(12) United States Patent
Fan et al.

(10) Patent No.: US 9,567,646 B2
(45) Date of Patent: Feb. 14, 2017

(54) MASSIVELY PARALLEL SINGLE CELL ANALYSIS

(71) Applicant: Cellular Research, Inc., Palo Alto, CA (US)

(72) Inventors: Christina Fan, Fremont, CA (US); Stephen P. A. Fodor, Palo Alto, CA (US); Glenn Fu, Dublin, CA (US); Geoffrey Richard Facer, Redwood City, CA (US); Julie Wilhelmy, Santa Cruz, CA (US)

(73) Assignee: Cellular Research, Inc., Menlo Park, CA (US)

( * ) Notice: Subject to any disclaimer, the term of this patent is extended or adjusted under 35 U.S.C. 154(b) by 0 days.

(21) Appl. No.: 14/800,526

(22) Filed: Jul. 15, 2015

(65) Prior Publication Data

US 2016/0010151 A1 Jan. 14, 2016

Related U.S. Application Data

(63) Continuation of application No. 14/472,363, filed on Aug. 28, 2014.

(60) Provisional application No. 62/012,237, filed on Jun. 13, 2014, provisional application No. 61/952,036, filed on Mar. 12, 2014, provisional application No. 61/871,232, filed on Aug. 28, 2013.

(51) Int. Cl.
*C12Q 1/68* (2006.01)

(52) U.S. Cl.
CPC ........... *C12Q 1/6888* (2013.01); *C12Q 1/6874* (2013.01); *C12Q 1/6876* (2013.01); *C12Q 1/6881* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 4,510,244 A * | 4/1985 | Parks | C12N 5/163 435/325 |
| 4,725,536 A | 2/1988 | Fritsch et al. | |
| 5,124,246 A | 6/1992 | Urdea et al. | |
| 5,149,625 A | 9/1992 | Church et al. | |
| 5,200,314 A | 4/1993 | Urdea | |
| 5,424,186 A | 6/1995 | Fodor et al. | |
| 5,424,413 A | 6/1995 | Hogan et al. | |
| 5,445,934 A | 8/1995 | Fodor et al. | |
| 5,604,097 A | 2/1997 | Brenner | |
| 5,635,352 A | 6/1997 | Urdea et al. | |
| 5,635,400 A | 6/1997 | Brenner | |
| 5,648,245 A | 7/1997 | Fire et al. | |
| 5,654,413 A | 8/1997 | Brenner | |
| 5,656,731 A | 8/1997 | Urdea | |
| 5,658,737 A | 8/1997 | Nelson et al. | |
| 5,714,330 A | 2/1998 | Brenner et al. | |
| 5,744,305 A | 4/1998 | Fodor et al. | |
| 5,759,778 A | 6/1998 | Li et al. | |
| 5,763,175 A | 6/1998 | Brenner | |
| 5,800,992 A | 9/1998 | Fodor et al. | |
| 5,846,719 A | 12/1998 | Brenner et al. | |
| 5,854,033 A | 12/1998 | Lizardi | |
| 5,871,928 A | 2/1999 | Fodor et al. | |
| 5,925,525 A | 7/1999 | Fodor et al. | |
| 5,935,793 A | 8/1999 | Wong | |
| 5,968,740 A | 10/1999 | Fodor et al. | |
| 5,981,176 A | 11/1999 | Wallace | |
| 5,981,179 A | 11/1999 | Lorinez et al. | |
| 6,013,445 A | 1/2000 | Albrecht et al. | |
| 6,040,138 A | 3/2000 | Lockhart et al. | |
| 6,046,005 A | 4/2000 | Ju et al. | |
| 6,060,596 A | 5/2000 | Lerner et al. | |
| 6,114,149 A | 9/2000 | Fry et al. | |
| 6,117,631 A | 9/2000 | Nilsen | |
| 6,124,092 A | 9/2000 | O'Neill et al. | |
| 6,138,077 A | 10/2000 | Brenner | |
| 6,140,489 A | 10/2000 | Brenner | |
| 6,172,214 B1 | 1/2001 | Brenner | |
| 6,197,506 B1 | 3/2001 | Fodor et al. | |
| 6,235,475 B1 | 5/2001 | Brenner et al. | |
| 6,268,152 B1 | 7/2001 | Fodor et al. | |
| 6,284,460 B1 | 9/2001 | Fodor et al. | |

(Continued)

FOREIGN PATENT DOCUMENTS

| | | | |
|---|---|---|---|
| DE | 102008025656 A1 | 12/2009 | |
| DE | EP 2805769 A1 * | 11/2014 | ........... C12Q 1/6834 |

(Continued)

OTHER PUBLICATIONS

Feldhaus et al. (Oligonucleotide-conjugated beads for transdominant genetic experiments, Nucleic Acids Res. Jan. 15, 2000; 28(2): 534-543).*
Sasuga et al. (Single-Cell Chemical Lysis Method for Analyses of Intracellular Molecules Using an Array of Picoliter-Scale Microwells, Anal Chem. Dec. 1, 2008;80(23):9141-9).*
Blainey (The future is now: single-cell genomics of bacteria and archaea, FEMS Microbiol Rev. May 2013 ; 37(3)).*
Parameswaran et al. (A pyrosequencing-tailored nucleotide barcode design unveils opportunities for large-scale sample multiplexing, Nucleic Acids Res. 2007;35(19):e130. Epub Oct. 11, 2007).*
Kivioja et al. (Counting absolute numbers of molecules using unique molecular identifiers, Nature Methods 9, 72-74 (2012), Nov. 20, 2011).*

(Continued)

*Primary Examiner* — Aaron Priest
(74) *Attorney, Agent, or Firm* — Knobbe, Martens, Olson & Bear, LLP

(57) ABSTRACT

The disclosure provides for methods, compositions, and kits for multiplex nucleic acid analysis of single cells. The methods, compositions and systems may be used for massively parallel single cell sequencing. The methods, compositions and systems may be used to analyze thousands of cells concurrently. The thousands of cells may comprise a mixed population of cells (e.g., cells of different types or subtypes, different sizes).

27 Claims, 135 Drawing Sheets

(56) References Cited

U.S. PATENT DOCUMENTS

| | | |
|---|---|---|
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'Neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,155,050 B1 | 12/2006 | Sloge |
| 7,393,665 B2 | 7/2008 | Brenner |
| 7,424,368 B2 | 9/2008 | Huang et al. |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,822,555 B2 | 10/2010 | Huang et al. |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,148,068 B2 | 4/2012 | Brenner |
| 8,168,385 B2 | 5/2012 | Brenner |
| 8,241,850 B2 | 8/2012 | Brenner |
| 8,298,767 B2 | 10/2012 | Brenner et al. |
| 8,318,433 B2 | 11/2012 | Brenner |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,228,229 B2 | 1/2016 | Olson et al. |
| 2002/0072058 A1 | 6/2002 | Voelker et al. |
| 2002/0168665 A1 | 11/2002 | Okawa |
| 2003/0003490 A1 | 1/2003 | Fan et al. |
| 2003/0049616 A1 | 3/2003 | Brenner et al. |
| 2003/0082818 A1* | 5/2003 | Bahnson ............... C12Q 1/24 436/63 |
| 2003/0104436 A1 | 6/2003 | Morris et al. |
| 2003/0175908 A1 | 9/2003 | Linnarson |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0259118 A1 | 12/2004 | Macevicz |
| 2005/0019776 A1 | 1/2005 | Callow et al. |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0041385 A1 | 2/2006 | Bauer |
| 2006/0073506 A1 | 4/2006 | Christians et al. |
| 2006/0211030 A1 | 9/2006 | Brenner |
| 2006/0263709 A1 | 11/2006 | Matsumura et al. |
| 2006/0263789 A1 | 11/2006 | Kincaid |
| 2007/0020640 A1 | 1/2007 | McCloskey et al. |
| 2007/0065823 A1 | 3/2007 | Dressman et al. |
| 2007/0117134 A1 | 5/2007 | Kou |
| 2007/0172873 A1* | 7/2007 | Brenner ............... C12Q 1/6816 435/6.12 |
| 2007/0178478 A1 | 8/2007 | Dhallan et al. |
| 2008/0070303 A1* | 3/2008 | West ................... C12N 5/0652 435/377 |
| 2008/0194414 A1 | 8/2008 | Albert et al. |
| 2008/0261204 A1 | 10/2008 | Lexow |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0061513 A1* | 3/2009 | Andersson Svahn .. C12M 23/12 435/366 |
| 2009/0105959 A1 | 4/2009 | Braverman et al. |
| 2009/0137407 A1 | 5/2009 | Church et al. |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0298709 A1 | 12/2009 | Ma |
| 2010/0069250 A1 | 3/2010 | White, III et al. |
| 2010/0105049 A1 | 4/2010 | Ehrich et al. |
| 2010/0105886 A1 | 4/2010 | Woudenberg et al. |
| 2010/0120630 A1 | 5/2010 | Huang et al. |
| 2010/0255471 A1 | 10/2010 | Clarke |
| 2010/0291666 A1 | 11/2010 | Collier et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0294689 A1 | 12/2011 | Namsaraev |
| 2012/0010091 A1 | 1/2012 | Linnarson |
| 2012/0040843 A1* | 2/2012 | Ducree ............ B01L 3/502753 506/7 |
| 2012/0045844 A1 | 2/2012 | Rothberg et al. |
| 2012/0065081 A1 | 3/2012 | Chee |
| 2012/0071331 A1* | 3/2012 | Casbon ................ C12Q 1/6855 506/4 |
| 2012/0156675 A1 | 6/2012 | Lueerssen et al. |
| 2012/0163681 A1 | 6/2012 | Lohse |
| 2012/0173159 A1* | 7/2012 | Davey .................... G06F 19/22 702/20 |
| 2012/0190020 A1* | 7/2012 | Oliphant ............... C12Q 1/6883 435/6.11 |
| 2012/0220022 A1 | 8/2012 | Ehrlich et al. |
| 2012/0220494 A1* | 8/2012 | Samuels ............ C12N 15/1075 506/16 |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1* | 2/2013 | Shinozuka ........... C07D 401/12 514/338 |
| 2013/0116130 A1* | 5/2013 | Fu ....................... C12Q 1/6837 506/4 |
| 2013/0190206 A1 | 7/2013 | Leonard |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0237458 A1 | 9/2013 | Casbon et al. |
| 2013/0267424 A1 | 10/2013 | Casbon et al. |

(56) References Cited

U.S. PATENT DOCUMENTS

| | | |
|---|---|---|
| 2013/0274117 A1 | 10/2013 | Church |
| 2013/0323732 A1* | 12/2013 | Anderson ............ C12Q 1/6813 435/6.11 |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0206547 A1 | 7/2014 | Wang |
| 2014/0216128 A1 | 8/2014 | Sahin et al. |
| 2014/0227684 A1 | 8/2014 | Hindson et al. |
| 2014/0227705 A1 | 8/2014 | Vogelstein et al. |
| 2014/0228255 A1 | 8/2014 | Hindson et al. |
| 2014/0235506 A1 | 8/2014 | Hindson et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0309945 A1 | 10/2014 | Park et al. |
| 2014/0315211 A1 | 10/2014 | Sugino et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005185 A1 | 1/2015 | Fodor et al. |
| 2015/0005199 A1 | 1/2015 | Hindson et al. |
| 2015/0005200 A1 | 1/2015 | Hindson et al. |
| 2015/0066385 A1 | 3/2015 | Schnall-Levin et al. |
| 2015/0099661 A1 | 4/2015 | Fodor et al. |
| 2015/0099673 A1 | 4/2015 | Fodor et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0141292 A1 | 5/2015 | Fodor et al. |
| 2015/0225778 A1 | 8/2015 | Hindson et al. |
| 2015/0299784 A1 | 10/2015 | Fan et al. |
| 2015/0376609 A1 | 12/2015 | Hindson et al. |
| 2016/0026758 A1 | 1/2016 | Jabara et al. |
| 2016/0055632 A1 | 2/2016 | Fu et al. |
| 2016/0145683 A1 | 5/2016 | Fan et al. |
| 2016/0222378 A1 | 8/2016 | Fodor et al. |
| 2016/0244828 A1 | 8/2016 | Mason |
| 2016/0253584 A1 | 9/2016 | Fodor et al. |
| 2016/0257993 A1 | 9/2016 | Fu et al. |
| 2016/0265069 A1 | 9/2016 | Fan et al. |

FOREIGN PATENT DOCUMENTS

| | | | |
|---|---|---|---|
| EP | 0799897 A1 | 10/1997 | |
| EP | 1473080 A2 | 11/2004 | |
| EP | 1647600 A2 | 4/2006 | |
| EP | 2 623 613 | 8/2013 | |
| WO | WO-8901050 A1 | 2/1989 | |
| WO | WO-9710365 A1 | 3/1997 | |
| WO | WO-9928505 A1 | 6/1999 | |
| WO | WO-0058516 A2 | 10/2000 | |
| WO | WO-02056014 A2 | 7/2002 | |
| WO | WO-2004017374 A2 | 2/2004 | |
| WO | WO 2005/071110 | 8/2005 | |
| WO | WO-2005080604 A2 | 9/2005 | |
| WO | WO-2005111242 A2 | 11/2005 | |
| WO | WO-2006071776 A2 | 7/2006 | |
| WO | WO-2006102264 A1 | 9/2006 | |
| WO | WO 2007/087310 | 8/2007 | |
| WO | WO 2007/087312 | 8/2007 | |
| WO | WO-2008096318 A2 | 8/2008 | |
| WO | WO 2009/148560 | 12/2009 | |
| WO | WO-2009152928 A2 | 12/2009 | |
| WO | WO-2009152928 A3 | 2/2010 | |
| WO | WO-2010117620 A2 | 10/2010 | |
| WO | WO-2011123246 A2 | 10/2011 | |
| WO | WO-2011143659 A2 | 11/2011 | |
| WO | WO-2012038839 A2 | 3/2012 | |
| WO | WO 2012/047297 | 4/2012 | |
| WO | WO-2012042374 A2 | 4/2012 | |
| WO | WO 2012048341 A1 * | 4/2012 | ............ C12Q 1/6869 |
| WO | WO-2012048341 A1 | 4/2012 | |
| WO | WO-2012083225 A2 | 6/2012 | |
| WO | WO-2012129363 A2 | 9/2012 | |
| WO | WO 2012129363 A2 * | 9/2012 | ............ C12Q 1/6853 |
| WO | WO-2012140224 A1 | 10/2012 | |
| WO | WO-2012142213 A2 | 10/2012 | |
| WO | WO 2012/149042 | 11/2012 | |
| WO | WO-2012148477 A1 | 11/2012 | |
| WO | WO-2013019075 A2 | 2/2013 | |
| WO | WO 2013130674 A1 * | 9/2013 | ............ C12Q 1/6806 |
| WO | WO-2013130674 A1 | 9/2013 | |
| WO | WO 2013/173394 | 11/2013 | |
| WO | WO 2013/177206 | 11/2013 | |
| WO | WO 2013/188831 | 12/2013 | |
| WO | WO 2013188872 A1 * | 12/2013 | ............ C12Q 1/6806 |
| WO | WO-2013188872 A1 | 12/2013 | |
| WO | WO 2014/015084 | 1/2014 | |
| WO | WO-2014018460 A1 | 1/2014 | |
| WO | WO-2014028537 A1 | 2/2014 | |
| WO | WO-2014093676 A1 | 6/2014 | |
| WO | WO-2014108850 A2 | 7/2014 | |
| WO | WO 2014/126937 | 8/2014 | |
| WO | WO-2014124336 A2 | 8/2014 | |
| WO | WO-2014124338 A1 | 8/2014 | |
| WO | WO 2014/144495 | 9/2014 | |
| WO | WO 2014/201273 | 12/2014 | |
| WO | WO-2014210353 A2 | 12/2014 | |
| WO | WO 2015/035087 | 3/2015 | |
| WO | WO-2015031691 A1 | 3/2015 | |
| WO | WO 2015/044428 | 4/2015 | |
| WO | WO 2015/047186 | 4/2015 | |
| WO | WO 2014/071361 | 5/2015 | |
| WO | WO 2015/103339 | 7/2015 | |
| WO | WO 2015/200869 | 12/2015 | |

OTHER PUBLICATIONS

Fu et al. (Counting individual DNA molecules by the stochastic attachment of diverse labels, Proc Natl Acad Sci U S A. May 31, 2011;108(22):9026-31. Epub May 11, 2011).*

Kinde et al. (Detection and quantification of rare mutations with massively parallel sequencing, Proc Natl Acad Sci U S A. Jun. 7, 2011;108(23):9530-5. Epub May 17, 2011).*

Novak et al. (Single-cell multiplex gene detection and sequencing with microfluidically generated agarose emulsions, Angew Chem Int Ed Engl. Jan. 10, 2011;50(2):390-5).*

Plessy et al. (Population transcriptomics with single-cell resolution: a new field made possible by microfluidics: a technology for high throughput transcript counting and data-driven definition of cell types, Bioessays. Feb. 2013;35(2):131-40. Epub Dec. 27, 2012).*

Miller et al. (Directed evolution by in vitro compartmentalization, Nature Methods—3, 561-570 (2006), Dec. 31, 2006).*

Leamon et al. (A massively parallel PicoTiterPlate based platform for discrete picoliter-scale polymerase chain reactions, Electrophoresis. Nov. 2003;24(21):3769-77).*

Marguiles et al. (Genome sequencing in microfabricated high-density picolitre reactors, Nature 437, 376-380, Published online Jul. 31, 2005).*

Bionumbers (Useful fundamental numbers in molecular biology, attached, available at http://bionumbers.hms.harvard.edu/KeyNumbers.aspx, Aug. 21, 2010).*

Shiroguchi et al. (Digital RNA sequencing minimizes sequence-dependent bias and amplification noise with optimized single-molecule barcodes, Proc Natl Acad Sci U S A. Jan. 24, 2012;109(4):1347-52. Epub Jan. 9, 2012).*

Lee et al. (Large-scale arrays of picolitre chambers for single-cell analysis of large cell populations, Lab Chip. Nov. 7, 2010;10(21):2952-8. Epub Sep. 13, 2010).*

Schmitt et al. (Detection of ultra-rare mutations by next-generation sequencing, Proc Natl Acad Sci U S A. Sep. 4, 2012;109(36):14508-13. doi: 10.1073/pnas.1208715109. Epub Aug. 1, 2012).*

(56) References Cited

OTHER PUBLICATIONS

Craig et al. (Identification of genetic variants using bar-coded multiplexed sequencing, Nat Methods. Oct. 2008;5(10):887-93. doi: 10.1038/nmeth.1251. Epub Sep. 14, 2008).*
Casbon et al. (A method for counting PCR template molecules with application to next-generation sequencing, Nucl. Acids Res. (2011), doi: 10.1093/nar/gkr217, First published online: Apr. 13, 2011).*
Cai et al. (Turning single cells into microarrays by super-resolution barcoding, Brief Funct Genomics. Mar. 2013;12(2):75-80. doi: 10.1093/bfgp/els054. Epub Nov. 22, 2012).*
Marcus et al. (Microfluidic single-cell mRNA isolation and analysis, Anal Chem. May 1, 2006;78(9):3084-9).*
Warren et al. (Transcription factor profiling in individual hematopoietic progenitors by digital RT-PCR, Proc Natl Acad Sci U S A. Nov. 21, 2006;103(47):17807-12. Epub Nov. 10, 2006).*
Gong et al. (Massively parallel detection of gene expression in single cells using subnanolitre wells, Lab Chip. Sep. 21, 2010;10(18):2334-7. doi: 10.1039/c004847j. Epub Aug. 4, 2010).*
White et al. (High-throughput microfluidic single-cell RT-qPCR, Proc Natl Acad Sci U S A., Aug. 23, 2011; 108(34): 13999-14004. Published online Aug. 1, 2011).*
Nagai et al. (Development of a microchamber array for picoliter PCR, Anal Chem. Mar. 1, 2001;73(5):1043-7).*
Achim; et al., "High-throughput spatial mapping of single-cell RNA-seq data to tissue of origin. Nature Biotechnology, vol. 33, No. 5, May 2015, p. 503-511.".
Alkan, et al. Personalized copy number and segmental duplication maps using next-generation sequencing. Nat Genet. Oct. 2009;41(10):1061-7. doi: 10.1038/ng.437. Epub Aug. 30, 2009.
Anderson; et al., "2010, HIV-1 populations in semen arise through multiple mechanisms, PLOS Pathogens, 6(8) e1001053 (12 pages).".
Ansorge. Next-generation DNA sequencing techniques. New Biotechnology, 25(4): 195-203 (2009).
Atanur, et al. The genome sequence of the spontaneously hypertensive rat: Analysis and functional significance. Genome Res. Jun. 2010;20(6):791-803. doi: 10.1101/gr.103499.109. Epub Apr. 29, 2010.
Audic, et al. The Significance of Digital Gene Expression Profiles. Genome Research, 7: 986-995 (1997).
Bendall, et al. Single-cell mass cytometry of differential immune and drug responses across a human hematopoietic continuum. Science. May 6, 2011;332(6030):687-96. doi: 10.1126/science. 1198704.
Bonaldo, et al. Normalization and subtraction: two approaches to facilitate gene discovery. Genome Res. Sep. 1996;6(9):791-806.
Braha, et al. Simultaneous stochastic sensing of divalent metal ions. Nature Biotechnology, 18: 1005-1007 (2000).
Bratke, et al. Differential expression of human granzymes A, B, and K in natural killer cells and during CD8+ T cell differentiation in peripheral blood. Eur J Immunol. Sep. 2005;35(9):2608-16.
Brenner, et al. Gene expression analysis by massively parallel signature sequencing (MPSS) on microbead arrays. Nature Biotechnology, 18: 630-634 (2000).
Brenner, et al. In vitro cloning of complex mixtures of DNA on microbeads: physical separation of differentially expressed cDNAs. Proc Natl Aced Sci U S A. Feb. 15, 2000;97(4):1665-70.
Carr, et al. Inferring relative proportions of DNA variants from sequencing electropherograms. Bioinformatics. Dec. 15, 2009;25(24):3244-50. doi: 10.1093/bioinformatics/btp583. Epub Oct. 9, 2009.
Casbon, et al. A method for counting PCR template molecules with application to next-generation sequencing. Nucleic Acids Res. Jul. 2011;39(12):e81. doi: 10.1093/nar/gkr217. Epub Apr. 13, 2011.
Castle, et al. DNA copy number, including telomeres and mitochondria, assayed using next-generation sequencing. BMC Genomics. Apr. 16, 2010;11:244. doi: 10.1186/1471-2164-11-244.
Chang, et al. Detection of allelic imbalance in ascitic supernatant by digital single nucleotide polymorphism analysis. Clin Cancer Res. Aug. 2002;8(8):2580-5.

Chee. Enzymatic multiplex DNA sequencing. Nucleic Acids Research, 19(12): 3301-3305 (1991).
Chee, et al. Accessing genetic information with high-density DNA arrays. Science, 274: 610-6 14 (1996).
Chen; et al., "Spatially resolved, high multiplexed RNA profiling in single cells. Sciencexpress, Apr. 9, 2015, p. 1-21.".
Church, et al. Multiplex DNA sequencing. Science, 240: 185-188 (1988).
Co-pending U.S. Appl. No. 14/381,526, filed Aug. 27, 2014.
Co-pending U.S. Appl. No. 14/472,363, filed Aug. 28, 2014.
Co-pending U.S. Appl. No. 14/508,911, filed Oct. 7, 2014.
Costello, et al. Discovery and characterization of artifactual mutations in deep coverage targeted capture sequencing data due to oxidative DNA damage during sample preparation. Nucleic Acids Res. Apr. 1, 2013; 41(6):e67. doi: 10.1093/nar/gks1443. Epub Jan. 8, 2013.
Cox. Bar coding objects with DNA. Analyst. May 2001;126(5):545-7.
Craig, et al. Identification of genetic variants using bar-coded multiplexed sequencing. Nat Methods. Oct. 2008;5(10):887-93. doi: 10.1038/nmeth.1251. Epub Sep. 14, 2008.
Cusanovich; et al., "Multiplex single-cell profiling of chromatin accessibility by combinatorial cellular indexing. Sciencexpress, May 7, 2014, p. 1-9.".
Daines, et al. High-throughput multiplex sequencing to discover copy nymber variants in *Drosophila*. Genetics. Aug. 2009;182(4):935-41. doi: 10.1534/genetics.109.103218. Epub Jun. 15, 2009.
D'Antoni, et al. Rapid quantitative analysis using a single molecule counting approach. Anal Biochem. May 1, 2006;352(1):97-109. Epub Feb. 10, 2006.
Daser, et al. Interrogation of genomes by molecular copy-number counting (MCC). Nature Methods, 3(6): 447-453 (2006).
De Saizieu, et al. Bacterial transcript imaging by hybridization of total RNA to oligonucleotide arrays. Nature Biotechnology, 16: 45-48 (1998).
Dirks; et al., "Triggered amplification by hybridization chain reaction.", Oct. 26, 2004, 101(43), 15275-8.
"European search report and search opinion dated Jul. 17, 2015 for EP Application No. 13755319.4.".
Fan; et al., "Expression profiling. Combinatorial labeling of single cells for gene expression cytometry. Science. Feb. 6, 2015;347(6222):1258367. doi: 10.1126/science.1258367.".
Fan, et al. Microfluidic digital PCR enables rapid prenatal diagnosis of fetal aneuploidy. Am Obstet Gynecol. 2009; 200:543.e1-543.e7.
Fan, et al. Non-invasive prenatal measurement of the fetal genome. Nature. Jul. 19, 2012;487(7407):320-4. doi: 10.1038/nature11251.
Fan, et al. Parallel Genotyping of Human SNPs Using Generic High-density Oligonucleotide Tag Arrays. Genome Research, 10: 853-860 (2000).
Fox-Walsh et al., "A multiplex RNA-seq strategy to profile poly(A+) RNA: application to analysis of transcription response and 3' end formation.", Oct. 2011, 98(4), 266-71.
Fu, et al. Counting individual DNA molecules by the stochastic attachment of diverse labels. Proc Natl Aced Sci U S A. May 31, 2011;108(22):9026-31. Epub May 11, 2011.
Fu, et al. Digital encoding of cellular mRNAs enabling precise and absolute gene expression measurement by single-molecule counting. Anal Chem. Mar. 18, 2014;86(6):2867-70. doi: 10.1021/ac500459p. Epub Mar. 4, 2014.
Gerry, et al. Universal DNA microarray method for multiplex detection of low abundance point mutations. Journal of Molecular Biology, 292(2): 251-262 (1999).
Gillespie. .Exact stochastic simulation of coupled chemical reactions. The Journal of Physical Chemistry, 81(25): 2340-2361 (1977).
Grant, et al. SNP genotyping on a genome-wide amplified DOP-PCR template. Nucleic Acids Res. Nov. 15, 2002;30(22):e125.
Gunderson; et al., "Decoding randomly ordered DNA arrays. Genome Res. May 2004;14(5):870-7. Epub Apr. 12, 2004.".
Gundry, et al. Direct, genome-wide assessment of DNA mutations in single cells. Nucleic Acids Res. Mar. 2012;40(5):2032-40. doi: 10.1093/nar/gkr949. Epub Nov. 15, 2011.

(56) References Cited

OTHER PUBLICATIONS

Gundry, et al. Direct mutation analysis by high-throughput sequencing: from germline to low-abundant, somatic variants. Mutat Res. Jan. 3, 2012;729(1-2):1-15. doi: 10.1016/mrfmmm.2011.10.001. Epub Oct. 12, 2011.
Hacia, et al. Determination of ancestral alleles for human single-nucleotide polymorphisms using high-density oligonucleotide arrays. Nature Genetics, 22: 164-167 (1999).
Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.
Harrington; et al., "2009, Cross-sectional characterization of HIV-1 env compartmentalization in cerebrospinal fluid over the full disease course, AIDS, 23(8) 907-915.".
Hashimshony, et al. CEL-Seq: single-cell RNA-Seq by multiplexed linear amplification Cell Rep. Sep. 27, 2012;2(3):666-73. doi: 10.1016/j.celrep.2012.08.003. Epub Aug. 30, 2012.
Hensel, et al. Simultaneous identification of bacterial virulence genes by negative selection. Science. Jul. 21, 1995;269(5222):400-3.
Hiatt, et al. Parallel, tag-directed assembly of locally derived short sequence reads. Nat Methods. Feb. 2010;7(2):119-22. doi: 10.1038/nmeth.1416. Epub Jan. 17, 2010.
Hiatt, et al. Single molecule molecular inversion probes for targeted, high-accuracy detection of low-frequency variation. Genome Res. May 2013;23(5):843-54. doi: 10.1101/gr.147686.112. Epub Feb. 4, 2013.
Hollas, et al. A stochastic approach to count RNA molecules using DNA sequencing methods. Lecture Notes in Computer Science, 2812: 55-62 (2003).
Hug, et al. Measurement of the number Of molecules of a single mRNA species in a complex mRNA preparation. J Theor Biol. Apr. 21, 2003;221(4):615-24.
Ingolia, et al. Genome-wide analysis in vivo of translation with nucleotide resolution using ribosome profiling. Science. Apr. 10, 2009;324(5924):218-23. Epub Feb. 12, 2009.
"International search report and written opinion dated Feb. 3, 2015 for PCT/US2014/053301.".
International search report and written opinion dated May 7, 2012 for PCT/IB2011/003160.
International search report and written opinion dated Jun. 6, 2012 for PCT/US2011/065291.
International search report and written opinion dated Aug. 16, 2013 for PCT/US2013/027891.
International search report and written opinion dated Dec. 19, 2014 for PCT Application No. US2014/059542.
International search report dated Aug. 6, 2014 for PCT Application No. GB1408829.8.
Islam; et al., "Characterization of the single-cell transcriptional landscape by highly multiplex RNA-seq. Genome Research, 2011, 21: 1160-1167.".
Jabara, et al. Accurate sampling and deep sequencing of the HIV-1 protease gene using a Primer ID, Dec. 3, 2011, PNAS, vol. 108, No. 50, p. 20166-20171.
Kanagawa. Bias and artifacts in multitemplate polymerase chain reactions (PCR), 2003, Journal of Bioscience and Bioengineering, vol. 96, No. 4, p. 317-323.
Kinde, et al. Detection and quantification of rare mutations with massively parallel sequencing. Proc Natl Aced Sci U S A. Jun. 7, 2011;108(23):9530-5. doi: 10.1073/pnas.1105422108. Epub May 17, 2011.
Kivioja, et al. Counting absolute numbers of molecules using unique molecular identifiers. Nat Methods. Nov. 20, 2011;9(1):72-4. doi: 10.1038/nmeth.1778.
Koboldt, et al. VarScan: variant detection in massively parallel sequencing of individual and pooled samples. Bioinformatics. Sep. 1, 2009;25(17):2283-5. doi: 10.1093/bioinformatics/btp373. Epub Jun. 19, 2009.
Konig, et al. iCLIP reveals the function of hnRNAP particles in splicing at individual nucleotide resolution, Jul. 2010, Nature Structural & Molecular Biology, 17(7):909-916.
Larson, et al. A single molecule view of of gene expression. Trends Cell Biol. Nov. 2009;19(11):630-7. Epub Oct. 8, 2009.
Lee; et al., "Highly multiplexed subcellular RNA sequencing in situ. Science. Mar. 21, 2014;343(6177):1360-3. doi: 10.1126/science.1250212. Epub Feb. 27, 2014.".
Lizardi, et al. Mutation detection and single-molecule counting using isothermal rolling-circle amplification. Nat Genet. Jul. 1998;19(3):225-32.
Lockhart, et al. Expression monitoring by hybridization to high-density oligonucleotide arrays. Nature Biotechnology, 14: 1675-1680 (1996).
Lovatt; et al., "Transcriptome in vivo analysis (TIVA) of spatially defined single cells in live tissue. Nat Methods. Feb. 2014;11(2):190-6. doi: 10.1038/nmeth.2804. Epub Jan. 12, 2014.".
Lucito, et al. Representational Oligonucleotide Microarray Analysis: A High-Resolution Method to Detect Genome Copy Number Variation. Genome Research, 13: 2291-2305.
Maamar, et al. Noise in Gene Expression Determines Cell Fate in Bacillus subtilis. Science, 317: 526-529 (2007).
MaCaulay; et al., "G&T-seq: parallel sequencing of single-cell genomes and transcriptomes. Nature Methods, 2015, p. 1-7.".
Makrigiorgos, et al., A PCR-Based amplification method retaining quantative difference between two complex genomes. Nature Biotech, vol. 20, No. 9, pp. 939-939 (Sep. 2002).
McCloskey, et al. Encoding PCR products with batch-stamps and barcodes. Biochem Genet. Dec. 2007;45(11-12):761-7. Epub Oct. 23, 2007.
Medvedev, et al. Detecting copy number variation with mated short reads. Genome Res. Nov. 2010;20(11):1613-22. doi: 10.1101/gr.106344.110. Epub Aug. 30, 2010.
Mei, et al. Identification of recurrent regions of Copy-Number Variants across multiple individuals. BMC Bioinformatics. Mar. 22, 2010;11:147. doi: 10.1186/1471-2105-11-147.
Mortazavi, et al. Mapping and quantifying mammalian transcriptomes by RNA-Seq. Nat. Methods. 2008; 5, 621-628.
Newell, et al. Cytometry by time-of-flight shows combinatorial cytokine expression and virus-specific cell niches within a continuum of CD8+ T cell phenotypes. Immunity. Jan. 27, 2012;36(1):142-52. doi: 10.1016/j.immuni.2012.01.002.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Feb. 18, 2015 for U.S. Appl. No. 14/540,007.
Office action dated Feb. 26, 2015 for U.S. Appl. No. 14/540,029.
Office action dated Mar. 19, 2015 for U.S. Appl. No. 14/540,018.
Office action dated May 7, 2015 for U.S. Appl. No. 13/327,526.
"Office action dated Sep. 1, 2015 for U.S. Appl. No. 14/540,029.".
"Office action dated Sep. 24, 2015 for U.S. Appl. No. 14/540,007.".
Office action dated Oct. 3, 2013 for U.S. Appl. No. 12/969,581.
"Office action dated Oct. 6, 2015 for U.S. Appl. No. 14/540,018.".
Ogino, et al. Quantification of PCR bias caused by a single nucleotide polymorphism in SMN gene dosage analysis. J Mol Diagn. Nov. 2002;4(4):185-90.
Park, et al. Discovery of common Asian copy number variants using integrated high-resolution array CGH and massively parallel DNA sequencing. Nat Genet. May 2010;42(5):400-5. doi: 10.1038/ng.555. Epub Apr. 4, 2010.
Pihlak, et al. Rapid genome sequencing with short universal tiling probes. Nature Biotechnology, 26: 676-684 (2008).
Pinkel, et al. Comparative Genomic Hybridization. Annual Review of Genomics and Human Genetics, 6: 331-354 (2005).
Pleasance, et al. A small-cell lung cancer genome with complex signatures of tobacco exposure. Nature. Jan. 14, 2010;463(7278):184-90. doi: 10.1038/nature08629. Epub Dec. 16, 2009.

(56) References Cited

OTHER PUBLICATIONS

Qiu, et al. DNA sequence-based "bar codes" for tracking the origins of expressed sequence tags from a maize cDNA library constructed using multiple mRNA sources. Plant Physiol. Oct. 2003;133(2):475-81.
Response with alllowed claims dated Mar. 4, 2014 for U.S. Appl. No. 12/969,581.
Sasagawa; et al., "Quartz-Seq: a highly reproducible and sensitive single-cell RNA sequencing method, reveals non-genetic gene-expression heterogeneity. Genome Biology, 2013, 14:R31.".
Satija; et al., "Spatial reconstruction of single-cell gene expression data. Nature Biotechnology, vol. 33, No. 5, May 2015, p. 495-508.".
Schmitt, et al. Detection of ultra-rare mutations by next-generation sequencing. Proc Natl Acad Sci U S A. Sep. 4, 2012;109(36):14508-13. doi: 10.1073/pnas.1208715109. Epub Aug. 1, 2012.
Sebat, et al. Large-Scale Copy Number Polymorphism in the Human Genome. Science, 305: 525-528 (2004).
Shalek, et al. Single-cell transcriptomics reveals bimodality in expression and splicing in immune cells. Nature. Jun. 13, 2013;498(7453):236-40. doi: 10.1038/nature12172. Epub May 19, 2013.
Shiroguchi, et al. Digital RNA sequencing minimizes sequence-dependent bias and amplification noise with optimized single-molecule barcodes. Proc Natl Acad Sci U S A. Jan. 24, 2012;109(4):1347-52. doi: 10.1073/pnas.1118018109. Epub Jan. 9, 2012.
Shoemaker, et al. Quantitative phenotypic analysis of yeast deletion mutants using a highly parallel molecular bar-coding strategy. Nature Genetics, 14: 450-456 (1996).
Simpson, et al. Copy number variant detection in inbred strains from short read sequence data. Bioinformatics. Feb. 15, 2010;26(4):565-7. doi: 10.1093/bioinformatics/btp693. Epub Dec. 18, 2009.
Smith, et al. Highly-multiplexed barcode sequencing: an efficient method for parallel analysis of pooled samples. Nucleic Acids Research, 38(13): e142 (2010).
Tan, et al. Genome-wide comparison of DNA hydroxymethylation in mouse embryonic stem cells and neural progenitor cells by a new comparative hMeDIP-seq method. Nucleic Acids Res. Apr. 2013;41(7):e84. doi: 10.1093/nar/gkt091. Epub Feb. 13, 2013.
Taudien, et al. Haplotyping and copy number estimation of the highly polymorphic human beta-defensin locus on 8p23 by 454 amplicon sequencing. BMC Genomics. Apr. 19, 2010;11:252. doi: 10.1186/1471-2164-11-252.
Tomaz, et al. Differential methylation as a cause of allele dropout at the imprinted GNAS locus. Genet Test Mol Biomarkers. Aug, 2010;14(4):455-60. doi: 10.1089/gtmb.2010.0029.
Treutlein, et al. Reconstructing lineage hierarchies of the distal lung epithelium using single-cell RNA-seq. Nature. May 15, 2014;509(7500):371-5. doi: 10.1038/nature13173. Epub Apr. 13, 2014.
U.S. Appl. No. 61/384,001, filed Sep. 17, 2010.
U.S. Appl. No. 61/432,119, filed Jan. 12, 2011.
Velculescu, et al. Characterization of the Yeast Transcriptome. Cell, 88: 243-251 (1997).
Velculescu, et al. Serial Analysis of Gene Expression. Science, 270: 484-487 (1995).
Vogelstein, et al. Digital PCR. Proc. Natl. Acad. Sci., 96(16): 9236-9241 (1999).
Walker, et al. Isothermal in vitro amplification of DNA by a restriction enzyme/DNA polymerase system. Proc Natl Acad Sci U S A. Jan. 1, 1992;89(1):392-6.
Walsh, et al. Detection of inherited mutations for breast and ovarian cancer using genomic capture and massively parallel sequencing. Proc Natl Aced Sci U S A. Jul. 13, 2010;107(28):12629-33. doi: 10.1073/pnas.1007983107. Epub Jun. 28, 2010.
Wang, et al. iCLIP predicts the dual splicing effects of TIA-RNA interactions, Oct. 2010, PLoS Biol, 8(10):e1000530.
Wang, et al. RNA-Seq: a revolutionary tool for transcriptomics. Nature Reviews Genetics, 10: 57-63 (2009).

Weber, et al. A real-time polymerase chain reaction assay for quantification of allele ratios and correction of amplification bias. Anal Biochem. Sep. 15, 2003;320(2):252-8.
Wittes, et al. Searching for Evidence of Altered Gene Expression: a Comment on Statistical Analysis of Microarray Data. Journal of the National Cancer Institute, 91(5): 400-401 (1999).
Wodicka, et al. Genome-wide expression monitoring in Saccharomyces cerevisiae. Nature Biotechnology, 15: 1359-1367 (1997).
Wojdacs, et al. Primer design versus PCR bias in methylation independent PCR amplifications. Epigenetics. May 16, 2009;4(4):231-4. Epub May 14, 2009.
Wood, et al. Using next-generation sequencing for high resolution multiplex analysis of copy number variation from nanogram quantities of DNA from formalin-fixed paraffin-embedded specimens. Nucleic Acids Res. Aug. 2010;38(14):e151. doi: 10.1093/nar/gkq510. Epub Jun. 4, 2010.
Wu, et al. Quantitative assessment of single-cell RNA-sequencing methods. Nat Methods. Jan. 2014;11(1):41-6. doi: 10.1038/nmeth.2694. Epub Oct. 20, 2013.
Yandell, et al. A probabilistic disease-gene finder for personal genomes. Genome Res. Sep. 2011;21(9):1529-42. doi: 10.1101/gr.123158.111. Epub Jun. 23, 2011.
Ye, et al. Fluorescent microsphere-based readout technology for multiplexed human single nucleotide polymorphism analysis and bacterial identification. Human Mutation, 17(4): 305-316 (2001).
Yoon, et al. Sensitive and accurate detection of copy number variants using read depth of coverage. Genome Res. Sep. 2009;19(9):1586-92. doi: 10.1101/gr.092981.109. Epub Aug. 5, 2009.
Zhang; et al., "DNA-based hybridization chain reaction for amplified bioelectronic signal and ultrasensitive detection of proteins.", Jun. 19, 2012, 84(12), 5392-9.
Zhang, et al. The impact of next-generation sequencing on genomics. J Genet Genomics. Mar. 20, 2011;38(3):95-109. doi: 10.1016/j.jgg.2011.02.003. Epub Mar. 15, 2011.
Zhao, et al. Homozygous Deletions and Chromosome Amplifications in Human Lung Carcinomas Revealed by Single Nucleotide Polymorphism Array Analysis. Cancer Research, 65: 5561-5570 (2005).
Zhou, et al. Counting alleles reveals a connection between chromosomes 18q loss and vascular invasion. Nature Biotechnology, 19: 78-81 (2001).
Blainey, May 2013, The future is now: single-cell genomics of bacteria and archaea, FEMS Microbiol Rev., 37(3):407-427.
Brodin et al., 2015, Challenges with using primer IDs to improve accuracy of next generation sequencing, 19(3):1-12.
Chamberlain et al., Dec. 9, 1988, Deletion screening of the Duchenne muscular dystrophy locus via multiplex DNA amplification. Nucleic Acids Res., 16(23):11141-11156.
Feldhaus et al., Jan. 15, 2000, Oligonucleotide-conjugated beads for transdominant genetic experiments, Nucleic Acids Res., 28(2):534-543.
Jabara, Apr. 23, 2010, Capturing the cloud: High throughput sequencing of multiple individual genomes from a retroviral population. Biology Lunch Bunch Series, Training Initiatives in Biomedical & Biological Sciences of the University of North Carolina at Chapel Hill.
Keys et al., Jun. 2015, Primer ID informs next-generation sequencing platforms and reveals preexisting drug resistance mutations in the HIV-1 reverse transcriptase coding domain, AIDS Research and Human Retroviruses, 31(6):658-668.
Macosko et al., 2015, Highly parallel genome-wide expression profiling of individual cells using nanoliter droplets, Cell 161:1202-1214 (and supplemental information).
Miner et al., 2004, Molecular barcodes detect redundancy and contamination in hairpin-bisulfite PCR, Nucleic Acids Research, 32(17):e135.
Ogino et al., Nov. 2002, Quantification of PCR bias caused by a single nucleotide polymorphism in SMN gene dosage analysis, Journal of Molecular Diagnostics, 4(4):185-190.

(56) References Cited

OTHER PUBLICATIONS

Parameswaran et al., 2007, A pyrosequencing-tailored nucleotide barcode design unveils opportunities for large-scale sample multiplexing. Nucleic Acids Res. 35(19):e130.
Sasuga et al., Dec. 2008, Single-cell chemical lysis method for analyses of intracellular molecules using an array of picoliter-scale microwells, Anal Chem, 80(23):9141-9149.
The Tibbs Times, UNC bioscience newsletter, Apr. 2010, 17 pages.
Zhou et al., 2001, Counting alleles reveals a connection between chromosome 18q loss and vascular invasion. Nature Biotechnology, 19:78-81.
Office action dated Dec. 3, 2015 for U.S. Appl. No. 14/281,706.
Notice of allowance dated Jan. 21, 2016 for U.S. Appl. No. 13/327,526.
Notice of allowance dated Dec. 15, 2015 for U.S. Appl. No. 14/540,007.
Notice of allowance dated Dec. 21, 2015 for U.S. Appl. No. 14/540,018.
Restriction Requirement dated Mar. 15, 2016 in U.S. Appl. No. 14/381,488.
International search report dated Sep. 6, 2013 in PCT/US13/028103.
Search Report and Written Opinion mailed Mar. 1, 2016 in Singapore Patent Application No. 1120140527W.
Extended European Search Report dated Dedember 15, 2015 in European Patent Application No. 13754428.4.
Restriction Requirement dated Mar. 17, 2016 in U.S. Appl. No. 14/472,363.
Examination Report dated Feb. 19, 2016 in Great Britain Patent Application No. GB1511591.8.
Notice of opposition dated Jul. 22, 2015 for EP Application No. 11810645.9.
Notice of opposition dated Jul. 9, 2015 for EP Application No. 11810645.9.
Roche Diagnostics GmbH, 2006, Genome Sequencer 20 System: First to the Finish (product brochure), 40 pages.
Cai, Mar. 2013, Turning single cells in microarrays by super-resolution bar-coding, Brief Funct Genomics, 12(2):75-80.
Dalerba et al., Single-cell dissection of transcriptional heterogeneity in human colon tumors, Nat Biotechnol., 29(12):1120-1127 and Supplementary Material.
Kim et al., Jun. 8, 2007, Polony multiplex analysis of gene expression (PMAGE) in mouse hypertrophic cardiomyopathy, Science, 316(5830):1481-1484.
Kurimoto et al., Mar. 17, 2006, An improved single-cell cDNA amplification method for efficient high-density oligonucleotide microarray analysis, Nucleic Acids Res., 34(5):e42.
Picelli et al., Jul. 30, 2014, Tn5 transposase and tagmentation procedures for massively scaled sequencing projects, Genome Research 24(12):2033-2040.
Soumillon et al., Mar. 5, 2014, Characterization of directed differentiation by high-throughput single-cell RNA-Seq, bioRxiv preprint, http://biorxiv.org/content/early/2014/03/05/003236.full.pdf, 13 pp.
Wang et al., May 21, 2015, Advances and applications of single-cell sequencing technologies, Molecular Cell, 58(4):598-609.
International Search Report and Written Opinion dated May 3, 2016 in PCT/US16/018354.
Office Action dated May 10, 2016 in U.S. Appl. No. 14/381,488.
Search and Examination Report dated Jan. 27, 2016 in GB patent application No. 1408829.8.
Office Action dated Apr. 11, 2016 in U.S. Appl. No. 14/472,363.
Search and Examination Report dated Aug. 26, 2015 in GB patent application No. 1511591.8.
Office Action dated May 13, 2016 in U.S. Appl. No. 14/508,911.

Castellarnau et al., Jan. 2015, Stochastic particle barcoding for single-cell tracking and multiparametric analysis, Small, 11(4):489-498.
Fan Nov. 2010, Molecular counting: from noninvasive prenatal diagnostics to whole-genome haplotyping, doctoral dissertation, Stanford University, 185 pp.
Haff, 1994, Improved quantitative PCR using nested primers, PCR Methods and Applications, 3:332-337.
Kebschull et al., Jul. 17, 2015, Sources of PCR-induced distortions in high-throughput sequencing data sets, Nucleic Acids Research, 15 pp.
Kotake et al., 1996, A simple nested RT-PCR method for quantitation of the relative amounts of multiple cytokine mRNAs in small tissue samples, Journal of Immunological Methods, 199:193-203.
Speicher et al., Oct. 2005, The new cytogenetics: blurring the boundaries with molecular biology, Nature Reviews Genetics, 6(10):782-792.
Takahashi et al., Mar. 2006, Novel technique of quantitative nested real-time PCR assay for mycobacterium tuberculosis DNA, Journal of Clinical Microbiology, 44(3):1029-1039.
Zheng et al., Feb. 2016, Haplotyping germline and cancer genomes with high-throughput linked-read sequencing, Nature Biotechnology, 34(3):303-311.
Examination Report dated Jun. 8, 2016 in GB Patent Application No. 1408829.8.
International Search Report and Written Opinion dated Jun. 20, 2016 in PCT/US16/14612.
International Search Report and Written Opinion dated Jun. 17, 2016 in PCT/US16/019962.
Invitation to Pay Additional Search Fees dated Jun. 2, 2016 in PCT/US16/019971.
International Search Report and Written Opinion dated Jun. 9, 2016 in PCT/US16/022712.
Anderson, Feb. 11, 2014, Study describes RNA sequencing applications for molecular indexing methods, genomeweb.com, 5 pp.
Bioscribe, Feb. 5, 2015, Massively parallel sequencing technology for single-cell gene expression published (press release), 3 pp.
Butkus, Feb. 6, 2014, Cellular research set to launch first gene expression platform using 'molecular indexing' technology, genomeweb.com, 5 pp.
Junker et al., May 21, 2015, Single-cell transcriptomics enters the age of mass production, Molecular Cell, 58:563-564.
Klein et al., May 21, 2015, Droplet barcoding for single-cell transcriptomics applied to embryonic stem cells, Cell, 161:1187-1201.
Kolodziejczyk et al., May 21, 2015, The technology and biology of single-cell RNA sequencing, Molecular Cell, 58:610-620.
Liu et al., Single-cell transcriptome sequencing: recent advances and remaining challenges, F1000 Research 2016, 5(F1000 Faculty Rev):182, 9 pp.
Navin, 2015, The first five years of single-cell cancer genomics and beyond, Genome Research, 25:1499-1507.
Office action dated Jul. 20, 2016 for U.S. Appl. No. 14/281,706.
Office Action dated Aug. 12, 2016 in U.S. Appl. No. 14/381,488.
Second Office Action dated Jun. 6, 2016 in Chinese Patent Application No. 201380022187.9.
Examination report dated Jul. 12, 2016 in European Patent Application No. 13755319.4.
Examination Report dated Jun. 15, 2016 in Great Britain Patent Application No. GB1511591.8.
Written Opinion dated Jul. 5, 2016 in PCT/US16/019962.
International Search Report and Written Opinion dated Aug. 9, 2016 in PCT/US16/019971.

* cited by examiner

| well volume | 2.12E-14 | m3 |
|---|---|---|
| bead volume | 4.19E-15 | m3 |
| well volume-bead volume | 1.70E-14 | m3 |
| well volume-bead volume | 1.70E-11 | L |
| #mRNA per cell | 2.50E+05 | molecules |
| concentration of mRNA | 1.47E+16 | molecules per L |
| concentration of mRNA | 2.44E-08 | moles per L |
| concentration of mRNA | 24.40 | nM |

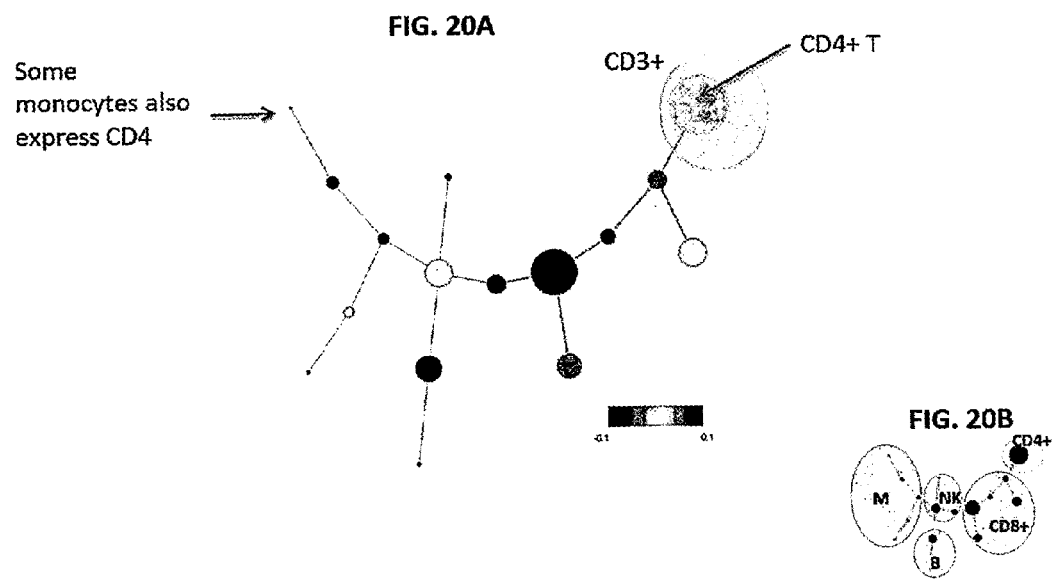
FIG. 20A-B
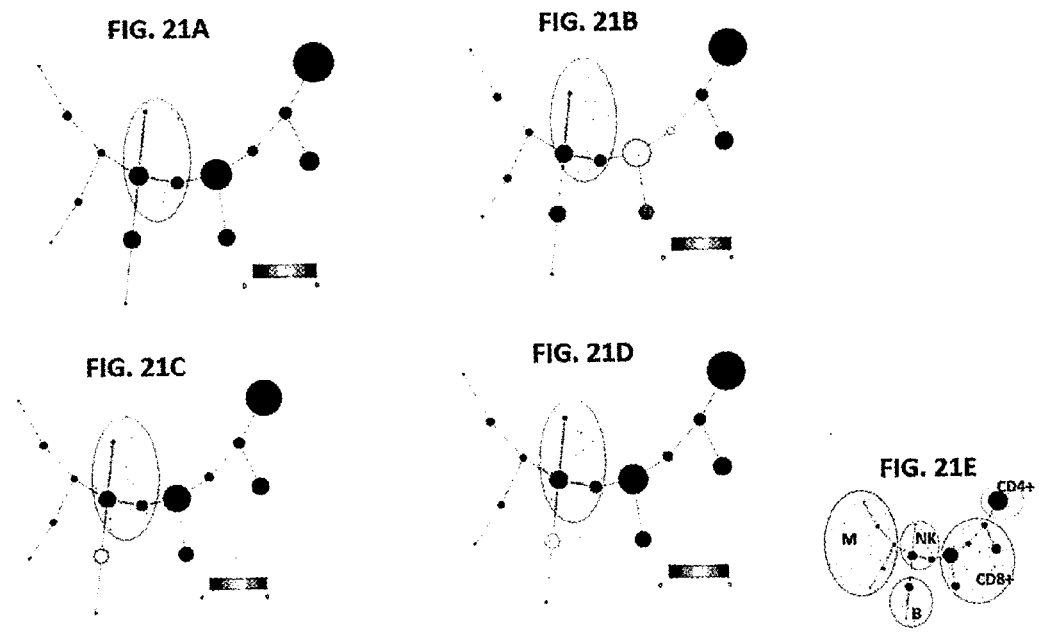
FIG. 21A-E

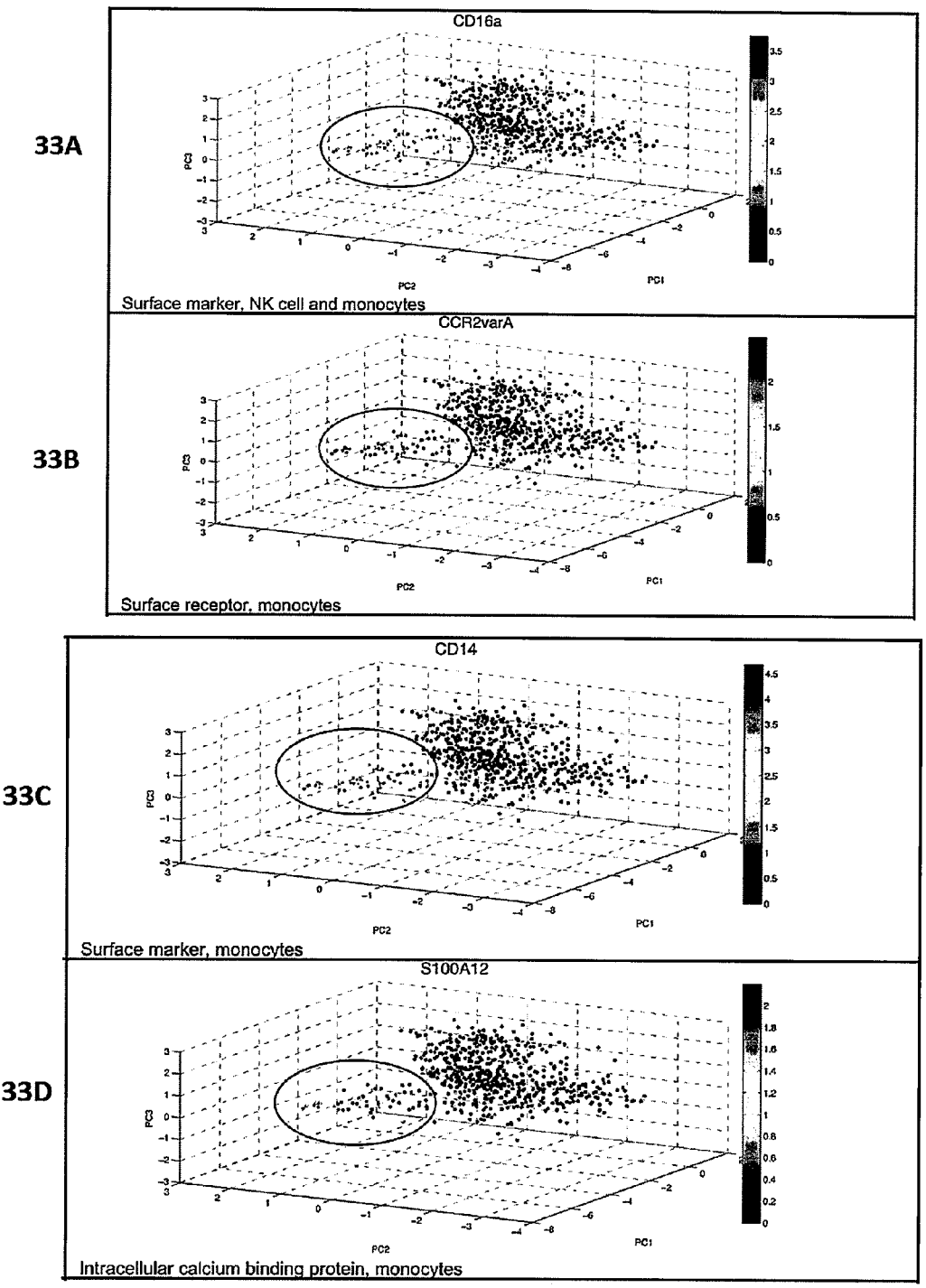
FIG. 33A-D

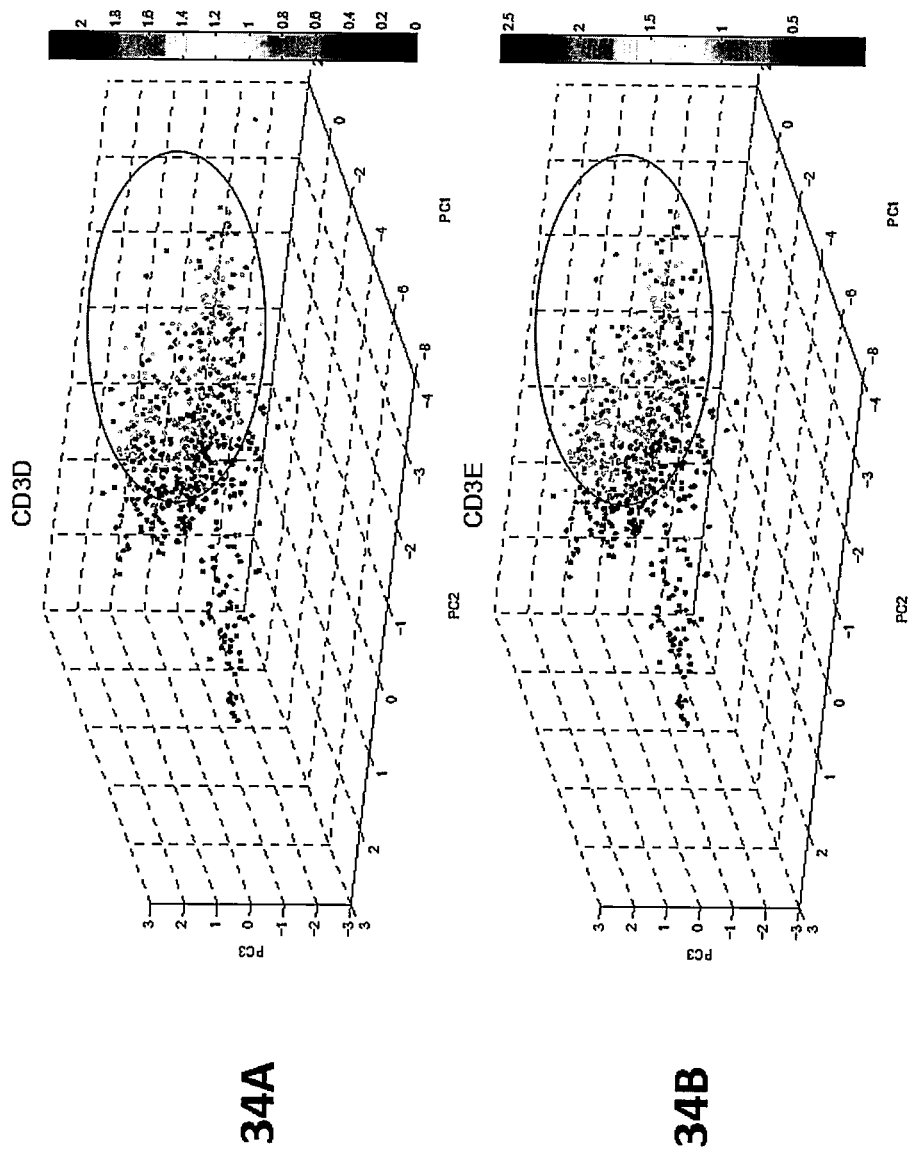
FIG. 34A-B

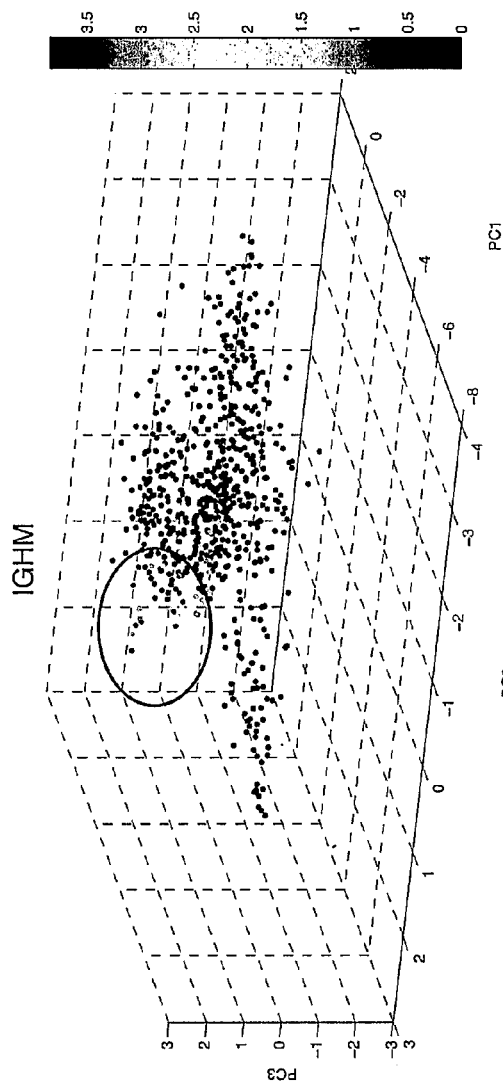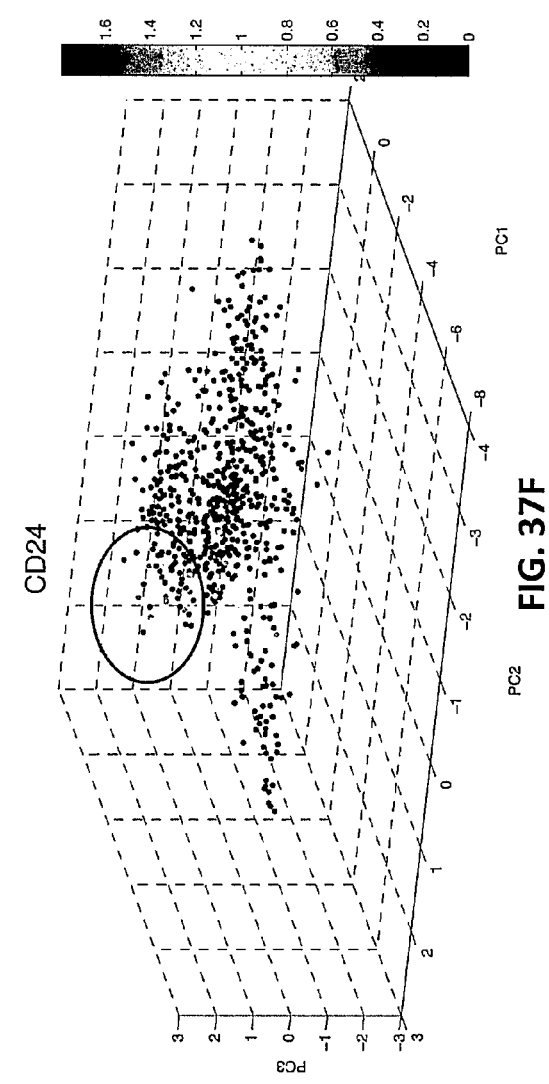

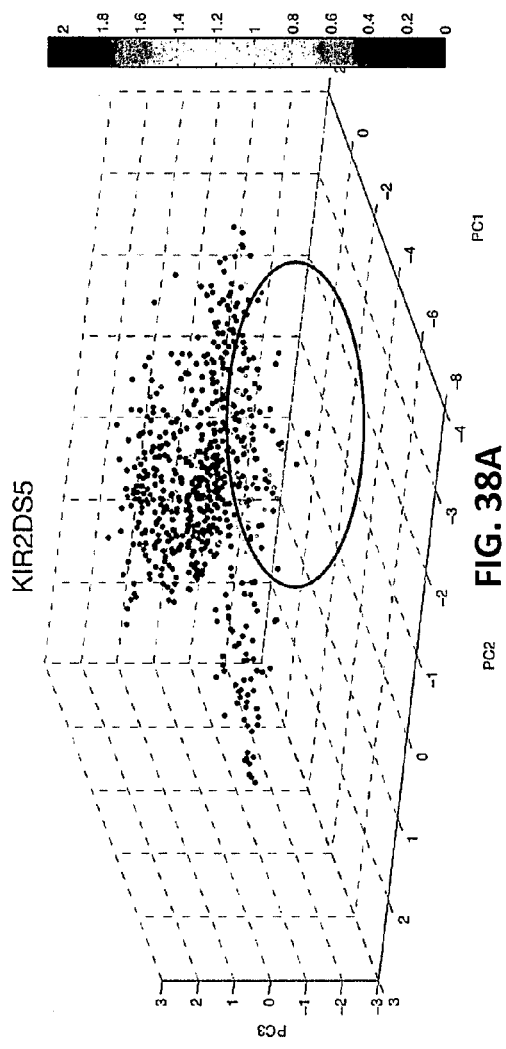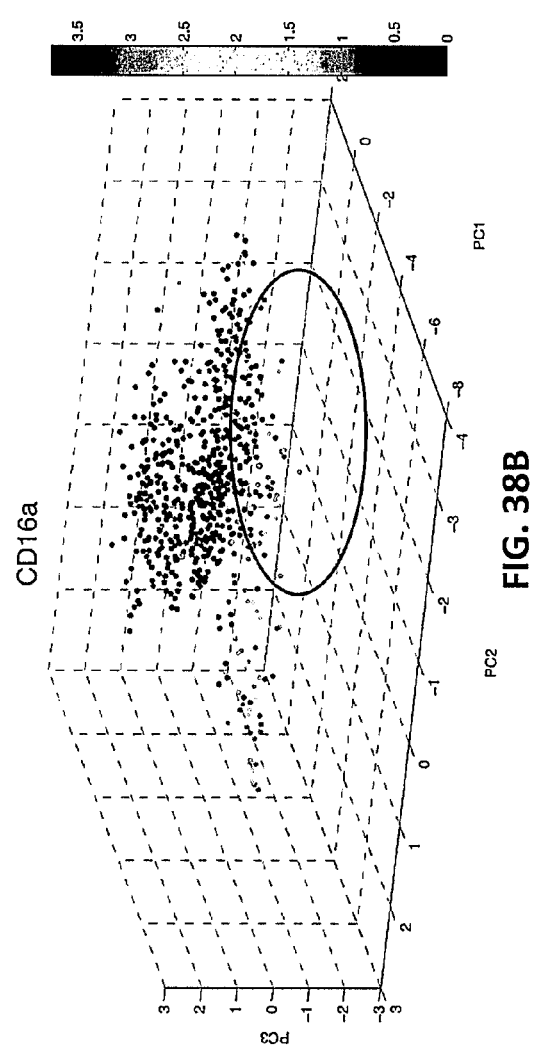

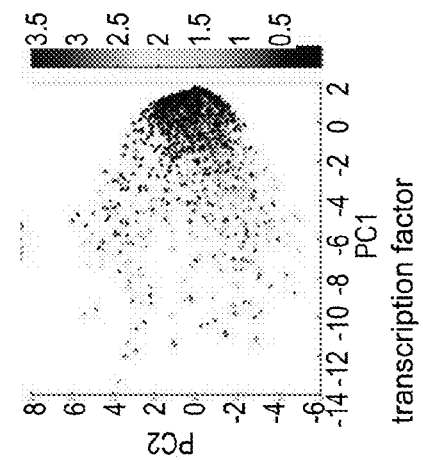
FIG. 44BA — transcription factor
Selected genes that are known to be associated with activated T cells
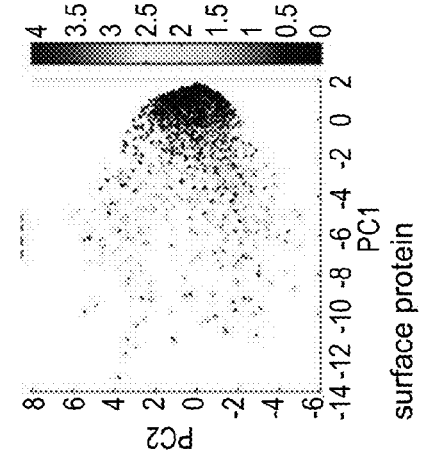
FIG. 44BB — surface protein
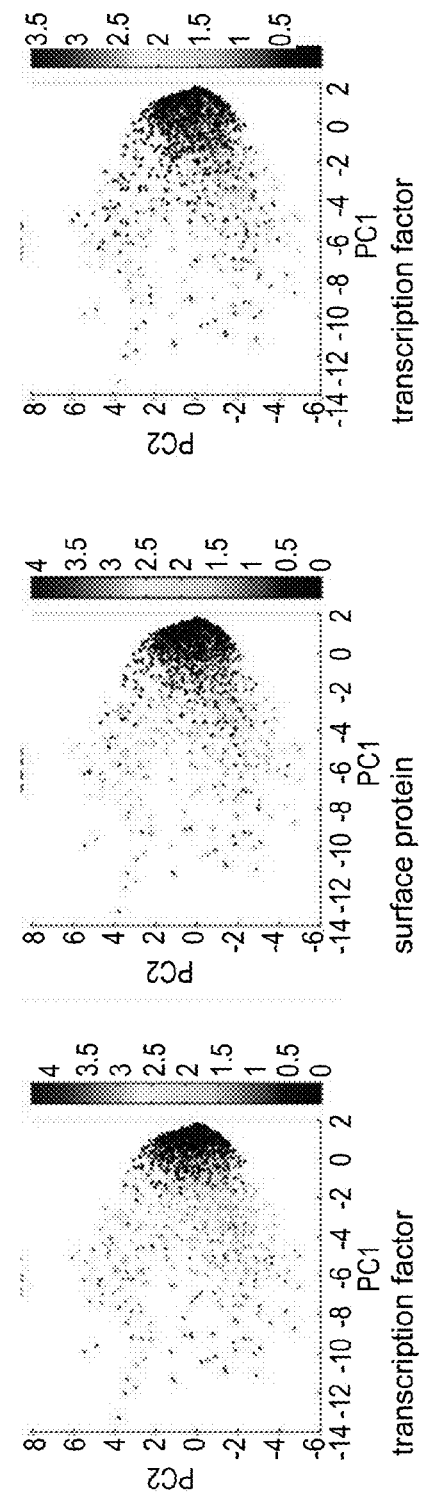
FIG. 44BC — transcription factor
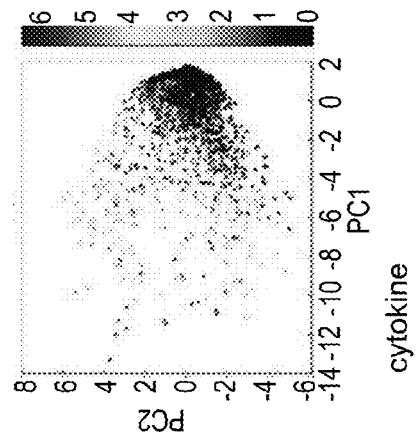
FIG. 44BD — intracellular protein
Selected genes that are known to be associated with activated T cells
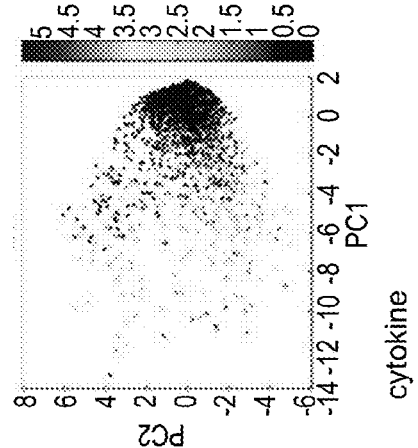
FIG. 44BE — cytokine
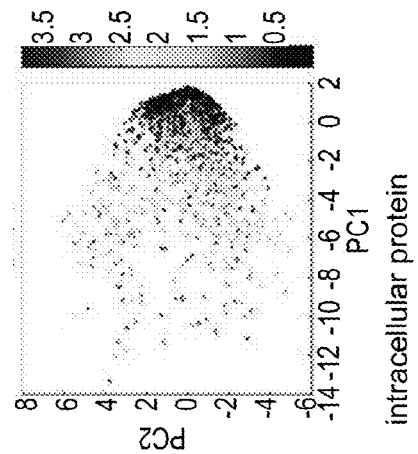
FIG. 44BF — cytokine

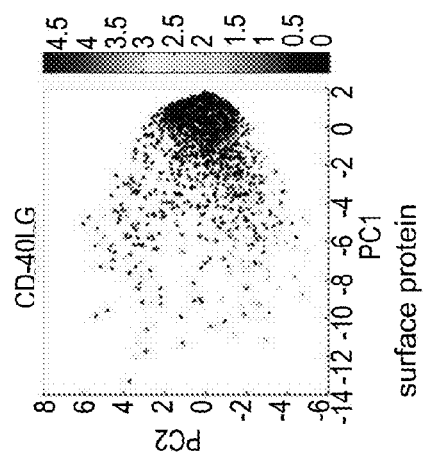
FIG. 44BI
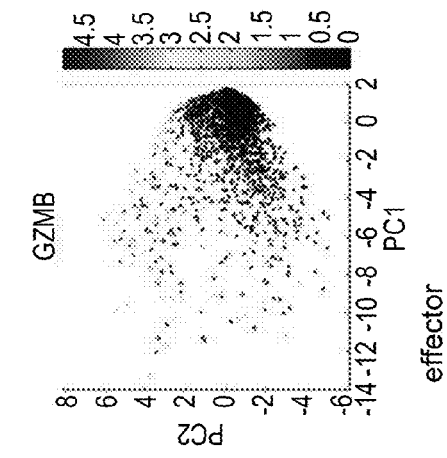
FIG. 44BL
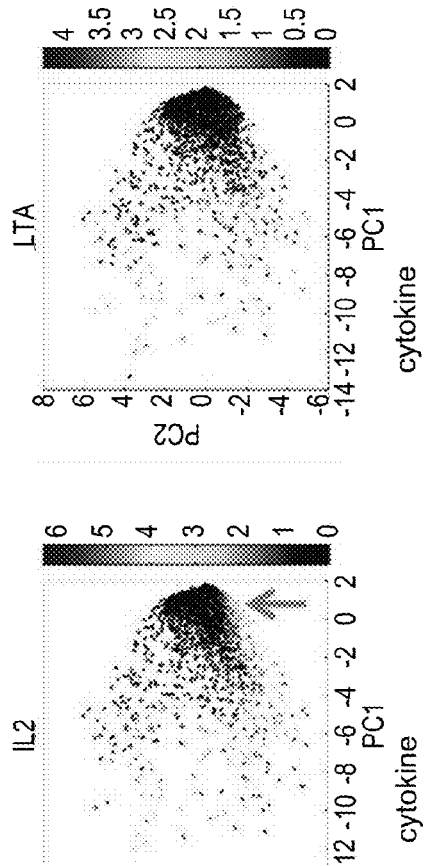
FIG. 44BH
FIG. 44BG
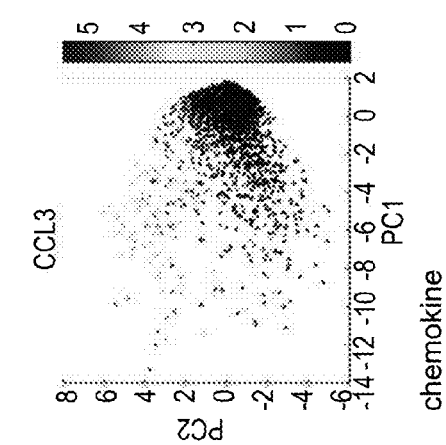
FIG. 44BK
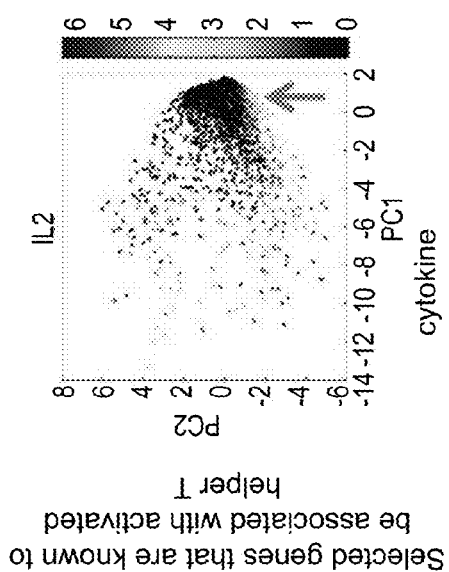
FIG. 44BJ

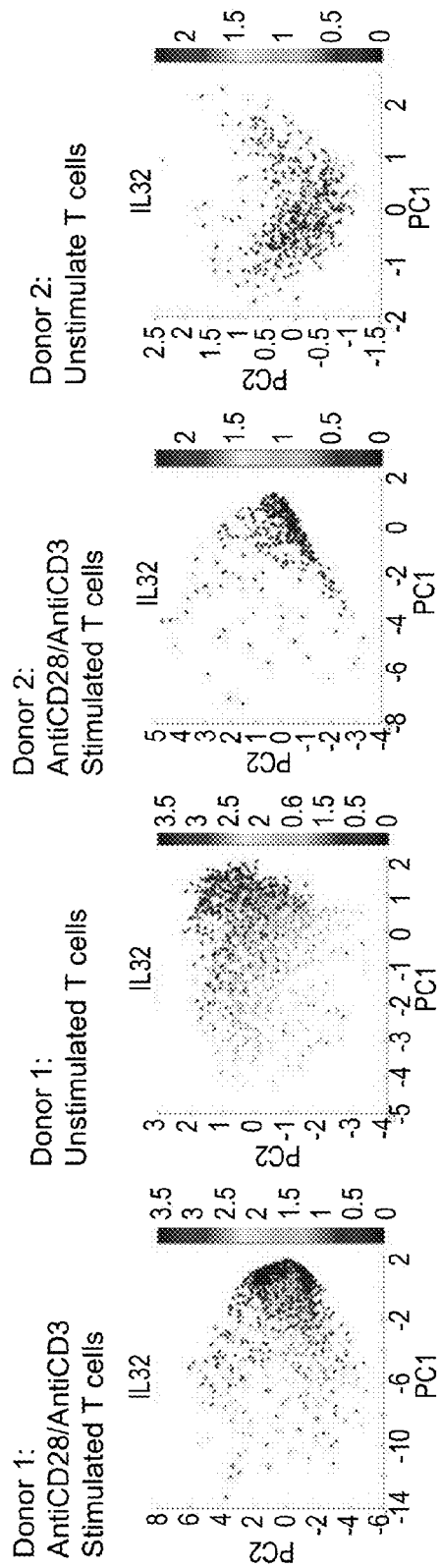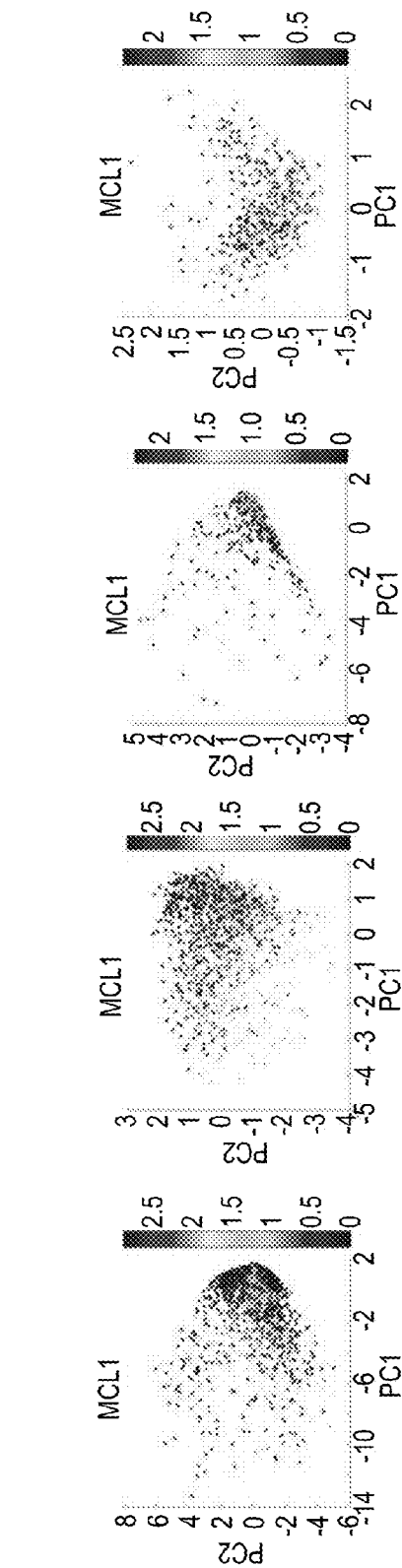

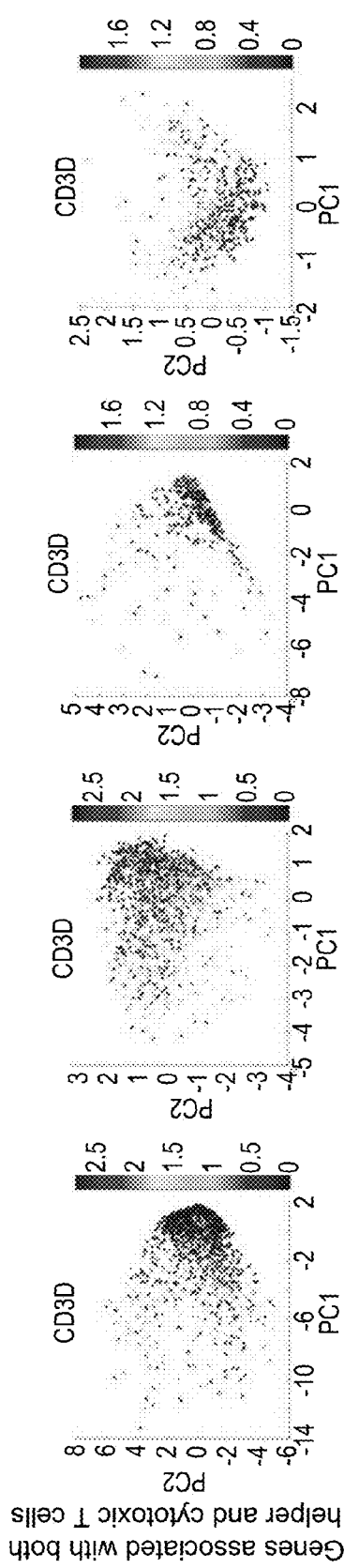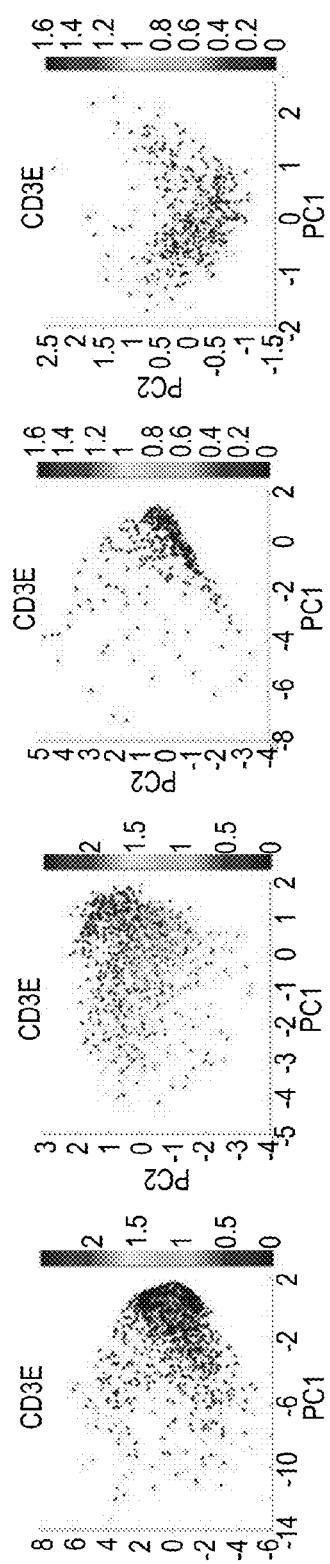

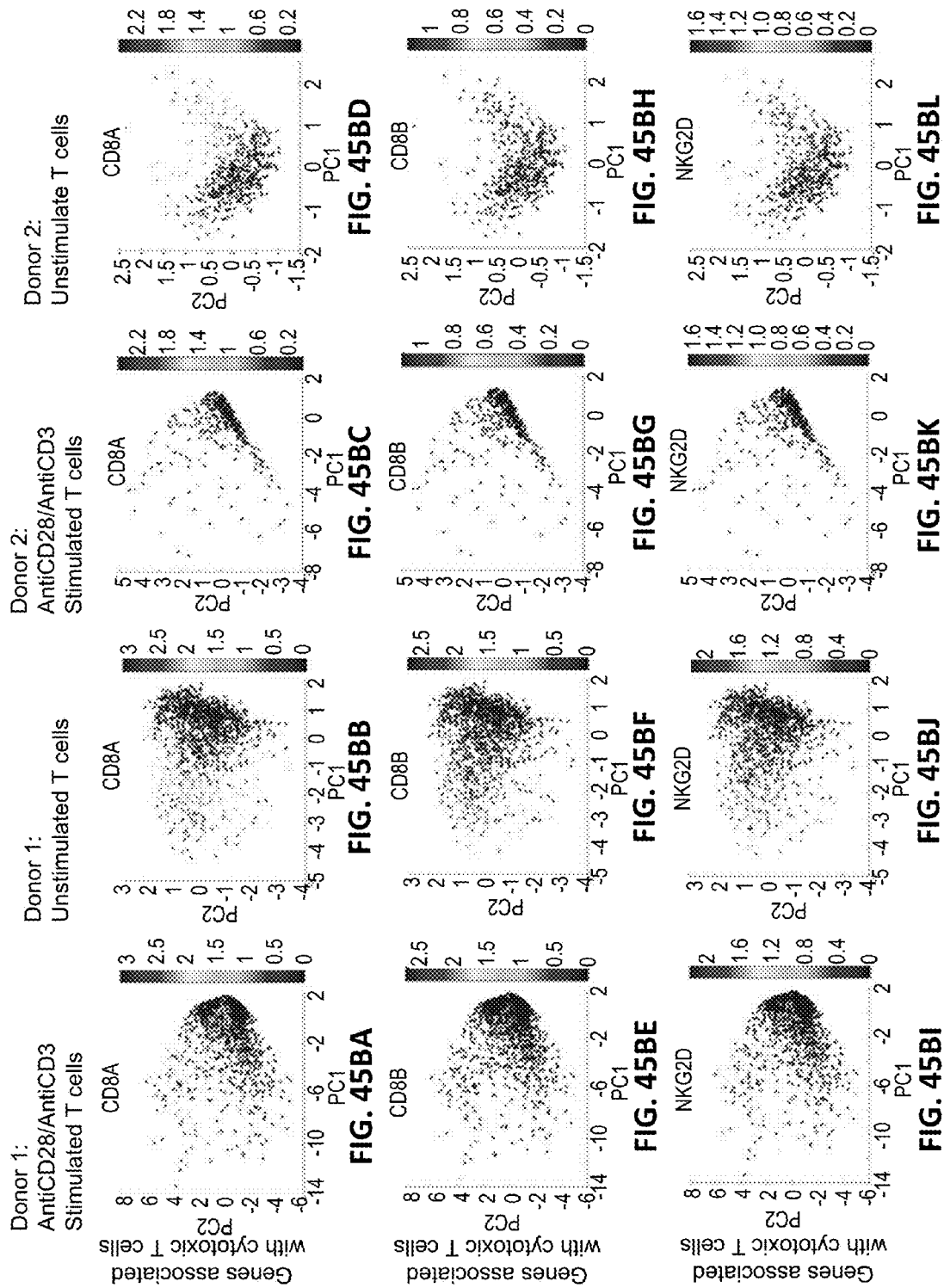

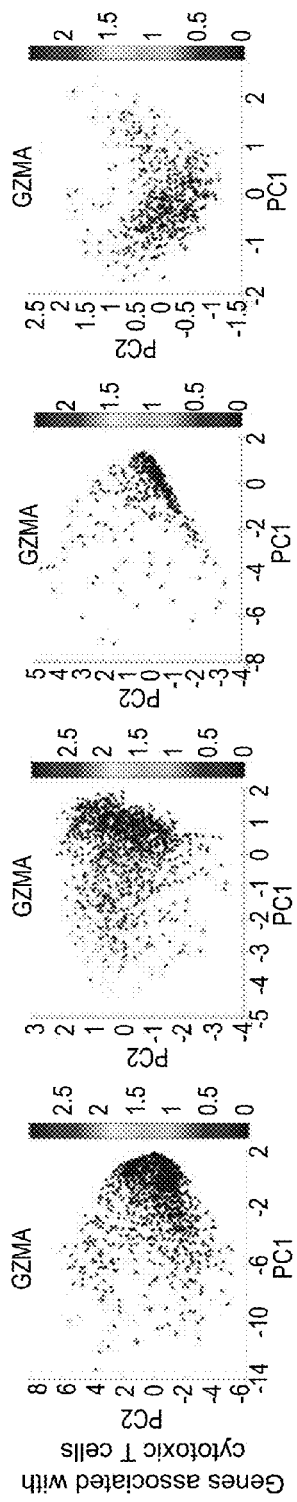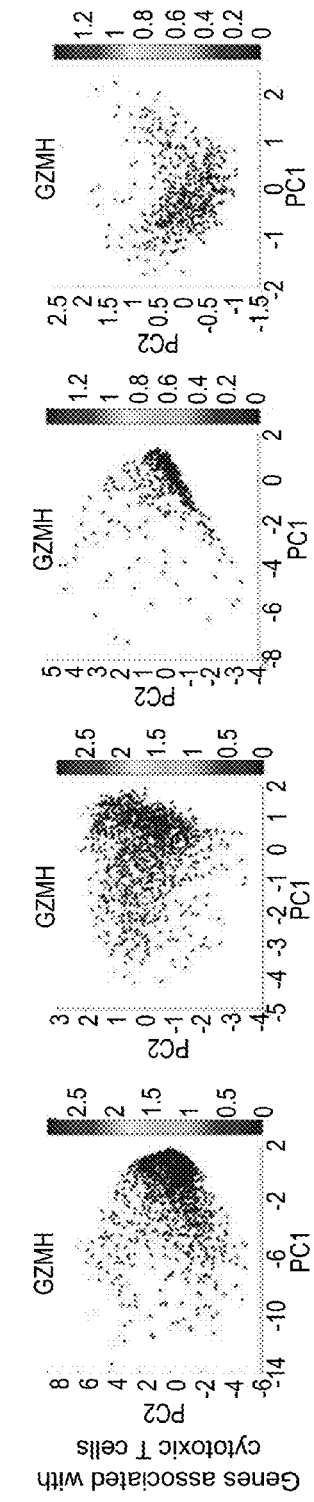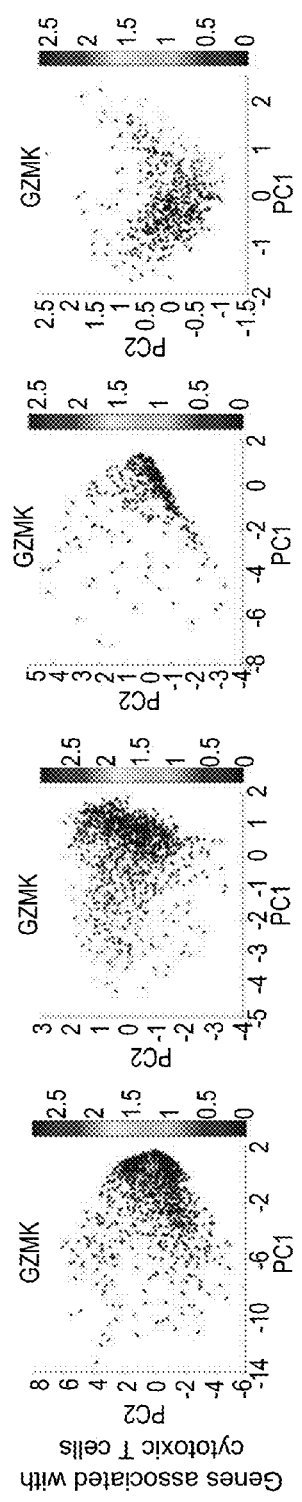

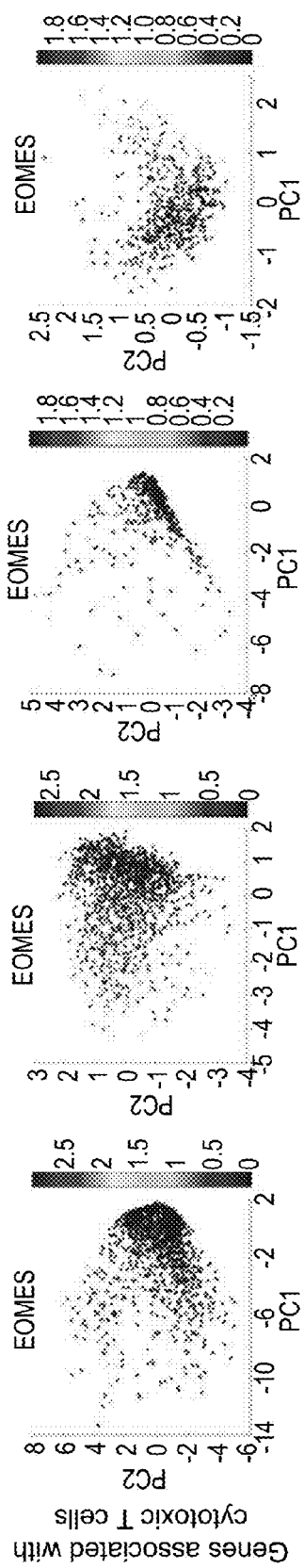

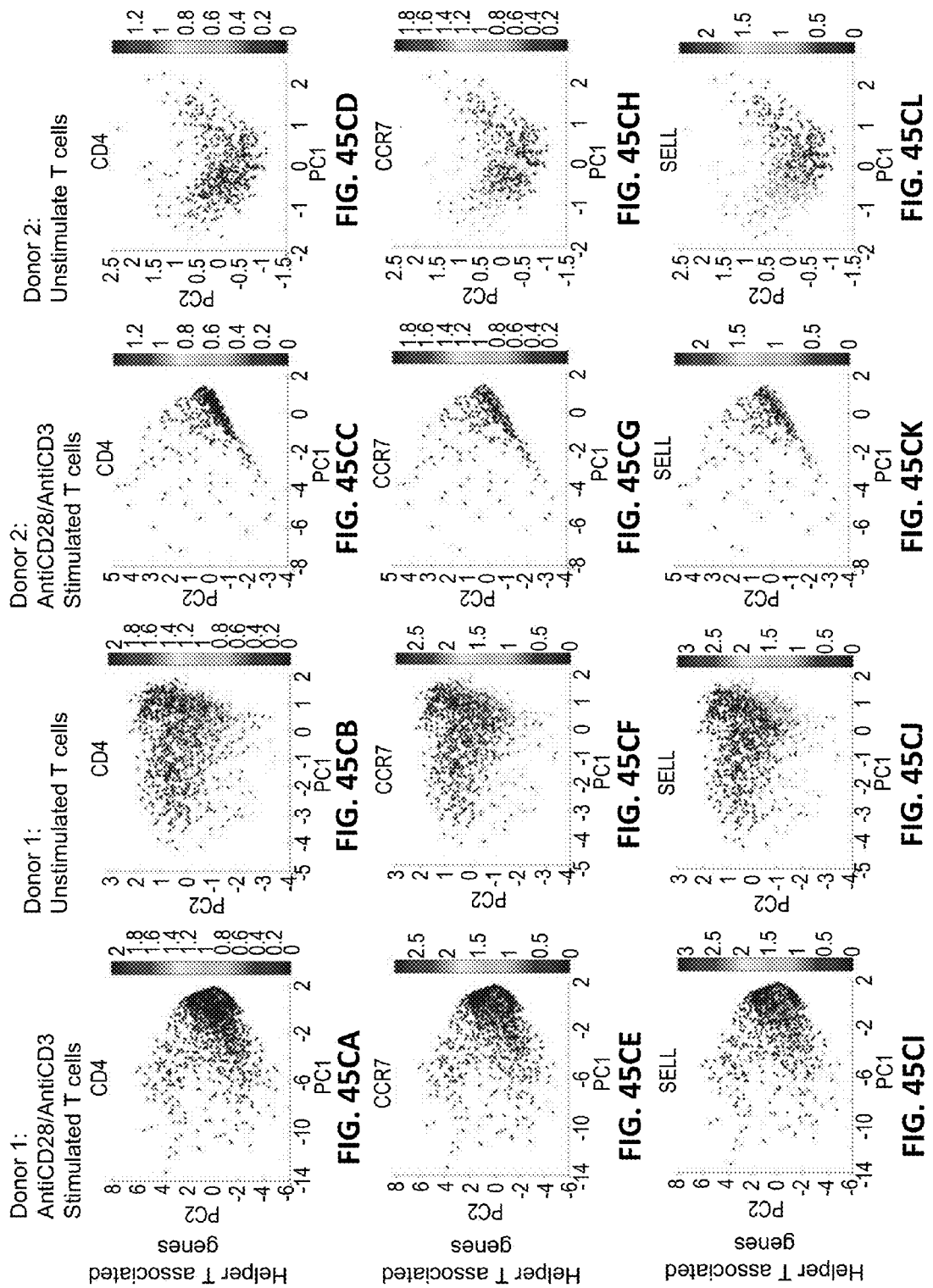

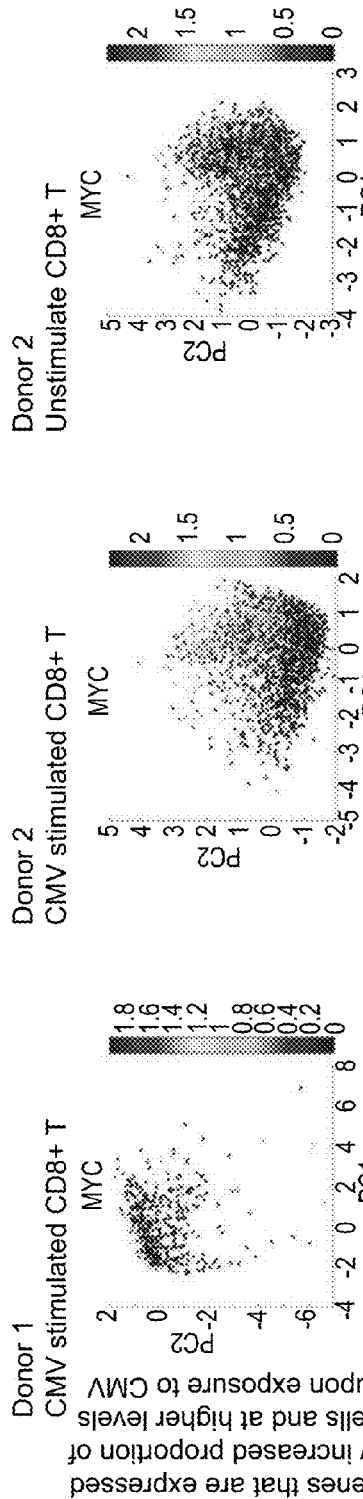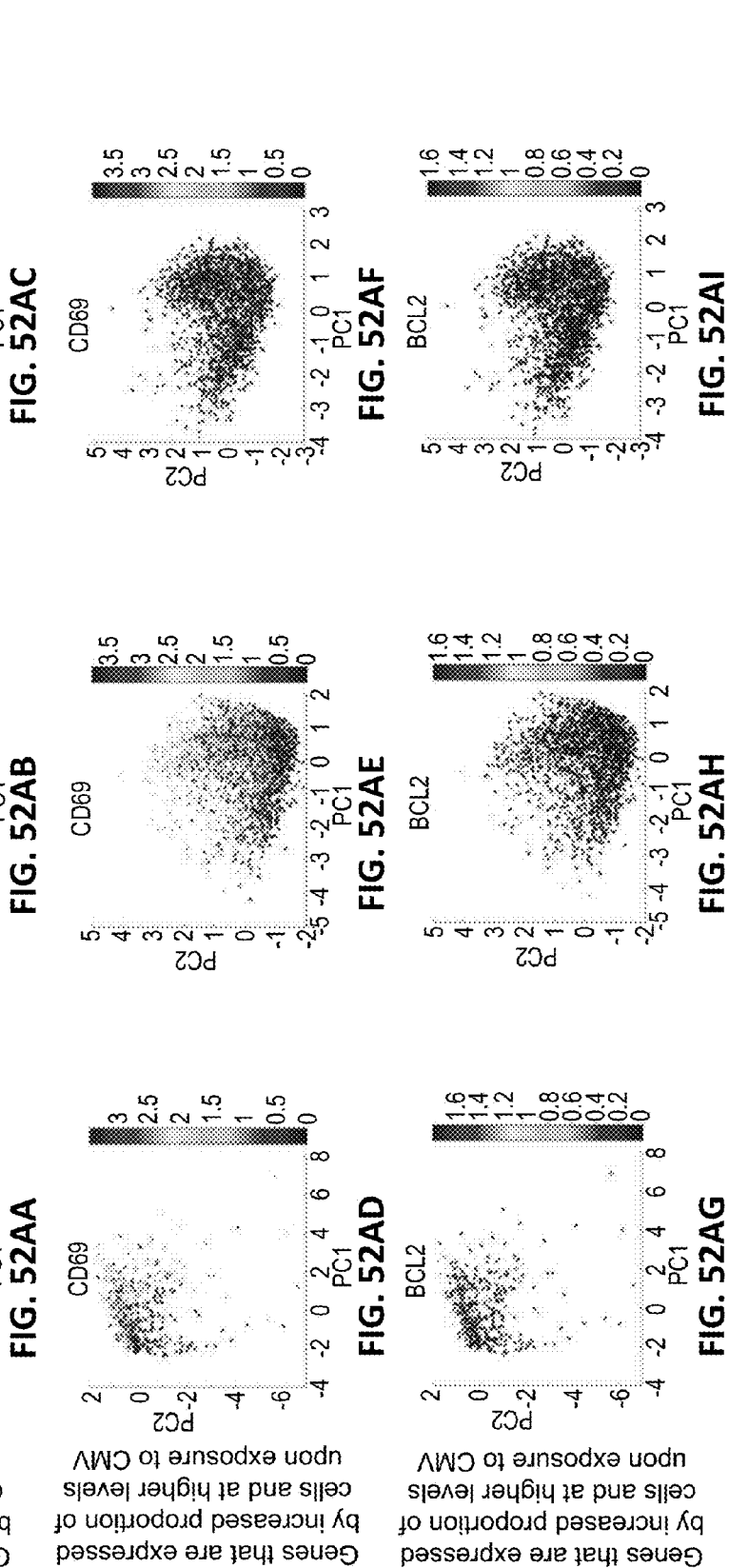

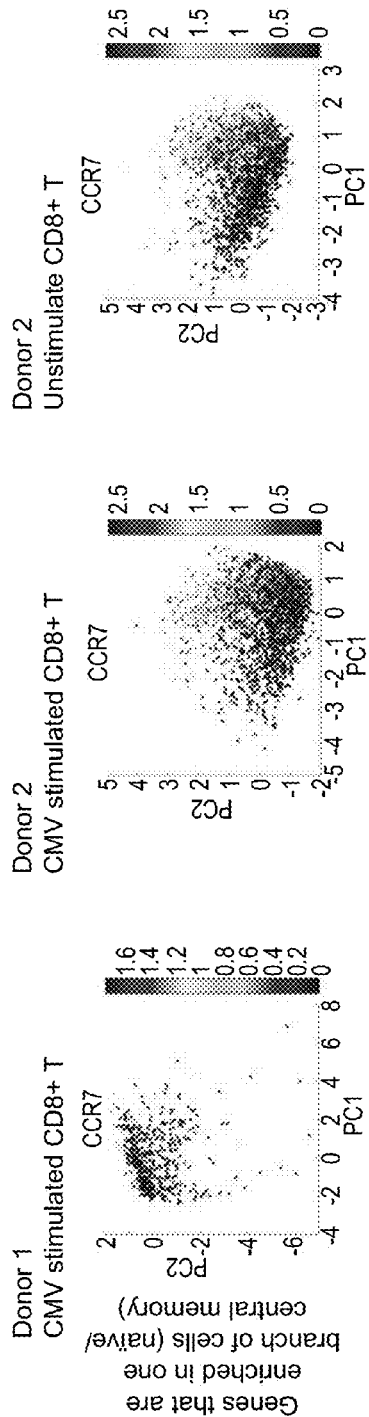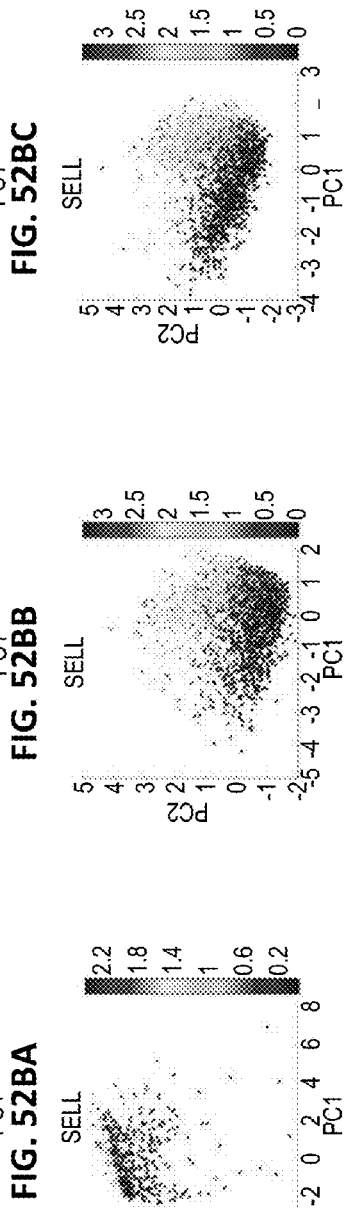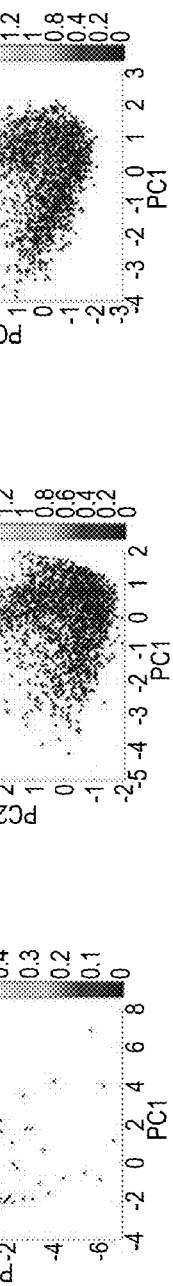

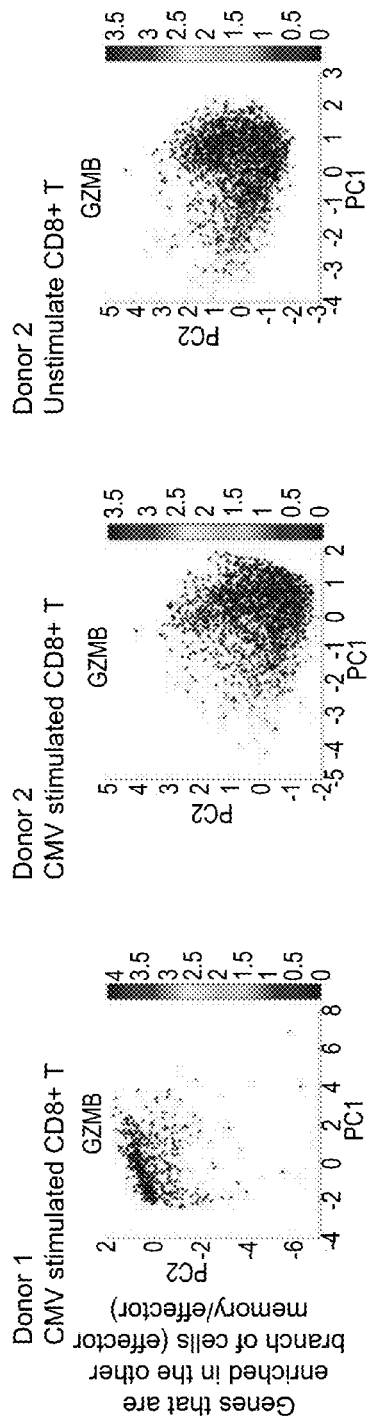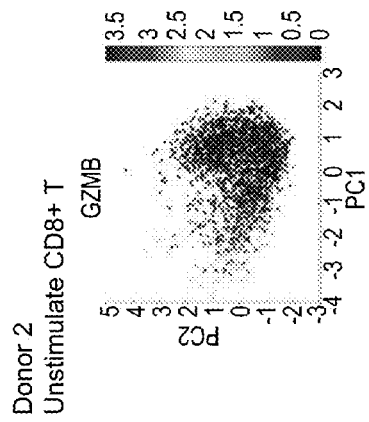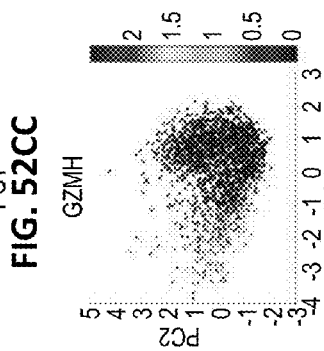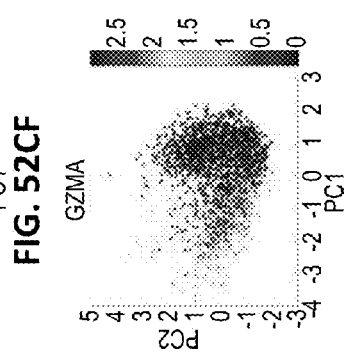

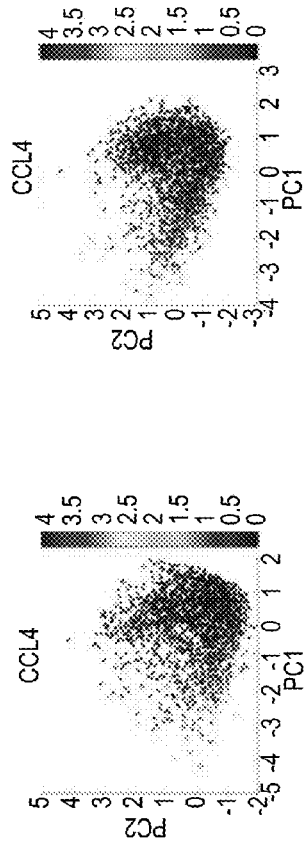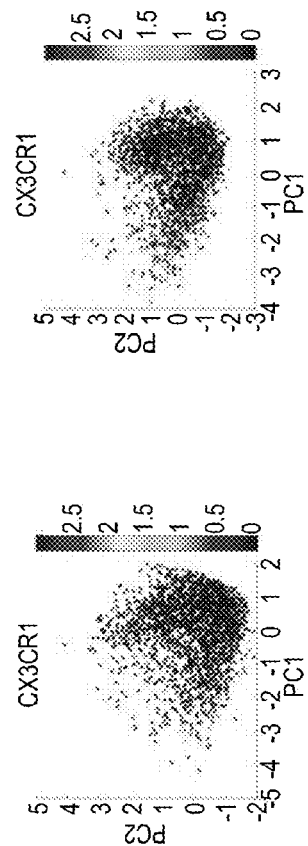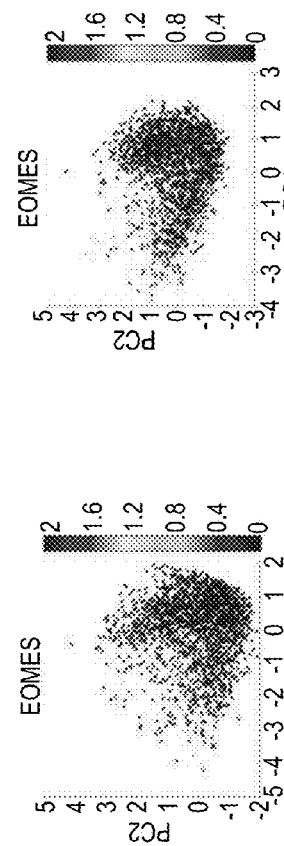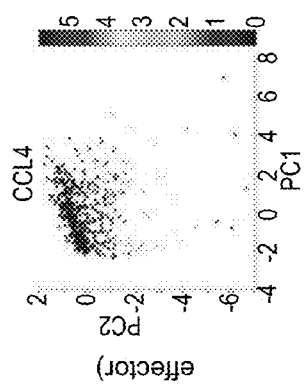
FIG. 52CJ, FIG. 52CK, FIG. 52CL, FIG. 52CM, FIG. 52CN, FIG. 52CO, FIG. 52CP, FIG. 52CQ, FIG. 52CR

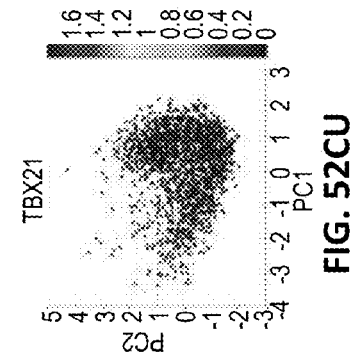
FIG. 52CU
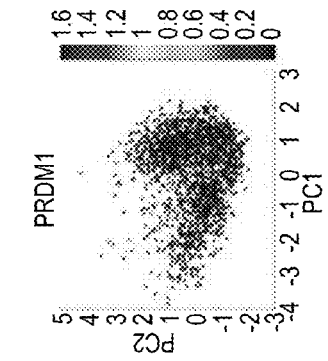
FIG. 52CX
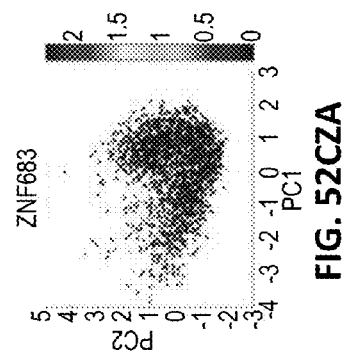
FIG. 52CZA
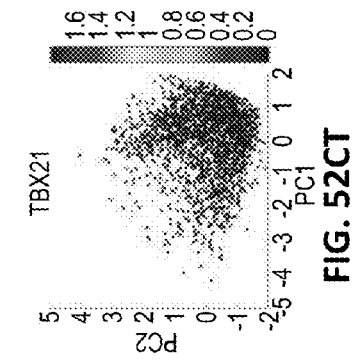
FIG. 52CT
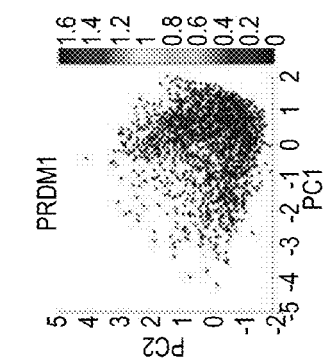
FIG. 52CW
FIG. 52CZ
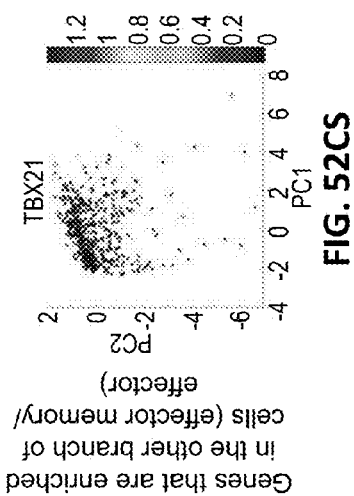
FIG. 52CS
Genes that are enriched in the other branch of cells (effector memory/effector)
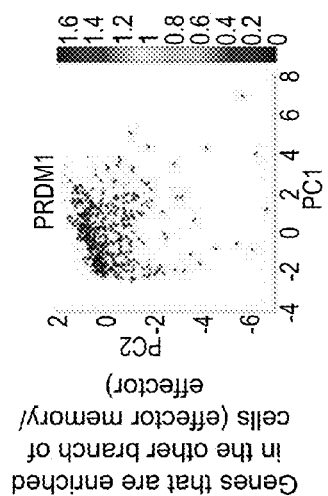
FIG. 52CV
Genes that are enriched in the other branch of cells (effector memory/effector)
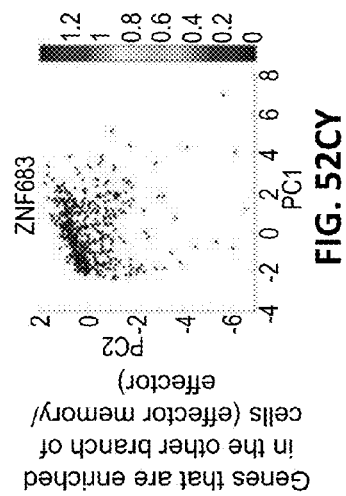
FIG. 52CY
Genes that are enriched in the other branch of cells (effector memory/effector)

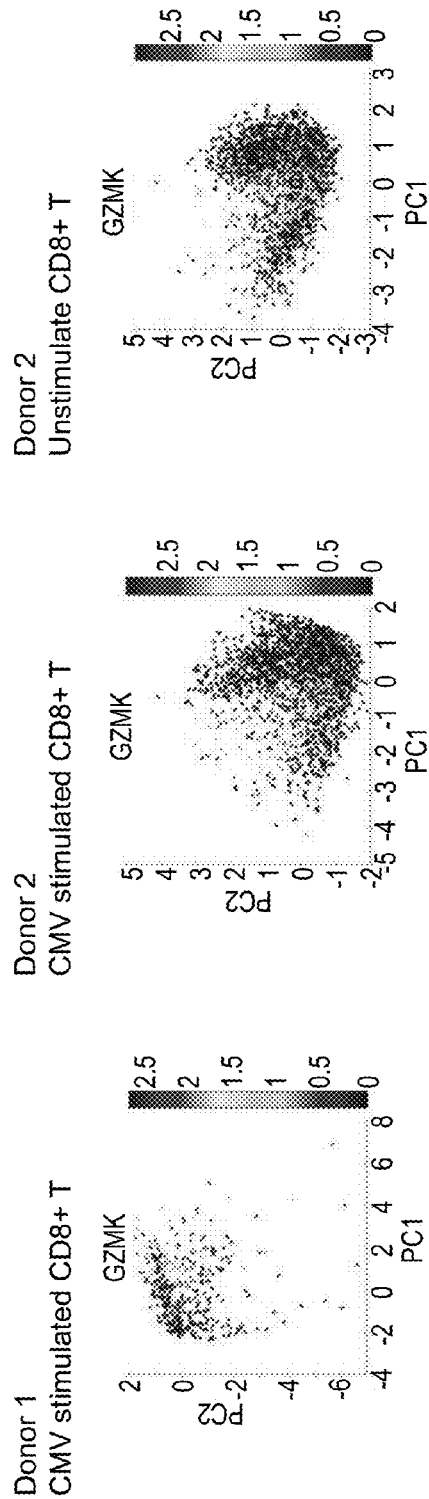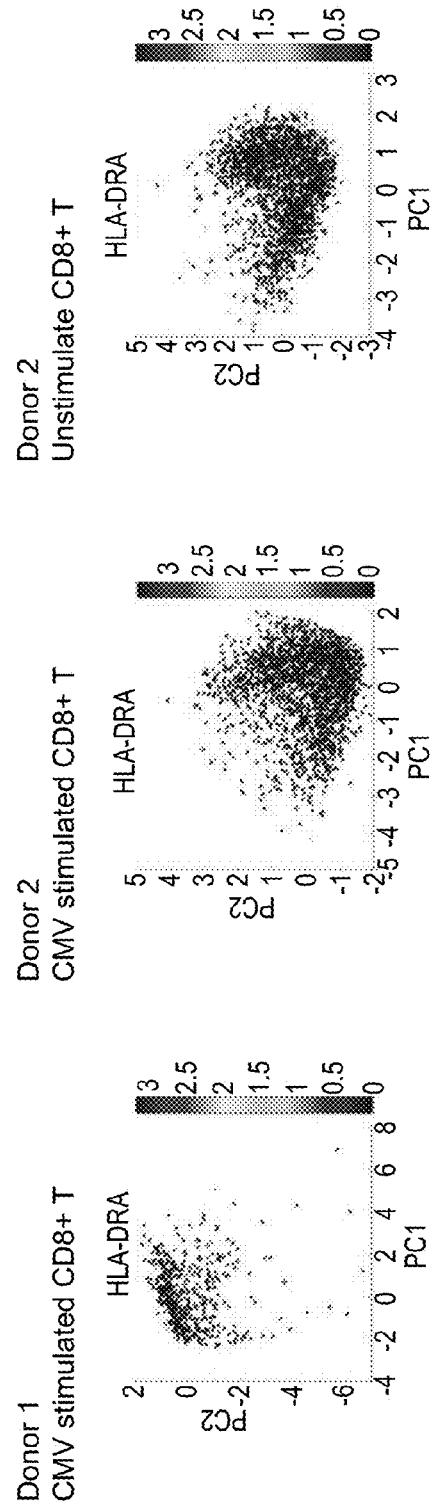
FIG. 52DA  FIG. 52DB  FIG. 52DC
FIG. 52EA  FIG. 52EB  FIG. 52EC

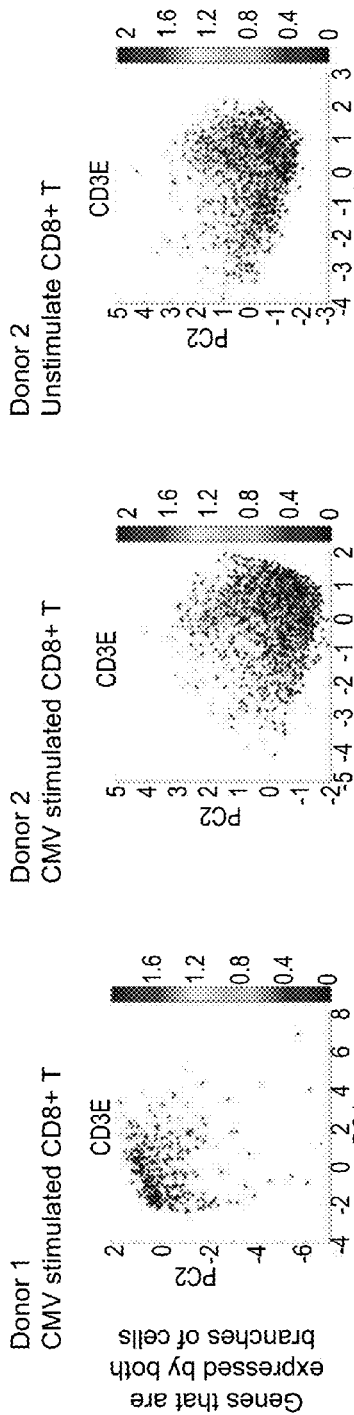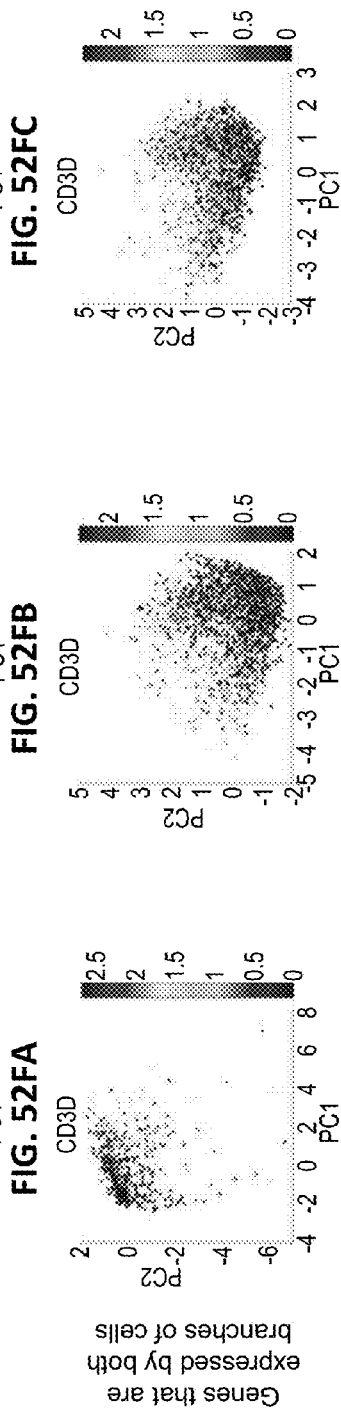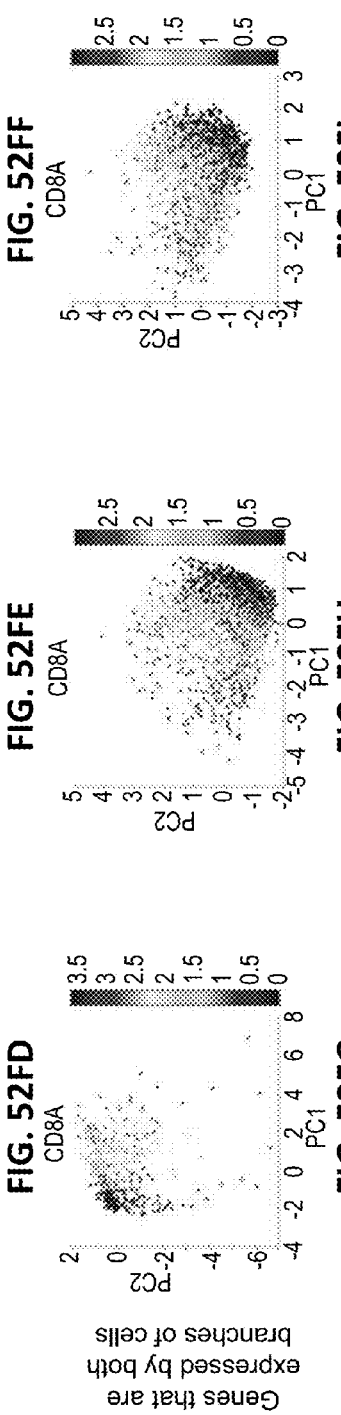

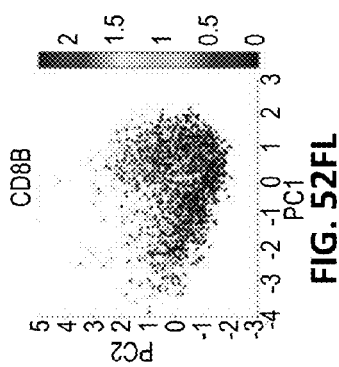
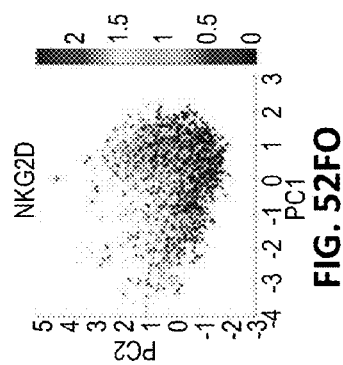
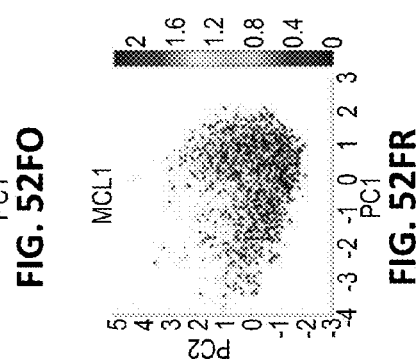
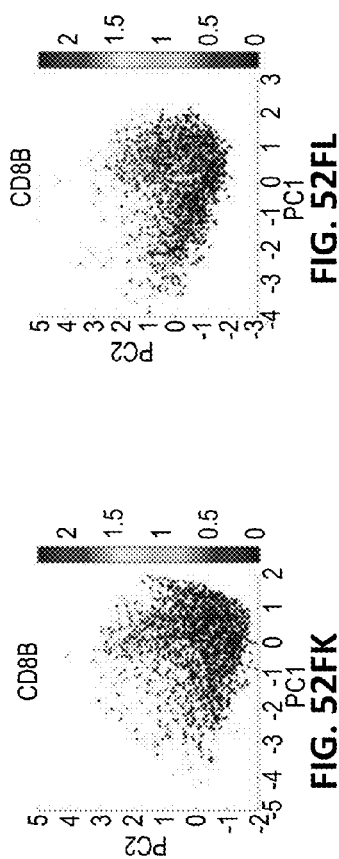
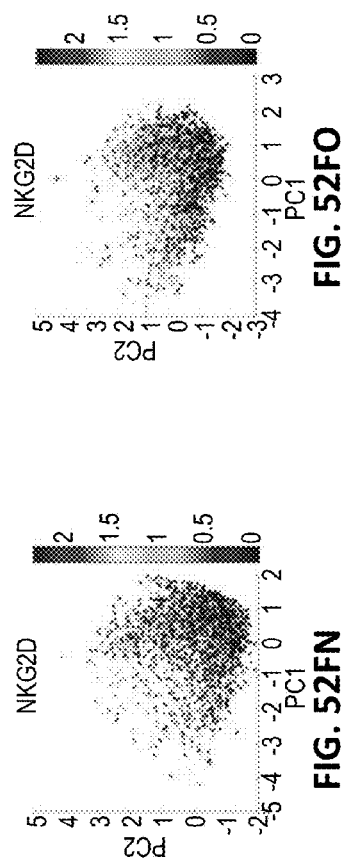
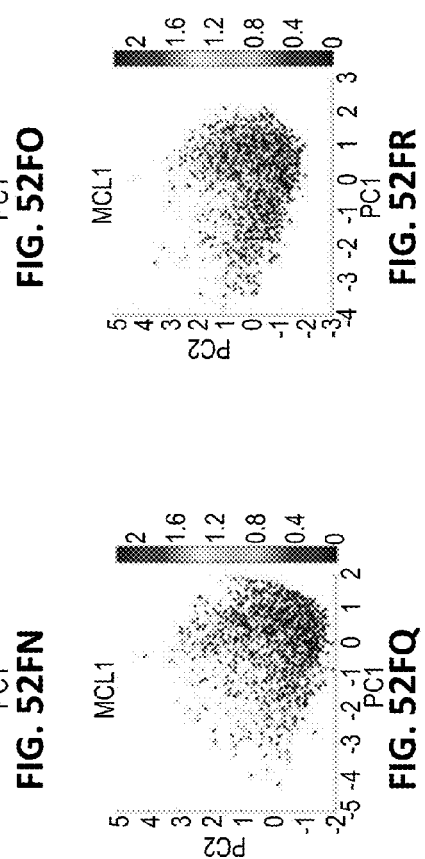
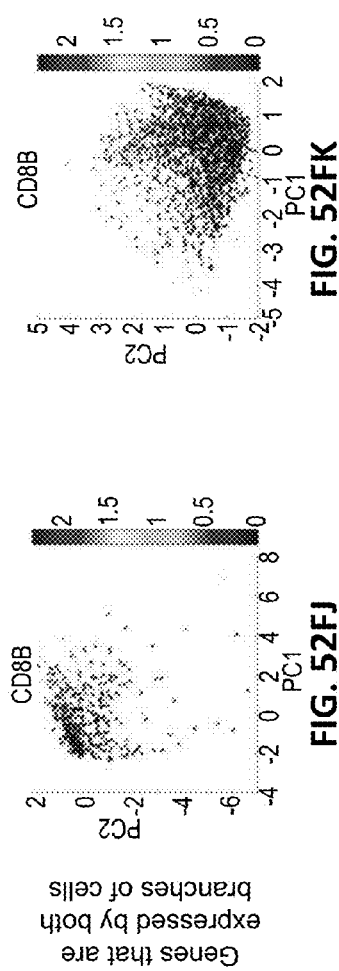
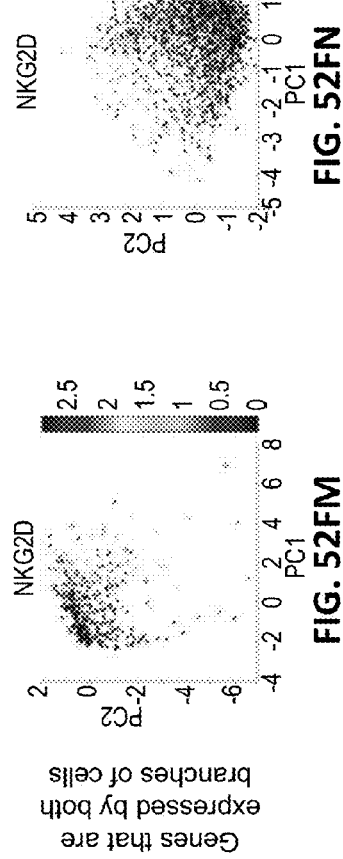
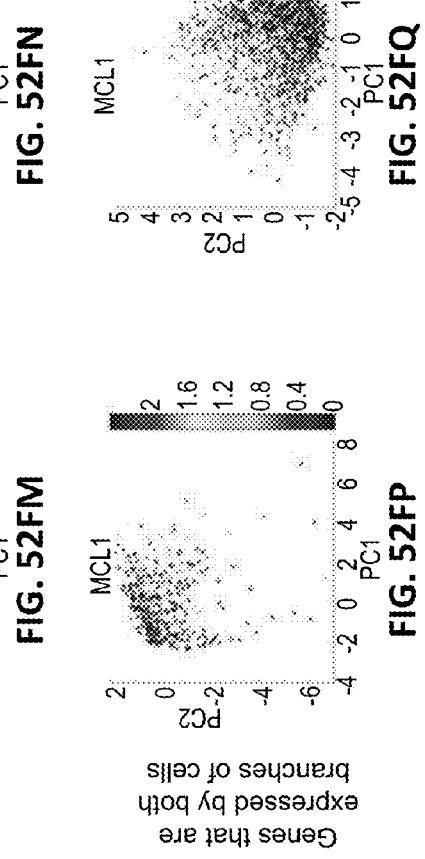

Genes that are expressed by both branches of cells

Genes that are expressed by both branches of cells

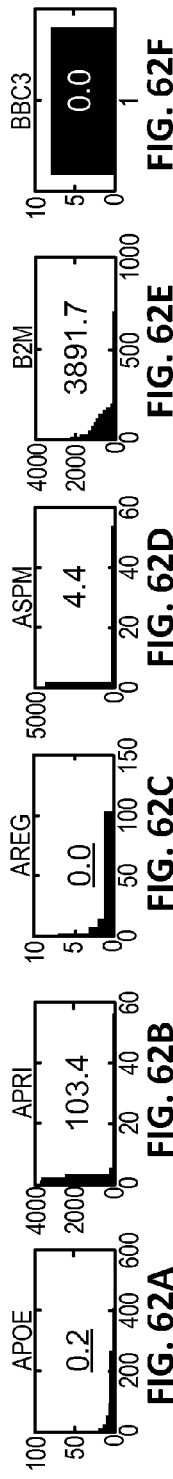
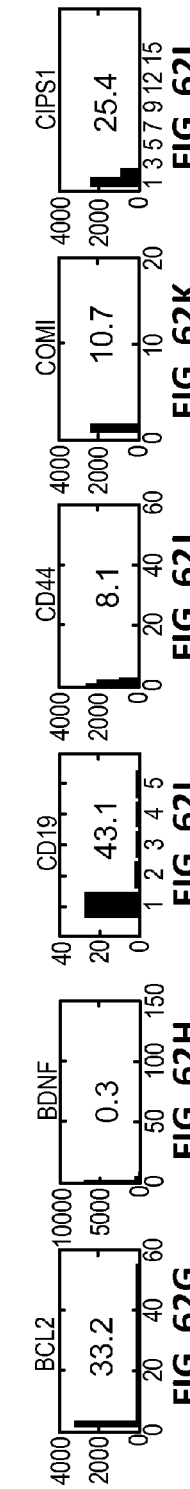
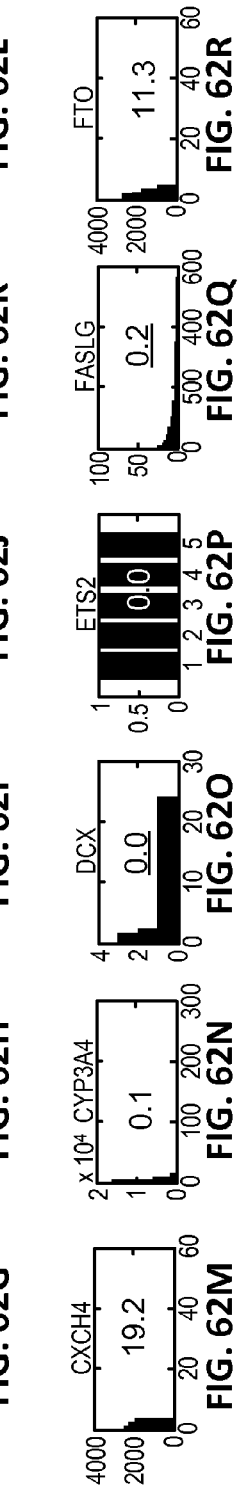
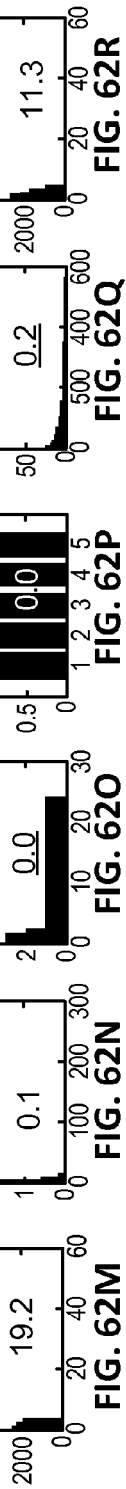

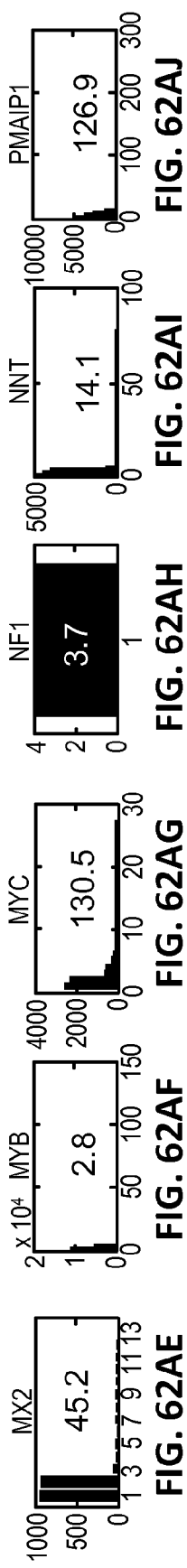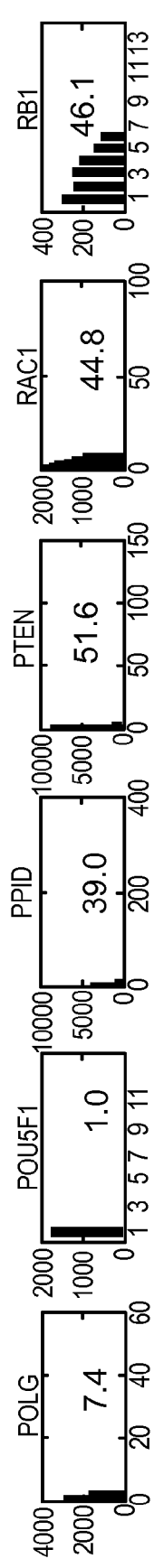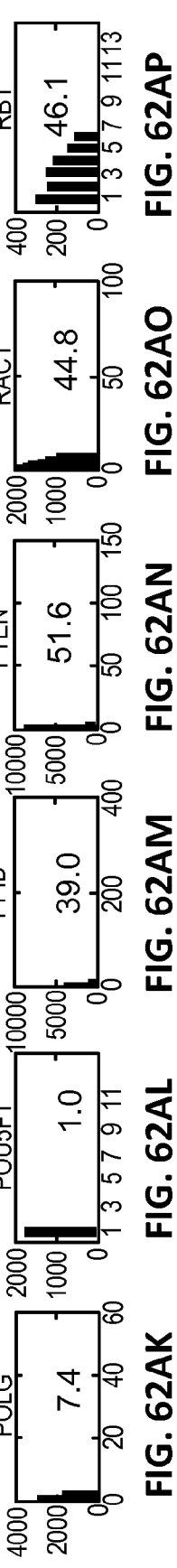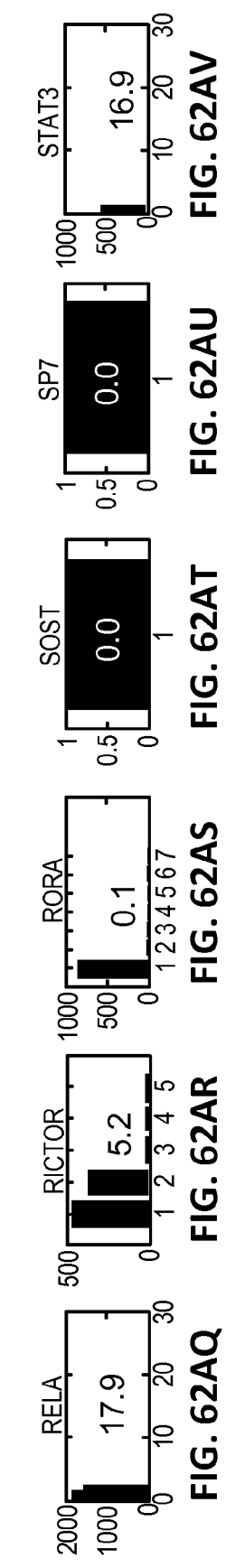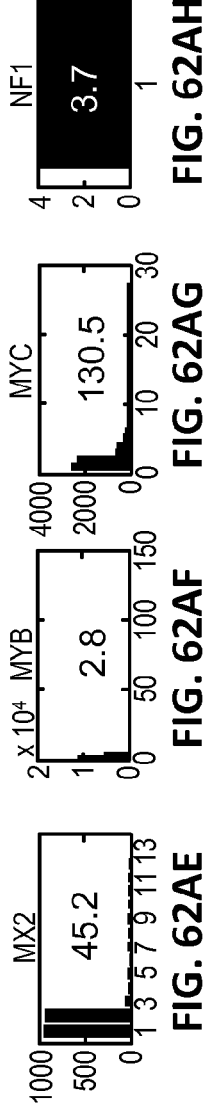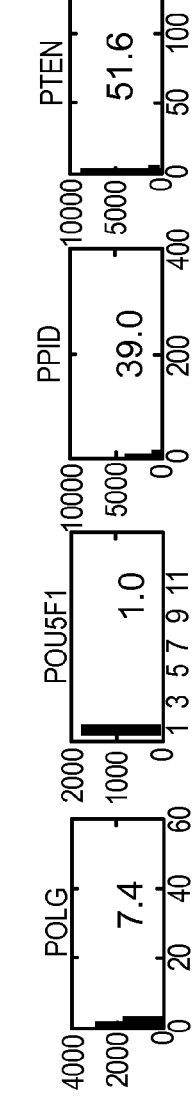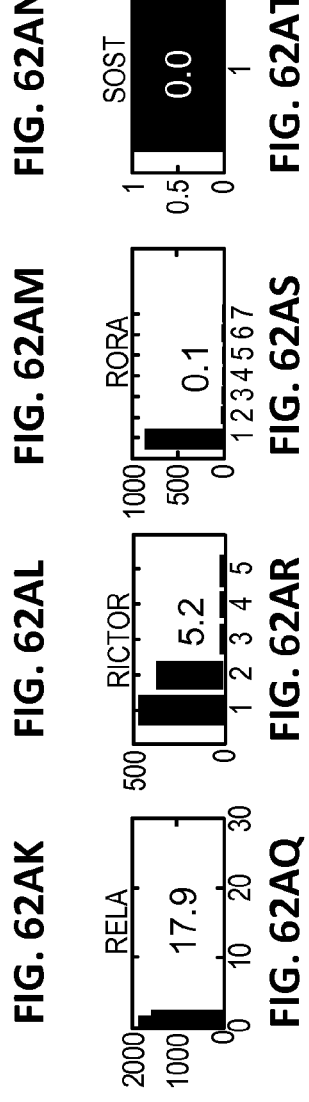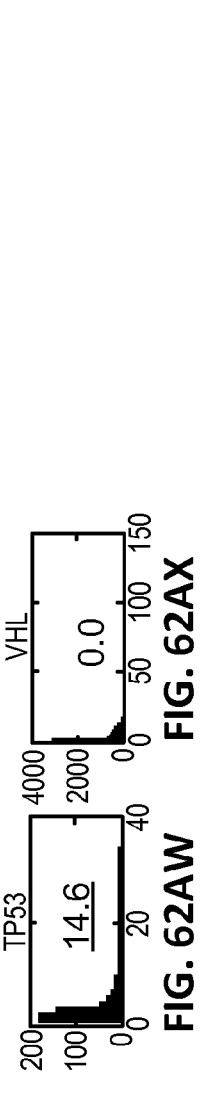
FIG. 62AE, FIG. 62AF, FIG. 62AG, FIG. 62AH, FIG. 62AI, FIG. 62AJ, FIG. 62AK, FIG. 62AL, FIG. 62AM, FIG. 62AN, FIG. 62AO, FIG. 62AP, FIG. 62AQ, FIG. 62AR, FIG. 62AS, FIG. 62AT, FIG. 62AU, FIG. 62AV, FIG. 62AW, FIG. 62AX

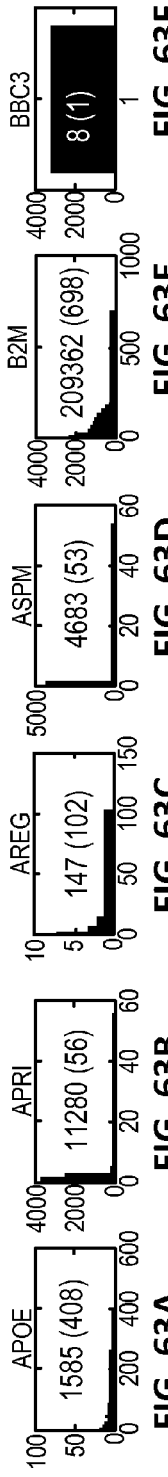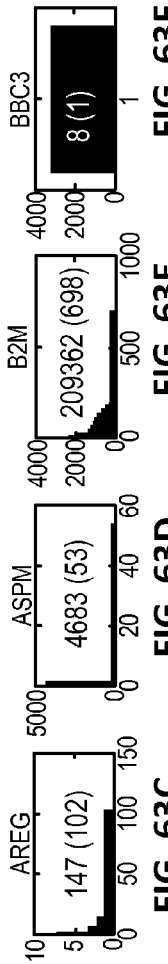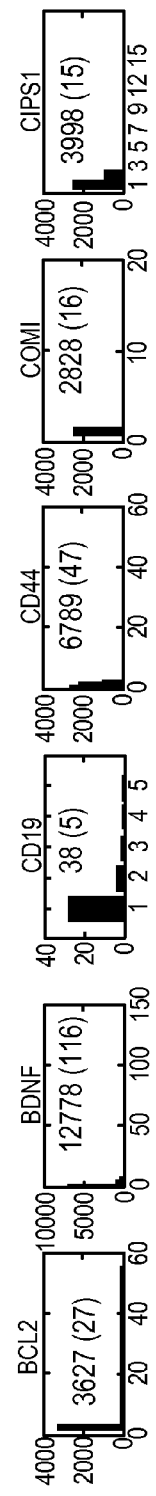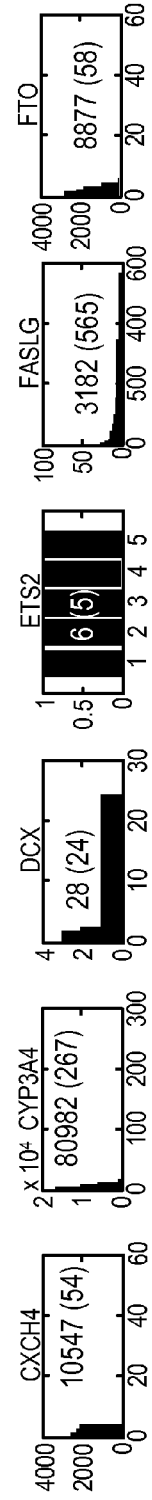
FIG. 63A – FIG. 63AD

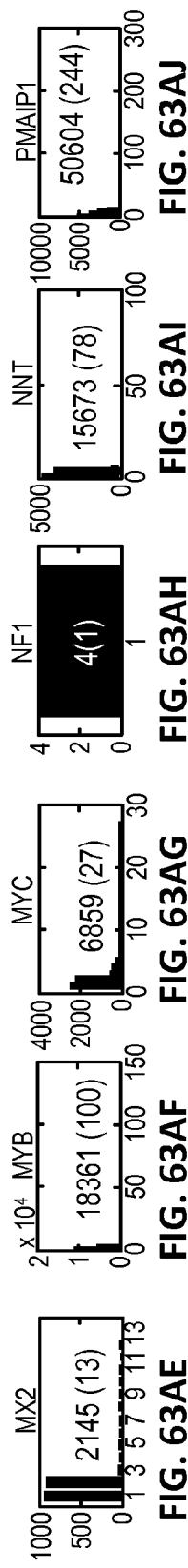
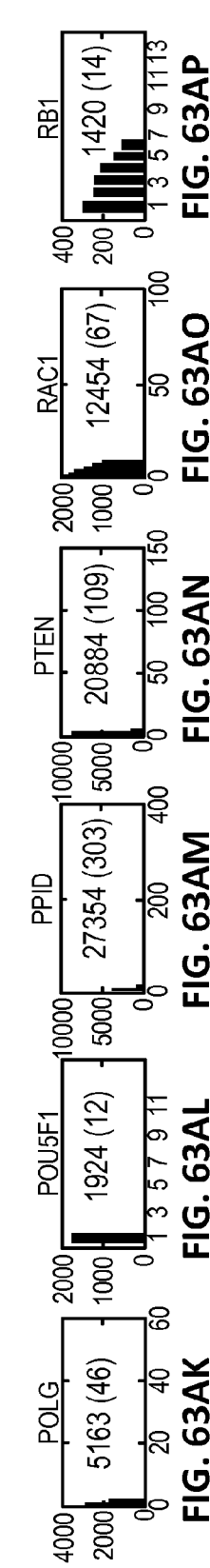
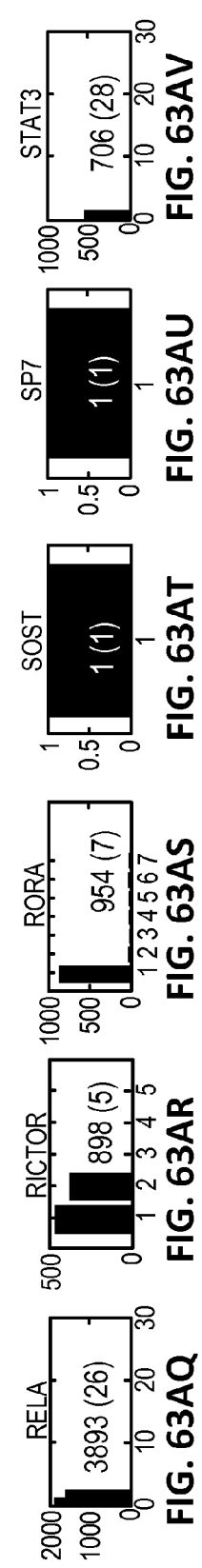

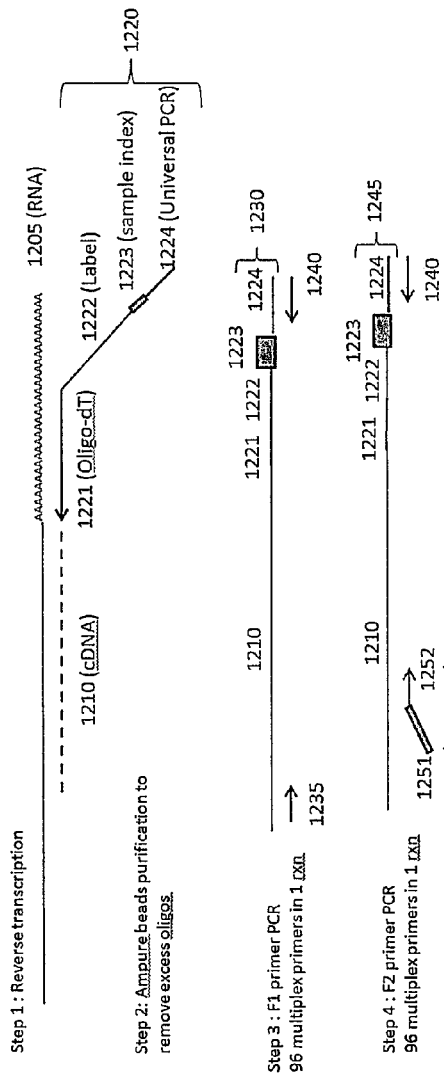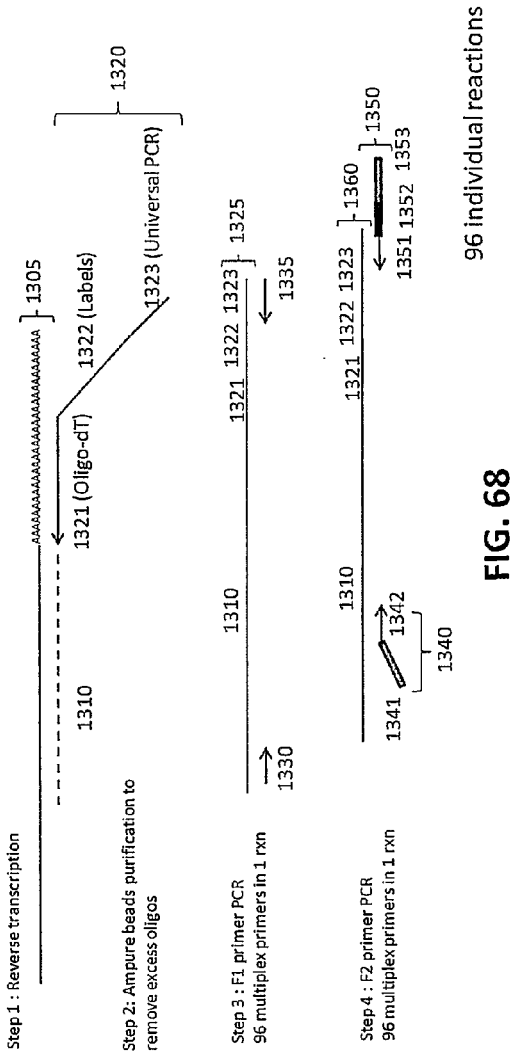

US 9,567,646 B2

SEQUENCE LISTING

```
<160> NUMBER OF SEQ ID NOS: 843

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(18)
<223> OTHER INFORMATION: This sequence may encompass 12-18 nucleotides

<400> SEQUENCE: 1
tttttttttt tttttttt                                                    18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cccctggaag aagatgatga                                                  20

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagacgtgtg ctcttccgat ctttctccaa caagttgcct cc                         42

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaggaaatga agccaaacac a                                                21

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
```

-continued

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cagacgtgtg ctcttccgat ctaatcgtga ccttaaaggc cc                              42

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttagccacct catgcctttc                                                       20

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cagacgtgtg ctcttccgat ctctactgtg gtggctccgc t                               41

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggaggaggat tgtgctgatg                                                       20

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cagacgtgtg ctcttccgat ctgtgtccgc ataagaaaaa gaatc                           45

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcaagaaggt gctgacttcc                                                       20

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 11
cagacgtgtg ctcttccgat ctctgcatgt ggatcctgag aa                        42

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctgcagtccc atcctcttgt                                                 20

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cagacgtgtg ctcttccgat ctgatgaggt ggagagtggg aa                        42

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggacataaca gacttggaag ca                                              22

<210> SEQ ID NO 15
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cagacgtgtg ctcttccgat ctcaatccat tttgtaactg aacctt                    46

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aagcctctgg gtcagtggt                                                  19

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
```
cagacgtgtg ctcttccgat cttggaaaag ggatagaggt tgg                43

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tagacagatc cccgttcctg                                          20

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagacgtgtg ctcttccgat ctacagggag aagggataac cc                 42

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagcatccca gccttgag                                            18

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagacgtgtg ctcttccgat ctcctcaatg gcctttgct ac                  42

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cctctaaact gccccacctc                                          20

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cagacgtgtg ctcttccgat ctccttaatc gctgcctcta gg                              42

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 24
cacatggccu ccaaggagua a                                                     21

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cagacgtgtg ctcttccgat ctcagcaaga gcacaagagg aa                              42

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcagggtccc agtcctatg                                                        19

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cagacgtgtg ctcttccgat ctccaatcat gaggaagatg ca                              42

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tccaggagga ttaccgaaaa                                                       20

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 29
cagacgtgtg ctcttccgat ctccatccaa gggagagtga ga                              42

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aatggcaaag gaaggtggat                                                       20

<210> SEQ ID NO 31
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cagacgtgtg ctcttccgat ctgcagacac cttggacatc ct                              42

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agatctgagc cagtcgctgt                                                       20

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cagacgtgtg ctcttccgat cttggtgcag agctgaagat ttt                             43

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aaaagtgggc ttgattctgc                                                       20

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
```
cagacgtgtg ctcttccgat cttttttgttc gcatggtcac ac                42

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atattccttt gggcctctgc                                          20

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cagacgtgtg ctcttccgat cttcaagttt gggtctgtgc tg                 42

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cccccgaaaa tgttcaataa                                          20

<210> SEQ ID NO 39
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cagacgtgtg ctcttccgat cttgctcttg tcataccccc a                  41

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tagcttcctc ctctggtggt                                          20

<210> SEQ ID NO 41
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
cagacgtgtg ctcttccgat cttttgcctt tccataatca ctca          44
```

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
ctggctctcc ccaatatcct                                     20
```

<210> SEQ ID NO 43
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
cagacgtgtg ctcttccgat ctgctctgag gactgcacca tt            42
```

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

```
gtggtgttgg ggtatggttt                                     20
```

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

```
cagacgtgtg ctcttccgat ctatacacag atgcccattg ca            42
```

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

```
agacaggtcc ttttcgatgg                                     20
```

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

```
cagacgtgtg ctcttccgat cttgtgcaat atgtgatgtg gc            42
```

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ttgagacagg cacatacagc tt                                              22

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cagacgtgtg ctcttccgat ctttgcttcc tcaatctgtc ca                        42

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccccaaccac ttcattcttg                                                 20

<210> SEQ ID NO 51
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cagacgtgtg ctcttccgat ctttcaattc ctctgggaat gtt                       43

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tgcctagagg tgctcattca                                                 20

<210> SEQ ID NO 53
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cagacgtgtg ctcttccgat ctgttgatgc tggaggcaga at                        42

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
agcctgggtc acagatcaag                                                    20

<210> SEQ ID NO 55
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
cagacgtgtg ctcttccgat ctaggtagga gggtggatgg ag                           42

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
ccagcaccag ggagtttcta                                                    20

<210> SEQ ID NO 57
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
cagacgtgtg ctcttccgat ctaggaaagg attggaacag ca                           42

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
gggtttcagg ttccaatcag                                                    20

<210> SEQ ID NO 59
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
cagacgtgtg ctcttccgat cttttgtaac tttttgcaag gca                          43

-continued

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gtgaggagtg ggtccagaaa                                                    20

<210> SEQ ID NO 61
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cagacgtgtg ctcttccgat ctagtgggga ggagcaggag                              40

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ccattccctt cttcctcctc                                                    20

<210> SEQ ID NO 63
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cagacgtgtg ctcttccgat cttacctaca agatcccgcg tc                           42

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ttggacatag cccaagaaca                                                    20

<210> SEQ ID NO 65
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cagacgtgtg ctcttccgat cttgtgcctc actggacttg tc                           42

<210> SEQ ID NO 66

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acctgaagct gaatgcctga                                                    20

<210> SEQ ID NO 67
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cagacgtgtg ctcttccgat ctctggaggc cacctcttct aa                           42

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggtaaacacg cctgcaaac                                                     19

<210> SEQ ID NO 69
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cagacgtgtg ctcttccgat ctcaggactc agaagcctct gg                           42

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
caacaaagca cagtgttaaa tgaa                                               24

<210> SEQ ID NO 71
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cagacgtgtg ctcttccgat cttgtgtcag ctactgcgga aa                           42

<210> SEQ ID NO 72
<211> LENGTH: 20
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tgagcagatc cacaggaaaa                                                      20

<210> SEQ ID NO 73
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cagacgtgtg ctcttccgat ctgaaatgga gtctcaaagc ttca                           44

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tcccaactac gctgatttga                                                      20

<210> SEQ ID NO 75
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cagacgtgtg ctcttccgat ctgaccaaaa ggaatgtgtg gg                             42

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tgcaagagtg acagtggatt g                                                    21

<210> SEQ ID NO 77
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cagacgtgtg ctcttccgat cttcaaccaa ggtttgcttt tgt                            43

<210> SEQ ID NO 78
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 78
agaggctgaa agaggccaat                                                 20

<210> SEQ ID NO 79
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cagacgtgtg ctcttccgat ctaatatggg ttgcatttgg tca                       43

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
aaatctgcag aaggaaaaat gtg                                             23

<210> SEQ ID NO 81
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cagacgtgtg ctcttccgat ctagttttca atgatgggcg ag                        42

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gctcaaggga gagctgaaga                                                 20

<210> SEQ ID NO 83
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cagacgtgtg ctcttccgat ctgactacct gcccccagag at                        42

<210> SEQ ID NO 84
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 84
gtggcgtgta tgagtggaga                                                    20

<210> SEQ ID NO 85
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cagacgtgtg ctcttccgat ctcactcgcc cagagactca g                            41

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gcacatctca tggcagctaa                                                    20

<210> SEQ ID NO 87
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
cagacgtgtg ctcttccgat ctgcttcaca aaccttgctc ct                           42

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
acattttctg ccacccaaac                                                    20

<210> SEQ ID NO 89
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cagacgtgtg ctcttccgat ctaacagcac cctctccaga tg                           42

<210> SEQ ID NO 90
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 90
gcctggtaga attggctttt c                                              21

<210> SEQ ID NO 91
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
cagacgtgtg ctcttccgat cttttgtag ccaacattca ttcaa                     45

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
caattggcag ccctatttca                                                20

<210> SEQ ID NO 93
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cagacgtgtg ctcttccgat ctgttcagca gactggtttg ca                       42

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ccgtgaggat gtcactcaga                                                20

<210> SEQ ID NO 95
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cagacgtgtg ctcttccgat ctacgaggaa gccctaagac gt                       42

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
    primer

<400> SEQUENCE: 96
ttgagcctgg ggtgtaagac                                                  20

<210> SEQ ID NO 97
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cagacgtgtg ctcttccgat ctgtcttcca ggattcacgg tg                         42

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gagcacctcc tggaagattg                                                  20

<210> SEQ ID NO 99
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cagacgtgtg ctcttccgat cttaagcacc agtgggactg tg                         42

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
taggagcagg cctgagaaaa                                                  20

<210> SEQ ID NO 101
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cagacgtgtg ctcttccgat ctgattcctc tccaaaccca tg                         42

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 102
tgttttgggg aaagttggag                                                   20

<210> SEQ ID NO 103
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cagacgtgtg ctcttccgat ctctgtttgc ccagtgtttg tg                          42

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
tgcaacccaa ctgtgtgtta                                                   20

<210> SEQ ID NO 105
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
cagacgtgtg ctcttccgat cttttcacca actgttctct gagc                        44

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gccctgagca acaatagcag                                                   20

<210> SEQ ID NO 107
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
cagacgtgtg ctcttccgat ctttcagctc ttcactccag ca                          42

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 108
aggaaaagat gtggctcacg                                              20

<210> SEQ ID NO 109
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cagacgtgtg ctcttccgat ctggagttgg ggagaactgt ca                     42

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tcgaataatc cagggaaacc                                              20

<210> SEQ ID NO 111
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cagacgtgtg ctcttccgat ctaccaaagc atcacgttga ca                     42

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ggctttacaa agctggcaat                                              20

<210> SEQ ID NO 113
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
cagacgtgtg ctcttccgat cttatgcctc ttcgattgct cc                     42

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
```
ccttgagtgt gtctgcgtgt                                                    20

<210> SEQ ID NO 115
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
cagacgtgtg ctcttccgat ctccacagaa ttgggttcca ag                           42

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
aactgggaag gccaggtaac                                                    20

<210> SEQ ID NO 117
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
cagacgtgtg ctcttccgat cttgttttca aattgccatt gc                           42

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ctttctccac gccatttgat                                                    20

<210> SEQ ID NO 119
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cagacgtgtg ctcttccgat ctactaggat atggggtggg ct                           42

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120

```
gggatctgct cgtcatcatt                                                    20
```

<210> SEQ ID NO 121
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121

```
cagacgtgtg ctcttccgat ctgtttctgc tctgaggga aa                            42
```

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122

```
gcgtgcgcgt tatttattta                                                    20
```

<210> SEQ ID NO 123
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123

```
cagacgtgtg ctcttccgat cttgtctggg gaaggcaagt ta                           42
```

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124

```
gcagtcagcc agaaatcaca                                                    20
```

<210> SEQ ID NO 125
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125

```
cagacgtgtg ctcttccgat cttttttctcc tctctgggac ca                          42
```

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126

```
tgaaaagtct ccctttccag a                                                  21
```

<210> SEQ ID NO 127
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
cagacgtgtg ctcttccgat ctccttcaga cagattccag gc                            42

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ggagaggaga gatggggatt                                                     20

<210> SEQ ID NO 129
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
cagacgtgtg ctcttccgat ctgagtgagt gcccctttc tt                             42

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ctcatgccaa caagaacctg                                                     20

<210> SEQ ID NO 131
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
cagacgtgtg ctcttccgat cttgacccac acctgacact tc                            42

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
tcgtggaaca caggcaaac                                                      19

```
<210> SEQ ID NO 133
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
cagacgtgtg ctcttccgat ctttgcattt gtactggcaa gg                          42

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
tcaaggcaac cagaggaaac                                                   20

<210> SEQ ID NO 135
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
cagacgtgtg ctcttccgat ctactaaggg atggggcagt ct                          42

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
accttttcgt tggcatgtgt                                                   20

<210> SEQ ID NO 137
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
cagacgtgtg ctcttccgat cttcagggaa aggactcacc tg                          42

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
atgctgaagg catttcttgg                                                   20
```

```
<210> SEQ ID NO 139
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
cagacgtgtg ctcttccgat ctctgtgagc atggtgcttc at          42

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gaggggagtg gtgggtttat                                    20

<210> SEQ ID NO 141
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
cagacgtgtg ctcttccgat ctcaaaaggg aagggagga tt            42

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
aggggaaaac tcatgagcag                                    20

<210> SEQ ID NO 143
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
cagacgtgtg ctcttccgat cttcactgtg cctggaccat ag           42

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ttgggcagaa agaaaaatgg                                    20

<210> SEQ ID NO 145
```

```
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
cagacgtgtg ctcttccgat ctcaaaagat tccaccagac tgaa            44

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
cctcccccag tctctcttct                                       20

<210> SEQ ID NO 147
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
cagacgtgtg ctcttccgat ctgagtcagg ccgttgctag tc              42

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ggctgatctt cccacaacac                                       20

<210> SEQ ID NO 149
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cagacgtgtg ctcttccgat ctacgagggc aaagatgcta aa              42

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
attcccgtgt tgcttcaaac                                       20

<210> SEQ ID NO 151
<211> LENGTH: 42
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
cagacgtgtg ctcttccgat ctagaactgc cagcaggtag ga                         42

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
cacttccctg ggacattctc                                                  20

<210> SEQ ID NO 153
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
cagacgtgtg ctcttccgat ctctcactct tctccaggcc ag                         42

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
tgatgtctgt ctggctgagg                                                  20

<210> SEQ ID NO 155
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
cagacgtgtg ctcttccgat ctccacacac agaggaagag ca                         42

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
ccagcctgta ggaaaccaaa                                                  20

<210> SEQ ID NO 157
<211> LENGTH: 42
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 157
cagacgtgtg ctcttccgat ctctccttct atctccaggg cc                        42

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
ggatgcaggt ggtttttgat                                                 20

<210> SEQ ID NO 159
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
cagacgtgtg ctcttccgat ctcattgtac ccattttaca ttttctt                   47

<210> SEQ ID NO 160
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
caaaccttaa acacccagaa gc                                              22

<210> SEQ ID NO 161
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
cagacgtgtg ctcttccgat ctataacaat tcggcagttg gc                        42

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gaaccagttt cctcctgtgc                                                 20

<210> SEQ ID NO 163
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
cagacgtgtg ctcttccgat ctaagatgtg gaggctgttg ct                        42

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gactgcggat ctctgtgtca                                                 20

<210> SEQ ID NO 165
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
cagacgtgtg ctcttccgat cttctgcact attcctttgc cc                        42

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
tcagtatgat cttgtgctgt gct                                             23

<210> SEQ ID NO 167
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
cagacgtgtg ctcttccgat cttacccatg aagattggtg gg                        42

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
cacagcatga gaggctctgt                                                 20

<210> SEQ ID NO 169
<211> LENGTH: 42
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 169
cagacgtgtg ctcttccgat cttctcagtt ccgatttccc ag                         42

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
tcaggatctg aggtcccaac                                                  20

<210> SEQ ID NO 171
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
cagacgtgtg ctcttccgat cttcacctgt gtatctcacg ca                         42

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
agagctgtct agcccaggtg                                                  20

<210> SEQ ID NO 173
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
cagacgtgtg ctcttccgat cttggtgtcc tttctctgct cc                         42

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
cttaacgtgg gagtggaacc                                                  20

<210> SEQ ID NO 175
<211> LENGTH: 42
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 175
cagacgtgtg ctcttccgat ctgtgtgcaa atggcagcta ga                              42

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
tctcagcttc caccaaggtt                                                      20

<210> SEQ ID NO 177
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
cagacgtgtg ctcttccgat cttcactggg acactttgc ct                              42

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
caggggagag tgtggtgttt                                                      20

<210> SEQ ID NO 179
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
cagacgtgtg ctcttccgat ctgacatgca ctcagctctt gg                             42

<210> SEQ ID NO 180
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
tgcatagttc ccatgttaaa tcc                                                  23

<210> SEQ ID NO 181
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
cagacgtgtg ctcttccgat cttaccagga atggatgtcg ct                42

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
acatcctacg gtcccaaggt                                         20

<210> SEQ ID NO 183
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
cagacgtgtg ctcttccgat ctgcagaagt gcaggcacct a                 41

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
tgcatgatca aatgcaacct                                         20

<210> SEQ ID NO 185
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
cagacgtgtg ctcttccgat ctttggactt tgggcataaa aga              43

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
aaatcacggc agttttcagc                                         20

<210> SEQ ID NO 187
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 187
cagacgtgtg ctcttccgat ctctcatctg tgcactctcc cc                         42

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
gtgggaagag aagctgatgc                                                  20

<210> SEQ ID NO 189
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
cagacgtgtg ctcttccgat cttcaagcat tatccacgtc ca                         42

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
tgtgatgcca tatcaagtcc a                                                21

<210> SEQ ID NO 191
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
cagacgtgtg ctcttccgat cttcagtgta tgcgaaaagg ttttt                      45

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
agcctctctt gggctttctt                                                  20

<210> SEQ ID NO 193
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
```

```
cagacgtgtg ctcttccgat ctgttttccc tgcctggaac tt          42

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
ctttgctgct gaaggctcat                                    20

<210> SEQ ID NO 195
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
cagacgtgtg ctcttccgat ctacaagtgg tggtaaccct gg          42

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
tgcttcctaa aaagcgaggt                                    20

<210> SEQ ID NO 197
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
cagacgtgtg ctcttccgat ctgaactagg gaggggaaa ga           42

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
gcagccaacc taagcaagat                                    20

<210> SEQ ID NO 199
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
```

```
cagacgtgtg ctcttccgat ctatccagtt actgccggtt tg                         42
```

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200

```
gaatgctgca ggacttgaga                                                  20
```

<210> SEQ ID NO 201
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201

```
cagacgtgtg ctcttccgat ctacttcctt gagacacgga gc                         42
```

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202

```
acccagggac ttaatcagca                                                  20
```

<210> SEQ ID NO 203
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203

```
cagacgtgtg ctcttccgat ctgctgatga gacagcaacc att                        43
```

<210> SEQ ID NO 204
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204

```
gacatctttg ctgcctcca                                                   19
```

<210> SEQ ID NO 205
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205

```
cagacgtgtg ctcttccgat ctatgagaag gacactcgct gc                         42
```

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
ttaaggagtt cctgcagtcc a                                              21

<210> SEQ ID NO 207
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
cagacgtgtg ctcttccgat cttccactgg gcacagaact ta                       42

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
tccttcgctt tgcttgtctt                                                20

<210> SEQ ID NO 209
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
cagacgtgtg ctcttccgat ctaggtggaa aaatagatgc cagtc                    45

<210> SEQ ID NO 210
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
cccggaagtc tatgcgttt                                                 19

<210> SEQ ID NO 211
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
cagacgtgtg ctcttccgat ctaggacatc tcggtgcagt g                        41

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tgtgtgaggt gtctggcttc                                                    20

<210> SEQ ID NO 213
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
cagacgtgtg ctcttccgat ctaggagcac cacgttctgg                              40

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
cccggagaag tatgtgacca                                                    20

<210> SEQ ID NO 215
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
cagacgtgtg ctcttccgat ctgtacttcg cccacagcat c                            41

<210> SEQ ID NO 216
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
ctgaacgagc tggtgacg                                                      18

<210> SEQ ID NO 217
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
cagacgtgtg ctcttccgat ctagtacctg acttgggcat cc                           42

```
<210> SEQ ID NO 218
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
caagggccca tcggtctt                                                        18

<210> SEQ ID NO 219
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
cagacgtgtg ctcttccgat ctttgtgaca aaactcacac atgc                           44

<210> SEQ ID NO 220
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
caagggccca tcggtctt                                                        18

<210> SEQ ID NO 221
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
cagacgtgtg ctcttccgat ctcaaatatg gtcccccatg c                              41

<210> SEQ ID NO 222
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
caagggccca tcggtctt                                                        18

<210> SEQ ID NO 223
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
cagacgtgtg ctcttccgat ctgcaaatgt tgtgtcgagt gc                             42

<210> SEQ ID NO 224
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
caagggccca tcggtctt                                                    18

<210> SEQ ID NO 225
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
cagacgtgtg ctcttccgat ctaccccact tggtgacaca ac                         42

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
ccattccgca gtactccatt                                                  20

<210> SEQ ID NO 227
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
cagacgtgtg ctcttccgat ctaaggaaaa gagcaaacgt gg                         42

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
ttggttgact tcatggatgc                                                  20

<210> SEQ ID NO 229
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
cagacgtgtg ctcttccgat ctggaaacag cacaaatgaa cttaa                      45

<210> SEQ ID NO 230
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
catcatgcag ttcaacaagc                                                 20

<210> SEQ ID NO 231
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
cagacgtgtg ctcttccgat ctatgcactc tgtttgcgaa ga                        42

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
gggtgtgttt ccatgtctca                                                 20

<210> SEQ ID NO 233
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
cagacgtgtg ctcttccgat ctttgaaagt gtgtgtgtcc gc                        42

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
tcaggctgtt gcatgaagaa                                                 20

<210> SEQ ID NO 235
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
cagacgtgtg ctcttccgat ctgtatgccc ttgctggacc ta                        42

<210> SEQ ID NO 236
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 236
atgcgcagta aaaactcgtg                                                   20

<210> SEQ ID NO 237
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
cagacgtgtg ctcttccgat cttacagttc cacgctgagc tg                          42

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
gcctgtactt tcagctgggt a                                                 21

<210> SEQ ID NO 239
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
cagacgtgtg ctcttccgat ctaaggtgtt tgtgccattt gg                          42

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
ggtgagctct gattgcttca                                                   20

<210> SEQ ID NO 241
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
cagacgtgtg ctcttccgat cttatcagga ggcagggatc ac                          42

<210> SEQ ID NO 242
<211> LENGTH: 19
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 242
gaccgggtca gtggtctct                                                    19

<210> SEQ ID NO 243
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
cagacgtgtg ctcttccgat ctggtgatcc tgagccctga c                           41

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
tgcagtgagc tgagatcgag                                                   20

<210> SEQ ID NO 245
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
cagacgtgtg ctcttccgat ctatggaaaa catcctcatg gc                          42

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 246
cacatggccu ccaaggagua a                                                 21

<210> SEQ ID NO 247
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
cagacgtgtg ctcttccgat ctcagcaaga gcacaagagg aa                          42

<210> SEQ ID NO 248
<211> LENGTH: 19

<212> TYPE: DNA
<213> ORGANISM: Artificial Sequence
<220> FEATURE:
<223> OTHER INFORMATION: Description of Artificial Sequence: Synthetic primer

<400> SEQUENCE: 248
gcagggtccc agtcctatg                                                    19

<210> SEQ ID NO 249
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 249
cagacgtgtg ctcttccgat ctccaatcat gaggaagatg ca                          42

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 250
taggagcagg cctgagaaaa                                                   20

<210> SEQ ID NO 251
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 251
cagacgtgtg ctcttccgat ctgattcctc tccaaaccca tg                          42

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 252
tccttcgctt tgcttgtctt                                                   20

<210> SEQ ID NO 253
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 253
cagacgtgtg ctcttccgat ctaggtggaa aaatagatgc cagtc                       45

<210> SEQ ID NO 254
<211> LENGTH: 19
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 254
ggtaaacacg cctgcaaac                                                  19

<210> SEQ ID NO 255
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
cagacgtgtg ctcttccgat ctcaggactc agaagcctct gg                        42

<210> SEQ ID NO 256
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
caacaaagca cagtgttaaa tgaa                                            24

<210> SEQ ID NO 257
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
cagacgtgtg ctcttccgat cttgtgtcag ctactgcgga aa                        42

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
tgtgtgaggt gtctggcttc                                                 20

<210> SEQ ID NO 259
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
cagacgtgtg ctcttccgat ctaggagcac cacgttctgg                           40

<210> SEQ ID NO 260
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 260
cccggagaag tatgtgacca                                                    20

<210> SEQ ID NO 261
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
cagacgtgtg ctcttccgat ctgtacttcg cccacagcat c                            41

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
tccaggagga ttaccgaaaa                                                    20

<210> SEQ ID NO 263
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
cagacgtgtg ctcttccgat ctccatccaa gggagagtga ga                           42

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
agatctgagc cagtcgctgt                                                    20

<210> SEQ ID NO 265
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
cagacgtgtg ctcttccgat cttggtgcag agctgaagat ttt                          43

<210> SEQ ID NO 266
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 266
aaaagtgggc ttgattctgc                                                  20

<210> SEQ ID NO 267
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
cagacgtgtg ctcttccgat cttttgttc gcatggtcac ac                          42

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
tgagcagatc cacaggaaaa                                                  20

<210> SEQ ID NO 269
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
cagacgtgtg ctcttccgat ctgaaatgga gtctcaaagc ttca                       44

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
cccccgaaaa tgttcaataa                                                  20

<210> SEQ ID NO 271
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
cagacgtgtg ctcttccgat cttgctcttg tcataccccc a                          41

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 272 atattcctttt gggcctctgc                                           20

<210> SEQ ID NO 273
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
cagacgtgtg ctcttccgat cttcaagttt gggtctgtgc tg                   42

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
ccccaaccac ttcattcttg                                            20

<210> SEQ ID NO 275
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
cagacgtgtg ctcttccgat ctttcaattc ctctgggaat gtt                  43

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
aatggcaaag gaaggtggat                                            20

<210> SEQ ID NO 277
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
cagacgtgtg ctcttccgat ctgcagacac cttggacatc ct                   42

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 278
tgcatagttc ccatgttaaa tcc                                         23

<210> SEQ ID NO 279
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
cagacgtgtg ctcttccgat cttaccagga atggatgtcg ct                    42

<210> SEQ ID NO 280
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
aaatctgcag aaggaaaaat gtg                                         23

<210> SEQ ID NO 281
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
cagacgtgtg ctcttccgat ctagttttca atgatgggcg ag                    42

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
tcgaataatc cagggaaacc                                             20

<210> SEQ ID NO 283
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
cagacgtgtg ctcttccgat ctaccaaagc atcacgttga ca                    42

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
ctggctctcc ccaatatcct                                                      20

<210> SEQ ID NO 285
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
cagacgtgtg ctcttccgat ctgctctgag gactgcacca tt                             42

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
gcagccaacc taagcaagat                                                      20

<210> SEQ ID NO 287
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
cagacgtgtg ctcttccgat ctatccagtt actgccggtt tg                             42

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
tgcctagagg tgctcattca                                                      20

<210> SEQ ID NO 289
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
cagacgtgtg ctcttccgat ctgttgatgc tggaggcaga at                             42

<210> SEQ ID NO 290
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
gacatctttg ctgcctcca                                                19

<210> SEQ ID NO 291
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
cagacgtgtg ctcttccgat ctatgagaag gacactcgct gc                      42

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
ttggacatag cccaagaaca                                               20

<210> SEQ ID NO 293
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
cagacgtgtg ctcttccgat cttgtgcctc actggacttg tc                      42

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
aaatcacggc agttttcagc                                               20

<210> SEQ ID NO 295
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
cagacgtgtg ctcttccgat ctctcatctg tgcactctcc cc                      42

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296

```
atgctgaagg catttcttgg                                                  20

<210> SEQ ID NO 297
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
cagacgtgtg ctcttccgat ctctgtgagc atggtgcttc at                         42

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
gactgcggat ctctgtgtca                                                  20

<210> SEQ ID NO 299
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
cagacgtgtg ctcttccgat cttctgcact attcctttgc cc                         42

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
ccgtgaggat gtcactcaga                                                  20

<210> SEQ ID NO 301
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
cagacgtgtg ctcttccgat ctacgaggaa gccctaagac gt                         42

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
agacaggtcc ttttcgatgg                                                  20
```

<210> SEQ ID NO 303
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
cagacgtgtg ctcttccgat cttgtgcaat atgtgatgtg gc                    42

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
tgttttgggg aaagttggag                                             20

<210> SEQ ID NO 305
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
cagacgtgtg ctcttccgat ctctgtttgc ccagtgtttg tg                    42

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
acatcctacg gtcccaaggt                                             20

<210> SEQ ID NO 307
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
cagacgtgtg ctcttccgat ctgcagaagt gcaggcacct a                     41

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
agagctgtct agcccaggtg                                             20

<210> SEQ ID NO 309
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
cagacgtgtg ctcttccgat cttggtgtcc tttctctgct cc                              42

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
tgacgtgtgt tgcttttgtg                                                       20

<210> SEQ ID NO 311
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
cagacgtgtg ctcttccgat ctacttggga gaaaacaggg gt                              42

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
gctttccact cccagctatg                                                       20

<210> SEQ ID NO 313
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
cagacgtgtg ctcttccgat cttgctttga gtgctacgga ga                              42

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
gggggaggga tgtgaagtta                                                       20

```
<210> SEQ ID NO 315
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
cagacgtgtg ctcttccgat ctatcttgtc tgtgattccg gg                           42

<210> SEQ ID NO 316
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
acagatgacc caatgcaatt c                                                  21

<210> SEQ ID NO 317
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
cagacgtgtg ctcttccgat ctgagcacct gtgatatgtg cg                           42

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
agaccgatgc acagtcttcc                                                    20

<210> SEQ ID NO 319
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
cagacgtgtg ctcttccgat ctcttcacgt ctggcctcag tc                           42

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
ggagcactca agtgtgacga                                                    20

<210> SEQ ID NO 321
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
cagacgtgtg ctcttccgat cttttctat ggagccttcc ga                           42

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
catccaattc ccaaggacag                                                    20

<210> SEQ ID NO 323
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
cagacgtgtg ctcttccgat ctggtgaagg tgccgagcta ta                           42

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
gctcttcctc aaaccacgaa                                                    20

<210> SEQ ID NO 325
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
cagacgtgtg ctcttccgat ctcacactcc tttgcttagc cc                           42

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
tcctcacacc acgaatctga                                                    20

<210> SEQ ID NO 327
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
cagacgtgtg ctcttccgat ctcactcctt tgcttagccc ac                    42

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
ccagctcacc tgttctccag                                             20

<210> SEQ ID NO 329
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
cagacgtgtg ctcttccgat ctgaatcccg tacctgctgc t                     41

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
ctaaaggact gccagccaag                                             20

<210> SEQ ID NO 331
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
cagacgtgtg ctcttccgat ctataacctg acactggacg gg                    42

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
cacattcctg tgcattgagg                                             20

<210> SEQ ID NO 333
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 333
cagacgtgtg ctcttccgat ctatactcag ttcggaaggg gc                          42

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
gaaggaggga gacatgagca                                                   20

<210> SEQ ID NO 335
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
cagacgtgtg ctcttccgat ctactggtcc ttagccccat ct                          42

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
tcagttggct gacttccaca                                                   20

<210> SEQ ID NO 337
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
cagacgtgtg ctcttccgat ctttagtttg ggggttttgc tg                          42

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
tcttggccag ggtagtaaga a                                                 21

<210> SEQ ID NO 339
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 339
cagacgtgtg ctcttccgat ctgtcagttc caatgaggtg gg                    42

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
cgtccagacc ttgttcacac                                             20

<210> SEQ ID NO 341
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
cagacgtgtg ctcttccgat ctccacaaat agtgctcgct ttc                   43

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
tagagggcca ggacatcatc                                             20

<210> SEQ ID NO 343
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
cagacgtgtg ctcttccgat ctttgctcct tttgctatgc ct                    42

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
tgctattgac cgatgcttca                                             20

<210> SEQ ID NO 345
<211> LENGTH: 42
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 345
cagacgtgtg ctcttccgat ctgcaacggg ctacagcttt at                              42

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
gctcttgttc ttgccgtttt                                                      20

<210> SEQ ID NO 347
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
cagacgtgtg ctcttccgat ctgagtccct cagtggagca ag                              42

<210> SEQ ID NO 348
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
cacaagcaca ttcatctctt cc                                                   22

<210> SEQ ID NO 349
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
cagacgtgtg ctcttccgat ctattcaggg ccagcttcat aa                              42

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
tacttcaagg gagccattcc                                                      20

<210> SEQ ID NO 351
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 351
cagacgtgtg ctcttccgat cttttgtaac tgtgcagggc ag                42

<210> SEQ ID NO 352
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
agcaacgtgg agtcagtctg t                                       21

<210> SEQ ID NO 353
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
cagacgtgtg ctcttccgat ctctcacctt ctcttgcctt gg                42

<210> SEQ ID NO 354
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
ttattttctg gggctgtcag a                                       21

<210> SEQ ID NO 355
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
cagacgtgtg ctcttccgat ctcattctgg cactcaggtg aa                42

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
tgatcaagca cctgagaacg                                         20

<210> SEQ ID NO 357
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
cagacgtgtg ctcttccgat cttaccagtg caccatctgc ac				42

<210> SEQ ID NO 358
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
tgcaaaaccc agaagctaaa a				21

<210> SEQ ID NO 359
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
cagacgtgtg ctcttccgat ctgttctgtg caaatggcat tc				42

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
agagctgtgt ggagctggat				20

<210> SEQ ID NO 361
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
cagacgtgtg ctcttccgat ctggagtctt ctgctttgct gg				42

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
gccctcttgc caggatattt				20

<210> SEQ ID NO 363
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
cagacgtgtg ctcttccgat ctgcatgtaa gttgtccccc at                          42

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
ctggcctctg ctcaactagc                                                   20

<210> SEQ ID NO 365
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
cagacgtgtg ctcttccgat ctatggtaca agcaatgcct gc                          42

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
cagcctcaag gggaaggtat                                                   20

<210> SEQ ID NO 367
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
cagacgtgtg ctcttccgat cttgcttaac ccatggatcc tg                          42

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
ccctgcagtc acagctacac                                                   20

<210> SEQ ID NO 369
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
cagacgtgtg ctcttccgat cttcagggct ggtcttttag ga                              42

<210> SEQ ID NO 370
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
tgggataatg taaaactggt gct                                                   23

<210> SEQ ID NO 371
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
cagacgtgtg ctcttccgat ctcatcccca tgatatttgg ga                              42

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
agctagcctg agagggaacc                                                       20

<210> SEQ ID NO 373
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
cagacgtgtg ctcttccgat cttcctccag accattcagg ac                              42

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
ggctctgcct tgcactattt                                                       20

<210> SEQ ID NO 375
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
cagacgtgtg ctcttccgat ctctcttcct cccttccatg c				41

<210> SEQ ID NO 376
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
taaggcccaa agtgggtaca				20

<210> SEQ ID NO 377
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
cagacgtgtg ctcttccgat cttaggaagc acgaggaaag ga				42

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
accctctctc cctcccttc				20

<210> SEQ ID NO 379
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
cagacgtgtg ctcttccgat cttagttggc tatgctggca tg				42

<210> SEQ ID NO 380
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
gcctggtaga attggctttt c				21

<210> SEQ ID NO 381
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
cagacgtgtg ctcttccgat cttttttgtag ccaacattca ttcaa				45

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382 cagggagag tgtggtgttt                                                   20

<210> SEQ ID NO 383
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
cagacgtgtg ctcttccgat ctactcagct cttggctcca ct                         42

<210> SEQ ID NO 384
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
acatcaagct ccattgtttc g                                                21

<210> SEQ ID NO 385
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
cagacgtgtg ctcttccgat cttttgcctg cactctttgt agg                        43

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
gcctggcacg taatagcttg                                                  20

<210> SEQ ID NO 387
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
cagacgtgtg ctcttccgat ctaggaaaga aatgcccttg gt                         42

<210> SEQ ID NO 388
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 388
gaggatgtgt ggcattttca    20

<210> SEQ ID NO 389
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 389
cagacgtgtg ctcttccgat ctggttccta ggtgagcagg tg    42

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 390
agcaggctgt acacagcaga    20

<210> SEQ ID NO 391
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 391
cagacgtgtg ctcttccgat ctgacactag gcacattggc tg    42

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 392
actgtgccct catccagaac    20

<210> SEQ ID NO 393
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 393
cagacgtgtg ctcttccgat ctaacgacgc caaggtgata ct    42

```
<210> SEQ ID NO 394
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
tggtgaaatg cagagtcaat g                                              21

<210> SEQ ID NO 395
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
cagacgtgtg ctcttccgat cttcaggagg aaggcttaca cc                       42

<210> SEQ ID NO 396
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
tgaattttgc ttggtggatg                                                20

<210> SEQ ID NO 397
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
cagacgtgtg ctcttccgat cttgtcagtg gaagaagcag atg                      43

<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
cagtgagaat gagggccaag                                                20

<210> SEQ ID NO 399
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
cagacgtgtg ctcttccgat ctgaatgagg gccaagaaag ag                       42

<210> SEQ ID NO 400
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
aaaatgaaac cctcccaaa                                                    20

<210> SEQ ID NO 401
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
cagacgtgtg ctcttccgat cttcctttgg agattaaggc cc                          42

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
ctgcatcaat gctcaaggaa                                                   20

<210> SEQ ID NO 403
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
cagacgtgtg ctcttccgat ctccaaggct gctctgtttc tt                          42

<210> SEQ ID NO 404
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
aaatcaagct cccaaggtca                                                   20

<210> SEQ ID NO 405
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
cagacgtgtg ctcttccgat cttgtgaatg acttggtccc tg                          42

<210> SEQ ID NO 406
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
atgccccaaa gcgattttt                                                    19

<210> SEQ ID NO 407
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
cagacgtgtg ctcttccgat ctcaaaggaa accaatgcca ct                          42

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
tccctcattg aaagatgcaa                                                   20

<210> SEQ ID NO 409
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
cagacgtgtg ctcttccgat cttagaatca ttaggccagg cg                          42

<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
tgcaagccat ttatgggaat                                                   20

<210> SEQ ID NO 411
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
cagacgtgtg ctcttccgat ctccttgggt tttcttttca attc                        44

<210> SEQ ID NO 412
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 412
atttccatgg tgctccagtc                                        20

<210> SEQ ID NO 413
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 413
cagacgtgtg ctcttccgat ctagagaagc agaagtcgct cg               42

<210> SEQ ID NO 414
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 414
ctgctggccc tgtacctg                                          18

<210> SEQ ID NO 415
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 415
cagacgtgtg ctcttccgat ctctccaccc tggccaagat                  40

<210> SEQ ID NO 416
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 416
ttcagctgac ttggacaacc t                                      21

<210> SEQ ID NO 417
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 417
cagacgtgtg ctcttccgat ctggacaacc tgactggctt tg               42

<210> SEQ ID NO 418
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 418
gggtgttggt gaacttggtt                                                    20

<210> SEQ ID NO 419
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
cagacgtgtg ctcttccgat cttttaatat ggatgccgtg gg                           42

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
gttgcccagt gtgtttctga                                                    20

<210> SEQ ID NO 421
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
cagacgtgtg ctcttccgat ctaaccaggc aacttgggaa ct                           42

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422
ccattccgca gtactccatt                                                    20

<210> SEQ ID NO 423
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
cagacgtgtg ctcttccgat ctaaggaaaa gagcaaacgt gg                           42

<210> SEQ ID NO 424
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 424
ttggttgact tcatggatgc                                                    20

<210> SEQ ID NO 425
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 425
cagacgtgtg ctcttccgat ctggaaacag cacaaatgaa cttaa                        45

<210> SEQ ID NO 426
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 426
catcatgcag ttcaacaagc                                                    20

<210> SEQ ID NO 427
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 427
cagacgtgtg ctcttccgat ctatgcactc tgtttgcgaa ga                           42

<210> SEQ ID NO 428
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 428
gggtgtgttt ccatgtctca                                                    20

<210> SEQ ID NO 429
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 429
cagacgtgtg ctcttccgat ctttgaaagt gtgtgtgtcc gc                           42

<210> SEQ ID NO 430
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 430
tcaggctgtt gcatgaagaa                                                 20

<210> SEQ ID NO 431
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 431
cagacgtgtg ctcttccgat ctgtatgccc ttgctggacc ta                        42

<210> SEQ ID NO 432
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 432
atgcgcagta aaaactcgtg                                                 20

<210> SEQ ID NO 433
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
cagacgtgtg ctcttccgat cttacagttc cacgctgagc tg                        42

<210> SEQ ID NO 434
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 434
gcctgtactt tcagctgggt a                                               21

<210> SEQ ID NO 435
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
cagacgtgtg ctcttccgat ctaaggtgtt tgtgccattt gg                        42

<210> SEQ ID NO 436
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 436
ggtgagctct gattgcttca                                              20

<210> SEQ ID NO 437
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 437
cagacgtgtg ctcttccgat cttatcagga ggcagggatc ac                     42

<210> SEQ ID NO 438
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
gaccgggtca gtggtctct                                               19

<210> SEQ ID NO 439
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
cagacgtgtg ctcttccgat ctggtgatcc tgagccctga c                      41

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 440
tgcagtgagc tgagatcgag                                              20

<210> SEQ ID NO 441
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
cagacgtgtg ctcttccgat ctatggaaaa catcctcatg gc                     42

<210> SEQ ID NO 442
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
```

```
<223> OTHER INFORMATION: Description of Combined DNA/RNA Molecule:
      Synthetic primer

<400> SEQUENCE: 442
cacatggccu ccaaggagua a                                                    21

<210> SEQ ID NO 443
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 443
cagacgtgtg ctcttccgat ctcagcaaga gcacaagagg aa                             42

<210> SEQ ID NO 444
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 444
gacttcaaca gcgacaccca                                                      20

<210> SEQ ID NO 445
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 445
cagacgtgtg ctcttccgat ctgccctcaa cgaccacttt gt                             42

<210> SEQ ID NO 446
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 446
gaaaacgcat cctggaccca                                                      20

<210> SEQ ID NO 447
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 447
cagacgtgtg ctcttccgat cttgatgtca ttgccactct gct                            43

<210> SEQ ID NO 448
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 448
aagttgtccc ccatcccaaa                                            20

<210> SEQ ID NO 449
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
cagacgtgtg ctcttccgat ctctggggat ggactgggta aat                  43

<210> SEQ ID NO 450
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 450
actgctgtcc caaacatgca                                            20

<210> SEQ ID NO 451
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 451
cagacgtgtg ctcttccgat ctatgcctgc ccattggaga gaa                  43

<210> SEQ ID NO 452
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 452
ccaccatctt tgcaggttgc                                            20

<210> SEQ ID NO 453
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 453
cagacgtgtg ctcttccgat ctgctgtcca gttcccagaa gg                   42

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 454
ctgggagagg gggtagctag                                               20

<210> SEQ ID NO 455
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 455
cagacgtgtg ctcttccgat ctaccacttc cctcagtccc aa                      42

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456
acagaagcag cgtcagtacc                                               20

<210> SEQ ID NO 457
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
cagacgtgtg ctcttccgat ctgggtctct tgagtcccgt g                       41

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
ggggagagtg tggtgtttcc                                               20

<210> SEQ ID NO 459
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
cagacgtgtg ctcttccgat ctctcttggc tccactggga tg                      42

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 460
atcaatggtc caagccgcat                                                    20

<210> SEQ ID NO 461
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
cagacgtgtg ctcttccgat ctaggtcaca gatcttcccc cg                           42

<210> SEQ ID NO 462
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 462
ctttccagtc ctacggagcc                                                    20

<210> SEQ ID NO 463
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463
cagacgtgtg ctcttccgat cttgctctga accccaatcc tc                           42

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 464
accatcacag gcatgttcct                                                    20

<210> SEQ ID NO 465
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465
cagacgtgtg ctcttccgat cttgtagatg acctggcttg cc                           42

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 466
```
gcatctcatg agtgccaagc                                                       20

<210> SEQ ID NO 467
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 467
cagacgtgtg ctcttccgat ctcctgcccc cagaccttt atc                              43

<210> SEQ ID NO 468
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 468
tgcagagcct tgtcgttaca                                                       20

<210> SEQ ID NO 469
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 469
cagacgtgtg ctcttccgat ctcgtgacag agtgccttt cg                               42

<210> SEQ ID NO 470
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 470
aggtgaagat gacagtgcag g                                                     21

<210> SEQ ID NO 471
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 471
cagacgtgtg ctcttccgat ctaggccctc ttgtgtgtaa ca                              42

<210> SEQ ID NO 472
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 472
ggaaccatgt gccaagttgc    20

<210> SEQ ID NO 473
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 473
cagacgtgtg ctcttccgat ctcctttgtt gtgcgagggt gt    42

<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 474
agtgttgctg acagtgcaga    20

<210> SEQ ID NO 475
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 475
cagacgtgtg ctcttccgat ctccaaagaa gacacagacc ggt    43

<210> SEQ ID NO 476
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 476
ttgccacaaa gcctggaatc    20

<210> SEQ ID NO 477
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 477
cagacgtgtg ctcttccgat ctaaagcaac cttgtcccgc ct    42

<210> SEQ ID NO 478
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 478
ggagtccagc gaatgacgtc    20

<210> SEQ ID NO 479
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 479
cagacgtgtg ctcttccgat ctcatggcca cgttgtcatt gt        42

<210> SEQ ID NO 480
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 480
caacacccag gggatcagtg        20

<210> SEQ ID NO 481
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 481
cagacgtgtg ctcttccgat ctccaccctc cacaggaaat tg        42

<210> SEQ ID NO 482
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 482
agctgtacca gggggagag        19

<210> SEQ ID NO 483
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 483
cagacgtgtg ctcttccgat ctctttggag aagacagtgg cga        43

<210> SEQ ID NO 484
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 484
ggaagacagc cagatccagt g        21

```
<210> SEQ ID NO 485
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 485
cagacgtgtg ctcttccgat ctttgtgcag accaagagca cc                              42

<210> SEQ ID NO 486
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 486
gggctgagaa tgaggcagtt                                                       20

<210> SEQ ID NO 487
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 487
cagacgtgtg ctcttccgat ctggaaagcg acaagggtga ac                              42

<210> SEQ ID NO 488
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 488
acttaacagc tgcaggggc                                                        19

<210> SEQ ID NO 489
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 489
cagacgtgtg ctcttccgat ctactaactt gaaccgtgtt taagg                           45

<210> SEQ ID NO 490
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 490
ttataaccat cagcccgcca                                                       20
```

<210> SEQ ID NO 491
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 491
cagacgtgtg ctcttccgat ctagaaaagg ggctggaaag gg          42

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 492
accaaagcat cacgttgaca t                                 21

<210> SEQ ID NO 493
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 493
cagacgtgtg ctcttccgat ctacatgtga atgttgagcc ca          42

<210> SEQ ID NO 494
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 494
ctcttcagca tcccccgtac                                   20

<210> SEQ ID NO 495
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 495
cagacgtgtg ctcttccgat ctgcccccaa atgaaagctt ga          42

<210> SEQ ID NO 496
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 496
ggagagcgtc cattccagtg                                   20

<210> SEQ ID NO 497

```
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 497
cagacgtgtg ctcttccgat ctatccacct gaagctgcac c                 41

<210> SEQ ID NO 498
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 498
aatgtaccag ccagtcagcg                                          20

<210> SEQ ID NO 499
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 499
cagacgtgtg ctcttccgat ctggttttgg tggagctgac ga                42

<210> SEQ ID NO 500
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 500
tttactcatc gggcagccac                                          20

<210> SEQ ID NO 501
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 501
cagacgtgtg ctcttccgat cttgtttgcc cagtgtttgt gc                42

<210> SEQ ID NO 502
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 502
gctgtagaca ggtccttttc g                                       21

<210> SEQ ID NO 503
<211> LENGTH: 47
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 503
cagacgtgtg ctcttccgat ctagtgttgg aaaatgtgca atatgtg        47

<210> SEQ ID NO 504
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 504
gggtctggtg ggcatcatta        20

<210> SEQ ID NO 505
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 505
cagacgtgtg ctcttccgat ctgcctcttc gattgctccg ta        42

<210> SEQ ID NO 506
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 506
aggtcaatgc cagagacgga        20

<210> SEQ ID NO 507
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 507
cagacgtgtg ctcttccgat ctatcagcat acctttattg tgatctatc        49

<210> SEQ ID NO 508
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 508
tggcatgtga gtcattgctc        20

<210> SEQ ID NO 509
<211> LENGTH: 42
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 509
cagacgtgtg ctcttccgat cttttttgatg tgaggggcgg at                             42

<210> SEQ ID NO 510
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 510 tacttttttcg cctcccaggg                                                     20

<210> SEQ ID NO 511
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 511
cagacgtgtg ctcttccgat cttcctgccc caccaagatc at                             42

<210> SEQ ID NO 512
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 512
tgccacggcc tttccttaaa                                                      20

<210> SEQ ID NO 513
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 513
cagacgtgtg ctcttccgat ctttgtctaa gtgcaaccgc ct                             42

<210> SEQ ID NO 514
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 514
ctcctgacag aaggtgccac                                                      20

<210> SEQ ID NO 515
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 515
cagacgtgtg ctcttccgat ctggtgattg gaccaggcca tt                          42

<210> SEQ ID NO 516
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 516
gactggctac gtagttcggg                                                   20

<210> SEQ ID NO 517
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 517
cagacgtgtg ctcttccgat cttttgctta gaaggatggc gc                          42

<210> SEQ ID NO 518
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 518
agctacggaa ctcttgtgcg                                                   20

<210> SEQ ID NO 519
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 519
cagacgtgtg ctcttccgat ctcaaccttg gctgagtctt ga                          42

<210> SEQ ID NO 520
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 520 tcagtctttta ggggttgggc                                                  20

<210> SEQ ID NO 521
<211> LENGTH: 45
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 521
cagacgtgtg ctcttccgat ctatgtgcat ttcaatccca cgtac              45

<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 522
ccagtctagt ttctgggcag g                                        21

<210> SEQ ID NO 523
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 523
cagacgtgtg ctcttccgat ctatgtaaac cattgctgtg ccatt              45

<210> SEQ ID NO 524
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 524
ccagttcttc ctgacaccgg                                          20

<210> SEQ ID NO 525
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 525
cagacgtgtg ctcttccgat ctccaaagtt tgcagcctat acc                43

<210> SEQ ID NO 526
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 526
accaaccaga ccaggactta                                          20

<210> SEQ ID NO 527
<211> LENGTH: 43
<212> TYPE: DNA
<213> ORGANISM: Artificial Sequence
<220> FEATURE:
<223> OTHER INFORMATION: Description of Artificial Sequence: Synthetic
```

```
                       primer

<400> SEQUENCE: 527
cagacgtgtg ctcttccgat cttcactagg agacgtggaa ttg                        43

<210> SEQ ID NO 528
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 528
cacccgtcca gaccttgtt                                                   19

<210> SEQ ID NO 529
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 529
cagacgtgtg ctcttccgat cttgttttcc tcttaacgtt agaccac                    47

<210> SEQ ID NO 530
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 530
tgcaagagtg acagtggatt g                                                21

<210> SEQ ID NO 531
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 531
cagacgtgtg ctcttccgat ctgctgatat tctgcaacac tgtaca                     46

<210> SEQ ID NO 532
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 532
tgtcctcacg gtgcctttt                                                   19

<210> SEQ ID NO 533
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 533
cagacgtgtg ctcttccgat ctgtaggcag acacagggac tt                          42

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 534
cctcaagggg gactgtctttt c                                                21

<210> SEQ ID NO 535
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 535
cagacgtgtg ctcttccgat ctgcatatcc tgagccatcg gt                          42

<210> SEQ ID NO 536
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 536
attgctggta gagaccccca                                                   20

<210> SEQ ID NO 537
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 537
cagacgtgtg ctcttccgat ctcccccatt tccccgatgt                             40

<210> SEQ ID NO 538
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 538
cccagccagc tgtggtattc                                                   20

<210> SEQ ID NO 539
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 539
cagacgtgtg ctcttccgat cttggaactg aactgagctg ct                          42

<210> SEQ ID NO 540
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 540
ctaggcagcc aacctaagca                                                   20

<210> SEQ ID NO 541
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 541
cagacgtgtg ctcttccgat ctcctgcaat ctgagccagt gc                          42

<210> SEQ ID NO 542
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 542
agtggacctt aggccttcct                                                   20

<210> SEQ ID NO 543
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 543
cagacgtgtg ctcttccgat ctggctcaga catgttttcc gtg                         43

<210> SEQ ID NO 544
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 544
tcacttaaga cccagggact t                                                 21

<210> SEQ ID NO 545
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 545

```
cagacgtgtg ctcttccgat ctaagcatca tctcaacact gactt              45
```

<210> SEQ ID NO 546
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 546

```
accatgagaa ggacactcgc                                           20
```

<210> SEQ ID NO 547
<211> LENGTH: 42
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 547

```
cagacgtgtg ctcttccgat ctcgggcttg aattcctgtc ct                  42
```

<210> SEQ ID NO 548
<211> LENGTH: 19
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 548

```
cggcaaatgt agcatgggc                                            19
```

<210> SEQ ID NO 549
<211> LENGTH: 43
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 549

```
cagacgtgtg ctcttccgat ctggaaagtg gctatgcagt ttg                 43
```

<210> SEQ ID NO 550
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 550

```
ggcatcctcc acaatagcag a                                         21
```

<210> SEQ ID NO 551
<211> LENGTH: 43
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 551

```
cagacgtgtg ctcttccgat ctgcattttg gtccaagttg tgc          43
```

<210> SEQ ID NO 552
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 552

```
cttaaagccc gcctgacaga                                    20
```

<210> SEQ ID NO 553
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 553

```
cagacgtgtg ctcttccgat ctacattctg atgagcaacc gc           42
```

<210> SEQ ID NO 554
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 554

```
acagacgact ttgagcctcg                                    20
```

<210> SEQ ID NO 555
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 555

```
cagacgtgtg ctcttccgat ctatttcacc ttttcctgcg gc           42
```

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 556

```
ggagccaagg gttcagagac                                    20
```

<210> SEQ ID NO 557
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 557

```
cagacgtgtg ctcttccgat cttgctacct cactggggtc ct           42
```

<210> SEQ ID NO 558
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 558
ggccatctct tcctttcgga                                               20

<210> SEQ ID NO 559
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 559
cagacgtgtg ctcttccgat ctgtgtggga actctgccgt g                       41

<210> SEQ ID NO 560
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 560
ctcaccccat catccctttc c                                             21

<210> SEQ ID NO 561
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 561
cagacgtgtg ctcttccgat ctgcccagtg agactgtgtt gt                      42

<210> SEQ ID NO 562
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 562
tactgacggc atgttaggtg                                               20

<210> SEQ ID NO 563
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 563
cagacgtgtg ctcttccgat cttgtgtgtg gagtgggatg tg                      42

<210> SEQ ID NO 564
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 564
aggcagggag gggactattt                                               20

<210> SEQ ID NO 565
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 565
cagacgtgtg ctcttccgat ctggagaaac agagacaggc cc                      42

<210> SEQ ID NO 566
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 566
gcagtgagaa tgagggcca                                                19

<210> SEQ ID NO 567
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 567
cagacgtgtg ctcttccgat ctaggcatac tgacactttg cc                      42

<210> SEQ ID NO 568
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 568
agccagtcca ggagtgagac                                               20

<210> SEQ ID NO 569
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 569
cagacgtgtg ctcttccgat ctggccacac tgaccctgat ac                      42

```
<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 570
cccaaggtca agatcgccac                                                   20

<210> SEQ ID NO 571
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 571
cagacgtgtg ctcttccgat ctctgccagc tccagaagat gt                          42

<210> SEQ ID NO 572
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 572
tgggaagcca aactccatca t                                                 21

<210> SEQ ID NO 573
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 573
cagacgtgtg ctcttccgat ctggaaacca atgccacttt tgt                         43

<210> SEQ ID NO 574
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 574
gccttcaaga ctgaacaccg a                                                 21

<210> SEQ ID NO 575
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 575
cagacgtgtg ctcttccgat ctgcccctca gagatcaaca gac                         43

<210> SEQ ID NO 576
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 576
ttggagaagg tgctggtgac                                                    20

<210> SEQ ID NO 577
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 577
cagacgtgtg ctcttccgat ctcttaccca gtgctctgca ac                           42

<210> SEQ ID NO 578
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 578
tattcctttg cccggcatca                                                    20

<210> SEQ ID NO 579
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 579
cagacgtgtg ctcttccgat ctaccttggg cactgttgaa gt                           42

<210> SEQ ID NO 580
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 580
acttgcacat catggagggt                                                    20

<210> SEQ ID NO 581
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 581
cagacgtgtg ctcttccgat cttccataag ctattttggt ttagtgc                      47

<210> SEQ ID NO 582
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 582
ggtccctcca aaccgttgtc                                            20

<210> SEQ ID NO 583
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 583
cagacgtgtg ctcttccgat ctgaactagg gagggggaaa gaag                 44

<210> SEQ ID NO 584
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 584
tgggagttga tcgcctttcc                                            20

<210> SEQ ID NO 585
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 585
cagacgtgtg ctcttccgat ctctcattct gaaggagccc cat                  43

<210> SEQ ID NO 586
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 586
tggactggtt gttgccaaac                                            20

<210> SEQ ID NO 587
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 587
cagacgtgtg ctcttccgat ctctctgaga gttcccctgt cc                   42

<210> SEQ ID NO 588
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 588
ttcctcctca tcaccatcgc                                                    20

<210> SEQ ID NO 589
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 589
cagacgtgtg ctcttccgat ctcttaccac ccctcagagt gc                           42

<210> SEQ ID NO 590
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 590
gaagctgaat gcctgagggg                                                    20

<210> SEQ ID NO 591
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 591
cagacgtgtg ctcttccgat ctgtcccatc tgctatgccc a                            41

<210> SEQ ID NO 592
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 592
gagtgctgcc tggagtactt                                                    20

<210> SEQ ID NO 593
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 593
cagacgtgtg ctcttccgat ctctcacccc agactcctga ct                           42

<210> SEQ ID NO 594
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 594
gctatggtga gccgtgattg                                                    20

<210> SEQ ID NO 595
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 595
cagacgtgtg ctcttccgat cttcctcacc cccacctctc ta                           42

<210> SEQ ID NO 596
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 596
gacctcagag gcctcctact                                                    20

<210> SEQ ID NO 597
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 597
cagacgtgtg ctcttccgat ctccaatatc ctcgctcccg g                            41

<210> SEQ ID NO 598
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 598
ttcaggactc cctccagcat                                                    20

<210> SEQ ID NO 599
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 599
cagacgtgtg ctcttccgat ctaggtacca aatgcctgtg cc                           42

<210> SEQ ID NO 600
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 600
tgaacttcag ggagggtggt                                                    20

<210> SEQ ID NO 601
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 601
cagacgtgtg ctcttccgat cttcctcgta tgcatggaac cc                           42

<210> SEQ ID NO 602
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 602
ccaaagggaa gagtgcaggg                                                    20

<210> SEQ ID NO 603
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 603
cagacgtgtg ctcttccgat ctattctgta taacactcat atctttgcc                    49

<210> SEQ ID NO 604
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 604
agaatcatta ggccaggcgt g                                                  21

<210> SEQ ID NO 605
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 605
cagacgtgtg ctcttccgat ctctggccaa tatgctgaaa ccc                          43

<210> SEQ ID NO 606
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 606
atttgaggct gcagtgagct                                               20

<210> SEQ ID NO 607
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 607
cagacgtgtg ctcttccgat ctagacaaga gctggctcac ct                      42

<210> SEQ ID NO 608
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 608
cctccccagc ctttgatcag                                               20

<210> SEQ ID NO 609
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 609
cagacgtgtg ctcttccgat cttcctcgca agctgggtaa tc                      42

<210> SEQ ID NO 610
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 610
ccagcaccag ggagtttcta                                               20

<210> SEQ ID NO 611
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 611
cagacgtgtg ctcttccgat ctacagcatg tcacaaggct gt                      42

<210> SEQ ID NO 612
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 612
aggcagatgg aacttgagcc                                              20

<210> SEQ ID NO 613
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 613
cagacgtgtg ctcttccgat ctgcattcga agatccccag actt                   44

<210> SEQ ID NO 614
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 614
tccccatcgt cctccttgtc                                              20

<210> SEQ ID NO 615
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 615
cagacgtgtg ctcttccgat ctttgccggc tctccagagt a                      41

<210> SEQ ID NO 616
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 616
gttcccatgt taaatcccat tcat                                         24

<210> SEQ ID NO 617
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 617
cagacgtgtg ctcttccgat cttaccagga atggatgtcg ctaatca                47

<210> SEQ ID NO 618
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 618
accctctctc cctcccttc                                          20

<210> SEQ ID NO 619
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 619
cagacgtgtg ctcttccgat cttagttggc tatgctggca tg                42

<210> SEQ ID NO 620
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 620
ccccaaccac ttcattcttg                                         20

<210> SEQ ID NO 621
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 621
cagacgtgtg ctcttccgat ctttcaattc tctgggaat gtt                43

<210> SEQ ID NO 622
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 622
cctcccccag tctctcttct                                         20

<210> SEQ ID NO 623
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 623
cagacgtgtg ctcttccgat ctgagtcagg ccgttgctag tc                42

<210> SEQ ID NO 624
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 624
ctgcctcggt gagttttctc                                              20

<210> SEQ ID NO 625
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 625
cttcccgtta cggttttgac                                              20

<210> SEQ ID NO 626
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 626
aaaaccggat taggccatta                                              20

<210> SEQ ID NO 627
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 627
tctcgtcatg accgaaaaag                                              20

<210> SEQ ID NO 628
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 628
caacgcctac aaaagccagt                                              20

<210> SEQ ID NO 629
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 629
gtggcaaagc aaaagttcaa                                              20

<210> SEQ ID NO 630
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 630
tgagaaagcg tttgatgatg ta                                        22

<210> SEQ ID NO 631
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 631
gccagtttat cccgtcaaag                                           20

<210> SEQ ID NO 632
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 632
cttcccgtta cggttttgac                                           20

<210> SEQ ID NO 633
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 633
aaaaccggat taggccatta                                           20

<210> SEQ ID NO 634
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 634
tctcgtcatg accgaaaaag                                           20

<210> SEQ ID NO 635
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 635
caacgcctac aaaagccagt                                           20

<210> SEQ ID NO 636
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 636
ttgactttgc cttggagagc                                           20

<210> SEQ ID NO 637
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 637
tttttcttac agtgtcttgg cata                                          24

<210> SEQ ID NO 638
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 638
cgtgaccctc agcgaggag                                                19

<210> SEQ ID NO 639
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 639
tttgcagtga tttgaagacc a                                             21

<210> SEQ ID NO 640
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 640
ggcattcctt cttctggtca                                               20

<210> SEQ ID NO 641
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 641
ctgggctata tacagtcctc aaa                                           23

<210> SEQ ID NO 642
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 642
ggggtgatta tgaccagttg a                                             21

<210> SEQ ID NO 643
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 643
tgcatgatca aatgcaacct                                                   20

<210> SEQ ID NO 644
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 644
tcttccgaaa aatcctcttc c                                                 21

<210> SEQ ID NO 645
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 645
ctggggtccc agtcctatg                                                    19

<210> SEQ ID NO 646
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 646
tgtactggga aggcaatttc a                                                 21

<210> SEQ ID NO 647
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 647
gagccgctgg ggttactc                                                     18

<210> SEQ ID NO 648
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 648
cagttagttg ctgcacatgg a                                                 21

```
<210> SEQ ID NO 649
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 649
ttgcatttct tttggggaag                                              20

<210> SEQ ID NO 650
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 650
gtcatgcatg cagatggaag                                              20

<210> SEQ ID NO 651
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 651
gctgcagtga gctgtgatgt                                              20

<210> SEQ ID NO 652
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 652
gttcctctcc gagctcacc                                               19

<210> SEQ ID NO 653
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 653
tccgaaagtt tccaattcca                                              20

<210> SEQ ID NO 654
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 654
ttgtttggga gactctgcat t                                            21

<210> SEQ ID NO 655
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 655
gaccccactt ggactggtag                                              20

<210> SEQ ID NO 656
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 656
gtgatcttga ttgcggcttt                                              20

<210> SEQ ID NO 657
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 657
gggggaaaaa ctacaagtgc                                              20

<210> SEQ ID NO 658
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 658
tgattccttt tcctgcctgt                                              20

<210> SEQ ID NO 659
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 659
aaaaacctcc aggccagact                                              20

<210> SEQ ID NO 660
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 660
aatcaaaata acgccccaga                                              20

<210> SEQ ID NO 661
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 661
ttgctaaaaa ttggcagagc                                              20

<210> SEQ ID NO 662
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 662
ttgttaagtg ccaaacaaag ga                                           22

<210> SEQ ID NO 663
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 663
aagctgggaa gagcaaagc                                               19

<210> SEQ ID NO 664
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 664
aggacagagg gtggtcgtc                                               19

<210> SEQ ID NO 665
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 665
tgagtgctgt ctccatgttt g                                            21

<210> SEQ ID NO 666
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 666
cctcacagct gttgctgtta tt                                           22

<210> SEQ ID NO 667
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 667
aaaacaccca gctaggacca                                                   20

<210> SEQ ID NO 668
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 668
aactgaggca cgagcaaagt                                                   20

<210> SEQ ID NO 669
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 669
gctttatggg tggatgctga                                                   20

<210> SEQ ID NO 670
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 670
ataatatcgc cagcctcagc                                                   20

<210> SEQ ID NO 671
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 671
tccagagtgt gctggatgac                                                   20

<210> SEQ ID NO 672
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 672
tgcaagccat ttatgggaat                                                   20

<210> SEQ ID NO 673
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 673
tggaatgagg tctcttagta cagtt                                           25

<210> SEQ ID NO 674
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 674
tcccagaaac acctgtaagg a                                               21

<210> SEQ ID NO 675
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 675
tgtctaggca ggacctgtgg                                                 20

<210> SEQ ID NO 676
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 676
agtgatgctg cgactcacac                                                 20

<210> SEQ ID NO 677
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 677
ggctcagaaa gtctctcttt cc                                              22

<210> SEQ ID NO 678
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 678
ctcccaaact caggctttca                                                 20

<210> SEQ ID NO 679
<211> LENGTH: 19
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 679
aaagcgctgg gattacagg                                                19

<210> SEQ ID NO 680
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 680
cgtccagttg cttggagaag                                               20

<210> SEQ ID NO 681
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 681
aataaccttg gctgccgtct                                               20

<210> SEQ ID NO 682
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 682
gggaattctc agtgccaact                                               20

<210> SEQ ID NO 683
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 683
gcatcctggg ctacactgag                                               20

<210> SEQ ID NO 684
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 684
tgctgggaac aatgactata aga                                           23

<210> SEQ ID NO 685
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 685
gcctaaaaca ctttgggtgg t                                              21

<210> SEQ ID NO 686
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 686
gggtgcccac aaaatagaga                                                20

<210> SEQ ID NO 687
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 687
gagactgggt ctcgctttgt                                                20

<210> SEQ ID NO 688
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 688
tggggaaggc tttctctagg                                                20

<210> SEQ ID NO 689
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 689
ttcaacttga gtgatctgag ctg                                            23

<210> SEQ ID NO 690
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 690
tatgggcaac cctaaggtga                                                20

<210> SEQ ID NO 691
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 691
cgctgcgaca ctacatcaac 20

<210> SEQ ID NO 692
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 692
tggagtcttg ctctgtcacc 20

<210> SEQ ID NO 693
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 693
acgaggtgaa ggagcaggt 19

<210> SEQ ID NO 694
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 694
cgatgccttt gggtagagag 20

<210> SEQ ID NO 695
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 695
actgatcgtc caaggactgg 20

<210> SEQ ID NO 696
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 696
aaaaagaaat ctggtcttgt tagaaaa 27

<210> SEQ ID NO 697
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 697
ttgaaaagtg gtaaggaatt gtga                                          24

<210> SEQ ID NO 698
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 698
caccaagaat tgattttgta gcc                                           23

<210> SEQ ID NO 699
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 699
aaaaatgggg gaaaatggtg                                               20

<210> SEQ ID NO 700
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 700
catggttgaa accccatctc                                               20

<210> SEQ ID NO 701
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 701
ttcaaagcct ccacgactct                                               20

<210> SEQ ID NO 702
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 702
gctggaacag gtgcctaaag                                               20

<210> SEQ ID NO 703
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 703
```
ccctaaggga acgacactca 20

<210> SEQ ID NO 704
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 704
acctgctaca agccctgga 19

<210> SEQ ID NO 705
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 705
ggatccctaa gaccgtggag 20

<210> SEQ ID NO 706
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 706
ccacctcaga ggctccaa 18

<210> SEQ ID NO 707
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 707
tgctgtattt taaaagaatg attatga 27

<210> SEQ ID NO 708
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 708
gtagctggga cgctggttta 20

<210> SEQ ID NO 709
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 709 attccttcc ccctacaaga        20

<210> SEQ ID NO 710
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 710
cctgagtgca acgacatcac        20

<210> SEQ ID NO 711
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 711
gggggaacca gcagaaat        18

<210> SEQ ID NO 712
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 712
gacctagggc gagggttc        18

<210> SEQ ID NO 713
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 713
aattcctgaa gccagatcca        20

<210> SEQ ID NO 714
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 714
aaaatgttta ttgttgtagc tctgg        25

<210> SEQ ID NO 715
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 715
tttcaagagc tcaacagatg aca        23

```
<210> SEQ ID NO 716
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 716
gactgcccgg acaagtttt                                                  19

<210> SEQ ID NO 717
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 717
gagaaggtgc cccaaaatg                                                  19

<210> SEQ ID NO 718
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 718
agccactgga ctgacgactt                                                 20

<210> SEQ ID NO 719
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 719
ggaggactag tgagggaggt g                                               21

<210> SEQ ID NO 720
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 720
ggcaagtgat gtggcaatta                                                 20

<210> SEQ ID NO 721
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 721
gttggagcac ctggaaagaa                                                 20
```

<210> SEQ ID NO 722
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 722
atgcctgcct caccttcat                                                   19

<210> SEQ ID NO 723
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 723
acaggggcac tgtcaacac                                                   19

<210> SEQ ID NO 724
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 724
aaaaatcatg tgttgcagct tt                                               22

<210> SEQ ID NO 725
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 725
tgctttcaca acatttgcag                                                  20

<210> SEQ ID NO 726
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 726
aatgtttcct tgtgcctgct                                                  20

<210> SEQ ID NO 727
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 727
atatcctgag ccatcggtga                                                  20

```
<210> SEQ ID NO 728
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 728
ttttggtacc ccaggctatg                                                20

<210> SEQ ID NO 729
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 729
accccgtggc attacataac                                                20

<210> SEQ ID NO 730
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 730
cttccaggag gcacagaaat                                                20

<210> SEQ ID NO 731
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 731
ctaacctggg cgacagagtg                                                20

<210> SEQ ID NO 732
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 732
atatttggac ataacagact tggaa                                          25

<210> SEQ ID NO 733
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 733
tgctgacttt taaaataagt gattcg                                         26

<210> SEQ ID NO 734
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 734
gcggcagagt agccctaac                                              19

<210> SEQ ID NO 735
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 735
tgggctattt ctattgctgc t                                           21

<210> SEQ ID NO 736
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 736
aatggaaagt ggctatgcag                                             20

<210> SEQ ID NO 737
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 737
ggttgtagtc actttagatg gaaaa                                       25

<210> SEQ ID NO 738
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 738
tttgtttgac tttgagcacc a                                           21

<210> SEQ ID NO 739
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 739
aatgtttctc tgtaaatatt gccatt                                      26

<210> SEQ ID NO 740
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 740
cacccccata tggtcatagc                                                 20

<210> SEQ ID NO 741
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 741
agcaccaggt gatcctcag                                                  19

<210> SEQ ID NO 742
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 742
tgttttgctg taacattgaa gga                                             23

<210> SEQ ID NO 743
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 743
taatgccaca gtggggatg                                                  19

<210> SEQ ID NO 744
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 744
gggcctaaac tttggcagtt                                                 20

<210> SEQ ID NO 745
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 745
ttttaccttc catggctctt tt                                              22

<210> SEQ ID NO 746
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 746
gccttactct gattcagcct ctt                                              23

<210> SEQ ID NO 747
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 747
cgtaacaaaa ttcattgtgg tgt                                              23

<210> SEQ ID NO 748
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 748
agaaccgctc ctacagcaag                                                  20

<210> SEQ ID NO 749
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 749
gtgctttctt ttgtgggaca                                                  20

<210> SEQ ID NO 750
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 750
gggagttctg catttgatcc                                                  20

<210> SEQ ID NO 751
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 751
tgggtcagag gacttcaagg                                                  20

<210> SEQ ID NO 752
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 752
agggttctga tcacattgca c                                              21

<210> SEQ ID NO 753
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 753
ctgcaggact ggtcgttttt                                                20

<210> SEQ ID NO 754
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 754
agggcagggt agagagggta                                                20

<210> SEQ ID NO 755
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 755
ttcttccatg cggagaaatc                                                20

<210> SEQ ID NO 756
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 756
catggctgaa ggaaaccagt                                                20

<210> SEQ ID NO 757
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 757
ttgccagcta tcacatgtcc                                                20

<210> SEQ ID NO 758
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 758
tcttttcctg taccaggttt ttc                                              23

<210> SEQ ID NO 759
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 759
tgactgggaa catcttgctg                                                  20

<210> SEQ ID NO 760
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 760
tggcacctgt acccttcttc                                                  20

<210> SEQ ID NO 761
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 761
ttcaatctct tgcactcaaa gc                                               22

<210> SEQ ID NO 762
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 762
tggagtcact gccaagtcat                                                  20

<210> SEQ ID NO 763
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 763
tttgcatgat gtttgtgtgc                                                  20

<210> SEQ ID NO 764
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 764
gcacccactc tgctttgact					20

<210> SEQ ID NO 765
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 765
accatgtagc cagctttcaa					20

<210> SEQ ID NO 766
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 766
gcaactgggc atgagtacct					20

<210> SEQ ID NO 767
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 767
ccacaccccc ttcctactc					19

<210> SEQ ID NO 768
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 768
agtctgctta tttccagctg ttt				23

<210> SEQ ID NO 769
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 769
tcctgttcaa aagtcaggat ga				22

<210> SEQ ID NO 770
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 770
aaatcacaaa tccctgcaa                                              20

<210> SEQ ID NO 771
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 771
ctgaacattc cagagcgtgt                                             20

<210> SEQ ID NO 772
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 772
cagtgggacc accctcact                                              19

<210> SEQ ID NO 773
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 773
tctgtagatg acctggcttg c                                           21

<210> SEQ ID NO 774
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 774
tcagaaccaa gatgccaaca                                             20

<210> SEQ ID NO 775
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 775
catgacccag cctatggttt                                             20

<210> SEQ ID NO 776
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 776
acctcctgca agaagagctg                                              20

<210> SEQ ID NO 777
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 777
ttgggaggct ttgcttattt t                                            21

<210> SEQ ID NO 778
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 778
ctgggaaaca ctccttgcat                                              20

<210> SEQ ID NO 779
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 779
caacgaattt ggctacagca                                              20

<210> SEQ ID NO 780
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 780
caaaggtcat aatgctttca gc                                           22

<210> SEQ ID NO 781
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 781
tttgacgtat cttttcatcc aa                                           22

<210> SEQ ID NO 782
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 782
```

```
tgttgttggt ttccaaaaag g                                                 21

<210> SEQ ID NO 783
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 783
gccaactttt gcatgttttg                                                   20

<210> SEQ ID NO 784
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 784
cccaagctga tctggtggt                                                    19

<210> SEQ ID NO 785
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 785
tgctgtgaaa gaaacaaaca ttg                                               23

<210> SEQ ID NO 786
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 786
gcacgtggat cctgagaact                                                   20

<210> SEQ ID NO 787
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 787
ccagcccaga gacactgatt                                                   20

<210> SEQ ID NO 788
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 788
```

```
cacgcccagc taattttttgt                                                20
```

<210> SEQ ID NO 789
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 789

```
cctggtggaa gacatgcag                                                  19
```

<210> SEQ ID NO 790
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 790

```
tcacacctgt aatcccagca                                                 20
```

<210> SEQ ID NO 791
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 791

```
cagagctccg cctcattagt                                                 20
```

<210> SEQ ID NO 792
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 792

```
tccatttcat cattgtttct gc                                              22
```

<210> SEQ ID NO 793
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 793

```
tggtgtttgt aggtcactga aca                                             23
```

<210> SEQ ID NO 794
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 794

```
aacatggtcc attcacctttt atg                                            23
```

<210> SEQ ID NO 795
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 795
agagcgagac tccgtctcaa                                               20

<210> SEQ ID NO 796
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 796
agtgagctga gattgcacca                                               20

<210> SEQ ID NO 797
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 797
agacggcctt gagtctcagt                                               20

<210> SEQ ID NO 798
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 798
gggaatccct tcctggtc                                                 18

<210> SEQ ID NO 799
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 799
cttcctgcct ttctcagcag                                               20

<210> SEQ ID NO 800
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 800
tgcaggtgat caagaagacg                                               20

<210> SEQ ID NO 801
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 801
ggttttgagc atgggttcat                                               20

<210> SEQ ID NO 802
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 802
ccagcccact cctatggat                                                19

<210> SEQ ID NO 803
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 803
aaactgggac aggggagaac                                               20

<210> SEQ ID NO 804
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 804
tttgggtagg tgacctgctt                                               20

<210> SEQ ID NO 805
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 805
tcactgaacg aatgagtgct g                                             21

<210> SEQ ID NO 806
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 806
acgatgtgca ggaccagtg                                                19

```
<210> SEQ ID NO 807
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 807
aatttgcact gaaacgtgga                                                    20

<210> SEQ ID NO 808
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 808
ctgttgtggc ccattaaaga a                                                  21

<210> SEQ ID NO 809
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 809
ttccctccag cagtggtatt                                                    20

<210> SEQ ID NO 810
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 810
caccaggaag gaagctgttg                                                    20

<210> SEQ ID NO 811
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 811
tttccttgtg ttcttccaag c                                                  21

<210> SEQ ID NO 812
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 812
tcgcaggcat tactaatctg aa                                                 22

<210> SEQ ID NO 813
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 813
ctctggctgg ctaactggaa                                              20

<210> SEQ ID NO 814
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 814
agagccccac cctcagat                                                18

<210> SEQ ID NO 815
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 815
tgtgcagagt tctccatctg a                                            21

<210> SEQ ID NO 816
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 816
tgcctgttac aaatatcaag gaa                                          23

<210> SEQ ID NO 817
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 817
tttcccttct tgcatccttc                                              20

<210> SEQ ID NO 818
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 818
tgtgaccact ggcattcatt                                              20

<210> SEQ ID NO 819
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 819
ctcacacaca cggcctgtta                                              20

<210> SEQ ID NO 820
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 820
cacttgacca atactgaccc tct                                          23

<210> SEQ ID NO 821
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 821
gtgtgtgccc tgtaacctga                                              20

<210> SEQ ID NO 822
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 822
ccacttccca cttgcagtct                                              20

<210> SEQ ID NO 823
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 823
tgtgtgtgtg tgtgtgtgtg t                                            21

<210> SEQ ID NO 824
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 824
tctcccatgc attcaaactg                                              20

<210> SEQ ID NO 825
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 825
tctaagtgtt cctcactgac agg                                             23

<210> SEQ ID NO 826
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 826
tactctgcag cgaagtgcaa                                                 20

<210> SEQ ID NO 827
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 827
ccaagatcac accattgcac                                                 20

<210> SEQ ID NO 828
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 828
atatttggac ataacagact tggaa                                           25

<210> SEQ ID NO 829
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 829
tttttttttt tttttttv                                                   18

<210> SEQ ID NO 830
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 830
aaaaaaaaaa                                                            10

<210> SEQ ID NO 831
<211> LENGTH: 31
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 831
aaaaaaaaaa aaaaaaaaaa aaaaaaaaaa a                                      31

<210> SEQ ID NO 832
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 832
cgactacgac gactacg                                                      17

<210> SEQ ID NO 833
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 833
atgatacgac tagcggat                                                     18

<210> SEQ ID NO 834
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 834
cgactacgac gactacgcga catcgactac gagtcggt                               38

<210> SEQ ID NO 835
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 835
aatgctatga tacgactagc ggat                                              24

<210> SEQ ID NO 836
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 836
cgactacgac gactacgcga catcgactac gagtcggtaa tgctatgata cgactagcgg       60
at                                                                      62

<210> SEQ ID NO 837
<211> LENGTH: 12
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 837
agcattaccg ac     12

<210> SEQ ID NO 838
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 838
cgactacgac gactacgcga catcgactac gagtcggt     38

<210> SEQ ID NO 839
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 839
atccgctagt cgtatcatac cgac     24

<210> SEQ ID NO 840
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 840
cgactacgac gactacgcga catcgactac gagtcggtat gatacgacta gcggat     56

<210> SEQ ID NO 841
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 841
cgactacgac gactacgcga catcgactac gagtcggt     38

<210> SEQ ID NO 842
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 842
auccgcuagu cguaucauac cgac     24

<210> SEQ ID NO 843
<211> LENGTH: 56
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 843
cgactacgac gactacgcga catcgactac gagtcggtat gatacgacta gcggat          56
```

MASSIVELY PARALLEL SINGLE CELL ANALYSIS

CROSS REFERENCE

This application is a Continuation application which claims the benefit of U.S. application Ser. No. 14/472,363, filed Aug. 28, 2014, which claims the benefit of U.S. Provisional Application No. 62/012,237, filed on Jun. 13, 2014, U.S. Provisional Application No. 61/952,036, filed on Mar. 12, 2014, and U.S. Provisional Application No. 61/871,232, filed on Aug. 28, 2013, each of which applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 2, 2015, is named 41977_710.301_SL.txt and is 192,992 bytes in size.

BACKGROUND

Multicellular masses, such as tissues and tumors, may comprise a heterogeneous cellular milieu. These complex cellular environments may often display multiple phenotypes, which may be indicative of multiple genotypes. Distilling multicellular complexity down to single cell variability is an important facet of understanding multicellular heterogeneity. This understanding may be important in the development of therapeutic regimens to combat diseases with multiple resistance genotypes.

SUMMARY OF THE INVENTION

One aspect provided is a method, comprising obtaining a sample comprising a plurality of cells; labeling at least a portion of two or more polynucleotide molecules, complements thereof, or reaction products therefrom, from a first cell of the plurality and a second cell of the plurality with a first same cell label specific to the first cell and a second same cell label specific to the second cell; and a molecular label specific to each of the two or more polynucleotide molecules, complements thereof, or reaction products therefrom, wherein each molecular label of the two or more polynucleotide molecules, complements thereof, or reaction products therefrom, from the first cell are unique with respect to each other, and wherein each molecular label of the two or more polynucleotide molecules, complements thereof, or reaction products therefrom, from the second cell are unique with respect to each other. In some embodiments, the method further comprises sequencing the at least a portion of two or more polynucleotide molecules, complements thereof, or reaction products therefrom. In some embodiments, the method further comprises analyzing sequence data from the sequencing to identify a number of individual molecules of the polynucleotides in a specific one of the cells. In some embodiments, the cells are cancer cells. In some embodiments, the cells are infected with viral polynucleotides. In some embodiments, the cells are bacteria or fungi. In some embodiments, the sequencing comprises sequencing with read lengths of at least 100 bases. In some embodiments, the sequencing comprises sequencing with read lengths of at least 500 bases. In some embodiments, the polynucleotide molecules are mRNAs or micro RNAs, and the complements thereof and reaction products thereof are complements of and reaction products therefrom the mRNAs or micro RNAs. In some embodiments, the molecular labels are on a bead. In some embodiments, the label specific to an individual cell is on a bead. In some embodiments, the label specific to an individual cell and the molecular labels are on beads. In some embodiments, the method is performed at least in part in an emulsion. In some embodiments, the method is performed at least in part in a well or microwell of an array. In some embodiments, the presence of a polynucleotide that is associated with a disease or condition is detected. In some embodiments, the disease or condition is a cancer. In some embodiments, at least a portion of a microRNA, complement thereof, or reaction product therefrom is detected. In some embodiments, the disease or condition is a viral infection. In some embodiments, the viral infection is from an enveloped virus. In some embodiments, the viral infection is from a non-enveloped virus. In some embodiments, the virus contains viral DNA that is double stranded. In some embodiments, the virus contains viral DNA that is single stranded. In some embodiments, the virus is selected from the group consisting of a pox virus, a herpes virus, a vericella zoster virus, a cytomegalovirus, an Epstein-Barr virus, a hepadnavirus, a papovavirus, polyomavirus, and any combination thereof. In some embodiments, the first cell is from a person not having a disease or condition and the second cell is from a person having the disease or condition. In some embodiments, the persons are different. In some embodiments, the persons are the same but cells are taken at different time points. In some embodiments, the first cell is from a person having the disease or condition and the second cell is from the same person. In some embodiments, the cells in the sample comprise cells from a tissue or organ. In some embodiments, the cells in the sample comprise cells from a thymus, white blood cells, red blood cells, liver cells, spleen cells, lung cells, heart cells, brain cells, skin cells, pancreas cells, stomach cells, cells from the oral cavity, cells from the nasal cavity, colon cells, small intestine cells, kidney cells, cells from a gland, brain cells, neural cells, glial cells, eye cells, reproductive organ cells, bladder cells, gamete cells, human cells, fetal cells, amniotic cells, or any combination thereof.

One aspect provided is a solid support comprising a plurality of oligonucleotides each comprising a cellular label and a molecular label, wherein each cellular label of the plurality of oligonucleotides are the same, and each molecular label of the plurality of oligonucleotides are different; and wherein the solid support is a bead, the cellular label is specific to the solid support, the solid support, when placed at the center of a three dimensional Cartesian coordinate system, has oligonucleotides extending into at least seven of eight octants, or any combination thereof. In some embodiments, the plurality of oligonucleotides further comprises at least one of a sample label; a universal label; and a target nucleic acid binding region. In some embodiments, the solid support comprises the target nucleic acid binding region, wherein the target nucleic acid binding region comprises a sequence selected from the group consisting of a gene-specific sequence, an oligo-dT sequence, a random multimer, and any combination thereof. In some embodiments, the solid support further comprises a target nucleic acid or complement thereof. In some embodiments, the solid support comprises a plurality of target nucleic acids or complements thereof comprising from about 0.01% to about 100% of transcripts of a transcriptome of an organism or complements thereof, or from about 0.01% to about 100% of genes of a genome of an organism or complements thereof. In some embodiments, the cellular labels of the plurality of oligonucleotides comprise a first random sequence connected to a second random sequence by a first label linking sequence; and the molecular labels of the plurality of oligonucleotides comprise random sequences. In some embodiments, the solid support is selected from the group consisting of a polydimethylsiloxane (PDMS) solid support, a polystyrene solid support, a glass solid support, a polypropylene solid support, an agarose solid support, a gelatin solid support, a magnetic solid support, a pluronic solid support, and any combination thereof. In some embodiments, the plurality of oligonucleotides comprise a linker comprising a linker functional group, and the solid support comprises a solid support functional group; wherein the solid support functional group and linker functional group connect to each other. In some embodiments, the linker functional group and the solid support functional group are individually selected from the group consisting of C6, biotin, streptavidin, primary amine(s), aldehyde(s), ketone(s), and any combination thereof. In some embodiments, molecular labels of the plurality of oligonucleotides comprise at least 15 nucleotides.

One aspect provided is a kit comprising any of the solid supports described herein, and instructions for use. In some embodiments, the kit further comprises a well. In some embodiments, the well is comprised in an array. In some embodiments, the well is a microwell. In some embodiments, the kit further comprises a buffer. In some embodiments, the kit is contained in a package. In some embodiments, the package is a box. In some embodiments, the package or box has a volume of 2 cubic feet or less. In some embodiments, the package or box has a volume of 1 cubic foot or less.

One aspect provided is an emulsion comprising any of the solid supports described herein.

One aspect provided is a composition comprising a well and any of the solid supports described herein.

One aspect provided is a composition comprising a cell and any of the solid supports described herein.

In some embodiments, the emulsion or composition further comprises a cell. In some embodiments, the cell is a single cell. In some embodiments, the well is a microwell. In some embodiments, the microwell has a volume ranging from about 1,000 $\mu m^3$ to about 120,000 $\mu m^3$.

One aspect provided is a method, comprising contacting a sample with any solid support disclosed herein, hybridizing a target nucleic acid from the sample to an oligonucleotide of the plurality of oligonucleotides. In some embodiments, the method further comprises amplifying the target nucleic acid or complement thereof. In some embodiments, the method further comprises sequencing the target nucleic acid or complement thereof, wherein the sequencing comprises sequencing the molecular label of the oligonucleotide to which the target nucleic acid or complement thereof is bound. In some embodiments, the method further comprises determining an amount of the target nucleic acid or complement thereof, wherein the determining comprises quantifying levels of the target nucleic acid or complement thereof; counting a number of sequences comprising the same molecular label; or a combination thereof. In some embodiments, the method does not comprise aligning any same molecular labels or any same cellular labels. In some embodiments, the amplifying comprises reverse transcribing the target nucleic acid. In some embodiments, the amplifying employs a method selected from the group consisting of: PCR, nested PCR, quantitative PCR, real time PCR, digital PCR, and any combination thereof. In some embodiments, the amplifying is performed directly on the solid support; on a template transcribed from the solid support; or a combination thereof. In some embodiments, the sample comprises a cell. In some embodiments, the cell is a single cell. In some embodiments, the contacting occurs in a well. In some embodiments, the well is a microwell and is contained in an array of microwells.

One aspect provided is a device, comprising a plurality of microwells, wherein each microwell of the plurality of microwells has a volume ranging from about 1,000 $\mu m^3$ to about 120,000 $\mu m^3$. In some embodiments, each microwell of the plurality of microwells has a volume of about 20,000 $\mu m^3$. In some embodiments, the plurality of microwells comprises from about 96 to about 200,000 microwells. In some embodiments, the microwells are comprised in a layer of a material. In some embodiments, at least about 10% of the microwells further comprise a cell. In some embodiments, the device further comprises any of the solid supports described herein.

One aspect provided is an apparatus comprising any of the devices described herein, and a liquid handler. In some embodiments, the liquid handler delivers liquid to the plurality of microwells in about one second. In some embodiments, the liquid handler delivers liquid to the plurality of microwells from a single input port. In some embodiments, the apparatus further comprises a magnet. In some embodiments, the apparatus further comprises at least one of: an inlet port, an outlet port, a pump, a valve, a vent, a reservoir, a sample collection chamber, a temperature control apparatus, or any combination thereof. In some embodiments, the apparatus comprises the sample collection chamber, wherein the sample collection chamber is removable from the apparatus. In some embodiments, the apparatus further comprises an optical imager. In some embodiments, the optical imager produces an output signal which is used to control the liquid handler. In some embodiments, the apparatus further comprises a thermal cycling mechanism configured to perform a polymerase chain reaction (PCR) amplification of oligonucleotides.

One aspect provided is a method of producing a clinical diagnostic test result, comprising producing the clinical diagnostic test result with any device or apparatus described herein; any solid support described herein; any method described herein; or any combination thereof. In some embodiments, the clinical diagnostic test result is transmitted via a communication medium.

One aspect provided is a method of making any of the solid supports described herein, comprising attaching to a solid support: a first polynucleotide comprising a first portion of the cellular label, and a first linker; and contacting a second polynucleotide comprising a second portion of the cellular label, a sequence complementary to the first liker, and the molecular label. In some embodiments, the third polynucleotide further comprises a target nucleic acid binding region.

In some embodiments, an emulsion, microwell, or well contains only one cell. In some embodiments, from 1 to 2,000,000 emulsions, microwells, or wells each contain only one cell. In some embodiments, the method comprises distributing at most one cell into each emulsion, microwell, or well. In some embodiments, a single solid support and a single cell are distributed to an emulsion, microwell, or well. In some embodiments, from 1 to 2,000,000 emulsions, microwells, or wells each have distributed thereto one cell and one solid support. In some embodiments, the method comprises distributing at most one solid support per emulsion, microwell, or well. In some embodiments, the method comprises distributing one solid support and one cell to each of from 1 to 2,000,000 microwells, emulsions, or wells. In some embodiments, cell distribution is random or non-random. In some embodiments, cell distribution is stochastic. In some embodiments, a cell is distributed by a cell sorter. In some embodiments, a cell is distributed by contacting one or more wells, microwells, or emulsions with a dilute solution of cells diluted so that at most one cell is distributed to the one or more wells, microwells, or emulsions.

In some embodiments, the target specific regions, target specific regions of the plurality of oligonucleotides, or the target specific region of the two or more polynucleotide molecules, comprise sequences complementary to two or more targets of a target panel. In some embodiments, the two or more targets of the target panel are biomarkers. In some embodiments, the biomarkers are biomarkers for a disease or condition. In some embodiments, the disease or condition is a cancer, an infection, a viral infection, an inflammatory disease, a neurodegenerative disease, a fungal disease, a bacterial infection, or any combination thereof. In some embodiments, the panel comprises from: 2-50,000, 2-40,000, 2-30,000, 2-20,000, 2-10,000, 2-9000, 2-8,000, 2-7,000, 2-6,000, 2-5,000, 2-1,000, 2-800, 2-700, 2-600, 2-500, 2-400, 2-300, 2-200, 2-100, 2-75, 2-50, 2-40, 2-30, 2-20, 2-10, or 2-5 biomarkers.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 discloses "dT (17)V" as SEQ ID NO: 829.

FIG. 3 discloses "dT(17)V" as SEQ ID NO: 829.

FIG. 6A shows the distribution of K562 cells (large cell size). FIG. 6B shows the distribution of Ramos cells (small cell size). FIG. 6C shows the distribution of Ramos cells and oligonucleotide coupled beads onto microwell arrays, with solid arrows pointing to the Ramos cells and dashed arrows pointing to the oligonucleotide coupled beads.

FIG. 8A-B show images of a microarray well with cells and oligonucleotide beads distributed into wells of a microarray well and with larger sephadex beads used to seal the wells. Dotted arrows point to the cells, dashed arrows point to the oligonucleotide coupled beads and the solid arrows point to the sephadex beads. FIG. 8C depicts a schematic of the cell and oligonucleotide bead (e.g., oligobead) deposited within a well with a sephadex bead used to seal the well.

FIG. 20A shows the analysis of CD4+ T cell specific markers. FIG. 20B shows the cell cluster depicted in FIG. 16.

FIGS. 21A-D show the analysis of Natural Killer (NK) cell specific markers. FIG. 21E shows the cell cluster depicted in FIG. 16.

FIG. 30 discloses "dT(17)V" as SEQ ID NO: 829 and "AAAAAAAAAA" as SEQ ID NO: 830.

FIGS. 33A-F shows the principal component analysis (PCA) for monocyte associated genes. FIG. 33A shows the PCA for CD16. FIG. 33B shows the PCA for CCRvarA. FIG. 33C shows the PCA for CD14. FIG. 33D shows the PCA for S100A12. FIG. 33E shows the PCA for CD209. FIG. 33F shows the PCA for IFNGR1.

FIGS. 34A-B shows the principal component analysis (PCA) for pan-T cell markers (CD3). FIG. 34A shows the PCA for CD3D and FIG. 34B shows the PCA for CD3E.

FIG. 35A shows the PCA for CD8A. FIG. 35B shows the PCA for EOMES. FIG. 35C shows the PCA for CD8B. FIG. 35D shows the PCA for PRF1. FIG. 35E shows the PCA for RUNX3.

FIG. 36A shows the PCA for CD4. FIG. 36B shows the PCA for CCR7. FIG. 36C shows the PCA for CD62L.

FIGS. 37A-F shows the principal component analysis (PCA) for B cell associated genes. FIG. 37A shows the PCA for CD20. FIG. 37B shows the PCA for IGHD. FIG. 37C shows the PCA for PAX5. FIG. 37D shows the PCA for TCL1A. FIG. 37E shows the PCA for IGHM. FIG. 37F shows the PCA for CD24.

FIGS. 38A-C shows the principal component analysis (PCA) for Natural Killer cell associated genes. FIG. 38A shows the PCA for KIR2DS5. FIG. 38B shows the PCA for CD16. FIG. 38C shows the PCA for CD62L.

FIG. 43A. Experimental procedure for CytoSeq. FIG. 43B. Structure of oligonucleotides attached to beads.

FIGS. 44 AA-C illustrate dissecting sub-populations of CD3+ T cells. FIGS. 44BA-BL. PCA of Donor 1 anti-CD3/anti-CD28 stimulated sample showing enrichment of expression of indicated genes to one of the two main branches representing helper and cytotoxic T cells. These genes are present at low amounts in the unstimulated sample. First two rows show genes that are known to be associated with activated T cells and include (from left to right) in the first row IRF4, CD69 and MYC and in the second row GAPDH, TNF and IFNG. The third row shows genes that are known to be associated with activated helper T cells and include (from left to right) IL2, LTA and CD40LG. The fourth row shows genes that are known to be associated with activated cytotoxic T cells and include (from left to right) CCL4, CCL3 and GZMB.

FIGS. 45AA-CL illustrate PCA plots of T cell samples that have undergone stimulation with anti-CD28/anti-CD3 beads in the two donors, and the corresponding unstimulated samples, with emphasis on the expression of genes that clearly show preferential expression in either helper or cytotoxic subsets in the unstimulated samples. The color of each data point (single cell) indicates log (number of unique transcript molecule) per cell for the indicated gene. For each pair of stimulated and unstimulated graphs in each donor, the color range is adjusted to be the same. FIGS. 45AA-AP. Genes that are known to be associated with both helper and cytotoxic T cells. FIGS. 45BA-BZB. Genes that are known to be associated with cytotoxic T cells. FIGS. 45CA-CL. Genes that are known to be associated with helper T cells.

FIG. 47 Top: Heatmap showing correlation between each pair of cells. Cells that are highly correlated are grouped together. FIG. 47 Bottom: Heatmap showing the level of expression of each gene of each cell. Cells and genes are ordered via bidirectional hierarchical clustering.

FIG. 48 Top: Heatmap showing correlation between each pair of cells. Cells that are highly correlated are grouped together. FIG. 48 Bottom: Heatmap showing the level of expression of each gene of each cell. Cells and genes are ordered via bidirectional hierarchical clustering.

FIGS. 49A-C In donor 1, large overall fold change was observed for various cytokines in the antiCD28/antiCD3 stimulated sample, as compared to the unstimulated one. A-B: The large fold changes of these cytokines were mostly contributed by only a few single cells (dots that are enclosed with squares or circles). A number of these cytokines were contributed by the same small number of cells. C: The co-expression patterns of these cytokines coincide with the signature cytokine combination for the Th2 and Th17 subsets of helper T cells.

FIG. 50A. Clustering of CytoSeq data defines two major groups of CD8+ cells—one group expresses genes shared by central memory/naïve cells, and the other group expresses genes shared by effector memory/effector cells. Shown here is data of Donor 2's unstimulated sample. FIG. 50A Top: Heatmap showing correlation between each pair of cells. FIG. 50A Bottom: Heatmap showing the level of expression of each gene in each cell. Cells and genes are ordered via bidirectional hierarchical clustering. FIG. 50B. Identification of rare antigen specific T cell by expression of gamma interferon (IFNG) in CD8+ T cells from two donors after stimulation with CMV peptide pool. FIG. 50B Top: data for donor 1. FIG. 50B bottom: data for donor 2. Each cell is plotted on the 2D principal component space. Cells expressing IFNG (circled) are usually among those with the most total detected transcripts in the panel (indicated by the color). In donor 2, the top expressing cell (square) does not produce IFNG but expresses cytokines IL6 and IL1B. Number next to each circle indicates the rank in descending order the number of total unique transcript molecules detected for that cell.

FIG. 51 Top: Heatmap showing correlation between each pair of cells. FIG. 51 Bottom: Heatmap showing the level of expression of each gene in each cell. Cells and genes are ordered via bidirectional hierarchical clustering.

FIGS. 52 AA-FX illustrate data plotted in principal component space. Color indicates log(number of unique transcript molecule detected) for the particular gene. FIGS. 52AA-AI. Genes that appear to be expressed by larger proportion of cells upon stimulation by CMV peptide pool. FIGS. 52BA-BI. Genes that are enriched in one branch of cells. These genes are also known to be associated with naïve and central memory CD8+ T cells. FIGS. 52CA-CZA. Genes that are enriched in the other branch of cells. These genes are known to be associated with effector and effector memory CD8+ T cells. FIGS. 52DA-DC. Granzyme K expressing cells occupy a region between the naïve/central memory and effector/effector memory cells on the PC space. FIGS. 52EA-EC. HLA-DRA expressing cells constitute a special subset.

FIG. 53 Top: data from donor 1. FIG. 53 Bottom: data from donor 2. None of the cells in Donor 1's sample expressed IFNG, while one cell in Donor 2's sample expressed IFNG yet with overall low expression across the entire gene panel (rank 1069). Color scale is adjusted to match that of the respective graph for the stimulated sample.

FIG. 54 Left: data from donor 1. FIG. 54 Right: data from donor 2. Also shown is the cell that carries most total transcripts detected in Donor 2. This particular cell does not express IFNG but expresses strongly IL6, IL1B and CCL4. The cells and genes are ordered by bidirectional hierarchical clustering based on correlation. Cell ID refers to the rank in total number of detected transcripts of the gene panel, and are indicated in the PCA plots in FIG. 50.

FIG. 56 discloses "AAAAAAAAAAAAAAAAAAAAAAAAAAAAAA" as SEQ ID NO: 831.

FIGS. 62A-62AX depict plots of the reads observed per label detected (RPLD) for various genes.

FIGS. 63A-AX depict plots of total reads (labels) versus rpld for various genes.

FIG. 65 discloses "1001" as SEQ ID NO: 832 and "1003" as SEQ ID NO: 833 and "1005" as SEQ ID NOS 832 and 833, respectively, in order of appearance.

FIG. 66A discloses "1121" as SEQ ID NO: 834, "1127" as SEQ ID NO: 835, "1128" as SEQ ID NO: 836 and "1129" as SEQ ID NO: 837. FIG. 66B discloses "1150" as SEQ ID NO: 838, "1159" as SEQ ID NO: 839 and "1158" as SEQ ID NO: 840. FIG. 66C discloses "1170" as SEQ ID NO: 841, "1176" as SEQ ID NO: 842 and "1177" as SEQ ID NO: 843.

FIG. 67 shows a schematic of a workflow for stochastically labeling nucleic acids. FIG. 67 discloses "AAAAAAAAAAAAAAAAAAAAAAAAAAAAAA" as SEQ ID NO: 831.

FIG. 68 is a schematic of a workflow for stochastically labeling nucleic acids. FIG. 68 discloses "AAAAAAAAAAAAAAAAAAAAAAAAAAAAAA" as SEQ ID NO: 831.

FIG. 69 Upper: exploded view showing the upper and lower parts of the fixture and an elastomeric gasket for forming a leak-proof seal with the microwell array substrate. FIG. 69 Lower: exploded side-view of the fixture.

FIG. 72 Left: An exploded view of the cartridge illustrating (from bottom to top) the microwell array substrate, a gasket that defines the flow cell or array chamber, a reagent and/or waste reservoir component for defining compartments to contain pre-loaded assay reagents or store spent reagents, and a cover for sealing the reagent and waste reservoirs and defining the sample inlet and outlet ports. FIG. 72 Right: An assembled view of one embodiment of the cartridge design illustrating relief for bringing an external magnet into close proximity with the microwell array.

DETAILED DESCRIPTION

Figure 1:
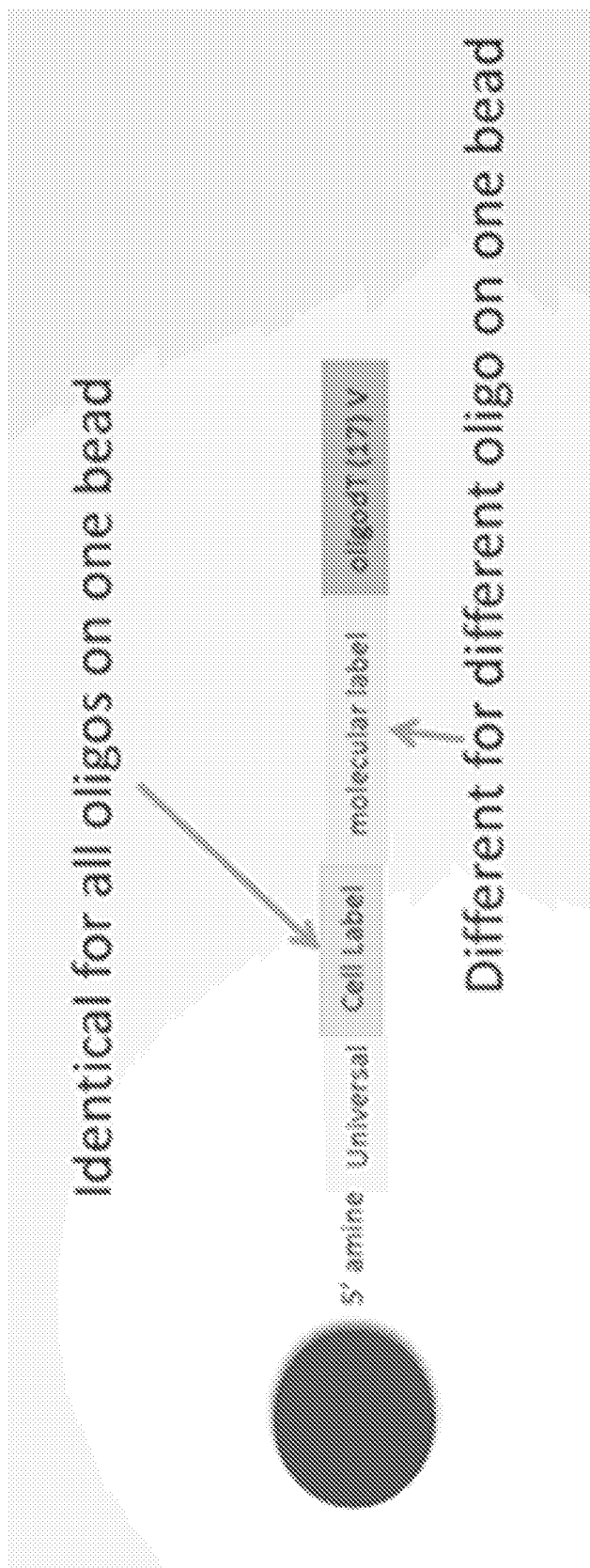
FIG. 1 depicts an exemplary solid support conjugated with an exemplary oligonucleotide.

Disclosed herein are methods, kits, and compositions for analyzing molecules in a plurality of samples. Generally, the methods, kits, and compositions comprise (a) stochastically labeling molecules in two or more samples with molecular barcodes to produce labeled molecules; and (b) detecting the labeled molecules. The molecular barcodes may comprise one or more target specific regions, label regions, sample index regions, universal PCR regions, adaptors, linkers, or a combination thereof. The labeled molecules may comprise a) a molecule region; b) a sample index region; and c) a label region. The molecule region may comprise at least a portion of the molecule from the molecular barcode was originally attached to. The molecule region may comprise a fragment of the molecule from the molecular barcode was originally attached to. The sample index region may be used to determine the source of the molecule region. The sample index region may be used to determine from which sample the molecule region originated from. The sample index region may be used to differentiate molecule regions from two or more different samples. The label region may be used to confer a unique identity to identical molecule regions originating from the same source. The label region may be used to confer a unique identity to identical molecule regions originating from the same sample.

The method for analyzing molecules in a plurality of samples may comprise: a) producing a plurality of sample-tagged nucleic acids by: i) contacting a first sample comprising a plurality of nucleic acids with a plurality of first sample tags to produce a plurality of first sample-tagged nucleic acids; and ii) contacting a second sample comprising a plurality of nucleic acids with a plurality of second sample tags to produce a plurality of second sample-tagged nucleic acids, wherein the plurality of second sample tags are different from the first sample tags; b) contacting the plurality of sample-tagged nucleic acids with a plurality of molecular identifier labels to produce a plurality of labeled nucleic acids; and c) detecting at least a portion of the labeled nucleic acids, thereby determining a count of a plurality of nucleic acids in a plurality of samples. The plurality of samples may comprise a single cell.

Alternatively, the method for analyzing molecules in a plurality of samples may comprise: a) producing a plurality of labeled nucleic acids comprising: i) contacting a first sample with a first plurality of sample tags, wherein the first plurality of sample tags comprises identical nucleic acid sequences; ii) contacting the first sample with a first plurality of molecular identifier labels may comprise different nucleic acid sequences, wherein contacting the first sample with the first plurality of sample tags or first plurality of molecular identifier labels occurs simultaneously or sequentially to produce a plurality of first-labeled nucleic acids; iii) contacting a second sample with a second plurality of sample tags, wherein the second plurality of sample tags may comprise identical nucleic acid sequences; iv) contacting the second sample with a second plurality of molecular identifier labels may comprise different nucleic acid sequences, wherein contacting the second sample with the second plurality of sample tags or second plurality of molecular identifier labels occurs simultaneously or sequentially to produce a plurality of second-labeled nucleic acids, wherein the plurality of labeled nucleic acids may comprise the plurality of first-labeled nucleic acids and the second-labeled nucleic acids; and b) determining a number of different labeled nucleic acids, thereby determining a count of a plurality of nucleic acids in a plurality of samples.

The method for analyzing molecules in a plurality of samples may comprise: a) contacting a plurality of samples may comprise two or more different nucleic acids with a plurality of sample tags and a plurality of molecular identifier labels to produce a plurality of labeled nucleic acids, wherein: i) the plurality of labeled nucleic acids may comprise two or more nucleic acids attached to two or more sample tags and two or more molecular identifier labels; ii) the sample tags attached to nucleic acids from a first sample of the plurality of samples are different from the sample tags attached to nucleic acid molecules from a second sample of the plurality of samples; and iii) two or more identical nucleic acids in the same sample are attached to two or more different molecular identifier labels; and b) detecting at least a portion of the labeled nucleic acids, thereby determining a count of two or more different nucleic acids in the plurality of samples.

Figure 56:
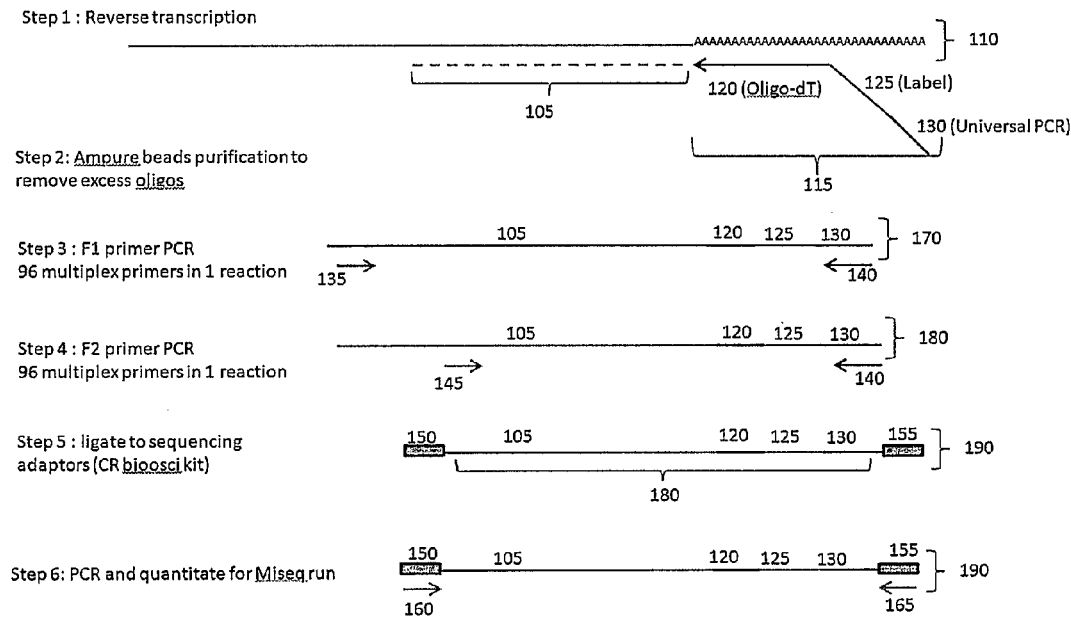
FIG. 56 depicts a schematic of a workflow for analyzing molecules from a sample.

FIG. 56 depicts an exemplary workflow for the quantification of RNA molecules in a sample. As shown in Step 1 of FIG. 56, RNA molecules (110) may be reverse transcribed to produce cDNA molecules (105) by the stochastic hybridization of a set of molecular identifier labels (115) to the polyA tail region of the RNA molecules. The molecular identifier labels (115) may comprise an oligodT region (120), label region (125), and universal PCR region (130). The set of molecular identifier labels may contain 960 different types of label regions. As shown in Step 2 of FIG. 56, the labeled cDNA molecules (170) may be purified to remove excess molecular identifier labels (115). Purification may comprise Ampure bead purification. As shown in Step 3 of FIG. 56, the labeled cDNA molecules (170) may be amplified to produce a labeled amplicon (180). Amplification may comprise multiplex PCR amplification. Amplification may comprise a multiplex PCR amplification with 96 multiplex primers in a single reaction volume. Amplification may comprise a custom primer (135) and a universal primer (140). The custom primer (135) may hybridize to a region within the cDNA (105) portion of the labeled cDNA molecule (170). The universal primer (140) may hybridize to the universal PCR region (130) of the labeled cDNA molecule (170). As shown in Step 4, the labeled amplicons (180) may be further amplified by nested PCR. The nested PCR may comprise multiplex PCR with 96 multiplex primers in a single reaction volume. Nested PCR may comprise a custom primer (145) and a universal primer (140). The custom primer (135) may hybridize to a region within the cDNA (105) portion of the labeled amplicon (180). The universal primer (140) may hybridize to the universal PCR region (130) of the labeled amplicon (180). As shown in Step 5, one or more adaptors (150, 155) may be attached to the labeled amplicon (180) to produce an adaptor-labeled amplicon (190). The one or more adaptors may be attached to the labeled amplicon (180) via ligation. As shown in Step 6, the one or more adaptors (150, 155) may be used to conduct one or more additional assays on the adaptor-labeled amplicon (190). The one or more adaptors (150, 155) may be hybridized to one or more primers (160, 165). The one or more primers (160, 165) be PCR amplification primers. The one or more primers (160, 165) may be sequencing primers. The one or more adaptors (150, 155) may be used for further amplification of the adaptor-labeled amplicons. The one or more adaptors (150, 155) may be used for sequencing the adaptor-labeled amplicon.

Figure 57:
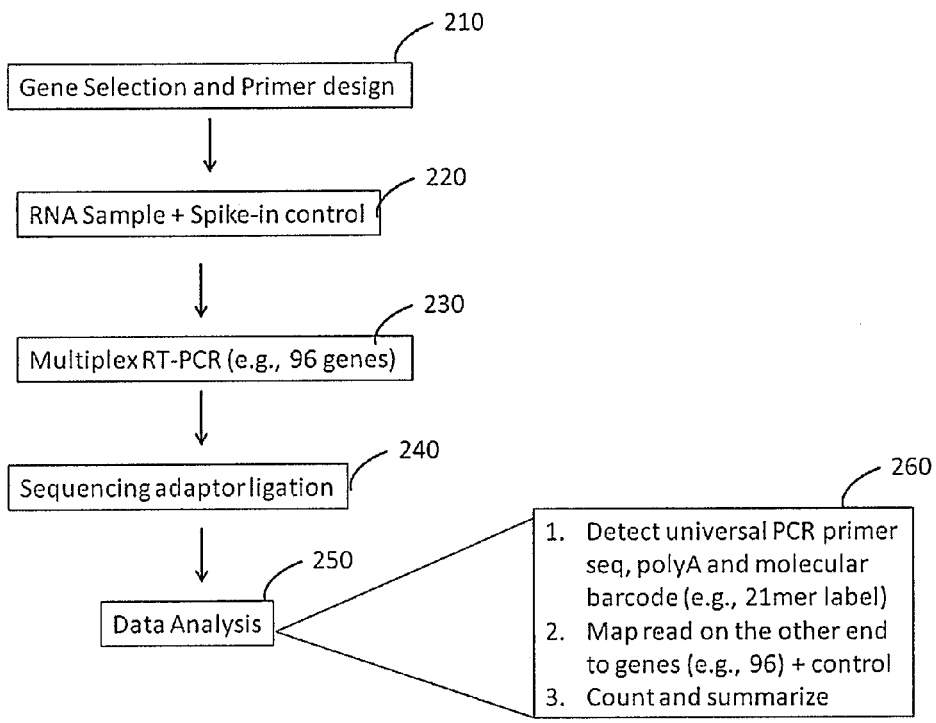
FIG. 57 depicts a schematic of a workflow for analyzing molecules from a sample.

FIG. 57 depicts an exemplary schematic of a workflow for analyzing nucleic acids from two or more samples. As shown in FIG. 57, a method for analyzing nucleic acids from two or more samples may comprise selecting two or more genes for analysis and designing custom primers based on the selected genes (210). The method may further comprise supplementing one or more samples comprising nucleic acids (e.g., RNA) with one or more spike-in controls (220). The nucleic acids in the sample may be amplified by multiplex RT-PCR (230) with molecular barcodes (or sample tags or molecular identifier labels) and the custom primers to produce labeled amplicons. The labeled amplicons may further treated with one or more sequencing adaptors to produce adaptor labeled amplicons (240). The adaptor labeled amplicons can be analyzed (250). As shown in FIG. 57, analysis of the labeled amplicons (250) may comprise one or more of (1) detection of a universal PCR primer seq, polyA and/or molecular barcode (or sample tag, molecular identifier label); (2) map read on the end of the adaptor labeled amplicons (e.g., 96 genes and spike-in controls) that is not attached to the adaptor and/or barcode (e.g., molecular barcode, sample tag, molecular identifier label); and (3) count and/or summarize the number of different adaptor labeled amplicons.

FIG. 67 shows a schematic of a workflow for stochastically labeling nucleic acids with molecular barcodes (1220). As shown in step 1 of FIG. 67, RNA molecules may be stochastically labeled with a set of molecular barcodes (1220). The molecular barcodes (1220) may comprise a target binding region (1221), label region (1222), sample index region (1223) and universal PCR region (1224). In some instances, the target binding region comprises an oligodT sequence that hybridizes to a polyA sequence in the RNA molecules. The label region (1222) may contain a unique sequence that may be used to distinguish two or more different molecular barcodes. When the molecular barcode hybridizes to an RNA molecule, the label region may be used to confer a unique identity to identical RNA molecules. The sample index region (1223) may be identical for a set of molecular barcodes. The sample index region (1223) may be used to distinguish labeled nucleic acids from different samples. The universal PCR region (1224) may serve as a primer binding site for amplification of the labeled molecules. Once the RNA molecules are labeled with the molecular barcodes, the RNA molecules may be reverse transcribed to produce labeled cDNA molecules (1230) containing a cDNA copy of the RNA molecule (1210) and the molecular barcode (1220).

As shown in Step 2 of FIG. 67, excess oligos (e.g., molecular barcodes) may be removed by Ampure bead purification. As shown in Step 3 of FIG. 67, the labeled cDNA molecules may be amplified by multiplex PCR. Multiplex PCR of the labeled cDNA molecules may be performed by using a first set of forward primers (F1, 1235 in FIG. 67) and universal primers (1240) in a single reaction volume to produce labeled amplicons (1245). As shown in Step 4 of FIG. 67, the labeled amplicons may be further amplified by multiplex PCR using nested primers. Nested primer amplification of the labeled amplicons may be performed by using a second set of forward primers (F2, 1250 in FIG. 67) and universal primers (1240) in a single reaction volume to produce labeled nested PCR amplicons. In some instances, the F2 primers (1250) contain an adaptor (1251) and a target binding region (1252). The target binding region (1252) of the F2 primers may hybridize to the labeled amplicons and may prime amplification of the labeled amplicons. The adaptor (1251) and the universal PCR region (1224) of the nested PCR amplicons may be used in the sequencing of the labeled nested PCR amplicons. The amplicons may be sequenced by MiSeq. Alternatively, the amplicons may be sequenced by HiSeq.

FIG. 68 shows a schematic of a workflow for stochastically labeling nucleic acids. As shown in Step 1 of FIG. 68, RNA molecules (1305) may be stochastically labeled with a set molecular barcodes (1320). The molecular barcodes may comprise a target binding region (1321), label region (1322), and universal PCR region (1323). Once the molecular barcodes are attached to the RNA molecules, the RNA molecules (1305) may be reverse transcribed to produce labeled cDNA molecules (1325) comprising a cDNA copy of the RNA molecule (1310) and the molecular barcode (1320). As shown in Step 2 of FIG. 68, the labeled cDNA molecules may be purified by Ampure bead purification to remove excess oligos (e.g., molecular barcodes). As shown in Step 3 of FIG. 68, the labeled amplicons may be amplified by multiplex PCR. Multiplex PCR of the labeled cDNA molecules may be performed by using a first set of forward primers (F1, 1330 in FIG. 68) and universal primers (1335) in a single reaction volume to produce labeled amplicons (1360). As shown in Step 4 of FIG. 67, the labeled amplicons may be further amplified by multiplex PCR using nested primers. Nested primer amplification of the labeled amplicons may be performed by using a second set of forward primers (F2, 1340 in FIG. 68) and sample index primers (1350) in a single reaction volume to produce labeled nested PCR amplicons. In some instances, the F2 primers (1340) contain an adaptor (1341) and a target binding region (1342). The target binding region (1342) of the F2 primers may hybridize to the labeled amplicons and may prime amplification of the labeled amplicons. The sample index primers (1350) may comprise a universal primer region (1351), sample index region (1352), and adaptor region (1353). As shown in Step 4 of FIG. 68, the universal primer region (1351) of the sample index primer may hybridize to the universal PCR region of the labeled amplicons. The sample index region (1352) of the sample index primer may be used to distinguish two or more samples. The adaptor regions (1341, 1353) may be used to sequence the labeled nested PCR amplicons. The amplicons may be sequenced by MiSeq. Alternatively, the amplicons may be sequenced by HiSeq.

Further disclosed herein are methods of producing one or more libraries. The one or more libraries may comprise a plurality of labeled molecules. The one or more libraries may comprise a plurality of labeled amplicons. The one or more libraries may comprise a plurality of enriched molecules or a derivative thereof (e.g., labeled molecules, labeled amplicons). Generally, the method of producing one or more libraries comprises (a) stochastically labeling a plurality of molecules from two or more samples to produce a plurality of labeled molecules, wherein the labeled molecules comprise a molecule region, a sample index region, and label region; and (b) producing one or more libraries from the plurality of labeled molecules, wherein (i) the one or more libraries comprise two or more different labeled molecules, (ii) the two or more different labeled molecules differ by the molecule region, sample index region, label region, or a combination thereof.

The method for producing one or more libraries may comprise: a) producing a plurality of sample-tagged nucleic acids by: i) contacting a first sample comprising a plurality of nucleic acids with a plurality of first sample tags to produce a plurality of first sample-tagged nucleic acids; and ii) contacting a second sample comprising a plurality of nucleic acids with a plurality of second sample tags to produce a plurality of second sample-tagged nucleic acids, wherein the plurality of first sample tags are different from the second sample tags; and b) contacting the plurality of sample-tagged nucleic acids with a plurality of molecular identifier labels to produce a plurality of labeled nucleic acids, thereby producing a labeled nucleic acid library.

The contacting to a sample can be random or non-random. For example, the contacting of a sample with sample tags can be a random or non-random contacting. In some embodiments, the sample is contacted with sample tags randomly. In some embodiments, the sample is contacted with sample tags non-randomly. The contacting to a plurality of nucleic acids can be random or non-random. For example, the contacting of a plurality of nucleic acids with sample tags can be a random or non-random contacting. In some embodiments, the plurality of nucleic acids is contacted with sample tags randomly. In some embodiments, the plurality of nucleic acids is contacted with sample tags non-randomly.

Further disclosed herein are methods of producing one or more sets of labeled beads. The method of producing the one or more sets of labeled beads may comprise attaching one or more nucleic acids to one or more beads, thereby producing one or more sets of labeled beads. The one or more nucleic acids may comprise one or more molecular barcodes. The one or more nucleic acids may comprise one or more sample tags. The one or more nucleic acids may comprise one or more molecular identifier labels. The one or more nucleic acids may comprise a) a primer region; b) a sample index region; and c) a linker or adaptor region. The one or more nucleic acids may comprise a) a primer region; b) a label region; and c) a linker or adaptor region. The one or more nucleic acids may comprise a) a sample index region; and b) a label region. The one or more nucleic acids may further comprise a primer region. The one or more nucleic acids may further comprise a target specific region. The one or more nucleic acids may further comprise a linker region.

The one or more nucleic acids may further comprise an adaptor region. The one or more nucleic acids may further comprise a sample index region. The one or more nucleic acids may further comprise a label region.

Further disclosed herein are methods for selecting one or more custom primers. The method of selecting a custom primer for analyzing molecules in a plurality of samples may comprise: a) a first pass, wherein primers chosen may comprise: i) no more than three sequential guanines, no more than three sequential cytosines, no more than four sequential adenines, and no more than four sequential thymines; ii) at least 3, 4, 5, or 6 nucleotides that are guanines or cytosines; and iii) a sequence that does not easily form a hairpin structure; b) a second pass, comprising: i) a first round of choosing a plurality of sequences that have high coverage of all transcripts; and ii) one or more subsequent rounds, selecting a sequence that has the highest coverage of remaining transcripts and a complementary score with other chosen sequences no more than 4; and c) adding sequences to a picked set until coverage saturates or total number of customer primers is less than or equal to about 96.

Further disclosed herein are kits for use in analyzing two or more molecules from two or more samples. The kit may comprise (a) a first container comprising a first set of molecular barcodes, wherein (i) a molecular barcode of the first set of molecular barcodes comprise a sample index region and a label region; (ii) the sample index region of two or more barcodes of the first set of molecular barcodes are the same; and (iii) the label region of two or more barcodes of the first set of molecular barcodes are different; and (b) a second container comprising a second set of molecular barcodes, wherein (i) a molecular barcode of the second set of molecular barcodes comprise a sample index region and a label region; (ii) the sample index region of two or more barcodes of the second set of molecular barcodes are the same; (iii) the label region of two or more barcodes of the second set of molecular barcodes are different; (iv) the sample index region of the barcodes of the second set of molecular barcodes are different from the sample index region of the barcodes of the first set of molecular barcodes; and (v) the label region of two or more barcodes of the second set of molecular barcodes are identical to the label region of two or more barcodes of the first set of molecular barcodes.

Alternatively, the kit comprises: a) a plurality of beads, wherein one or more beads of the plurality of beads may comprise at least one of a plurality of nucleic acids, wherein at least one of a plurality nucleic acids may comprise: i) at least one primer sequence, wherein the primer sequence of at least one of the plurality of nucleic acids is the same for the plurality of beads; ii) a bead-specific sequence, wherein the bead-specific sequence of any one of the plurality of nucleic acids is the same, and wherein the bead-specific sequence is different for any one of the plurality of beads; and iii) a stochastic sequence, wherein the stochastic sequence is different for any one of the plurality of nucleic acids; b) a primer may comprise a sequence complementary to the primer sequence; and c) one or more amplification agents suitable for nucleic acid amplification.

Alternatively, the kit comprises: a) a first container comprising a first set of sample tags, wherein (i) a sample tag of the first set of sample tags comprises a sample index region; and (ii) the sample index regions of the sample tags of the first set of sample tags are at least about 80% identical; and b) a second container comprising a first set of molecular identifier labels, wherein (i) a molecular identifier label of the first set of molecular identifier labels comprises a label region; and (ii) at least about 30% of the label regions of the total molecular identifier labels of the first set of molecular identifier labels are different Before the present methods, kits and compositions are described in greater detail, it is to be understood that this invention is not limited to particular method, kit or composition described, as such may, of course, vary. It is also to be understood that the terminology used herein is for the purpose of describing particular embodiments only, and is not intended to be limiting, since the scope of the present invention will be limited only by the appended claims. Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods, kits and compositions are provided for stochastic labeling of nucleic acids in a plurality of samples or in a complex nucleic acid preparation. These methods, kits and compositions find use in unraveling mechanisms of cellular response, differentiation or signal transduction and in performing a wide variety of clinical measurements. These and other objects, advantages, and features of the invention will become apparent to those persons skilled in the art upon reading the details of the methods, kits and compositions as more fully described below.

The methods disclosed herein comprise attaching one or more molecular barcodes, sample tags, and/or molecular identifier labels to two or more molecules from two or more samples. The molecular barcodes, sample tags and/or molecular identifier labels may comprise one or more oligonucleotides. In some instances, attachment of molecular barcodes, sample tags, and/or molecular identifier labels to the molecules comprises stochastic labeling of the molecules. Methods for stochastically labeling molecules may be found, for example, in U.S. Ser. Nos. 12/969,581 and 13/327,526. Generally, the stochastic labeling method comprises the random attachment of a plurality of the tag and label oligonucleotides to one or more molecules. The molecular barcodes, sample tags, and/or molecular identifier labels are provided in excess of the one or more molecules to be labeled. In stochastic labeling, each individual molecule to be labeled has an individual probability of attaching to the plurality of the molecular barcodes, sample tags, and/or molecular identifier labels. The probability of each individual molecule to be labeled attaching to a particular molecular barcodes, sample tags, and/or molecular identifier labels may be about the same as any other individual molecule to be labeled. Accordingly, in some instances, the probability of any of the molecules in a sample finding any of the tags and labels is assumed to be equal, an assumption that may be used in mathematical calculations to estimate the number of molecules in the sample. In some circumstances the probability of attaching may be manipulated by, for example electing tags and labels with different properties that would increase or decrease the binding efficiency of that molecular barcodes, sample tags, and/or molecular identifier labels with an individual molecule. The tags and labels may also be varied in numbers to alter the probability that a particular molecular barcodes, sample tags, and/or molecular identifier labels will find a binding partner during the stochastic labeling. For example, one label is overrepresented in a pool of labels, thereby increasing the chances that the overrepresented label finds at least one binding partner.

The methods disclosed herein may further comprise combining two or more samples. The methods disclosed herein may further comprise combining one or more molecules from two or more samples. For example, the methods disclosed herein comprise combining a first sample and a second sample. The two or more samples may be combined after conducting one or more stochastic labeling procedures. The two or more samples may be combined after attachment of one or more sets of molecular barcodes to two or more molecules from the two or more samples. The two or more samples may be combined after attachment of one or more sets of sample tags to two or more molecules from the two or more samples. The two or more samples may be combined after attachment of one or more sets of molecular identifier labels to two or more molecules from the two or more samples. For example, the first and second samples are combined prior to contact with the plurality of molecular identifier labels.

Alternatively, the two or more samples may be combined prior to conducting one or more stochastic labeling procedures. The two or more samples may be combined prior to attachment of one or more sets of molecular barcodes to two or more molecules from the two or more samples. The two or more samples may be combined prior to attachment of one or more sets of sample tags to two or more molecules from the two or more samples. The two or more samples may be combined prior to attachment of one or more sets of molecular identifier labels to two or more molecules from the two or more samples.

The two or more samples may be combined after conducting one or more assays on two or more molecules or derivatives thereof (e.g., labeled molecules, amplicons) from the two or more samples. The one or more assays may comprise one or more amplification reactions. The one or more assays may comprise one or more enrichment assays. The one or more assays may comprise one or more detection assays. For example, the first and second samples are combined after detecting the labeled nucleic acids.

The two or more samples may be combined prior to conducting one or more assays on two or more molecules or derivatives thereof (e.g., labeled molecules, amplicons) from the two or more samples. The one or more assays may comprise one or more amplification reactions. The one or more assays may comprise one or more enrichment assays. The one or more assays may comprise one or more detection assays. For example, the first and second samples are combined prior to detecting the labeled nucleic acids.

Supports

The present disclosure comprises compositions and methods for multiplex sequence analysis from single cells. The methods and compositions of the present disclosure provide for the use of solid supports. In some instances, the methods, kits, and compositions disclosed herein comprise a support.

The terms "support", "solid support", "semi-solid support", and "substrate" may be used interchangeably and refer to a material or group of materials having a rigid or semi-rigid surface or surfaces. A support may refer to any surface that is transferable from solution to solution or forms a structure for conducting oligonucleotide-based assays. The support or substrate may be a solid support. Alternatively, the support is a non-solid support. A support may refer to an insoluble, semi-soluble, or insoluble material. A support may be referred to as "functionalized" when it includes a linker, a scaffold, a building block, or other reactive moiety attached thereto, whereas a solid support may be "nonfunctionalized" when it lack such a reactive moiety attached thereto. The support may be employed free in solution, such as in a microtiter well format; in a flow-through format, such as in a column; or in a dipstick.

The support or substrate may comprise a membrane, paper, plastic, coated surface, flat surface, glass, slide, chip, or any combination thereof. In many embodiments, at least one surface of the support may be substantially flat, although in some embodiments it may be desirable to physically separate synthesis regions for different compounds with, for example, wells, raised regions, pins, etched trenches, or the like. According to other embodiments, the solid support(s) may take the form of resins, gels, microspheres, or other geometric configurations. Alternatively, the solid support(s) comprises silica chips, microparticles, nanoparticles, plates, and arrays. Solid supports may include beads (e.g., silica gel, controlled pore glass, magnetic beads, Dynabeads, Wang resin; Merrifield resin, Sephadex/Sepharose beads, cellulose beads, polystyrene beads etc.), capillaries, flat supports such as glass fiber filters, glass surfaces, metal surfaces (steel, gold silver, aluminum, silicon and copper), glass supports, plastic supports, silicon supports, chips, filters, membranes, microwell plates, slides, or the like. plastic materials including multiwell plates or membranes (e.g., formed of polyethylene, polypropylene, polyamide, polyvinylidenedifluoride), wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

Methods and techniques applicable to polymer (including protein) array synthesis have been described in U.S. Patent Pub. No. 20050074787, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Publication No. WO 99/36760 and WO 01/58593, which are all incorporated herein by reference in their entirety for all purposes. Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but many of the same techniques may be applied to polypeptide arrays. Additional exemplary substrates are disclosed in U.S. Pat. No. 5,744,305 and US Patent Pub. Nos. 20090149340 and 20080038559.

The attachment of the labeled nucleic acids to the support may comprise amine-thiol crosslinking, maleimide crosslinking, N-hydroxysuccinimide or N-hydroxysulfosuccinimide, Zenon or SiteClick. Attaching the labeled nucleic acids to the support may comprise attaching biotin to the plurality of labeled nucleic acids and coating the one or more beads with streptavadin.

In some instances, a solid support may comprise a molecular scaffold. Exemplary molecular scaffolds may include antibodies, antigens, affinity reagents, polypeptides, nucleic acids, cellular organelles, and the like. Molecular scaffolds may be linked together (e.g., a solid support may comprise a plurality of connected molecular scaffolds). Molecular scaffolds may be linked together by an amino acid linker, a nucleic acid linker, a small molecule linkage (e.g., biotin and avidin), and/or a matrix linkage (e.g., PEG or glycerol). Linkages may be non-covalent. Linkages may be covalent. In some instances, molecular scaffolds may not be linked. A plurality of individual molecular scaffolds may be used in the methods of the disclosure.

In some instances a support may comprise a nanoparticle. The nanoparticle may be a nickel, gold, silver, carbon, copper, silicate, platinum cobalt, zinc oxide, silicon dioxide crystalline, and/or silver nanoparticle. Alternatively, or additionally, the nanoparticle may be a gold nanoparticle embedded in a porous manganese oxide. The nanoparticle may be an iron nanoparticle. The nanoparticle may be a nanotetrapod studded with nanoparticles of carbon.

A support may comprise a polymer. A polymer may comprise a matrix. A matrix may further comprise one or more beads. A polymer may comprise PEG, glycerol, polysaccharide, or a combination thereof. A polymer may be a plastic, rubber, nylon, silicone, neoprene, and/or polystyrene. A polymer may be a natural polymer. Examples of natural polymers include, but are not limited to, shellac, amber, wool, silk, cellulose, and natural rubber. A polymer may be a synthetic polymer. Examples of synthetic polymers include, but are not limited to, synthetic rubber, phenol formaldehyde resin (or Bakelite), neoprene, nylon, polyvinyl chloride (PVC or vinyl), polystyrene, polyethylene, polypropylene, polyacrylonitrile, PVB, and silicone.

A support may be a semi-solid support. A support may comprise a gel (e.g., a hydrogel). The terms "hydrogel", "gel" and the like, are used interchangeably herein and may refer to a material which is not a readily flowable liquid and not a solid but a gel which gel is comprised of from 0.5% or more and preferably less than 40% by weight of gel forming solute material and from 95% or less and preferably more than 55% water. The gels of the invention may be formed by the use of a solute which is preferably a synthetic solute (but could be a natural solute, e.g., for forming gelatin) which forms interconnected cells which binds to, entrap, absorb and/or otherwise hold water and thereby create a gel in combination with water, where water includes bound and unbound water. The gel may be the basic structure of the hydrogel patch of the invention will include additional components beyond the gel forming solute material and water such as an enzyme and a salt which components are further described herein. The gel may be a polymer gel.

A solid support may comprise a structured nanostructure. For example, the structured nanostructure may comprise capture containers (e.g., a miniaturized honeycomb) which may comprise the oligonucleotides to capture the cell and/or contents of the cell. In some instances, structured nanostructures may not need the addition of exogenous reagents.

In some instances, the support comprises a bead. A bead may encompass any type of solid or hollow sphere, ball, bearing, cylinder, or other similar configuration composed of plastic, ceramic, metal, or polymeric material onto which a nucleic acid may be immobilized (e.g., covalently or non-covalently). A bead may comprise nylon string or strings. A bead may be spherical in shape. A bead may be non-spherical in shape. Beads may be unpolished or, if polished, the polished bead may be roughened before treating, (e.g., with an alkylating agent). A bead may comprise a discrete particle that may be spherical (e.g., microspheres) or have an irregular shape. Beads may comprise a variety of materials including, but not limited to, paramagnetic materials, ceramic, plastic, glass, polystyrene, methylstyrene, acrylic polymers, titanium, latex, sepharose, cellulose, nylon and the like. A bead may be attached to or embedded into one or more supports. A bead may be attached to a gel or hydrogel. A bead may be embedded into a gel or hydrogel. A bead may be attached to a matrix. A bead may be embedded into a matrix. A bead may be attached to a polymer. A bead may be embedded into a polymer. The spatial position of a bead within the support (e.g., gel, matrix, scaffold, or polymer) may be identified using the oligonucleotide present on the bead which serves as a location address. Examples of beads include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, oligodT conjugated beads, silica beads, silica-like beads, anti-biotin microbead, anti-fluorochrome microbead, and BcMag™ Carboxy-Terminated Magnetic Beads. The diameter of the beads may be about 5 µm, 10 µm, 20 µm, 25 µm, 30 µm, 35 µm, 40 µm, 45 µm or 50 µm. A bead may refer to any three dimensional structure that may provide an increased surface area for immobilization of biological particles and macromolecules, such as DNA and RNA.

A support may be porous. A support may be permeable or semi-permeable. A support may be solid. A support may be semi-solid. A support may be malleable. A support may be flexible. In some instances, a support may be molded into a shape. For example, a support may be placed over an object and the support may take the shape of the object. In some instances, the support is placed over an organ and takes the shape of the organ. In some instances, the support is produced by 3D-printing.

The support (e.g., beads, nanoparticles) may be at least about 0.1, 0.5, 1, 2, 3, 4, 5, 6, 7, 8, 9, 10, 20, 30, 100, 500, 1000, or 2000 or more micrometers in diameter. The solid supports (e.g., beads) may be at most about 0.1, 0.5, 1, 2, 3, 4, 5, 6, 7, 8, 9, 10, 20, 30, 100, 500, 1000, or 2000 or more micrometers in diameter. The diameter of the bead may be about 20 microns.

In some instances, a solid support comprises a dendrimer. A dendrimer may be smaller than a bead. A dendrimer may be subcellular. A dendrimer may be less than 1, 0.9, 0.8, 0.7, 0.6, 0.5, 0.4, 0.3, 0.2, or 0.1 micron in diameter. A dendrimer may be less than 0.09, 0.08, 0.07, 0.06, 0.05, 0.04, 0.03, or 0.01 micron in diameterA dendrimer may comprise three major portions, a core, an inner shell, and an outer shell. A dendrimer may be synthesized to have different functionality in each of these portions. The different functionality of the portions of the dendrimer may control properties such as solubility, thermal stability, and attachment of compounds for particular applications. A dendrimer may be synthetically processed. A dendrimer may be synthesized by divergent synthesis. Divergent synthesis may comprise assembling a dendrimer from a multifunctional core, which is extended outward by a series of reactions. Divergent synthesis may comprise a series of Michael reactions. Alternatively, a dendrimer may be synthesized by convergent synthesis. Convergent synthesis may comprise building dendrimers from small molecules that end up at the surface of the sphere, and reactions may proceed inward and are eventually attached to a core. Dendrimers may also be prepared by click chemistry. Click chemistry may comprise Diels-Alder reactions, thiol-yne reactions, azide-alkyne reactions, or a combination thereof. Examples of dendrimers include, but are not limited to, poly(amidoamine) (PAMAM) dendrimer, PEG-core denderimer, phosphorous dendrimer, polypropylenimine dendrimer, and polylysine dendrimer. A dendrimer may be a chiral dendrimer. Alternatively, a dendrimer may be an achiral dendrimer.

A solid support may comprise a portion of a dendrimer. The portion of the dendrimer may comprise a dendron. A dendron may comprise monodisperse wedge-shaped dendrimer sections with multiple terminal groups and a single reaction function at the focal point. A solid support may comprise a polyester dendrom. Examples of dendrons include, but are not limited to, polyester-8-hydroxyl-1-acetylene bis-MPA dendron, polyester-16-hydroxyl-1-acetylene bis-MPA dendron, polyester-32-hydroxyl-1-acetylene bis-MPA dendron, polyester-8-hydroxyl-1-carboxyl bis-MPA dendron, polyester-16-hydroxyl-1-carboxyl bis-MPA dendron, and polyester-32-hydroxyl-1-carboxyl bis-MPA dendron.

A solid support may comprise a hyberbranched polymer. A hyperbranched polymer may comprise polydisperse dendritic macromolecules that possess dendrimer-like properties. Often, hyberbranched polymers are prepared in a single synthetic polymerization step. The hyperbranched polymer may be based on 2,2-bis(hydroxymethyl)propanoic acid (bis-MPA) monomer. Examples of hyperbranched polymers include, but are not limited to, hyperbranched bis-MPA polyester-16-hydroxyl, hyperbranched bis-MPA polyester-32-hydroxyl, and hyperbranched bis-MPA polyester-64-hydroxyl.

The solid support may be an array or microarray. The solid support may comprise discrete regions. The solid support may be an addressable array. In some instances, the array comprises a plurality of probes fixed onto a solid surface. The plurality of probes enables hybridization of the labeled-molecule and/or labeled-amplicon to the solid surface. The plurality of probes comprises a sequence that is complementary to at least a portion of the labeled-molecule and/or labeled-amplicon. In some instances, the plurality of probes comprises a sequence that is complementary to at least a portion of the sample tag, molecular identifier label, nucleic acid, or a combination thereof. In other instances, the plurality of probes comprises a sequence that is complementary to the junction formed by the attachment of the sample tag or molecular identifier label to the nucleic acid.

The array may comprise one or more probes. The probes may be in a variety of formats. The array may comprise a probe comprising a sequence that is complementary to at least a portion of the target nucleic acid and a sequence that is complementary to the unique identifier region of a sample tag or molecular identifier label, wherein the sample tag or molecular identifier label comprises an oligonucleotide. The sequence that is complementary to at least a portion of the target nucleic acid may be attached to the array. The sequence that is complementary to the unique identifier region may be attached to the array. The array may comprise a first probe comprising a sequence that is complementary to at least a portion of the target nucleic acid and a second probe that is complementary to the unique identifier region. There are various ways in which a stochastically labeled nucleic acid may hybridize to the arrays. For example, the junction of the unique identifier region and the target nucleic acid of the stochastically labeled nucleic acid may hybridize to the probe on the array. There may be a gap in the regions of the stochastically labeled nucleic acid that may hybridize to the probe on the array. Different regions of the stochastically labeled nucleic acid may hybridize to two or more probes on the array. Thus, the array probes may be in many different formats. The array probes may comprise a sequence that is complementary to a unique identifier region, a sequence that is complementary to the target nucleic acid, or a combination thereof. Hybridization of the stochastically labeled nucleic acid to the array may occur by a variety of ways. For example, two or more nucleotides of the stochastically labeled nucleic acid may hybridize to one or more probes on the array. The two or more nucleotides of the stochastically labeled nucleic acid that hybridize to the probes may be consecutive nucleotides, non-consecutive nucleotides, or a combination thereof. The stochastically labeled nucleic acid that is hybridized to the probe may be detected by any method known in the art. For example, the stochastically labeled nucleic acids may be directly detected. Directly detecting the stochastically labeled nucleic acid may comprise detection of a fluorophore, hapten, or detectable label. The stochastically labeled molecules may be indirectly detected. Indirect detection of the stochastically labeled nucleic acid may comprise ligation or other enzymatic or non-enzymatic methods.

The array may be in a variety of formats. For example, the array may be in a 16-, 32-, 48-, 64-, 80-, 96-, 112-, 128-, 144-, 160-, 176-, 192-, 208-, 224-, 240-, 256-, 272-, 288-, 304-, 320-, 336-, 352-, 368-, 384-, or 400-format. Alternatively, the array is in an 8×60K, 4×180K, 2×400K, 1×1M format. In other instances, the array is in an 8×15K, 4×44K, 2×105K, 1×244K format.

The array may comprise a single array. The single array may be on a single substrate. Alternatively, the array is on multiple substrates. The array may comprise multiple formats. The array may comprise a plurality of arrays. The plurality of arrays may comprise two or more arrays. For example, the plurality of arrays may comprise at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 arrays. In some instances, at least two arrays of the plurality of arrays are identical. Alternatively, at least two arrays of the plurality of arrays are different.

In some instances, the array comprises symmetrical chambered areas. For example, the array comprises 0.5×0.5 millimeters (mm), 1×1 mm, 1.5×1.5 mm, 2×2 mm, 2.5×2.5 mm, 3×3 mm, 3.5×3.5 mm, 4×4 mm, 4.5×4.5 mm, 5×5 mm, 5.5×5.5 mm, 6×6 mm, 6.5×6.5 mm, 7×7 mm, 7.5×7.5 mm, 8×8 mm, 8.5×8.5 mm, 9×9 mm, 9.5×9.5 mm, 10×10 mm, 10.5×10.5 mm, 11×11 mm, 11.5×11.5 mm, 12×12 mm, 12.5×12.5 mm, 13×13 mm, 13.5×13.5 mm, 14×14 mm, 14.5×14.5 mm, 15×15 mm, 15.5×15.5 mm, 16×16 mm, 16.5×16.5 mm, 17×17 mm, 17.5×17.5 mm, 18×18 mm, 18.5×18.5 mm, 19×19 mm, 19.5×19.5 mm, or 20×20 mm chambered areas. In some instances, the array comprises 6.5×6.5 mm chambered areas. Alternatively, the array comprises asymmetrical chambered areas. For example, the array comprises 6.5×0.5 mm, 6.5×1 mm, 6.5×1.5 mm, 6.5×2 mm, 6.5×2.5 mm, 6.5×3 mm, 6.5×3.5 mm, 6.5×4 mm, 6.5×4.5 mm, 6.5×5 mm, 6.5×5.5 mm, 6.5×6 mm, 6.5×6.5 mm, 6.5×7 mm, 6.5×7.5 mm, 6.5×8 mm, 6.5×8.5 mm, 6.5×9 mm, 6.5×9.5 mm, 6.5×10 mm, 6.5×10.5 mm, 6.5×11 mm, 6.5×11.5 mm, 6.5×12 mm, 6.5×12.5 mm, 6.5×13 mm, 6.5×13.5 mm, 6.5×14 mm, 6.5×14.5 mm, 6.5×15 mm, 6.5×15.5 mm, 6.5×16 mm, 6.5×16.5 mm, 6.5×17 mm, 6.5×17.5 mm, 6.5×18 mm, 6.5×18.5 mm, 6.5×19 mm, 6.5×19.5 mm, or 6.5×20 mm chambered areas.

The array may comprise at least about 1 micron (μm), 2 μm, 3 μm, 4 μm, 5 μm, 6 μm, 7 μm, 8 μm, 9 μm, 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 125 μm, 150 μm, 175 μm, 200 μm, 225 μm, 250 μm, 275 μm, 300 μm, 325 μm, 350 μm, 375 μm, 400 μm, 425 μm, 450 μm, 475 μm, or 500 μm spots. In some instances, the array comprises 70 μm spots.

The array may comprise at least about 1 μm, 2 μm, 3 μm, 4 μm, 5 μm, 6 μm, 7 μm, 8 μm, 9 μm, 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 125 μm, 150 μm, 175 μm, 200 μm, 225 μm, 250 μm, 275 μm, 300 μm, 325 μm, 350 μm, 375 μm, 400 μm, 425 μm, 450 μm, 475 μm, 500 μm, 525 μm, 550 μm, 575 μm, 600 μm, 625 μm, 650 μm, 675 μm, 700 μm, 725 μm, 750 μm, 775 μm, 800 μm, 825 μm, 850 μm, 875 μm, 900 μm, 925 μm, 950 μm, 975 μm, 1000 μm feature pitch. In some instances, the array comprises 161 μm feature pitch.

The array may comprise one or more probes. In some instances, the array comprises at least about 5, 10, 15, 20, 25, 30, 40, 50, 60, 70, 80, 90, or 100 probes. Alternatively, the array comprises at least about 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 probes. The array may comprise at least about 3500, 4000, 4500, 5000, 5500, 6000, 6500, 7000, 7500, 8000, 8500, 9000, 9500, or 10000 probes. In some instances, the array comprises at least about 960 probes. Alternatively, the array comprises at least about 2780 probes. The probes may be specific for the plurality of oligonucleotide tags. The probes may be specific for at least a portion of the plurality of oligonucleotide tags. The probes may be specific for at least about 5%, 10%, 20%, 30%, 40%, 50%, 60%, 70%, 80%, 90%, 95%, 97% or 100% of the total number of the plurality of oligonucleotide tags. Alternatively, the probes are specific for at least about 5%, 10%, 20%, 30%, 40%, 50%, 60%, 70%, 80%, 90%, 95%, 97% or 100% of the total number of different oligonucleotide tags of the plurality of oligonucleotide tags. The probes may be oligonucleotides. The oligonucleotides may be at least about 1, 2, 5, 10, 20, 30, 40, 50, 60, 70, 80, 90, 100 nucleotides long. In other instances, the probes are non-specific probes. For example, the probes may be specific for a detectable label that is attached to the labeled-molecule. The probe may be streptavidin.

The array may be a printed array. In some instances, the printed array comprises one or more oligonucleotides attached to a substrate. For example, the printed array comprises 5' amine modified oligonucleotides attached to an epoxy silane substrate.

Alternatively, the array comprises a slide with one or more wells. The slide may comprise at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 wells. Alternatively, the slide comprises at least about 125, 150, 175, 200, 250, 300, 350, 400, 450, 500, 650, 700, 750, 800, 850, 900, 950, or 1000 wells. In some instances, the slide comprises 16 wells. Alternatively, the slide comprises 96 wells. In other instances, the slide comprises at least about 80, 160, 240, 320, 400, 480, 560, 640, 720, 800, 880, or 960 wells.

In some instances, the solid support is an Affymetrix 3K tag array, Arrayjet non-contact printed array, or Applied Microarrays Inc (AMI) array. Alternatively, the support comprises a contact printer, impact printer, dot printer, or pin printer.

The solid support may comprise the use of beads that self-assemble in microwells. For example, the solid support comprises Illumina's BeadArray Technology. Alternatively, the solid support comprises Abbott Molecular's Bead Array technology, and Applied Microarray's FlexiPlex™ system.

In other instances, the solid support is a plate. Examples of plates include, but are not limited to, MSD multi-array plates, MSD Multi-Spot® plates, microplate, ProteOn microplate, AlphaPlate, DELFIA plate, IsoPlate, and LumaPlate.

The method may further comprise attaching at least one of a plurality of labeled nucleic acids to a support. The support may comprise a plurality of beads. The support may comprise an array. The support may comprise a glass slide.

The glass slide may comprise one or more wells. The one or more wells may be etched on the glass slide. The one or more wells may comprise at least 960 wells. The glass slide may comprise one or more probes. The one or more probes may be printed onto the glass slide. The one or more wells may further comprise one or more probes. The one or more probes may be printed within the one or more wells. The one or more probes may comprise 960 nucleic acids.

The methods and kits disclosed herein may further comprise distributing the plurality of first sample tags, the plurality of second sample tags, the plurality of molecular identifier labels, or any combination thereof in a microwell plate. The methods and kits disclosed herein may further comprise distributing one or more beads in the microwell plate. The methods and kits disclosed herein may further comprise distributing the plurality of samples in a plurality of wells of a microwell plate. The one or more of the plurality of samples may comprise a plurality of cells. One or more of the plurality of samples may comprise a plurality of nucleic acids. The method may further comprise distributing one or fewer cells to the plurality of wells. The plurality of cells may be lysed in the microwell plate. The method may further comprise synthesizing cDNA in the microwell plate. Synthesizing cDNA may comprise reverse transcription of mRNA. The microwell plate may comprise a microwell plate fabricated on PDMS by soft lithography, etched on a silicon wafer, etched on a glass slide, patterned photoresist on a glass slide, or a combination thereof. The microwell may comprise a hole on a microcapillary plate. The microwell plate may comprise a water-in-oil emulsion. The microwell plate may comprise at least one or more wells. The microwell plate may comprise at least about 6 wells, 12 wells, 48 wells, 96 wells, 384 wells, 960 wells or 1000 wells.

The methods and kits may further comprise a chip. The microwell plate may be attached to the chip. The chip may comprise at least about 6 wells, 12 wells, 48 wells, 96 wells, 384 wells, 960 wells, 1000 wells, 2000 wells, 3000 wells, 4000 wells, 5000 wells, 6000 wells, 7000 wells, 8000 wells, 9000 wells, 10,000 wells, 20,000 wells, 30,000 wells, 40,000 wells, 50,000 wells, 60,000 wells, 70,000 wells, 80,000 wells, 90,000 wells, 100,000 wells, 200,000 wells, 500,000 wells, or a million wells. The wells may comprise an area of at least about 300 microns$^2$, 400 microns$^2$, 500 microns$^2$, 600 microns$^2$, 700 microns$^2$, 800 microns$^2$, 900 microns$^2$, 1000 microns$^2$, 1100 microns$^2$, 1200 microns$^2$, 1300 microns$^2$, 1400 microns$^2$, 1500 microns$^2$. The method may further comprise distributing between about 10,000 and 30,000 samples on the chip.

Functionalized Surfaces and Oligonucleotides

The bead may comprise a functionalized surface. A functionalized surface may refer to the surface of the solid support comprising a functional group. A functional group may be a group capable of forming an attachment with another functional group. For example, a functional group may be biotin, which may form an attachment with streptavidin, another functional group. Exemplary functional groups may include, but are not limited to, aldehydes, ketones, carboxy groups, amino groups, biotin, streptavidin, nucleic acids, small molecules (e.g., for click chemistry), homo- and hetero-bifunctional reagents (e.g., N-succinimidyl(4-iodoacetyl)aminobenzoate (SIAB), dimaleimide, dithio-bis-nitrobenzoic acid (DTNB), N-succinimidyl-S-acetyl-thioacetate (SATA), N-succinimidyl-3-(2-pyridyldithio) propionate (SPDP), succinimidyl 4-(N-mafeimidomethyl)-cyclohexane-1-carboxylate (SMCC) and 6-hydrazinonicotimide (HYNIC), and antibodies. In some instances the functional group is a carboxy group (e.g., COOH).

Oligonucleotides (e.g., nucleic acids) may be attached to functionalized solid supports. The immobilized oligonucleotides on solid supports or similar structures may serve as nucleic acid probes, and hybridization assays may be conducted wherein specific target nucleic acids may be detected in complex biological samples.

The solid support (e.g., beads) may be functionalized for the immobilization of oligonucleotides. An oligonucleotide may be conjugated to a solid support through a covalent amide bond formed between the solid support and the oligonucleotide.

A support may be conjugated to at least about 10, 20, 30, 40, 50, 60, 70, 80, 90, 100, 200, 300, 400, 500, 600, 700, 800, 900 or 1000 or more oligonucleotides. A support may be conjugated to at least about 100000, 200000, 300000, 400000, 500000, 600000, 700000, 800000, 900000, 1000000, 2000000, 3000000, 4000000, 5000000, 6000000, 7000000, 8000000, 9000000 or 10000000, 100000000, 500000000, 1000000000 or more oligonucleotides. A support may be conjugated to at least about 100000, 200000, 300000, 400000, 500000, 600000, 700000, 800000, 900000, 1000000, 2000000, 3000000, 4000000, 5000000, 6000000, 7000000, 8000000, 9000000 or 10000000, 100000000, 500000000, 1000000000 or more oligonucleotides. A support may be conjugated to at least 1 million oligonucleotides. A support may be conjugated to at least 10 million oligonucleotides. A support may be conjugated to at least 25 million oligonucleotides. A support may be conjugated to at least 50 million oligonucleotides. A support may be conjugated to at least 100 million oligonucleotides. A support may be conjugated to at least 250 million oligonucleotides. A support may be conjugated to at least 500 million oligonucleotides. A support may be conjugated to at least 750 million oligonucleotides. A support may be conjugated to at least about 1, 2, 3 4, 5, 6, 7, 8, 9, 10, 11, 12 13, 14, or 15 billion oligonucleotides. A support may be conjugated to at least 1 billion oligonucleotides. A support may be conjugated to at least 5 billion oligonucleotides.

The oligonucleotides may be attached to the support (e.g., beads, polymers, gels) via a linker. Conjugation may comprise covalent or non-covalent attachment. Conjugation may introduce a variable spacer between the beads and the nucleic acids. The linker between the support and the oligonucleotide may be cleavable (e.g., photocleavable linkage, acid labile linker, heat sensitive linker, and enzymatically cleavable linker).

Cross-linking agents for use for conjugating molecules to supports may include agents capable of reacting with a functional group present on a surface of the solid support and with a functional group present in the molecule. Reagents capable of such reactivity may include aldehydes, ketones, carboxy groups, amino groups, biotin, streptavidin, nucleic acids, small molecules (e.g., for click chemistry), homo- and hetero-bifunctional reagents (e.g., N-succinimidyl(4-iodoacetyl)aminobenzoate (SIAB), dimaleimide, dithio-bis-nitrobenzoic acid (DTNB), N-succinimidyl-S- acetyl-thioacetate (SATA), N-succinimidyl-3-(2-pyridyldithio) propionate (SPDP), succinimidyl 4-(N-mafeimidomethyl)-cyclohexane-1-carboxylate (SMCC) and 6-hydrazinonicotimide (HYNIC).

A bead may be functionalized with a carboxy functional group and an oligonucleotide may be functionalized with an amino functional group.

A support may be smooth. Alternatively, or additionally, a support may comprise divets, ridges, or wells. A support may comprise a microwell array. A microwell array may be functionalized with functional groups that facilitate the attachment of oligonucleotides. The functional groups on the microwell array may be different for different positions on the microwell array. The functional groups on the microwell array may be the same for all regions of the microwell array.

Assay System Components
Microwell Arrays

As described above, microwell arrays are used to entrap single cells and beads (one bead per cell) within a small reaction chamber of defined volume. Each bead comprises a library of oligonucleotide probes for use in stochastic labeling and digital counting of the entire complement of cellular mRNA molecules, which are released upon lysis of the cell. In one embodiment of the present disclosure, the microwell arrays are a consumable component of the assay system. In other embodiments, the microwell arrays may be reusable. In either case, they may be configured to be used as a stand-alone device for use in performing assays manually, or they may be configured to comprise a removable or fixed component of an instrument that provides for full or partial automation of the assay procedure.

The microwells of the array can be fabricated in a variety of shapes and sizes, which are chosen to optimize the efficiency of trapping a single cell and bead in each well. Appropriate well geometries include, but are not limited to, cylindrical, conical, hemispherical, rectangular, or polyhedral (e.g., three dimensional geometries comprised of several planar faces, for example, hexagonal columns, octagonal columns, inverted triangular pyramids, inverted square pyramids, inverted pentagonal pyramids, inverted hexagonal pyramids, or inverted truncated pyramids). The microwells may comprise a shape that combines two or more of these geometries. For example, in one embodiment it may be partly cylindrical, with the remainder having the shape of an inverted cone. In another embodiment, it may include two side-by-side cylinders, one of larger diameter than the other, that are connected by a vertical channel (that is, parallel to the cylinder axes) that extends the full length (depth) of the cylinders. In general, the open end (or mouth) of each microwell will be located at an upper surface of the microwell array, but in some embodiments the openings may be located at a lower surface of the array. In general, the closed end (or bottom) of the microwell will be flat, but curved surfaces (e.g., convex or concave) are also possible. In general, the shape (and size) of the microwells will be determined based on the types of cells and/or beads to be trapped in the microwells.

Microwell dimensions may be characterized in terms of the diameter and depth of the well. As used herein, the diameter of the microwell refers to the largest circle that can be inscribed within the planar cross-section of the microwell geometry. In one embodiment of the present disclosure, the diameter of the microwells may range from about 0.1 to about 5-fold the diameter of the cells and/or beads to be trapped within the microwells. In other embodiments, the microwell diameter is at least 0.1-fold, at least 0.5-fold, at least 1-fold, at least 2-fold, at least 3-fold, at least 4-fold, or at least 5-fold the diameter of the cells and/or beads to be trapped within the microwells. In yet other embodiments, the microwell diameter is at most 5-fold, at most 4-fold, at most 3-fold, at most 2-fold, at most 1-fold, at most 0.5-fold, or at most 0.1-fold the diameter of the cells and/or beads to be trapped within the microwells. In one embodiment, the microwell diameter is about 2.5-fold the diameter of the cells and/or beads to be trapped within the microwells. Those of skill in the art will appreciate that the microwell diameter may fall within any range bounded by any of these values (e.g., from about 0.2-fold to about 3.5-fold the diameter of the cells and/or beads to be trapped within the microwells). Alternatively, the diameter of the microwells can be specified in terms of absolute dimensions. In one embodiment of the present disclosure, the diameter of the microwells may range from about 5 to about 50 microns. In other embodiments, the microwell diameter is at least 5 microns, at least 10 microns, at least 15 microns, at least 20 microns, at least 25 microns, at least 30 microns, at least 35 microns, at least 40 microns, at least 45 microns, or at least 50 microns. In yet other embodiments, the microwell diameter is at most 50 microns, at most 45 microns, at most 40 microns, at most 35 microns, at most 30 microns, at most 25 microns, at most 20 microns, at most 15 microns, at most 10 microns, or at most 5 microns. In one embodiment, the microwell diameter is about 30 microns. Those of skill in the art will appreciate that the microwell diameter may fall within any range bounded by any of these values (e.g., from about 28 microns to about 34 microns).

The microwell depth is chosen to optimize cell and bead trapping efficiency while also providing efficient exchange of assay buffers and other reagents contained within the wells. In one embodiment of the present disclosure, the depth of the microwells may range from about 0.1 to about 5-fold the diameter of the cells and/or beads to be trapped within the microwells. In other embodiments, the microwell depth is at least 0.1-fold, at least 0.5-fold, at least 1-fold, at least 2-fold, at least 3-fold, at least 4-fold, or at least 5-fold the diameter of the cells and/or beads to be trapped within the microwells. In yet other embodiments, the microwell depth is at most 5-fold, at most 4-fold, at most 3-fold, at most 2-fold, at most 1-fold, at most 0.5-fold, or at most 0.1-fold the diameter of the cells and/or beads to be trapped within the microwells. In one embodiment, the microwell depth is about 2.5-fold the diameter of the cells and/or beads to be trapped within the microwells. Those of skill in the art will appreciate that the microwell depth may fall within any range bounded by any of these values (e.g., from about 0.2-fold to about 3.5-fold the diameter of the cells and/or beads to be trapped within the microwells). Alternatively, the diameter of the microwells can be specified in terms of absolute dimensions. In one embodiment of the present disclosure, the depth of the microwells may range from about 10 to about 60 microns. In other embodiments, the microwell depth is at least 10 microns, at least 20 microns, at least 25 microns, at least 30 microns, at least 35 microns, at least 40 microns, at least 50 microns, or at least 60 microns. In yet other embodiments, the microwell depth is at most 60 microns, at most 50 microns, at most 40 microns, at most 35 microns, at most 30 microns, at most 25 microns, at most 20 microns, or at most 10 microns. In one embodiment, the microwell depth is about 30 microns. Those of skill in the art will appreciate that the microwell depth may fall within any range bounded by any of these values (e.g., from about 24 microns to about 36 microns).

The wells of the microwell array are arranged in a one dimensional, two dimensional, or three dimensional array, where three dimensional arrays may be achieved, for example, by stacking a series of two or more two dimensional arrays (that is, by stacking two or more substrates comprising microwell arrays). The pattern and spacing between wells is chosen to optimize the efficiency of trapping a single cell and bead in each well, as well as to maximize the number of wells per unit area of the array. The wells may be distributed according to a variety of random or non-random patterns, for example, they may be distributed entirely randomly across the surface of the array substrate, or they may be arranged in a square grid, rectangular grid, or hexagonal grid. In one embodiment of the present disclosure, the center-to-center distance (or spacing) between wells may vary from about 15 microns to about 75 microns. In other embodiments, the spacing between wells is at least 15 microns, at least 20 microns, at least 25 microns, at least 30 microns, at least 35 microns, at least 40 microns, at least 45 microns, at least 50 microns, at least 55 microns, at least 60 microns, at least 65 microns, at least 70 microns, or at least 75 microns. In yet other embodiments, the microwell spacing is at most 75 microns, at most 70 microns, at most 65 microns, at most 60 microns, at most 55 microns, at most 50 microns, at most 45 microns, at most 40 microns, at most 35 microns, at most 30 microns, at most 25 microns, at most 20 microns, or at most 15 microns. In one embodiment, the microwell spacing is about 55 microns. Those of skill in the art will appreciate that the microwell depth may fall within any range bounded by any of these values (e.g., from about 18 microns to about 72 microns).

The microwell array may comprise surface features between the microwells that are designed to help guide cells and beads into the wells and/or prevent them from settling on the surfaces between wells. Examples of suitable surface features include, but are not limited to, domed, ridged, or peaked surface features that encircle the wells and/or straddle the surface between wells.

The total number of wells in the microwell array is determined by the pattern and spacing of the wells and the overall dimensions of the array. In one embodiment of the present disclosure, the number of microwells in the array may range from about 96 to about 5,000,000 or more. In other embodiments, the number of microwells in the array is at least 96, at least 384, at least 1,536, at least 5,000, at least 10,000, at least 25,000, at least 50,000, at least 75,000, at least 100,000, at least 500,000, at least 1,000,000, or at least 5,000,000. In yet other embodiments, the number of microwells in the array is at most 5,000,000, at most 1,000,000, at most 75,000, at most 50,000, at most 25,000, at most 10,000, at most 5,000, at most 1,536, at most 384, or at most 96 wells. In one embodiment, the number of microwells in the array is about 96. In another embodiment, the number of microwells is about 150,000. Those of skill in the art will appreciate that the number of microwells in the array may fall within any range bounded by any of these values (e.g., from about 100 to 325,000).

Microwell arrays may be fabricated using any of a number of fabrication techniques known to those of skill in the art. Examples of fabrication methods that may be used include, but are not limited to, bulk micromachining techniques such as photolithography and wet chemical etching, plasma etching, or deep reactive ion etching; micro-molding and micro-embossing; laser micromachining; 3D printing or other direct write fabrication processes using curable materials; and similar techniques.

Microwell arrays may be fabricated from any of a number of substrate materials known to those of skill in the art, where the choice of material typically depends on the choice of fabrication technique, and vice versa. Examples of suitable materials include, but are not limited to, silicon, fused-silica, glass, polymers (e.g., agarose, gelatin, hydrogels, polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), and epoxy resins), metals or metal films (e.g., aluminum, stainless steel, copper, nickel, chromium, and titanium), and the like. Typically, a hydrophilic material is desirable for fabrication of the microwell arrays (to enhance wettability and minimize non-specific binding of cells and other biological material), but hydrophobic materials that can be treated or coated (e.g., by oxygen plasma treatment, or grafting of a polyethylene oxide surface layer) can also be used. The use of porous, hydrophilic materials for the fabrication of the microwell array may be desirable in order to facilitate capillary wicking/venting of entrapped air bubbles in the device. In some embodiments, the microwell array is fabricated with an optical adhesive. In some embodiments, the microwell array is fabricated with a plasma or corona treated material. The use of plasma or corona treated materials can make the material hydrophillic. In some embodiments, plasma or corona treated materials, such as a hydrophillic material, can be more stable than non-treated materials. In some embodiments, the microwell array is fabricated from a single material. In other embodiments, the microwell array may comprise two or more different materials that have been bonded together or mechanically joined.

A variety of surface treatments and surface modification techniques may be used to alter the properties of microwell array surfaces. Examples include, but are not limited to, oxygen plasma treatments to render hydrophobic material surfaces more hydrophilic, the use of wet or dry etching techniques to smooth (or roughen) glass and silicon surfaces, adsorption and/or grafting of polyethylene oxide or other polymer layers to substrate surfaces to render them more hydrophilic and less prone to non-specific adsorption of biomolecules and cells, the use of silane reactions to graft chemically-reactive functional groups to otherwise inert silicon and glass surfaces, etc. Photodeprotection techniques can be used to selectively activate chemically-reactive functional groups at specific locations in the array structure, for example, the selective addition or activation of chemically-reactive functional groups such as primary amines or carboxyl groups on the inner walls of the microwells may be used to covalently couple oligonucleotide probes, peptides, proteins, or other biomolecules to the walls of the microwells. In general, the choice of surface treatment or surface modification utilized will depend both on the type of surface property that is desired and on the type of material from which the microwell array is made.

In some embodiments, it may be advantageous to seal the openings of microwells during, for example, cell lysis steps, to prevent cross hybridization of target nucleic acid between adjacent microwells. A microwell may be sealed using a cap such as a solid support or a bead, where the diameter of the bead is larger than the diameter of the microwell. For example, a bead used as a cap can be at least about 10, 20, 30, 40, 50, 60, 70, 80 or 90% larger than the diameter of the microwell. Alternatively, a cap may be at most about 10, 20, 30, 40, 50, 60, 70, 80 or 90% larger than the diameter of the microwell.

A bead used as a cap may comprise cross-linked dextran beads (e.g., Sephadex). Cross-linked dextran can range from about 10 micrometers to about 80 micrometers. The cross-linked dextran of the bead cap can be from 20 micrometers to about 50 micrometers. A cap can comprise, for example, inorganic nanopore membranes (e.g., aluminum oxides), dialysis membranes, glass slides, coverslips, and/or hydrophilic plastic film (e.g., film coated with a thin film of agarose hydrated with lysis buffer).

In some embodiments, the cap may allow buffer to pass into and out of the microwell, while preventing macromolecules (e.g., nucleic acids) from migrating out of the well. A macromolecule of at least about 1, 2, 3, 4, 5, 6, 7, 8, 9, 10, 12, 13, 14, 15, 16, 17, 18, 19, or 20 or more nucleotides can be blocked from migrating into or out of the microwell by the cap. A macromolecule of at most about 1, 2, 3, 4, 5, 6, 7, 8, 9, 10, 12, 13, 14, 15, 16, 17, 18, 19, or 20 or more nucleotides can be blocked from migrating into or out of the microwell by the cap.

In some embodiments, a sealed microwell array can comprise a single layer of beads on top of the microwells. In some embodiments, a sealed microwell array can comprise multiple layers of beads on top of the microwells. A sealed microwell array can comprise about 1, 2, 3, 4, 5, or 6 or more layers of beads.

Mechanical Fixtures

Figure 69:
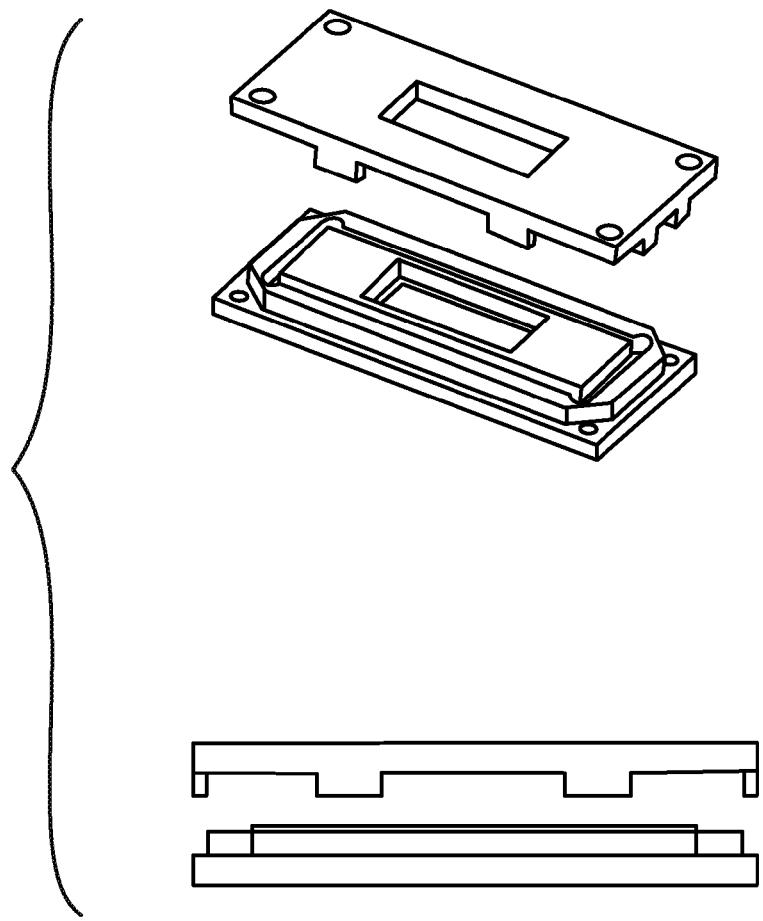
FIG. 69 illustrates a mechanical fixture within which microwell array substrates may be clamped, thereby forming a reaction chamber or well into which samples and reagents may be pipetted for performing multiplexed, single cell stochastic labeling/molecular indexing experiments.
Figure 70:
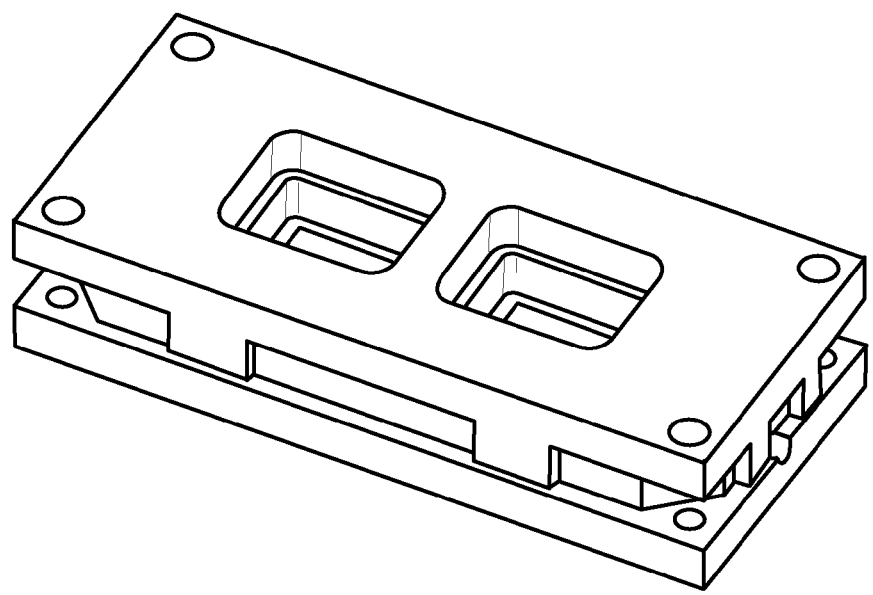
FIG. 70 illustrates a mechanical fixture which creates two reaction chambers or wells when a microwell array substrate is clamped within the fixture.

When performing multiplexed, single cell stochastic labeling/molecular indexing assays manually, it is convenient to mount the microwell array in a mechanical fixture to create a reaction chamber and facilitate the pipetting or dispensing of cell suspensions and assay reagents onto the array (FIGS. 69 and 70). In the example illustrated in FIG. 69, the fixture accepts a microwell array fabricated on a 1 mm thick substrate, and provides mechanical support in the form of a silicone gasket to confine the assay reagents to a reaction chamber that is 16 mm wide×35 mm long×approximately 4 mm deep, thereby enabling the use of 800 microliters to 1 milliliter of cell suspension and bead suspension (comprising bead-based oligonucleotide labels) to perform the assay.

The fixture consists of rigid, machined top and bottom plates (e.g., aluminum) and a compressible (e.g., silicone, polydimethylsiloxane) gasket for creating the walls of the chamber or well. Design features include: (i) Chamfered aperture edges and clearance for rotating microscope objectives in and out of position as needed (for viewing the microwell array at different magnifications). (ii) Controlled compression of the silicone gasket to ensure uniform, repeatable formation of a leak-proof seal with the microwell array substrate. (iii) Captive fasteners for convenient operation. (iv) A locating clamp mechanism for secure and repeatable positioning of the array. (v) Convenient disassembly for removal of the array during rinse steps.

The top and bottom plates may be fabricated using any of a variety of techniques (e.g., conventional machining, CNC machining, injection molding, 3D printing, etc.) using a variety of materials (e.g., aluminum, anodized aluminum, stainless steel, teflon, polymethylmethacrylate (PMMA), polycarbonate (PC), or similar rigid polymer materials).

Figure 71:
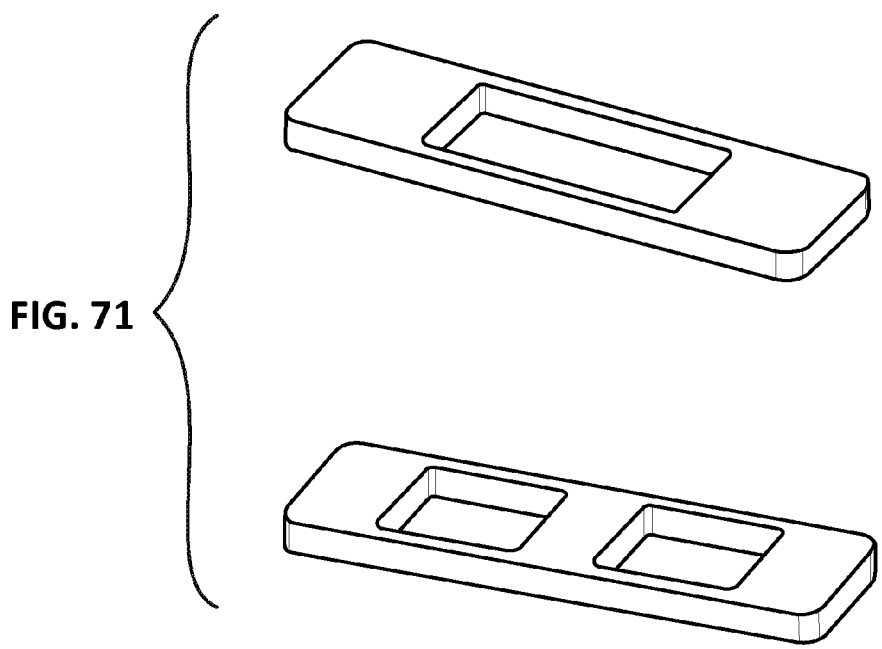
FIG. 71 illustrates two examples of elastomeric (e.g., polydimethylsiloxane) gaskets for use with the mechanical fixtures illustrated in FIGS. 69 and 70. The elastomeric gaskets provide for a leak-proof seal with the microwell array substrate to create a reagent well around the microwell array. The gaskets may contain one (FIG. 71 Upper), two (FIG. 71 Lower), or more openings for creating reagent wells.

The silicone (polydimethylsiloxane; PDMS) gasket may be configured to create multiple chambers (see FIG. 71) in order to run controls and experiments (or replicate experiments, or multiple independent experiments) in parallel. The gasket is molded from PDMS or similar elastomeric material using a Teflon mold that includes draft angles for the vertical gasket walls to provide for good release characteristics. Alternatively, molds can be machined from aluminum or other materials (e.g., black delrin, polyetherimide (ultem), etc.), and coated with Teflon if necessary to provide for good release characteristics. The gasket mold designs are inverted, i.e. so that the top surface of the molded part (i.e. the surface at the interface with a glass slide or silicon wafer used to cover the mold during casting) becomes the surface for creating a seal with the microwell array substrate during use, thereby avoiding potential problems with mold surface roughness and surface contamination in creating a smooth gasket surface (to ensure a leak-proof seal with the array substrate), and also providing for a flexible choice of substrate materials and the option of pre-assembly by using the microwell array substrate as a base during casting. The gasket mold designs may also include force focusing ridges at the boundaries of the well areas, i.e. the central mesa(s) in the mold (which form the well(s)) have raised ridges at the locations which become the perimeter of the well(s), so that a cover placed on top of the mold after filling rests on a small contact area at the precise location where good edge profile is critical for forming a leak-proof seal between the gasket and substrate during use.

Instrument Systems

The present disclosure also includes instrument systems and consumables to support the automation of multiplexed, single cell stochastic labeling/molecular indexing assays. Such systems may include consumable cartridges that incorporate microwell arrays integrated with flow cells, as well as the instrumentation necessary to provide control and analysis functionality such as (i) fluidics control, (ii) temperature control, (iii) cell and/or bead distribution and collection mechanisms, (iv) cell lysis mechanisms, (v) imaging capability, and (vi) image processing. In some embodiments, the input for the system comprises a cell sample and the output comprises a bead suspension comprising beads having attached oligonucleotides that incorporate sample tags, cell tags, and molecular indexing tags. In other embodiments, the system may include additional functionality, such as thermal cycling capability for performing PCR amplification, in which case the input for the system comprises a cell sample and the output comprises an oligonucleotide library resulting from amplification of the oligonucleotides incorporating sample tags, cell tags, and molecular indexing tags that were originally attached to beads. In yet other embodiments, the system may also include sequencing capability, with or without the need for oligonucleotide amplification, in which case the input for the system is a cell sample and the output comprises a dataset further comprising the sequences of all sample tag, cell tag, and molecular indexing tags associated with the target sequences of interest.

Microwell Array Flow Cells

In many embodiments of the automated assay system, the microwell array substrate will be packaged within a flow cell that provides for convenient interfacing with the rest of the fluid handling system and facilitates the exchange of fluids, e.g., cell and bead suspensions, lysis buffers, rinse buffers, etc., that are delivered to the microwell array. Design features may include: (i) one or more inlet ports for introducing cell samples, bead suspensions, and/or other assay reagents, (ii) one or more microwell array chambers designed to provide for uniform filling and efficient fluid-exchange while minimizing back eddies or dead zones, and (iii) one or more outlet ports for delivery of fluids to a sample collection point and/or a waste reservoir. In some embodiments, the design of the flow cell may include a plurality of microarray chambers that interface with a plurality of microwell arrays such that one or more cell samples may be processed in parallel. In some embodiments, the design of the flow cell may further include features for creating uniform flow velocity profiles, i.e. "plug flow", across the width of the array chamber to provide for more uniform delivery of cells and beads to the microwells, for example, by using a porous barrier located near the chamber inlet and upstream of the microwell array as a "flow diffuser", or by dividing each array chamber into several subsections that collectively cover the same total array area, but through which the divided inlet fluid stream flows in parallel. In some embodiments, the flow cell may enclose or incorporate more than one microwell array substrate. In some embodiments, the integrated microwell array/flow cell assembly may constitute a fixed component of the system. In some embodiments, the microwell array/flow cell assembly may be removable from the instrument.

In general, the dimensions of fluid channels and the array chamber(s) in flow cell designs will be optimized to (i) provide uniform delivery of cells and beads to the microwell array, and (ii) to minimize sample and reagent consumption. In some embodiments, the width of fluid channels will be between 50 microns and 20 mm. In other embodiments, the width of fluid channels may be at least 50 microns, at least 100 microns, at least 200 microns, at least 300 microns, at least 400 microns, at least 500 microns, at least 750 microns, at least 1 mm, at least 2.5 mm, at least 5 mm, at least 10 mm, or at least 20 mm. In yet other embodiments, the width of fluid channels may at most 20 mm, at most 10 mm, at most 5 mm, at most 2.5 mm, at most 1 mm, at most 750 microns, at most 500 microns, at most 400 microns, at most 300 microns, at most 200 microns, at most 100 microns, or at most 50 microns. In one embodiment, the width of fluid channels is about 2 mm. Those of skill in the art will appreciate that the width of the fluid channels may fall within any range bounded by any of these values (e.g., from about 250 microns to about 3 mm).

In some embodiments, the depth of the fluid channels will be between 50 microns and 10 mm. In other embodiments, the depth of fluid channels may be at least 50 microns, at least 100 microns, at least 200 microns, at least 300 microns, at least 400 microns, at least 500 microns, at least 750 microns, at least 1 mm, at least 1.25 mm, at least 1.5 mm, at least 1.75 mm, at least 2 mm, at least 2.5 mm, at least 3 mm, at least 3.5 mm, at least 4 mm, at least 4.5 mm, at least 5 mm, at least 5.5 mm, at least 6 mm, at least 6.5 mm, at least 7 mm, at least 7.5 mm, at least 8 mm, at least 8.5 mm, at least 9 mm, or at least 9.5 mm. In other embodiments, the depth of fluid channels may be at most 10 mm, at most 9.5 mm, at most 9 mm, at most 8.5 mm, at most 8 mm, at most 7.5 mm, at most 7 mm, at most 6.5 mm, at most 6 mm, at most 5.5 mm, at most 5 mm, at most 4.5 mm, at most 4 mm, at most 3.5 mm, at most 3 mm, at most 2 mm, at most 1.75 mm, at most 1.5 mm, at most 1.25 mm, at most 1 mm, at most 750 microns, at most 500 microns, at most 400 microns, at most 300 microns, at most 200 microns, at most 100 microns, or at most 50 microns. In one embodiment, the depth of the fluid channels is about 1 mm. Those of skill in the art will appreciate that the depth of the fluid channels may fall within any range bounded by any of these values (e.g., from about 800 microns to about 1 mm).

Flow cells may be fabricated using a variety of techniques and materials known to those of skill in the art. In general, the flow cell will be fabricated as a separate part and subsequently either mechanically clamped or permanently bonded to the microwell array substrate. Examples of suitable fabrication techniques include conventional machining, CNC machining, injection molding, 3D printing, alignment and lamination of one or more layers of laser or die-cut polymer films, or any of a number of microfabrication techniques such as photolithography and wet chemical etching, dry etching, deep reactive ion etching, or laser micromachining Once the flow cell part has been fabricated it may be attached to the microwell array substrate mechanically, e.g., by clamping it against the microwell array substrate (with or without the use of a gasket), or it may be bonded directly to the microwell array substrate using any of a variety of techniques (depending on the choice of materials used) known to those of skill in the art, for example, through the use of anodic bonding, thermal bonding, ultrasonic welding, or any of a variety of adhesives or adhesive films, including epoxy-based, acrylic-based, silicone-based, UV curable, polyurethane-based, or cyanoacrylate-based adhesives.

Flow cells may be fabricated using a variety of materials known to those of skill in the art. Examples of suitable materials include, but are not limited to, silicon, fused-silica, glass, any of a variety of polymers, e.g., polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, metals (e.g., aluminum, stainless steel, copper, nickel, chromium, and titanium), or a combination of these materials.

Cartridges

In many embodiments of the automated assay system, the microwell array, with or without an attached flow cell, will be packaged within a consumable cartridge that interfaces with the instrument system and which may incorporate additional functionality. Design features of cartridges may include (i) one or more inlet ports for creating fluid connections with the instrument and/or manually introducing cell samples, bead suspensions, and/or other assay reagents into the cartridge, (ii) one or more bypass channels, i.e. for self-metering of cell samples and bead suspensions, to avoid overfilling and/or back flow, (iii) one or more integrated microwell array/flow cell assemblies, or one or more chambers within which the microarray substrate(s) are positioned, (iv) integrated miniature pumps or other fluid actuation mechanisms for controlling fluid flow through the device, (v) integrated miniature valves for compartmentalizing pre-loaded reagents and/or controlling fluid flow through the device, (vi) vents for providing an escape path for trapped air, (vii) one or more sample and reagent waste reservoirs, (viii) one or more outlet ports for creating fluid connections with the instrument and/or providing a processed sample collection point, (ix) mechanical interface features for reproducibly positioning the removable, consumable cartridge with respect to the instrument system, and for providing access so that external magnets can be brought into close proximity with the microwell array, (x) integrated temperature control components and/or a thermal interface for providing good thermal contact with the instrument system, and (xi) optical interface features, e.g., a transparent window, for use in optical interrogation of the microwell array. In some embodiments, the cartridge is designed to process more than one sample in parallel. In some embodiments of the device, the cartridge may further comprise one or more removable sample collection chamber(s) that are suitable for interfacing with stand-alone PCR thermal cyclers and/or sequencing instruments. In some embodiments of the device, the cartridge itself is suitable for interfacing with stand-alone PCR thermal cyclers and/or sequencing instruments.

In some embodiments of the device, the cartridge may further comprise components that are designed to create physical and/or chemical barriers that prevent diffusion of (or increase path lengths and diffusion times for) large molecules in order to minimize cross-contamination between microwells. Examples of such barriers include, but are not limited to, a pattern of serpentine channels used for delivery of cells and beads to the microwell array, a retractable platen or deformable membrane that is pressed into contact with the surface of the microwell array substrate during lysis or incubation steps, the use of larger beads, e.g., Sephadex beads as described previously, to block the openings of the microwells, or the release of an immiscible, hydrophobic fluid from a reservoir within the cartridge during lysis or incubation steps, to effectively separate and compartmentalize each microwell in the array. Any or all of these barriers, or an embodiment without such barriers, may be combined with raising the viscosity of the solution in and adjacent to the microwells, e.g., through the addition of solution components such as glycerol or polyethylene glycol.

In general, the dimensions of fluid channels and the array chamber(s) in cartridge designs will be optimized to (i) provide uniform delivery of cells and beads to the microwell array, and (ii) to minimize sample and reagent consumption. In some embodiments, the width of fluid channels will be between 50 microns and 20 mm. In other embodiments, the width of fluid channels may be at least 50 microns, at least 100 microns, at least 200 microns, at least 300 microns, at least 400 microns, at least 500 microns, at least 750 microns, at least 1 mm, at least 2.5 mm, at least 5 mm, at least 10 mm, or at least 20 mm. In yet other embodiments, the width of fluid channels may at most 20 mm, at most 10 mm, at most 5 mm, at most 2.5 mm, at most 1 mm, at most 750 microns, at most 500 microns, at most 400 microns, at most 300 microns, at most 200 microns, at most 100 microns, or at most 50 microns. In one embodiment, the width of fluid channels is about 2 mm. Those of skill in the art will appreciate that the width of the fluid channels may fall within any range bounded by any of these values (e.g., from about 250 microns to about 3 mm).

In some embodiments, the depth of the fluid channels in cartridge designs will be between 50 microns and 10 mm. In other embodiments, the depth of fluid channels may be at least 50 microns, at least 100 microns, at least 200 microns, at least 300 microns, at least 400 microns, at least 500 microns, at least 750 microns, at least 1 mm, at least 1.25 mm, at least 1.5 mm, at least 1.75 mm, at least 2 mm, at least 2.5 mm, at least 3 mm, at least 3.5 mm, at least 4 mm, at least 4.5 mm, at least 5 mm, at least 5.5 mm, at least 6 mm, at least 6.5 mm, at least 7 mm, at least 7.5 mm, at least 8 mm, at least 8.5 mm, at least 9 mm, or at least 9.5 mm. In yet other embodiments, the depth of fluid channels may be at most 10 mm, at most 9.5 mm, at most 9 mm, at most 8.5 mm, at most 8 mm, at most 7.5 mm, at most 7 mm, at most 6.5 mm, at most 6 mm, at most 5.5 mm, at most 5 mm, at most 4.5 mm, at most 4 mm, at most 3.5 mm, at most 3 mm, at most 2 mm, at most 1.75 mm, at most 1.5 mm, at most 1.25 mm, at most 1 mm, at most 750 microns, at most 500 microns, at most 400 microns, at most 300 microns, at most 200 microns, at most 100 microns, or at most 50 microns. In one embodiment, the depth of the fluid channels is about 1 mm. Those of skill in the art will appreciate that the depth of the fluid channels may fall within any range bounded by any of these values (e.g., from about 800 microns to about 1 mm).

Cartridges may be fabricated using a variety of techniques and materials known to those of skill in the art. In general, the cartridges will be fabricated as a series of separate component parts (FIG. 72) and subsequently assembled (FIGS. 72 and 73) using any of a number of mechanical assembly or bonding techniques. Examples of suitable fabrication techniques include, but are not limited to, conventional machining, CNC machining, injection molding, thermoforming, and 3D printing. Once the cartridge components have been fabricated they may be mechanically assembled using screws, clips, and the like, or permanently bonded using any of a variety of techniques (depending on the choice of materials used), for example, through the use of thermal or ultrasonic bonding/welding or any of a variety of adhesives or adhesive films, including epoxy-based, acrylic-based, silicone-based, UV curable, polyurethane-based, or cyanoacrylate-based adhesives.

Cartridge components may be fabricated using any of a number of suitable materials, including but not limited to silicon, fused-silica, glass, any of a variety of polymers, e.g., polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, or metals (e.g., aluminum, stainless steel, copper, nickel, chromium, and titanium).

As described above, the inlet and outlet features of the cartridge may be designed to provide convenient and leak-proof fluid connections with the instrument, or may serve as open reservoirs for manual pipetting of samples and reagents into or out of the cartridge. Examples of convenient mechanical designs for the inlet and outlet port connectors include, but are not limited to, threaded connectors, swaged connectors, Luer lock connectors, Luer slip or "slip tip" connectors, press fit connectors, and the like. In some embodiments, the inlet and outlet ports of the cartridge may further comprise caps, spring-loaded covers or closures, phase change materials, or polymer membranes that may be opened or punctured when the cartridge is positioned in the instrument, and which serve to prevent contamination of internal cartridge surfaces during storage and/or which prevent fluids from spilling when the cartridge is removed from the instrument. As indicated above, in some embodiments the one or more outlet ports of the cartridge may further comprise a removable sample collection chamber that is suitable for interfacing with stand-alone PCR thermal cyclers and/or sequencing instruments.

As indicated above, in some embodiments the cartridge may include integrated miniature pumps or other fluid actuation mechanisms for control of fluid flow through the device. Examples of suitable miniature pumps or fluid actuation mechanisms include, but are not limited to, electromechanically- or pneumatically-actuated miniature syringe or plunger mechanisms, chemical propellants, membrane diaphragm pumps actuated pneumatically or by an external piston, pneumatically-actuated reagent pouches or bladders, or electro-osmotic pumps.

As described above, in some embodiments the cartridge may include miniature valves for compartmentalizing pre-loaded reagents and/or controlling fluid flow through the device. Examples of suitable miniature valves include, but are not limited to, one-shot "valves" fabricated using wax or polymer plugs that can be melted or dissolved, or polymer membranes that can be punctured; pinch valves constructed using a deformable membrane and pneumatic, hydraulic, magnetic, electromagnetic, or electromechanical (solenoid) acutation, one-way valves constructed using deformable membrane flaps, and miniature gate valves.

As indicated above, in some embodiments the cartridge may include vents for providing an escape path for trapped air. Vents may be constructed according to a variety of techniques known to those of skill in the art, for example, using a porous plug of polydimethylsiloxane (PDMS) or other hydrophobic material that allows for capillary wicking of air but blocks penetration by water. Vents may also be constructed as apertures through hydrophobic barrier materials, such that wetting to the aperture walls does not occur at the pressures used during operation.

Figure 72:
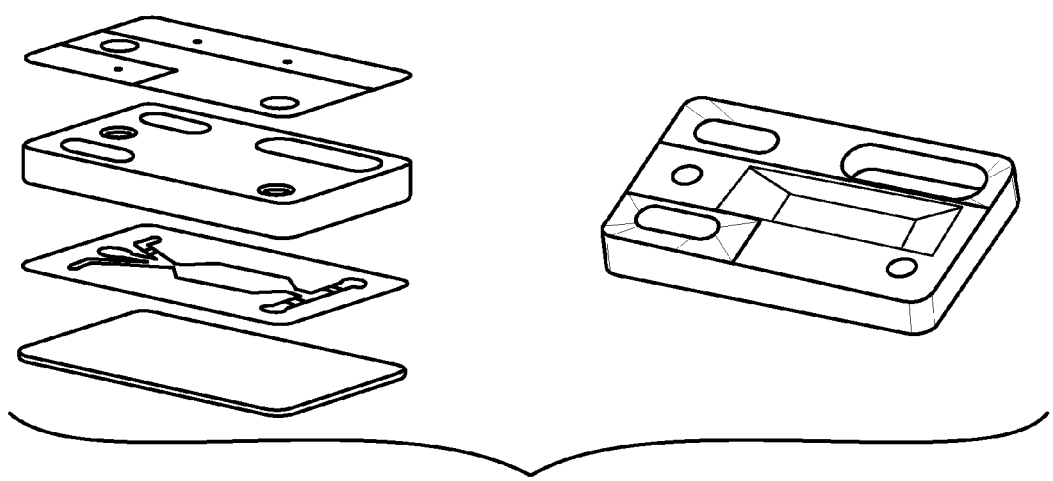
FIG. 72 depicts one embodiment of a cartridge within which a microwell array is packaged.
Figure 73:
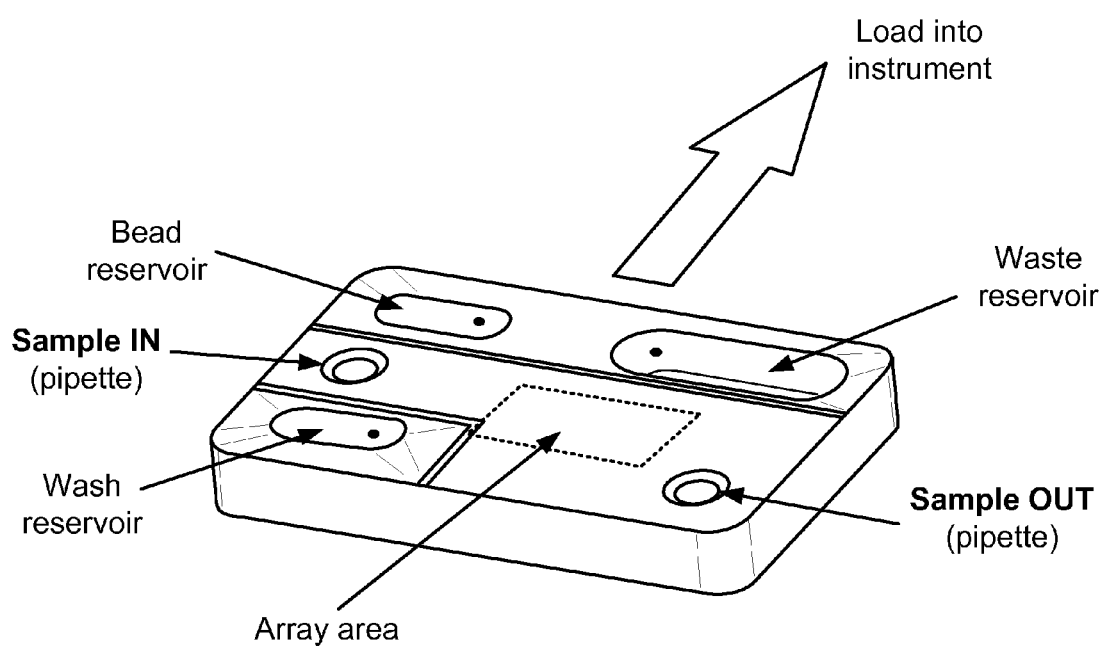
FIG. 73 depicts one embodiment of a cartridge designed to include onboard assay reagents with the packaged microwell array.

In general, the mechanical interface features of the cartridge provide for easily removable but highly precise and repeatable positioning of the cartridge relative to the instrument system. Suitable mechanical interface features include, but are not limited to, alignment pins, alignment guides, mechanical stops, and the like. In some embodiments, the mechanical design features will include relief features for bringing external apparatus, e.g., magnets or optical components, into close proximity with the microwell array chamber (FIG. 72).

In some embodiments, the cartridge will also include temperature control components or thermal interface features for mating to external temperature control modules. Examples of suitable temperature control elements include, but are not limited to, resistive heating elements, miniature infrared-emitting light sources, Peltier heating or cooling devices, heat sinks, thermistors, thermocouples, and the like. Thermal interface features will typically be fabricated from materials that are good thermal conductors (e.g., copper, gold, silver, aluminium, etc.) and will typically comprise one or more flat surfaces capable of making good thermal contact with external heating blocks or cooling blocks.

In many embodiments, the cartridge will include optical interface features for use in optical imaging or spectroscopic interrogation of the microwell array. Typically, the cartridge will include an optically transparent window, e.g., the microwell substrate itself or the side of the flow cell or microarray chamber that is opposite the microwell array, fabricated from a material that meets the spectral requirements for the imaging or spectroscopic technique used to probe the microwell array. Examples of suitable optical window materials include, but are not limited to, glass, fused-silica, polymethylmethacrylate (PMMA), polycarbonate (PC), cyclic olefin polymers (COP), or cyclic olefin copolymers (COC). Typically, the cartridge will include a second optically transparent or translucent window or region which can be used to illuminate the microwell array in transverse, reflected, or oblique illumination orientations.

Instruments

Figure 74:
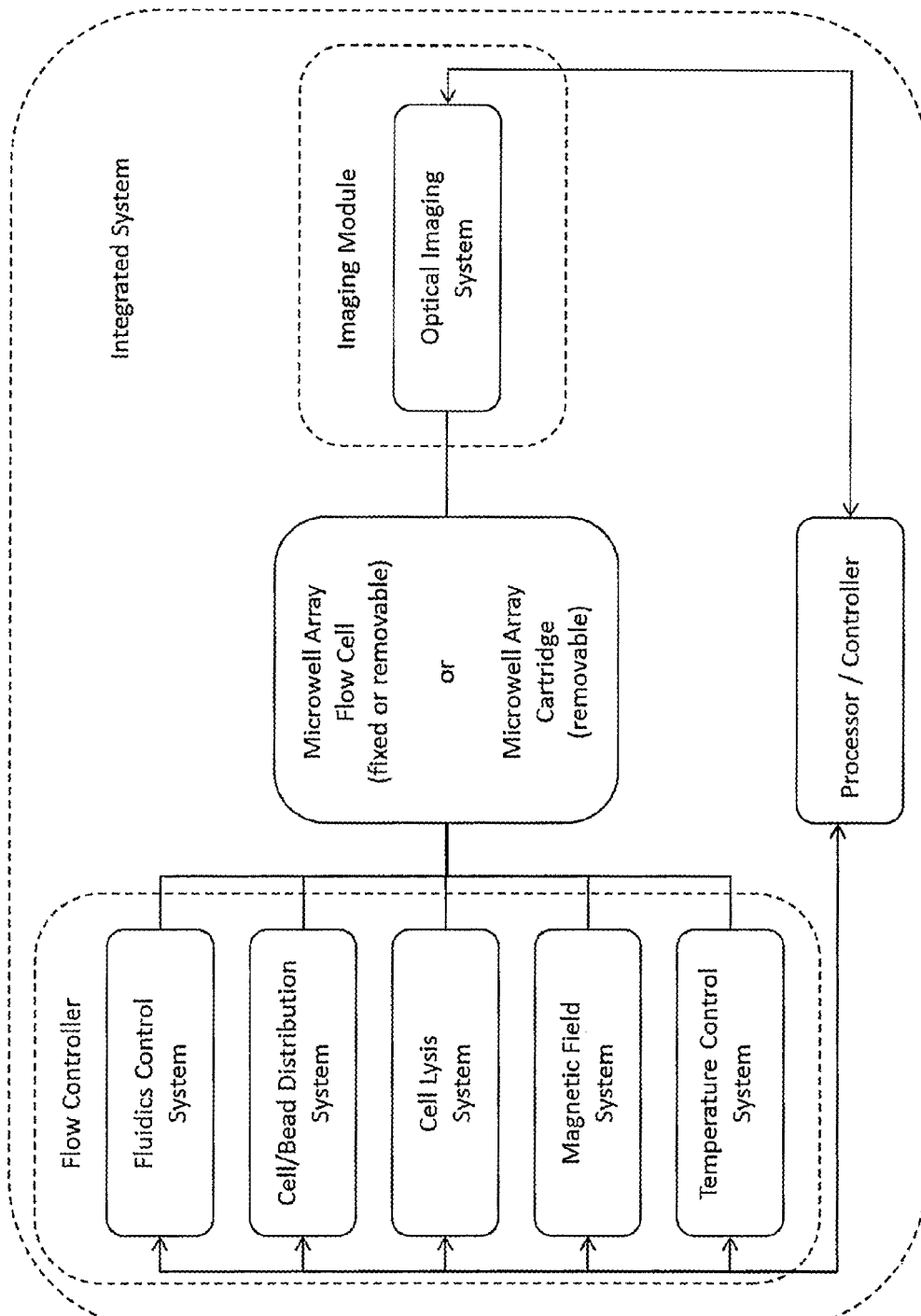
FIG. 74 provides a schematic illustration of an instrument system for performing multiplexed, single cell stochastic labeling/molecular indexing assay. The instrument system may provide a variety of control and analysis capabilities, and may be packaged as individual modules or as a fully integrated system. Microwell arrays may be integrated with flow cells that are either a fixed component of the system or are removable, or may be packaged within removable cartridges that further comprise pre-loaded assay reagent reservoirs and other functionality.
Figure 75:
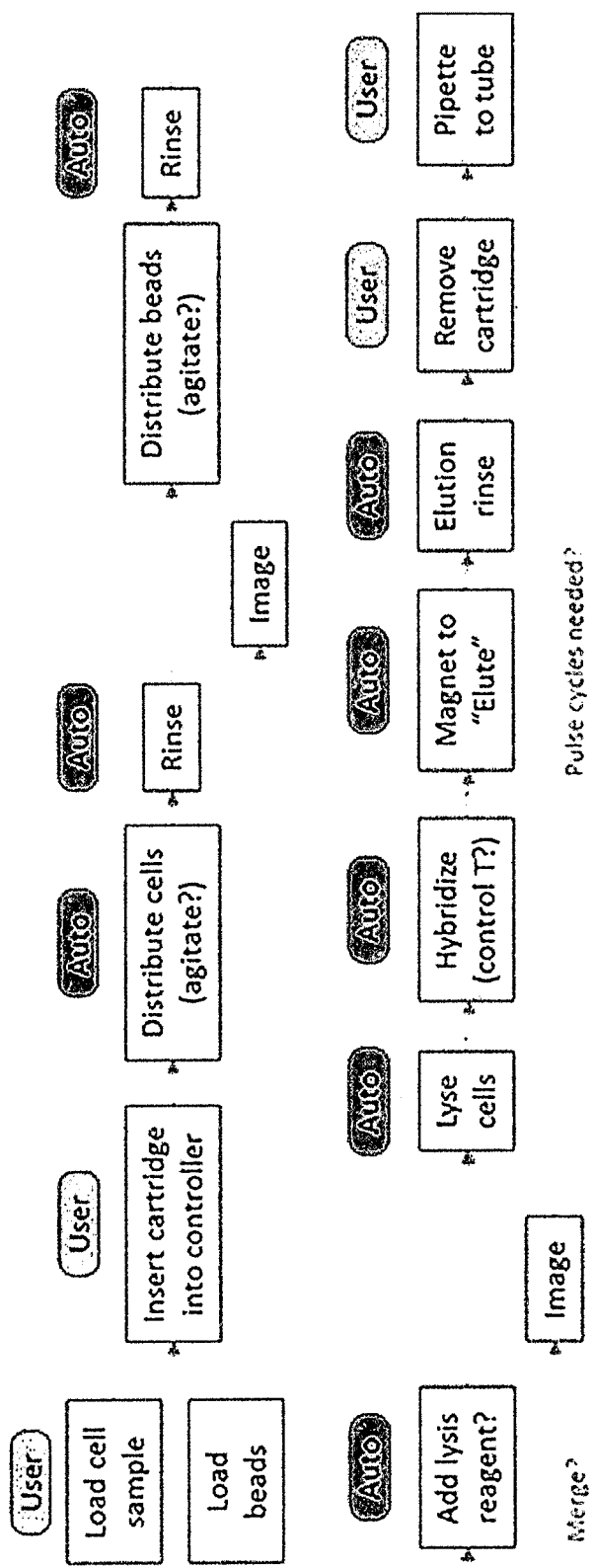
FIG. 75 illustrates one embodiment of the process steps to be performed by an automated system for performing multiplexed, single cell stochastic labeling/molecular indexing assays.

The present disclosure also includes instruments for use in the automation of multiplexed, single cell stochastic labeling/molecular indexing assays. As indicated above, these instruments may provide control and analysis functionality such as (i) fluidics control, (ii) temperature control, (iii) cell and/or bead distribution and collection mechanisms, (iv) cell lysis mechanisms, (v) magnetic field control, (vi) imaging capability, and (vii) image processing. In some embodiments, the instrument system may comprise one or more modules (one possible embodiment of which is illustrated schematically in FIG. 74), where each module provides one or more specific functional feature sets to the system. In other embodiments, the instrument system may be packaged such that all system functionality resides within the same package. FIG. 75 provides a schematic illustration of the process steps included in one embodiment of the automated system. As indicated above, in some embodiments, the system may comprise additional functional units, either as integrated components or as modular components of the system, that expand the functional capabilities of the system to include PCR amplification (or other types of oligonucleotide amplification techniques) and oligonucleotide sequencing.

In general, the instrument system will provide fluidics capability for delivering samples and/or reagents to the one or more microarray chamber(s) or flow cell(s) within one or more assay cartridge(s) connected to the system. Assay reagents and buffers may be stored in bottles, reagent and buffer cartridges, or other suitable containers that are connected to the cartridge inlets. The system may also include waste reservoirs in the form of bottles, waste cartridges, or other suitable waste containers for collecting fluids downstream of the assay cartridge(s). Control of fluid flow through the system will typically be performed through the use of pumps (or other fluid actuation mechanisms) and valves. Examples of suitable pumps include, but are not limited to, syringe pumps, programmable syringe pumps, peristaltic pumps, diaphragm pumps, and the like. In some embodiments, fluid flow through the system may be controlled by means of applying positive pneumatic pressure at the one or more inlets of the reagent and buffer containers, or at the inlets of the assay cartridge(s). In some embodiments, fluid flow through the system may be controlled by means of drawing a vacuum at the one or more outlets of the waste reservoirs, or at the outlets of the assay cartridge(s). Examples of suitable valves include, but are not limited to, check valves, electromechanical two-way or three-way valves, pneumatic two-way and three-way valves, and the like. In some embodiments, pulsatile flow may be applied during assay wash/rinse steps to facilitate complete and efficient exchange of fluids within the one or more microwell array flow cell(s) or chamber(s).

As indicated above, in some embodiments the instrument system may include mechanisms for further facilitating the uniform distribution of cells and beads over the microwell array. Examples of such mechanisms include, but are not limited to, rocking, shaking, swirling, recirculating flow, low frequency agitation (for example, using a rocker plate or through pulsing of a flexible (e.g., silicone) membrane that forms a wall of the chamber or nearby fluid channel), or high frequency agitation (for example, through the use of piezoelectric transducers). In some embodiments, one or more of these mechanisms is utilized in combination with physical structures or features on the interior walls of the flow cell or array chamber, e.g., mezzanine/top hat structures, chevrons, or ridge arrays, to facilitate mixing and/or to help prevent pooling of cells or beads within the array chamber. Flow-enhancing ribs on upper or lower surfaces of the flow cell or array chamber may be used to control flow velocity profiles and reduce shear across the microwell openings (i.e. to prevent cells or beads from being pulled out of the microwells during reagent exchange and rinse steps).

In some embodiments, the instrument system may include mechanical cell lysis capability as an alternative to the use of detergents or other reagents. Sonication using a high frequency piezoelectric transducer is one example of a suitable technique.

In some embodiments, the instrument system will include temperature control functionality for the purpose of facilitating the accuracy and reproducibility of assay results, for example, cooling of the microwell array flow cell or chamber may be advantageous for minimizing molecular diffusion between microwells. Examples of temperature control components that may be incorporated into the instrument system design include, but are not limited to, resistive heating elements, infrared light sources, Peltier heating or cooling devices, heat sinks, thermistors, thermocouples, and the like. In some embodiments of the system, the temperature controller may provide for programmable changes in temperature over specified time intervals.

As indicated elsewhere in this disclosure, many embodiments of the disclosed methods utilize magnetic fields for removing beads from the microwells upon completion of the assay. In some embodiments, the instrument system may further comprise use of magnetic fields for transporting beads into or out of the microwell array flow cell or chamber. Examples of suitable means for providing control of magnetic fields include, but are not limited to, use of electromagnets in fixed position(s) relative to the cartridge, or the use of permanent magnets that are mechanically repositioned as necessary. In some embodiments of the instrument system, the strength of the applied magnetic field(s) will be varied by varying the amount of current applied to one or more electromagnets. In some embodiments of the instrument system, the strength of the applied magnetic fields will be varied by changing the position of one or more permanent magnets relative to the position of the microarray chamber(s) using, for example, stepper motor-driven linear actuators, servo motor-driven linear actuators, or cam shaft mechanisms. In some embodiments of the instrument system, the use of pulsed magnetic fields may be advantageous, for example, to prevent clustering of magnetic beads. In some embodiments, a magnet in close proximity to the array or chamber may be moved, once or multiple times, between at least two positions relative to the microwell array. Motion of the magnets can serve to agitate beads within microwells, to facilitate removal of beads from microwells, or to collect magnetic beads at a desired location.

As indicated above, in many embodiments the instrument system will include optical imaging and/or other spectroscopic capabilities. Such functionality may be useful, for example, for inspection of the microwell array(s) to determine whether or not the array has been uniformly and optimally populated with cells and/or beads. Any of a variety of imaging modes may be utilized, including but not limited to, bright-field, dark-field, and fluorescence/luminescence imaging. The choice of imaging mode will impact the design of microwell arrays, flow cells, and cartridge chambers in that the array substrate and/or opposing wall of the flow cell or array chamber will necessarily need to be transparent or translucent over the spectral range of interest. In some embodiments, each microwell array may be imaged in its entirety within a single image. In some embodiments, a series of images may be "tiled" to create a high resolution image of the entire array. In some embodiment, a single image that represents a subsection of the array may be used to evaluate properties, e.g., cell or bead distributions, for the array as a whole. In some embodiments, dual wavelength excitation and emission (or multi-wavelength excitation and/or emission) imaging may be performed. Any of a variety of light sources may be used to provide the imaging and/or excitation light, including but not limited to, tungsten lamps, tungsten-halogen lamps, arc lamps, lasers, light emitting diodes (LEDs), or laser diodes. Any of a variety of image sensors may be used for imaging purposes, including but not limited to, photodiode arrays, charge-coupled device (CCD) cameras, or CMOS image sensors. The optical system will typically include a variety of optical components for steering, shaping, filtering, and/or focusing light beams through the system. Examples of suitable optical components include, but are not limited to, lenses, mirrors, prisms, diffraction gratings, colored glass filters, narrowband interference filters, broadband interference filters, dichroic reflectors, optical fibers, optical waveguides, and the like. In some embodiments, the instrument system may use an optically transparent microarray substrate as a waveguide for delivering excitation light to the microwell array. The choice of imaging mode may also enable the use of other types of assays to be run in parallel with stochastic labeling/molecular indexing assays, for example, the use of trypan blue live cell/dead cell assays with bright field imaging, the use of fluorescence-based live cell/dead cell assays with fluorescence imaging, etc. Correlation of viability data for individual cells with the cell tag associated with each bead in the associated microwell may provide an additional level of discrimination in analyzing the data from multiplexed, single cell assays. Alternatively, viability data in the form of statistics for multiple cells may be employed for enhancing the analytical capabilities and quality assurance of the assay.

In some embodiments, the system may comprise non-imaging and/or non-optical capabilities for probing the microwell array. Examples of non-imaging and/or non-optical techniques for detecting trapped air bubbles, determining the cell and/or bead distribution over the array, etc., include but are not limited to measurements of light scattering, ultraviolet/visible/infrared absorption measurements (e.g., using stained cells and/or beads that incorporate dyes), coherent raman scattering, and conductance measurements (e.g., using microfabricated arrays of electrodes in register with the microwell arrays).

System Processor and Software

In general, instrument systems designed to support the automation of multiplexed, single cell stochastic labeling/molecular indexing assays will include a processor or computer, along with software to provide (i) instrument control functionality, (ii) image processing and analysis capability, and (iii) data storage, analysis, and display functionality.

In many embodiments, the instrument system will comprise a computer (or processor) and computer-readable media that includes code for providing a user interface as well as manual, semi-automated, or fully-automated control of all system functions, i.e. control of the fluidics system, the temperature control system, cell and/or bead distribution functions, magnetic bead manipulation functions, and the imaging system. Examples of fluid control functions provided by the instrument control software include, but are not limited to, volumetric fluid flow rates, fluid flow velocities, the timing and duration for sample and bead addition, reagent addition, and rinse steps. Examples of temperature control functions provided by the instrument control software include, but are not limited to, specifying temperature set point(s) and control of the timing, duration, and ramp rates for temperature changes. Examples of cell and/or bead distribution functions provided by the instrument control software include, but are not limited to, control of agitation parameters such as amplitude, frequency, and duration. Examples of magnetic field functions provided by the instrument control software include, but are not limited to, the timing and duration of the applied magnetic field(s), and in the case of electromagnets, the strength of the magnetic field as well. Examples of imaging system control functions provided by the instrument control software include, but are not limited to, autofocus capability, control of illumination and/or excitation light exposure times and intensities, control of image acquisition rate, exposure time, and data storage options.

In some embodiments of the instrument system, the system will further comprise computer-readable media that includes code for providing image processing and analysis capability. Examples of image processing and analysis capability provided by the software include, but are not limited to, manual, semi-automated, or fully-automated image exposure adjustment (e.g., white balance, contrast adjustment, signal-averaging and other noise reduction capability, etc.), automated object identification (i.e. for identifying cells and beads in the image), automated statistical analysis (i.e. for determining the number of cells and/or beads identified per unit area of the microwell array, or for identifying wells that contain more than one cell or more than one bead), and manual measurement capabilities (e.g., for measuring distances between objects, etc.). In some embodiments, the instrument control and image processing/analysis software will be written as separate software modules. In some embodiments, the instrument control and image processing/analysis software will be incorporated into an integrated package. In some embodiments, the system software may provide integrated real-time image analysis and instrument control, so that cell and bead sample loading steps can be prolonged or repeated until optimal cell/bead distributions are achieved.

In some embodiments of the instrument system, the system will comprise computer-readable media that includes code for providing sequence data analysis. Examples of sequence data analysis functionality that may be provided by the data analysis software includes, but is not limited to, (i) algorithms for determining the number of reads per gene per cell, and the number of unique transcript molecules per gene per cell, based on the data provided by sequencing the oligonucleotide library created by running the assay, (ii) statistical analysis of the sequencing data, e.g., principal component analysis, for predicting confidence intervals for determinations of the number of transcript molecules per gene per cell, etc., (iii) sequence alignment capabilities for alignment of gene sequence data with known reference sequences, (iv) decoding/demultiplexing of sample barcodes, cell barcodes, and molecular barcodes, and (v) automated clustering of molecular labels to compensate for amplification or sequencing errors.

Figure 76:
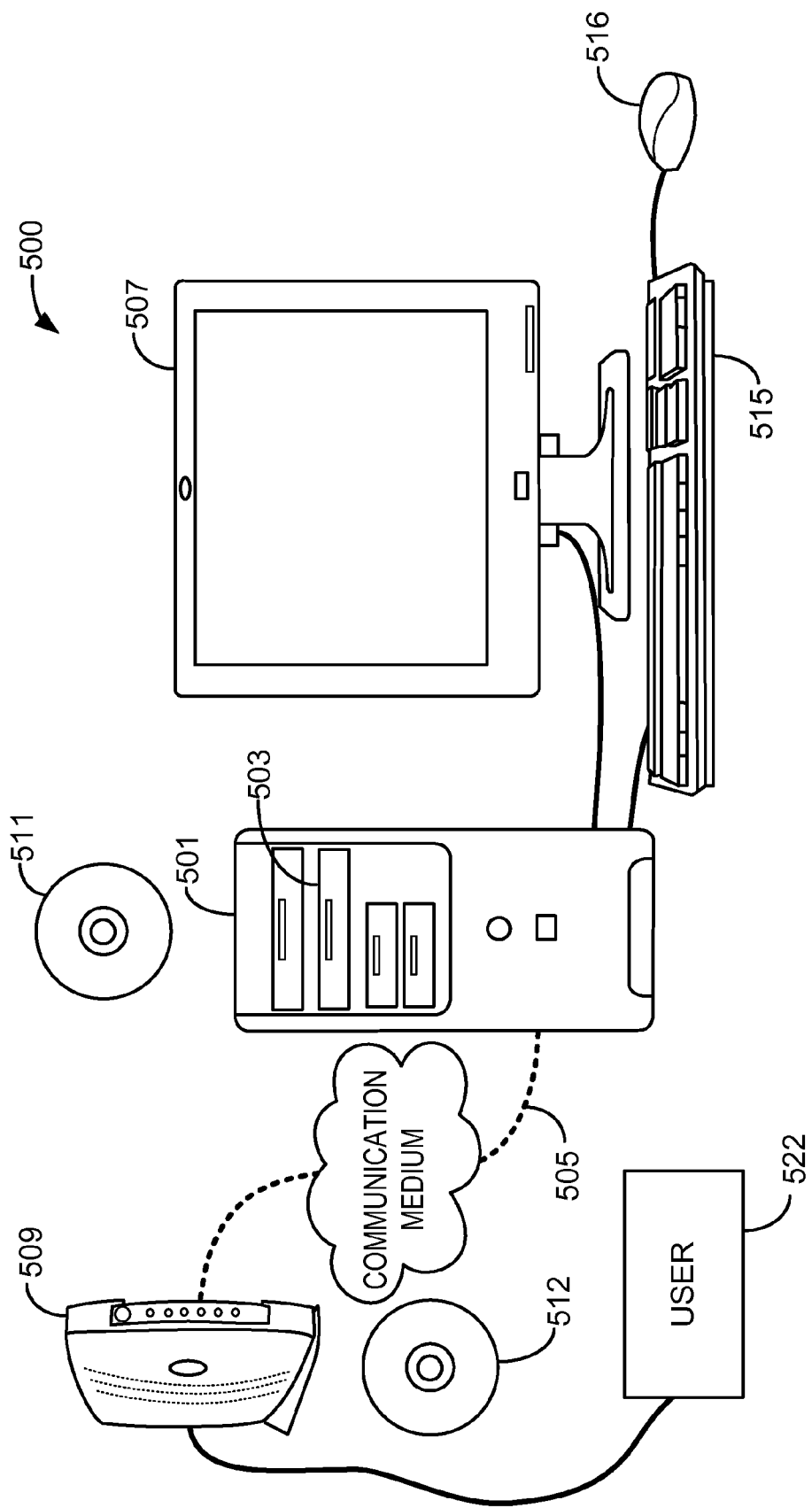
FIG. 76 illustrates one embodiment of a computer system or processor for providing instrument control and data analysis capabilities for the assay system presently disclosed.

In general, the computer or processor included in the presently disclosed instrument systems, as illustrated in FIG. 76, may be further understood as a logical apparatus that can read instructions from media 511 and/or a network port 505, which can optionally be connected to server 509 having fixed media 512. The system 500, such as shown in FIG. 76 can include a CPU 501, disk drives 503, optional input devices such as keyboard 515 and/or mouse 516 and optional monitor 507. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 522 as illustrated in FIG. 76.

Figure 77:
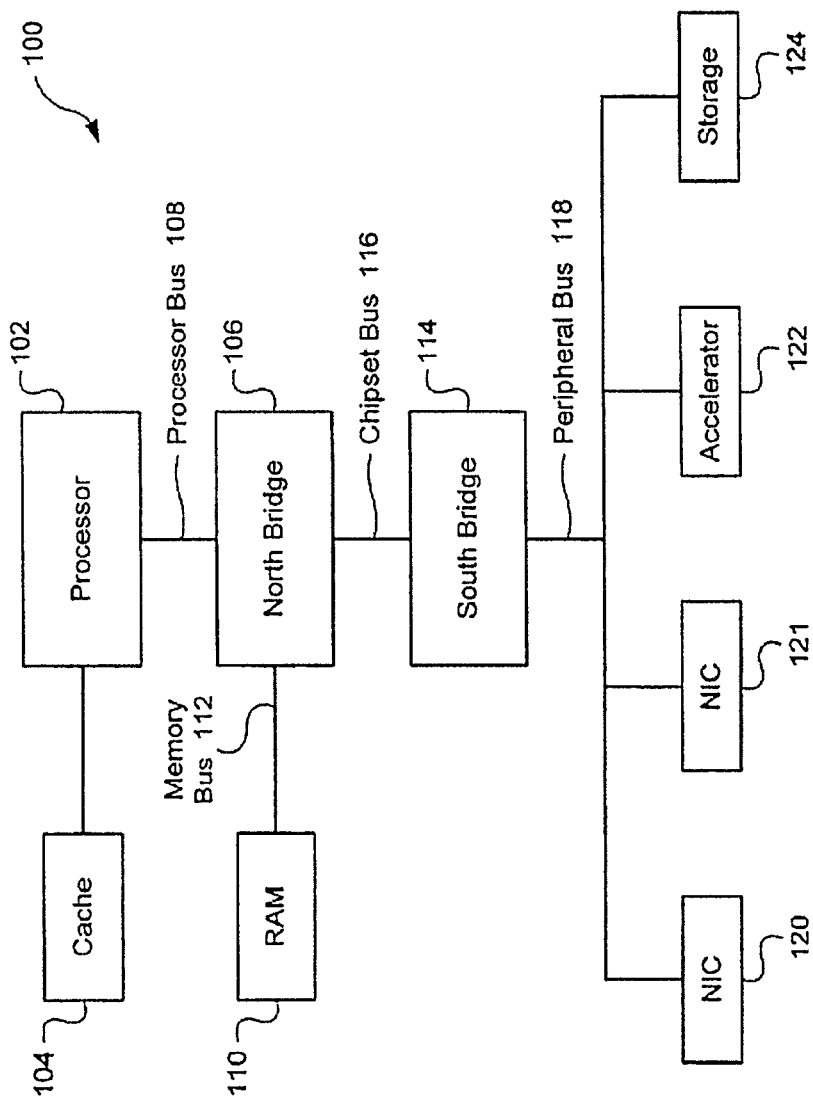
FIG. 77 shows a block diagram illustrating one example of a computer system architecture that can be used in connection with example embodiments of the assay systems of the present disclosure.

FIG. 77 is a block diagram illustrating a first example architecture of a computer system 100 that can be used in connection with example embodiments of the present disclosure. As depicted in FIG. 77, the example computer system can include a processor 102 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 77, a high speed cache 104 can be connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 can include an accelerator card 122 attached to the peripheral bus 118. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 78:
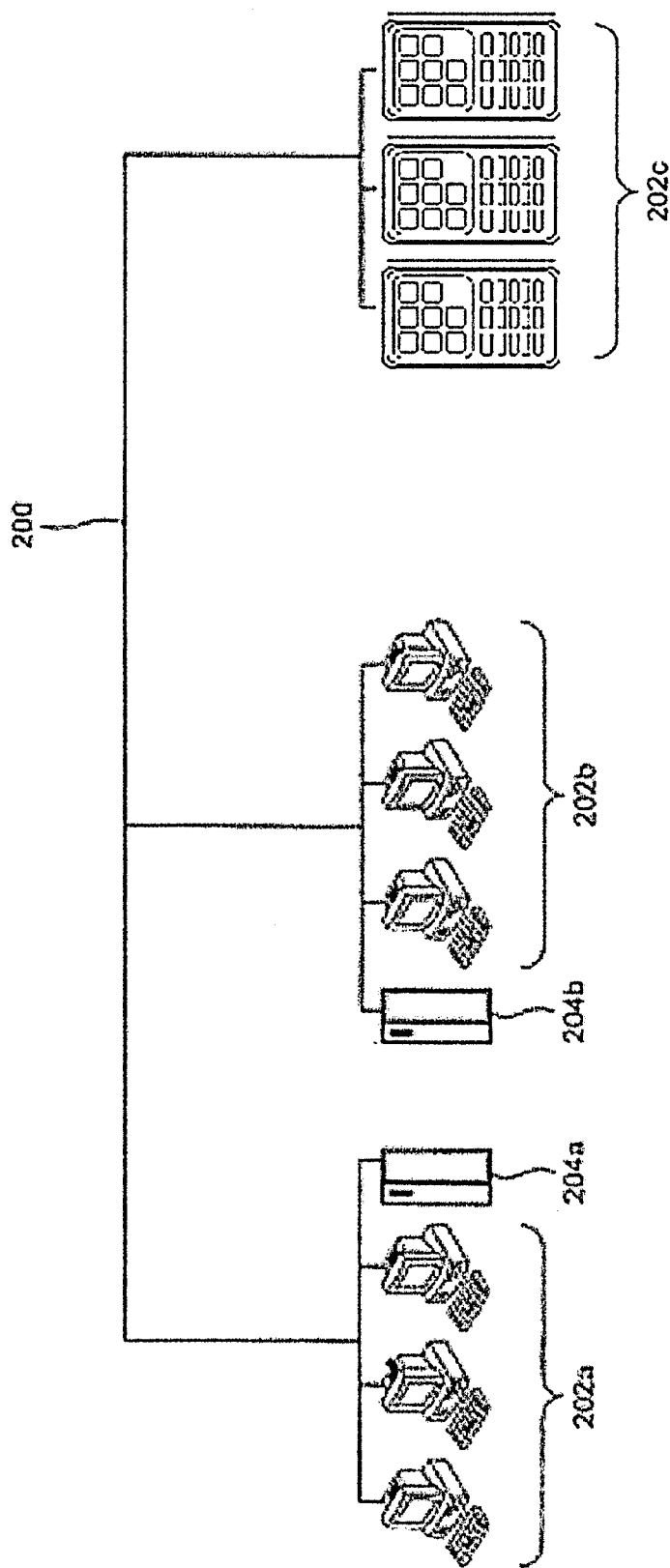
FIG. 78 depicts a diagram showing a network with a plurality of computer systems, cell phones, personal data assistants, and Network Attached Storage (NAS), that can be used with example embodiments of the assay systems of the present disclosure.

FIG. 78 is a diagram showing a network 200 with a plurality of computer systems 202a, and 202b, a plurality of cell phones and personal data assistants 202c, and Network Attached Storage (NAS) 204a, and 204b. In example embodiments, systems 212a, 212b, and 212c can manage data storage and optimize data access for data stored in Network Attached Storage (NAS) 214a and 214b. A mathematical model can be used for the data and be evaluated using distributed parallel processing across computer systems 212a, and 212b, and cell phone and personal data assistant systems 212c. Computer systems 212a, and 212b, and cell phone and personal data assistant systems 212c can also provide parallel processing for adaptive data restructuring of the data stored in Network Attached Storage (NAS) 214a and 214b. FIG. 78 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 79:
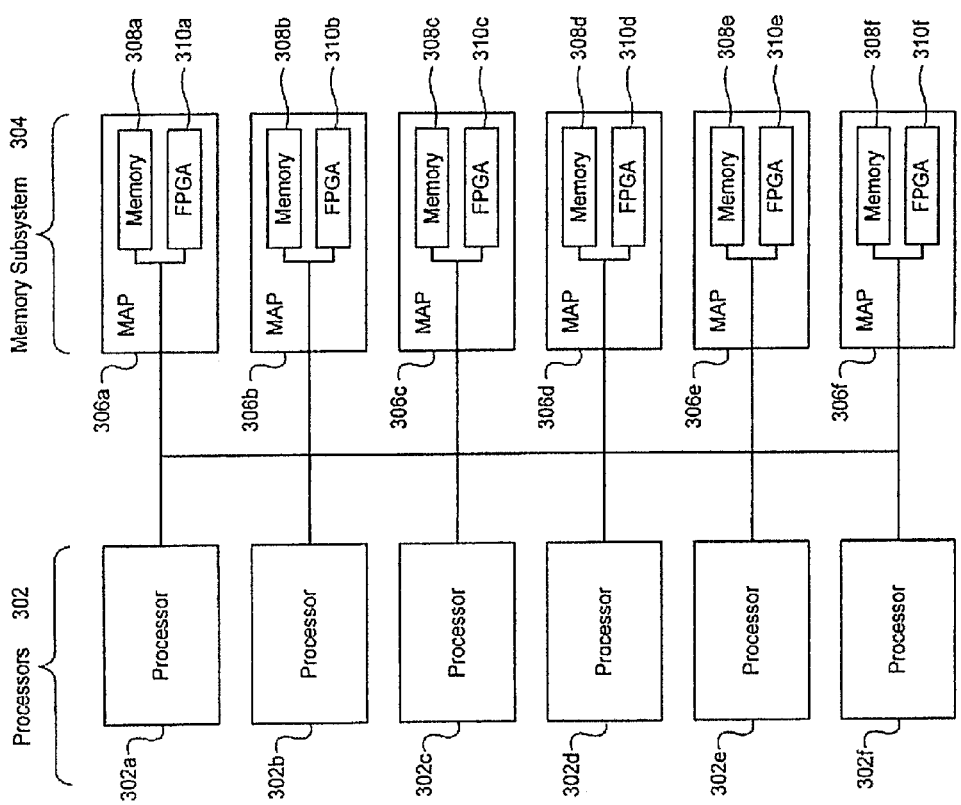
FIG. 79 depicts a block diagram of a multiprocessor computer system that can be used with example embodiments of the assay systems of the present disclosure.
Figure 80:
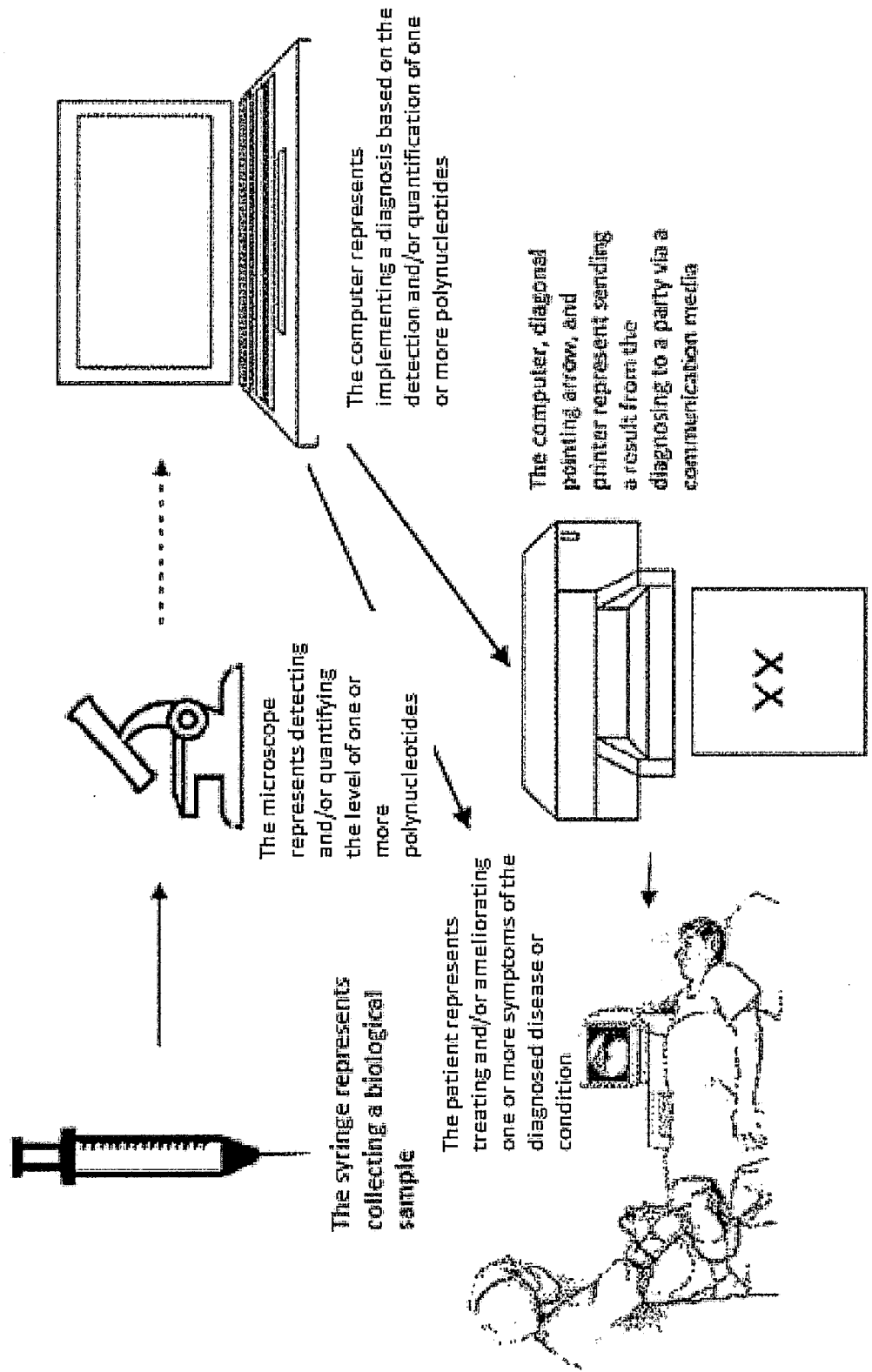
FIG. 80 depicts a diagram of the analysis of a test sample and communication of the test result obtained from the test sample via a communication media.

FIG. 79 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. Each MAP 306a-f can comprise a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 308a-f, allowing it to execute tasks independently of, and asynchronously from, the respective microprocessor 302a-f In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer subsystem of the present disclosure can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 79, system on chips (SOCs), application specific integrated circuits (ASICs), or other processing and logic elements. For example, the Set Processor and Optimizer can be implemented with hardware acceleration through the use of a hardware accelerator card, such as accelerator card 122 illustrated in FIG. 77.

Oligonucleotides (e.g., Molecular Barcodes)

The methods and kits disclosed herein may comprise one or more oligonucleotides or uses thereof. The oligonucleotides may be attached to a solid support disclosed herein. Attachment of the oligonucleotide to the solid support may occur through functional group pairs on the solid support and the oligonucleotide. The oligonucleotide may be referred to as a molecular bar code. The oligonucleotide may be referred to as a label (e.g., molecular label, cellular label) or tag (e.g., sample tag).

Oligonucleotides may comprise a universal label. A universal label may be the same for all oligonucleotides in a sample. A universal label may be the same for oligonucleotides in a set of oligonucleotides. A universal label may be the same for two or more sets of oligonucleotides. A universal label may comprise a sequence of nucleic acids that may hybridize to a sequencing primer. Sequencing primers may be used for sequencing oligonucleotides comprising a universal label. Sequencing primers (e.g., universal sequencing primers) may comprise sequencing primers associated with high-throughput sequencing platforms. A universal label may comprise a sequence of nucleic acids that may hybridize to a PCR primer. A universal label may comprise a sequence of nucleic acids that may hybridize to a sequencing primer and a PCR primer. The sequence of nucleic acids of the universal label that may hybridize to a sequencing and/or PCR primer may be referred to as a primer binding site. A universal label may comprise a sequence that may be used to initiate transcription of the oligonucleotide. A universal label may comprise a sequence that may be used for extension of the oligonucleotide or a region within the oligonucleotide. A universal label may be at least about 1, 2, 3, 4, 5, 10, 15, 20, 25, 30, 35, 40, 45, 50 or more nucleotides in length. A universal label may comprise at least about 10 nucleotides. A universal label may be at most about 1, 2, 3, 4, 5, 10, 15, 20, 25, 30, 35, 40, 45, 50 or more nucleotides in length.

Oligonucleotides may comprise a cellular label. A cellular label may comprise a nucleic acid sequence that may provide information for which cell the oligonucleotide is contacted to (e.g., determining which nucleic acid originated from which cell). At least 60%, 70%, 80%, 85%, 90%, 95%, 97%, 99% or 100% of oligonucleotides on the same solid support may comprise the same cellular label. At least 60% of oligonucleotides on the same solid support may comprise the same cellular label. At least 95% of oligonucleotides on the same solid support may comprise the same cellular label. All the oligonucleotides on a same solid support may comprise the same cellular label. The cellular label of the oligonucleotides on a first solid support may be different than the cellular labels of the oligonucleotides on the second solid support.

A cellular label may be at least about 1, 2, 3, 4, 5, 10, 15, 20, 25, 30, 35, 40, 45, 50 or more nucleotides in length. A cellular label may be at most about 300, 200, 100, 90, 80, 70, 60, 50, 40, 30, 20, 15, 12, 10, 9, 8, 7, 6, 5, 4 or fewer or more nucleotides in length. A cellular label may comprise between about 5 to about 200 nucleotides. A cellular label may comprise between about 10 to about 150 nucleotides. A cellular label may comprise between about 20 to about 125 nucleotides in length.

Oligonucleotides may comprise a molecular label. A molecular label may comprise a nucleic acid sequence that may provide identifying information for the specific nucleic acid species hybridized to the oligonucleotide. Oligonucleotides conjugated to a same solid support may comprise different molecular labels. In this way, the molecular label may distinguish the types of target nucleic acids (e.g., genes), that hybridize to the different oligonucleotides. A molecular label may be at least about 1, 2, 3, 4, 5, 10, 15, 20, 25, 30, 35, 40, 45, 50 or more nucleotides in length. A molecular label may be at most about 300, 200, 100, 90, 80, 70, 60, 50, 40, 30, 20, 15, 12, 10, 9, 8, 7, 6, 5, 4 or fewer nucleotides in length.

Oligonucleotides may comprise a sample label (e.g., sample index). A sample label may comprise a nucleic acid sequence that may provide information about from where a target nucleic acid originated. For example, a sample label may be different on different solid supports used in different experiments. A sample label may be at least about 1, 2, 3, 4, 5, 10, 15, 20, 25, 30, 35, 40, 45, 50 or more nucleotides in length. A sample label may be at most about 300, 200, 100, 90, 80, 70, 60, 50, 40, 30, 20, 15, 12, 10, 9, 8, 7, 6, 5, 4 or fewer nucleotides in length.

An oligonucleotide may comprise a universal label, a cellular label, a molecular label and a sample label, or any combination thereof. In combination, the sample label may be used to distinguish target nucleic acids between samples, the cellular label may be used to distinguish target nucleic acids from different cells in the sample, the molecular label may be used to distinguish the different target nucleic acids in the cell (e.g., different copies of the same target nucleic acid), and the universal label may be used to amplify and sequence the target nucleic acids.

A universal label, a molecular label, a cellular label, linker label and/or a sample label may comprise a random sequence of nucleotides. A random sequence of nucleotides may be computer generated. A random sequence of nucleotides may have no pattern associated with it. A universal label, a molecular label, a cellular label, linker label and/or a sample label may comprise a non-random (e.g., the nucleotides comprise a pattern) sequence of nucleotides. Sequences of the universal label, a molecular label, a cellular label, linker label and/or a sample label may be commercially available sequences. Sequences of the universal label, a molecular label, a cellular label, linker label and/or a sample label may be comprise randomer sequences. Randomer sequences may refer to oligonucleotide sequences composed of all possible sequences for a given length of the randomer. Alternatively, or additionally, a universal label, a molecular label, a cellular label, linker label and/or a sample label may comprise a predetermined sequence of nucleotides.

FIG. 1 shows an exemplary oligonucleotide of the disclosure comprising a universal label, a cellular label and a molecular label.

Figure 3:
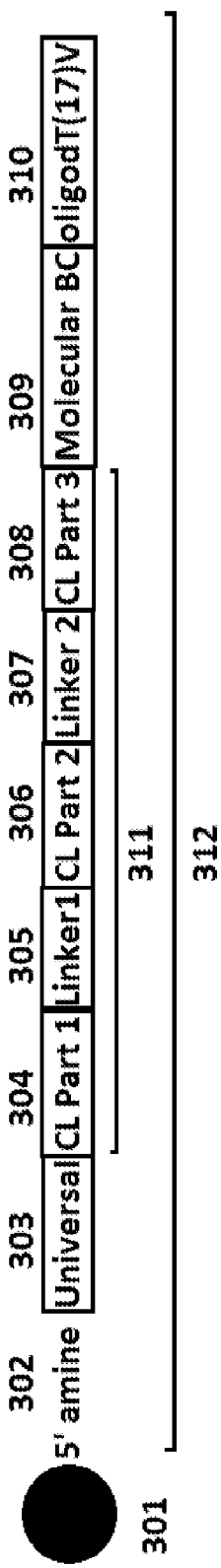
FIG. 3 depicts an exemplary oligonucleotide coupled bead.

FIG. 3 shows an exemplary oligonucleotide coupled solid support comprising a solid support (301) coupled to an oligonucleotide (312). The oligonucleotide (312) comprises a chemical group (5' amine, 302), a universal label (303), a cellular label (311), a molecular label (Molecular BC, 311), and a target binding region (oligodT, 310). In this schematic, the cellular label (311) comprises a first cell label (CL Part 1, 304), a first linker (Linker1, 305), a second cell label (CL Part 2, 306), a second linker (Linker2, 307), a third cell label (CL Part 3, 308). The cellular label (311) is common for each oligonucleotide on the solid support. The cellular labels (311) for two or more beads may be different. The cellular labels (311) for two or more beads may differ by the cell labels (e.g., CL Part 1 (304), CL Part 2 (306), CL Part 3 (308)). The cellular labels (311) for two or more beads may differ by the first cell label (304), second cell label (306), third cell label (308), or a combination thereof. The first and second linkers (303, 305) of the cellular labels (311) may be identical for two or more oligonucleotide coupled solid supports. The universal label (303) may be identical for two or more oligonucleotide coupled solid supports. The universal label (303) may be identical for two or more oligonucleotides on the same solid support. The molecular label (311) may be different for at least two or more oligonucleotides on the solid support. The solid support may comprise 100 or more oligonucleotides. The solid support may comprise 1000 or more oligonucleotides. The solid support may comprise 10000 or more oligonucleotides. The solid support may comprise 100000 or more oligonucleotides.

In addition to a universal label, a cellular label, and a molecular label, an oligonucleotide may comprise a target binding region. A target binding region may comprise a nucleic acid sequence that may bind to a target nucleic acid (e.g., a cellular nucleic acid to be analyzed). A target binding region may be a gene specific sequence. For example, a target binding region may comprise a nucleic acid sequence that may attach (e.g., hybridize) to a specific location of a specific target nucleic acid. A target binding region may comprise a non-specific target nucleic acid sequence. A non-specific target nucleic acid sequence may refer to a sequence that may bind to multiple target nucleic acids, independent of the specific sequence of the target nucleic acid. For example, target binding region may comprise a random multimer sequence or an oligo dT sequence (e.g., a stretch of thymidine nucleotides that may hybridize to a poly-adenylation tail on mRNAs). A random multimer sequence can be, for example, a random dimer, trimer, quatramer, pentamer, hexamer, septamer, octamer, nonamer, decamer, or higher multimer sequence of any length. A target binding region may be at least about 5, 10, 15, 20, 25, 30, 35, 40, 45, 50 or more nucleotides in length. A target binding region may be at most about 5, 10, 15, 20, 25, 30, 35, 40, 45, 50 or more nucleotides in length.

An oligonucleotide may comprise a plurality of labels. For example an oligonucleotide may comprise at least about 1, 2, 3, 4, 5, 6, 7, or 8 or more universal labels. An oligonucleotide may comprise at most about 1, 2, 3, 4, 5, 6, 7, or 8 or more universal labels. An oligonucleotide may comprise at least about 1, 2, 3, 4, 5, 6, 7, or 8 or more cellular labels. An oligonucleotide may comprise at most about 1, 2, 3, 4, 5, 6, 7, or 8 or more cellular labels. An oligonucleotide may comprise at least about 1, 2, 3, 4, 5, 6, 7, or 8 or more molecular labels. An oligonucleotide may comprise at most about 1, 2, 3, 4, 5, 6, 7, or 8 or more molecular labels. An oligonucleotide may comprise at least about 1, 2, 3, 4, 5, 6, 7, or 8 or more sample labels. An oligonucleotide may comprise at most about 1, 2, 3, 4, 5, 6, 7, or 8 or more sample labels. An oligonucleotide may comprise at least about 1, 2, 3, 4, 5, 6, 7, or 8 or more target binding regions. An oligonucleotide may comprise at most about 1, 2, 3, 4, 5, 6, 7, or 8 or more target binding regions.

When an oligonucleotide comprises more than one of a type of label (e.g., more than one cellular label or more than one molecular label), the labels may be interspersed with a linker label sequence. A linker label sequence may be at least about 5, 10, 15, 20, 25, 30, 35, 40, 45, 50 or more nucleotides in length. A linker label sequence may be at most about 5, 10, 15, 20, 25, 30, 35, 40, 45, 50 or more nucleotides in length. In some instances, a linker label sequence is 12 nucleotides in length. A linker label sequence may be used to facilitate the synthesis of the oligonucleotide, such as diagrammed in FIG. 2A.

The number of oligonucleotides conjugated to a solid support may be 1, 2, 3, 4, 5, 6, 7, 8, 9, or 10-fold more than the number of target nucleic acids in a cell. In some instances, at least 10, 20, 30, 40, 50, 60, 70, 80, 90 or 100% of the oligonucleotides are bound by a target nucleic acid. In some instances, at most 10, 20, 30, 40, 50, 60, 70, 80, 90 or 100% of the oligonucleotides are bound by a target nucleic acid. In some instances, at least 1, 2, 3, 4, 5, 6, 7, 8, 9, 10, 20, 30, 40, 50, 60, 70, 80, 90 or 100 or more different target nucleic acids are captured by the oligonucleotides on a solid support. In some instances, at most 1, 2, 3, 4, 5, 6, 7, 8, 9, 10, 20, 30, 40, 50, 60, 70, 80, 90 or 100 or more different target nucleic acids are captured by the oligonucleotides on a solid support.

A polymer may comprise additional solid supports. For example, a polymer may be dotted with beads. The beads may be spatially located at different regions of the polymer. The beads or supports comprising oligonucleotides of the disclosure may be spatially addressed. The beads or supports may comprise a barcode corresponding to a spatial address on the polymer. For example, each bead or support of a plurality of beads or supports may comprise barcode that corresponds to a position on a polymer, such as a position on an array or a particular microwall of a plurality of microwells. The spatial address can be decoded to determine the location from which a bead or support was positioned. For example, a spatial address, such as a barcode, can be decoded by hybridization of an oligonucleotide to the barcode or by sequencing the barcode. Alternatively, beads or supports can bear other types of barcodes, such as graphical features, chemical groups, colors, fluorescence, or combinations any combination thereof, for spatial address decoding purposes.

The methods and kits disclosed herein may comprise one or more sets of molecular barcodes. One or more molecular barcodes may comprise a sample index region and a label region. Two or more molecular barcodes of a set of molecular barcodes may comprise the same sample index region and two or more different label regions. Two or more molecular barcodes of two or more sets of molecular barcodes may comprise two or more different sample index regions. Two or more molecular barcodes from a set of molecular barcodes may comprise different label regions. Two or more molecular barcodes of two or more sets of molecular barcodes may comprise the same label region. Molecular barcodes from two or more sets of molecular barcodes may differ by their sample index regions. Molecular barcodes from two or more sets of molecular barcodes may be similar based on their label regions.

The molecular barcodes may further comprise a target specific region, an adapter region, a universal PCR region, a target specific region or any combination thereof. The molecular barcode may comprise a universal PCR region and a target specific region. The molecular barcode may comprise one or more secondary structures. The molecular barcode may comprise a hairpin structure. The molecular barcode may comprise a target specific region and a cleavable stem.

The methods and kits disclosed herein may comprise one or more sets of sample tags. One or more sample tags may comprise a sample index region. One or more sample tags may comprise a sample index region. Two or more sample tags of a set of sample tags may comprise the same sample index region. Two or more sample tags of two or more sets of sample tags may comprise two or more different sample index regions.

The sample tags may further comprise a target specific region, an adapter region, a universal PCR region, a target specific region or any combination thereof. The sample tag may comprise a universal PCR region and a target specific region. The sample tag may comprise one or more secondary structures. The sample tag may comprise a hairpin structure. The sample tag may comprise a target specific region and a cleavable stem.

The methods and kits disclosed herein may comprise one or more sets of, molecular identifier labels. One or more molecular identifier labels may comprise a label region. One or more molecular identifier labels may comprise a label region. Two or more molecular identifier labels of a set of molecular identifier labels may comprise two or more different label regions. Two or more molecular identifier labels of two or more sets of molecular identifier labels may comprise two or more identical label regions. The molecular identifier labels may further comprise a target specific region, an adapter region, a universal PCR region, a target specific region or any combination thereof. The molecular identifier label may comprise a universal PCR region and a target specific region. The molecular identifier label may comprise one or more secondary structures. The molecular identifier label may comprise a hairpin structure. The molecular identifier label may comprise a target specific region and a cleavable stem.

The molecular barcode, sample tag or molecular identifier label may comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the sample tag or molecular identifier label comprises at least about 1500, 2,000; 2500, 3,000; 3500, 4,000; 4500, 5,000; 5500, 6,000; 6500, 7,000; 7500, 8,000; 8500, 9,000; 9500, or 10,000 nucleotides or base pairs.

The molecular barcodes, sample tags or molecular identifier labels may be multimers, e.g., random multimers. A multimer sequence can be, for example, a non-random or random dimer, trimer, quatramer, pentamer, hexamer, septamer, octamer, nonamer, decamer, or higher multimer sequence of any length. The tags may be randomly generated from a set of mononucleotides. The tags may be assembled by randomly incorporating mononucleotides.

The molecular barcodes, sample tags or molecular identifier labels may also be assembled without randomness, to generate a library of different tags which are not randomly generated but which includes sufficient numbers of different tags to practice the methods.

In some embodiments a molecular barcode, sample tag or molecular identifier label may comprise a cutback in a target nucleic acid. The cutback may be, for example, an enzymatic digestion of one or both ends of a target nucleic acid. The cutback may be used in conjunction with the addition of added molecular barcodes, sample tags (e.g., sample index region, sample label), cellular label, and molecular identifier labels (e.g., molecular label). The combination of the cutback and the added tags may contain information related to the particular starting molecule. By adding a random cutback to the molecular barcode, sample tag or molecular identifier label, a smaller diversity of the added tags may be necessary for counting the number of target nucleic acids when detection allows a determination of both the random cutback and the added oligonucleotides.

The molecular barcode, sample tag or molecular identifier label may comprise a target specific region. The target specific region may comprise a sequence that is complementary to the molecule. In some instances, the molecule is an mRNA molecule and the target specific region comprises an oligodT sequence that is complementary to the polyA tail of the mRNA molecule. The target specific region may also act as a primer for DNA and/or RNA synthesis. For example, the oligodT sequence of the target specific region may act as a primer for first strand synthesis of a cDNA copy of the mRNA molecule. Alternatively, the target specific region comprises a sequence that is complementary to any portion of the molecule. In other instances, the target specific region comprises a random sequence that may be hybridized or ligated to the molecule. The target specific region may enable attachment of the sample tag or molecular identifier label to the molecule. Attachment of the sample tag or molecular identifier label may occur by any of the methods disclosed herein (e.g., hybridization, ligation). In some instances, the target specific region comprises a sequence that is recognized by one or more restriction enzymes. The target specific region may comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the target specific region comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. Preferably, the target specific region comprises at least about 5-10, 10-15, 10-20, 10-30, 15-30, or 20-30 nucleotides or base pairs.

In some instances, the target specific region is specific for a particular gene or gene product. For example, the target specific region comprises a sequence complementary to a region of a p53 gene or gene product. Therefore, the sample tags and molecular identifier labels may only attach to molecules comprising the p53-specific sequence. Alternatively, the target specific region is specific for a plurality of different genes or gene products. For example, the target specific region comprises an oligodT sequence. Therefore, the sample tags and molecular identifier labels may attach to any molecule comprising a polyA sequence. In another example, the target specific region comprises a random sequence that is complementary to a plurality of different genes or gene products. Thus, the sample tag or molecular identifier label may attach to any molecule with a sequence that is complementary to the target specific region. In other instances, the target specific region comprises a restriction site overhang (e.g., EcoRI sticky-end overhang). The sample tag or molecular identifier label may ligate to any molecule comprising a sequence complementary to the restriction site overhang.

In some instances, the target specific region is specific for a particular microRNA or microRNA product. For example, the target specific region comprises a sequence complementary to a region of a specific microRNA or microRNA product. For example, the target specific regions comprise sequences complementary to regions of a specific panel of microRNAs or panel of microRNA products. Therefore, the sample tags and molecular identifier labels may only attach to molecules comprising the micoRNA-specific sequence. Alternatively, the target specific region is specific for a plurality of different micoRNAs or micoRNA products. For example, the target specific region comprises a sequence complimentary to a region comprised in two or more microRNAs, such as a panel of microRNAs containing a common sequence. Therefore, the sample tags and molecular identifier labels may attach to any molecule comprising the common microRNA sequence. In another example, the target specific region comprises a random sequence that is complementary to a plurality of different microRNAs or microRNA products. Thus, the sample tag or molecular identifier label may attach to any microRNA molecule with a sequence that is complementary to the target specific region. In other instances, the target specific region comprises a restriction site overhang (e.g., EcoRI sticky-end overhang). The sample tag or molecular identifier label may ligate to any microRNA molecule comprising a sequence complementary to the restriction site overhang.

The molecular barcode or molecular identifier label disclosed herein often comprises a label region. The label region may be used to uniquely identify occurrences of target species thereby marking each species with an identifier that may be used to distinguish between two otherwise identical or nearly identical targets. The label region of the plurality of sample tags and molecular identifier labels may comprise a collection of different semiconductor nanocrystals, metal compounds, peptides, oligonucleotides, antibodies, small molecules, isotopes, particles or structures having different shapes, colors, barcodes or diffraction patterns associated therewith or embedded therein, strings of numbers, random fragments of proteins or nucleic acids, different isotopes, or any combination thereof. The label region may comprise a degenerative sequence. The label region may comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the label region comprises at least about 1500; 2,000; 2500, 3,000; 3500, 4,000; 4500, 5,000; 5500, 6,000; 6500, 7,000; 7500, 8,000; 8500, 9,000; 9500, or 10,000 nucleotides or base pairs. Preferably, the label region comprises at least about 10-30, 15-40, or 20-50 nucleotides or base pairs.

In some instances, the molecular barcode, sample tag or molecular identifier label comprises a universal primer binding site. The universal primer binding site allows the attachment of a universal primer to the labeled-molecule and/or labeled-amplicon. Universal primers are well known in the art and include, but are not limited to, −47F (M13F), alfaMF, AOX3', AOX5', BGH_r, CMV_-30, CMV_-50, CVM_f, LACrmt, lamgda gt10F, lambda gt10R, lambda gt11F, lambda gt11R, M13 rev, M13Forward(−20), M13Reverse, male, p10SEQP_pQE, pA_-120, pet_4, pGAP Forward, pGL_RVpr3, pGLpr2_R, pKLAC1_4, pQE_FS, pQE_RS, puc_U1, puc_U2, revers_A, seq_IRES_tam, seq_IRES_z-pet, seq_ori, seq_PCR, seq_pIRES−, seq_pIRES+, seq_p-SecTag, seq_pSecTag+, seq_retro+PSI, SP6, T3-prom, T7-prom, and T7-term_Inv. Attachment of the universal primer to the universal primer binding site may be used for amplification, detection, and/or sequencing of the labeled-molecule and/or labeled-amplicon. The universal primer binding site may comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the universal primer binding site comprises at least about 1500; 2,000; 2500, 3,000; 3500, 4,000; 4500, 5,000; 5500, 6,000; 6500, 7,000; 7500, 8,000; 8500, 9,000; 9500, or 10,000 nucleotides or base pairs. Preferably, the universal primer binding site comprises 10-30 nucleotides or base pairs.

The molecular barcode, sample tag or molecular identifier label may comprise an adapter region. The adapter region may enable hybridization of one or more probes. The adapter region may enable hybridization of one or more HCR probes.

The molecular barcode, sample tag or molecular identifier label may comprise one or more detectable labels.

The molecular barcode, sample tag or molecular identifier label may act as an initiator for a hybridization chain reaction (HCR). The adapter region of the sample tag or molecular identifier label may act as an initiation for HCR. The universal primer binding site may act as an initiator for HCR.

In some instances, the molecular barcode, sample tag or molecular identifier label is single-stranded. In other instances, the molecular barcode, sample tag or molecular identifier label is double-stranded. The molecular barcode, sample tag or molecular identifier label may be linear. Alternatively, the molecular barcode, sample tag or molecular identifier label comprises a secondary structure. As used herein, "secondary structure" includes tertiary, quaternary, etc. . . . structures. In some instances, the secondary structure is a hairpin, a stem-loop structure, an internal loop, a bulge loop, a branched structure or a pseudoknot, multiple stem loop structures, cloverleaf type structures or any three dimensional structure. In some instances, the secondary structure is a hairpin. The hairpin may comprise an overhang sequence. The overhang sequence of the hairpin may act as a primer for a polymerase chain reaction and/or reverse transcription reaction. The overhang sequence comprises a sequence that is complementary to the molecule to which the sample tag or molecular identifier label is attached and the overhang sequence hybridizes to the molecule. The overhang sequence may be ligated to the molecule and acts as a template for a polymerase chain reaction and/or reverse transcription reaction. In some embodiments, molecular barcode, the sample tag, or molecular identifier label comprises nucleic acids and/or synthetic nucleic acids and/or modified nucleic acids.

In some instances, the plurality of molecular barcodes, sample tags (e.g., sample index region, sample label), cellular label, and molecular identifier labels (e.g., molecular label) comprises at least about 2, 3, 4, 5, 6, 7, 8, 9, 10, 15, 20, 25, 30, 35, 40, 45, 50, 55, 60, 65, 70, 75, 80, 85, 90, 95, or 100 different molecular barcodes, sample tags (e.g., sample index region, sample label), cellular label, and molecular identifier labels (e.g., molecular label). In other instances, the plurality of molecular barcodes, sample tags (e.g., sample index region, sample label), cellular label, and molecular identifier labels (e.g., molecular label) comprises at least about 200; 300; 400; 500; 600; 700; 800; 900; 1,000; 2,000; 3,000; 4,000; 5,000; 6,000; 7,000; 8,000; 9,000; or 10000 different molecular barcodes, sample tags (e.g., sample index region, sample label), cellular label, and molecular identifier labels (e.g., molecular label). Alternatively; the plurality of molecular barcodes, sample tags (e.g., sample index region, sample label), cellular label, and molecular identifier labels (e.g., molecular label) comprises at least about 20,000; 30,000; 40,000; 50,000; 60,000; 70,000; 80,000; 90,000; or 100,000 different molecular barcodes, sample tags (e.g., sample index region, sample label), cellular label, and molecular identifier labels (e.g., molecular label).

The number of molecular barcodes, sample tags (e.g., sample index region, sample label), cellular label, and molecular identifier labels (e.g., molecular label) in the plurality of molecular barcodes, sample tags (e.g., sample index region, sample label), cellular label, and molecular identifier labels (e.g., molecular label) is often in excess of the number of molecules to be labeled. In some instances, the number of molecular barcodes, sample tags (e.g., sample index region, sample label), cellular label, and molecular identifier labels (e.g., molecular label) in the plurality of molecular barcodes, sample tags (e.g., sample index region, sample label), cellular label, and molecular identifier labels (e.g., molecular label) is at least about 2, 3, 4, 5, 6, 7, 8, 9, 10, 15, 20, 30, 40, 50, 60, 70, 80, 90, or 100 times greater than the number of molecules to be labeled.

The number of different molecular barcodes, sample tags (e.g., sample index region, sample label), cellular label, and molecular identifier labels (e.g., molecular label) in the plurality of molecular barcodes, sample tags (e.g., sample index region, sample label), cellular label, and molecular identifier labels (e.g., molecular label) is often in excess of the number of different molecules to be labeled. In some instances, the number of different molecular barcodes, sample tags (e.g., sample index region, sample label), cellular label, and molecular identifier labels (e.g., molecular label) in the plurality of molecular barcodes, sample tags (e.g., sample index region, sample label), cellular label, and molecular identifier labels (e.g., molecular label) is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled.

In some instances, stochastic labeling of a molecule comprises a plurality of molecular barcodes, sample tags (e.g., sample index region, sample label), cellular label, and molecular identifier labels (e.g., molecular label), wherein the concentration of the different molecular barcodes, sample tags (e.g., sample index region, sample label), cellular label, and molecular identifier labels (e.g., molecular label) in the plurality of molecular barcodes, sample tags (e.g., sample index region, sample label), cellular label, and molecular identifier labels (e.g., molecular label) is the same. In such instances, the plurality of molecular barcodes, sample tags (e.g., sample index region, sample label), cellular label, and molecular identifier labels (e.g., molecular label) comprises equal numbers of each different molecular barcode, sample tag or molecular identifier label.

In some instances, stochastic labeling of a molecule comprises a plurality of molecular barcodes, sample tags (e.g., sample index region, sample label), cellular label, and molecular identifier labels (e.g., molecular label), wherein the concentration of the different molecular barcodes, sample tags (e.g., sample index region, sample label), cellular label, and molecular identifier labels (e.g., molecular label) in the plurality of molecular barcodes, sample tags (e.g., sample index region, sample label), cellular label, and molecular identifier labels (e.g., molecular label) is different. In such instances, the plurality of molecular barcodes, sample tags (e.g., sample index region, sample label), cellular label, and molecular identifier labels (e.g., molecular label) comprises different numbers of each different molecular barcode, sample tag or molecular identifier label.

In some instances, some molecular barcodes, sample tags (e.g., sample index region, sample label), cellular label, and molecular identifier labels (e.g., molecular label) are present at higher concentrations than other molecular barcodes, sample tags (e.g., sample index region, sample label), cellular label, and molecular identifier labels (e.g., molecular label) in the plurality of molecular barcodes, sample tags (e.g., sample index region, sample label), cellular label, and molecular identifier labels (e.g., molecular label). In some instances, stochastic labeling with different concentrations of molecular barcodes, sample tags (e.g., sample index region, sample label), cellular label, and molecular identifier labels (e.g., molecular label) extends the sample measurement dynamic range without increasing the number of different labels used. For example, consider stochastically labeling 3 nucleic acid sample molecules with 10 different molecular barcodes, sample tags (e.g., sample index region, sample label), cellular label, and molecular identifier labels (e.g., molecular label) all at equal concentration. We expect to observe 3 different labels. Now instead of 3 nucleic acid molecules, consider 30 nucleic acid molecules, and we expect to observe all 10 labels. In contrast, if we still used 10 different stochastic labels and alter the relative ratios of the labels to 1:2:3:4 . . . 10, then with 3 nucleic acid molecules, we would expect to observe between 1-3 labels, but with 30 molecules we would expect to observe only approximately 5 labels thus extending the range of measurement with the same number of stochastic labels.

The relative ratios of the different molecular barcodes, sample tags (e.g., sample index region, sample label), cellular label, and molecular identifier labels (e.g., molecular label) in the plurality of molecular barcodes, sample tags (e.g., sample index region, sample label), cellular label, and molecular identifier labels (e.g., molecular label) may be 1:X, where X is at least about 1, 2, 3, 4, 5, 6, 7, 8, 9, 10, 15, 20, 25, 30, 35, 40, 45, 50, 55, 60, 65, 70, 75, 80, 85, 90, 95, or 100. Alternatively, the relative ratios of "n" different molecular barcodes, sample tags (e.g., sample index region, sample label), cellular label, and molecular identifier labels (e.g., molecular label) in the plurality of molecular barcodes, sample tags (e.g., sample index region, sample label), cellular label, and molecular identifier labels (e.g., molecular label) is 1:A:B:C: . . . Zn, where A, B, C . . . Zn is at least about 1, 2, 3, 4, 5, 6, 7, 8, 9, 10, 15, 20, 25, 30, 35, 40, 45, 50, 55, 60, 65, 70, 75, 80, 85, 90, 95, or 100.

In some instances, the concentration of two or more different molecular barcodes, sample tags (e.g., sample index region, sample label), cellular label, and molecular identifier labels (e.g., molecular label) in the plurality of molecular barcodes, sample tags (e.g., sample index region, sample label), cellular label, and molecular identifier labels (e.g., molecular label) is the same. For "n" different molecular barcodes, sample tags (e.g., sample index region, sample label), cellular label, and molecular identifier labels (e.g., molecular label), the concentration of at least 2, 3, 4, . . . n different molecular barcodes, sample tags (e.g., sample index region, sample label), cellular label, and molecular identifier labels (e.g., molecular label) is the same. Alternatively, the concentration of two or more different molecular barcodes, sample tags (e.g., sample index region, sample label), cellular label, and molecular identifier labels (e.g., molecular label) in the plurality of molecular barcodes, sample tags (e.g., sample index region, sample label), cellular label, and molecular identifier labels (e.g., molecular label) is different. For "n" different molecular barcodes, sample tags (e.g., sample index region, sample label), cellular label, and molecular identifier labels (e.g., molecular label), the concentration of at least 2, 3, 4, . . . n different molecular barcodes, sample tags (e.g., sample index region, sample label), cellular label, and molecular identifier labels (e.g., molecular label) is different. In some instances, for "n" different molecular barcodes, sample tags (e.g., sample index region, sample label), cellular label, and molecular identifier labels (e.g., molecular label), the difference in concentration for at least 2, 3, 4, . . . n different molecular barcodes, sample tags (e.g., sample index region, sample label), cellular label, and molecular identifier labels (e.g., molecular label) is at least about 0.1, 0.2, 0.3, 0.4, 0.5, 0.6, 0.7, 0.8, 0.9, 1, 1.25, 1.5, 1.75, 2, 2.25, 2.5, 2.75, 3, 4, 5, 6, 7, 8, 9, 10, 15, 20, 30, 40, 50, 60, 70, 80, 90, 100, 200, 300, 400, 500, 600, 700, 800, 900, or 1000-fold.

In some instances, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different molecular barcodes, sample tags (e.g., sample index region, sample label), cellular label, and molecular identifier labels (e.g., molecular label) in the plurality of molecular barcodes, sample tags (e.g., sample index region, sample label), cellular label, and molecular identifier labels (e.g., molecular label) have the same concentration. Alternatively, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different molecular barcodes, sample tags (e.g., sample index region, sample label), cellular label, and molecular identifier labels (e.g., molecular label) in the plurality of molecular barcodes, sample tags (e.g., sample index region, sample label), cellular label, and molecular identifier labels (e.g., molecular label) have a different concentration.

Figure 65:
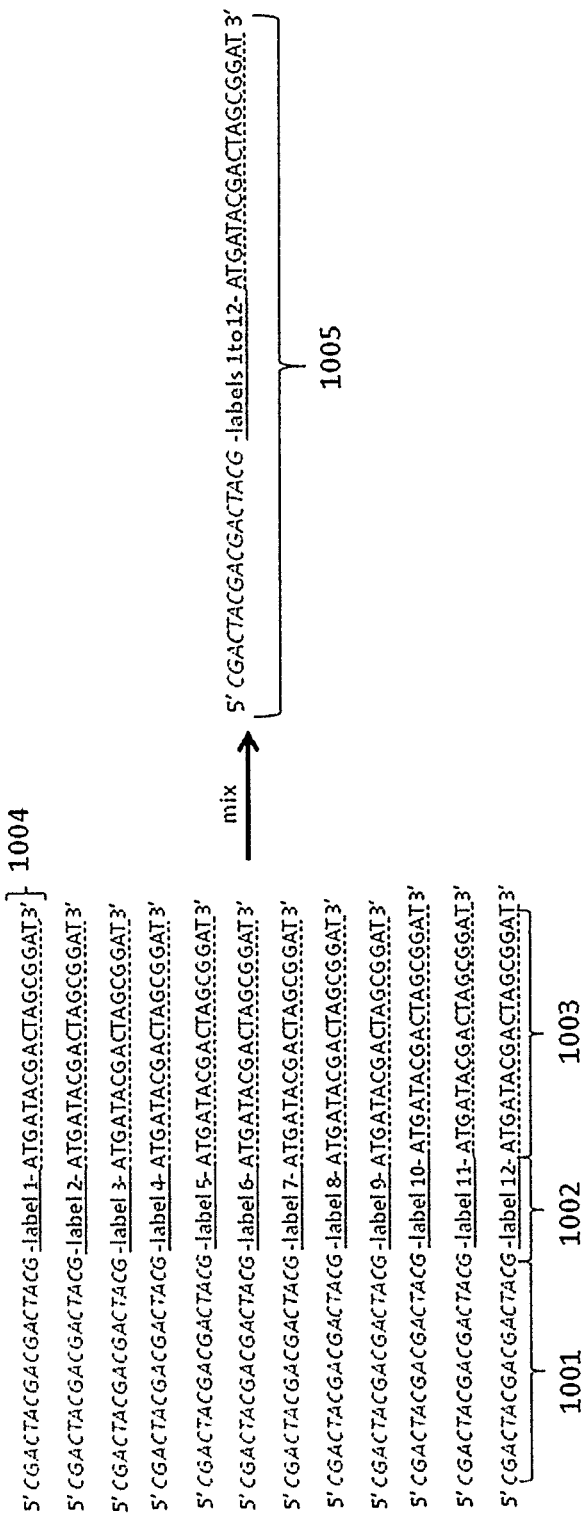
FIG. 65 depicts a schematic for the synthesis of molecular barcodes.

As shown in FIG. 65, molecular barcodes (1004) may be synthesized separately. The molecular barcodes (1004) may comprise a universal PCR region (1001), one or more identifier regions (1002), and a target specific region. The one or more identifier regions may comprise a sample index region, label region, or a combination thereof. The one or more identifier regions may be adjacent. The one or more identifier regions may be non-adjacent. The individual molecular barcodes may be pooled to produce a plurality of molecular barcodes (1005) comprising a plurality of different identifier regions. Sample tags may be synthesized in a similar manner as depicted in FIG. 65, wherein the one or more identifier regions comprise a sample index region. Molecular identifier labels may be synthesized in a similar manner as depicted in FIG. 65, wherein the one or more identifier regions comprises a label region.

The target specific region may be ligated to the identifier region to produce a molecular barcode comprising a target specific region. 5' and 3' exonucleases may be added to the reaction to remove non-ligated products. The molecular barcode may comprise the universal primer binding site, label region and target specific region and may be resistant to 5' and 3' exonucleases. As used herein, the terms "universal primer binding site" and "universal PCR region" may be used interchangeably and refer to a sequence that can be used to prime an amplification reaction. The 3' phosphate group from the ligated identifier region may be removed to produce a molecular barcode without a 3' phosphate group. The 3' phosphate group may be removed enzymatically. For example, a T4 polynucleotide kinase may be used to remove the 3' phosphate group.

Figure 66A:
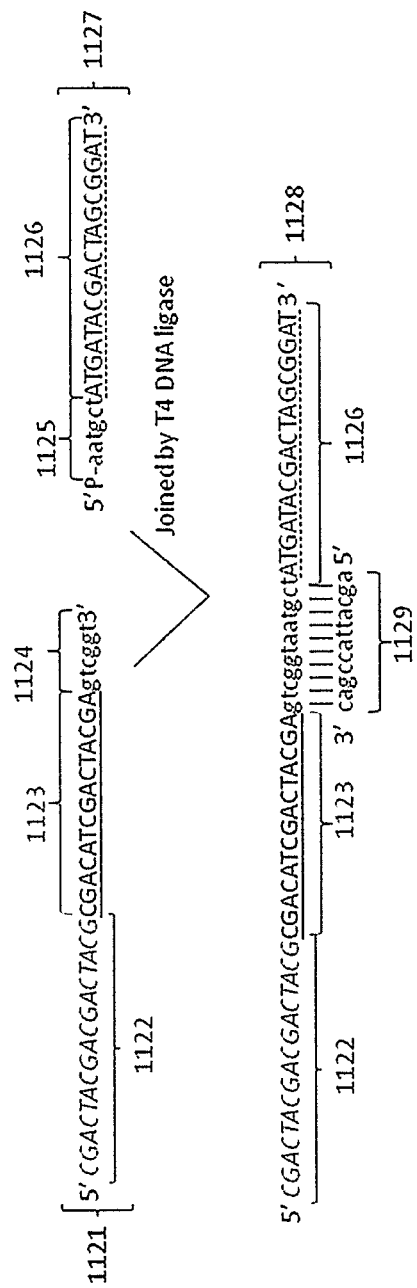
FIGS. 66A-C depict schematics for the synthesis of molecular barcodes.

Another method of synthesizing molecular barcodes is depicted in FIG. 66A. As shown in FIG. 66A, a molecular barcode (1128) may be synthesized by ligating two or more oligonucleotide fragments (1121 and 1127). One oligonucleotide fragment (1121) may comprise a universal primer binding site (1122), identifier region (1123) and a first splint (1123). The other oligonucleotide fragment (1128) may comprise a second splint (1125) and a target specific region (1126). A ligase (e.g., T4 DNA ligase) may be used to join the two oligonucleotide fragments (1121 and 1127) to produce a molecular barcode (1128). Double stranded ligation of the first splint (1124) and second splint (1125) may produce a molecular barcode (1128) with a bridge splint (1129).

Figure 66B:
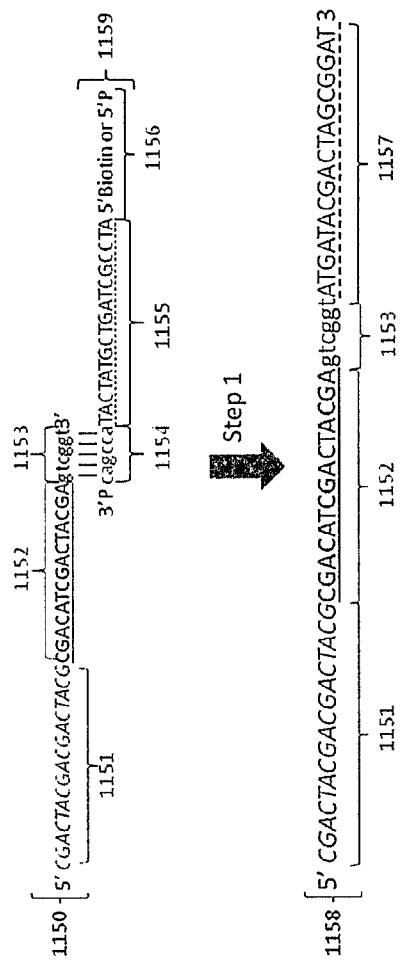

An alternative method of synthesizing a molecular barcode by ligating two oligonucleotide fragments is depicted in FIG. 66B. As shown in FIG. 66B, a molecular barcode (1158) is synthesized by ligating two oligonucleotide fragments (1150 and 1158). One oligonucleotide fragment (1150) may comprise a universal primer binding site (1151), one or more identifier region (1152), and a ligation sequence (1153). The other oligonucleotide fragment (1158) may comprise a ligation sequence (1154) that is complementary to the ligation sequence (1153) of the first oligonucleotide fragment (1150), a complement of a target specific region (1155), and a label (1156). The oligonucleotide fragment (1159) may also comprise a 3' phosphate which prevents extension of the oligonucleotide fragment. As shown in Step 1 of FIG. 66B, the ligation sequences (1153 and 1154) of the two oligonucleotide fragments may anneal and a polymerase may be used to extend the 3' end of the first oligonucleotide fragment (1150) to produce molecular barcode (1158). The molecular barcode (1158) may comprise a universal primer binding site (1151), one or more identifier regions (1152), ligation sequence (1153), and a target specific sequence (1157). The target specific sequence (1157) of the molecular barcode (1158) may be the complement of the complement of the target specific region (1155) of the second oligonucleotide fragment (1159). The oligonucleotide fragment comprising the label (1156) may be removed from the molecular barcode (1158). For example, the label (1156) may comprise biotin and oligonucleotide fragments (1159) comprising the biotin label (1156) may be removed via streptavidin capture. In another example, the label (1156) may comprise a 5' phosphate and oligonucleotide fragments (1159) comprising the 5' phosphate (1156) may be removed via an exonuclease (e.g., Lambda exonuclease).

Figure 66C:
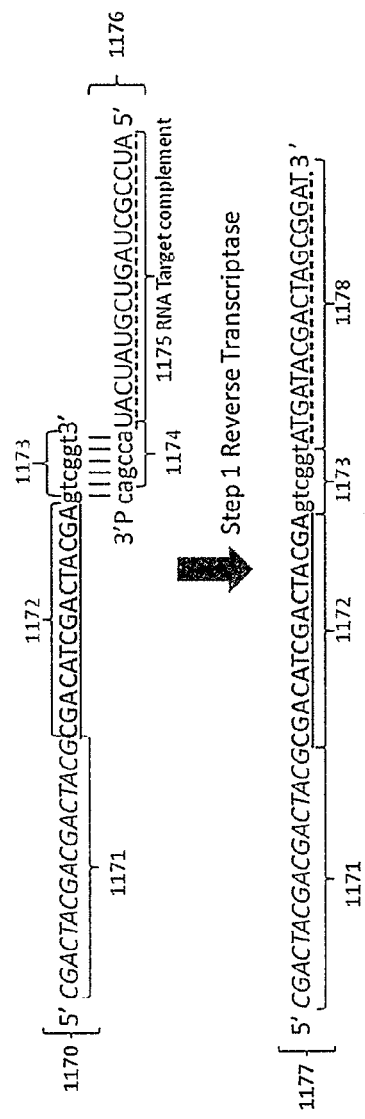

As depicted in FIG. 66C, a first oligonucleotide fragment (1170) comprising a universal primer binding site (1171), one or more identifier regions (1172), a first ligation sequence (1173) is annealed to a second oligonucleotide fragment (1176) comprising a second ligation sequence (1174) and an RNA complement of the target sequence (1175). Step 1 may comprise annealing the first and second ligation sequences (1173 and 1174) followed by reverse transcription of the RNA complement of the target sequence (1175) to produce molecular barcode (1177) comprising a universal primer binding site (1171), one or more identifier regions (1172), a first ligation sequence (1173), and a target specific region (1178). The oligonucleotide fragments comprising the RNA complement of the target sequence may be selectively degraded by RNAse treatment.

The sequences of the molecular barcodes, sample tags (e.g., sample index region, sample label), cellular label, and molecular identifier labels (e.g., molecular label) may be optimized to minimize dimerization of molecular barcodes, sample tags (e.g., sample index region, sample label), cellular label, and molecular identifier labels (e.g., molecular label). The molecular barcode, sample tag or molecular identifier label dimer may be amplified and result in the formation of an amplicon comprising two universal primer binding sites on each end of the amplicon and a target specific region and a unique identifier region. Because the concentration of the molecular barcodes, sample tags (e.g., sample index region, sample label), cellular label, and molecular identifier labels (e.g., molecular label) are far greater that the number of DNA templates, these molecular barcode, sample tag or molecular identifier label dimers may outcompete the labeled DNA molecules in an amplification reaction. Unamplified DNAs lead to false negatives, and amplified molecular barcode, sample tag or molecular identifier label dimers lead to high false positives. Thus, the molecular barcodes, sample tags (e.g., sample index region, sample label), cellular label, and molecular identifier labels (e.g., molecular label) may be optimized to minimize molecular barcode, sample tag or molecular identifier label dimer formation. Alternatively, molecular barcodes, sample tags (e.g., sample index region, sample label), cellular label, and molecular identifier labels (e.g., molecular label) that dimerize are discarded, thereby eliminating molecular barcode, sample tag or molecular identifier label dimer formation.

Alternatively, molecular barcode, sample tag or molecular identifier label dimer formation may be eliminated or reduced by incorporating one or more modifications into the molecular barcode, sample tag or molecular identifier label sequence. A molecular barcode, sample tag or molecular identifier label comprising a universal primer binding site, unique identifier region, and target specific region comprising uracils and a 3' phosphate group is annealed to a target nucleic acid. The target nucleic acid may be a restriction endonuclease digested fragment. The restriction endonuclease may recognize the recognition site. PCR amplification may comprise one or more forward primers and one or more reverse primers. PCR amplification may comprise nested PCR with a forward primer specific for the universal primer binding site of the molecular barcode, sample tag or molecular identifier label and a forward primer specific for the target specific region of the molecular barcode, sample tag or molecular identifier label and reverse primers that are specific for the target nucleic acid. The target nucleic acid may be amplified using a Pfu DNA polymerase, which cannot amplify template comprising one or more uracils. Thus, any dimerized molecular barcodes, sample tags (e.g., sample index region, sample label), cellular label, and molecular identifier labels (e.g., molecular label) cannot be amplified by Pfu DNA polymerase.

Methods to Synthesize Oligonucleotides (e.g., Molecular Barcodes)

An oligonucleotide may be synthesized. An oligonucleotide may be synthesized, for example, by coupling (e.g., by 1-Ethyl-3-(3-dimethylaminopropyl) carbodiimide) of a 5' amino group on the oligonucleotide to the carboxyl group of the functionalized solid support.

Uncoupled oligonucleotides may be removed from the reaction mixture by multiple washes. The solid supports may be split into wells (e.g., 96 wells). Each solid support may be split into a different well. Oligonucleotide synthesis may be performed using the split/pool method of synthesis. The split/pool method may utilize a pool of solid supports comprising reactive moieties (e.g., oligonucleotides to be synthesized). This pool may be split into a number of individual pools of solid supports. Each pool may be subjected to a first reaction that may result in a different modification to the solid supports in each of the pools (e.g., a different nucleic acid sequence added to the oligonucleotide). After the reaction, the pools of solid supports may be combined, mixed, and split again. Each split pool may be subjected to a second reaction or randomization that again is different for each of the pools. The process may be continued until a library of target compounds is formed.

Using split/pool synthesis, the nucleic acid sequence to be added to the oligonucleotide may be incorporated by primer extension (e.g., Klenow extension). The nucleic acid sequence to be added to the oligonucleotide may be referred to as a primer fragment. Each primer fragment for each individual pool may comprise a different sequence (e.g., either in the cellular label, the molecular label, the sample label, or any combination thereof). The primer fragment may comprise a sequence that may hybridize to the linker label sequence of the oligonucleotide (e.g., the oligonucleotide coupled to the solid support). The primer fragment may further comprise a second cell label and a second linker label sequence. Primer extension may be used to introduce the second cell label sequence and the second linker label sequence onto the oligonucleotide coupled to the solid support (See FIG. 2B). After primer extension incorporates the new sequences, the solid supports may be combined. The combined solid supports may be heated to denature the enzyme. The combined solid supports may be heated to disrupt hybridization. The combined solid supports may be split into wells again. The process may be repeated to add additional sequences to the solid support-conjugated oligonucleotide.

The split/pool process may lead to the creation of at least about 1000, 10000, 100000, 500000, or 1000000 or more different oligonucleotides. The process may lead to the creation of at most about 1000, 10000, 100000, 500000, or 1000000 or more different oligonucleotides.

Split pool synthesis may comprise chemical synthesis. Different oligonucleotides may be synthesized using DMT chemistry on solid supports in individual reactions, then pooled into reactions for synthesis. The split/pool process may be repeated 1, 2, 3, 4, 5, 6, 7, 8, 9, 10 or more times. The split/pool process may be repeated 11, 12, 13, 14, 15, 16, 17, 18, 19, 20, 25, 30, 35, 40, 45, 50, 55, 60, 65, 70, 75, 80, 85, 90, 95, 100 or more times. The split/pool process may be repeated 2 or more times. The split/pool process may be repeated 3 or more times. The split/pool process may be repeated 5 or more times. The split/pool process may be repeated 10 or more times.

Further disclosed herein are methods of producing one or more sets of labeled beads (e.g., oligonucleotide conjugated beads). The method of producing the one or more sets of labeled beads may comprise attaching one or more nucleic acids to one or more beads, thereby producing one or more sets of labeled beads. The one or more nucleic acids may comprise one or more molecular barcodes. The one or more nucleic acids may comprise one or more sample tags (e.g., sample labels, sample index regions). The one or more nucleic acids may comprise one or more cellular labels. The one or more nucleic acids may comprise one or more molecular identifier labels (e.g., molecular labels). The one or more nucleic acids may comprise a) a primer region; b) a sample index region; and c) a linker or adaptor region. The one or more nucleic acids may comprise a) a primer region; b) a label region (e.g., molecular label); and c) a linker or adaptor region. The one or more nucleic acids may comprise a) a sample index region (e.g., sample tag); and b) a label region (e.g., molecular label). The one or more nucleic acids may comprise a) a sample index region; and b) a cellular label. The one or more nucleic acids may comprise a) a cellular label; and b) a molecular label. The one or more nucleic acids may comprise a) a sample index region; b) cellular label; and c) a molecular label. The one or more nucleic acids may further comprise a primer region. The one or more nucleic acids may further comprise a target specific region. The one or more nucleic acids may further comprise a linker region. The one or more nucleic acids may further comprise an adaptor region. The one or more nucleic acids may further comprise a sample index region. The one or more nucleic acids may further comprise a label region.

Alternatively, the method comprises: a) depositing a plurality of first nucleic acids into a plurality of wells, wherein two or more different wells of the plurality of wells may comprise two or more different nucleic acids of the plurality of nucleic acids; b) contacting one or more wells of the plurality of wells with one or fewer beads to produce a plurality of single label beads, wherein a single label bead of the plurality of first labeled beads comprises a bead attached to a nucleic acid of the plurality of first nucleic acids; c) pooling the plurality of first labeled beads from the plurality of wells to produce a pool of first labeled beads; d) distributing the pool of first labeled beads to a subsequent plurality of wells, wherein two or more wells of the subsequent plurality of wells comprise two or more different nucleic acids of a plurality of subsequent nucleic acids; and e) attaching one or more nucleic acids of the plurality of subsequent nucleic acids to one or more first labeled beads to produce a plurality of uniquely labeled beads.

Libraries

Disclosed herein are methods of producing molecular libraries. The method may comprise: (a) stochastically labeling two or more molecules from two or more samples to produce labeled molecules, wherein the labeled molecules comprise (i) a molecule region based on or derived from the two or more molecules, (ii) a sample index region for use in differentiating two or more molecules from two or more samples; and (iii) a label region for use in differentiating two or more molecules from a single sample. Stochastic labeling may comprise the use of one or more sets of molecular barcodes. Stochastic labeling may comprise the use of one or more sets of sample tags. Stochastic labeling may comprise the use of one or more sets of molecular identifier labels.

Stochastically labeling the two or more molecules may comprise contacting the two or more samples with a plurality of sample tags and the plurality of molecule specific labels to produce the plurality of labeled nucleic acids. The contacting can be random. The method may further comprise amplifying one or more of the labeled molecules, thereby producing an enriched population of labeled molecules of the library. The method may further comprise conducting one or more assays on the two or more molecules from the two or more samples. The method may further comprise conducting one or more pull-down assays.

The method of producing a labeled nucleic acid library may further comprise adding one or more controls to the two or more of samples. The one or more controls may be stochastically labeled to produce labeled controls. The one or more controls may be used to measure an efficiency of producing the labeled molecules.

The libraries disclosed herein may be used in a variety of applications. For example, the library could be used for sequencing applications. The library may be stored and used multiple times to generate samples for analysis. Some applications include, for example, genotyping polymorphisms, studying RNA processing, and selecting clonal representatives to do sequencing.

Sample Preparation and Applications

The oligonucleotides (e.g., molecular bar code, sample tag, molecular label, cellular label) disclosed herein may be used in a variety of methods. The oligonucleotides may be in methods for nucleic acid analysis. Nucleic acid analysis may include, but is not limited to, genotyping, gene expression, copy number variation, and molecular counting.

The disclosure provides for methods of multiplex nucleic acid analysis. The method may comprise (a) contacting one or more oligonucleotides from a cell with one or more oligonucleotides attached to a support, wherein the one or more oligonucleotides attached to the support comprise (i) a cell label region comprising two or more randomer sequences connected by a non-random sequence; and (ii) a molecular label region; and (b) conducting one or more assays on the one or more oligonucleotides from the cell.

Further disclosed herein are methods of producing single cell nucleic acid libraries. The method may comprise (a) contacting one or more oligonucleotides from a cell with one or more oligonucleotides attached to a support, wherein the one or more oligonucleotides attached to the support comprise (i) a cell label region comprising two or more randomer sequences connected by a non-random sequence; and (ii) a molecular label region; and (b) conducting one or more assays on the one or more oligonucleotides from the cell.

Figure 6A:
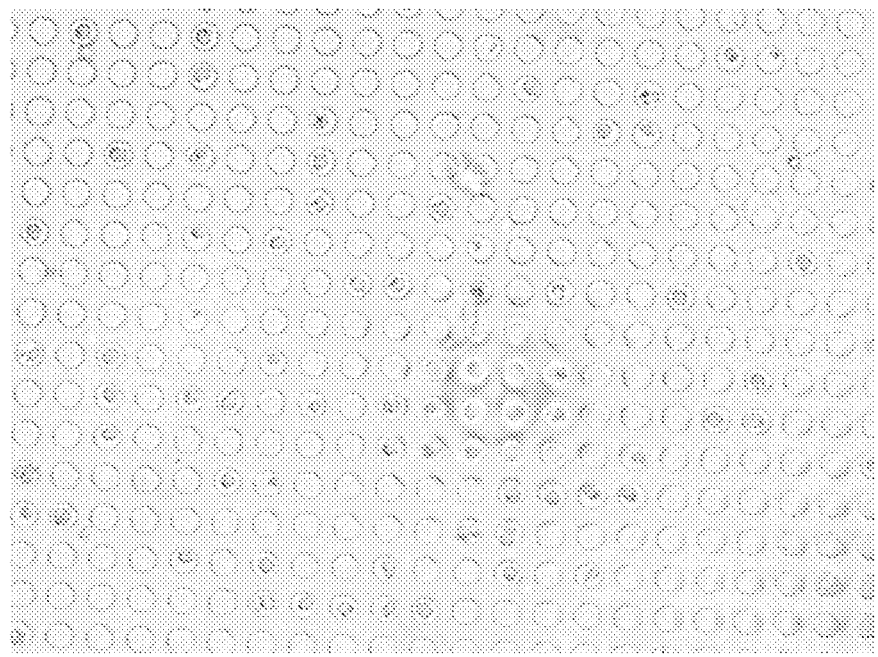
FIGS. 6A-C show exemplary distribution cells onto microwell arrays.
Figure 6B:
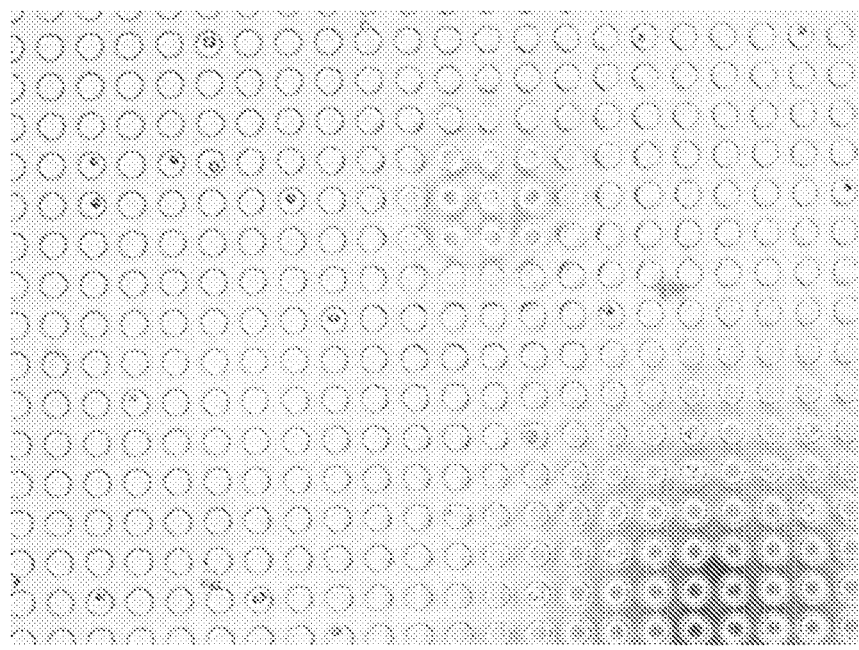

In some instances, the method comprises adding a one or more cells onto a microwell array. The number of cells to be added may be determined from counting. Excess or unbound cells may be washed away using a buffer (e.g., phosphobuffered saline buffer, HEPES, Tris). The number of cells that may be captured by the wells of the microwell array may be related to the size of the cell. For example, depending on the design of the microwell, larger cells may be more easily captured than smaller cells, as depicted in FIG. 6. Different microwells (e.g., different dimensions) may be used for capturing different cell types.

The methods described here allow for the addition of sequences that can nucleic acids for sequencing or other molecular analyses. These methods can allow detection of nucleic acid variants, mutants, polymorphisms, inversions, deletions, reversions and other qualitative events found in a population of RNA or DNA molecules. For example, the methods can allow for identification of target frequencies (e.g., gene expression or allelic distribution). For example, the methods also allow for identification of mutations or SNPs in a genome or transcriptome, such as from a diseased or non-diseased subject. The methods also allow for determining the presence or absence of contamination or infections in a biological sample from a subject, such as foreign organisms or viruses, such as a bacteria or a fungus.

Cells can be added into microwells by any method. In some embodiments, cells are added to microwells as a diluted cell sample. In some embodiments, cells are added to microwells and allowed to settle in the microwells by gravity. In some embodiments, cells are added to microwells and centrifugation is used to settle the cells in the microwells. In some embodiments, cells are added to microwells by injecting one or more cells into one or more microwells. For example, a single cell can be added to a microwell by injecting the single cell in to a microwell. The injecting of a cell can be through the use of any device or method, such as through the use of a micro manipulator. In some embodiments, cell can be added to microwells using a magnet. For example, cells can coated on their surface with magnetic particles, such as magnetic microparticles or magnetic nanoparticles and added to microwells using a magnet or a magnetic field.

Figure 5:
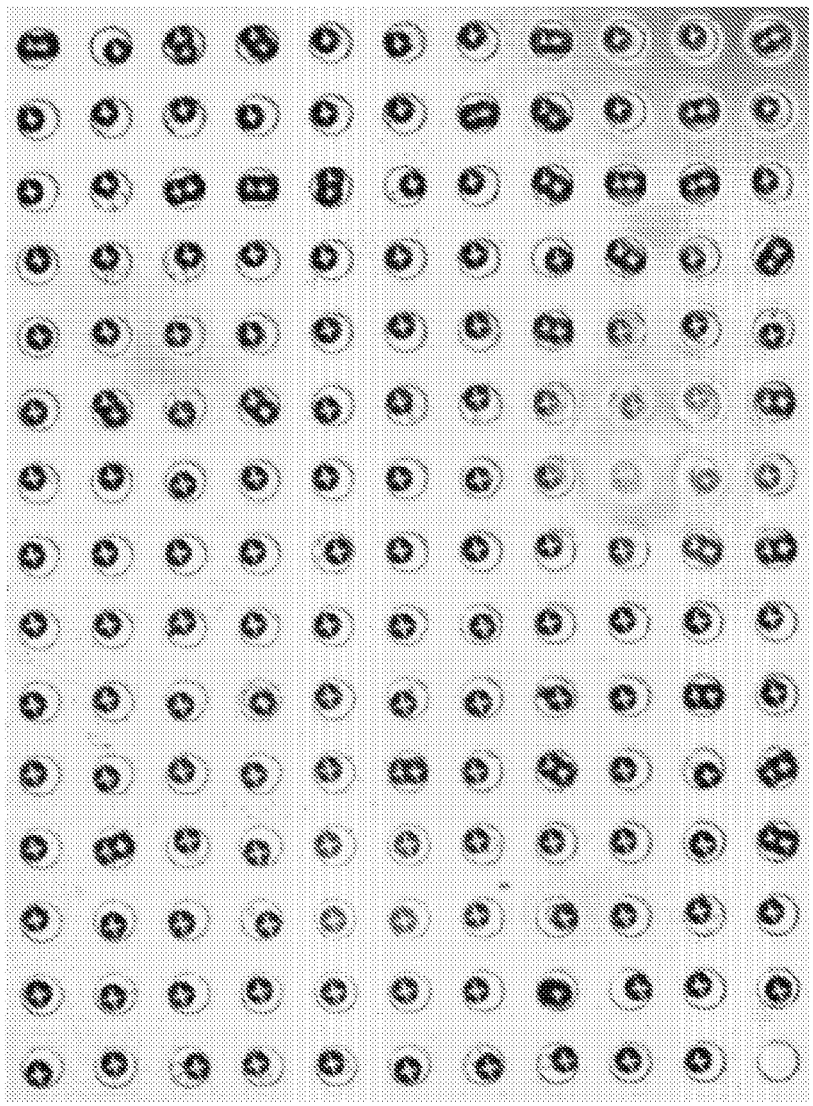
FIG. 5 depicts an exemplary distribution of solid supports in a microwell array.

The microwell array comprising cells may be contacted with an oligonucleotide conjugated solid support (e.g., bead). Uncaptured oligonucleotide conjugated solid supports may be removed (e.g., washed away with buffer). FIG. 5 depicts a microwell array with captured solid supports. A microwell may comprise at least one solid support. A microwell may comprise at least two solid supports. A microwell may comprise at most one solid support. A microwell may comprise at most two solid supports. A microwell may comprise at least about 1, 2, 3, 4, 5, 6, 7, 8, 9, or 10 or more solid supports. A microwell may comprise at most about 1, 2, 3, 4, 5, 6, 7, 8, 9, or 10 or more solid supports. Some of the microwells of the microwell array may comprise one solid support and some of the microwells of the microwell array may comprise two or more solid supports, as shown in FIG. 5. The microwell may not need to be covered for any of the methods of the disclosure. In other words, microwells may not need to be sealed during the method. When the microwells are not covered (e.g., sealed), the wells may be spaced apart such that the contents of one microwell may not diffuse into another microwell.

Alternatively, or additionally, cells may be captured and/or purified prior to being contacted with an oligonucleotide conjugated support. Methods to capture and/or purify cells may comprise use of antibodies, molecular scaffolds, and/or beads. Cells may be purified by flow cytometry. Commercially available kits may be used to capture or purify cells. For example, Dynabeads® may be used to isolate cells. Magnetic isolation may be used to purify cells. Cells may be purified by centrifugation.

Cells may be contacted with oligonucleotide conjugated supports by creating a suspension comprising cells and the supports. The suspension may comprise a gel. Cells may be immobilized on a support or in a solution prior to contact with the oligonucleotide conjugated supports. Alternatively, cells may be added to a suspension comprising the oligonucleotide conjugated support. For example, cells may be added to a hydrogel that is embedded with oligonucleotide conjugated supports.

A single cell may be contacted with a single oligonucleotide coupled solid support. A single cell may be contacted with multiple oligonucleotide conjugated solid supports. Multiple cells may interact with a single oligonucleotide conjugated solid support. Multiple cells may interact with multiple oligonucleotide conjugated solid supports. The oligonucleotide conjugated solid supports may be cell-type specific. Alternatively, the oligonucleotide conjugated support may interact with two or more different cell types.

Lysis

Cells in the microwells may be lysed. Lysis may be performed by mechanical lysis, heat lysis, optical lysis, and/or chemical lysis. Chemical lysis may include the use of digestive enzymes such as proteinase K, pepsin, and trypsin. Lysis may be performed by the addition of a lysis buffer to the microwells. A lysis buffer may comprise Tris HCl. A lysis buffer may comprise at least about 0.01, 0.05, 0.1, 0.5, or 1M or more Tris HCl. A lysis buffer may comprise at most about 0.01, 0.05, 0.1, 0.5, or 1M or more Tris HCL. A lysis buffer may comprise about 0.1 M Tris HCl. The pH of the lysis buffer may be at least about 1, 2, 3, 4, 5, 6, 7, 8, 9, or 10 or more. The pH of the lysis buffer may be at most about 1, 2, 3, 4, 5, 6, 7, 8, 9, or 10 or more. In some instances, the pH of the lysis buffer is about 7.5. The lysis buffer may comprise a salt (e.g., LiCl). The concentration of salt in the lysis buffer may be at least about 0.1, 0.5, or 1M or more. The concentration of salt in the lysis buffer may be at most about 0.1, 0.5, or 1M or more. In some instances, the concentration of salt in the lysis buffer is about 0.5M. The lysis buffer may comprise a detergent (e.g., SDS, Li dodecyl sulfate, triton X, tween, NP-40). The concentration of the detergent in the lysis buffer may be at least about 0.0001, 0.0005, 0.001, 0.005, 0.01, 0.05, 0.1, 0.5, 1, 2, 3, 4, 5, 6, or 7% or more. The concentration of the detergent in the lysis buffer may be at most about 0.0001, 0.0005, 0.001, 0.005, 0.01, 0.05, 0.1, 0.5, 1, 2, 3, 4, 5, 6, or 7% or more. In some instances, the concentration of the detergent in the lysis buffer is about 1% Li dodecyl sulfate. The time used in the method for lysis may be dependent on the amount of detergent used. In some instances, the more detergent used, the less time needed for lysis. The lysis buffer may comprise a chelating agent (e.g., EDTA, EGTA). The concentration of a chelating agent in the lysis buffer may be at least about 1, 5, 10, 15, 20, 25, or 30 mM or more. The concentration of a chelating agent in the lysis buffer may be at most about 1, 5, 10, 15, 20, 25, or 30 mM or more. In some instances, the concentration of chelating agent in the lysis buffer is about 10 mM. The lysis buffer may comprise a reducing reagent (e.g., beta-mercaptoethanol, DTT). The concentration of the reducing reagent in the lysis buffer may be at least about 1, 5, 10, 15, or 20 mM or more. The concentration of the reducing reagent in the lysis buffer may be at most about 1, 5, 10, 15, or 20 mM or more. In some instances, the concentration of reducing reagent in the lysis buffer is about 5 mM. In some instances, a lysis buffer may comprise about 0.1M TrisHCl, about pH 7.5, about 0.5M LiCl, about 1% lithium dodecyl sulfate, about 10 mM EDTA, and about 5 mM DTT.

Figures 6C, 7:
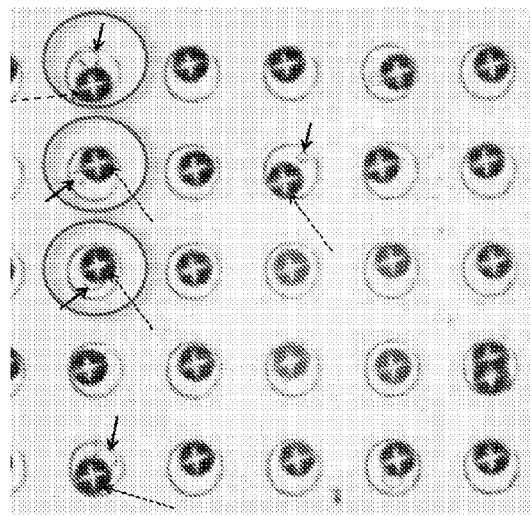
FIG. 7 shows exemplary statistics of the microwell volume, solid support volume, and amount of biological material obtained from lysis.

Lysis may be performed at a temperature of about 4, 10, 15, 20, 25, or 30 C. Lysis may be performed for about 1, 5, 10, 15, or 20 or more minutes. A lysed cell may comprise at least about 100000, 200000, 300000, 400000, 500000, 600000, or 700000 or more target nucleic acid molecules. A lysed cell may comprise at most about 100000, 200000, 300000, 400000, 500000, 600000, or 700000 or more target nucleic acid molecules. FIG. 7 illustrates exemplary statistics about the concentration of target nucleic acid (i.e., mRNA) that may be obtained from lysis.

Sealing

Figure 8A:
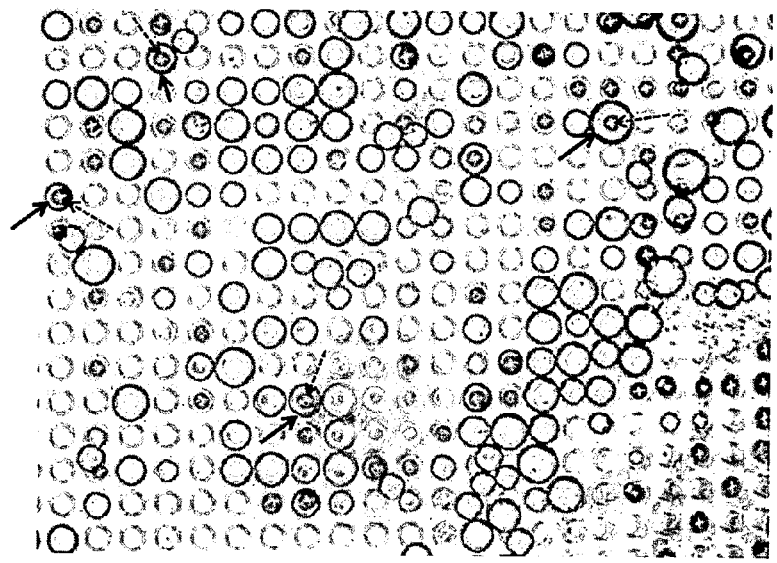
FIGS. 8A-C illustrates an exemplary embodiment of bead cap sealing.

The microwells of the microwell array may be sealed during lysis. Sealing may be useful for preventing cross hybridization of target nucleic acid between adjacent microwells. A microwell may be sealed using a cap as shown in FIGS. 8A and B. A cap may be a solid support. A cap may comprise a bead. The diameter of the bead may be larger than the diameter of the microwell. For example, a cap may be at least about 10, 20, 30, 40, 50, 60, 70, 80 or 90% larger than the diameter of the microwell. For example, a cap may be at most about 10, 20, 30, 40, 50, 60, 70, 80 or 90% larger than the diameter of the microwell.

A cap may comprise cross-linked dextran beads (e.g., Sephadex). Cross-linked dextran may range from about 10 micrometers to about 80 micrometers. The cross-linked dextran of the cap may be from 20 micrometers to about 50 micrometers. A cap may comprise, for example, nanopore inorganic membranes (e.g., aluminum oxides), dialysis membranes, glass slides, coverslips, and/or hydrophilic plastic film (e.g., film coated with a thin film of agarose hydrated with lysis buffer).

The cap may allow buffer to pass through into and out of the microwell, but may prevent macromolecules (e.g., nucleic acid) from migrating out of the well. A macromolecule of at least about 1, 2, 3, 4, 5, 6, 7, 8, 9, 10, 12, 13, 14, 15, 16, 17, 18, 19, or 20 or more nucleotides may be blocked from migrating into or out of the microwell by the cap. A macromolecule of at most about 1, 2, 3, 4, 5, 6, 7, 8, 9, 10, 12, 13, 14, 15, 16, 17, 18, 19, or 20 or more nucleotides may be blocked from migrating into or out of the microwell by the cap.

A sealed microwell array may comprise a single layer of beads on top of the microwells. A sealed microwell array may comprise multiple layers of beads on top of the microwells. A sealed microwell array may comprise about 1, 2, 3, 4, 5, or 6 or more layers of beads.

Depositing a bead, or plurality of beads, onto a solid support (e.g., a microwell array) can be random or non-random. For example, contacting a bead with a microwell array can be a random or non-random contacting. In some embodiments, the bead is contacted with a microwell array randomly. In some embodiments, the bead is contacted with a microwell array non-randomly. Depositing of a plurality of beads to a microwell array can be random or non-random. For example, the contacting of a plurality of beads to a microwell array can be a random or non-random contacting. In some embodiments, the plurality of beads is contacted to a microwell array randomly. In some embodiments, the plurality of beads is contacted to a microwell array non-randomly.

Stochastic Labeling of Molecules

Wherein the sample tag or molecular identifier label is an oligonucleotide, attachment of the oligonucleotide to a nucleic acid may occur by a variety of methods, including, but not limited to, hybridization of the oligonucleotide to the nucleic acid. In some instances, the oligonucleotide comprises a target specific region. The target specific region may comprise a sequence that is complementary to at least a portion of the molecule to be labeled. The target specific region may hybridize to the molecule, thereby producing a labeled nucleic acid. Hybridization of the oligonucleotide to the nucleic acid may be followed by a nucleic acid extension reaction. The nucleic acid extension reaction may be reverse transcription.

Attaching, alternatively referred to as contacting, the plurality of nucleic acids with the sample tag may comprise hybridizing the sample tag to one or more of the plurality of nucleic acids. Contacting the plurality of nucleic acids with the sample tag may comprise performing a nucleic acid extension reaction. The nucleic acid extension reaction may be a reverse transcription reaction.

Contacting the plurality of nucleic acids with the molecular identifier label may comprise hybridizing the molecular identifier label to one or more of the plurality of nucleic acids. Contacting the plurality of nucleic acids with the molecular identifier label may comprise performing a nucleic acid extension reaction. The nucleic acid extension reaction may comprise reverse transcription.

Contacting the plurality of nucleic acids with the molecular identifier label may comprise hybridizing the sample tag to one or more of the plurality of nucleic acids. Contacting the plurality of nucleic acids with the molecular identifier label may comprise hybridizing the molecular identifier label to the sample tag.

Contacting the plurality of nucleic acids with the sample tag may comprise hybridizing the molecular identifier label to one or more of the plurality of nucleic acids. Contacting the plurality of nucleic acids with the sample tag may comprise hybridizing the sample tag to the molecular identifier label.

Attachment of the sample tag and/or the molecular identifier label to a nucleic acid may occur by ligation. Contacting the plurality of nucleic acids with the sample tag may comprise ligating the sample tag to any one of the plurality of nucleic acids. Contacting the plurality of nucleic acids with the molecular identifier label may comprise ligating the molecular identifier label to one or more of the plurality of nucleic acids. Contacting the plurality of nucleic acids with the sample tag may comprise ligating the molecular identifier label one or more the nucleic acids. Contacting the plurality of nucleic acids with the molecular identifier label may comprise ligating the sample tag to one or more of the nucleic acids. Ligation techniques comprise blunt-end ligation and sticky-end ligation. Ligation reactions may include DNA ligases such as DNA ligase I, DNA ligase III, DNA ligase IV, and T4 DNA ligase. Ligation reactions may include RNA ligases such as T4 RNA ligase I and T4 RNA ligase II.

Methods of ligation are described, for example in Sambrook et al. (2001) and the New England BioLabs catalog both of which are incorporated herein by reference for all purposes. Methods include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; E. coli DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'→5' phosphodiester bond, substrates include single-stranded RNA and DNA as well as dinucleoside pyrophosphates; or any other methods described in the art. Fragmented DNA may be treated with one or more enzymes, for example, an endonuclease, prior to ligation of adaptors to one or both ends to facilitate ligation by generating ends that are compatible with ligation.

In some instances, both ends of the oligonucleotide are attached to the molecule. For example, both ends of the oligonucleotide may be hybridized and/or ligated to one or more ends of the molecule. In some instances, attachment of both ends of the oligonucleotide to both ends of the molecule results in the formation of a circularized labeled nucleic acid. Both ends of the oligonucleotide may also be attached to the same end of the molecule. For example, the 5' end of the oligonucleotide is ligated to the 3' end of the molecule and the 3' end of the oligonucleotide is hybridized to the 3' end of the molecule, resulting in a labeled nucleic acid with a hairpin structure at one end. In some instances the oligonucleotide is attached to the middle of the molecule.

In some instances, attachment of the oligonucleotide to the nucleic acid comprises attaching one or more oligonucleotide linkers to the plurality of nucleic acids. The method may further comprise attaching one or more oligonucleotide linkers to the sample-tagged nucleic acids. The method may further comprise attaching one or more oligonucleotide linkers to the labeled nucleic acids. Attaching one or more oligonucleotide linkers to a nucleic acid, sample tag or molecular identifier label may comprise ligating one or more oligonucleotide linkers to a nucleic acid, sample tag or molecular identifier label. The one or more linkers may comprise at least about 1, 2, 3, 4, 5, 6, 7, 8, 9, 10, 11, 12, 13, 14, 15, 16, 17, 18, 19, 20, 25, 30, 35, 40, 45, 50, 55, 60, 70, 80, 90, 100 nucleotides. In some instances, the linker may comprise at least about 1000 nucleotides.

In some instances, attachment of the molecular barcode to the molecule comprises the use of one or more adaptors. As used herein, the terms "adaptors" and "adaptor regions" may be used interchangeably. Adaptors may comprise a target specific region, which allows the attachment of the adaptor to the molecule, and an oligonucleotide specific region, which allows attachment of the molecular barcode to the adaptor. Adaptors may further comprise a universal primer. Adaptors may further comprise a universal PCR region. Adaptors may be attached to the molecule and/or molecular barcodes by methods including, but not limited to, hybridization and/or ligation.

Methods for ligating adaptors to fragments of nucleic acid are well known. Adaptors may be double-stranded, single-stranded or partially single-stranded. In some aspects, adaptors are formed from two oligonucleotides that have a region of complementarity, for example, about 10 to 30, or about 15 to 40 bases of perfect complementarity; so that when the two oligonucleotides are hybridized together they form a double stranded region. Optionally, either or both of the oligonucleotides may have a region that is not complementary to the other oligonucleotide and forms a single stranded overhang at one or both ends of the adaptor. Single-stranded overhangs may be about 1 to about 8 bases, or about 2 to about 4. The overhang may be complementary to the overhang created by cleavage with a restriction enzyme to facilitate "sticky-end" ligation. Adaptors may include other features, such as primer binding sites and restriction sites. In some aspects the restriction site may be for a Type IIS restriction enzyme or another enzyme that cuts outside of its recognition sequence, such as EcoP15I (see, Mucke et al. J Mol Biol 2001, 312(4):687-698 and U.S. Pat. No. 5,710,000 which is incorporated herein by reference in its entirety).

In some instances, stochastically counting the number of copies of a nucleic acid in a plurality of samples comprises detecting the adaptor, a complement of the adaptor, a reverse complement of the adaptor or a portion thereof to determine the number of different labeled nucleic acids. Detecting the adaptor, a complement of the adaptor, a reverse complement of the adaptor or a portion thereof may comprise sequencing the adaptor, a complement of the adaptor, a reverse complement of the adaptor or a portion thereof.

The molecular barcode may be attached to any region of a molecule. For example, the molecular barcode may be attached to the 5' or 3' end of a polynucleotide (e.g., DNA, RNA). For example, the target-specific region of the molecular barcode comprises a sequence that is complementary to a sequence in the 5' region of the molecule. The target-specific region of the molecular barcode may also comprise a sequence that is complementary to a sequence in the 3' region of the molecule. In some instances, the molecular barcode is attached a region within a gene or gene product. For example, genomic DNA is fragmented and a sample tag or molecular identifier label is attached to the fragmented DNA. In other instances, an RNA molecule is alternatively spliced and the molecular barcode is attached to the alternatively spliced variants. In another example, the polynucleotide is digested and the molecular barcode is attached to the digested polynucleotide. In another example, the target-specific region of the molecular barcode comprises a sequence that is complementary to a sequence within the molecule.

A molecular barcode, sample tag (e.g., sample index), cellular label, or molecular identifier label (e.g., molecular label) comprising a hairpin may act as a probe for a hybridization chain reaction (HCR), and, thus, may be referred to as an HCR probe. The HCR probe may comprise a molecular barcode comprising a hairpin structure. The HCR probe may comprise a sample tag comprising a hairpin structure. The HCR probe may comprise a molecular identifier label comprising a hairpin structure. Further disclosed herein is a stochastic label-based hybridization chain reaction (HCR) method comprising stochastically labeling one or more nucleic acid molecules with an HCR probe, wherein the HCR probe comprises a molecular barcode comprising a hairpin and the one or more nucleic acid molecules act as initiators for a hybridization chain reaction. Further disclosed herein is a stochastic label-based hybridization chain reaction (HCR) method comprising stochastically labeling one or more nucleic acid molecules with an HCR probe, wherein the HCR probe comprises a sample tag comprising a hairpin and the one or more nucleic acid molecules act as initiators for a hybridization chain reaction. Further disclosed herein is a stochastic label-based hybridization chain reaction (HCR) method comprising stochastically labeling one or more nucleic acid molecules with an HCR probe, wherein the HCR probe comprises a molecular identifier label comprising a hairpin and the one or more nucleic acid molecules act as initiators for a hybridization chain reaction.

The HCR probe may comprise a hairpin with an overhang region. The overhang region of the hairpin may comprise a target specific region. The overhang region may comprise an oligodT sequence. The sample comprising the one or more nucleic acid molecules may be treated with one or more restriction nucleases prior to stochastic labeling. The overhang region may comprise a restriction enzyme recognition sequence. The sample comprising the one or more nucleic acid molecules may be contacted with one or more adapters prior to stochastic labeling to produce an adapter-nucleic acid molecule hybrid. The overhang region and the stem may be complementary to the one or more adapters. The HCR probe may comprise a hairpin with a loop. The loop of the HCR probe may comprise a label region and/or sample index region.

Hybridization of a first HCR probe to the nucleic acid molecules may result in the formation of a labeled nucleic acid, wherein the first HCR probe is linearized to produce a first linearized HCR probe. The first linearized HCR probe of the labeled nucleic acid may act as an initiator for hybridization of a second HCR probe to the labeled nucleic acid to produce a labeled nucleic acid with two linearized HCR probes. The second linearized HCR probe may act as an initiator for another hybridization reaction. This process may be repeated multiple times to produce a labeled nucleic acid with multiple linearized HCR probes. The detectable labels on the HCR probe may enable detection of the labeled nucleic acid. The detectable labels may be any type of label (e.g., fluorophore, chromophore, small molecule, nanoparticle, hapten, enzyme, antibody, magnet). The detectable labels may comprise fragments of a single label. The detectable labels may generate a detectable signal when they are in close proximity. When the HCR probe is a hairpin, the detectable labels may be too far away to produce a detectable signal. When the HCR probe is linearized and multiple linearized HCR probes are hybridized together, the detectable labels may be in close enough proximity to generate a detectable signal. For example, a HCR probe may comprise two pyrene moieties as detectable labels. Alternatively, the detectable labels may be nanoparticles. The stochastic label-based HCR method may enable attachment of multiple hairpin HCR probes to a labeled nucleic acid, which may result in signal amplification. Stochastic label-based HCR may increase the sensitivity of detection, analysis and/or quantification of the nucleic acid molecules. Stochastic label-based HCR may increase the accuracy of detection, analysis, and/or quantification of one or more nucleic acid molecules.

After lysis the target nucleic acid of the cells may hybridize to the oligonucleotide conjugated to the solid support. The target nucleic acid may hybridize to the target binding region of the oligonucleotide. The nucleic acid may hybridize to any region of the olignucleotide.

In some instances, not all oligonucleotides may bind a target nucleic acid. This is because in some instances, the number of oligonucleotides is larger than the number of target nucleic acids. The number of oligonucleotides conjugated to a solid support may be 1, 2, 3, 4, 5, 6, 7, 8, 9, or 10-fold more than the number of target nucleic acids in a cell. At least 10, 20, 30, 40, 50, 60, 70, 80, 90 or 100% of the oligonucleotides may be bound by a target nucleic acid. At most 10, 20, 30, 40, 50, 60, 70, 80, 90 or 100% of the oligonucleotides may be bound by a target nucleic acid. In some instances, at least 1, 2, 3, 4, 5, 6, 7, 8, 9, 10, 20, 30, 40, 50, 60, 70, 80, 90 or 100 or more different target nucleic acids may be captured by the oligonucleotides on a solid support. In some instances, at most 1, 2, 3, 4, 5, 6, 7, 8, 9, 10, 20, 30, 40, 50, 60, 70, 80, 90 or 100 or more different target nucleic acids may be captured by the oligonucleotides on a solid support.

In some instances, at least about 40, 50, 60, 70, 80, 90, 95, 96, 97, 98, 99, or 100% of the number of copies of a target nucleic acid are bound to oligonucleotides on a solid support. In some instances, at most about 40, 50, 60, 70, 80, 90, 95, 96, 97, 98, 99, or 100% of the number of copies of a target nucleic acid are bound to oligonucleotides on a solid support.

Retrieval

After lysis, the solid supports may be retrieved. Retrieval of the solid supports may be performed by using a magnet. Retrieval of the solid supports may be performed by melting the microwell array and/or sonication. Retrieval of the solid supports may comprise centrifugation. Retrieval of the solid supports may comprise size exclusion. In some instances, at least about 50, 60, 70, 80, 90, 95, or 100% of the solid supports are recovered from the microwells. In some instances, at most about 50, 60, 70, 80, 90, 95, or 100% of the solid supports are recovered from the microwells.

Reverse Transcription

The methods disclosed herein may further comprise reverse transcription of a labeled-RNA molecule to produce a labeled-cDNA molecule. In some instances, at least a portion of the oligonucleotide acts as a primer for the reverse transcription reaction. The oligodT portion of the oligonucleotide may act as a primer for first strand synthesis of the cDNA molecule.

In some instances the labeled cDNA molecule may be used as a molecule for a new stochastic labeling reaction. The labeled cDNA may have a first tag or set of tags from attachment to the RNA prior to reverse transcription and a second tag or set of tags attached to the cDNA molecule. These multiple labeling reactions can, for example, be used to determine the efficiency of events that occur between the attachment of the first and second tags, e.g., an optional amplification reaction or the reverse transcription reaction.

In another example, an oligonucleotide is attached to the 5' end of an RNA molecule to produce a labeled-RNA molecule. Reverse transcription of the labeled-RNA molecule may occur by the addition of a reverse transcription primer. In some instances, the reverse transcription primer is an oligodT primer, random hexanucleotide primer, or a target-specific oligonucleotide primer. Generally, oligodT primers are 12-18 nucleotides in length (SEQ ID NO: 1) and bind to the endogenous poly(A)+ tail at the 3' end of mammalian mRNA. Random hexanucleotide primers may bind to mRNA at a variety of complementary sites. Target-specific oligonucleotide primers typically selectively prime the mRNA of interest.

In some instances, the method comprises repeatedly reverse transcribing the labeled-RNA molecule to produce multiple labeled-cDNA molecules. The methods disclosed herein may comprise conducting at least about 1, 2, 3, 4, 5, 6, 7, 8, 9, 10, 11, 12, 13, 14, 15, 16, 17, 18, 19, or 20 reverse transcription reactions. The method may comprise conducting at least about 25, 30, 35, 40, 45, 50, 55, 60, 65, 70, 75, 80, 85, 90, 95, or 100 reverse transcription reactions.

Nucleic acid synthesis (e.g., cDNA synthesis) may be performed on the retrieved solid supports. Nucleic acid synthesis may be performed in a tube and/or on a rotor to keep the solid supports suspended. The resulting synthesized nucleic acid may be used in subsequent nucleic acid amplification and/or sequencing technologies. Nucleic acid synthesis may comprise generating cDNA copies on a RNA attached to the oligonucleotide on the solid support. Generating cDNA copies may comprise using a reverse transcriptase (RT) or DNA polymerases having RT activity. This may result in the production of single-stranded cDNA molecules. After nucleic acid synthesis, unused oligonucleotides may be removed from the solid support. Removal of the oligonucleotides may occur by exonuclease treatment (e.g., by ExoI).

In some embodiments, nucleic acids can be removed from the solid support using chemical cleavage. For example, a chemical group or a modified base present in a nucleic acid can be used to facilitate its removal from a solid support. For example, an enzyme can be used to remove a nucleic acid from a solid support. For example, a nucleic acid can be removed from a solid support through a restriction endonuclease digestion. For example, treatment of a nucleic acid containing a dUTP or ddUTP with uracil-d-glycosylase (UDG) can be used to remove a nucleic acid from a solid support. For example, a nucleic acid can be removed from a solid support using an enzyme that performs nucleotide excision, such as a base excision repair enzyme, such as an apurinic/apyrimidinic (AP) endonuclease. In some embodiments, a nucleic acid can be removed from a solid support using a photocleavable group and light. In some embodiments, a cleavable linker can be used to remove a nucleic acid from the solid support. For example, the cleavable linker can comprise at least one of biotin/avidin, biotin/streptavidin, biotin/neutravidin, Ig-protein A, a photo-labile linker, acid or base labile linker group, or an aptamer.

In some embodiments, nucleic acids are not amplified. In some embodiments, nucleic acids are not amplified prior to sequencing the nucleic acids. In some embodiments, nucleic acids not attached to a solid support can be directly sequenced without prior amplification. In some embodiments, nucleic acids can be directly sequenced without performing amplification when attached to a solid support, for example, nucleic acids attached to a solid support can be directly sequenced while attached to the solid support. In some embodiments, a nucleic acid that has been removed from a solid support can be directly sequenced. For example, a nucleic acid that has been removed from a solid support can be directly sequenced without performing amplification. Any sequencing platform conducive to sequencing without amplification can be used to perform the sequencing.

Amplification

After the nucleic acid has been synthesized (e.g., reverse transcribed), it may be amplified. Amplification may be performed in a multiplex manner, wherein multiple target nucleic acid sequences are amplified simultaneously. Amplification may add sequencing adaptors to the nucleic acid. Amplification may be performed by polymerase chain reaction (PCR). PCR may refer to a reaction for the in vitro amplification of specific DNA sequences by the simultaneous primer extension of complementary strands of DNA. PCR may encompass derivative forms of the reaction, including but not limited to, RT-PCR, real-time PCR, nested PCR, quantitative PCR, multiplexed PCR, digital PCR, and assembly PCR.

The method may further comprise conducting one or more amplification reactions to produce labeled nucleic acid amplicons. The labeled nucleic acids may be amplified prior to detecting the labeled nucleic acids. The method may further comprise combining the first and second samples prior to conducting the one or more amplification reactions.

The amplification reactions may comprise amplifying at least a portion of the sample tag. The amplification reactions may comprise amplifying at least a portion of the label. The amplification reactions may comprise amplifying at least a portion of the sample tag, label, nucleic acid, or a combination thereof. The amplification reactions may comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids. The method may further comprise conducting one or more cDNA synthesis reactions to produce one or more cDNA copies of the sample-tagged nucleic acids or molecular identifier labeled nucleic acids.

Amplification of the labeled nucleic acids may comprise PCR-based methods or non-PCR based methods. Amplification of the labeled nucleic acids may comprise exponential amplification of the labeled nucleic acids. Amplification of the labeled nucleic acids may comprise linear amplification of the labeled nucleic acids.

In some instances, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets (WO 89/01050; WO 88/10315; and U.S. Pat. Nos. 5,130,238; 5,409,818; 5,466,586; 5,514,545; 5,554,517; 5,888,779; 6,063,603; and 6,197,554), a ligase chain reaction (LCR), a Qβ replicase (Qβ) method as described in U.S. Pat. No. 4,786,600, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity (U.S. Pat. No. 6,214,587), rolling circle amplification, and ramification extension amplification (RAM) (U.S. Pat. No. 5,942,391).

Amplification of the labeled nucleic acids may comprise hybridization chain reaction (HCR) based methods (Dirks and Pierce, PNAS, 2004; Zhang et al., Anal Chem, 2012). HCR based methods may comprise DNA-based HCR. HCR based methods may comprise one or more labeled probes. The one or more labeled probes may comprise one or more sample tags or molecular identifier labels, or the complement thereof, disclosed herein.

In some instances, the methods disclosed herein further comprise conducting a polymerase chain reaction on the labeled nucleic acid (e.g., labeled-RNA, labeled-DNA, labeled-cDNA) to produce a labeled-amplicon. The labeled-amplicon may be double-stranded molecule. The double-stranded molecule may comprise a double-stranded RNA molecule, a double-stranded DNA molecule, or a RNA molecule hybridized to a DNA molecule. One or both of the strands of the double-stranded molecule may comprise the sample tag or molecular identifier label. Alternatively, the labeled-amplicon is a single-stranded molecule. The single-stranded molecule may comprise DNA, RNA, or a combination thereof. The nucleic acids of the present invention may comprise synthetic or altered nucleic acids.

The polymerase chain reaction may be performed by methods such as PCR, HD-PCR, Next Gen PCR, digital RTA, or any combination thereof. Additional PCR methods include, but are not limited to, allele-specific PCR, Alu PCR, assembly PCR, asymmetric PCR, droplet PCR, emulsion PCR, helicase dependent amplification HDA, hot start PCR, inverse PCR, linear-after-the-exponential (LATE)-PCR, long PCR, multiplex PCR, nested PCR, hemi-nested PCR, quantitative PCR, RT-PCR, real time PCR, single cell PCR, touchdown PCR or combinations thereof.

Multiplex PCR reactions may comprise nested PCR reactions. The method may comprise a pair of primers wherein a first primer that anneals to any one of the plurality of nucleic acids at least 300 to 400 nucleotides from the 3' end of any one of the plurality of nucleic acids and a second primer that anneals to any one of the plurality of nucleic acids at least 200 to 300 nucleotides from the 3' end of any one of the plurality of nucleic acids, wherein the first primer and second primer generate complementary DNA synthesis towards the 3' end of any one of the plurality of nucleic acids.

In some instances, conducting a polymerase chain reaction comprises annealing a first target specific primer to the labeled nucleic acid. Alternatively or additionally, conducting a polymerase chain reaction further comprises annealing a universal primer to a universal primer binding site region of the sample tag or molecular identifier label, wherein the sample tag or molecular identifier label is on a labeled nucleic acid or labeled-amplicon. The methods disclosed herein may further comprise annealing a second target specific primer to the labeled nucleic acid and/or labeled-amplicon.

In some instances, the method comprises repeatedly amplifying the labeled nucleic acid to produce multiple labeled-amplicons. The methods disclosed herein may comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245), rolling circle amplification (RCA) (for example, Fire and Xu, PNAS 92:4641 (1995) and Liu et al., J. Am. Chem. Soc. 118:1587 (1996)) and U.S. Pat. No. 5,648,245, strand displacement amplification (see Lasken and Egholm, Trends Biotechnol. 2003 21(12):531-5; Barker et al. Genome Res. 2004 May; 14(5):901-7; Dean et al. Proc Natl Acad Sci USA. 2002; 99(8):5261-6; Walker et al. 1992, Nucleic Acids Res. 20(7):1691-6, 1992 and Paez, et al. Nucleic Acids Res. 2004; 32(9):e71), Qbeta Replicase, described in PCT Patent Application No. PCT/US87/00880 and nucleic acid based sequence amplification (NABSA). (See, U.S. Pat. Nos. 5,409,818, 5,554,517, and 6,063,603, each of which is incorporated herein by reference), Other amplification methods that may be used are described in, U.S. Pat. Nos. 6,582,938, 5,242,794, 5,494,810, 4,988,617, and US Pub. No. 20030143599 each of which is incorporated herein by reference. DNA may also be amplified by multiplex locus-specific PCR or using adaptor-ligation and single primer PCR (See Kinzler and Vogelstein, NAR (1989) 17:3645-53. Other available methods of amplification, such as balanced PCR (Makrigiorgos, et al. (2002), Nat Biotechnol, Vol. 20, pp. 936-9), may also be used.

Molecular inversion probes ("MIPs") may also be used for amplification of selected targets. MIPs may be generated so that the ends of the pre-circle probe are complementary to regions that flank the region to be amplified. The gap may be closed by extension of the end of the probe so that the complement of the target is incorporated into the MIP prior to ligation of the ends to form a closed circle. The closed circle may be amplified and detected by sequencing or hybridization as previously disclosed in Hardenbol et al., Genome Res. 15:269-275 (2005) and in U.S. Pat. No. 6,858,412.

Amplification may further comprise adding one or more control nucleic acids to one or more samples comprising a plurality of nucleic acids. Amplification may further comprise adding one or more control nucleic acids to a plurality of nucleic acids. The control nucleic acids may comprise a control label.

Amplification may comprise use of one or more non-natural nucleotides. Non-natural nucleotides may comprise photolabile and/or triggerable nucleotides. Examples of non-natural nucleotides include, but are not limited to, peptide nucleic acid (PNA), morpholino and locked nucleic acid (LNA), as well as glycol nucleic acid (GNA) and threose nucleic acid (TNA). Non-natural nucleotides may be added to one or more cycles of an amplification reaction. The addition of the non-natural nucleotides may be used to identify products as specific cycles or time points in the amplification reaction.

Conducting the one or more amplification reactions may comprise the use of one or more primers. The one or more primers may comprise one or more oligonucleotides. The one or more oligonucleotides may comprise at least about 7-9 nucleotides. The one or more oligonucleotides may comprise less than 12-15 nucleotides. The one or more primers may anneal to at least a portion of the plurality of labeled nucleic acids. The one or more primers may anneal to the 3' end and/or 5' end of the plurality of labeled nucleic acids. The one or more primers may anneal to an internal region of the plurality of labeled nucleic acids. The internal region may be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers may comprise a fixed panel of primers. The one or more primers may comprise at least one or more custom primers. The one or more primers may comprise at least one or more control primers. The one or more primers may comprise at least one or more housekeeping gene primers. The one or more oligonucleotides may comprise a sequence selected from a group consisting of sequences in Table 23. The one or more primers may comprise a universal primer. The universal primer may anneal to a universal primer binding site. The one or more custom primers may anneal to the first sample tag, the second sample tag, the molecular identifier label, the nucleic acid or a product thereof. The one or more primers may comprise a universal primer and a custom primer. The custom primer may be designed to amplify one or more target nucleic acids. The target nucleic acids may comprise a subset of the total nucleic acids in one or more samples. The target nucleic acids may comprise a subset of the total labeled nucleic acids in one or more samples The one or more primers may comprise at least 96 or more custom primers. The one or more primers may comprise at least 960 or more custom primers. The one or more primers may comprise at least 9600 or more custom primers. The one or more custom primers may anneal to two or more different labeled nucleic acids. The two or more different labeled nucleic acids may correspond to one or more genes.

Disclosed herein is a method of selecting a custom primer comprising: a) a first pass, wherein primers chosen may comprise: i) no more than three sequential guanines, no more than three sequential cytosines, no more than four sequential adenines, and no more than four sequential thymines; ii) at least 3, 4, 5, or 6 nucleotides that are guanines or cytosines; and iii) a sequence that does not easily form a hairpin structure; b) a second pass, comprising: i) a first round of choosing a plurality of sequences that have high coverage of all transcripts; and ii) one or more subsequent rounds, selecting a sequence that has the highest coverage of remaining transcripts and a complementary score with other chosen sequences no more than 4; and c) adding sequences to a picked set until coverage saturates or total number of customer primers is less than or equal to about 96.

The method of selecting the custom primer may further comprise selecting the at least one common primer based on one or more mRNA transcripts, non-coding transcripts including structural RNAs, transcribed pseudogenes, model mRNA provided by a genome annotation process, sequences corresponding to the genomic contig, or any combination thereof.

The method of selecting the custom primer may further comprise a primer selection method that enriches for one or more subsets of nucleic acids. The one or more subsets may comprise low abundance mRNAs.

The method of selecting the custom primer may further comprise a computational algorithm. Primers used in the method may be designed with the use of the Primer 3, a computer program which suggests primer sequences based on a user defined input sequence. Other primer designs may also be used, or primers may be selected by eye without the aid of computer programs. There are many options available with the program to tailor the primer design to most applications. Primer3 may consider many factors, including, but not limited to, oligo melting temperature, length, GC content, 3' stability, estimated secondary structure, the likelihood of annealing to or amplifying undesirable sequences (for example interspersed repeats) and the likelihood of primer-dimer formation between two copies of the same primer. In the design of primer pairs, Primer3 may consider product size and melting temperature, the likelihood of primer-dimer formation between the two primers in the pair, the difference between primer melting temperatures, and primer location relative to particular regions of interest to be avoided.

The methods, compositions and kits disclosed herein may comprise one or more primers disclosed in Tables 23-24.

Sequencing

In some aspects, determining the number of different labeled nucleic acids may comprise determining the sequence of the labeled nucleic acid or any product thereof (e.g., labeled-amplicons, labeled-cDNA molecules). In some instances, an amplified target nucleic acid may be subjected to sequencing. Determining the sequence of the labeled nucleic acid or any product thereof may comprise conducting a sequencing reaction to determine the sequence of at least a portion of the sample tag, molecular identifier label, at least a portion of the labeled nucleic acid, a complement thereof, a reverse complement thereof, or any combination thereof. In some instances only the sample tag or a portion of the sample tag is sequenced. In some instances only the molecular identifier label or a portion of the molecular identifier label is sequenced.

Determining the sequence of the labeled nucleic acid or any product thereof may be performed by sequencing methods such as Helioscope™ single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent™, Ion semiconductor sequencing, Single Molecule SMRT(™) sequencing, Polony sequencing, DNA nanoball sequencing, and VisiGen Biotechnologies approach. Alternatively, determining the sequence of the labeled nucleic acid or any product thereof may use sequencing platforms, including, but not limited to, Genome Analyzer IIx, HiSeq, and MiSeq offered by Illumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, Mass.).

In some embodiments, the labeled nucleic acids comprise nucleic acids representing from about 0.01% of the genes of an organism's genome to about 100% of the genes of an organism's genome. For example, about 0.01% of the genes of an organism's genome to about 100% of the genes of an organism's genome can be sequenced using a target complimentary region comprising a plurality of multimers by capturing the genes containing a complimentary sequence from the sample. In some embodiments, the labeled nucleic acids comprise nucleic acids representing from about 0.01% of the transcripts of an organism's transcriptome to about 100% of the transcripts of an organism's transcriptome. For example, about 0.501% of the transcripts of an organism's transcriptome to about 100% of the transcripts of an organism's transcriptome can be sequenced using a target complimentary region comprising a poly-T tail by capturing the mRNAs from the sample.

In some instances, determining the sequence of the labeled nucleic acid or any product thereof comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the labeled nucleic acid or any product thereof may be determined by electron microscopy or a chemical-sensitive field effect transistor (chemFET) array.

Determination of the sequence of a nucleic acid (e.g., amplified nucleic acid, labeled nucleic acid, cDNA copy of a labeled nucleic acid, etc.) may be performed using variety of sequencing methods including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads, wobble sequencing, multiplex sequencing, polymerized colony (POLONY) sequencing; nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, such as cyclic array sequencing using platforms such as Roche 454, Illumina Solexa, ABI-SOLiD, ION Torrents, Complete Genomics, Pacific Bioscience, Helicos, Polonator platforms, may also be utilized. Sequencing may comprise MiSeq sequencing. Sequencing may comprise HiSeq sequencing. Sequencing may read the cell label, the molecular label and/or the gene that was on the original oligonucleotide.

In another example, determining the sequence of labeled nucleic acids or any product thereof comprises RNA-Seq or microRNA sequencing. Alternatively, determining the sequence of labeled nucleic acids or any products thereof comprises protein sequencing techniques such as Edman degradation, peptide mass fingerprinting, mass spectrometry, or protease digestion.

The sequencing reaction can, in certain embodiments, occur on a solid or semi-solid support, in a gel, in an emulsion, on a surface, on a bead, in a drop, in a continuous follow, in a dilution, or in one or more physically separate volumes.

Sequencing may comprise sequencing at least about 10, 20, 30, 40, 50, 60, 70, 80, 90, 100 or more nucleotides or base pairs of the labeled nucleic acid. In some instances, sequencing comprises sequencing at least about 200, 300, 400, 500, 600, 700, 800, 900, 1000 or more nucleotides or base pairs of the labeled nucleic acid. In other instances, sequencing comprises sequencing at least about 1500; 2,000; 3,000; 4,000; 5,000; 6,000; 7,000; 8,000; 9,000; or 10,000 or more nucleotides or base pairs of the labeled nucleic acid.

Sequencing may comprise at least about 200, 300, 400, 500, 600, 700, 800, 900, 1000 or more sequencing reads per run. In some instances, sequencing comprises sequencing at least about 1500; 2,000; 3,000; 4,000; 5,000; 6,000; 7,000; 8,000; 9,000; or 10,000 or more sequencing reads per run. Sequencing may comprise less than or equal to about 1,600,000,000 sequencing reads per run. Sequencing may comprise less than or equal to about 200,000,000 reads per run.

Determining the number of different labeled nucleic acids may comprise one or more arrays.

Determining the number of different labeled nucleic acids may comprise contacting the labeled nucleic acids with the one or more probes.

Probes, as described herein, may comprise a sequence that is complementary to at least a portion of the labeled nucleic acid or labeled-amplicon. The plurality of probes may be arranged on the solid support in discrete regions, wherein a discrete region on the solid support comprises probes of identical or near-identical sequences. In some instances, two or more discrete regions on the solid support comprise two different probes comprising sequences complementary to the sequence of two different unique identifier regions of the oligonucleotide tag.

In some instances, the plurality of probes is hybridized to the array. The plurality of probes may allow hybridization of the labeled-molecule to the array. The plurality of probes may comprise a sequence that is complementary to the stochastic label oligo dT. Alternatively, or additionally, the plurality of probes comprises a sequence that is complementary to the molecule.

Determining the number of different labeled nucleic acids may comprise contacting the labeled nucleic acids with an array of a plurality of probes. Determining the number of different labeled nucleic acids may comprise contacting the labeled nucleic acids with a glass slide of a plurality of probes.

Determining the number of different labeled nucleic acids may comprise labeled probe hybridization, target-specific amplification, target-specific sequencing, sequencing with labeled nucleotides specific for target small nucleotide polymorphism, sequencing with labeled nucleotides specific for restriction enzyme digest patterns, sequencing with labeled nucleotides specific for mutations, or a combination thereof.

Determining the number of different labeled nucleic acids may comprise flow cytometry sorting of a sequence-specific label. Determining the number of different labeled nucleic acids may comprise detection of the labeled nucleic acids attached to the beads. Detection of the labeled nucleic acids attached to the beads may comprise fluorescence detection.

Determining the number of different labeled nucleic acids may comprise counting the plurality of labeled nucleic acids by fluorescence resonance energy transfer (FRET), between a target-specific probe and a labeled nucleic acid or a target-specific labeled probe.

Detection of Labeled Nucleic Acids

The methods disclosed herein may further comprise detection of the labeled nucleic acids and/or labeled-amplicons. Detection of the labeled nucleic acids and/or labeled-amplicons may comprise hybridization of the labeled nucleic acids to surface, e.g., a solid support. The method may further comprise immunoprecipitation of a target sequence with a nucleic-acid binding protein. Detection of the labeled nucleic acids and/or labeled amplicons may enable or assist in determining the number of different labeled nucleic acids.

In some instances, the method further comprises contacting the labeled nucleic acids and/or labeled-amplicons with a detectable label to produce a detectable-label conjugated labeled nucleic acid. The methods disclosed herein may further comprise detecting the detectable-label conjugated labeled nucleic acid. Detection of the labeled nucleic acids or any products thereof (e.g., labeled-amplicons, detectable-label conjugated labeled nucleic acid) may comprise detection of at least a portion of the sample tag or molecular identifier label, molecule, detectable label, a complement of the sample tag or molecular identifier label, a complement of the molecule, or any combination thereof.

Detection of the labeled nucleic acids or any products thereof may comprise an emulsion or a droplet. For example, the labeled nucleic acids or any products thereof may be in an emulsion or droplet. A droplet can be a small volume of a first liquid that is encapsulated by an immiscible second liquid, such as a continuous phase of an emulsion (and/or by a larger droplet). The volume of a droplet, and/or the average volume of droplets in an emulsion, can, for example, be less than about one microliter (or between about one microliter and one nanoliter or between about one microliter and one picoliter), less than about one nanoliter (or between about one nanoliter and one picoliter), or less than about one picoliter (or between about one picoliter and one femtoliter), among others. A droplet (or droplets of an emulsion) can have a diameter (or an average diameter) of less than about 1000, 100, or 10 micrometers, or about 1000 to 10 micrometers, among others. A droplet can be spherical or nonspherical. Droplets can be generated having an average diameter of about, less than about, or more than about 0.001, 0.01, 0.05, 0.1, 1, 5, 10, 20, 30, 40, 50, 60, 70, 80, 100, 120, 130, 140, 150, 160, 180, 200, 300, 400, or 500 microns. Droplets can have an average diameter of about 0.001 to about 500, about 0.01 to about 500, about 0.1 to about 500, about 0.1 to about 100, about 0.01 to about 100, or about 1 to about 100 microns. A droplet can be a simple droplet or a compound droplet. The term emulsion, as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase. When an emulsion or droplet is used to isolate, for example, spatially isolate, single cells, a solid support may not be used. Thus the nucleic acids to be tagged and analyzed may not be bound to a solid support and in such instances; a cellular label can correspond to the single cell or population of cells present in the emulsion or droplet when tagged. The emulsion or droplet can thus effectively isolate the tagging or labeling steps with a single cell or plurality of cells and the cellular label can be used to identify the nucleic acids that came from the single cell or plurality of cells. In some embodiments, droplets can be applied to microwells, for example, similarly to application of beads to microwell arrays.

Alternatively, detection of the labeled nucleic acids or any products thereof comprises one or more solutions. In other instances, detection of the labeled nucleic acids comprises one or more containers.

Detection of the labeled nucleic acids or any products thereof (e.g., labeled-amplicons, detectable-label conjugated labeled nucleic acid) may comprise detecting each labeled nucleic acid or products thereof. For example, the methods disclosed herein comprise sequencing at least a portion of each labeled nucleic acid, thereby detecting each labeled nucleic acid.

In some instances, detection of the labeled nucleic acids and/or labeled-amplicons comprises electrophoresis, spectroscopy, microscopy, chemiluminescence, luminescence, fluorescence, immunofluorescence, colorimetry, or electrochemiluminescence methods. For example, the method comprises detection of a fluorescent dye. Detection of the labeled nucleic acid or any products thereof may comprise colorimetric methods. For example, the colorimetric method comprises the use of a colorimeter or a colorimetric reader. A non-limiting list of colorimeters and colorimetric readers include Sensovation's Colorimetric Array Imaging Reader (CLAIR), ESEQuant Lateral Flow Immunoassay Reader, SpectraMax 340PC 38, SpectraMax Plus 384, SpectraMax 190, VersaMax, VMax, and EMax.

Additional methods used alone or in combination with other methods to detect the labeled nucleic acids and/or amplicons may comprise the use of an array detector, fluorescence reader, non-fluorescent detector, CR reader, luminometer, or scanner. In some instances, detecting the labeled nucleic acids and/or labeled-amplicons comprises the use of an array detector. Examples of array detectors include, but are not limited to, diode-array detectors, photodiode array detectors, HLPC photodiode array detectors, array detectors, Germanium array detectors, CMOS and CCD array detectors, Gated linear CCD array detectors, InGaAs photodiode array systems, and TE cooled CCD systems. The array detector may be a microarray detector. Non-limiting examples of microarray detectors include microelectrode array detectors, optical DNA microarray detection platforms, DNA microarray detectors, RNA microarray detectors, and protein microarray detectors.

In some instances, a fluorescence reader is used to detect the labeled nucleic acid and/or labeled-amplicons. The fluorescence reader may read 1, 2, 3, 4, 5, or more color fluorescence microarrays or other structures on biochips, on slides, or in microplates. In some instances, the fluorescence reader is a Sensovation Fluorescence Array imaging Reader (FLAIR). Alternatively, the fluorescence reader is a fluorescence microplate reader such as the Gemini XPS Fluorescence microplate reader, Gemini EM Fluorescence microplate reader, Finstruments® Fluoroskan filter based fluorescence microplate reader, PHERAstar microplate reader, FlUOstar microplate reader, POLARstar Omega microplate reader, FLUOstar OPTIMA multi-mode microplate reader and POLARstar OPTIMA multi-mode microplate reader. Additional examples of fluorescence readers include PharosFX™ and PharosFX Plus systems.

In some instances, detection of the labeled nucleic acid and/or labeled-amplicon comprises the use of a microplate reader. In some instances, the microplate reader is an xMark™ microplate absorbance spectrophotometer, iMark microplate absorbance reader, EnSpire® Multimode plate reader, EnVision Multilabel plate reader, VICTOR X Multilabel plate reader, FlexStation, SpectraMax Paradigm, SpectraMax M5e, SpectraMax M5, SpectraMax M4, SpectraMax M3, SpectraMax M2-M2e, FilterMax F series, Fluoroskan Ascent FL Microplate Fluoremeter and Luminometer, Fluoroskan Ascent Microplate Fluoremeter, Luminoskan Ascent Microplate Luminometer, Multiskan EX Microplate Photometer, Muliskan FC Microplate Photometer, and Muliskan GO Microplate Photometer. In some instances, the microplate reader detects absorbance, fluorescence, luminescence, time-resolved fluorescence, light scattering, or any combination thereof. In some embodiments, the microplate reader detects dynamic light scattering. The microplate reader, may in some instances, detect static light scattering. In some instances, detection of the labeled nucleic acids and/or labeled-amplicons comprises the use of a microplate imager. In some instances, the microplate imager comprises ViewLux uHTS microplate imager and BioRad microplate imaging system.

Detection of labeled nucleic acids and/or products thereof may comprise the use of a luminometer. Examples of luminometers include, but are not limited to, SpectraMax L, GloMax®-96 microplate luminometer, GloMax®-20/20 single-tube luminometer, GloMax®-Multi+ with Instinct™ software, GloMax®-Multi Jr single tube multimode reader, LUMIstar OPTIMA, LEADER HC+ luminometer, LEADER 450i luminometer, and LEADER 50i luminometer.

In some instances, detection of the labeled nucleic acids and/or labeled-amplicons comprises the use of a scanner. Scanners include flatbed scanners such as those provided by Cannon, Epson, HP, Fujitsu, and Xerox. Additional examples of flatbed scanners include the FMBIO® fluorescence imaging scanners (e.g., FMBIO® II, III, and III Plus systems). Scanners may include microplate scanners such as the Arrayit ArrayPix™ microarray microplate scanner. In some instances, the scanner is a Personal Molecular Imager™ (PMI) system provided by Bio-rad.

Detection of the labeled nucleic acid may comprise the use of an analytical technique that measures the mass-to-charge ratio of charged particles, e.g., mass spectrometry. In some embodiments the mass-to-charge ratio of charged particles is measured in combination with chromatographic separation techniques. In some embodiments sequencing reactions are used in combination with mass-to-charge ratio of charged particle measurements. In some embodiments the tags comprise isotopes. In some embodiments the isotope type or ratio is controlled or manipulated in the tag library.

Detection of the labeled nucleic acids or any products thereof comprises the use of small particles and/or light scattering. For example, the amplified molecules (e.g., labeled-amplicons) are attached to haptens or directly to small particles and hybridized to the array. The small particles may be in the nanometer to micrometer range in size. The particles may be detected when light is scattered off of its surface.

A colorimetric assay may be used where the small particles are colored, or haptens may be stained with colorimetric detection systems. In some instances, a flatbed scanner may be used to detect the light scattered from particles, or the development of colored materials. The methods disclosed herein may further comprise the use of a light absorbing material. The light absorbing material may be used to block undesirable light scatter or reflection. The light absorbing material may be a food coloring or other material. In some instances, detection of the labeled nucleic acid or any products thereof comprises contacting the labeled nucleic acids with an off-axis white light.

In some embodiments, two or more different types of biological materials from a sample can be detected simultaneously. For example, two or more different types of biological materials selected from the group consisting of DNA, RNA (e.g., microRNA, mRNA, etc.), nucleotide, protein, and carbohydrate, from a sample can be detected simultaneously. For example, DNA and RNA from a sample can be detected simultaneously using the methods described herein.

Data Analysis

The sequencing data may be used to count the number of target nucleic acid molecules in a cell. For example, a plurality of copies of a target nucleic acid in a cell may bind to a different oligonucleotide on the solid support. When the plurality of target nucleic acids are amplified and sequenced, they may comprise different molecular labels. The number of molecular labels for a same target nucleic acid may be indicative of the number of copies of the target nucleic acid in the cell. Determining the copy number of a target nucleic acid may be useful for removing amplification bias when determining the concentration of a target nucleic acid in a cell.

The sequencing data may be used to genotype a subject. By comparing target nucleic acids with different cellular labels, the copy number variation and/or concentration of the target nucleic acid may be determined. By comparing concentrations of target nucleic acids with different cellular labels, the sequencing data may be used to determine cellular genotype heterogeneity. For example, a first cell of a sample may comprise a target nucleic acid at high concentrations, whereas a second cell of the sample may not comprise the target nucleic acid, or may comprise the target nucleic acid at low concentrations, thereby indicating the heterogeneity of the cellular sample.

Determining cellular genotype heterogeneity may be useful for diagnosing, prognosing, and determining a course of treatment of a disease. For example, if a first cell of a sample comprises the target nucleic acid, but a second cell of the sample does not comprise the target nucleic acid, but comprises a second target nucleic acid, then a course of a treatment may include an agent (e.g., drug) to target the first genotype and an agent (e.g., drug) to target the second genotype.

In some embodiments, certain sequence types can be linked to a DNA or RNA profile. For example, T-cell receptor and/or B-cell receptor sequences can be linked to a transcription profile, microRNA profile, or genomic mutation profile of a sample, such as a single cell. In some embodiments, certain sequence types can be linked to an antigenicity or protein expression profile. For example, T-cell receptor and/or B-cell receptor sequences can be linked to an antigenicity or protein expression profile via binding antibodies to a surface, such as a surface comprising proteins, such as protein targets of antibodies comprising the T-cell receptor and/or B-cell receptor sequences.

In some embodiments, the presence or absence of a sequence, such as a viral sequence, can be linked to a DNA or RNA profile. For example, the presence or absence of a sequence, such as a viral sequence, can be linked to a transcription profile, microRNA profile, or genomic mutation profile of a sample, such as a single cell.

Kits

The present disclosure provides kits for carrying out the methods of the disclosure. A kit may comprise one or more of: a microwell array, an oligonucleotide, and a solid support. A kit may comprise a reagent for reconstituting and/or diluting the oligonucleotides and/or solid support. A kit may comprise reagents for conjugating the oligonucleotides to the solid support. A kit may further comprise one or more additional reagents, where such additional reagents may be selected from: a wash buffer; a control reagent, an amplification agent for amplifying (e.g., performing cDNA synthesis and PCR) a target nucleic acid, and a conjugation agent for conjugating an oligonucleotide to the solid support. Components of a subject kit may be in separate containers, or may be combined in a single container.

A kit may comprise instructions for using the components of the kit to practice the subject methods. The instructions for practicing the subject methods may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In some embodiments, the instructions may be present as an electronic storage data file present on a suitable computer readable storage medium, e.g., CD-ROM, diskette, flash drive, etc. In some embodiments, the actual instructions may not be present in the kit, but means for obtaining the instructions from a remote source, e.g., via the internet, are provided. For example a kit may comprise a web address where the instructions may be viewed and/or from which the instructions may be downloaded. As with the instructions, this means for obtaining the instructions is recorded on a suitable substrate.

Further disclosed herein are kits for use in analyzing two or more molecules from two or more samples. The kits disclosed herein may comprise a plurality of beads, a primer and amplification agents sufficient to process at least about 384 samples. Any one of the samples may comprise a single cell. The nucleic acid amplification may result in a measurement of about 1, 2, 5, 10, 15, 20, 25, 30, 35, 40, 45, 50, 55, 60, 65, 70, 75, 80, 85, 90, 95, 100, 200, 300, 400, 500, 600, 700, 800, 900 or 1000 targeted nucleic acids in a sample. The nucleic acid amplification may result in a measurement of about 1000 targeted nucleic acids in a sample. The nucleic acid amplification may result in a measurement of about 100 targeted nucleic acids in a sample. The nucleic acid amplification may result in a measurement of about 5%, 10%, 15%, 20%, 25%, 30%, 35%, 40%, 45%, 50%, 55%, 60%, 65%, 70%, 75%, 80%, 85%, 90%, 95%, 100% of total nucleic acids in single cells. The nucleic acid amplification may result in a global measurement of all nucleic acid sequences in single cells. The nucleic acid amplification may result in a measurement of targeted nucleic acid sequences in single cells by sequencing. The nucleic acid amplification may result in a measurement of targeted nucleic acid sequences in single cells by an array.

The amplification agents may comprise a fixed panel of primers. The amplification agents may comprise at least one pair of custom primers. The amplification agents may comprise at least one pair of control primers. The amplification agents may comprise at least one pair of housekeeping gene primers. The amplification agents suitable may comprise a PCR master mix. The kit may further comprise instructions for primer design and optimization. The kit may further comprise a microwell plate, wherein the microwell plate may comprise at least one well in which no more than one bead is distributed. The kit may further comprise one or more additional containers. The one or more additional containers may comprise one or more additional plurality of sample tags. The plurality of one or more additional sample tags in the one or more additional containers are different from the first plurality of sample tags in the first container. The one or more additional containers may comprise one or more additional molecular identifier labels. The one or more additional molecular identifier labels of the one or more additional containers are the same as the one or more additional molecular identifier labels of the second container.

The methods and kits disclosed herein may comprise the use of one or more pipette tips and/or containers (e.g., tubes, vials, multiwell plates, microwell plates, eppendorf tubes, glass slides, beads). In some instances, the pipet tips are low binding pipet tips. Alternatively, or additionally, the containers may be low binding containers. Low binding pipet tips and low binding containers may have reduced leaching and/or subsequent sample degradation associated with silicone-based tips and non-low binding containers. Low binding pipet tips and low binding containers may have reduced sample binding as compared to non-low binding pipet tips and containers. Examples of low binding tips include, but are not limited to, Corning® DeckWorks™ low binding tips and Avant Premium low binding graduated tips. A non-limiting list of low-binding containers include Corning® Costar® low binding microcentrifuge tubes and Cosmobrand low binding PCR tubes and microcentrifuge tubes.

Any of the kits disclosed herein can further comprise software. For example, a kit can comprise software for analyzing sequences, such as barcodes or target sequences. For example, a kit can comprise software for analyzing sequences, such as barcodes or target sequences for counting unique target molecules, such as unique target molecules from a single cell. For example, a kit can comprise software for analyzing sequences, such as barcodes or target sequences for counting unique target molecules, such as unique target molecules from a gene, such as a gene from a single cell.

Microwells and Microwell Arrays

In some instances, the methods of the disclosure provide for contacting a solid support comprising a conjugated oligonucleotide with a cell. The contacting step may be performed on a surface. Exemplary surfaces may include a microwell, a tube, a flask, and chip. In some instances, the surface comprises a microwell. In some instances, the microwell is part of a microwell array.

The microwells of a microwell array may be of a size and shape capable of containing at least 1, 2, 3, 4, 5, 6, 7, 8, 9, or 10 or more cells per microwell. The microwells may be of a size and shape capable of containing at most 1, 2, 3, 4, 5, 6, 7, 8, 9, or 10 or more cells per microwell. The microwells of a microwell array may be of a size and shape capable of containing at least 1, 2, 3, 4, 5, 6, 7, 8, 9, or 10 or more solid supports per microwell. The microwells may be of a size and shape capable of containing at most 1, 2, 3, 4, 5, 6, 7, 8, 9, or 10 or more solid supports per microwell. A microwell may comprise at most one cell and one solid support. A microwell may comprise at most one cell and two solid supports. A microwell may comprise at least one cell and at most one solid support. A microwell may comprise at least one cell and at most two solid supports.

Microwells on the microwell array may be arranged horizontally. The microwells may be arranged vertically. The microwells may be arranged with equal or near equal spacing. The microwell array may have markers associated with one or more microwells. For example, the microwells of the microwell array may be divided into groups each comprised of a prescribed number of microwells. These groups may be provided on the principal surface of the substrate. Markers may be provided so that the position of each group may be determined. A marker may be detectable by the naked eye. A marker may be a marker that requires optics to see (e.g., fluorescent marker, emission marker, UV marker).

A microwell array may comprise at least about 96, 384, 1000, 5000, 10000, 15000, 100000, 150000, 500000, 1000000, or 5000000 or more microwells. A microwell array may comprise at most about 96, 384, 1000, 5000, 10000, 15000, 100000, 150000 500000, 1000000, or 5000000 or more microwells.

The shape of the microwell may be cylindrical. The shape of the microwell may be noncylindrical, such as a polyhedron comprised of multiple faces (for example, a parallelepiped, hexagonal column, or octagonal column), an inverted cone, an inverted pyramid (inverted triangular pyramid, inverted square pyramid, inverted pentagonal pyramid, inverted hexagonal pyramid, or an inverted polygonal pyramid with seven or more angles). The microwell may comprise a shape combining two or more of these shapes. For example, it may be partly cylindrical, with the remainder having the shape of an inverted cone. The shape of the microwell may be one in which a portion of the top of an inverted cone or inverted pyramid is cut off. The mouth of the microwell may be on the top of the microwell or the bottom of the microwell. The bottom of the microwell may be flat, but curved surfaces (e.g., convex or concave) are also possible. The shape and size of the microwell may be determined in consideration of the type of cell and/or solid substrate (e.g., shape, size) to be stored in the microwell.

The diameter of the microwell may refer to the largest circle that may be inscribed in the planar shape of the microwell. The diameter of the microwell may be at least about 0.1, 0.5, 1, 2, or 3-fold or more the diameter of the cell and/or solid support to be contained in the microwell. The diameter of the microwell may be at most about 0.1, 0.5, 1, 2, or 3-fold or more the diameter of the cell and/or solid support to be contained in the microwell. The diameter of the microwell may be at least about 10, 20, 30, 40, or 50% or more the diameter of the solid support. The diameter of the microwell may be at most about 10, 20, 30, 40, or 50% or more the diameter of the solid support. The diameter of the microwell may be at least about 5, 10, 15, 20, 25, 30, 35, 40, 45, or 50 or more micrometers. The diameter of the microwell may be at most about 5, 10, 15, 20, 25, 30, 35, 40, 45, or 50 or more micrometers. The diameter of the microwell is about 25 micrometers. In some instances, the diameter of the microwell is about 30 micrometers. In some instances, the diameter of the microwell is about 28 micrometers.

The difference between the microwell volume and the solid support volume may be at least about $1\times10^{-14}$ m$^3$, $1.5\times10^{-14}$ m$^3$, $1.7\times10^{-14}$ m$^3$, $2.0\times10^{-14}$ m$^3$, $2.5\times10^{-14}$ m$^3$, or $3.0\times10^{-14}$ m$^3$ or more. The difference between the microwell volume and the solid support volume may be at most about $1\times10^{-14}$ m$^3$, $1.5\times10^{-14}$ m$^3$, $1.7\times10^{-14}$ m$^3$, $2.0\times10^{-14}$ m$^3$, $2.5\times10^{-14}$ m$^3$, or $3.0\times10^{-14}$ m$^3$ or more. The difference between the microwell volume and the solid support volume may be at least about $1\times10^{-11}$ L, $1.5\times10^{-11}$ L, $1.7\times10^{-11}$ L, $2.0\times10^{-11}$ L, $2.5\times10^{-11}$ L, or $3.0\times10^{-11}$ L or more. The difference between the microwell volume and the solid support volume may be at most about $1\times10^{-11}$ L, $1.5\times10^{-11}$ L, $1.7\times10^{-11}$ L, $2.0\times10^{-11}$ L, $2.5\times10^{-11}$ L, or $3.0\times10^{-11}$ L or more. FIG. 7 illustrates exemplary statistics about the volume of the microwell, the solid support, and the differences between the microwell and the solid support volumes.

The depth of the microwell may be at least about 0.1, 0.5, 1, 2, 3, 4, or 5-fold or more the diameter of the cell and/or solid support to be contained in the microwell. The depth of the microwell may be at most about 0.1, 0.5, 1, 2, 3, 4, or 5-fold or more the diameter of the cell and/or solid support to be contained in the microwell. The depth of the microwell may be at least about 10, 20, 30, 40, or 50% or more the depth of the solid support. The depth of the microwell may be at most about 10, 20, 30, 40, or 50% or more the depth of the solid support. The depth of the microwell may be at least about 5, 10, 15, 20, 25, 30, 35, 40, 45, or 50 or more micrometers. The depth of the microwell may be at most about 5, 10, 15, 20, 25, 30, 35, 40, 45, or 50 or more micrometers. The depth of the microwell may be about 30 micrometers. The depth of the microwell may be about 28 micrometers. The microwell may be flat, or substantially flat.

A microwell array may comprise spacing between the wells. The spacing between the wells may be at least about 5, 10, 25, 20, 25, 30, 35, 40, 45, or 50 or more micrometers. The spacing between the wells may be at most about 5, 10, 25, 20, 25, 30, 35, 40, 45, or 50 or more micrometers. The spacing between the wells may be about 15 micrometers. The spacing between the wells may be about 25 micrometers.

There may be differences in the height of dips and rises at any position on the inner wall of a microwell. By creating dips and rises on a portion of the inner wall of a well that has been treated for smoothness, functionality may be added to the well. The inner wall of a microwell may be smoothed by etching. The degree of vacuum in the etching device, the type of etching gas, the etching steps, and the like may be suitably selected. For example, smoothing of the inner wall of a microwell may be conducted by wet etching or by combining a hot oxidation step with oxide film etching. The inner wall of the microwell may be functionalized (e.g., functionalized with an oligonucleotide, a reactive group, a functional group).

The microwell array may be made of silicon, metal (e.g., aluminum, stainless steel, copper, nickel, chromium, and titanium), PDMS (elastomer), glass, polypropylene, agarose, gelatin, pluoronic (e.g., pluronic F127), plastics (e.g., plastics that are naturally hydrophilic, such as PMMA), plastics (e.g., PP, COP, COC) and elastomer (e.g., PDMS) that are hydrophobic but may be treated to be made hydrophilic, hydrogels (e.g., polyacrylamide, alginate), or resin (e.g., polyimide, polyethylene, vinyl chloride, polypropylene, polycarbonate, acrylic, and polyethylene terephthalate).

The microwell array may be made of a material that is hydrophobic. The microwell array may be made of a material that is hydrophobic but coated to be made hydrophilic (e.g., by oxygen plasma treatment). The microwell array may be made of a material that is hydrophilic but coated to be made hydrophobic.

A microwell array may be assembled. Microwell array assembly may comprise obtaining a silicon wafter with patterning (e.g., patterned posts made with SU8 photoresist) and incubating it with PDMS material to create arrays of wells through soft lithography (e.g., at 80 C for a few hours). For example, uncured PDMS may be liquid. Uncured PDMS may fill gaps between posts. When PDMS is cured by heat, it may be come solid, thereby generating the array of wells. An optical adhesive (e.g., NOA81/NOA63) may be applied to the PDMS material (e.g., using UV light) to create an array of posts (e.g., a plurality of arrays). The application may be performed for at least about 1 second, 2 seconds, 3 seconds, 4 seconds, 5 seconds, 6 seconds, 7 seconds, 8 seconds, 9 seconds, 10 seconds or 1 minute, 2 minutes, 3 minutes, 4 minutes, or 5 or more minutes. A layer comprising agarose may be applied to the optical adhesive. The agarose layer may be at least about 1, 2, 3, 4, 5, 6, 7, 8, 9, 10% or more agarose. The agarose layer may be most about 1, 2, 3, 4 5, 6, 7, 8, 9, 10% or more agarose. The agarose layer may be about 5% agarose. The agarose layer may be set on Gelbond film, or any hydrophilic substrate that the agarose may adhere to. The incubation of the agarose layer on the optical surface may be at least about 1, 2, 3, 4, 5, 6, 7, 8, 9, 10 or more minutes. The incubation of the agarose layer on the optical surface may be at most about 1, 2, 3, 4, 5, 6, 7, 8, 9, 10 or more minutes.

In some instances, the methods of the disclosure may use a surface that may not comprise microwells. The surface may be glass, plastic, metal. The surface may be coated with solid supports, extracellular matrix, polymers. The surface may not comprise wells. The surface may comprise solid supports spatially arranged to limit molecular diffusion. The methods of the disclosure of capturing cells and/or cell contents may occur on a flat surface. The methods of the disclosure of capturing cells and/or cell contents may occur in a suspension.

Cells and Samples

The cell and of the disclosure may be a cell from an animal (e.g., human, rat, pig, horse, cow, dog, mouse). In some instances, the cell is a human cell. The cell may be a fetal human cell. The fetal human cell may be obtained from a mother pregnant with the fetus. The cell may be a cell from a pregnant mother. The cell may be a cell from a vertebrate, invertebrate, fungi, archae, or bacteria. The cell may be from a multicellular tissue (e.g., an organ (e.g., brain, liver, lung, kidney, prostate, ovary, spleen, lymph node, thyroid, pancreas, heart, skeletal muscle, intestine, larynx, esophagus, and stomach), a blastocyst). The cell may be a cell from a cell culture. The cell may be a HeLa cell, a K562 cell, a Ramos cell, a hybridoma, a stem cell, an undifferentiated cell, a differentiated cell, a circulating cell, a CHO cell, a 3T3 cell, and the like.

In some instances, the cell is a cancerous cell. Non-limiting examples of cancer cells may include a prostate cancer cell, a breast cancer cell, a colon cancer cell, a lung cancer cell, a brain cancer cell, and an ovarian cancer cell. In some instances, the cell is from a cancer (e.g., a circulating tumor cell). Non-limiting examples of cancers may include, adenoma, adenocarcinoma, squamous cell carcinoma, basal cell carcinoma, small cell carcinoma, large cell undifferentiated carcinoma, chondrosarcoma, and fibrosarcoma.

In some instances, the cell is a rare cell. A rare cell can be a circulating tumor cell (CTC), circulating epithelial cell (CEC), circulating stem cell (CSC), stem cells, undifferentiated stem cells, cancer stem cells, bone marrow cells, progenitor cells, foam cells, fetal cells, mesenchymal cells, circulating endothelial cells, circulating endometrial cells, trophoblasts, immune system cells (host or graft), connective tissue cells, bacteria, fungi, or pathogens (for example, bacterial or protozoa), microparticles, cellular fragments, proteins and nucleic acids, cellular organelles, other cellular components (for example, mitochondria and nuclei), and viruses.

In some instances, the cell is from a tumor. In some instances, the tumor is benign or malignant. The tumor cell may comprise a metastatic cell. In some instances, the cell is from a solid tissue that comprises a plurality of different cell types (e.g., different genotypes).

The cell may comprise a virus, bacterium, fungus, and parasite. Viruses may include, but are not limited to, DNA or RNA animal viruses (e.g., Picornaviridae (e.g., polioviruses), Reoviridae (e.g., rotaviruses), Togaviridae (e.g., encephalitis viruses, yellow fever virus, rubella virus), Orthomyxoviridae (e.g., influenza viruses), Paramyxoviridae (e.g., respiratory syncytial virus, measles virus, mumps virus, parainfluenza virus), Rhabdoviridae (e.g., rabies virus), Coronaviridae, Bunyaviridae, Flaviviridae, Filoviridae, Arenaviridae, Bunyaviridae and Retroviridae (e.g., human T cell lymphotropic viruses (HTLV), human immunodeficiency viruses (HIV), Papovaviridae (e.g., papilloma viruses), Adenoviridae (e.g., adenovirus), Herpesviridae (e.g., herpes simplex viruses), and Poxviridae (e.g., variola viruses)).

Exemplary bacteria that may be used in the methods of the disclosure may include *Actinomedurae, Actinomyces israelii, Bacillus anthracis, Bacillus cereus, Clostridium botulinum, Clostridium difficile, Clostridium perfringens, Clostridium tetani, Corynebacterium, Enterococcus faecalis, Listeria monocytogenes, Nocardia, Propionibacterium acnes, Staphylococcus aureus, Staphylococcus epiderm, Streptococcus mutans, Streptococcus pneumoniae* and the like. Gram negative bacteria include, but are not limited to, *Afipia felis, Bacteroides, Bartonella bacilliformis, Bortadella pertussis, Borrelia burgdorferi, Borrelia recurrentis, Brucella, Calymmatobacterium granulomatis, Campylobacter, Escherichia coli, Francisella tularensis, Gardnerella vaginalis, Haemophilius aegyptius, Haemophilius ducreyi, Haemophilius influenziae, Heliobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis* and the like. Other bacteria may include *Myobacterium avium, Myobacterium leprae, Myobacterium tuberculosis, Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium, Meningococci* and the like.

Exemplary fungi to be used in the methods of the disclosure may include, but are not limited to *Aspergilli, Candidae, Candida albicans, Coccidioides immitis, Cryptococci*, and combinations thereof.

Exemplary parasites to be used in the methods of the disclosure may include, but are not limited to, *Balantidium coli, Cryptosporidium parvum, Cyclospora cayatanensis, Encephalitozoa, Entamoeba histolytica, Enterocytozoon bieneusi, Giardia lamblia, Leishmaniae, Plasmodii, Toxoplasma gondii, Trypanosomae*, trapezoidal amoeba, worms (e.g., helminthes), particularly parasitic worms including, but not limited to, *Nematoda* (roundworms, e.g., whipworms, hookworms, pinworms, ascarids, filarids and the like), *Cestoda* (e.g., tapeworms).

The sample of the disclosure may be a sample from an animal (e.g., human, rat, pig, horse, cow, dog, mouse). In some instances, the sample is a human sample. The sample may be a fetal human sample. The fetal human sample may be obtained from a mother pregnant with the fetus. The sample may be a sample from a pregnant mother. The sample may be a sample from a vertebrate, invertebrate, fungi, archae, or bacteria. The sample may be from a multicellular tissue (e.g., an organ (e.g., brain, liver, lung, kidney, prostate, ovary, spleen, lymph node, thyroid, pancreas, heart, skeletal muscle, intestine, larynx, esophagus, and stomach), a blastocyst). The sample may be a cell from a cell culture.

The sample may comprise a plurality of cells. The sample may comprise a plurality of the same type of cell. The sample may comprise a plurality of different types of cells. The sample may comprise a plurality of cells at the same point in the cell cycle and/or differentiation pathway. The sample may comprise a plurality of cells at different points in the cell cycle and/or differentiation pathway. A sample may comprise a plurality of samples.

The plurality of samples may comprise at least 5, 10, 20, 30, 40, 50, 60, 70, 80, 90 or 100 or more samples. The plurality of samples may comprise at least about 100, 200, 300, 400, 500, 600, 700, 800, 900 or 1000 or more samples. The plurality of samples may comprise at least about 1000, 2000, 3000, 4000, 5000, 6000, 7000, 8000 samples, 9000, or 10,000 samples, or 100,000 samples, or 1,000,000 or more samples. The plurality of samples may comprise at least about 10,000 samples.

The one or more nucleic acids in the first sample may be different from one or more nucleic acids in the second sample. The one or more nucleic acids in the first sample may be different from one or more nucleic acids in a plurality of samples. The one or more nucleic acids may comprise a length of at least about 1 nucleotide, 2 nucleotides, 5 nucleotides, 10 nucleotides, 20 nucleotides, 50 nucleotides, 100 nucleotides, 200 nucleotides, 300 nucleotides, 500 nucleotides, 1000 nucleotides, 2000 nucleotides, 3000 nucleotides, 4000 nucleotides, 5000 nucleotides, 10,000 nucleotides, 100,000 nucleotides, 1,000,000 nucleotides.

The first sample may comprise one or more cells and the second sample may comprise one or more cells. The one or more cells of the first sample may be of the same cell type as the one or more cells of the second sample. The one or more cells of the first sample may be of a different cell type as one or more different cells of the plurality of samples. The cell type may be chondrocyte, osteoclast, adipocyte, myoblast, stem cell, endothelial cell or smooth muscle cell. The cell type may be an immune cell type. The immune cell type may be a T cell, B cell, thrombocyte, dendritic cell, neutrophil, macrophage or monocyte.

The plurality of samples may comprise one or more malignant cell. The one or more malignant cells may be derived from a tumor, sarcoma or leukemia.

The plurality of samples may comprise at least one bodily fluid. The bodily fluid may comprise blood, urine, lymphatic fluid, saliva. The plurality of samples may comprise at least one blood sample.

The plurality of samples may comprise at least one cell from one or more biological tissues. The one or more biological tissues may be a bone, heart, thymus, artery, blood vessel, lung, muscle, stomach, intestine, liver, pancreas, spleen, kidney, gall bladder, thyroid gland, adrenal gland, mammary gland, ovary, prostate gland, testicle, skin, adipose, eye or brain.

The biological tissue may comprise an infected tissue, diseased tissue, malignant tissue, calcified tissue or healthy tissue.

The plurality of samples may be from one or more sources. The plurality of samples may be from two or more sources. The plurality of samples may be from one or more subjects. The plurality of samples may be from two or more subjects. The plurality of samples may be from the same subject. The one or more subjects may be from the same species. The one or more subjects may be from different species. The one or more subjects may be healthy. The one or more subjects may be affected by a disease, disorder or condition. The plurality of samples may comprise cells of an origin selected from a mammal, bacteria, virus, fungus or plant. The one or more samples may be from a human, horse, cow, chicken, pig, rat, mouse, monkey, rabbit, guinea pig, sheep, goat, dog, cat, bird, fish, frog and fruit fly.

The plurality of samples may be obtained concurrently. The plurality of samples may be obtained at the same time. The plurality of samples may be obtained sequentially. The plurality of samples may be obtained over a course of years, 100 years, 10 years, 5 years, 4 years, 3 years, 2 years or 1 year of obtaining one or more different samples. One or more samples may be obtained within about one year of obtaining one or more different samples. One or more samples may be obtained within 12 months, 11 months, 10 months, 9 months, 8 months, 7 months, 6 months, 4 months, 3 months, 2 months or 1 month of obtaining one or more different samples. One or more samples may be obtained within 30 days, 28 days, 26 days, 24 days, 21 days, 20 days, 18 days, 17 days, 16 days, 15 days, 14 days, 13 days, 12 days, 11 days, 10 days, 9 days, 8 days, 7 days, 6 days, 5 days, 4 days, 3 days, 2 days or one day of obtaining one or more different samples. One or more samples may be obtained within about 24 hours, 22 hours, 20 hours, 18 hours, 16 hours, 14 hours, 12 hours, 10 hours, 8 hours, 6 hours, 4 hours, 2 hours or 1 hour of obtaining one or more different samples. One or more samples may be obtained within about 60 sec, 45 sec, 30 sec, 20 sec, 10 sec, 5 sec, 2 sec or 1 sec of obtaining one or more different samples. One or more samples may be obtained within less than one second of obtaining one or more different samples.

Target Molecules

The methods and kits disclosed herein may be used in the stochastic labeling of molecules. Such molecules include, but are not limited to, polynucleotides and polypeptides. As used herein, the terms "polynucleotide" and "nucleic acid molecule" refers to a polymeric form of nucleotides of any length, either ribonucleotides, deoxyribonucleotides, locked nucleic acids (LNA) or peptide nucleic acids (PNAs), that comprise purine and pyrimidine bases, or other natural, chemically or biochemically modified, non-natural, or derivatized nucleotide bases. A "polynucleotide" or "nucleic acid molecule" may consist of a single nucleotide or base pair. Alternatively, the "polynucleotide" or "nucleic acid molecule" comprises two or more nucleotides or base pairs. For example, the "polynucleotide" or "nucleic acid molecule" comprises at least about 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the polynucleotide comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. The backbone of the polynucleotide may comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes may be tailor made to stabilize or destabilize hybrid formation or enhance the specificity of hybridization with a complementary nucleic acid sequence as desired. In some instances, the molecules are DNA, RNA, or DNA-RNA hybrids. The molecules may be single-stranded or double-stranded. In some instances, the molecules are RNA molecules, such as mRNA, rRNA, tRNA, ncRNA, lncRNA, siRNA, microRNA or miRNA. The RNA molecules may be polyadenylated. Alternatively, the mRNA molecules are not polyadenylated. Alternatively, the molecules are DNA molecules. The DNA molecules may be genomic DNA. The DNA molecules may comprise exons, introns, untranslated regions, or any combination thereof. In some instances, the molecules are a panel of molecules.

The methods and kits disclosed herein may be used to stochastically label individual occurrences of identical or nearly identical molecules and/or different molecules. In some instances, the methods and kits disclosed herein may be used to stochastically label identical or nearly identical molecules (e.g., molecules comprise identical or nearly identical sequences). For example, the molecules to be labeled comprise at least about 80%, 85%, 90%, 95%, 96%, 97%, 98%, 99%, or 100% sequence identity. The nearly identical molecules may differ by less than about 100, 90, 80, 70, 60, 50, 40, 30, 25, 20, 25, 10, 9, 8, 7, 6, 5, 4, 3, 2, or 1 nucleotide or base pair. The plurality of nucleic acids in one or more samples of the plurality of samples may comprise two or more identical sequences. At least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the total nucleic acids in one or more of the plurality of samples may comprise the same sequence. The plurality of nucleic acids in one or more samples of the plurality of samples may comprise at least two different sequences. At least about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 100% of the total nucleic acids in one or more of the plurality of samples may comprise at least two different sequences. In some instances, the molecules to be labeled are variants of each other. For example, the molecules to be labeled may contain single nucleotide polymorphisms or other types of mutations. In another example, the molecules to be labeled are splice variants. In some instances, at least one molecule is stochastically labeled. In other instances, at least 2, 3, 4, 5, 6, 7, 8, 9, or 10 identical or nearly identical molecules are stochastically labeled. Alternatively, at least 20, 30, 40, 50, 60, 70, 80, 90, 100, 200, 300, 400, 500, 600, 700, 800, 900, or 1000 identical or nearly identical molecules are stochastically labeled. In other instances, at least 1500; 2,000; 2500; 3,000; 3500; 4,000; 4500; 5,000; 6,000; 7,000; 8,000; 9,000; or 10000 identical or nearly identical molecules are stochastically labeled. In other instances; at least 15,000; 20,000; 25,000; 30,000; 35,000; 40,000; 45,000; 50,000; 60,000; 70,000; 80,000; 90,000; or 100,000 identical or nearly identical molecules are stochastically labeled.

In other instances, the methods and kits disclosed herein may be used to stochastically label different molecules. For example, the molecules to be labeled comprise less than 75%, 70%, 65%, 60%, 55%, 50%, 45%, 40%, 35%, 30%, 25%, 20%, 15%, 10%, 5%, 4%, 3%, 2%, 1% sequence identity. The different molecules may differ by at least about 1, 2, 3, 4, 5, 6, 7, 8, 9, 10, 15, 20, 25, 30, 40, 50, 60, 70, 80, 90, 100 or more nucleotides or base pairs. In some instances, at least one molecule is stochastically labeled. In other instances, at least 2, 3, 4, 5, 6, 7, 8, 9, or 10 different molecules are stochastically labeled. Alternatively, at least 20, 30, 40, 50, 60, 70, 80, 90, 100, 200, 300, 400, 500, 600, 700, 800, 900, or 1000 different molecules are stochastically labeled. In other instances, at least 1500; 2,000; 2500; 3,000; 3500; 4,000; 4500; 5,000; 6,000; 7,000; 8,000; 9,000; or 10000 different molecules are stochastically labeled. In other instances; at least 15,000; 20,000; 25,000; 30,000; 35,000; 40,000; 45,000; 50,000; 60,000; 70,000; 80,000; 90,000; or 100,000 different molecules are stochastically labeled.

The different molecules to be labeled may be present in the sample at different concentrations or amounts. For example, the concentration or amount of one molecule is greater than the concentration or amount of another molecule in the sample. In some instances, the concentration or amount of at least one molecule in the sample is at least about 1.5, 2, 3, 4, 5, 6, 7, 8, 9, 10, 11, 12, 13, 14, 15, 20, 25, 30, 35, 40, 45, 50, 60, 70, 80, 90, or 100 or more times greater than the concentration or amount of at least one other molecule in the sample. In some instances, the concentration or amount of at least one molecule in the sample is at least about 1000 or more times greater than the concentration or amount of at least one other molecule in the sample. In another example, the concentration or amount of one molecule is less than the concentration or amount of another molecule in the sample. The concentration or amount of at least one molecule in the sample may be at least about 1.5, 2, 3, 4, 5, 6, 7, 8, 9, 10, 11, 12, 13, 14, 15, 20, 25, 30, 35, 40, 45, 50, 60, 70, 80, 90, or 100 or more times less than the concentration or amount of at least one other molecule in the sample. The concentration or amount of at least one molecule in the sample may be at least about 1000 or more times less than the concentration or amount of at least one other molecule in the sample.

In some instances, the molecules to be labeled are in one or more samples. The molecules to be labeled may be in two or more samples. The two or more samples may contain different amounts or concentrations of the molecules to be labeled. In some instances, the concentration or amount of one molecule in one sample may be greater than the concentration or amount of the same molecule in a different sample. For example, a blood sample might contain a higher amount of a particular molecule than a urine sample. Alternatively, a single sample is divided into two or more subsamples. The subsamples may contain different amounts or concentrations of the same molecule. The concentration or amount of at least one molecule in one sample may be at least about 1.5, 2, 3, 4, 5, 6, 7, 8, 9, 10, 11, 12, 13, 14, 15, 20, 25, 30, 35, 40, 45, 50, 60, 70, 80, 90, or 100 or more times greater than the concentration or amount of the same molecule in another sample. Alternatively, the concentration or amount of one molecule in one sample may be less than the concentration or amount of the same molecule in a different sample. For example, a heart tissue sample might contain a higher amount of a particular molecule than a lung tissue sample. The concentration or amount of at least one molecule in one sample may be at least about 1.5, 2, 3, 4, 5, 6, 7, 8, 9, 10, 11, 12, 13, 14, 15, 20, 25, 30, 35, 40, 45, 50, 60, 70, 80, 90, or 100 or more times less than the concentration or amount of the same molecule in another sample. In some instances, the different concentrations or amounts of a molecule in two or more different samples is referred to as sample bias.

The methods and kits disclosed herein may be used for the analysis of two or more molecules from two or more samples. The two or more molecules may comprise two or more polypeptides. The method may comprise determining the identity of two or more labeled polypeptides. Determining the identity of two or more labeled polypeptides may comprise mass spectrometry. The method may further comprise combining the labeled polypeptides of the first sample with the labeled polypeptides of the second sample. The labeled polypeptides may be combined prior to determining the number of different labeled polypeptides. The method may further comprise combining the first sample-tagged polypeptides and the second sample-tagged polypeptides. The first sample-tagged polypeptides and the second sample-tagged polypeptides may be combined prior to contact with the plurality of molecular identifier labels. Determining the number of different labeled polypeptides may comprise detecting at least a portion of the labeled polypeptide. Detecting at least a portion of the labeled polypeptide may comprise detecting at least a portion of the sample tag, molecular identifier label, polypeptide, or a combination thereof.

As used herein, the term "polypeptide" refers to a molecule comprising at least one peptide. In some instances, the polypeptide consists of a single peptide. Alternatively, the polypeptide comprises two or more peptides. For example, the polypeptide comprises at least about 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 peptides. Examples of polypeptides include, but are not limited to, amino acids, proteins, peptides, hormones, oligosaccharides, lipids, glycolipids, phospholipids, antibodies, enzymes, kinases, receptors, transcription factors, and ligands.

Subjects

The methods and kits disclosed herein may comprise use of a cell or sample from one or more subjects. A subject may be a human or a non-human subject. A subject may be living. A subject may be dead. A subject may be a human that is under the care of a caregiver (e.g., medical professional). A subject may be suspected of having a disease. A subject may have a disease. A subject may have symptoms of a disease.

A subject may be a subject that provides one or more samples. A subject may be a mammal, reptile, amphibian, and/or bird. A subject may be a non-human primate.

Enzymes

The methods and kits disclosed herein may comprise one or more enzymes. Examples of enzymes include, but are not limited to ligases, reverse transcriptases, polymerases, and restriction nucleases. In some instances, attachment of the oligonucleotide tag to the molecules comprises the use of one or more ligases. Examples of ligases include, but are not limited to, DNA ligases such as DNA ligase I, DNA ligase III, DNA ligase IV, and T4 DNA ligase, and RNA ligases such as T4 RNA ligase I and T4 RNA ligase II.

The methods and kits disclosed herein may further comprise the use of one or more reverse transcriptases. In some instances, the reverse transcriptase is a HIV-1 reverse transcriptase, M-MLV reverse transcriptase, AMV reverse transcriptase, and telomerase reverse transcriptase. In some instances, the reverse transcriptase is M-MLV reverse transcriptase.

In some instances, the methods and kits disclosed herein comprise the use of one or more polymerases. Examples of polymerases include, but are not limited to, DNA polymerases and RNA polymerases. In some instances, the DNA polymerase is a DNA polymerase I, DNA polymerase II, DNA polymerase III holoenzyme, and DNA polymerase IV. Commercially available DNA polymerases include, but are not limited to, Bst 2.0 DNA Polymerase, Bst 2.0 WarmStart™ DNA Polymerase, Bst DNA Polymerase, Sulfolobus DNA Polymerase IV, Taq DNA Polymerase, 9° N™m DNA Polymerase, Deep VentR™ (exo–) DNA Polymerase, Deep VentR™ DNA Polymerase, Hemo KlenTaq™, LongAmp® Taq DNA Polymerase, OneTaq® DNA Polymerase, Phusion® DNA Polymerase, Q5™ High-Fidelity DNA Polymerase, Therminator™ γ DNA Polymerase, Therminator™ DNA Polymerase, Therminator™ II DNA Polymerase, Therminator™ III DNA Polymerase, VentR® DNA Polymerase, VentR® (exo–) DNA Polymerase, Bsu DNA Polymerase, phi29 DNA Polymerase, T4 DNA Polymerase, T7 DNA Polymerase, Terminal Transferase, Titanium® Taq Polymerase, KAPA Taq DNA Polymerase and KAPA Taq Hot Start DNA Polymerase.

Alternatively, the polymerase is an RNA polymerases such as RNA polymerase I, RNA polymerase II, RNA polymerase III, *E. coli* Poly(A) polymerase, phi6 RNA polymerase (RdRP), Poly(U) polymerase, SP6 RNA polymerase, and T7 RNA polymerase.

In some instances, the methods and kits disclosed herein comprise one or more restriction enzymes. Restriction enzymes include type I, type II, type III, and type IV restriction enzymes. In some instances, Type I enzymes are complex, multi-subunit, combination restriction-and-modification enzymes that cut DNA at random far from their recognition sequences. Generally, type II enzymes cut DNA at defined positions close to or within their recognition sequences. They may produce discrete restriction fragments and distinct gel banding patterns. Type III enzymes are also large combination restriction-and-modification enzymes. They often cleave outside of their recognition sequences and may require two such sequences in opposite orientations within the same DNA molecule to accomplish cleavage; they rarely give complete digests. In some instances, type IV enzymes recognize modified, typically methylated DNA and may be exemplified by the McrBC and Mrr systems of *E. coli*.

Additional Reagents

The methods and kits disclosed herein may comprise the use of one or more reagents. Examples of reagents include, but are not limited to, PCR reagents, ligation reagents, reverse transcription reagents, enzyme reagents, hybridization reagents, sample preparation reagents, and reagents for nucleic acid purification and/or isolation.

The methods and kits disclosed herein may comprise the use of one or more buffers. Examples of buffers include, but are not limited to, wash buffers, ligation buffers, hybridization buffers, amplification buffers, and reverse transcription buffers. In some instances, the hybridization buffer is a commercially available buffer, such as TMAC Hyb solution, SSPE hybridization solution, and ECONO™ hybridization buffer. The buffers disclosed herein may comprise one or more detergents.

The methods and kits disclosed herein may comprise the use of one or more carriers. Carriers may enhance or improve the efficiency of one or more reactions disclosed herein (e.g., ligation reaction, reverse transcription, amplification, hybridization). Carriers may decrease or prevent non-specific loss of the molecules or any products thereof (e.g., labeled-molecule, labeled-cDNA molecule, labeled-amplicon). For example, the carrier may decrease non-specific loss of a labeled-molecule through absorption to surfaces. The carrier may decrease the affinity of the molecule, labeled-molecule, or any product thereof to a surface or substrate (e.g., container, eppendorf tube, pipet tip). Alternatively, the carrier may increase the affinity of the molecule or any product thereof to a surface or substrate (e.g., bead, array, glass, slide, chip). Carriers may protect the molecule or any product thereof from degradation. For example, carriers may protect an RNA molecule or any product thereof from ribonucleases. Alternatively, carriers may protect a DNA molecule or any product thereof from a DNase. Examples of carriers include, but are not limited to, nucleic acid molecules such as DNA and/or RNA, or polypeptides. Examples of DNA carriers include plasmids, vectors, polyadenylated DNA, and DNA oligonucleotides. Examples of RNA carriers include polyadenylated RNA, phage RNA, phage MS2 RNA, *E. coli* RNA, yeast RNA, yeast tRNA, mammalian RNA, mammalian tRNA, short polyadenylated synthetic ribonucleotides and RNA oligonucleotides. The RNA carrier may be a polyadenylated RNA. Alternatively, the RNA carrier may be a non-polyadenylated RNA. In some instances, the carrier is from a bacteria, yeast, or virus. For example, the carrier may be a nucleic acid molecule or a polypeptide derived from a bacteria, yeast or virus. For example, the carrier is a protein from *Bacillus subtilis*. In another example, the carrier is a nucleic acid molecule from *Escherichia coli*. Alternatively, the carrier is a nucleic acid molecule or peptide from a mammal (e.g., human, mouse, goat, rat, cow, sheep, pig, dog, or rabbit), avian, amphibian, or reptile.

The methods and kits disclosed herein may comprise the use of one or more control agents. Control agents may include control oligos, inactive enzymes, non-specific competitors. Alternatively, the control agents comprise bright hybridization, bright probe controls, nucleic acid templates, spike-in controls, PCR amplification controls. The PCR amplification controls may be positive controls. In other instances, the PCR amplification controls are negative controls. The nucleic acid template controls may be of known concentrations. The control agents may comprise one or more labels.

Spike-in controls may be templates that are added to a reaction or sample. For example, a spike-in template may be added to an amplification reaction. The spike-in template may be added to the amplification reaction any time after the first amplification cycle. In some instances, the spike-in template is added to the amplification reaction after the 2nd, 3rd, 4th, 5th, 6th, 7th, 8th, 9th, 10th, 11th, 12th, 13th, 14th, 15th, 20th, 25th, 30th, 35th, 40th, 45th, or 50th amplification cycle. The spike-in template may be added to the amplification reaction any time before the last amplification cycle. The spike-in template may comprise one or more nucleotides or nucleic acid base pairs. The spike-in template may comprise DNA, RNA, or any combination thereof. The spike-in template may comprise one or more labels.

Detectable Labels

The methods, kits, and compositions disclosed herein may further comprise a detectable label. The terms "detectable label", "tag" or "label" may be used interchangeably and refer to any chemical moiety attached to a molecule (e.g., nucleotide, nucleotide polymer, or nucleic acid binding factor, molecular barcode). The chemical moiety may be covalently attached the molecule. The chemical moiety may be non-covalently attached to the molecule. The molecular barcodes, sample tags and molecular identifier labels may further comprise a detectable label, tag or label. Preferably, the label is detectable and renders the nucleotide or nucleotide polymer detectable to the practitioner of the invention. Detectable labels that may be used in combination with the methods disclosed herein include, for example, a fluorescent label, a chemiluminescent label, a quencher, a radioactive label, biotin, pyrene moiety, gold, or combinations thereof. Non-limiting example of detectable labels include luminescent molecules, fluorochromes, fluorescent quenching agents, colored molecules, radioisotopes or scintillants.

In some instances, the methods disclosed herein further comprise attaching one or more detectable labels to the molecular barcode, molecular identifier label, the sample tag, the labeled nucleic acid or any product thereof (e.g., labeled-amplicon). The methods may comprise attaching two or more detectable labels to the molecular barcode, molecular identifier label, the sample tag or the labeled nucleic acid. Alternatively, the method comprises attaching at least about 3, 4, 5, 6, 7, 8, 9, or 10 detectable labels to the molecular barcode, molecular identifier label, the sample tag or the labeled nucleic acid. In some instances, the detectable label is a Cy™ label. The Cy™ label is a Cy3 label. Alternatively, or additionally, the detectable label is biotin. In some embodiments the detectable label is attached to a probe which binds to the molecular barcode, molecular identifier label, the sample tag or the labeled nucleic acid. This may occur, for example, after the nucleic acid or labeled nucleic acid has been hybridized to an array. In one example the nucleic acid or labeled nucleic acid is bound to partners on an array. After the binding, a probe which may bind the labeled nucleic acid is bound to the molecules on the array. This process may be repeated with multiple probes and labels to decrease the likelihood that a signal is the result of nonspecific binding of a label or nonspecific binding of the molecule to the array.

A donor acceptor pair may be used as the detectable labels. Either the donor or acceptor may be attached to a probe that binds a nucleic acid. The probe may be, for example, a nucleic acid probe that may bind to a nucleic acid or the labeled nucleic acid. The corresponding donor or acceptor may be added to cause a signal.

In some instances, the detectable label is a Freedom dye, Alexa Fluor® dye, Cy™ dye, fluorescein dye, or LI-COR IRDyes®. In some instances, the Freedom dye is fluorescein (6-FAM™, 6-carboxyfluoroscein), MAX (NHS Ester), TYE™ 563, TEX 615, TYE™ 665, TYE 705. The detectable label may be an Alexa Fluor dye. Examples of Alexa Fluor® dyes include Alexa Fluor® 488 (NHS Ester), Alexa Fluor® 532 (NHS Ester), Alexa Fluor® 546 (NHS Ester), Alexa Fluor® 594 (NHS Ester), Alexa Fluor® 647 (NHS Ester), Alexa Fluor® 660 (NHS Ester), or Alexa Fluor® 750 (NHS Ester). Alternatively, the detectable label is a Cy™ dye. Examples of Cy™ dyes include, but are not limited to, Cy2, Cy3, Cy3B, Cy3.5, Cy5, Cy5.5, and Cy7. In some instances, the detectable label is a fluorescein dye. Non-limiting examples of fluorescein dyes include 6-FAM™ (Azide), 6-FAM™ (NHS Ester), Fluorescein dT, JOE (NHS Ester), TET™, and HEX™. In some instances, the detectable label is a LI-COR IRDyes®, such as 5' IRDye® 700, 5' IRDye® 800, or IRDye® 800CW (NHS Ester). In some instances, the detectable label is TYE™ 563. Alternatively, the detectable label is Cy3.

The detectable label may be Rhodamine dye. Examples of rhodamine dyes include, but are not limited to, Rhodamine Green™-X (NHS Ester), TAMRA™, TAMRA™ (NHS Ester), Rhodamine Red™-X(NHS Ester), ROX™ (NHS Ester), and 5'TAMRA™ (Azide). In other instances, the detectable label is a WellRED Dye. WellRED Dyes include, but are not limited to, WellRED D4 dye, WellRED D3 dye, and WellRED D2 dye. In some instances, the detectable label is Texas Red®-X (NHS Ester), Lightcycler® 640 (NHS Ester), or Dy 750 (NHS Ester).

In some instances, detectable labels include a linker molecule. Examples of linker molecules include, but are not limited to, biotin, avidin, streptavidin, HRP, protein A, protein G, antibodies or fragments thereof, Grb2, polyhistidine, Ni2+, FLAG tags, myc tags. Alternatively, detectable labels include heavy metals, electron donors/acceptors, acridinium esters, dyes and calorimetric substrates. In other instances, detectable labels include enzymes such as alkaline phosphatase, peroxidase and luciferase.

A change in mass may be considered a detectable label, as is the case of surface plasmon resonance detection. The skilled artisan would readily recognize useful detectable labels that are not mentioned herein, which may be employed in the operation of the present invention.

In some instances, detectable labels are used with primers. For example, the universal primer is a labeled with the detectable label (e.g., Cy3 labeled universal primer, fluorophore labeled universal primer). Alternatively, the target specific primer is labeled with the detectable label (e.g., TYE 563-labeled target specific primer). In other instances, detectable labels are used with the sample tags or molecular identifier labels. For example, the oligonucleotide tag is labeled with a detectable label (e.g., biotin-labeled oligonucleotide tag). In other instances, detectable labels are used with the nucleic acid template molecule. Detectable labels may be used to detect the labeled-molecules or labeled-amplicons. Alternatively, detectable labels are used to detect the nucleic acid template molecule.

In some instances, the detectable label is attached to the primer, molecular barcode, sample tag, molecular identifier label, labeled-molecule, labeled-amplicon, probe, HCR probe, and/or non-labeled nucleic acid. Methods for attaching the detectable label to the primer, oligonucleotide tag, labeled-molecule, labeled-amplicon, and/or non-labeled nucleic acid include, but are not limited to, chemical labeling and enzymatic labeling. In some instances, the detectable label is attached by chemical labeling. In some embodiments, chemical labeling techniques comprise a chemically reactive group. Non-limiting examples of reactive groups include amine-reactive succinimidyl esters such as NHS-fluorescein or NHS-rhodamine, amine-reactive isothiocyanate derivatives including FITC, and sulfhydryl-reactive maleimide-activated fluors such as fluorescein-5-maleimide. In some embodiments, reaction of any of these reactive dyes with another molecule results in a stable covalent bond formed between a fluorophore and the linker and/or agent. In some embodiments, the reactive group is isothiocyanates. In some embodiments, a label is attached to an agent through the primary amines of lysine side chains. In some embodiments, chemical labeling comprises a NHS-ester chemistry method.

Alternatively, the detectable label is attached by enzymatic labeling. Enzymatic labeling methods may include, but are not limited to, a biotin acceptor peptide/biotin ligase (AP/Bir A), acyl carrier protein/phosphopantetheine transferase (ACP/PPTase), human O6-alkylguanine transferase (hAGT), Q-tag/transglutaminase (TGase), aldehyde tag/formylglycine-generating enzyme, mutated prokaryotic dehalogenase (HaloTag™), and farnesylation motif/protein farnesyltransferase (PFTase) methods. Affinity labeling may include, but is not limited to, noncovalent methods utilizing dihydrofolate reductase (DHFR) and Phe36Val mutant of FK506-binding protein 12 (FKBP12(F36V)), and metal-chelation methods.

Crosslinking reagents may be used to attach a detectable label to the primer, oligonucleotide tag, labeled-molecule, labeled-amplicon, and/or non-labeled nucleic acid. In some instances, the crosslinking reagent is glutaraldehyde. Glutaraldehyde may react with amine groups to create crosslinks by several routes. For example, under reducing conditions, the aldehydes on both ends of glutaraldehyde couple with amines to form secondary amine linkages.

In some instances, attachment of the detectable label to the primer, oligonucleotide tag, labeled-molecule, labeled-amplicon, and/or non-labeled nucleic acid comprises periodate-activation followed by reductive amination. In some instances, Sulfo-SMCC or other heterobifunctional cross-linkers are used to conjugate the detectable to the primer, oligonucleotide tag, labeled-molecule, labeled-amplicon, and/or non-labeled nucleic acid. For example, Sulfo-SMCC is used to conjugate an enzyme to a drug. In some embodiments, the enzyme is activated and purified in one step and then conjugated to the drug in a second step. In some embodiments, the directionality of crosslinking is limited to one specific orientation (e.g., amines on the enzyme to sulfhydryl groups on the antibody).

Diseases/Conditions

Disclosed herein are methods, kits and compositions for diagnosing, monitoring, and/or prognosing a status or outcome of a disease or condition in a subject. Generally, the method comprises (a) stochastically labeling two or more molecules from two or more samples to produce two or more labeled nucleic acids; (b) detecting and/or quantifying the two or more labeled nucleic acids; and (c) diagnosing, monitoring, and/or prognosing a status or outcome of a disease or condition in a subject based on the detecting and/or quantifying of the two or more labeled nucleic acids. may The method may further comprise determining a therapeutic regimen. The two or more of samples may comprise one or more samples from a subject suffering from a disease or condition. The two or more samples may comprise one or more samples from a healthy subject. The two or more samples may comprise one or more samples from a control.

Monitoring a disease or condition may further comprise monitoring a therapeutic regimen. Monitoring a therapeutic regimen may comprise determining the efficacy of a therapeutic regimen. In some instances, monitoring a therapeutic regimen comprises administrating, terminating, adding, or altering a therapeutic regimen. Altering a therapeutic regimen may comprise increasing or reducing the dosage, dosing frequency, or mode of administration of a therapeutic regimen. A therapeutic regimen may comprise one or more therapeutic drugs. The therapeutic drugs may be an anticancer drug, antiviral drug, antibacterial drug, antipathogenic drug, or any combination thereof.

Cancer

In some instances, the disease or condition is a cancer. The molecules to be stochastically labeled may be from a cancerous cell or tissue. In some instances, the cancer is a sarcoma, carcinoma, lymphoma or leukemia. Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g., alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous cell carcinoma, melanoma, nonmelanoma, or actinic (solar) keratosis.

In some instances, the cancer is a lung cancer. Lung cancer may start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendrogliomas. Nongliomas include meningiomas, pituitary adenomas, primary CNS lymphomas, and medulloblastomas. In some instances, the cancer is a meningioma.

The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic leukemia.

Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Pathogenic Infection

In some instances, the disease or condition is a pathogenic infection. The molecules to be stochastically labeled may be from a pathogen. The pathogen may be a virus, bacterium, fungi, or protozoan. In some instances, the pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g., *I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora*, *Trachipleistophora* (e.g., *T. anthropophthera, T. hominis*), and *Vittaforma* (e.g., *V. corneae*). The pathogen may be a fungus, such as, *Candida, Aspergillus, Cryptococcus, Histoplasma, Pneumocystis*, and *Stachybotrys*.

The pathogen may be a bacterium. Exemplary bacteria include, but are not limited to, *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, or *Yersinia*.

The virus may be a reverse transcribing virus. Examples of reverse transcribing viruses include, but are not limited to, single stranded RNA-RT (ssRNA-RT) virus and double-stranded DNA-RT (dsDNA-RT) virus. Non-limiting examples of ssRNA-RT viruses include retroviruses, alpharetrovirus, betaretrovirus, gammaretrovirus, deltaretrovirus, epsilonretrovirus, lentivirus, spuma virus, metavirirus, and pseudoviruses. Non-limiting examples of dsDNA-RT viruses include hepadenovirus and caulimovirus. The virus can be a DNA virus. The virus can be a RNA virus. The DNA virus may be a double-stranded DNA (dsDNA) virus. In some instances, the dsDNA virus is an adenovirus, herpes virus, or pox virus. Examples of adenoviruses include, but are not limited to, adenovirus and infectious canine hepatitis virus. Examples of herpes viruses include, but are not limited to, herpes simplex virus, varicella-zoster virus, cytomegalovirus, and Epstein-Barr virus. A non-limiting list of pox viruses includes smallpox virus, cow pox virus, sheep pox virus, monkey pox virus, and vaccinia virus. The DNA virus may be a single-stranded DNA (ssDNA) virus. The ssDNA virus may be a parvovirus. Examples of parvoviruses include, but are not limited to, parvovirus B19, canine parvovirus, mouse parvovirus, porcine parvovirus, feline panleukopenia, and Mink enteritis virus.

The virus can be a RNA virus. The RNA virus may be a double-stranded RNA (dsRNA) virus, (+) sense single-stranded RNA virus ((+)ssRNA) virus, or (−) sense single-stranded ((−) ssRNA) virus. A non-limiting list of dsRNA viruses include reovirus, orthoreovirus, cypovirus, rotavirus, bluetongue virus, and phytoreovirus. Examples of (+) ssRNA viruses include, but are not limited to, picornavirus and togavirus. Examples of picornaviruses include, but are not limited to, enterovirus, rhinovirus, hepatovirus, cardiovirus, aphthovirus, poliovirus, parechovirus, erbovirus, kobuvirus, teschovirus, and coxsackie. In some instances, the togavirus is a rubella virus, Sindbis virus, Eastern equine encephalitis virus, Western equine encephalitis virus, Venezuelan equine encephalitis virus, Ross River virus, O'nyong'nyong virus, Chikungunya, or Semliki Forest virus. A non-limiting list of (−) ssRNA viruses include orthomyxovirus and rhabdovirus. Examples of orthomyxoviruses include, but are not limited to, influenzavirus a, influenzavirus B, influenzavirus C, isavirus, and thogotovirus. Examples of rhabdoviruses include, but are not limited to, cytorhabdovirus, dichorhabdovirus, ephemerovirus, lyssavirus, novirhabdovirus, and vesiculovirus.

Fetal Disorders

In some instances, the disease or condition is pregnancy. The methods and kits disclosed herein may comprise diagnosing a fetal condition in a pregnant subject. The methods and kits disclosed herein may comprise identifying fetal mutations or genetic abnormalities. The molecules to be stochastically labeled may be from a fetal cell or tissue. Alternatively, or additionally, the molecules to be labeled may be from the pregnant subject.

The methods and kits disclosed herein may be used in the diagnosis, prediction or monitoring of autosomal trisomies (e.g., Trisomy 13, 15, 16, 18, 21, or 22). In some cases the trisomy may be associated with an increased chance of miscarriage (e.g., Trisomy 15, 16, or 22). In other cases, the trisomy that is detected is a liveborn trisomy that may indicate that an infant will be born with birth defects (e.g., Trisomy 13 (Patau Syndrome), Trisomy 18 (Edwards Syndrome), and Trisomy 21 (Down Syndrome)). The abnormality may also be of a sex chromosome (e.g., XXY (Klinefelter's Syndrome), XYY (Jacobs Syndrome), or XXX (Trisomy X). The molecule(s) to be labeled may be on one or more of the following chromosomes: 13, 18, 21, X, or Y. For example, the molecule is on chromosome 21 and/or on chromosome 18, and/or on chromosome 13.

Further fetal conditions that may be determined based on the methods and kits disclosed herein include monosomy of one or more chromosomes (X chromosome monosomy, also known as Turner's syndrome), trisomy of one or more chromosomes (13, 18, 21, and X), tetrasomy and pentasomy of one or more chromosomes (which in humans is most commonly observed in the sex chromosomes, e.g., XXXX, XXYY, XXXY, XYYY, XXXXX, XXXXY, XXXYY, XYYYY and XXYYY), monoploidy, triploidy (three of every chromosome, e.g., 69 chromosomes in humans), tetraploidy (four of every chromosome, e.g., 92 chromosomes in humans), pentaploidy and multiploidy.

Further disclosed herein is a method of forensic analysis comprising any of the above described methods. Forensic scientists may use nucleic acids in various samples (e.g., blood, semen, skin, saliva, hair) found at a crime scene to identify the presence of an individual at the scene, such as a perpetrator. This process is formally termed DNA profiling, but may also be called "genetic fingerprinting." For example, DNA profiling comprises measuring and comparing the lengths of variable sections of repetitive DNA, such as short tandem repeats and minisatellites, in various samples and people. This method is usually an extremely reliable technique for matching a DNA sample from a person with DNA in a sample found at the crime scene. However, identification may be complicated if the scene is contaminated with DNA from several people. In this instance, as well as in other forensic applications, it may be advantageous to obtain absolute quantification of nucleic acids from a single cell or small number of cells.

In some instances, the disease or condition is an immune disorder. An immune disorder can be an inflammatory disorder, an autoimmune disorder, irritable bowel syndrome or ulcerative colitis. Examples of autoimmune diseases include Chrohn's disease, lupus, and Graves' disease.

In some instances, the disease or disorder is a neorlogical condition or disorder. A neorlogical condition or disorder can be Acquired Epileptiform Aphasia, Acute Disseminated Encephalomyelitis, Adrenoleukodystrophy, Agenesis of the corpus callosum, Agnosia, Aicardi syndrome, Alexander disease, Alpers' disease, Alternating hemiplegia, Alzheimer's disease, Amyotrophic lateral sclerosis (see Motor Neuron Disease), Anencephaly, Angelman syndrome, Angiomatosis, Anoxia, Aphasia, Apraxia, Arachnoid cysts, Arachnoiditis, Arnold-Chiari malformation, Arteriovenous malformation, Asperger's syndrome, Ataxia Telangiectasia, Attention Deficit Hyperactivity Disorder, Autism, Auditory processing disorder, Autonomic Dysfunction, Pain, Batten disease, Behcet's disease, Bell's palsy, Benign Essential Blepharospasm, Benign Focal Amyotrophy, Benign Intracranial Hypertension, Bilateral frontoparietal polymicrogyria, Binswanger's disease, Blepharospasm, Bloch-Sulzberger syndrome, Brachial plexus injury, Brain abscess, Brain damage, Brain injury, Brain tumor, Brown-Sequard syndrome, Canavan disease, Carpal tunnel syndrome (CTS), Causalgia, Central pain syndrome, Central pontine myelinolysis, Centronuclear myopathy, Cephalic disorder, Cerebral aneurysm, Cerebral arteriosclerosis, Cerebral atrophy, Cerebral gigantism, Cerebral palsy, Charcot-Marie-Tooth disease, Chiari malformation, Chorea, Chronic inflammatory demyelinating polyneuropathy (CIDP), Chronic pain, Chronic regional pain syndrome, Coffin Lowry syndrome, Coma, including Persistent Vegetative State, Complex I deficiency syndrome, Complex I deficiency syndrome, Complex II deficiency syndrome, Complex III deficiency syndrome, Complex IV/COX deficiency syndrome, Complex V deficiency syndrome, Congenital facial diplegia, Corticobasal degeneration, Cranial arteritis, Craniosynostosis, Creutzfeldt-Jakob disease, Cumulative trauma disorders, Cushing's syndrome, Cytomegalic inclusion body disease (CIBD), Cytomegalovirus Infection, Dandy-Walker syndrome, Dawson disease, Deficiency of mitochondrial NADH dehydrogenase component of Complex I, De Morsier's syndrome, Dejerine-Klumpke palsy, Dejerine-Sottas disease, Delayed sleep phase syndrome, Dementia, Dermatomyositis, Neurological Dyspraxia, Diabetic neuropathy, Diffuse sclerosis, Dysautonomia, Dyscalculia, Dysgraphia, Dyslexia, Dystonia, Early infantile epileptic encephalopathy, Empty sella syndrome, Encephalitis, Encephalocele, Encephalotrigeminal angiomatosis, Encopresis, Epilepsy, Erb's palsy, Erythromelalgia, Essential tremor, Fabry's disease, Fahr's syndrome, Fainting, Familial spastic paralysis, Febrile seizures, Fisher syndrome, Friedreich's ataxia, FART Syndrome, Gaucher's disease, Gerstmann's syndrome, Giant cell arteritis, Giant cell inclusion disease, Globoid cell Leukodystrophy, Gray matter heterotopia, Guillain-Barre syndrome, HTLV-1 associated myelopathy, Hallervorden-Spatz disease, Head injury, Headache, Hemifacial Spasm, Hereditary Spastic Paraplegia, Heredopathia atactica polyneuritiformis, Herpes zoster oticus, Herpes zoster, Hirayama syndrome, Holoprosencephaly, Huntington's disease, Hydranencephaly, Hydrocephalus, Hypercortisolism, Hypoxia, Immune-Mediated encephalomyelitis, Inclusion body myositis, Incontinentia pigmenti, Infantile phytanic acid storage disease, Infantile Refsum disease, Infantile spasms, Inflammatory myopathy, Intracranial cyst, Intracranial hypertension, Joubert syndrome, Kearns-Sayre syndrome, Kennedy disease, Kinsbourne syndrome, Klippel Feil syndrome, Krabbe disease, Kufor-Rakeb syndrome, Kugelberg-Welander disease, Kuru, Lafora disease, Lambert-Eaton myasthenic syndrome, Landau-Kleffner syndrome, Lateral medullary (Wallenberg) syndrome, Learning disabilities, Leigh's disease, Lennox-Gastaut syndrome, Lesch-Nyhan syndrome, Leukodystrophy, Lewy body dementia, Lissencephaly, Locked-In syndrome, Lou Gehrig's disease, Lumbar disc disease, Lyme disease—Neurological Sequelae, Machado-Joseph disease (Spinocerebellar ataxia type 3), Macrencephaly, Maple Syrup Urine Disease, Megalencephaly, Melkersson-Rosenthal syndrome, Menieres disease, Meningitis, Menkes disease, Metachromatic leukodystrophy, Microcephaly, Migraine, Miller Fisher syndrome, Mini-Strokes, Mitochondrial disease, Mitochondrial dysfunction, Mitochondrial Myopathies, Mitochondrial Respiratory Chain Complex I Deficiency, Mobius syndrome, Monomelic amyotrophy, Motor Neuron Disease, Motor skills disorder, Moyamoya disease, Mucopolysaccharidoses, Multi-Infarct Dementia, Multifocal motor neuropathy, Multiple sclerosis, Multiple system atrophy with postural hypotension, Muscular dystrophy, Myalgic encephalomyelitis, Myasthenia gravis, Myelinoclastic diffuse sclerosis, Myoclonic Encephalopathy of infants, Myoclonus, Myopathy, Myotubular myopathy, Myotonia congenita, NADH-coenzyme Q reductase deficiency, NADH:Q(1) oxidoreductase deficiency, Narcolepsy, Neurofibromatosis, Neuroleptic malignant syndrome, Neurological manifestations of AIDS, Neurological sequelae of lupus, Neuromyotonia, Neuronal ceroid lipofuscinosis, Neuronal migration disorders, Niemann-Pick disease, Non 24-hour sleep-wake syndrome, Nonverbal learning disorder, O'Sullivan-McLeod syndrome, Occipital Neuralgia, Occult Spinal Dysraphism Sequence, Ohtahara syndrome, Olivopontocerebellar atrophy, Opsoclonus myoclonus syndrome, Optic neuritis, Orthostatic Hypotension, Overuse syndrome, oxidative phosphorylation disorders, Palinopsia, Paresthesia, Parkinson's disease, Paramyotonia Congenita, Paraneoplastic diseases, Paroxysmal attacks, Parry-Romberg syndrome (also known as Rombergs Syndrome), Pelizaeus-Merzbacher disease, Periodic Paralyses, Peripheral neuropathy, Persistent Vegetative State, Pervasive neurological disorders, Photic sneeze reflex, Phytanic Acid Storage disease, Pick's disease, Pinched Nerve, Pituitary Tumors, PMG, Polio, Polymicrogyria, Polymyositis, Porencephaly, Post-Polio syndrome, Postherpetic Neuralgia (PHN), Postinfectious Encephalomyelitis, Postural Hypotension, Prader-Willi syndrome, Primary Lateral Sclerosis, Prion diseases, Progressive Hemifacial Atrophy also known as Rombergs Syndrome, Progressive multifocal leukoencephalopathy, Progressive Sclerosing Poliodystrophy, Progressive Supranuclear Palsy, Pseudotumor cerebri, Ramsay-Hunt syndrome (Type I and Type II), Rasmussen's encephalitis, Reflex sympathetic dystrophy syndrome, Refsum disease, Repetitive motion disorders, Repetitive stress injury, Restless legs syndrome, Retrovirus-associated myelopathy, Rett syndrome, Reye's syndrome, Romberg_s Syndrome, Rabies, Saint Vitus dance, Sandhoff disease, Schytsophrenia, Schilder's disease, Schizencephaly, Sensory Integration Dysfunction, Septo-optic dysplasia, Shaken baby syndrome, Shingles, Shy-Drager syndrome, Sjogren's syndrome, Sleep apnea, Sleeping sickness, Snatiation, Sotos syndrome, Spasticity, Spina bifida, Spinal cord injury, Spinal cord tumors, Spinal muscular atrophy, Spinal stenosis, Steele-Richardson-Olszewski syndrome, see Progressive Supranuclear Palsy, Spinocerebellar ataxia, Stiff-person syndrome, Stroke, Sturge-Weber syndrome, Subacute sclerosing panencephalitis, Subcortical arteriosclerotic encephalopathy, Superficial siderosis, Sydenham's chorea, Syncope, Synesthesia, Syringomyelia, Tardive dyskinesia, Tay-Sachs disease, Temporal arteritis, Tethered spinal cord syndrome, Thomsen disease, Thoracic outlet syndrome, Tic Douloureux, Todd's paralysis, Tourette syndrome, Transient ischemic attack, Transmissible spongiform encephalopathies, Transverse myelitis, Traumatic brain injury, Tremor, Trigeminal neuralgia, Tropical spastic paraparesis, Trypanosomiasis, Tuberous sclerosis, Vasculitis including temporal arteritis, Von Hippel-Lindau disease (VHL), Viliuisk Encephalomyelitis (VE), Wallenberg's syndrome, Werdnig-Hoffman disease, West syndrome, Whiplash, Williams syndrome, Wilson's disease, X-Linked Spinal and Bulbar Muscular Atrophy, or Zellweger syndrome.

Definitions

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

As used herein, the term "label" may refer to a unique oligonucleotide sequence that may allow a corresponding nucleic acid base and/or nucleic acid sequence to be identified. In some embodiments, the nucleic acid base and/or nucleic acid sequence may be located at a specific position on a larger polynucleotide sequence (e.g., a polynucleotide attached to a bead).

As used herein, the term "hybridization" may refer to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex."

As used herein, "nucleoside" may include natural nucleosides, such as 2'-deoxy and 2'-hydroxyl forms. "Analogs" in reference to nucleosides may include synthetic nucleosides comprising modified base moieties and/or modified sugar moieties, or the like. Analogs may be capable of hybridization. Analogs may include synthetic nucleosides designed to enhance binding properties, reduce complexity, increase specificity, and the like. Exemplary types of analogs may include oligonucleotide phosphoramidates (referred to herein as "amidates"), peptide nucleic acids (referred to herein as "PNAs"), oligo-2'-O-alkylribonucleotides, polynucleotides containing C-5 propynylpyrimidines, and locked nucleic acids (LNAs).

As used herein, the terms "nucleic acid molecule," "nucleic acid sequence," "nucleic acid fragment," "oligonucleotide," "oligonucleotide fragment" and "polynucleotide" may be used interchangeably and may be intended to include, but are not limited to, polymeric forms of nucleotides that may have various lengths, either deoxyribonucleotides or ribonucleotides, or analogs thereof. Nucleic acid molecules may include single stranded DNA (ssDNA), double stranded DNA (dsDNA), single stranded RNA (ssRNA) and double stranded RNA (dsRNA). Different nucleic acid molecules may have different three-dimensional structures, and may perform various functions. Non-limiting examples of nucleic acid molecules may include a gene, a gene fragment, a genomic gap, an exon, an intron, intergenic DNA (including, without limitation, heterochromatic DNA), messenger RNA (mRNA), transfer RNA, ribosomal RNA, ribozymes, small interfering RNA (siRNA), miRNA, small nucleolar RNA (snoRNA), cDNA, recombinant polynucleotides, branched polynucleotides, plasmids, vectors, isolated DNA of a sequence, isolated RNA of a sequence, nucleic acid probes, and primers.

Oligonucleotides may refer to a linear polymer of natural or modified nucleosidic monomers linked by phosphodiester bonds or analogs thereof. An "oligonucleotide fragment" refers to an oligonucleotide sequence that has been cleaved into two or more smaller oligonucleotide sequences. Oligonucleotides may be natural or synthetic. Oligonucleotides may include deoxyribonucleosides, ribonucleosides, and non-natural analogs thereof, such as anomeric forms thereof, peptide nucleic acids (PNAs), and the like. Oligonucleotides may be capable of specifically binding to a target genome by way of a regular pattern of monomer-to-monomer interactions, such as Watson-Crick type of base pairing, base stacking, Hoogsteen or reverse Hoogsteen types of base pairing, or the like. Oligonucleotides and the term "polynucleotides" may be used interchangeably herein.

Whenever an oligonucleotide is represented by a sequence of letters, such as "ATGCCTG," it may be understood that the nucleotides are in 5' to 3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted.

Oligonucleotides may include one or more non-standard nucleotide(s), nucleotide analog(s) and/or modified nucleotides. Examples of modified nucleotides may include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, oligonucleotide phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

As used herein, a "sample" may refer to a single cell or many cells. Nucleic acid molecules may be obtained from one or more samples. A sample may comprise a single cell type or a combination of two or more cell types. A sample may include a collection of cells that perform a similar function such as those found, for example, in a tissue. A sample may comprise one or more tissues. Examples of tissues may include, but are not limited to, epithelial tissue (e.g., skin, the lining of glands, bowel, skin and organs such as the liver, lung, kidney), endothelium (e.g., the lining of blood and lymphatic vessels), mesothelium (e.g., the lining of pleural, peritoneal and pericardial spaces), mesenchyme (e.g., cells filling the spaces between the organs, including fat, muscle, bone, cartilage and tendon cells), blood cells (e.g., erythrocytes, granulocytes, neutrophils, eosinophils, basophils, monocytes, T-lymphocytes (also known as T-cells), B-lymphocytes (also known as B-cells), plasma cells, megakaryocytes and the like), neurons, germ cells (e.g., spermatozoa, oocytes), amniotic fluid cells, placenta, stem cells and the like. A sample may be obtained from one or more of single cells in culture, metagenomic samples, embryonic stem cells, induced pluripotent stem cells, cancer samples, tissue sections, and biopsies, or any combination thereof.

As used herein, the term "organism" may include, but is not limited to, a human, a non-human primate, a cow, a horse, a sheep, a goat, a pig, a dog, a cat, a rabbit, a mouse, a rat, a gerbil, a frog, a toad, a fish (e.g., *Danio rerio*) a roundworm (e.g., *C. elegans*) and any transgenic species thereof. The term "organism" may also include, but is not limited to, a yeast (e.g., *S. cerevisiae*) cell, a yeast tetrad, a yeast colony, a bacterium, a bacterial colony, a virion, virosome, virus-like particle and/or cultures thereof, and the like.

As used herein, the term "attach," "conjugate," and "couple" may be used interchangeably and may refer to both covalent interactions and noncovalent interactions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

Enzymatic Split-Pool Synthesis

Figure 2A:
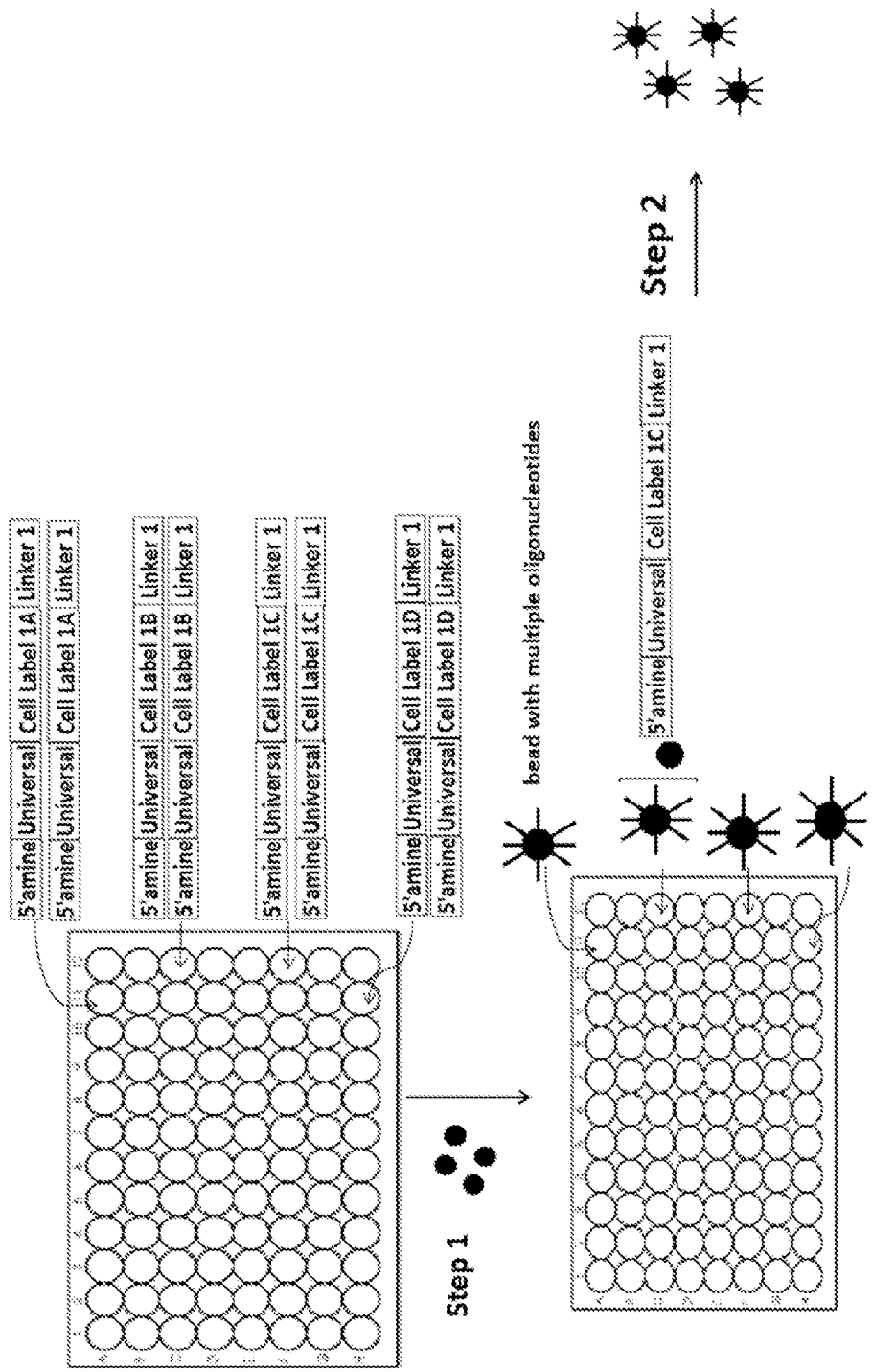
FIGS. 2A-C depicts an exemplary workflow for synthesizing oligonucleotide coupled beads using split-pool synthesis.

In this example, an enzymatic split-pool synthesis method was used to produce oligonucleotide coupled beads. As shown in FIG. 2A, a set of oligonucleotides was added to each well of a first plate. An oligonucleotide in a set of oligonucleotides comprises a 5'amine, universal sequence, cell label and a linker. The 5' amine, universal sequence and linker are the same for each set of oligonucleotides. The universal sequence and linker are different from each other. However, the cell label is different for each set of oligonucleotides. Thus, each well has a different cell label. In Step 1 of the enzymatic split-pool synthesis, oligonucleotide-coupled beads were synthesized by adding a single bead to each well and performing 1-Ethyl-3-(3-dimethylaminopropyl)carbodiimide (EDC) coupling reactions. The oligonucleotides beads resulting from Step 1 comprise a bead coupled to multiple oligonucleotides. The oligonucleotide comprises a 5'-amine, universal sequence, cellular label 1, and linker 1 (see FIG. 2A). The oligonucleotides on the same bead are the same. However, oligonucleotides on a first bead are different from oligonucleotides on a second bead.

In Step 2 of the enzymatic split-pool synthesis, multiple washes were performed to remove uncoupled oligonucleotides. Once the uncoupled oligonucleotides were removed, the oligonucleotide-coupled beads were pooled (see FIG. 2A). The oligonucleotide coupled beads resulting from Step 2 comprise a bead coupled to multiple single stranded oligonucleotides. The single stranded oligonucleotide comprises a 5' amine, universal sequence, cell label 1 and linker 1. Each oligonucleotide on a bead is identical. However, each bead comprises a different oligonucleotide. The oligonucleotides coupled to the different beads differ by the cell label 1 sequence.

Figure 2B:
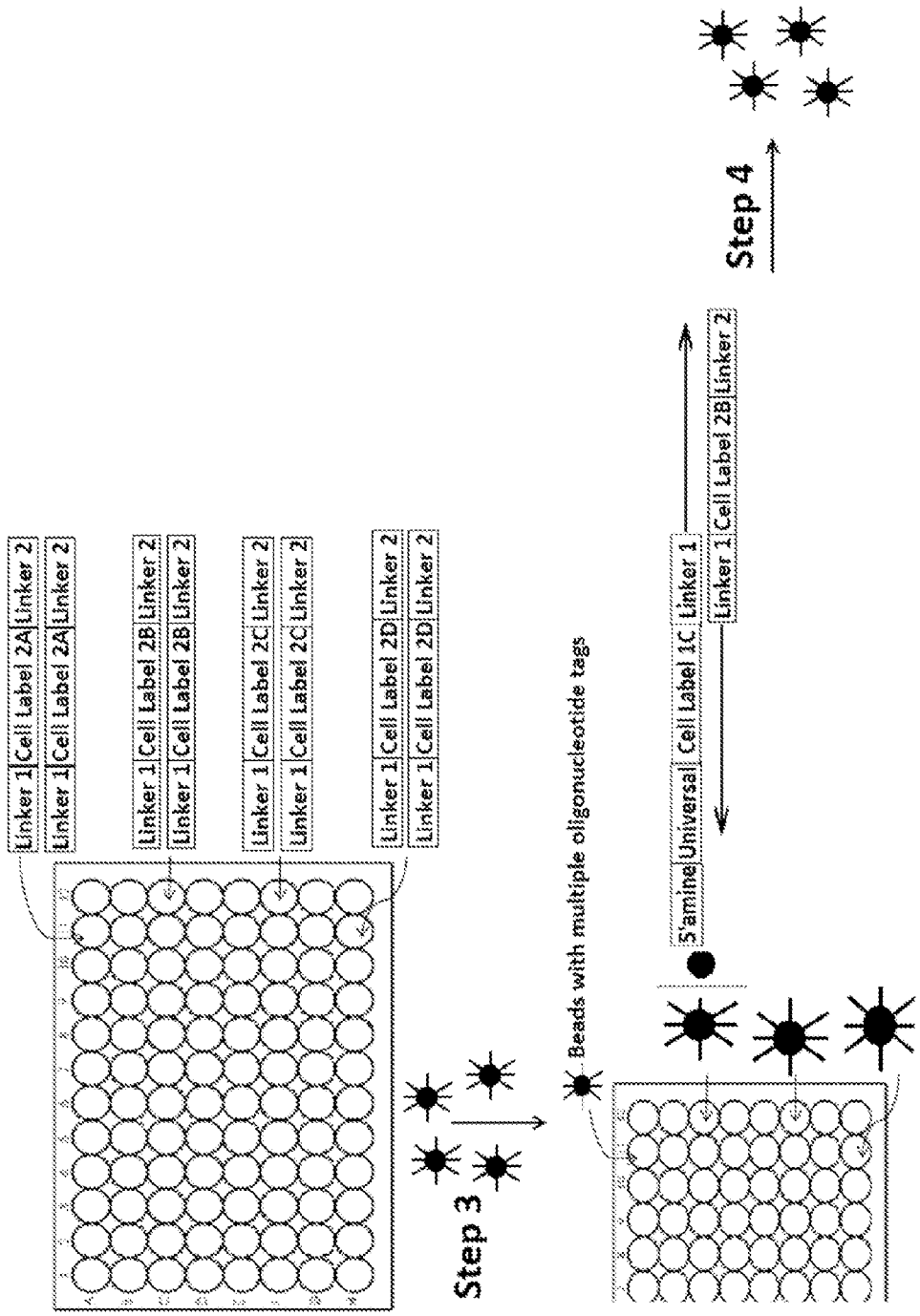

As shown in FIG. 2B, a set of oligonucleotides was added to each well of a second plate. An oligonucleotide in a set of oligonucleotides comprises a first linker, cell label, and a second linker. The first and second linkers are the same for each set of oligonucleotides. The first and second linkers are different from each other. However, the cell label is different for each set of oligonucleotides. Thus, each well has a different cell label.

In Step 3 of the enzymatic split-pool synthesis, the oligonucleotide coupled beads that were pooled in Step 2 were split into the wells of the second plate. Because the first linker of the oligonucleotides in the wells of the second plate are complementary to the linker of the oligonucleotides coupled to the beads, primer extension using Klenow large fragment was performed to couple the oligonucleotides from the second plate to the oligonucleotide coupled beads from Step 2. The oligonucleotides coupled beads resulting from Step 3 comprise a bead coupled to multiple double stranded oligonucleotides. The double stranded oligonucleotide comprises a 5' amine, universal sequence, cell label 1, linker 1, cell label 2, and linker 2 (see FIG. 2B).

In Step 4 of the enzymatic split-pool synthesis, multiple washes were performed to remove uncoupled oligonucleotides and the Klenow large fragment enzymes. The second plate was heated to denature the double stranded oligonucleotides, and the oligonucleotide coupled beads were pooled (see FIG. 2B). The oligonucleotide coupled beads resulting from Step 4 comprise a bead coupled to multiple single stranded oligonucleotides. The single stranded oligonucleotide comprises a 5' amine, universal sequence, cell label 1, linker 1, cell label 2, and linker 2. Each oligonucleotide on a bead is identical. However, each bead comprises a different oligonucleotide. The oligonucleotides coupled to the different beads differ by the combined cell label sequences. For example, a first bead may comprise oligonucleotides comprising a first cell label of cell label A and second cell label of cell label C and a second bead may comprise oligonucleotides comprising a first cell label of cell label C and a second cell label of cell label D. Thus, the first bead and the second bead may comprise the same cell label (in this case, cell label C), however, the combined cell label sequences of the first bead and the second bead are different (e.g., for the first bead, the combined cell label sequence is cell label A+cell label C; for the second bead, the combined cell label sequence is cell label C+cell label A). In other instances, two beads may comprise oligonucleotides comprising different cell labels. For example, a first bead may comprise oligonucleotides comprising cell label A and cell label B and a second bead may comprise oligonucleotides comprising cell label C and cell label D. In this instance, both of the cell labels of the first bead are different from both of the cell labels of the second bead.

Figure 2C:
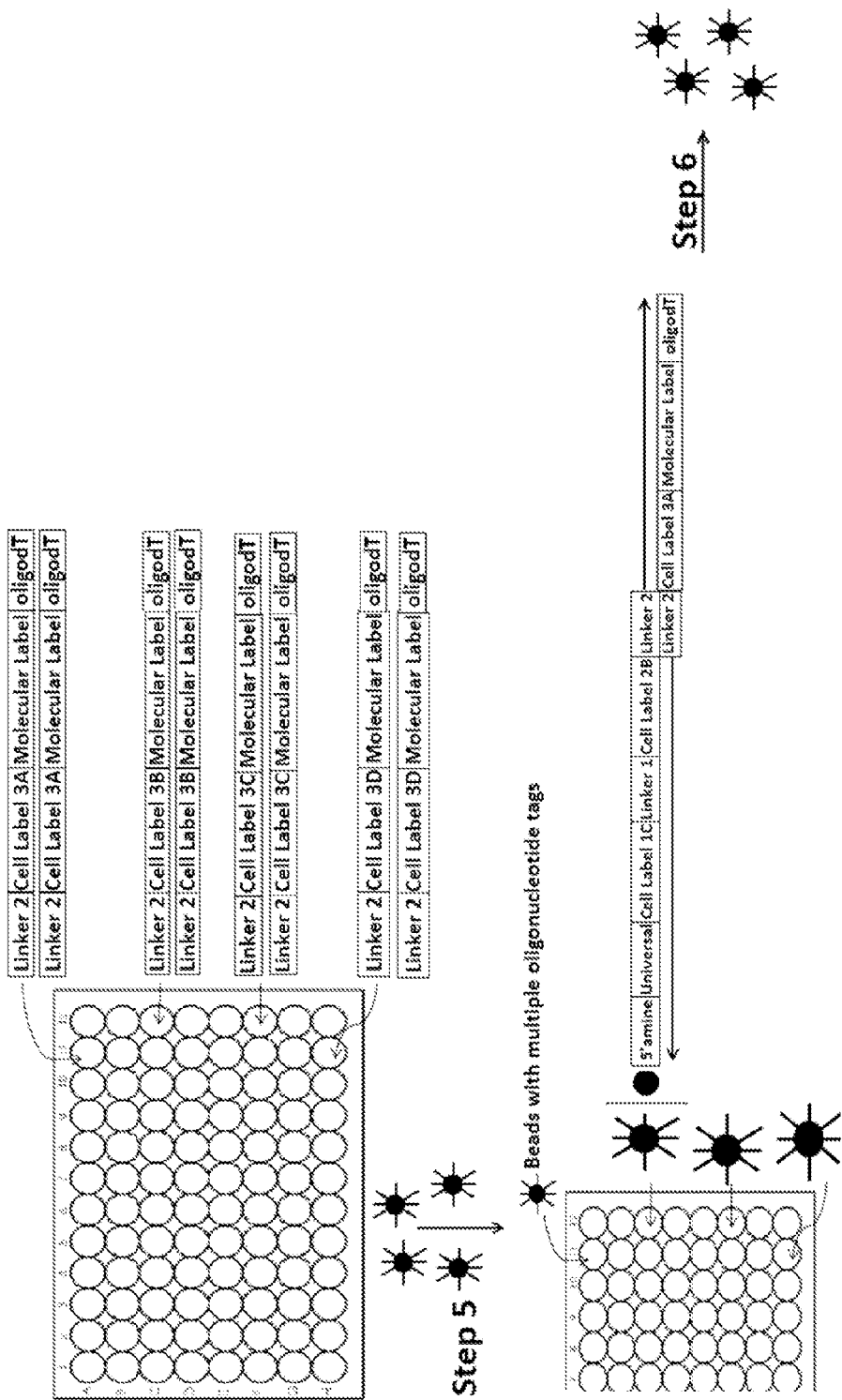

As shown in FIG. 2C, a set of oligonucleotides was added to each well of a third plate. An oligonucleotide in a set of oligonucleotides comprises a linker, cell label, molecular label, and an oligodT. The linker and oligodT sequences are the same for each set of oligonucleotides. However, the cell label is different for each set of oligonucleotides. Thus, each well has a different cell label. In addition, the molecular label is different for oligonucleotides within a set. Thus, a single well contains a plurality of oligonucleotides with the same cell label, but different molecular labels. The oligonucleotides from different wells may contain the same molecular label.

In Step 5 of the enzymatic split-pool synthesis, the oligonucleotide coupled beads that were pooled in Step 4 were split into the wells of the third plate. Because the linker of the oligonucleotides in the wells of the second plate are complementary to the second linker of the oligonucleotides coupled to the beads, primer extension using Klenow large fragment was performed to couple the oligonucleotides from the third plate to the oligonucleotide coupled beads from Step 4. The oligonucleotides coupled beads resulting from Step 5 comprise a bead coupled to multiple double stranded oligonucleotides. The double stranded oligonucleotide comprises a 5' amine, universal sequence, cell label 1, linker 1, cell label 2, linker 2, cell label 3, molecular label and oligodT (see FIG. 2C).

In Step 6 of the enzymatic split-pool synthesis, multiple washes were performed to remove uncoupled oligonucleotides and the Klenow large fragment enzymes. The third plate was heated to denature the double stranded oligonucleotides, and the oligonucleotide coupled beads were pooled (see FIG. 2C). The oligonucleotide coupled beads resulting from Step 4 comprise a bead coupled to multiple single stranded oligonucleotides. The single stranded oligonucleotide comprises a 5' amine, universal sequence, cell label 1, linker 1, cell label 2, linker 2, cell label 3, molecular label and oligodT. The multiple single stranded oligonucleotides on a single bead may be differentiated by the molecular label. The cell label portions of the multiple oligonucleotides on a single bead are identical. Each bead comprises different oligonucleotides. The oligonucleotides coupled to the different beads differ by the cell label sequences. The molecular label on the oligonucleotides from different beads may be the same. The molecular label on the oligonucleotides from different beads may be different. Two or more beads may differ by the combined cell label sequences. For example, a first bead may comprise an oligonucleotide comprising cell label A, cell label B and cell label C and a second bead may comprise an oligonucleotide comprising cell label B, cell label D and cell label A. In this instance, the first and second bead both contain cell label B, however the two other cell labels are different. Thus, two or more beads may comprise oligonucleotides differing by at least one cell label. Two or more beads may comprise oligonucleotides differing by at least two cell labels. Two or more beads may comprise oligonucleotides differing by at least three cell labels. However, a bead may comprise an oligonucleotide comprising two or more identical cell labels. For example, a bead may comprise an oligonucleotide comprising cell label A, cell label A and cell label D. A bead may comprise oligonucleotides comprising at least three identical cell labels. For example, a bead may comprise an oligonucleotide comprising cell label A, cell label A and cell label A. A bead may comprise oligonucleotides comprising three non-identical cell labels. For example, a bead may comprise an oligonucleotide comprising cell label A, cell label D and cell label E. A bead may comprise at least two oligonucleotides comprising at least two different molecular labels. For example, a bead may comprise a first oligonucleotide comprising molecular label A and a second oligonucleotide comprising molecular label D. However, a bead may comprise multiple copies of an oligonucleotide comprising a first molecular label. Thus, a bead may comprise at least two oligonucleotides comprising the same molecular label. For example, a bead may comprise a first oligonucleotide comprising molecular label A and a second oligonucleotide comprising molecular label A. At least 30% of the oligonucleotides on a bead may comprise different molecular labels. At least 40% of the oligonucleotides on a bead may comprise different molecular labels. At least 50% of the oligonucleotides on a bead may comprise different molecular labels. At least 60% of the oligonucleotides on a bead may comprise different molecular labels. Less than 30% of the oligonucleotides on a bead may comprise the same molecular label. Less than 20% of the oligonucleotides on a bead may comprise the same molecular label. Less than 15% of the oligonucleotides on a bead may comprise the same molecular label. Less than 10% of the oligonucleotides on a bead may comprise the same molecular label. Less than 5% of the oligonucleotides on a bead may comprise the same molecular label.

The enzymatic split-pool synthesis technique may be performed on multiple plates or plates with a greater number of wells to produce a larger number of oligonucleotide coupled beads. The use of three separate cell label portions may increase the diversity of the total cell label portions on the beads. With 96 different sequence options for each cell label portion, 884,736 different cell label combinations may be created.

Example 2

Comparison of Amplification in Tube and Microwell

The disclosure provides a method for capturing cells. About 5,000 Ramos cells were captured on a microwell array comprising microwells of about 30 micron in diameter. Some cells were not captured. The control for the experiment was an equivalent number of cells captured in a tube. Both the cells in the tube and the cells in the microwell array were lysed. The nucleic acid was allowed to hybridize to a conjugated bead. Real time PCR of GAPDH and RPL19 genes was performed.

Figure 9:
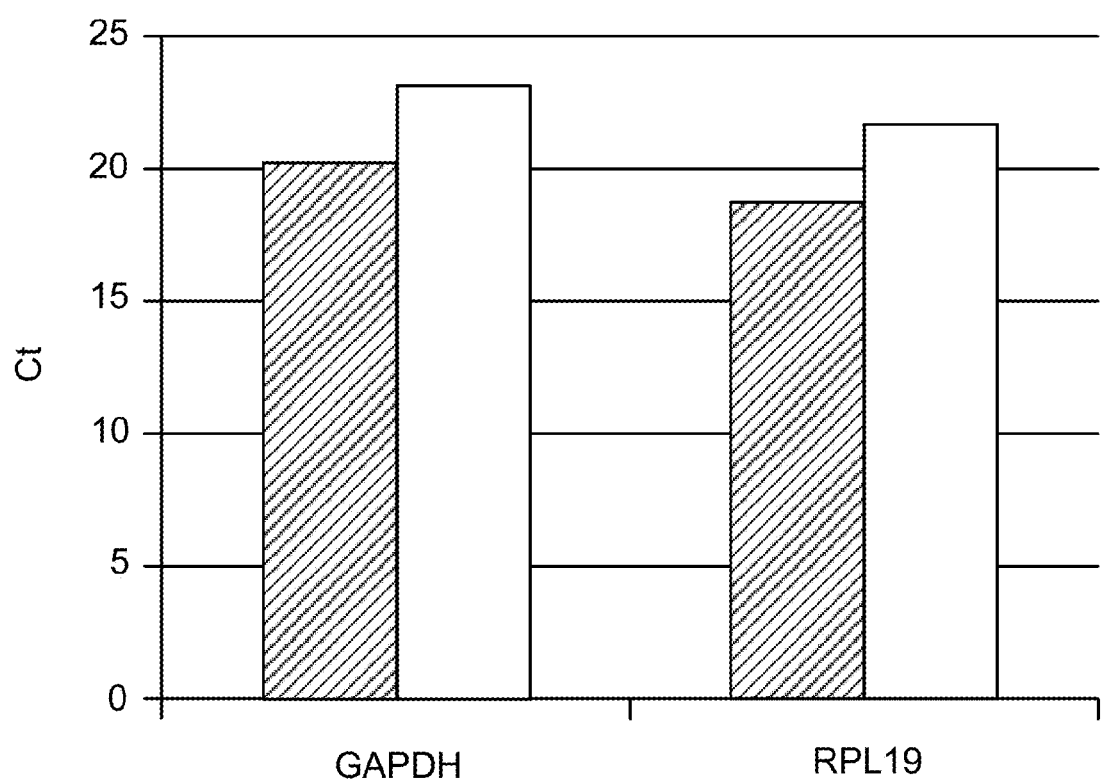
FIG. 9 depicts a bar graph comparing amplification efficiency of GAPDH and RPL19 amplified from microwells and tubes. The grey bars represent data from the microwell. The white bars represent data from the tube.

FIG. 9 shows the results of the real time PCR amplification. The yield from the microwell was larger than the yield from the nucleic acid in the tube, indicating that the hybridization of the nucleic acid to the oligonucleotide was more effective in the microwell than the tube (compare grey bar and white bar, respectively).

Example 3

Comparison of Amplification of Second Synthesized Strand and Synthesis on Bead

Figure 10:
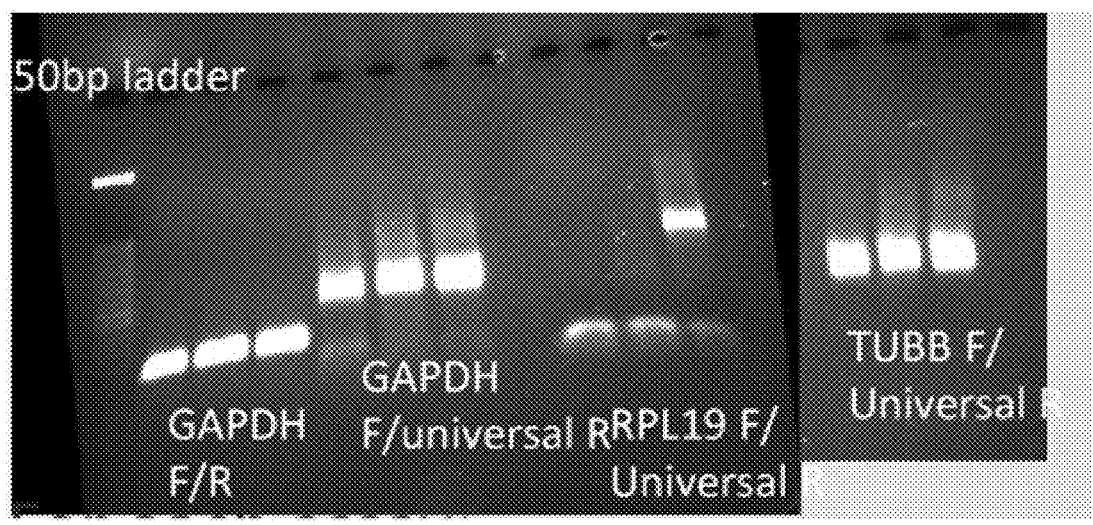
FIG. 10 depicts an agarose gel comparing amplification specificity of three different genes directly on a solid support.

Cells were obtained and lysed as described in Example 1. RPL19, TUBB, and GAPDH were amplified either off the second strand synthesized off the solid supports, or direct on the solid supports using a universal primer. FIG. 10 shows, amplification directly on the solid supports (FIG. 10) yielded less off-target amplification than amplification not directly off a solid support. GAPDH and TUBB amplifications produced correctly sized products regardless of method (the left lane of each triplet in FIG. 10 corresponds to solid support plus lysate in tube format, the middle lane of each triplet corresponds to solid supports from the microwell, and the right lane of each triplet corresponds to solid supports plus purified nucleic acid). The RPL19 product had minimal off-target amplification products, but only produced a strong product when purified nucleic acid was used with the solid support. These experiments indicate that amplification directly on the beads produces less off-target amplification products than amplification using a second strand synthesized off the solid support.

Example 4

Multiplex Analysis of Target Nucleic Acids

Cells are obtained and lysed as described in Example 1. Target nucleic acids are hybridized to the solid support comprising oligonucleotides. A plurality of copies of the target nucleic acid are hybridized to a target binding region comprising an oligodT sequence. The plurality of copies of the target nucleic acid are reverse transcribed using reverse transcriptase. Reverse transcription incorporates the features of the oligonucleotide to which the copy of the target nucleic acid was hybridized (e.g., the molecular label, the cellular label, and the universal label). The plurality of copies of the target nucleic acid are amplified using PCR. The amplified copies of the target nucleic acid are sequenced. The sequenced target nucleic acids are counted to determine the copy number of the target nucleic acid in the cell. The counting is performed by counting the number of different molecular labels for each of the same sequence read of target nucleic acid. In this way, amplification bias may be diminished.

Example 5

Figure 11A:
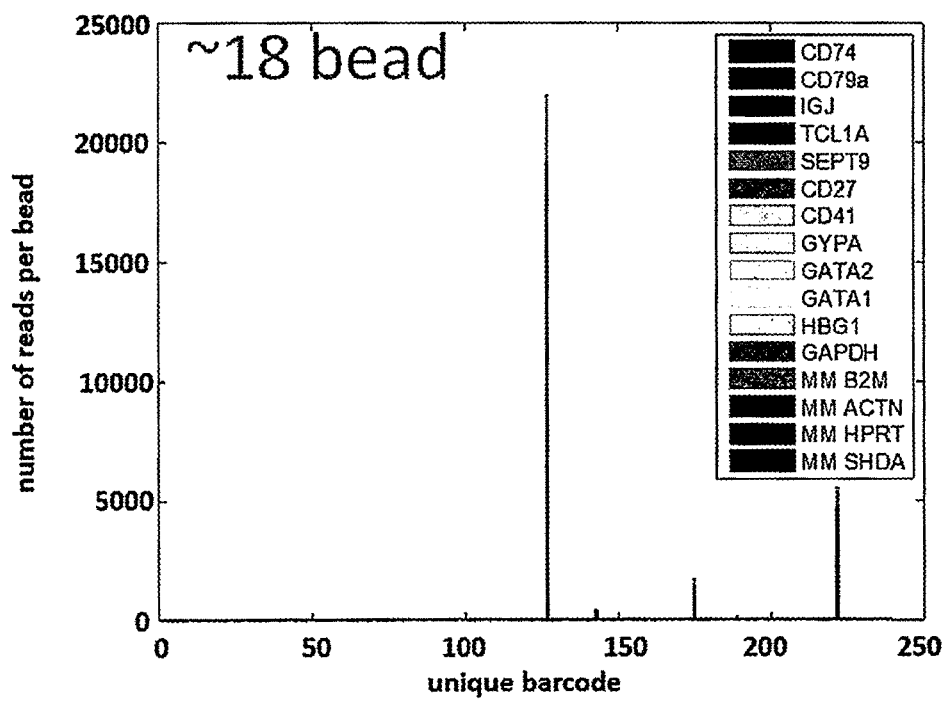
FIGS. 11A-I show graphical representations of the sequencing results.
Figure 11B:
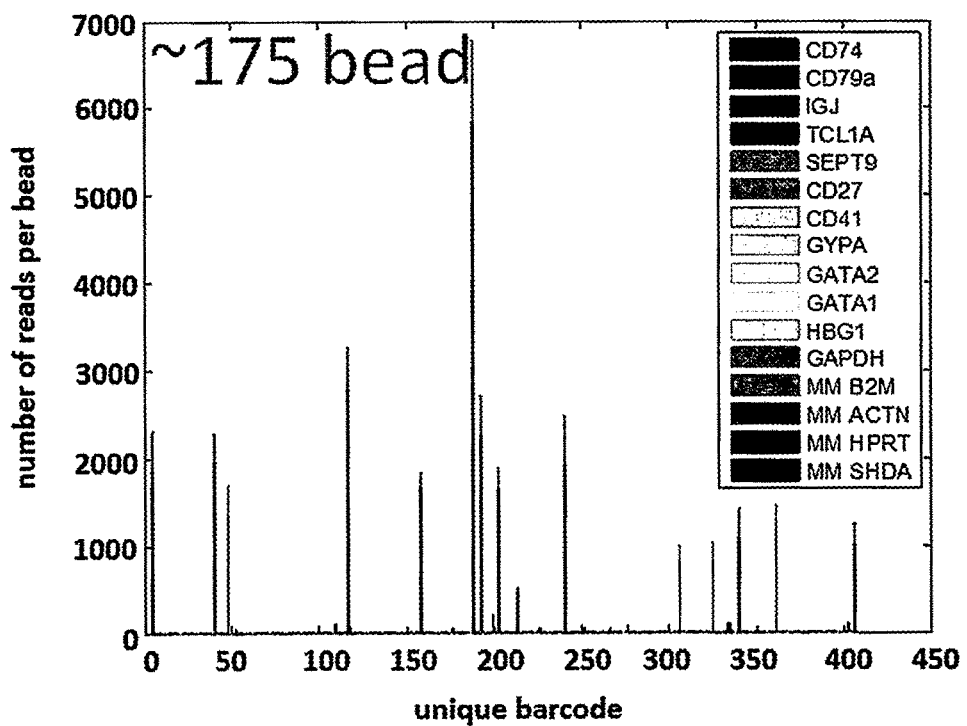
Figure 11C:
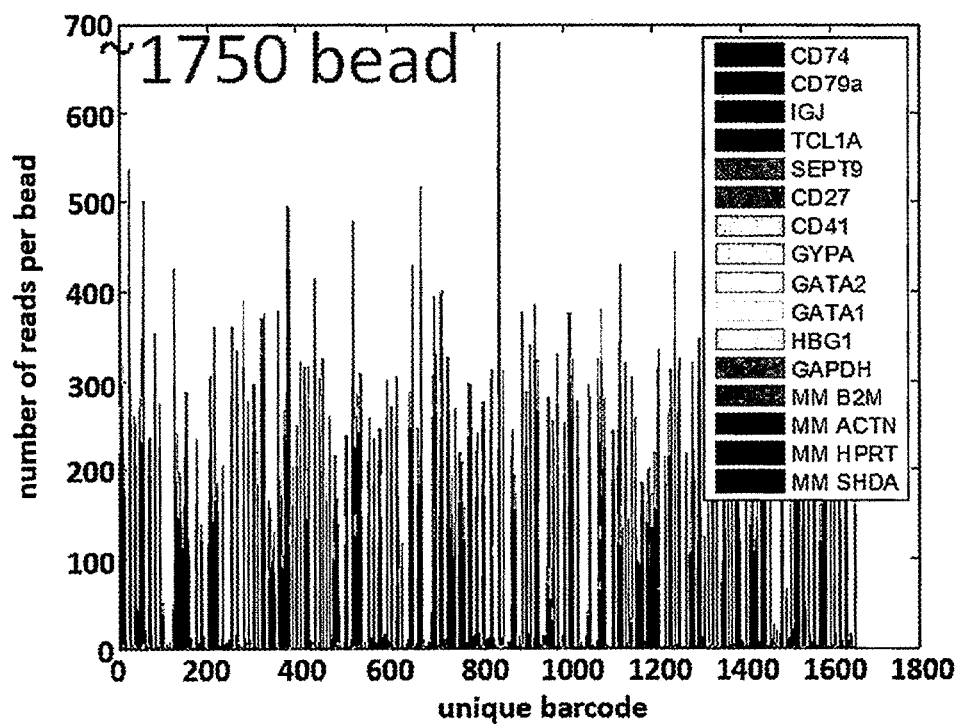
Figure 11D:
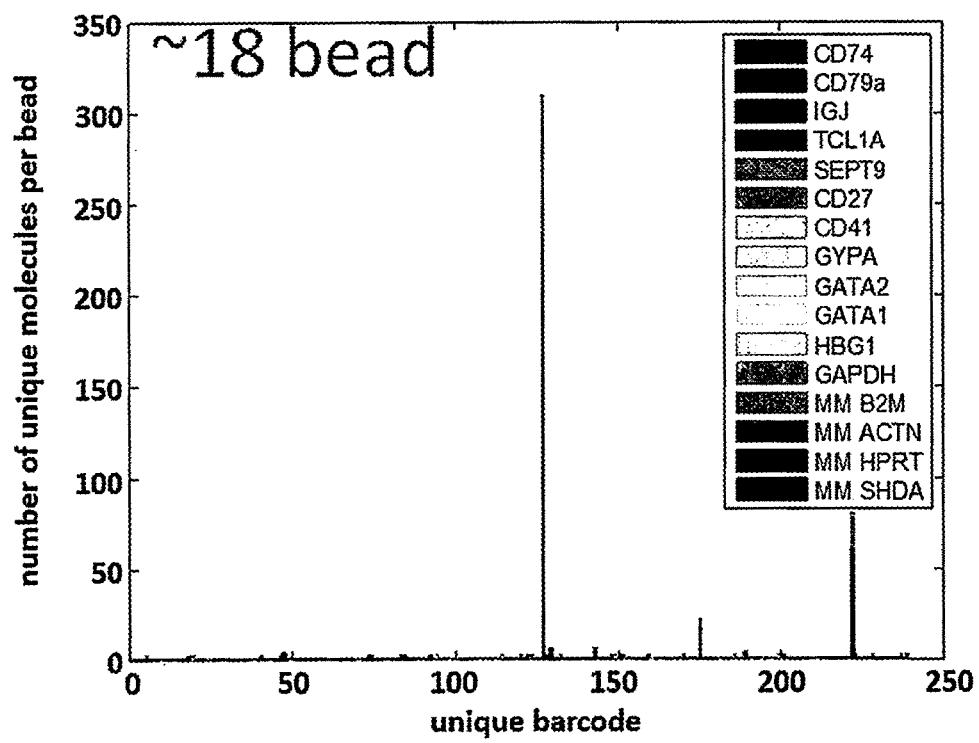
Figure 11E:
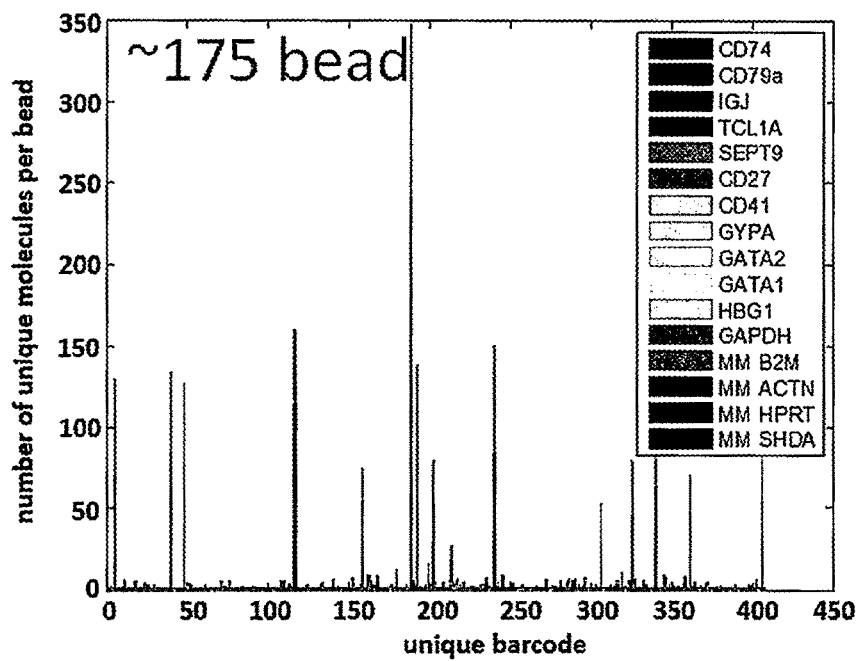
Figure 11F:
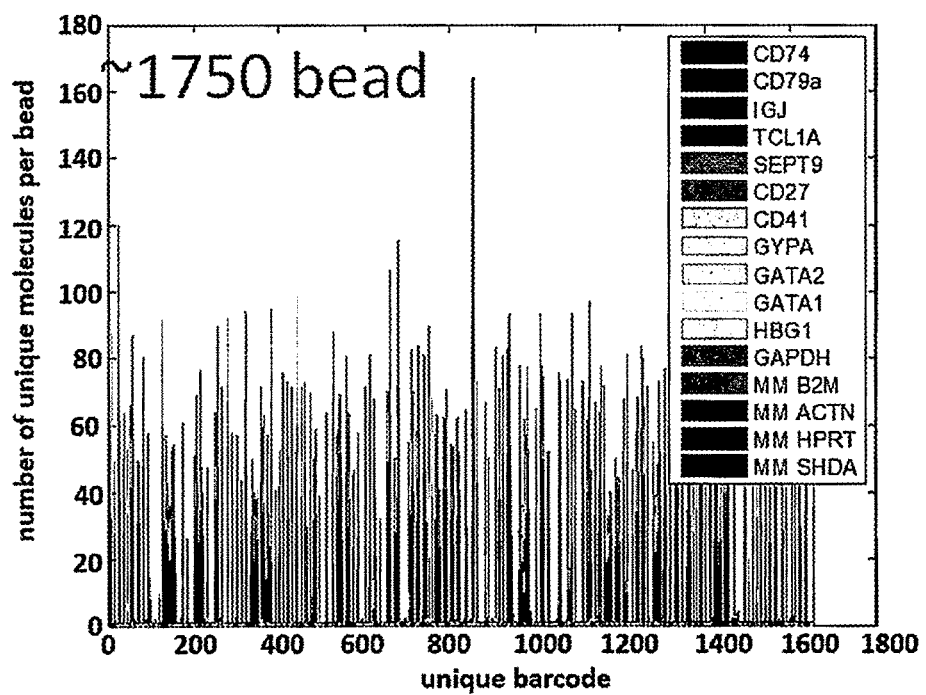
Figure 11G:
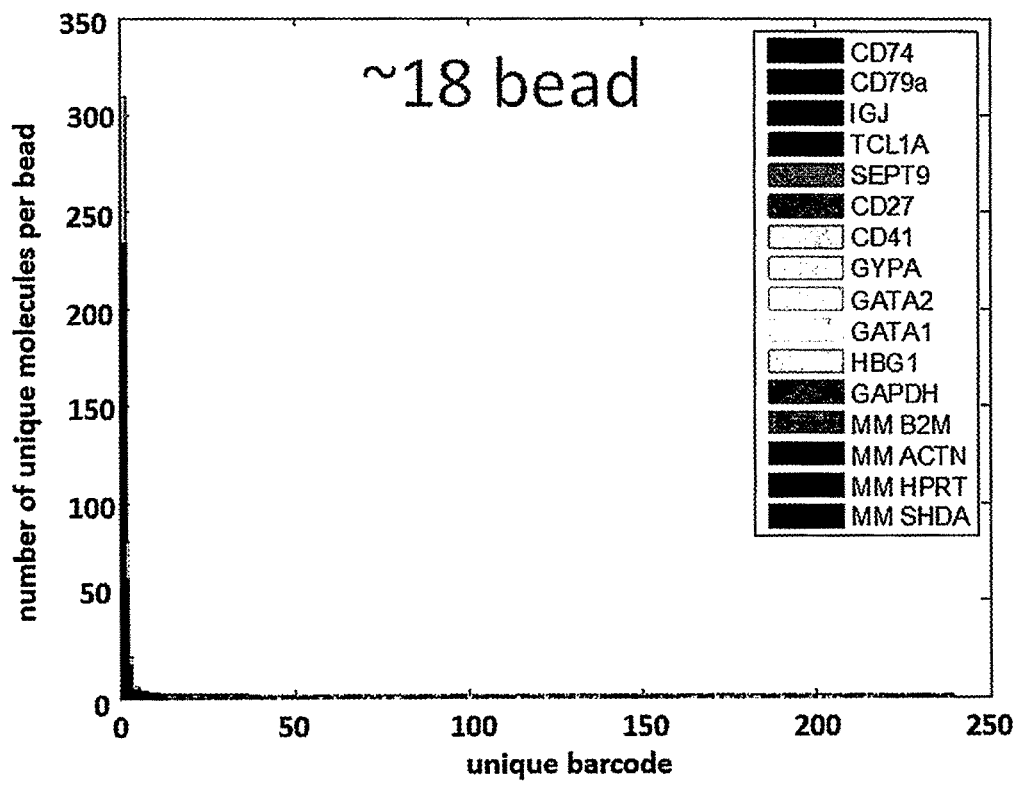
Figure 11H:
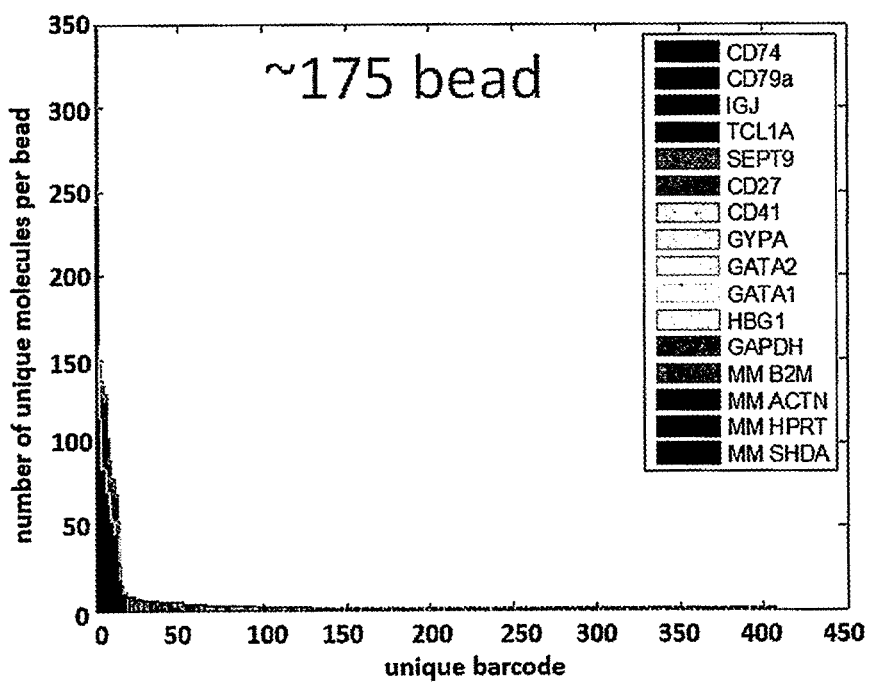
Figure 11I:
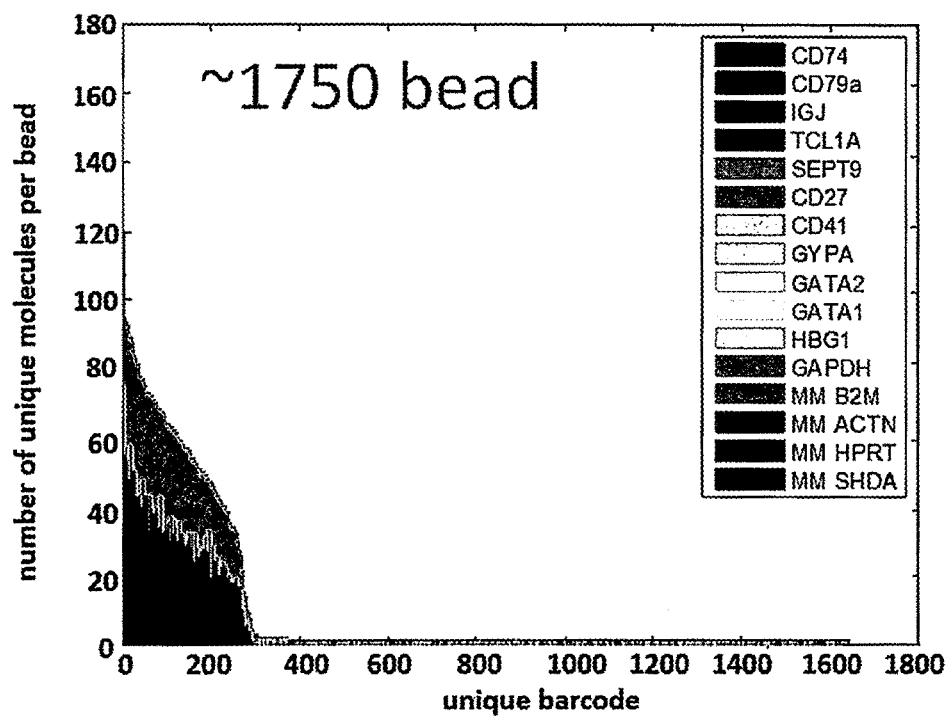

Evaluating Efficacy of Split-Pool Synthesis to Produce Beads with Clonal Copies of One Cell Label Combination In this example, the efficacy of split-pool synthesis to produce beads with clonal copies of one cell label combination was evaluated. Oligonucleotide coupled beads were synthesized by the enzymatic split-pool synthesis method as described in Example 1. 250 ng of total RNA was purified from Ramos cells, which is equivalent to RNA from 25,000 cells. The total RNA was contacted with 35,000 oligonucleotide coupled beads, resulting in hybridization of mRNA to the oligonucleotide coupled beads. cDNA synthesis was performed on the mRNA hybridized to the oligonucleotide coupled beads. Samples comprising 18, 175, and 1750 beads were used for further analysis. PCR amplification reactions using GAPDH-specific primers and IGJ-specific primers were performed on the cDNA bound to the beads from the 18-, 175- and 1750-bead samples. The cDNA molecules attached to the beads were sequenced. FIG. 11A-I show graphical representations of the sequencing results. For FIG. 11A-C, the number of reads per bead is plotted on the y-axis and the unique barcode (e.g., cell label combination) is plotted on the x-axis for the 18-bead, 175-bead and 1750-bead samples, respectively. For FIG. 11D-F, the number of unique molecules per bead is plotted on the y-axis and the unique barcode (e.g., cell label combination) is plotted on the x-axis for the 18-bead, 175-bead and 1750-bead samples, respectively. For FIG. 11G-I, the number of unique molecules per bead is plotted on the y-axis and the unique barcode is plotted on the x-axis for the 18-bead, 175-bead and 1750-bead samples, respectively. The results for FIG. 11G-I are sorted by the total number of molecules. The median number of unique molecules per bead for the various samples is shown in Table 1. Numerical values for the sequencing results are shown in Table 2. For FIG. 11J-L, the number of unique barcode (bc) combination using the index is plotted on the y-axis and the barcode (bc) segment index is plotted on the x-axis for the cell label 1, cell label 2, and cell label 3 for the 1750-bead sample, respectively. The barcode (bc) refers to the cell label (e.g., bc segment1=cell label part 1). As shown in FIG. 11J-L, the presence of almost all 96 barcodes within each segment was detected by sequencing. These results demonstrate the success of the enzymatic split-pool synthesis method to produce beads with clonal copies of one cell label combination.

TABLE 1

| | Median number of unique molecules | | |
|---|---|---|---|
| | 18 beads | 175 beads | 1750 beads |
| IGJ | 78 | 85 | 40 |
| GAPDH | 22 | 45 | 25 |

TABLE 2

| Expected # of beads | 17.5 | 175 | 1750 |
|---|---|---|---|
| Total number of reads | 58321 | 60308 | 133043 |
| >=8 match in constant 1 | 56385 | 57615 | 123349 |
| >=8 match in constant 2 | 54117 | 55187 | 115126 |
| >=8 match in constant 1 & 2 | 54114 | 55185 | 115107 |
| Perfect match in all 3 sub-barcodes | 38585 | 46066 | 95217 |
| Perfect match in gene (40 bp) | 29968 | 33775 | 72260 |
| Total number of unique barcode combination | 239 | 407 | 1654 |
| % useful reads | 51.388% | 56.00% | 54.31% |
| Number of unique barcode combinations >20 read | 5 | 26 | 288 |

Example 6

Single Cell RNA Labeling Using Oligonucleotide Coupled Beads

In this example, the efficacy of single cell RNA labeling using oligonucleotide coupled beads was evaluated. Three cell samples were prepared as follows:

| | Sample 1: K562 only | Sample 2: Ramos only | Sample 3: Ramos + K562 mixture |
|---|---|---|---|
| Number of microwells | ~10000 | ~10000 | ~10000 |
| Number of Ramos cells | 0 | 5000 | 3750 |
| Number of K562 cells | 1000 | 0 | 2500 |

The cell suspension of the samples was added to the top of a microwell and cells were allowed to settle into the wells of the microwell array. Cells not captured by the microwell array were washed away in a phosphate buffered saline (PBS) bath. Oligonucleotide coupled beads, as prepared by the enzymatic split-pool synthesis method described in Example 1, were added to the microwell array. The oligonucleotide coupled bead comprises a magnetic bead with a plurality of oligonucleotides. Each oligonucleotide on the bead comprises a 5'amine, universal sequence, cell label 1, linker 1, cell label 2, linker 2, cell label 3, molecular label, and oligodT. For each oligonucleotide on the same bead, the sequences of the oligonucleotides are identical except for the molecular label. For oligonucleotides on different beads, the cell label 1, 2, and 3 combinations are different. Approximately 5-6 beads were added per well of the microwell array.

Figure 12A:
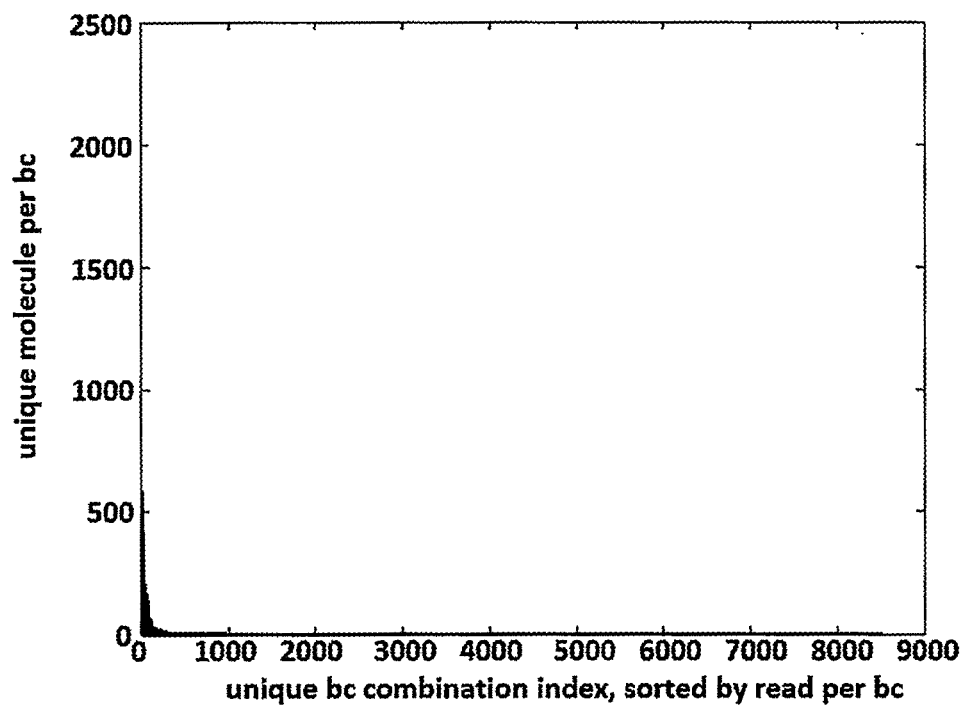
FIGS. 12A-C show a histogram of the sequencing results for the K562-only sample, Ramos-only sample, and K562+Ramos mixture sample, respectively.
Figure 12B:
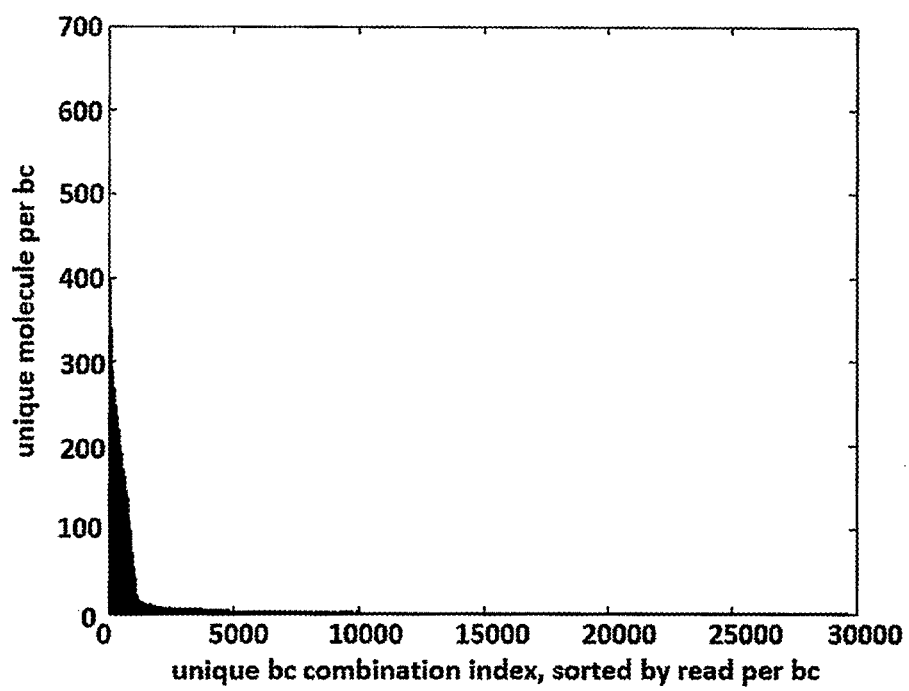
Figure 12C:
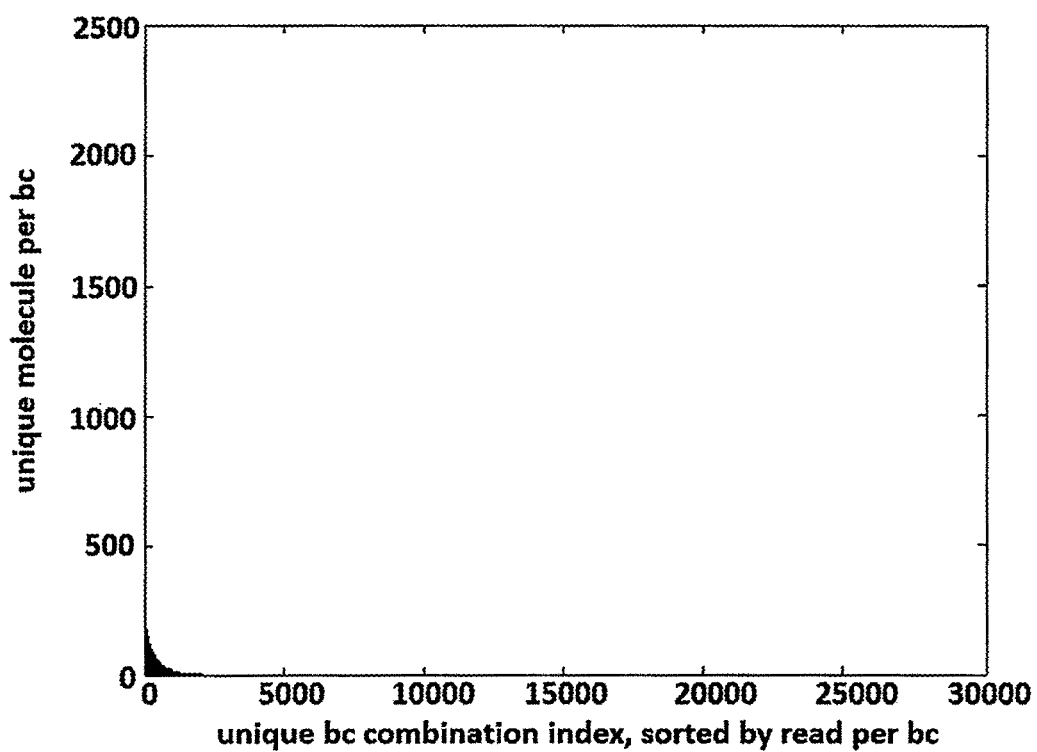

In some instances, for every 10 wells, 50 beads may be deposited on the array, with 0-2 beads falling into each well. The beads were allowed to settle into the wells and uncaptured beads were washed away in a PBS bath. A magnet was placed underneath the microwell array. Cells were lysed by the addition of cold lysis buffer. The array and magnet were placed on a cold aluminum block for 5 minutes. mRNA from the lysed cells were hybridized to the oligonucleotides coupled to the beads. The array was washed with excess lysis buffer to remove unbound mRNA. The beads were retrieved from the wells by placing a magnet on top of the microwell array. The retrieved beads were washed. cDNA synthesis was performed on the beads using Superscript III at 50° C. for 50 minutes on a rotor. Non-extended oligodT from the oligonucleotides on the beads were removed by ExoI treatment conducted at 37° C. for 30 minutes on a rotor. Gene-specific PCR amplification was conducted on the cDNA. The genes selected for the gene-specific PCR were cell-type specific and are shown in Table 3. The PCR amplified products were sequenced. Sequencing statistics are shown in Table 4. FIGS. 12A-C show a histogram of the sequencing results for the K562-only sample, Ramos-only sample, and K562+Ramos mixture sample, respectively. For FIG. 12A-C, the unique molecule per barcode plotted on the y-axis and the unique bc combination index, sorted by read per bc plotted on the x-axis.

TABLE 3

| Number | Gene | Cell-type |
|---|---|---|
| 1 | CD74 | Ramos-specific |
| 2 | CD79a | Ramos-specific |
| 3 | IGJ | Ramos-specific |
| 4 | TCL1A | Ramos-specific |
| 5 | SEPT9 | Ramos-specific |
| 6 | CD27 | Ramos-specific |
| 7 | CD41 | K562-specific |
| 8 | GYPA | K562-specific |
| 9 | GATA1 | K562-specific |
| 10 | GATA2 | K562-specific |
| 11 | HBG1 | K562-specific |
| 12 | GAPDH | common |

TABLE 4

| | Sample 1: K562 only | Sample 2: Ramos only | Sample 3: Ramos + K562 mixture |
|---|---|---|---|
| Number of Ramos cells | 0 | 5000 | 3750 |
| Number of K562 cells | 1000 | 0 | 2500 |
| Total number of reads | 717718 | 1329189 | 2399025 |
| >=8 match in constant 1 | 657911 | 1201081 | 2026726 |
| >=8 match in constant 2 | 581581 | 1071364 | 1513466 |
| >=8 match in constant 1 & 2 | 581508 | 1071153 | 1513102 |
| Perfect match in all 3 sub-barcodes | 481564 | 862348 | 1248073 |
| Perfect match in gene (40 bp) | 283463 | 575713 | 1004338 |
| % useful reads | 39.50% | 43.31% | 41.86% |
| Total number of unique barcode combination | 8501 | 29647 | 28783 |
| Number of unique barcode combinations >30 molecule | 145 | 1072 | 768 |
| Capture efficiency | 0.145 | 0.2144 | 0.12288 |

Figure 12D:
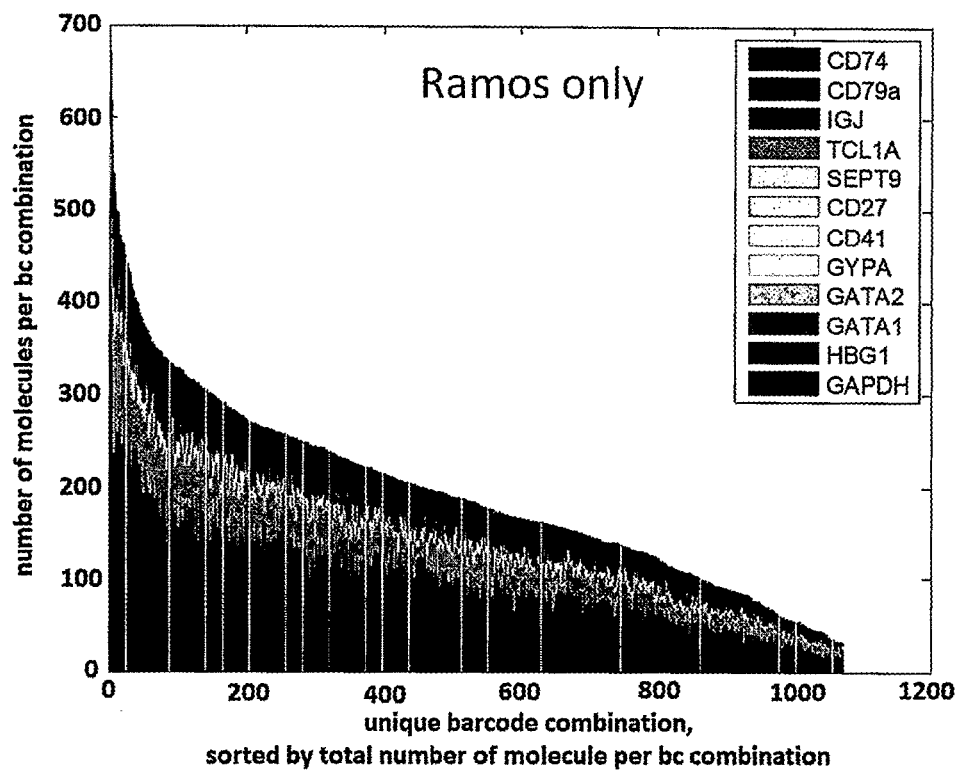
FIGS. 12D-E shows a graph of the copy number for genes listed in Table 3 for the Ramos-only cell sample and K562-only cell sample, respectively.
Figure 12E:
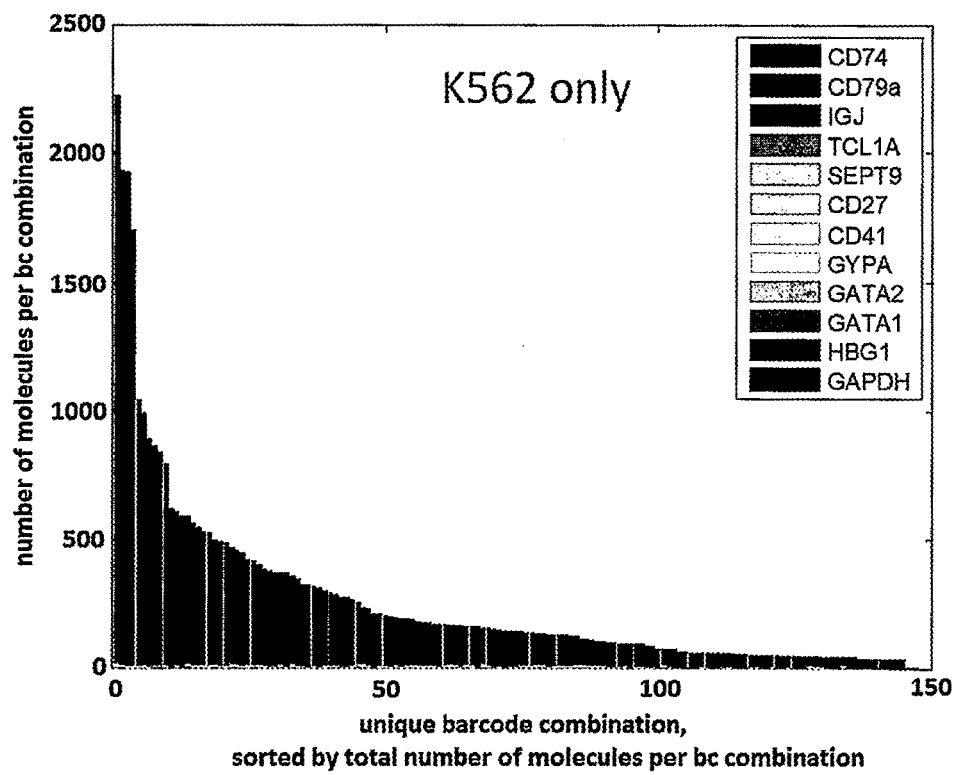
Figure 12F:
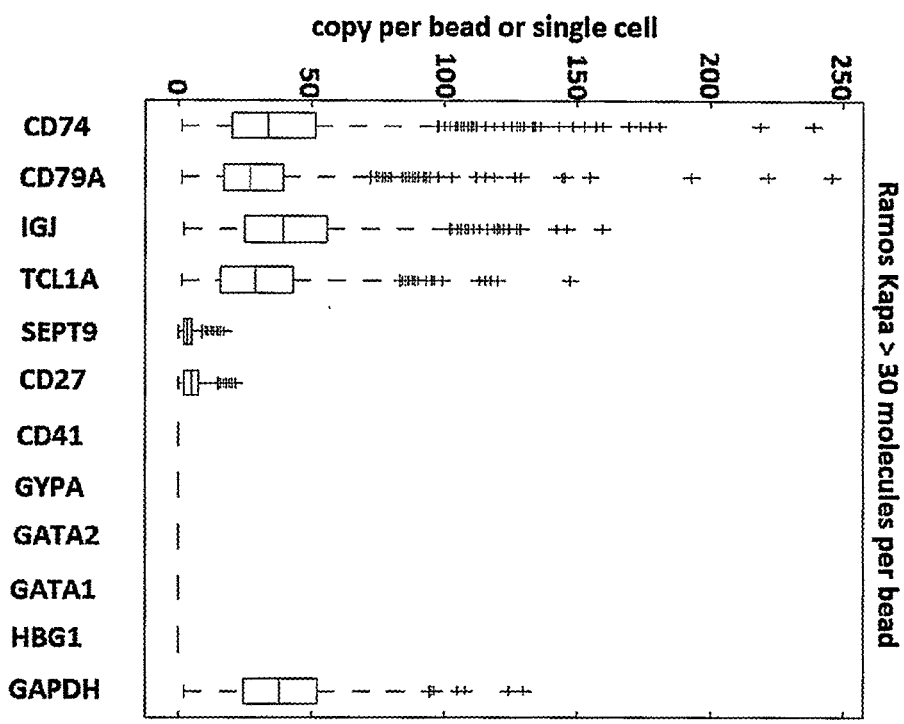
FIGS. 12F-I show the copy number for individual genes.
Figure 12G:
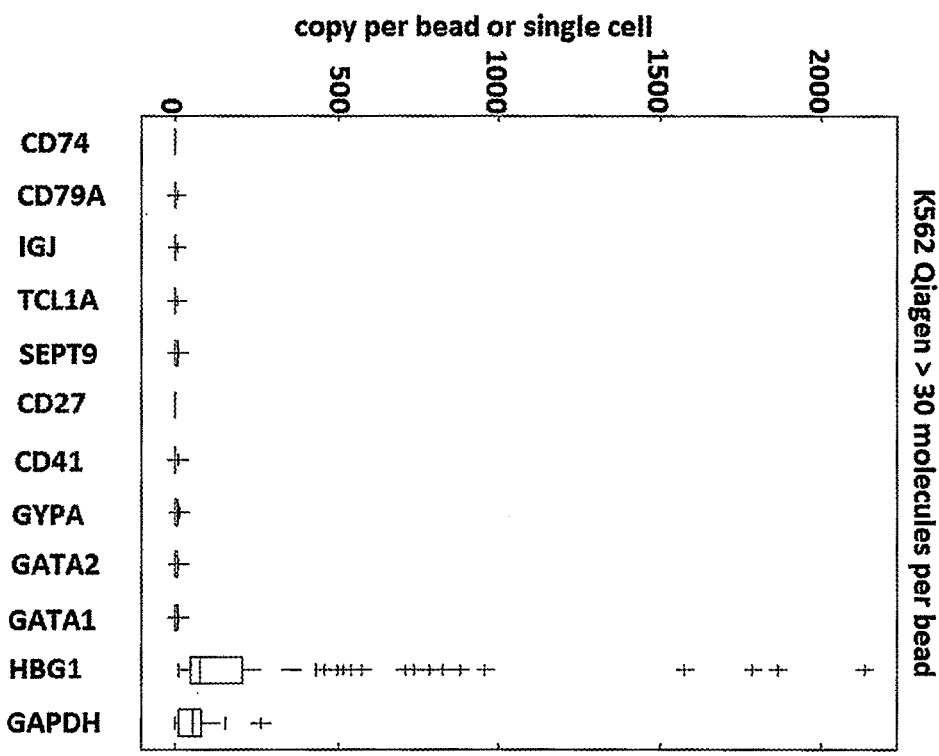
Figure 12H:
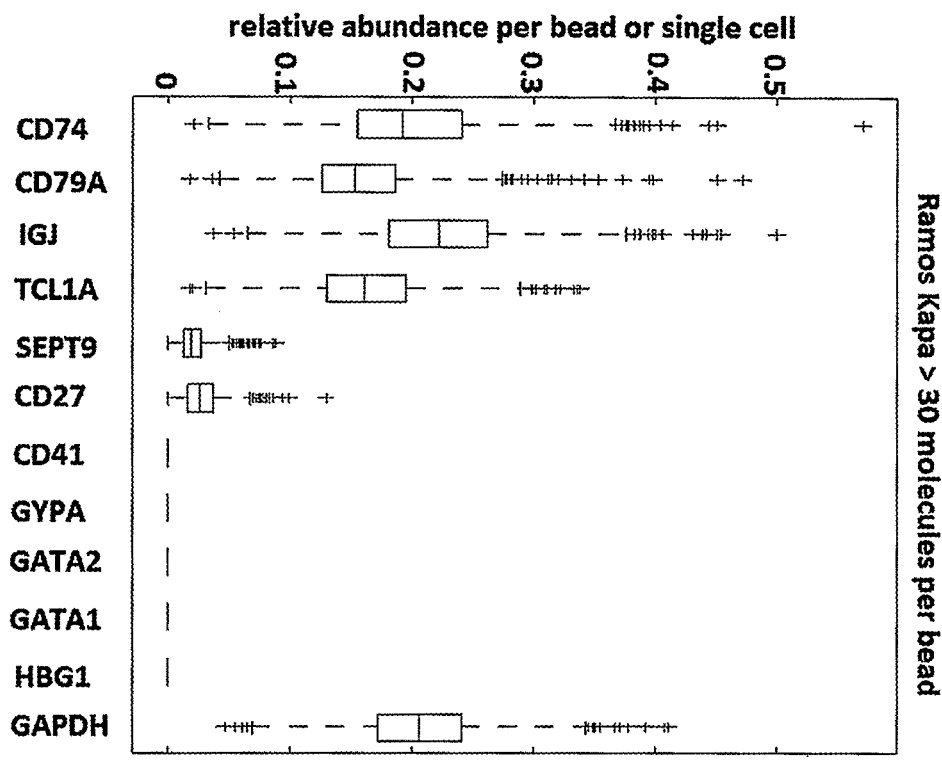
Figure 12I:
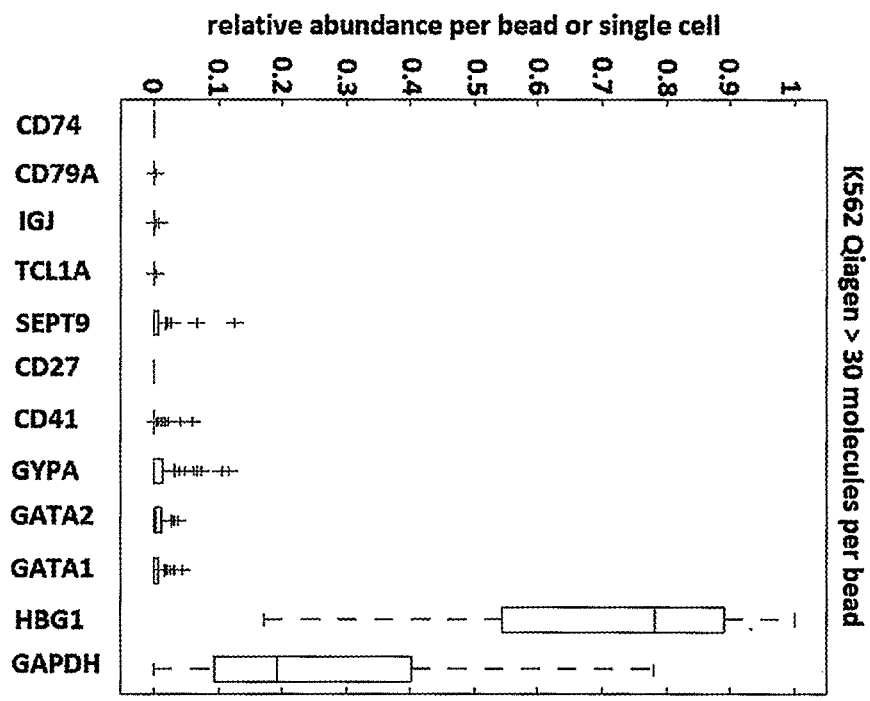
Figure 12J:
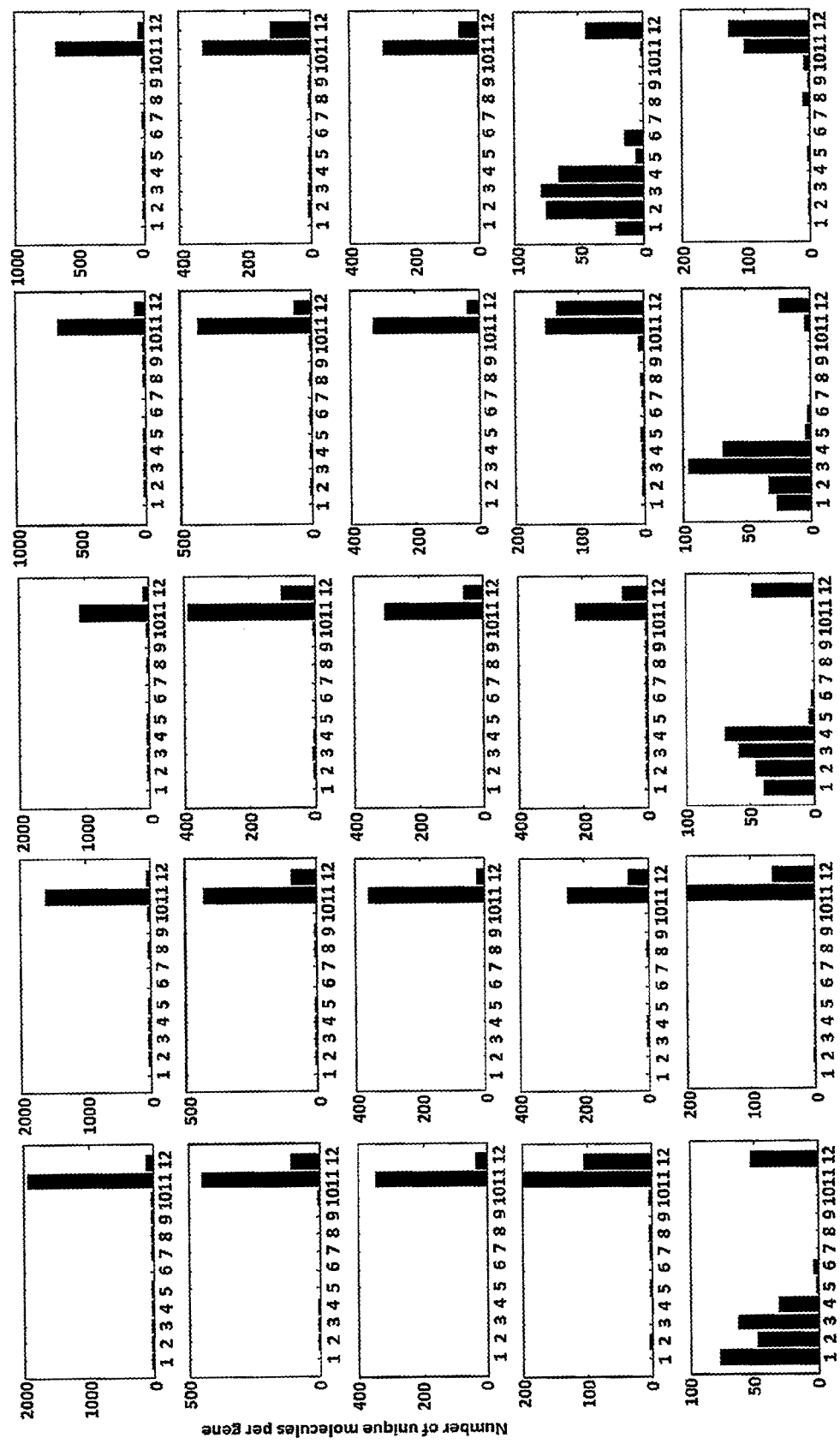
FIGS. 12J-M show graphs of the number of unique molecules per gene (y-axis) for the beads with the 100 unique barcode combinations.
Figure 12K:
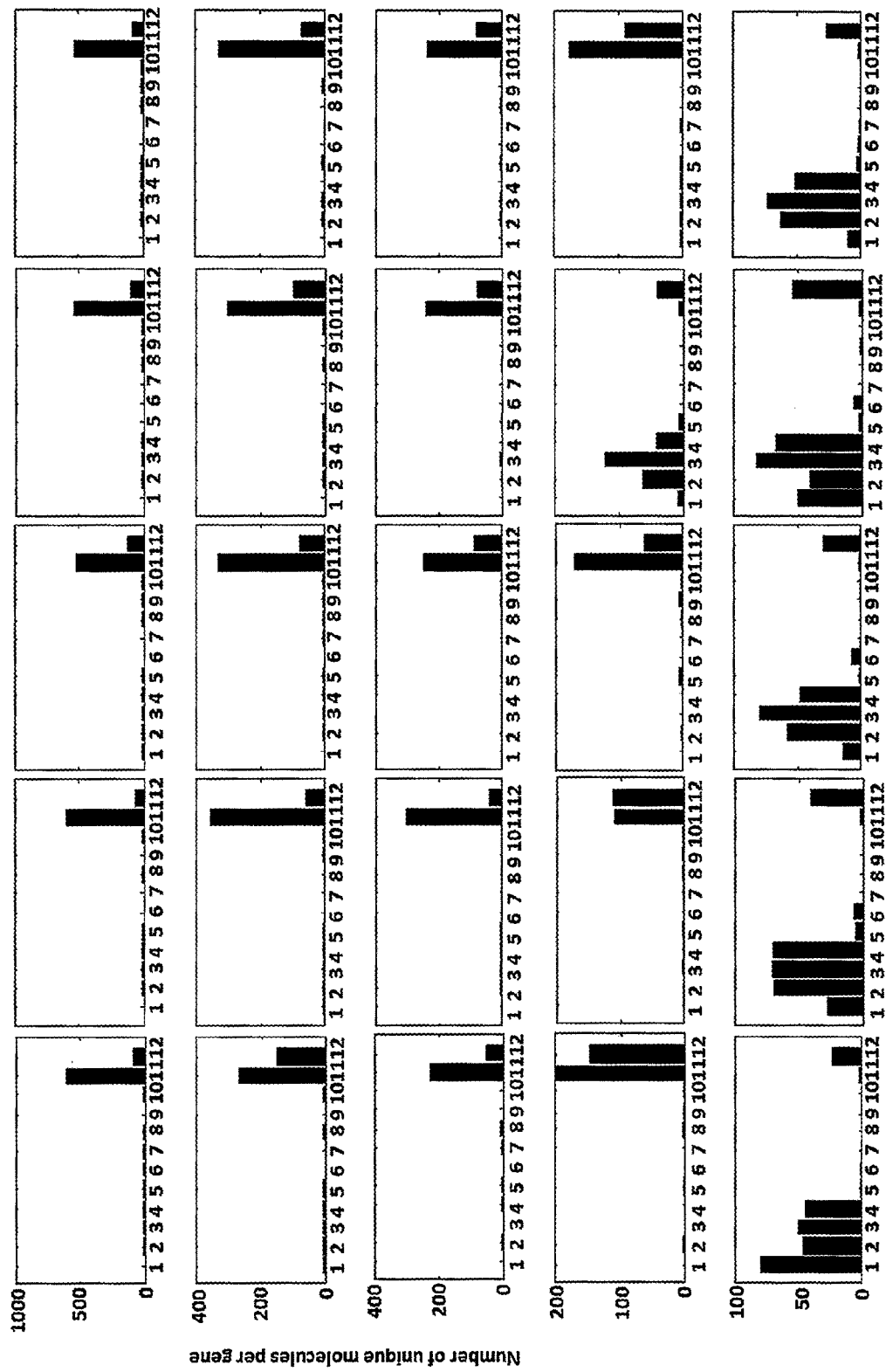
Figure 12L:
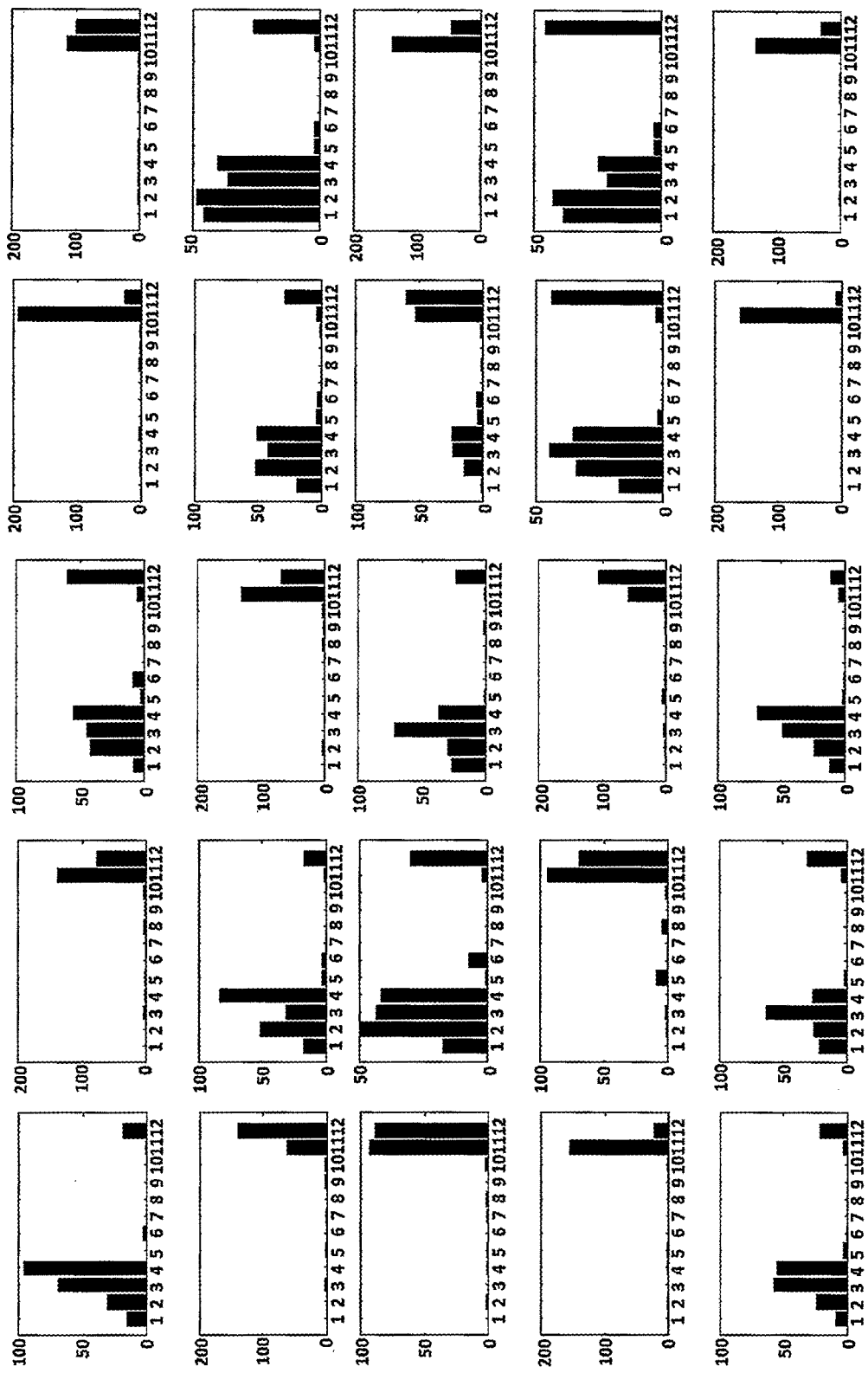
Figure 12M:
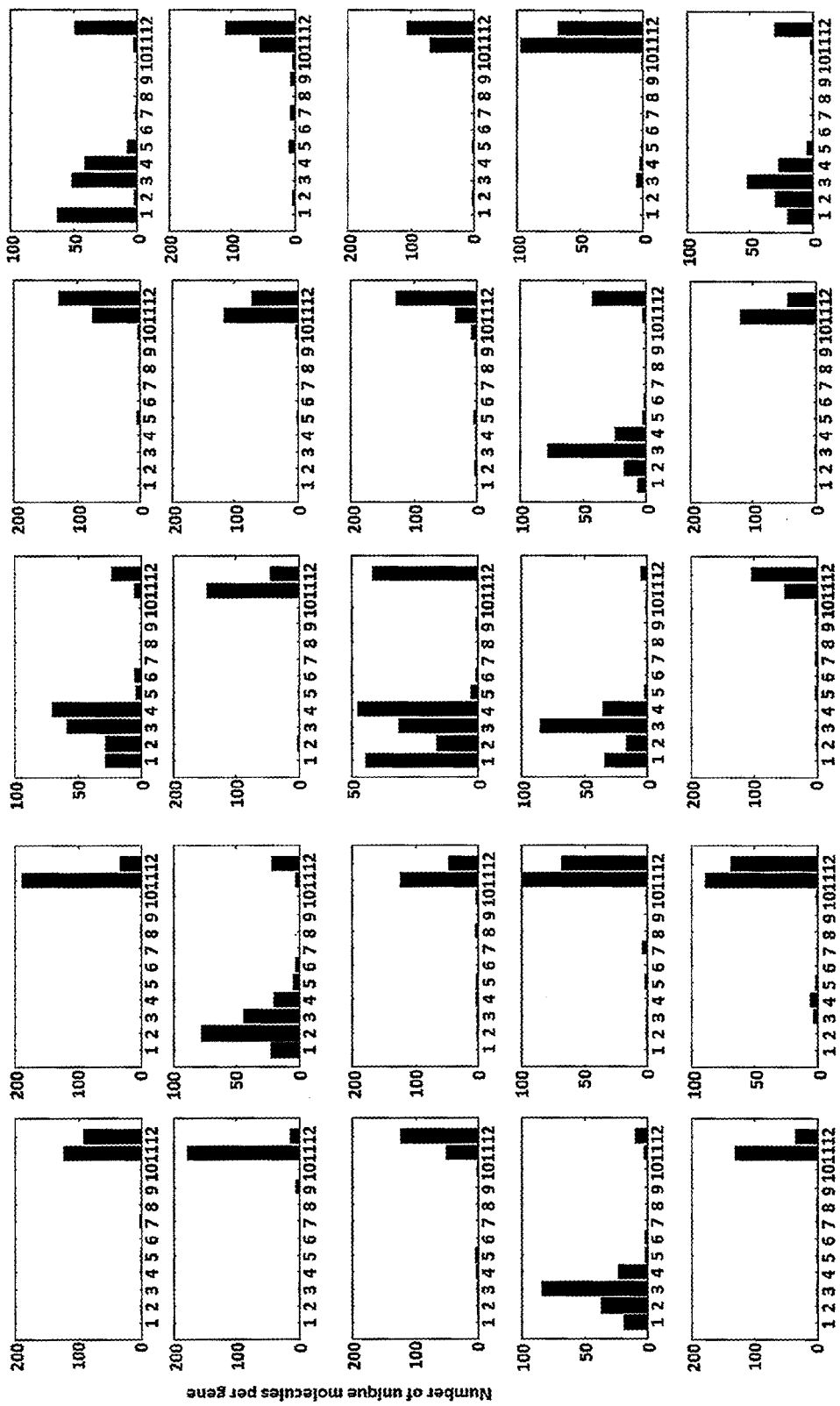

Single cell labeling was used to determine the copy number for the single-cell type samples (e.g., K562-only sample, Ramos-only sample). FIG. 12D-E shows a graph of the copy number for genes listed in Table 3 for the Ramos-only cell sample and K562-only cell sample, respectively. For FIG. 12D-E, the number of molecules per barcode (bc) combination is plotted on the y-axis and the unique barcode combination, sorted by total number of molecules per bc combination is plotted on the x-axis. The results shown in FIGS. 12D-E were based on sequencing data from beads with >30 total number of unique molecules. These results demonstrate that the proportion of molecules per amplicon per bead matches expectations for the cell type. For the K562-only cell sample, the skew of the number of molecules is more severe and it appears that HBG1, which is highly abundant in this cell type, has a variable copy number. However, GAPDH copy number appears to be constant even though the total number of molecules per bead is skewed. The copy number for the individual genes are shown in FIG. 12F-I. For FIG. 12F-G, the copy number is represented as copy per bead or single cell for Ramos-only cells and K562-only cells, respectively. For FIG. 12H-I, the copy number is represented as relative abundance per bead or single cell for Ramos-only cells and K562-only cells, respectively.

Figure 12N:
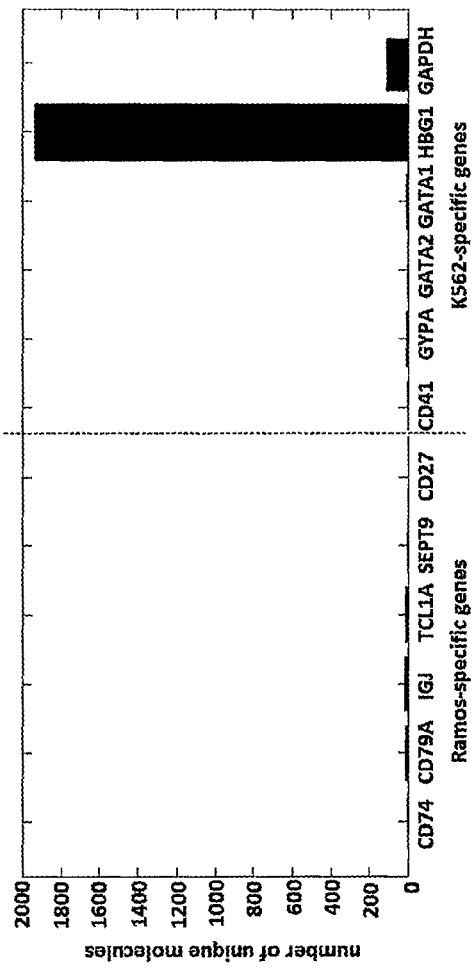
FIGS. 12N-O show enlarged graphs of two beads that depict the general pattern of gene expression profiles for the two cell types.
Figure 12O:
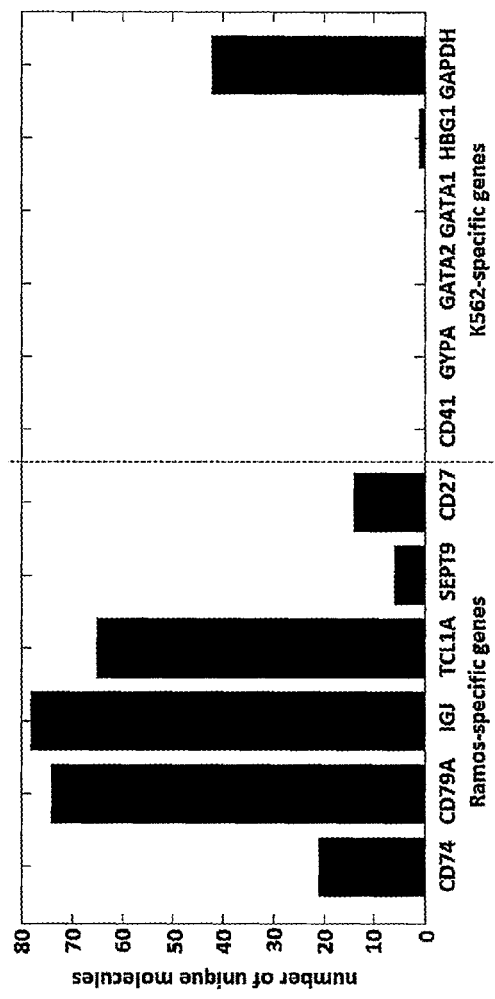
Figure 12P:
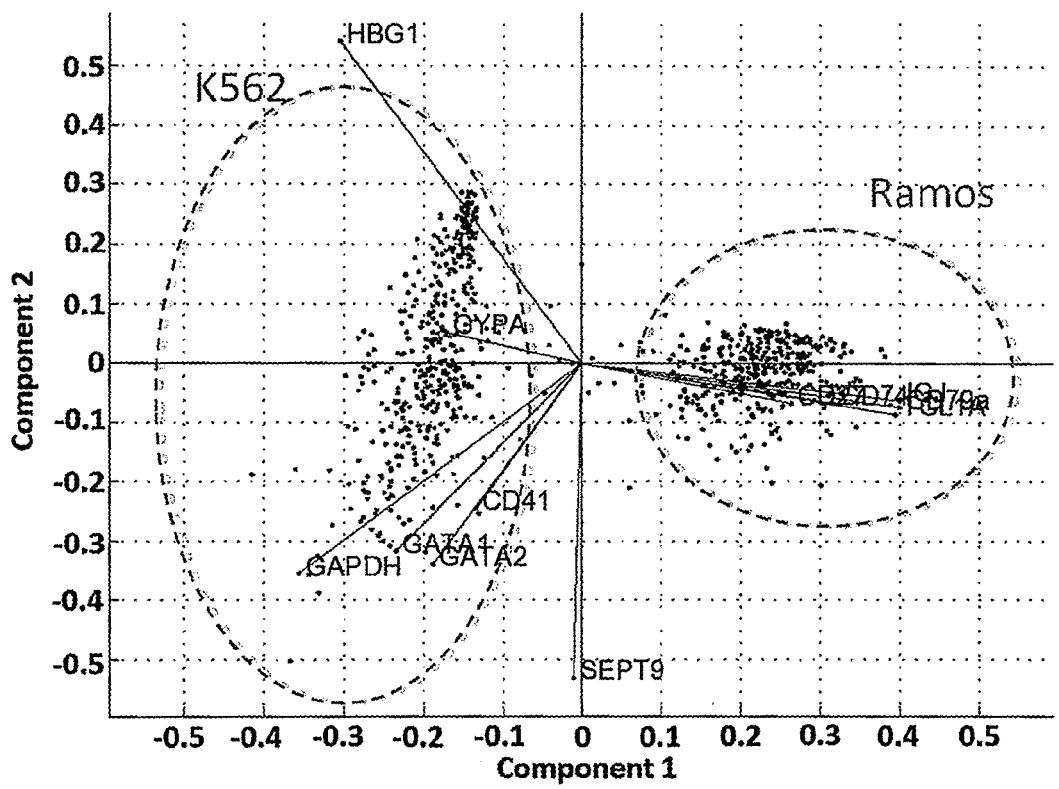
FIG. 12P shows a scatter plot of results based on principal component analysis of gene expression profile of 768 beads with >30 molecules per bead from the K562+Ramos mixture sample.
Figure 12Q:
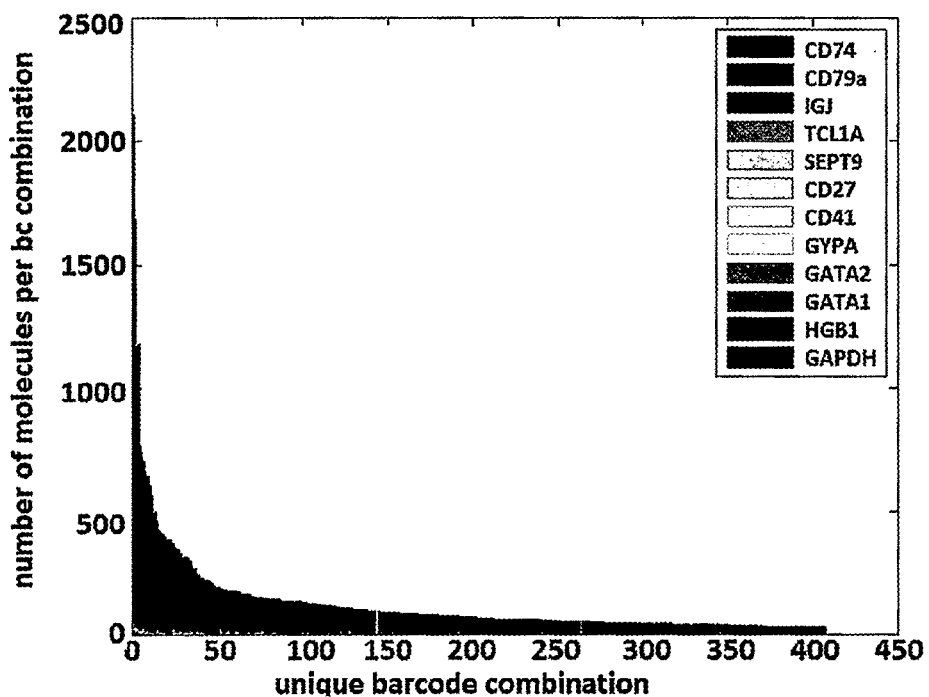
FIGS. 12Q-R show histograms of the copy number per amplicon per bead for the K562-like cells (beads on the left of the first principal component based on FIG. 12P) and Ramos-like cells (beads on the right of the first principal component based on FIG. 12P), respectively.
Figure 12R:
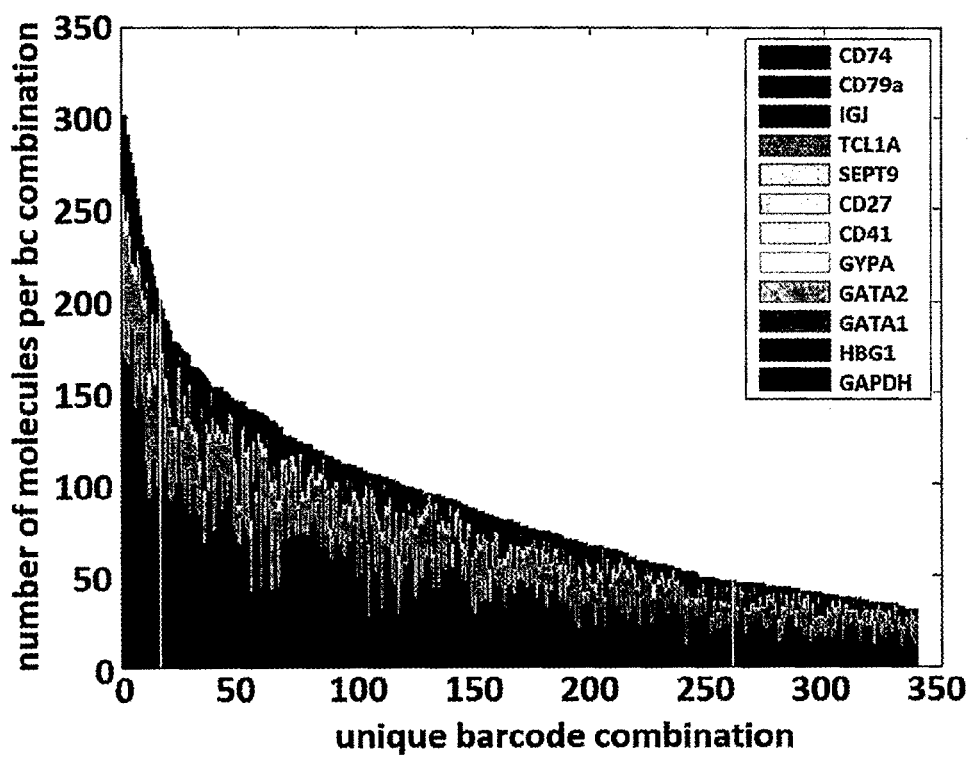
Figure 12S:
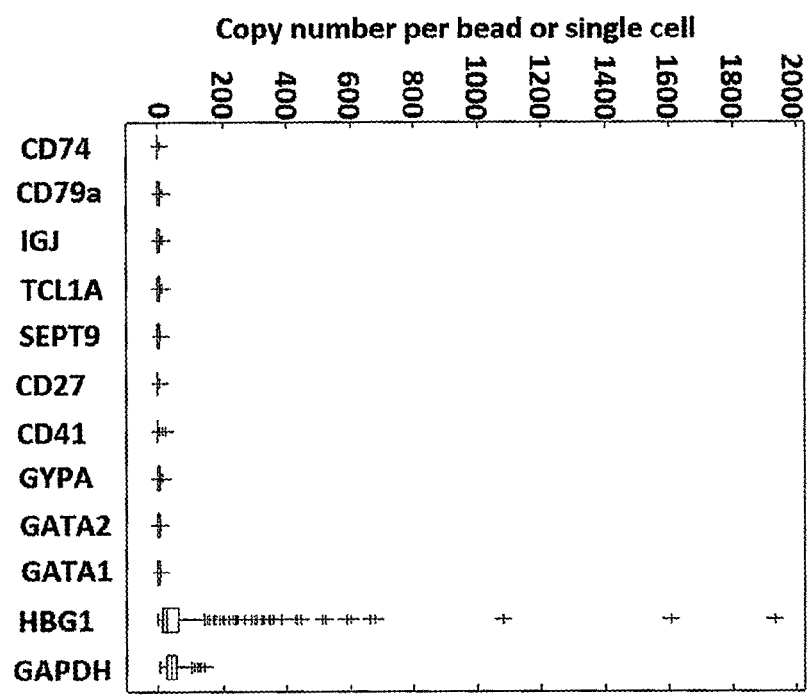
FIGS. 12S-T show the copy number per bead or single cell of the individual genes for the K562-like cells (beads on the left of the first principal component based on FIG. 12P) and Ramos-like cells (beads on the right of the first principal component based on FIG. 12P), respectively.
Figure 12T:
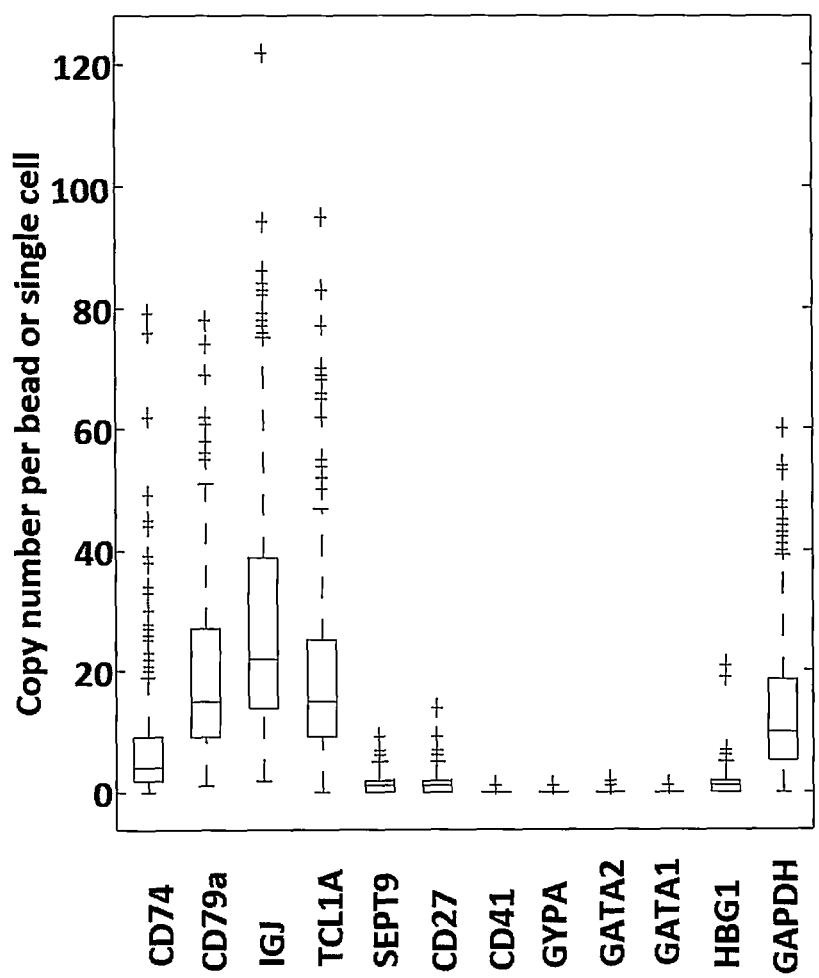

Single cell labeling was used to determine the cell type of single cells in the K562+Ramos mixture sample. Sequencing results from 100 unique barcode combinations with the most abundant molecules were analyzed to evaluate the efficacy of single cell labeling to determine the cell type of single cells in the K562+Ramos mixture sample. FIG. 12J-M show graphs of the number of unique molecules per gene (y-axis) for the beads with the 100 unique barcode combinations. The numbers on the x-axis refer to the gene (see Table 3). FIG. 12J-M clearly depict general gene expression patterns for the K562 and Ramos cells. FIG. 12N-O show enlarged graphs of two beads that depict the general pattern of gene expression profiles for the two cell types. FIG. 12N shows the general pattern of gene expression profile for K562-like cells and FIG. 12O shows the general pattern of gene expression profile for Ramos-like cells. FIG. 12P shows a scatter plot of results based on principal component analysis of gene expression profile of 768 beads with >30 molecules per bead from the K562+Ramos mixture sample. Component 1, which is plotted on the x-axis, separates the two cell types. Component 2, which is plotted on the y-axis, separates K562 cells with high and low HBG1 copy number. Each dot on the scatter plot represents one unique barcode combination, which is equivalent to one bead or one cell. Based on the principal component analysis, 409 beads corresponded to K562 cells and 347 beads corresponded to Ramos cells. The copy number of the genes from Table 3 was determined for the K562-like and Ramos-like cell types. FIG. 12Q-R show histograms of the copy number per amplicon per bead for the K562-like cells (beads on the left of the first principal component based on FIG. 12P) and Ramos-like cells (beads on the right of the first principal component based on FIG. 12P), respectively. For FIG. 12Q-R, number of per bc combination is on the y-axis and unique barcode combination, sorted by total number of molecules per bc combination is on the x-axis. FIG. 12S-T show the copy number per bead or single cell of the individual genes for the K562-like cells (beads on the left of the first principal component based on FIG. 12P) and Ramos-like cells (beads on the right of the first principal component based on FIG. 12P), respectively. Table 5 shows the mean copy number per bead for the single cell and mixture samples.

TABLE 5

| Gene | Single cell type samples | | K562 + Ramos mixture sample | |
|---|---|---|---|---|
| | K562-only | Ramos-only | K562-like | Ramos-like |
| CD74 | 0.00 | 39.95 | 0.10 | 7.50 |
| CD79a | 0.02 | 30.97 | 0.84 | 18.88 |
| IGJ | 0.03 | 42.43 | 0.81 | 27.76 |
| TCL1A | 0.01 | 31.78 | 0.71 | 19.44 |
| SEPT9 | 0.88 | 3.89 | 1.35 | 1.52 |
| CD27 | 0.00 | 5.31 | 0.03 | 1.30 |
| CD41 | 0.61 | 0.00 | 0.47 | 0.01 |
| GYPA | 1.92 | 0.00 | 0.73 | 0.02 |
| GATA2 | 1.38 | 0.00 | 0.60 | 0.04 |
| GATA1 | 0.94 | 0.00 | 1.04 | 0.04 |
| HBG1 | 201.09 | 0.00 | 72.27 | 1.37 |
| GAPDH | 51.77 | 39.13 | 44.94 | 13.53 |
| GAPDH read redundancy | 2.04 | 1.47 | 7.67 | 7.22 |

Example 7

Evaluating Cross-Talk Between Beads

In this example, the cross-talk between beads was evaluated. Samples comprising mixtures of mouse EL4 cells and Ramos cells were prepared as follows:

| | High density | Low density |
|---|---|---|
| Number of microwells | ~10000 | ~10000 |
| Number of mouse EL4 cells | 2500 | 1500 |
| Number of Ramos cells | 3750 | 1500 |

The cell suspension of the samples was added to the top of a microwell and cells were allowed to settle into the wells of the microwell array. Cells not captured by the microwell array were washed away in a phosphate buffered saline (PBS) bath. Oligonucleotide coupled beads, as prepared by the enzymatic split-pool synthesis method described in Example 1, were added to the microwell array. The oligonucleotide coupled bead comprises a magnetic bead with a plurality of oligonucleotides. Each oligonucleotide on the bead comprises a 5'amine, universal sequence, cell label 1, linker 1, cell label 2, linker 2, cell label 3, molecular label, and oligodT. For each oligonucleotide on the same bead, the sequences of the oligonucleotides are identical except for the molecular label. For oligonucleotides on different beads, the cell label 1, 2, and 3 combinations are different. Approximately 5-6 beads were added per well of the microwell array. The beads were allowed to settle into the wells and uncaptured beads were washed away in a PBS bath. A magnet was placed underneath the microwell array. Cells were lysed by the addition of cold lysis buffer. The array and magnet were placed on a cold aluminum block for 5 minutes. mRNA from the lysed cells were hybridized to the oligonucleotides coupled to the beads. The array was washed with excess lysis buffer to remove unbound mRNA. The beads were retrieved from the wells by placing a magnet on top of the microwell array. The retrieved beads were washed. cDNA synthesis was performed on the beads using Superscript III at 50° C. for 50 minutes on a rotor. Non-extended oligodT from the oligonucleotides on the beads were removed by ExoI treatment conducted at 37° C. for 30 minutes on a rotor. Gene-specific PCR amplification was conducted on the cDNA. The genes selected for the gene-specific PCR were cell-type specific and are shown in Table 6.

TABLE 6

| Number | Gene | Cell-type |
| --- | --- | --- |
| 1 | HS_CD74 | human |
| 2 | HS_CD79a | human |
| 3 | HS_IGJ | human |
| 4 | HS_TCL1A | human |
| 5 | HS_SEPT9 | human |
| 6 | HS_CD27 | human |
| 7 | HS_GAPDH | human |
| 8 | MM_B2M | mouse |
| 9 | MM_ACTM | mouse |
| 10 | MM_HPRT | mouse |
| 11 | MM_SHDA | mouse |

The PCR amplified products were sequenced. Sequencing statistics are shown in Table 7.

TABLE 7

|  | Low density | High density |
| --- | --- | --- |
| Number of Ramos cells | 15000 | 3750 |
| Number of mouse cells | 1500 | 2500 |
| Total number of reads | 2391780 | 4038217 |
| >=8 match in constant 1 | 2162945 | 3651643 |
| >=8 match in constant 2 | 1981835 | 3356493 |
| >=8 match in constant 1 & 2 | 1981626 | 3355787 |
| Perfect match in all 3 sub-barcodes | 1645994 | 2790879 |
| Perfect match in gene (40 bp) | 1083013 | 2171930 |
| % useful reads | 45% | 54% |
| Total number of unique barcode combination | 16695 | 36595 |
| Number of unique barcode combinations >30 molecule | 80 | 281 |
| Capture efficiency | 0.03 | 0.04 |

Figure 13A:
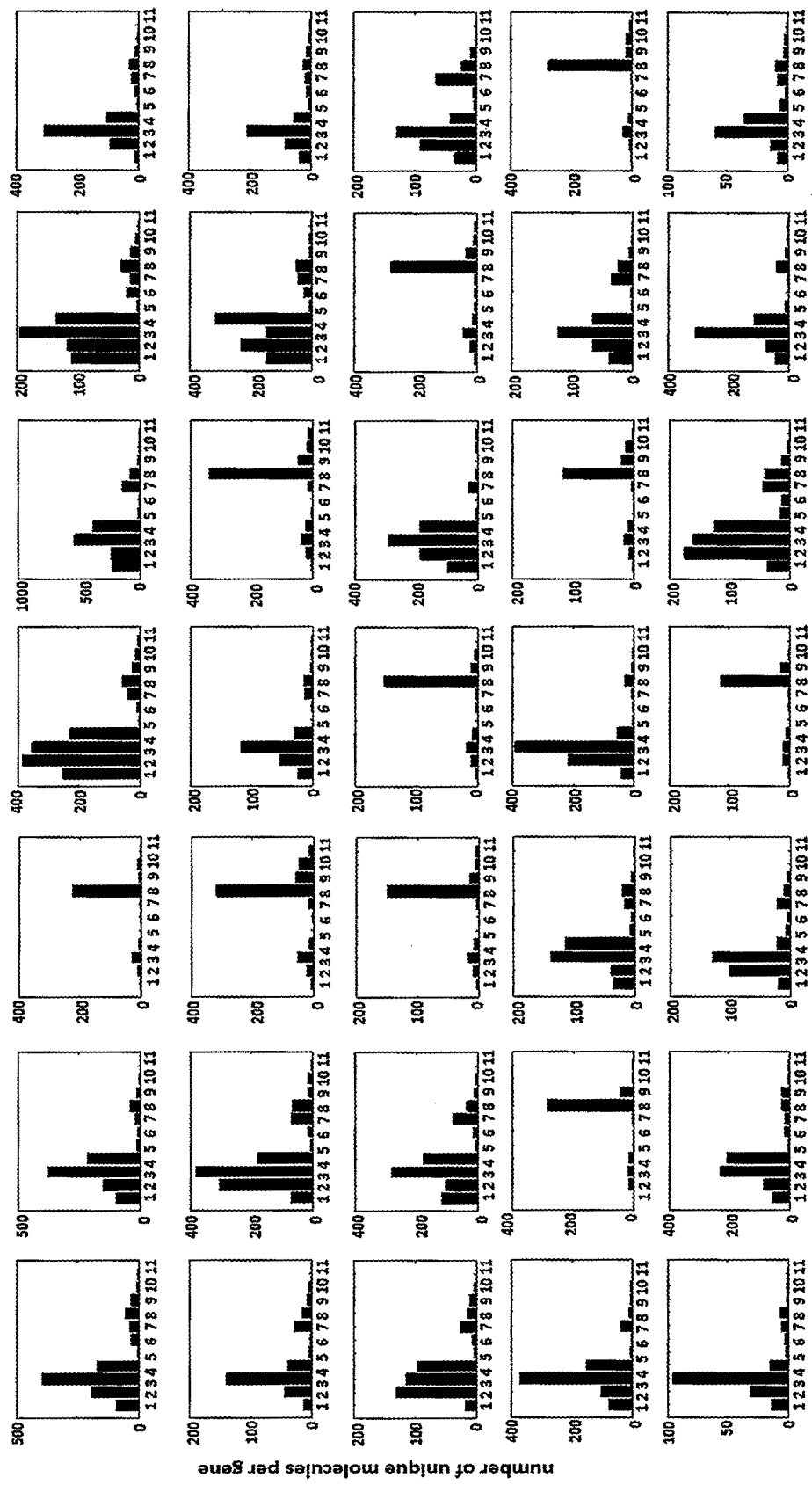
FIG. 13A depicts general gene expression patterns for the mouse and Ramos cells.
Figure 13B:
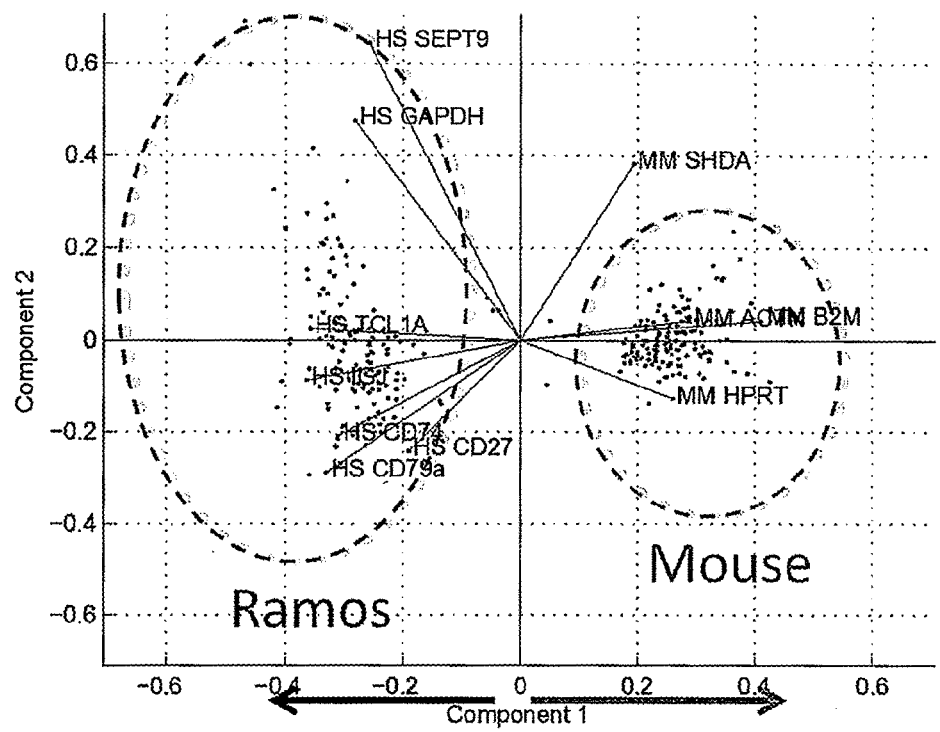
FIGS. 13B-C show scatter plots of results based on principal component analysis of gene expression profile of the high density sample and low density sample, respectively.
Figure 13C:
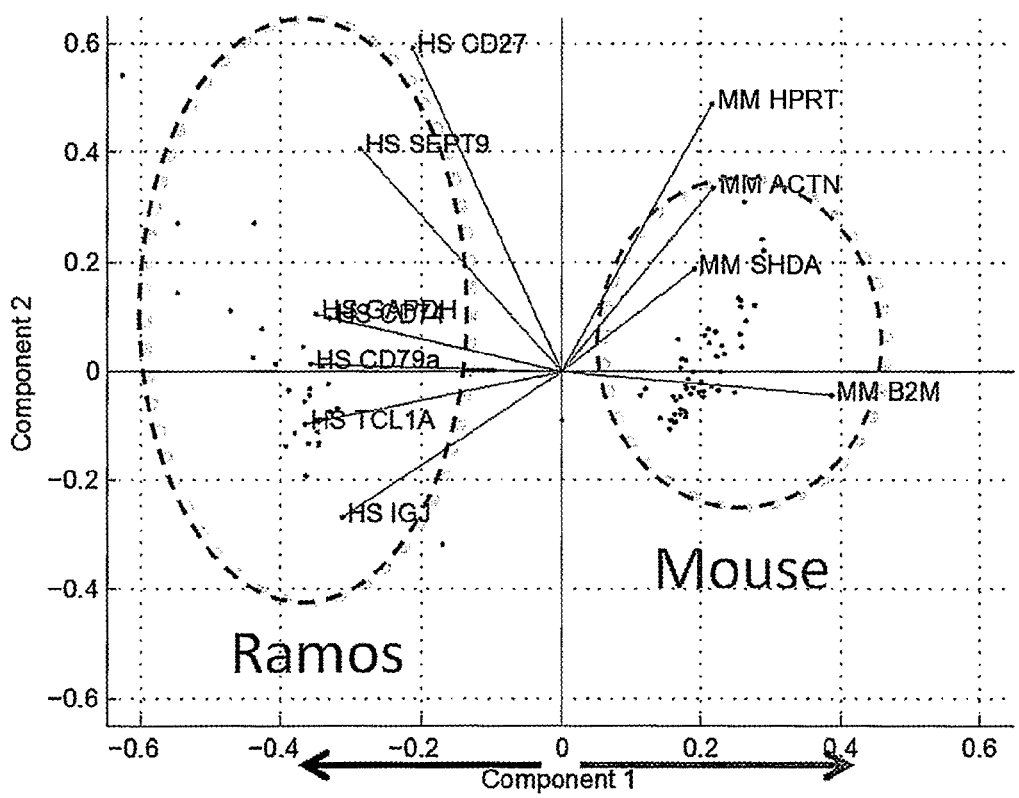

Gene expression profiles for 100 unique barcode combinations with the most abundant molecules were determined for the high density and low density samples. The gene expression profiles were generated based on the sequencing results. FIG. 13A shows graphs of the gene expression profile for 35 of the 100 unique barcode combinations from the high density sample. For FIG. 13A, the number of unique molecules is on the y-axis and the gene reference number is on the x-axis (see Table 6 for genes corresponding to the gene reference number). FIG. 13A clearly depicts general gene expression patterns for the mouse and Ramos cells. FIG. 13B-C show scatter plots of results based on principal component analysis of gene expression profile of the high density sample and low density sample, respectively. Component 1, which is plotted on the x-axis, separates the two cell types. Component 2, which is plotted on the y-axis, indicates variability in gene expression within the Ramos cell population. Each dot on the scatter plot represents one unique barcode combination, which is equivalent to one bead or one cell. Based on the principal component analysis of the high density sample, 144 beads corresponded to the mouse cells and 132 beads corresponded to Ramos cells. Based on the principal component analysis of the low density sample, 52 beads corresponded to the mouse cells and 27 beads corresponded to Ramos cells.

Figure 13D:
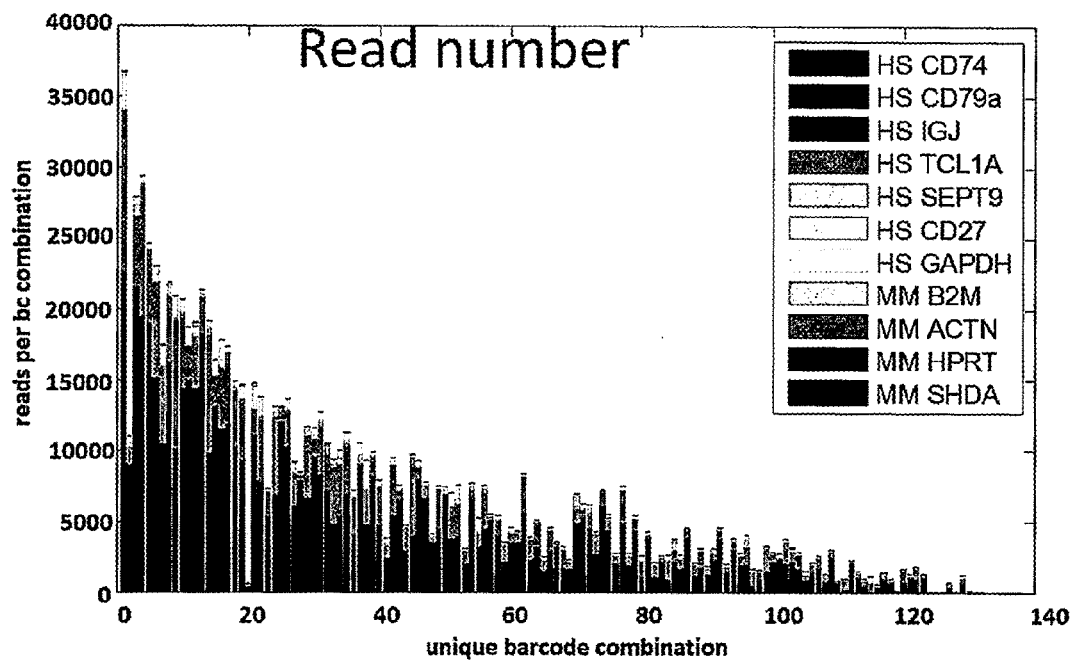
FIGS. 13D-E depict graphs of the read per barcode (bc) combination (y-axis) versus the unique barcode combination, sorted by the total number of molecules per bc combination (x-axis) for Ramos-like cells and mouse-like cells from the high density sample, respectively.
Figure 13E:
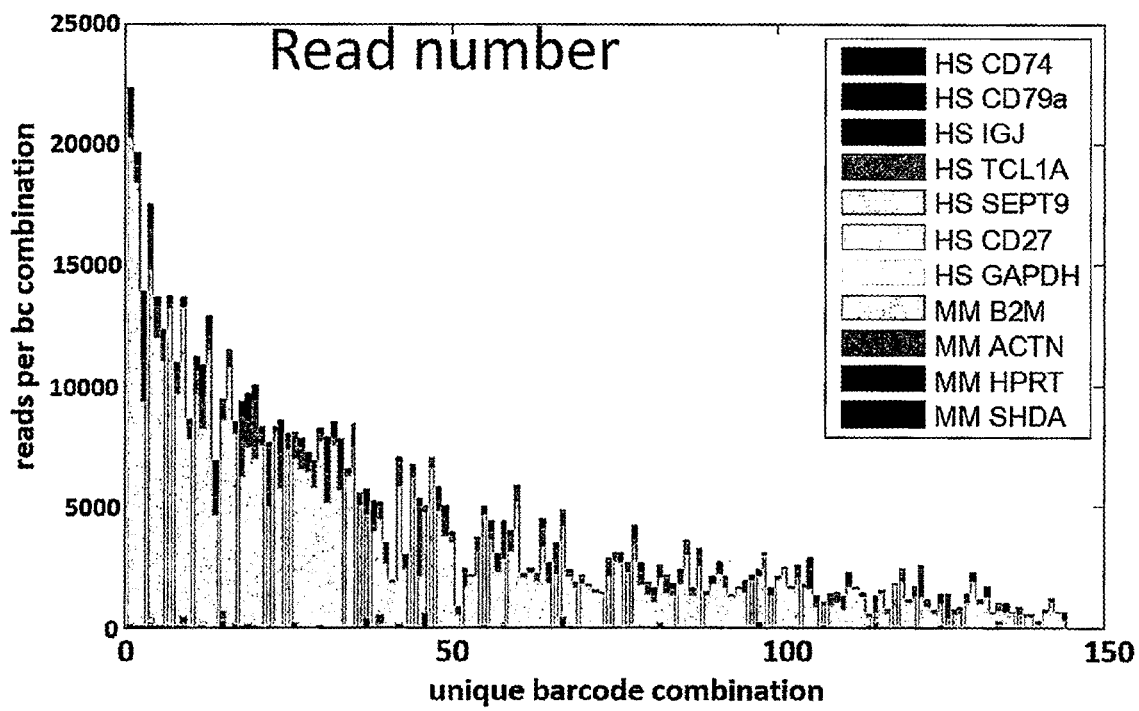
Figure 13F:
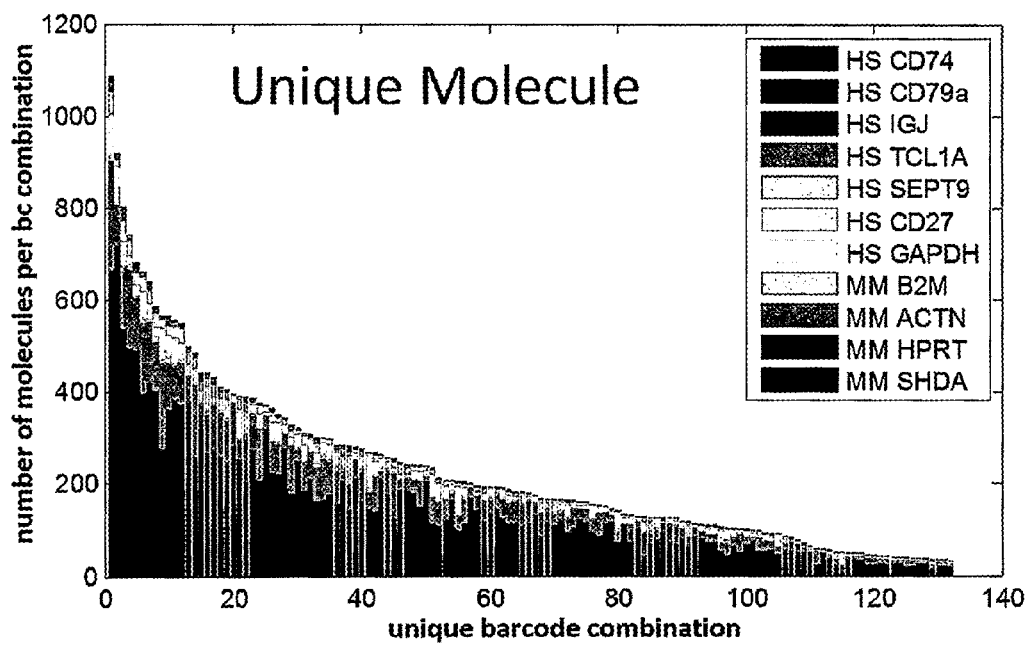
FIGS. 13F-G depict graphs of the number of molecules per barcode (bc) combination (y-axis) versus the unique barcode combination, sorted by the total number of molecules per bc combination (x-axis) for Ramos-like cells and mouse-like cells from the high density sample, respectively.
Figure 13G:
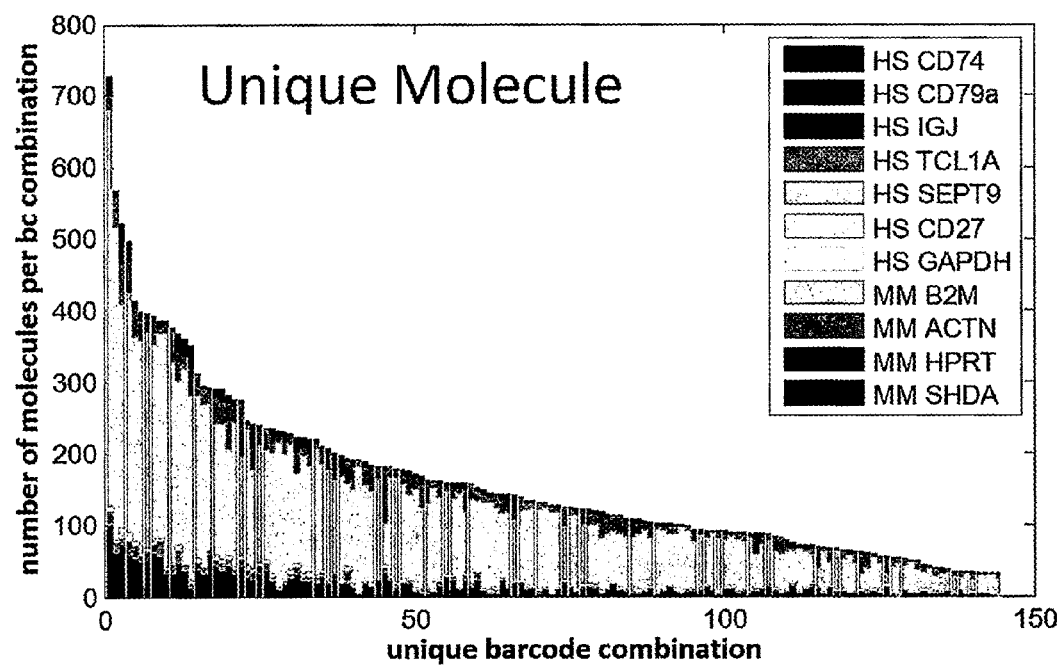
Figure 13H:
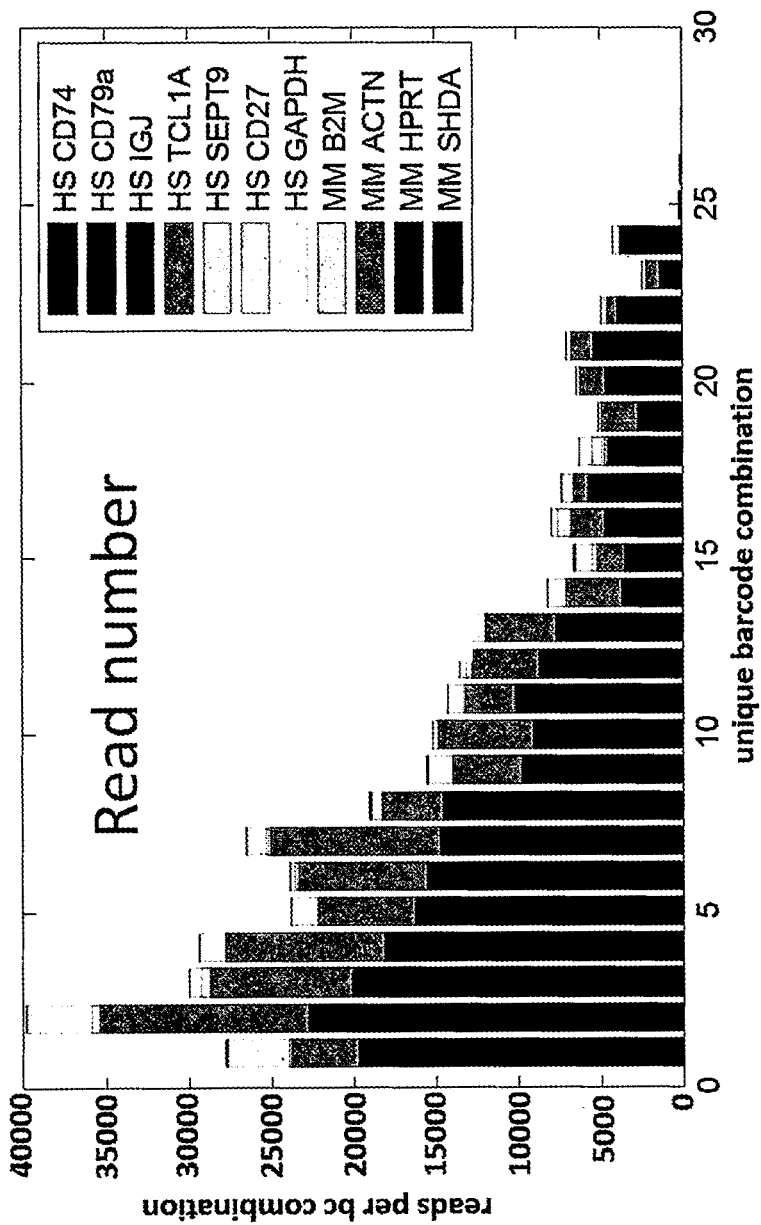
FIGS. 13H-I depict graphs of the read per barcode (bc) combination (y-axis) versus the unique barcode combination, sorted by the total number of molecules per bc combination (x-axis) for Ramos-like cells and mouse-like cells from the low density sample, respectively.
Figure 13I:
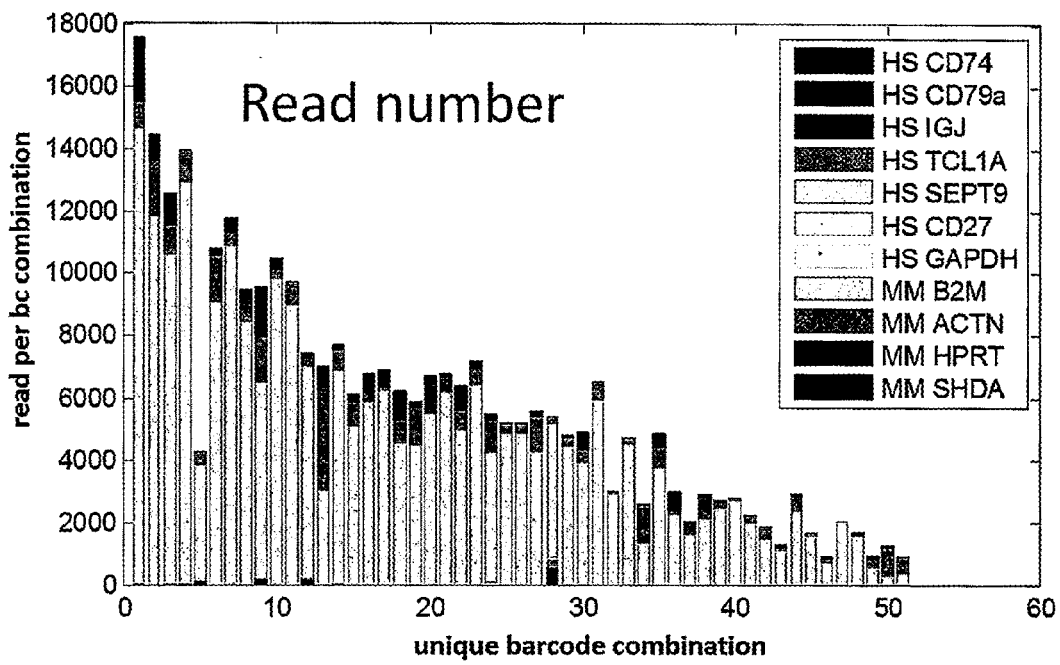
Figure 13J:
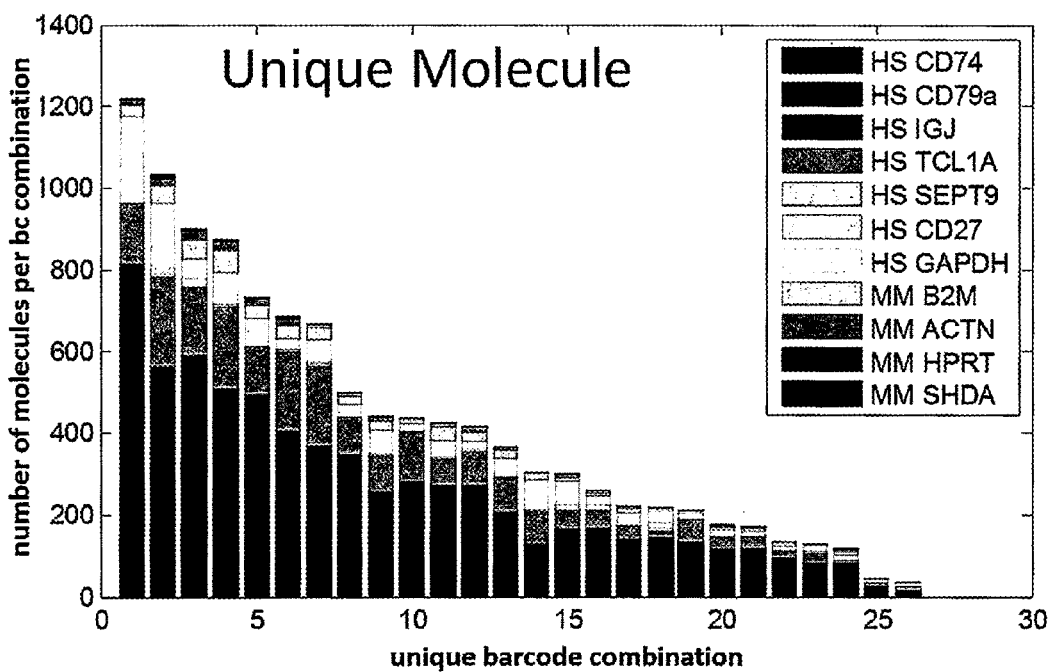
FIGS. 13J-K depict graphs of the number of molecules per barcode combination (y-axis) versus the unique barcode combination, sorted by the total number of molecules per barcode combination (x-axis) for Ramos-like cells and mouse-like cells from the low density sample, respectively.
Figure 13K:
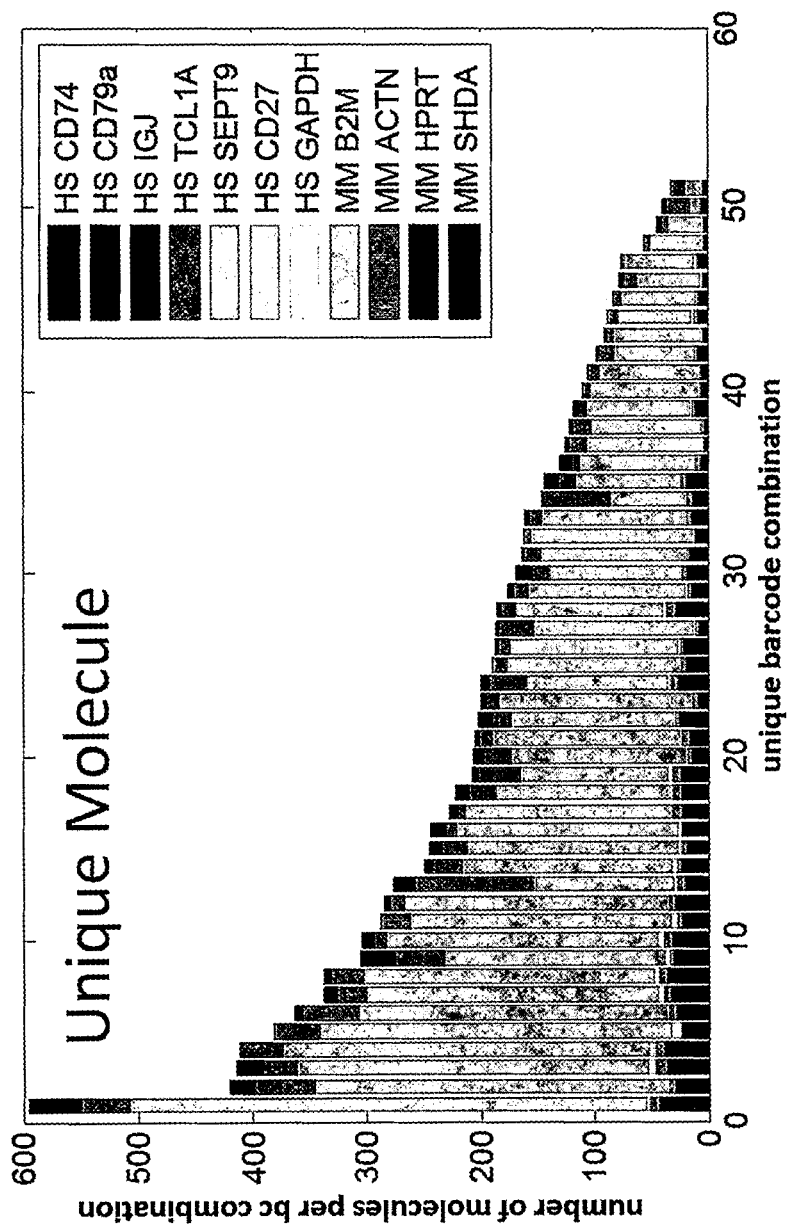

Once the cell types were determined, cross-talk between the beads was assessed by detecting the genes from Table 6 in the different cell types. FIG. 13D-E depict graphs of the read per barcode (bc) combination (y-axis) versus the unique barcode combination, sorted by the total number of molecules per bc combination (x-axis) for Ramos-like cells and mouse-like cells from the high density sample, respectively. FIG. 13F-G depict graphs of the number of molecules per bc combination (y-axis) versus the unique barcode combination, sorted by the total number of molecules per bc combination (x-axis) for Ramos-like cells and mouse-like cells from the high density sample, respectively. FIG. 13H-I depict graphs of the read per barcode (bc) combination (y-axis) versus the unique barcode combination, sorted by the total number of molecules per bc combination (x-axis) for Ramos-like cells and mouse-like cells from the low density sample, respectively. FIG. 13J-K depict graphs of the number of molecules per bc combination (y-axis) versus the unique barcode combination, sorted by the total number of molecules per bc combination (x-axis) for Ramos-like cells and mouse-like cells from the low density sample, respectively. Table 8 shows the average fold coverage or read redundancy per unique molecule for the low and high density samples.

TABLE 8

|  | Low density | | High density | |
| --- | --- | --- | --- | --- |
| Gene | Ramos-like cells | Mouse-like cells | Ramos-like cells | Mouse-like cells |
| HS_CD74 | 29.75 | 3.17 | 23.75 | 2.15 |
| HS_CD79a | 47.2 | 4.09 | 42.30 | 2.67 |
| HS_IGJ | 29.65 | 1.39 | 30.23 | 2.4 |
| HS_TCL1A | 45.74 | 2.26 | 39.00 | 4.13 |
| HS_SEPT9 | 11.85 | 1.00 | 12.75 | 1.18 |
| HS_CD27 | 37.99 | 1.00 | 32.12 | 1.10 |
| HS_GAPDH | 19.97 | 1.55 | 17.37 | 2.57 |
| MM_B2M | 1.21 | 31.98 | 3.05 | 31.48 |
| MM_ACTM | 1.05 | 29.08 | 1.90 | 28.38 |
| MM_HPRT | 1.02 | 39.96 | 1.03 | 43.65 |
| MM_SHDA | 1.00 | 39.60 | 1.02 | 29.60 |

The results in Table 8 show that average fold coverage per unique molecule was much higher for human genes than mouse genes in Ramos cells, and vice versa.

As a control, a mixture of mouse and human cells were lysed in a tube, converted to cDNA synthesis with the beads, and the cDNA was sequenced. FIG. 4XL shows a graphical representation of the sequencing results. As expected, a large number of unique barcode (bc) combinations was observed, and most beads only had one to two copies total.

These results demonstrate that there was minimal cross-talk between beads and that the cross-talk may be identified bioinformatically.

Example 8

Single Cell Nucleic Acid Library Production

The oligonucleotide conjugated supports disclosed herein may be used to produce single cell nucleic acid libraries. In this example, single cell nucleic acid libraries are produced by adding a cell sample to a surface (e.g., grid) that has the oligonucleotide conjugated supports. An oligonucleotide conjugated support comprises a plurality of oligonucleotides conjugated to a bead. An oligonucleotide comprises (a) a cell label region comprising at least two distinct regions connected by a linker; and (b) a molecular label region. Two or more oligonucleotides on a bead comprise identical cell label regions. Two or more oligonucleotides on a bead comprise two or more different molecular label regions. Two or more oligonucleotides on two or more different beads comprise two or more different cell label regions. Thus, each cell associated with an oligonucleotide conjugated support has a different cell label region. The concentration of cells in the cell sample is sufficiently dilute to enable association of one or fewer cells to one oligonucleotide conjugated support on the surface. Cells are lysed using a lysis buffer. mRNAs from a cell are hybridized to the oligonucleotides of the oligonucleotide conjugated support. Thus, all mRNAs from a cell are labeled with oligonucleotides comprising identical cell label regions. Two or more mRNAs from a cell are labeled with two or more oligonucleotides comprising two or more different molecular label regions. A magnet is applied to the surface to purify the oligonucleotide conjugated solid supports from the surface. The oligonucleotide conjugated solid supports may be individually purified from the surface. The mRNAs hybridized to the oligonucleotides on the oligonucleotide conjugated solid support are reverse transcribed to produce labeled cDNA. The labeled cDNA comprise a reverse complement of the mRNA and a copy of the oligonucleotide that the mRNA was hybridized to. The labeled cDNA are amplified by PCR to produce labeled amplicons. The labeled cDNA and/or labeled amplicons may be removed from the bead by restriction enzyme digestion. A library of nucleic acids from the single cell is produced from the labeled amplicons.

Alternatively, the oligonucleotide conjugated solid supports are purified together. Reverse transcription of the mRNA may be performed on the combined oligonucleotide conjugated solid supports. Because mRNAs from different cells are labeled with oligonucleotides comprising different cell label regions, the cell label regions may be used to determine which cell the labeled cDNA or labeled amplicons originated from. Thus, a library of nucleic acids from a plurality cells may be produced, wherein the identity of the cell from which the labeled amplicon originated from may be determined by the cell label region.

Single cell nucleic acid libraries may also be produced by contacting the cells with an agent prior to lysing the cell. The agent may be an antigen, drug, cell, toxin, etc. Thus, specialized single cell nucleic libraries may be produced. Analysis of the nucleic acid libraries may be used to generate single cell drug expression profiles. Signal transduction pathways on a single cell level may also be determined from these nucleic acid libraries. The nucleic acid libraries may also be used to determine the effects of antigens on specific cell types.

Example 9

Single Cell Expression Profiling

The oligonucleotide conjugated supports disclosed herein may be used to determine the expression profile of single cells. In this example, a cell sample comprising a mixture of cells is contacted with a plurality of antibodies. A subset of the cells is purified using flow cytometry. The subset of cells is added to a microwell array. A plurality of oligonucleotide conjugated supports is added to the microwell array. An oligonucleotide conjugated support comprises a plurality of oligonucleotides coupled to a nanoparticle. An oligonucleotide comprises (a) a cell label region comprising three distinct sequences connected by two predetermined sequences; and (b) a molecular label region. Two or more oligonucleotides on a nanoparticle comprise identical cell label regions. Two or more oligonucleotides on a nanoparticle comprise two or more different molecular label regions. Two or more oligonucleotides on two or more different nanoparticles comprise two or more different cell label regions. Thus, each cell associated with an oligonucleotide conjugated support has a different cell label region.

A magnet is applied to the microwell array and the cells that are not associated with an oligonucleotide conjugated support are washed away. A sponge comprising a lysis buffer is placed on top of the microwell array, thereby lysing the cells.

mRNAs from the lysed cells hybridize to the oligonucleotides on the bead. The mRNAs are reverse transcribed to produce labeled cDNA. The labeled cDNA comprise a reverse complement of the mRNA and a copy of the oligonucleotide that the mRNA was hybridized to. The labeled cDNA are amplified by PCR to produce labeled amplicons. The labeled amplicons are sequenced. Because each mRNA from a cell is labeled with the same cell label and mRNAs from different cells are labeled with different cell labels, the sequence information of the labeled amplicons is used to generate single cell expression profiles.

Example 10

Immunophenotyping by Single Cell Sequencing

A blood sample was collected from a subject and peripheral blood mononuclear cells (PMBCs) were isolated from the blood sample. PMBCs were cultured in RPMI1640 medium and placed in an incubator overnight. The PMBCs were washed multiple times in PBS to remove the serum. Approximately 7000 PMBCs were deposited onto a microwell array with 32,400 wells. Thus, most wells on the microwell array contained no cells and some wells on the cell contained only 1 cell. Oligonucleotide-conjugated beads were applied to the microwell array. Each oligonucleotide-conjugated bead contained approximately 1 billion oligonucleotides attached to a bead. Each oligonucleotide attached to the bead contained a 5' amine, universal sequence, three-part cellular label (e.g., three cell label sections connected by two linkers), molecular label, and oligodT. Each bead contained a unique three-part cellular label, which is a result of the unique combination of the three cell label sections. All of the oligonucleotides on a single bead contained the same three-part cellular label. Oligonucleotides from different beads contained different three-part cellular labels. Each well contained 1 or fewer oligonucleotide-conjugated bead. A cell lysis reagent was applied to the microwell array, resulting in lysis of the cells. Polyadenylated molecules (e.g., mRNA) from the cell hybridized to the oligodT sequence of the oligonucleotides from the oligonucleotide-conjugated beads. The polyadenylated molecules that were hybridized to the oligonucleotides from the oligonucleotide-conjugated bead were reverse transcribed with SuperScript II at 42° C. at 90 minutes on a rotor. The oligonucleotide from the oligonucleotide-conjugated bead served as a primer for first strand cDNA synthesis. A SMART oligo was incorporated in the cDNA synthesis such that the superscript II may add the complement of the SMART oligo sequence to the 3' end of the cDNA when it reaches the end. The cDNA synthesis reaction produces a bead conjugated to unextended oligonucleotides (e.g., oligonucleotides that were not attached to the polyadenylated molecule from the cell) and the extended oligonucleotides (e.g., oligonucleotides that were attached to the polyadenylated molecule and comprise a polyadenylated molecule/cDNA hybrid).

The beads are combined and the oligonucleotides comprising the polyadenylated molecule/cDNA hybrid were amplified. Multiplex PCR was performed to amplify a panel of 98 genes (see Table 9) from the cDNA on the beads. Primers for the multiplexed PCR comprised a first gene specific primer that was designed to sit approximately 500 base pairs from the 3' end of the mRNA and a nested gene-specific primer that was designed to sit approximately 300 base pairs from the 3' end of the mRNA. Primers for the multiplex PCR were designed to require no significant complementarity in the last 6 bases of the primers in the panel. If complementarity was detected in the multiplex PCR primers, then the primers were manually replaced. The multiplex PCR reaction comprised the following steps: 1) 15 cycles of first gene specific PCR (KAPA multiplex mix, 50 nM of each primer—first gene specific primer and universal primer that is complementary to the universal sequence of the oligonucleotide-conjugated bead), Ampure clean up (0.7× bead to template ratio), 15 cycles of nested gene specific PCR (KAPA multiplex mix, 50 nM of each primer—nested gene-specific primer and universal primer that is complementary to the universal sequence of the oligonucleotide-conjugated bead), Ampure clean up (0.7× bead to template ratio), 8 cycles of final PCR to add full length Illumina adaptor (KAPA HiFi ReadyMix), and Ampure clean up (1× bead to template ratio).

Figure 14:
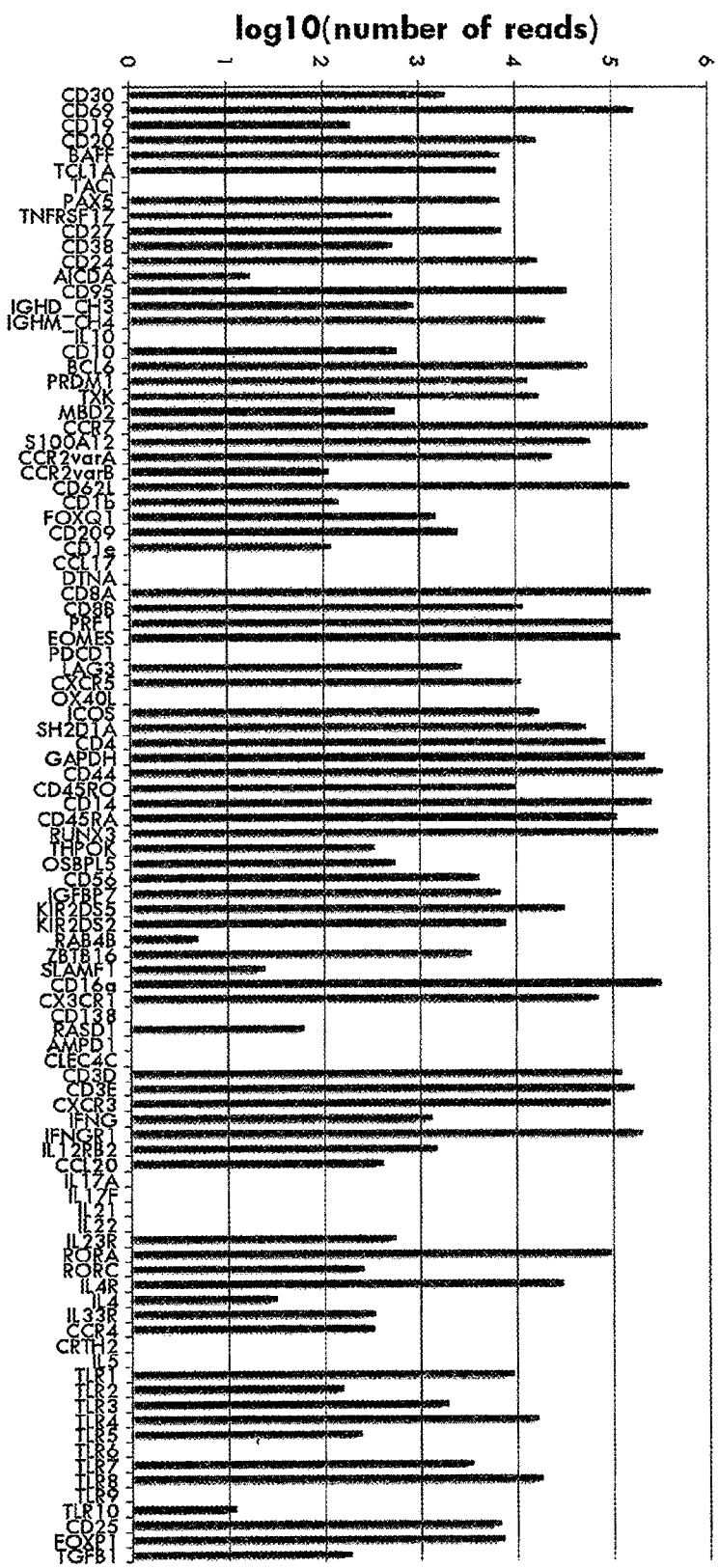
FIG. 14 shows a graph depicting the genes on the X-axis and the log 10 of the number of reads.

The amplified products were sequenced. The sequence reads with 150 bp were aligned to entire mRNA sequences of the 98 genes listed in Table 9 using Bowtie2. The results of the sequence alignment (see Table 10) demonstrate that the multiplex PCR reaction resulted in highly specific products. FIG. 14 shows a graph depicting the genes on the X-axis and the log 10 of the number of reads. 16 genes of the 98 genes were not present. Absence of these genes may be due to the fact that some of the genes target rare cells that may not be present in this blood sample. Overall, approximately, 84% of the genes from the 98 gene panel were detected.

TABLE 10

| | |
|---|---|
| total | 6357075 |
| aligned 0 times | 703616 |
| aligned exactly 1 time | 5584201 |
| aligned >1 time | 69258 |
| % aligned exactly once | 88% |

Table 11 shows the results of the overall sequencing statistics. For Read1, the total read1 match criteria required a perfect match to the three-part cellular label (e.g., cell barcode) and at most 1 mismatch to the linkers.

TABLE 11

| | |
|---|---|
| total num read | 6357075 |
| total read1 match criteria | 4384245 |

TABLE 9

Gene Panel

| Cell type | Gene | Cell type | Gene | Cell type | Gene | Cell type | Gene |
|---|---|---|---|---|---|---|---|
| B cell | PAX5 | monocytes | CD14 | naïve | CD62L (SELL) | Th17 | IL17A |
| | CD19 | classical | S100A12 | | CD45RA | | IL17F |
| | CD20 | monocytes | CCR2 | Naïve Th | THPOK/ZBTB7B | | IL21 |
| | BCMA/ | | SELL/CD62L | Naïve Tc | RUNX3 | | IL22 |
| | TNFRSF17 | | (L-selectin) | | | | |
| | BAFF | nonclassical | CD16/FCGR3B | memory | CD45RO/PTPRC | | CCL20 |
| | TCL1A | monocytes | CX3CR1 | | CD44 | | IL23R |
| | TACI | | ITGAL | Central | CCR7 | | RORa/RORA |
| B naïve | IGHD | conventional | CD1b | Memory | TXK | Follicular T | RORgamat/RORC |
| | IGHM | myeloid DC | FOXQ1 | CD8+/CD4+ | MBD2 | helper | OX40L/TNFSF4/ CD252 |
| B memory | CD27 | | CD209/ DC-SIGN | | BCL6 | | CXCR5 |
| | CD38 | | CD1e | Effector Memory CD8+/CD4+ | BLIMP1 | | SLAM/SLAMF1 |
| | CD24 | | CCL17 | Th1 | CXCR3 | | ICOS |
| | AICDA | | DTNA | | IFNGR1 | | SAP/SH2D1A |
| | CD95 | plasmacytoid dendritic cell (rare) | CLEC4C/ CD303 | | IL12RB2 | Activated T | CD69 |
| B transitional | CD10 | rare myeloid dendritic cell (0.02%) | CD141/TM | | IFN gamma | Activated T and B | CD30 |
| B reg | IL10 | NKT | | Th2 | IL33R/IL1RL1 | Toll-like | TLR1 |
| plasma | RASD1 | | PLZF/ZBTB16 | | IL4R | receptors | TLR2 |
| | AMPD1 | | SLAMF1 | | CCR4 | (innate) | TLR3 |
| | SDC1 (CD138) | T cell | CD3 (CD3D) | | CRTH2/PTGDR2 | | TLR4 |
| NK | OSBPL5 | | CD3 (CD3E) | | IL4 | | TLR5 |
| | CD56/NCAM1 | Cytotoxic T | CD8 (CD8A) | | IL5 | | TLR6 |
| | IGFBP7 | | CD8 (CD8B) | Treg | CD25 | | TLR7 |
| | KIR2DS5 | | PRF1 (perforin) | | FOXP1 | | TLR8 |
| | KIR2DS2 | | EOMES | | TGFbeta | | TLR9 |
| | RAB4B | Helper T | CD4 | | IL10 | | TLR10 |

TABLE 11-continued

| | |
|---|---|
| read2 also align | 3943667 |
| % read2 align | 89.95% |
| number of unique cell bc | 31129 |
| read count per unique bc >100 | 3228 |
| read count per unique bc >50 | 3721 |
| % useful reads | 62.04% |

Figure 15A:
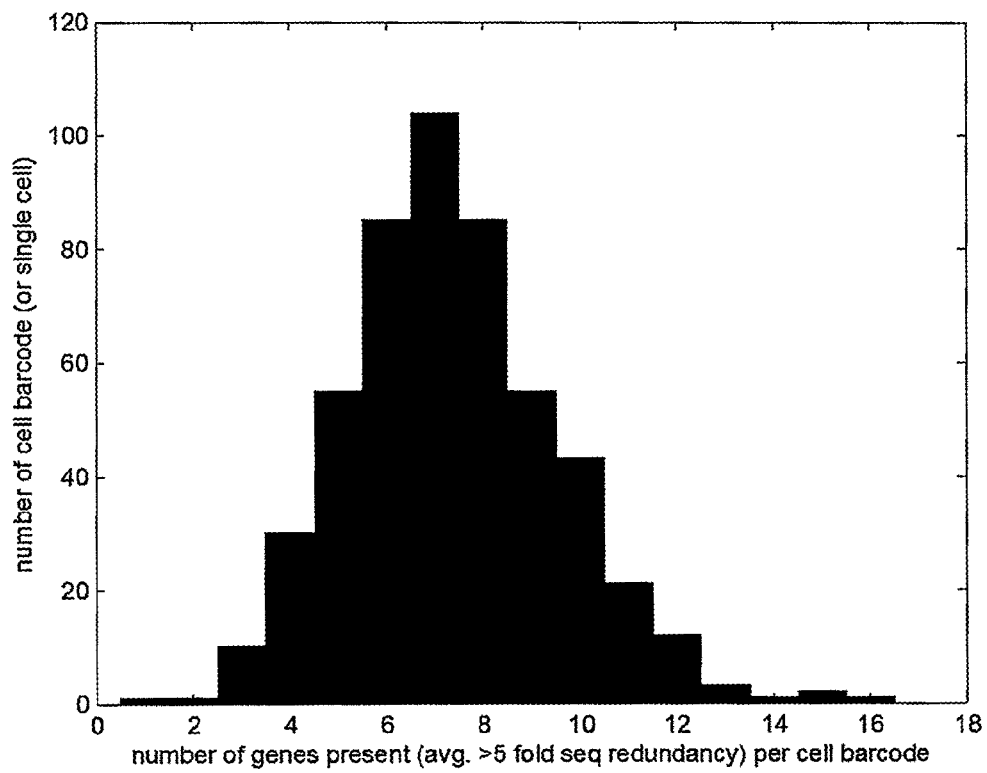
FIG. 15A shows a graph of the distribution of genes detected per three-part cell label (e.g., cell barcode).
Figure 15B:
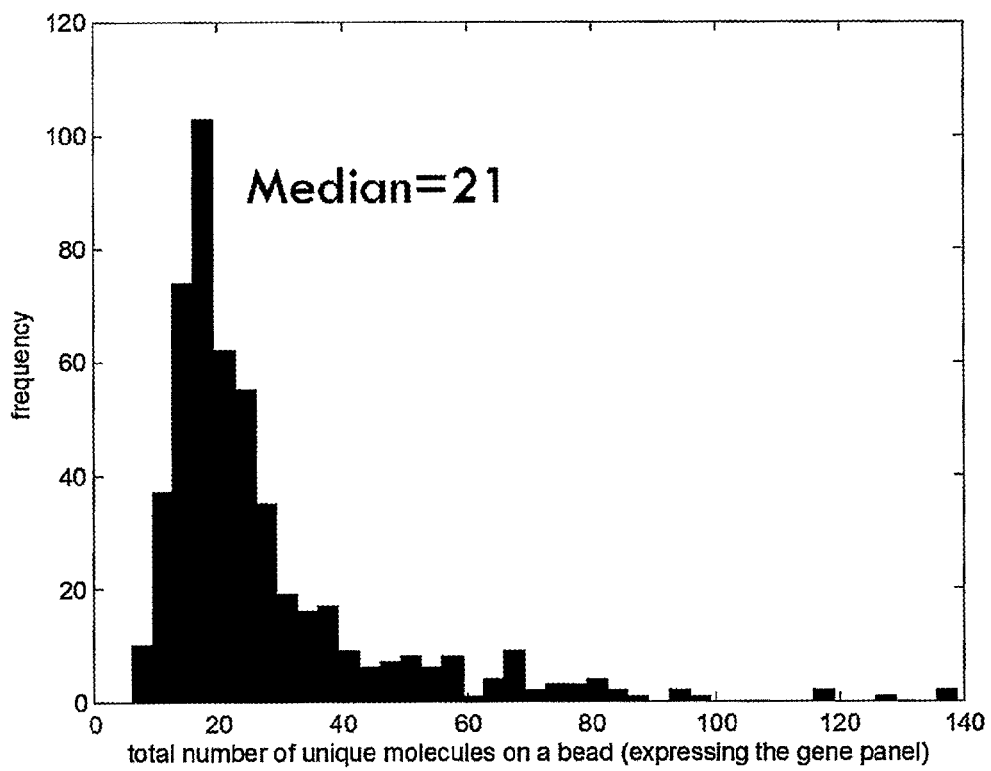
FIG. 15B shows a graph of the distribution of unique molecules detected per bead (expressing the gene panel).

FIG. 15A shows a graph of the distribution of genes detected per three-part cell label (e.g., cell barcode). FIG.

15B shows a graph of the distribution of unique molecules detected per bead (expressing the gene panel).

Figure 16:
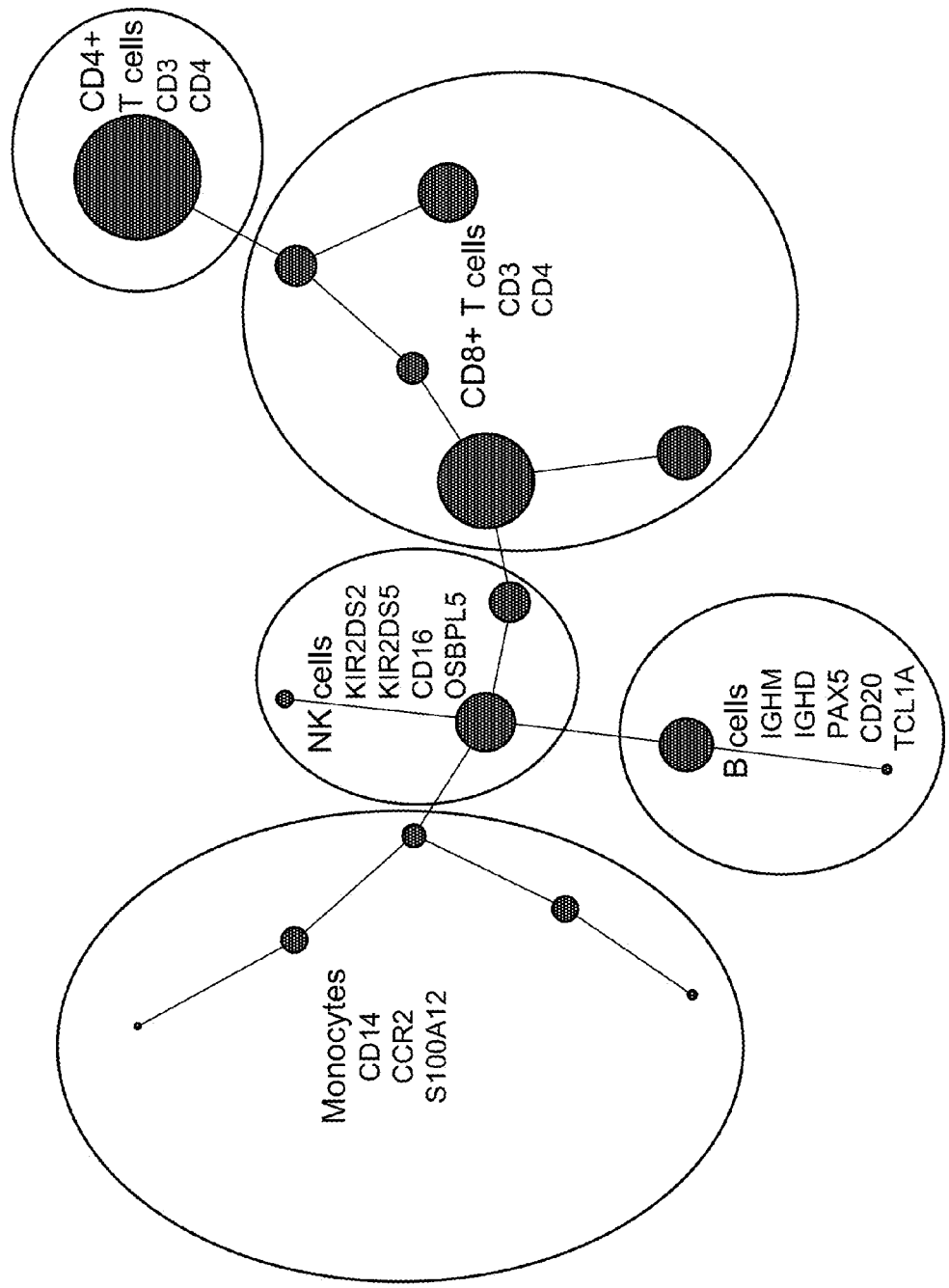
FIG. 16 depicts the cell clusters based on the genes associated with a cell barcode.

Cell clustering analysis was performed to determine whether the sequencing results could be used to analyze cell populations based on the cell barcode. SPADE (a minimum spanning tree algorithm developed by the Nolan lab for CyTOF data) was used to cluster cells based on the presence/absence of 17 genes. For a gene to be considered present, the average sequencing redundancy for the gen has to be greater than 5 fold. After sequence filtering, there were approximately 500 unique cell barcodes (e.g., cell labels) associated with greater than 20 unique molecules. Each unique cell barcode corresponds to a single cell. Based on the genes that were associated with a unique cell barcode, cells were clustered into cell types. Table 12 shows a list of genes that may be used to definitively identify a cell type. Thus, cell barcodes that are associated with CD20, IGHM, TCL1A and CD24 were designated as B-cells, whereas cell barcodes that are associated with CD8A, CD3D, CD3E, CD4 and CD62L were designated as T-cells. The remaining genes from Table 9 were mapped to the cell clusters. FIG. 16 depicts the cell clusters based on the genes associated with a cell barcode. The size of the cluster is proportionate to the number of cells that were assigned to the cluster. The results shown in FIG. 16 demonstrate that the combination of cell and molecular barcoding may be used to uniquely label copies of molecules from a single cell, which may enable immunophenotyping by single cell sequencing. In addition to clustering PMBCs into the major cell types based on the genes listed in Table 12, the 98 gene panel may also be used to identify clusters of sub-types of the major cell types. Table 13 shows the frequency of each major cell type detected by single cell sequencing. As shown in Table 13, with the exception of CD8+ T cells, the percentage of each cell type corresponded to the normal cell percentage range. A slightly higher percentage of CD8+ T cells was observed in the PMBC sample. Using the cell clusters based on FIG. 16, expression profiles of additional genes from the 98 gene panel were used to further analyze the cell clusters.

TABLE 12

| Major cell types | Genes |
| --- | --- |
| B cells | CD20, IGHM, TCL1A, CD24 |
| T cells | CD8A, CD3D, CD3E, CD4, CD62L |
| NKT cells | ZBTB16 |
| Dendritic cells | CD209 |
| Natural Killer cells | KIR2DS5, KIR2DS2, CD16 |
| Monocytes | CD16, CD14, CCR2, S100A12, CD62L |

TABLE 13

| Cell type | # cells | percentage | normal range |
| --- | --- | --- | --- |
| monocytes | 67 | 13.3% | 10-30% |
| NK | 85 | 16.9% | up to 15% |
| B | 47 | 9.3% | up to 15% |
| CD8 | 210 | 41.7% | 5-30% |
| CD4 | 94 | 18.7% | 25-60% |
| total assigned cluster | 503 | 100.0% | |

Figure 17A:
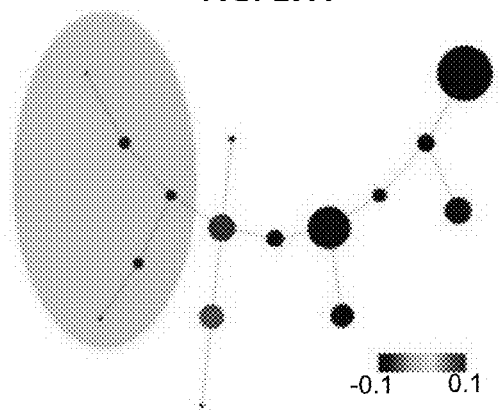
FIGS. 17A-D show the analysis of monocyte specific markers.
Figure 17B:
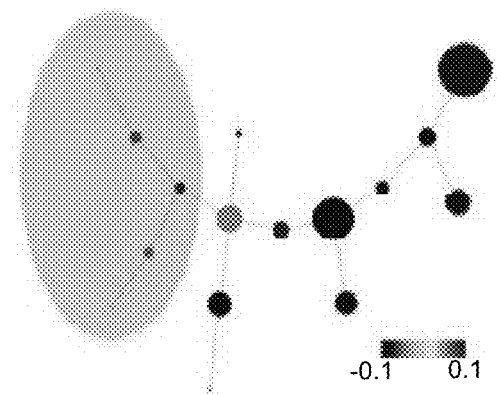
Figure 17C:
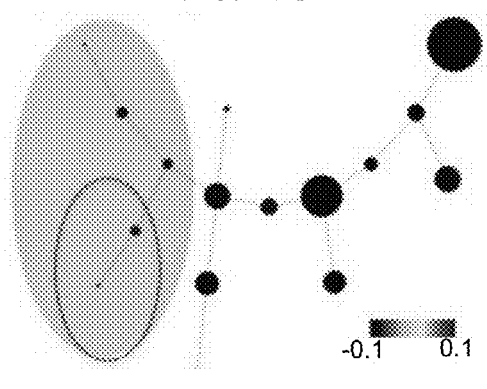
Figure 17D:
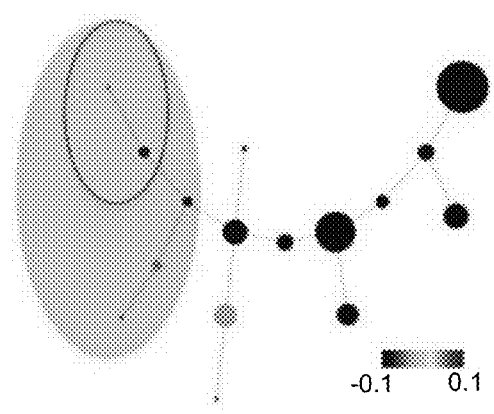
Figure 17E:
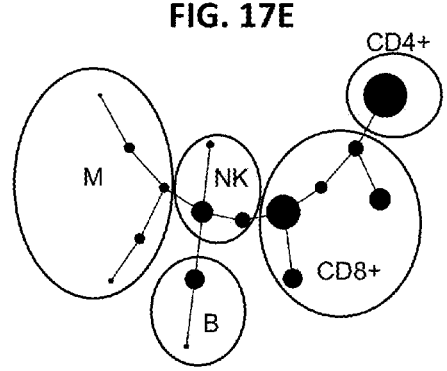
FIG. 17E shows the cell cluster depicted in FIG. 16.

FIG. 17A-D show the analysis of monocyte specific markers. FIG. 17E shows the cell cluster depicted in FIG. 16. FIG. 17A shows the cell expression profile for CD14, which is a monocyte specific marker. "Hot colors" (e.g., red) represent high gene expression and "cool colors" (e.g., blue) represent low gene expression. As shown in FIG. 17A, CD14 is highly expressed in the monocyte population and had low to no expression in the other cell types. The cell expression profile for CD16 which is known to be present in both monocytes and NK is shown in FIG. 17B. As shown in FIG. 17B, the monocyte and NK cell clusters had high expression of CD16, whereas the other cell types had low to no expression. CCR2 and S100A12 are known to be highly expressed in monocytes. The CCR2 and S100A12 monocyte-specific expression was also demonstrated in the cell expression profiles shown in FIGS. 17C and D, respectively. However, the expression of CCR2 and S100A12 separated into two branches of monocyte cells. The other cell types exhibited low to no expression of CCR2 and S100A12.

Figure 18A:
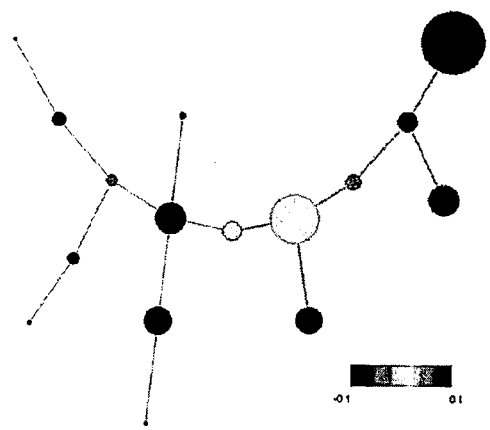
FIGS. 18A-B show the analysis of the T cell specific markers.
Figure 18B:
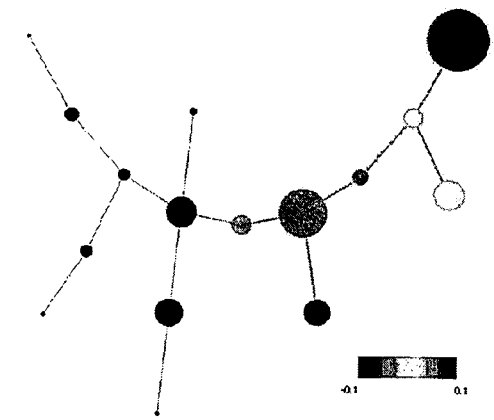
Figure 18C:
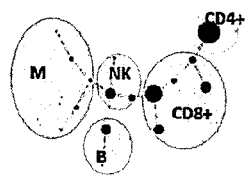
FIG. 18C shows the cell cluster depicted in FIG. 16.

FIG. 18A-B show the analysis of the T cell specific markers. FIG. 18C shows the cell cluster depicted in FIG. 16. FIG. 18A shows the cell expression profile for CD3D which is a chain of the CD3 molecule. CD3 is a pan T cell marker. FIG. 18A shows that CD3D is highly expressed in two branches of CD8+ T cells and moderately expressed in a third branch of CD8+ T cells. However, CD3D is not highly expressed in CD4+ T cells. Also, the other cell types have low to no expression of CD3D. FIG. 18B shows the cell expression profile for CD3E which is a chain of the CD3 molecule. FIG. 18B shows that CD3D is highly expressed in CD4+ T cells. Different branches of CD8+ T cells exhibit high to moderate expression of CD3D. Little to no expression of CD3D is observed in the other cell types.

Figure 19A:
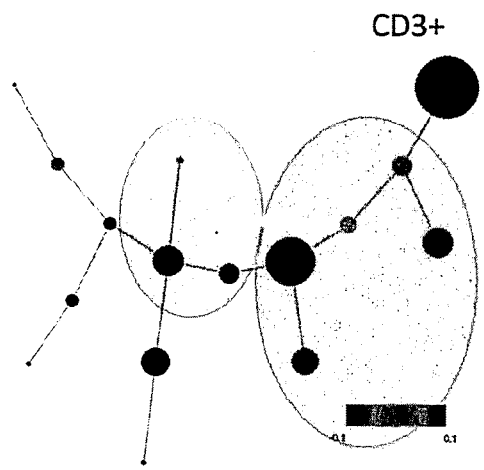
FIGS. 19A-B show the analysis of the CD8+ T cell specific markers.
Figure 19B:
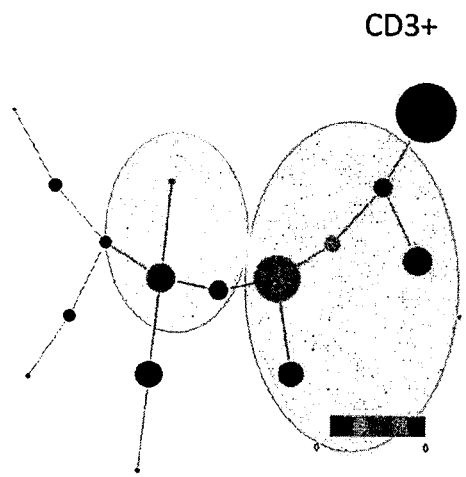
Figure 19C:
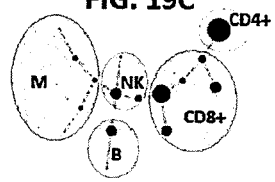
FIG. 19C shows the cell cluster depicted in FIG. 16.

FIG. 19A-B show the analysis of the CD8+ T cell specific markers. FIG. 19C shows the cell cluster depicted in FIG. 16. FIG. 19A shows the cell expression profile for CD8A which is a chain of the CD8 molecule. As shown in FIG. 19A, different branches of CD8+ T cells have various levels of CD8A expression, with some branches having high expression, other branches having moderate expression and one branch exhibiting low to no expression of CD8A. High CD8A expression was observed in a branch of the CD16+ NK cells. It has been reported in the literature that up to 80% of NK cells express CD8. Little to no CD8A expression was observed in the other cell types. FIG. 19B shows the cell expression profile for CD8B which is a chain of the CD8 model. As shown in FIG. 19B, different branches of CD8+ T cells have various levels of CD8B expression, with one branch having high expression, some branches having moderate expression and two branches exhibiting low to no expression of CD8B. High CD8B expression was also observed in a branch of the CD16+ NK cells. Little to no CD8B expression was observed in the other cell types.

FIG. 20A shows the analysis of CD4+ T cell specific markers. FIG. 20B shows the cell cluster depicted in FIG. 16. FIG. 20A shows the expression profile for CD4. Moderate expression of CD4 was observed in a subset of cells in the CD4+ T cell cluster and high expression of CD4 was observed in a branch of the monocyte cluster. It has previously been documented in the literature that monocytes also express CD4. Moderate to low expression of CD4 was observed in a branch of CD8+ T-cells and in NK cells. Low to no expression of CD4 was observed in the other cell types.

FIG. 21A-D show the analysis of Natural Killer (NK) cell specific markers. FIG. 20E shows the cell cluster depicted in FIG. 16. FIG. 20A shows the expression profile for KIR2DS2. All of the cell types exhibited little to no KIR2DS2 expression. FIG. 20B shows the expression profile for KIR2DS5. Killer immunoglobulin receptors (KIRs) are known to be expressed in NK cells and a subset of T cells. High expression of KIR2DS5 was observed in 2 branches of NK cells and moderate to low expression of KIR2DS5 was observed in one branch of NK cells. Moderate to high expression of KIR2DS5 was observed in 2 branches of CD8+ T cells. Low to no expression of KIR2DS5 was observed in all other cell types. OSBPL5 and IGFBP7 are known to be highly expressed in NK cells. FIG. 20C shows the expression profile for OSBPL5. OSBPL5 was highly expressed in one branch of NK cells. Moderate to low expression of OSBPL5 was observed in a branch of B cells. Low to no expression of OSBPL5 was observed in all other cell types. FIG. 20D shows the expression profile for IGFPBP7. High expression of IGFPBP7 was observed in two branches of NK cells and one branch of monocytes. Moderate expression of IGFPBP7 was observed in one branch of B cells. Low to no expression of IGFPBP7 was observed in all other cell types.

Figure 22A:
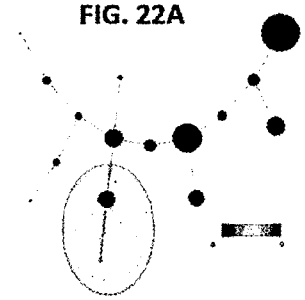
FIGS. 22A-E show the analysis of B cell specific markers.
Figure 22B:
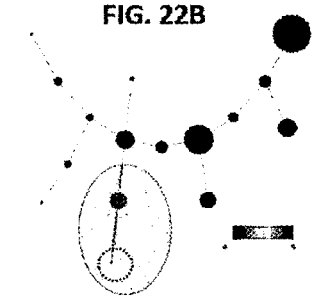
Figure 22C:
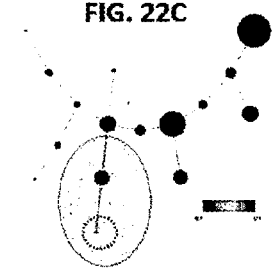
Figure 22D:
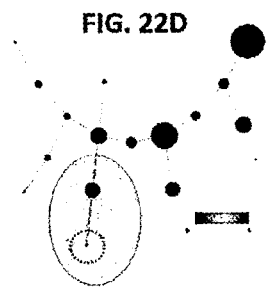
Figure 22E:
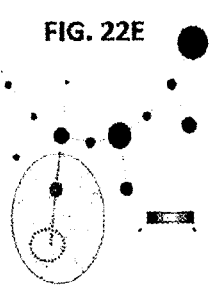
Figure 22F:
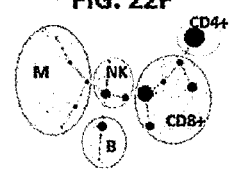
FIG. 22F shows the cell cluster depicted in FIG. 16.

FIG. 22A-E show the analysis of B cell specific markers. FIG. 22F shows the cell cluster depicted in FIG. 16. FIG. 22A shows the expression profile for IGHM CH4. IGHM CH4 was highly expressed in one branch of B cells and moderately expressed in the second branch of B cells. Low to no expression of IGHM CH4 was observed in all other cell types. FIG. 22B shows the expression profile for PAX5. PAX5 was highly expressed in one branch of B cells. Low to no expression of PAX5 was observed in all other cell types. FIG. 22C shows the expression profile for CD20. CD20 was highly expressed in one branch of B cells. Low to no expression of CD20 was observed in all other cell types. FIG. 22D shows the expression profile for TCL1A. Low to no expression of TCL1A was observed in all other cell types. FIG. 22E shows the expression profile for IGHD CH2. IGHD CH2 was highly expressed in one branch of B cells. Low to no expression of IGHD CH2 was observed in all other cell types.

Figure 23A:
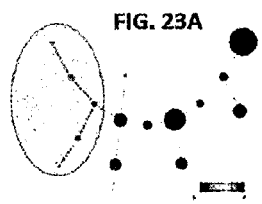
FIGS. 23A-F show the analysis of Toll-like receptors. Toll-like receptors are mainly expressed by monocytes and some B cells.
Figure 23B:
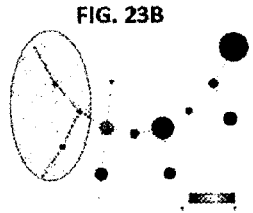
Figure 23C:
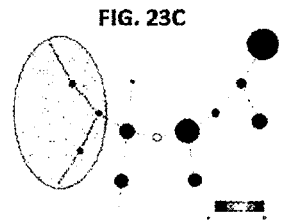
Figure 23D:
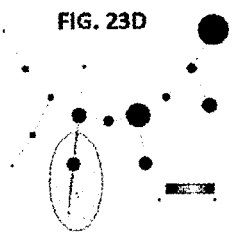
Figure 23E:
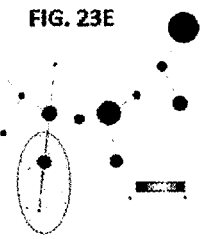
Figure 23F:
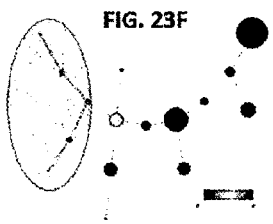
Figure 23G:
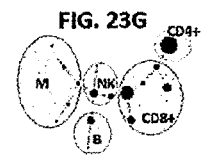
FIG. 23G shows the cell cluster depicted in FIG. 16.

FIG. 23A-F show the analysis of Toll-like receptors. Toll-like receptors are mainly expressed by monocytes and some B cells. FIG. 23G shows the cell cluster depicted in FIG. 16. FIG. 23A shows the expression profile for TLR1. One branch of monocytes exhibited high expression of TLR1 and two branches of monocytes exhibited moderate expression of TLR1. Low to no expression of TLR1 was observed in all other cell types. FIG. 23B shows the expression profile for TLR4. One branch of monocytes exhibited high expression of TLR4. Moderate TLR4 expression was observed in two branches of monocytes and one branch of NK cells. Low to no expression of TLR4 was observed in all other cell types. FIG. 23C shows the expression profile for TLR7. High expression of TLR7 was observed in one branch of monocytes and moderate expression of TLR7 was observed in one branch of NK cells. Low to no expression of TLR7 was observed in all other cell types. FIG. 23D shows the expression profile for TLR2. High expression of TLR2 was observed in one branch of B cells. Low to no expression of TLR2 was observed in all other cell types. FIG. 23E shows the expression profile for TLR3. High expression of TLR3 was observed in one branch of B cells. Low to no expression of TLR3 was observed in all other cell types. FIG. 23F shows the expression profile for TLR8. High expression of TLR8 was observed in three branches of monocytes. Moderate to low expression of TLR8 was observed in two branches of monocytes and one branch of NK cells. Low to no expression of TLR8 was observed in all other cell types.

These results demonstrate that massively parallel single cell sequencing may successfully identify major cell types in PMBCs. The sequencing results also determined that some cell markers that are used in FACs for identifying cell types do not have high mRNA expression (e.g., CD56 for NK cells, CD19 for B cells). In addition, many of the genes in the gene panel were expressed across multiple cell types. These expression profiles may be used to subtype cells within a major cell type (e.g., activated cell versus resting cell, etc.).

Example 11

Identifying Rare Cells in a Population

In this experiment, massively parallel single cell sequencing is used to identify cancer cells from a mixture of cancer and non-cancer cells. Ramos (Burkitt lymphoma) cells were spiked into a population of CD19+ B cells that were isolated from a healthy individual. The concentration of the Ramos cells in the mixed population was about 4-5%. Approximately 7000 normal B cells and 300 Ramos cells were deposited on a microwell array with 25,200 wells. Thus, most wells on the microwell array contained no cells and some wells on the cell contained only 1 cell. Oligonucleotide-conjugated beads were applied to the microwell array. Each oligonucleotide-conjugated bead contained approximately 1 billion oligonucleotides attached to a bead. Each oligonucleotide attached to the bead contained a 5' amine, universal sequence, three-part cellular label (e.g., three cell label sections connected by two linkers), molecular label, and oligodT. Each bead contained a unique three-part cellular label, which is a result of the unique combination of the three cell label sections. All of the oligonucleotides on a single bead contained the same three-part cellular label. Oligonucleotides from different beads contained different three-part cellular labels. Each well contained 1 or fewer oligonucleotide-conjugated bead. A cell lysis reagent was applied to the microwell array, resulting in lysis of the cells. Polyadenylated molecules (e.g., mRNA) from the cell hybridized to the oligodT sequence of the oligonucleotides from the oligonucleotide-conjugated beads. The polyadenylated molecules that were hybridized to the oligonucleotides from the oligonucleotide-conjugated bead were reverse transcribed with SuperScript II at 42° C. at 90 minutes on a rotor. The oligonucleotide from the oligonucleotide-conjugated bead served as a primer for first strand cDNA synthesis. A SMART oligo was incorporated in the cDNA synthesis such that the superscript II may add the complement of the SMART oligo sequence to the 3' end of the cDNA when it reaches the end. The cDNA synthesis reaction produces a bead conjugated to unextended oligonucleotides (e.g., oligonucleotides that were not attached to the polyadenylated molecule from the cell) and the extended oligonucleotides (e.g., oligonucleotides that were attached to the polyadenylated molecule and comprise a polyadenylated molecule/cDNA hybrid).

The beads are combined and the oligonucleotides comprising the polyadenylated molecule/cDNA hybrid were amplified. Multiplex PCR was performed to amplify a panel of 111 genes from the cDNA on the beads. The 111 genes represent markers for different subsets of B cells. Primers for the multiplexed PCR comprised a first gene specific primer that was designed to sit approximately 500 base pairs from the 3' end of the mRNA and a nested gene-specific primer that was designed to sit approximately 300 base pairs from the 3' end of the mRNA. Primers for the multiplex PCR were designed to require no significant complementarity in the last 6 bases of the primers in the panel. If complementarity was detected in the multiplex PCR primers, then the primers were manually replaced. The multiplex PCR reaction comprised the following steps: 1) 15 cycles of first gene specific PCR (KAPA multiplex mix, 50 nM of each primer—first gene specific primer and universal primer that is complementary to the universal sequence of the oligonucleotide-conjugated bead), Ampure clean up (0.7× bead to template ratio), 15 cycles of nested gene specific PCR (KAPA multiplex mix, 50 nM of each primer—nested gene-specific primer and universal primer that is complementary to the universal sequence of the oligonucleotide-conjugated bead), Ampure clean up (0.7× bead to template ratio), 8 cycles of final PCR to add full length Illumina adaptor (KAPA HiFi ReadyMix), and Ampure clean up (1× bead to template ratio).

Figure 24:
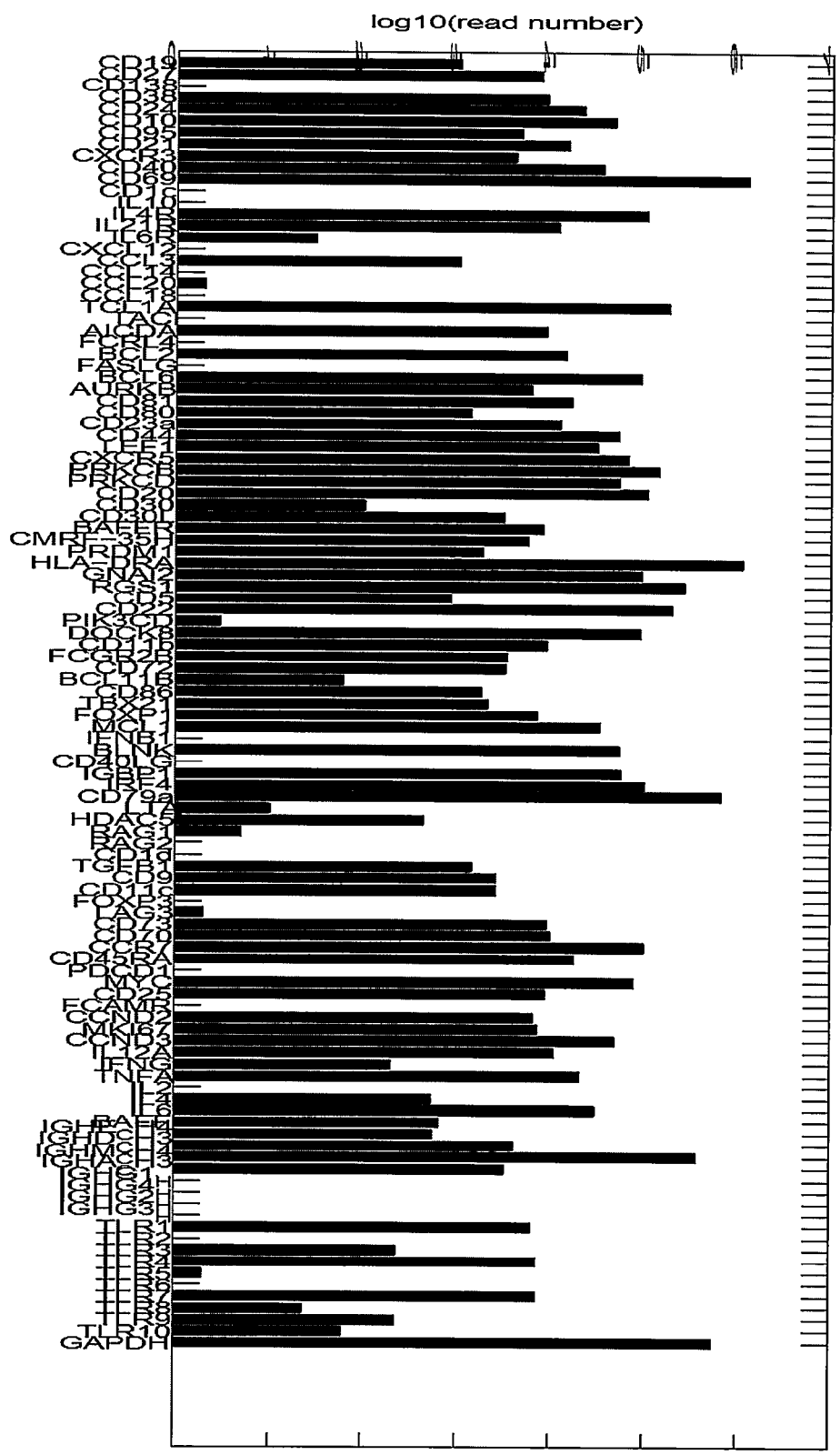
FIG. 24 depicts a graph of the genes versus the log 10 of the number of reads.

The amplified products were sequenced. The sequence reads comprising 150 bp were aligned to entire mRNA sequences of the 111 genes (Table 17) using Bowtie2. The results of the sequence alignment (see Table 14) demonstrate that the multiplex PCR reaction resulted in highly specific products. FIG. 24 depicts a graph of the genes versus the log 10 of the number of reads. 24 of the 111 genes were not present. At least two of the genes, RAG1 and RAG2 which are involved in VDJ recombination and should be present only in pre-B cells, should not be present. A few of the absent genes are specific for plasma cells, which are very rarely preserved in frozen cells.

(sorted by abundance) versus the log 10 of the number of reads for CD79. FIG. 25C shows a graph of the molecular barcode (sorted by abundance) versus the number of reads for GAPDH. FIG. 25D shows a graph of the molecular barcode (sorted by abundance) versus the log 10 of the number of reads for GAPDH.

Figure 26A:
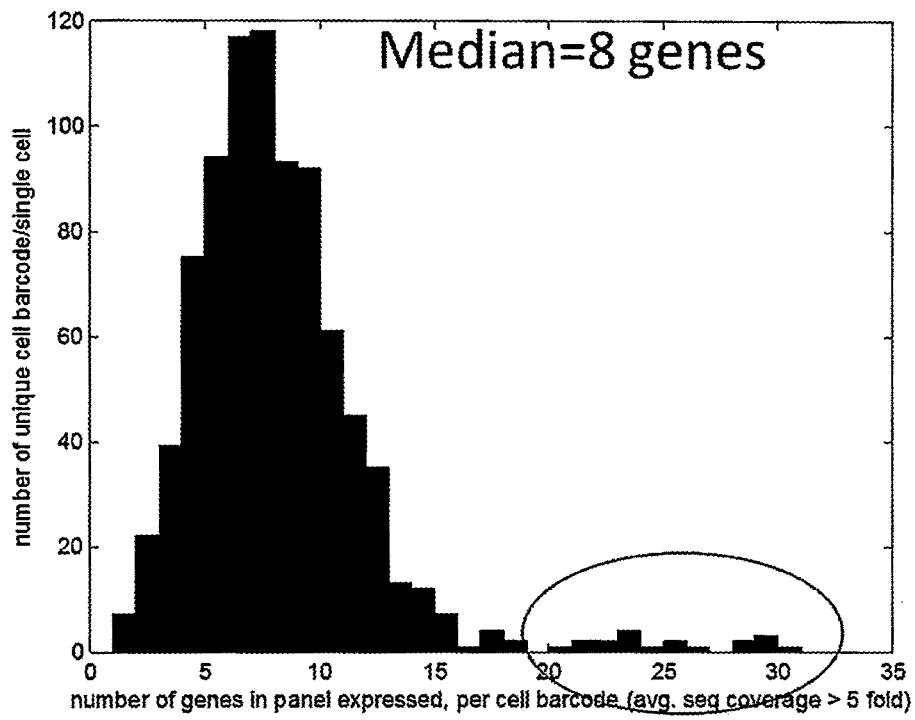
FIG. 26A shows a graph of the number of genes in the panel expressed per cell barcode versus the number of unique cell barcodes/single cell.
Figure 26B:
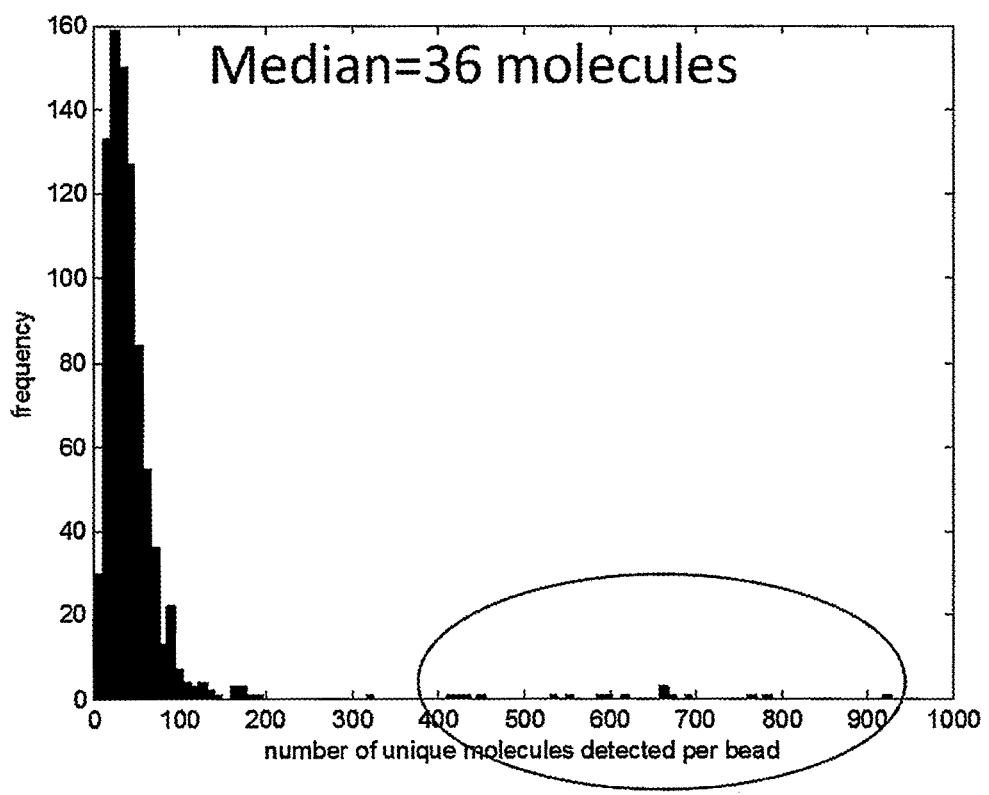
FIG. 26B shows a histogram of the number of unique molecules detected per bead versus frequency of the number of cells per unique cell barcode carrying a given number of molecules.
Figure 26C:
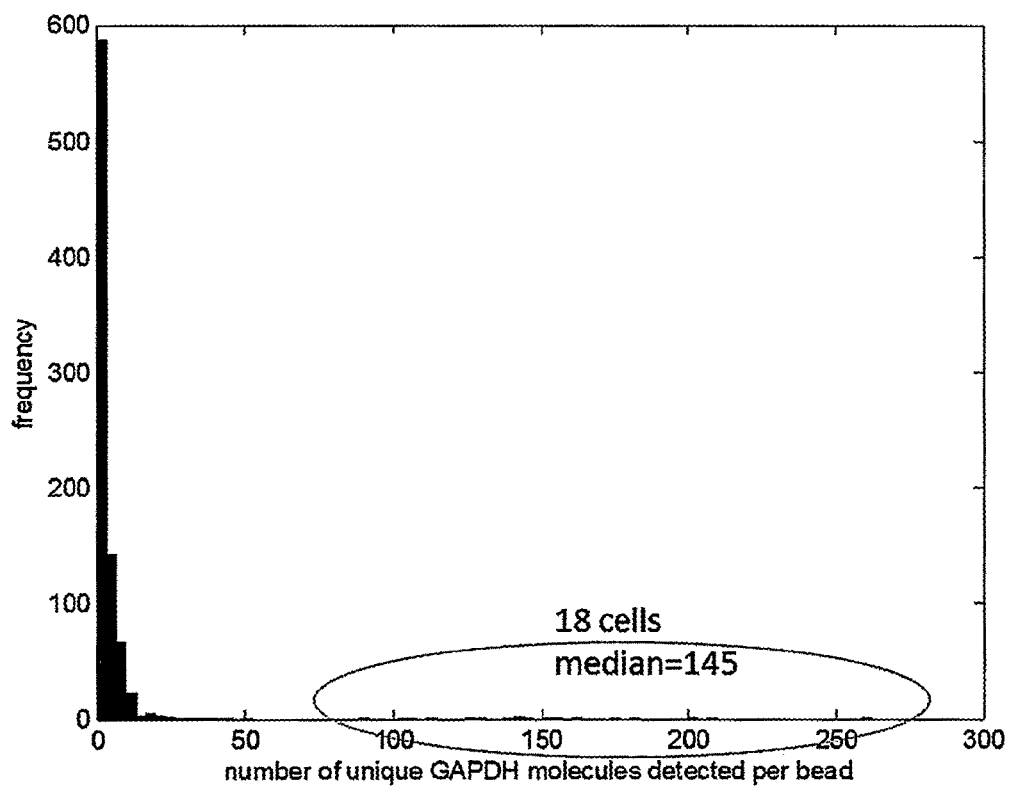
FIG. 26C shows a histogram of the number of unique GAPDH molecules detected per bead versus frequency of the number of cells/unique cell barcode carrying a given number of molecules.

856 cells were retained for analysis. FIG. 26A shows a graph of the number of genes in the panel expressed per cell barcode versus the number of unique cell barcodes/single cell. FIG. 26B shows a histogram of the number of unique molecules detected per bead versus frequency of the number of cells per unique cell barcode carrying a given number of molecules. A small subset of cells showed distinctly higher number of mRNA molecules and number of genes expressed from the 111 gene panel (see circled sections in FIG. 26A-B). FIG. 26C shows a histogram of the number of unique GAPDH molecules detected per bead versus frequency of the number of cells/unique cell barcode carrying a given number of molecules.

Figure 27:
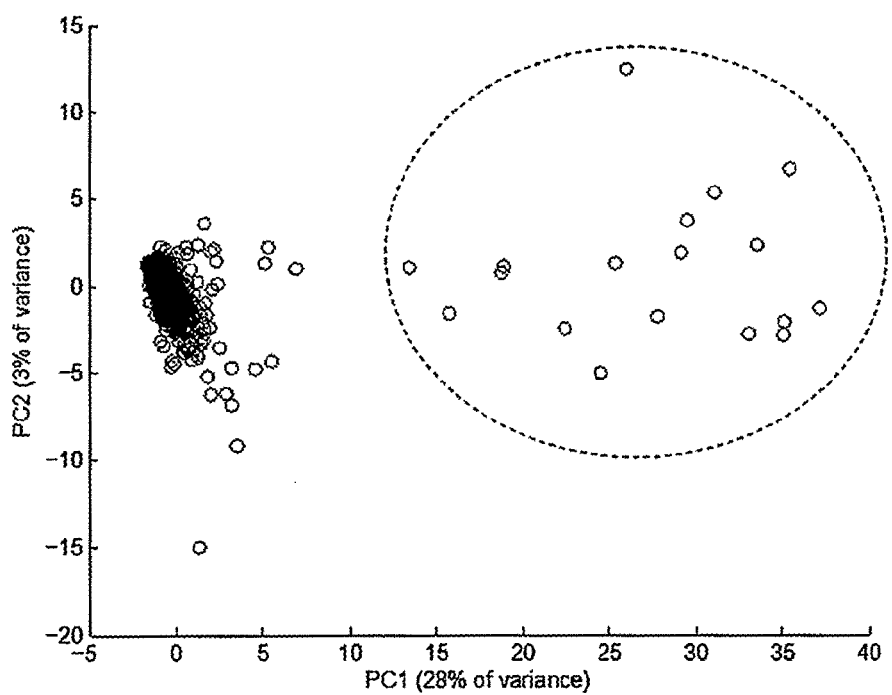
FIG. 27 shows a scatterplot of the 856 cells.

Principal component analysis (PCA) was used to generate a scatterplot of cells. FIG. 27 shows a scatterplot of the 856 cells. PCA identified the small subset of cells with a different gene expression pattern than the majority of cells. The

TABLE 17

| CD19 | AURKB | FOXP1 | CCND3 | TLR1 | FOXP3 | CXCL12 | GNAI2 |
|---|---|---|---|---|---|---|---|
| CD27 | CD81 | MCL1 | IL12A | TLR2 | LAG3 | CCL3 | RGS1 |
| CD138 | CD80 | IFNB1 | IFNG | TLR3 | CD73 | CCL14 | CD5 |
| CD38 | CD23a | BLNK | TNFA | TLR4 | CD70 | CCL20 | CD22 |
| CD24 | CD44 | CD40LG | IL2 | TLR5 | CCR7 | CCL18 | PIK3CD |
| CD10 | LEF1 | IGBP1 | IL4 | TLR6 | CD45RA | TCL1A | DOCK8 |
| CD95 | CXCR5 | IRF4 | IL6 | TLR7 | PDCD1 | TACI | CD11b |
| CD21 | PRKCB | CD79a | BAFF | TLR8 | MYC | AICDA | FCGR2B |
| CXCR3 | PRKCD | LTA | IGHE | TLR9 | CD25 | FCRL4 | CD72 |
| CD40 | CD20 | HDAC5 | IGHD | TLR10 | FCAMR | BCL2 | BCL11B |
| CD69 | CD30 | RAG1 | IGHM | GAPDH | CCND2 | FASLG | CD86 |
| CD1c | CD30L | RAG2 | IGHA | CD9 | MKI67 | BCL6 | TBX21 |
| IL10 | BAFFR | CD1d | IGHG1 | CD11c | IL21R | IGHG2 | PRDM1 |
| IL4R | CMRF-35H | TGFB1 | IGHG4 | IL6R | HLA-DRA | IGHG3 | |

TABLE 14

| total | 5711013 |
|---|---|
| aligned 0 times | 504775 |
| aligned exactly 1 time | 5203308 |
| aligned >1 time | 2930 |
| % aligned exactly once | 91.6% |

Table 15 shows the results of the overall sequencing statistics. For Read1, the total read1 match criteria required a perfect match to the three-part cellular label (e.g., cell barcode) and at most 1 mismatch to the linkers.

TABLE 15

| total num read | 5711013 |
|---|---|
| total read1 match criteria | 3795915 |
| read2 also align | 3495392 |
| % read2 align | 92% |
| number of unique cell bc | 40764 |
| read count per unique bc >100 | 3313 |
| read count per unique bc >50 | 4154 |
| % useful reads | 61% |

Figure 25A:
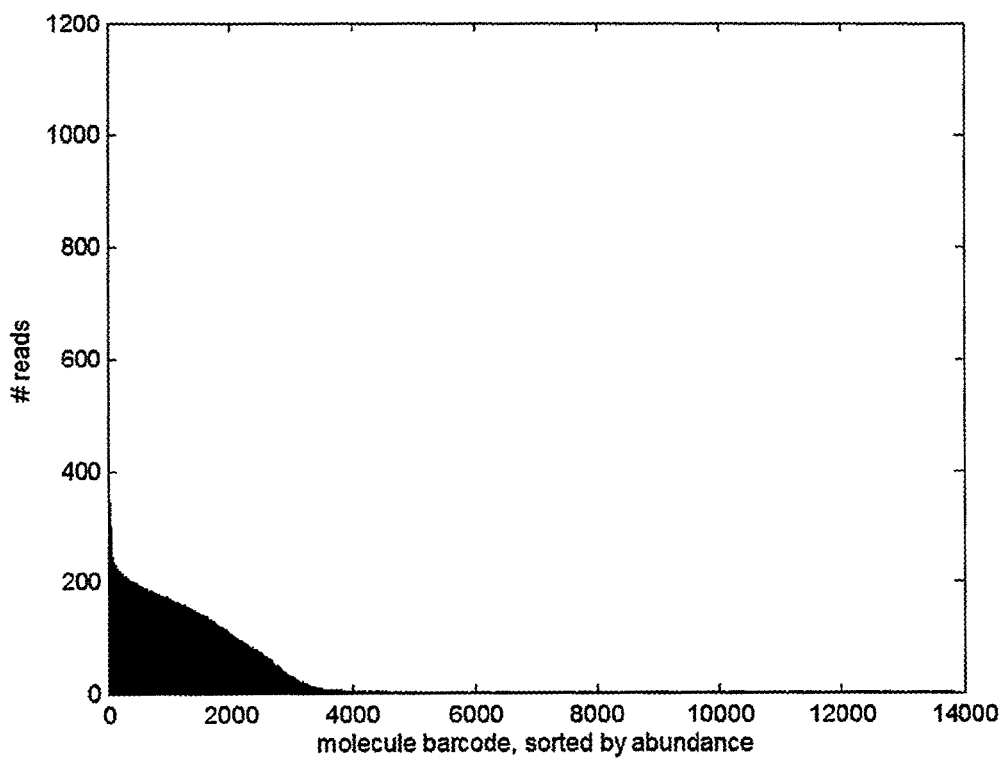
FIGS. 25A-D shows graphs of the molecular barcode versus the number of reads or log 10 of the number of reads for two genes.
Figure 25B:
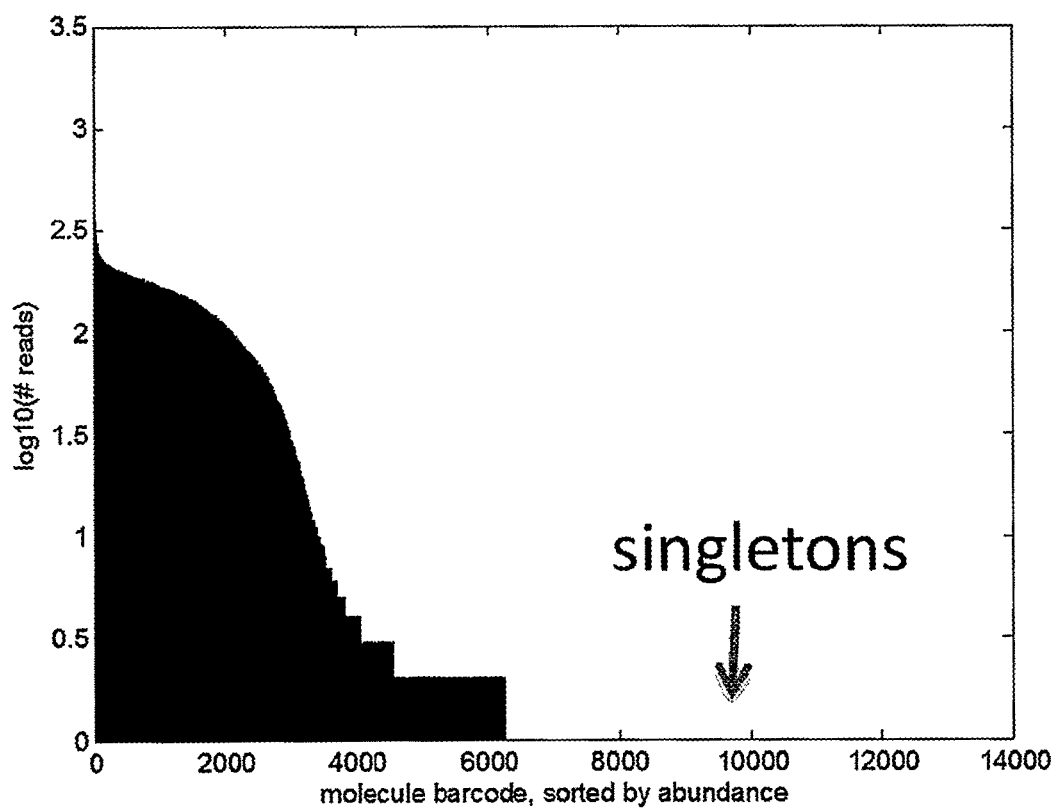
Figure 25C:
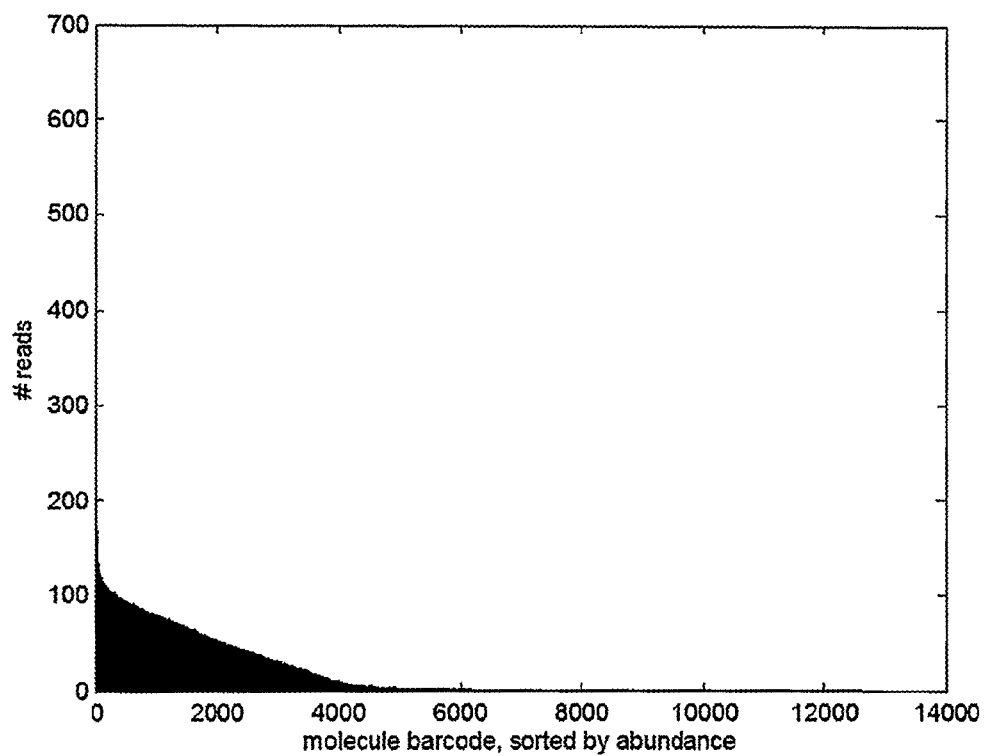
Figure 25D:
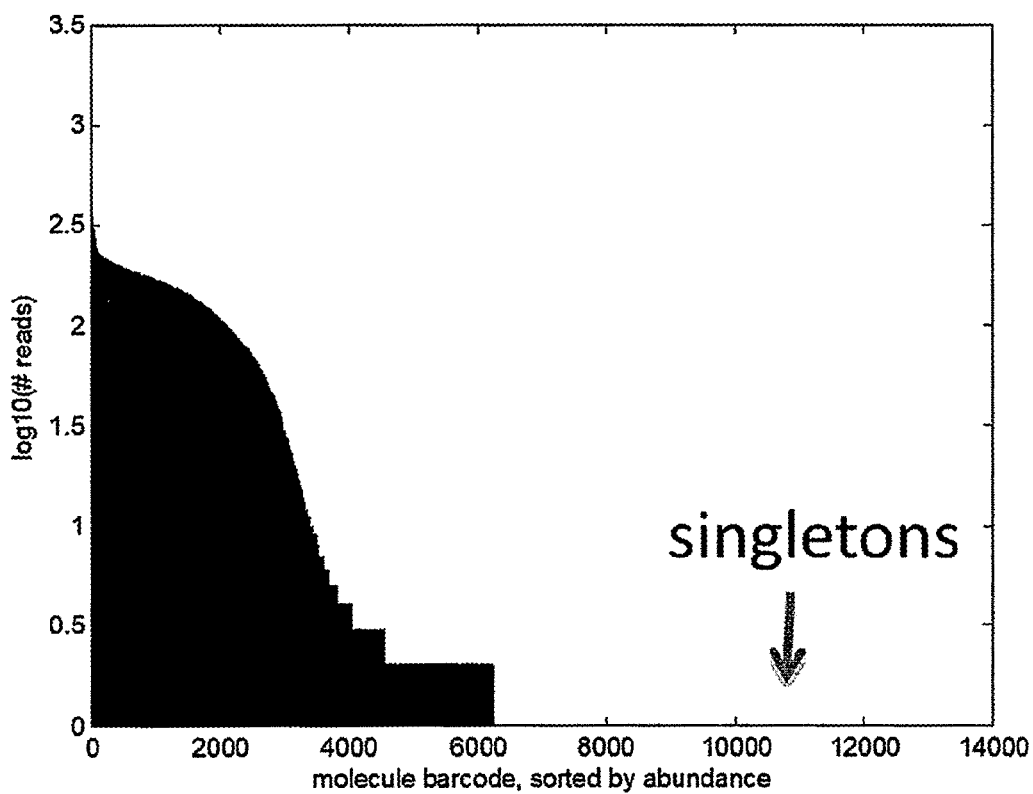

FIG. 25A-D shows graphs of the molecular barcode versus the number of reads or log 10 of the number of reads for two genes. FIG. 25A shows a graph of the molecular barcode (sorted by abundance) versus the number of reads for CD79. FIG. 25B shows a graph of the molecular barcode subset of cells contained 18 cells, which is approximately 2% of all of the cells analyzed. This percentage is similar to the percentage of Ramos cells that was spiked into the population.

Figure 28:
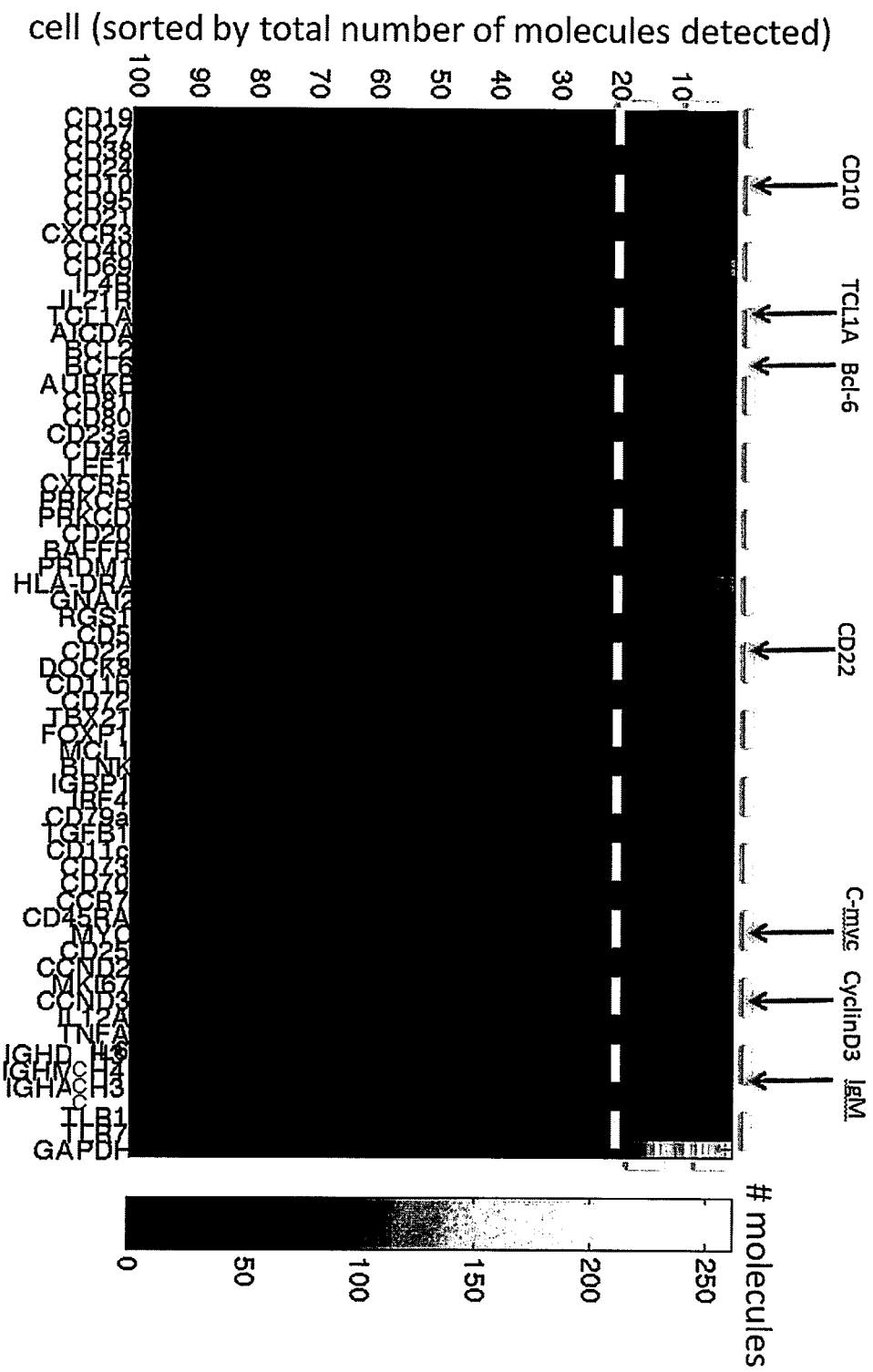
FIG. 28 shows a heat map of expression of the top 100 (in terms of the total number of molecules detected).

Ramos cells are derived from follicular B cells and strongly express B cell differentiation markers CD20, CD22, CD19, CD10 and BCL6. Ramos cells also express IgM and overexpress c-myc. FIG. 28 shows a heat map of expression of the top 100 (in terms of the total number of molecules detected). The subset of cells (18 cells) that express much higher levels of mRNA also strongly express genes that are known markers for Ramos cells (e.g., CD10, Bcl-6, CD22, C-my, and IgM).

These results demonstrate that massively parallel single cell sequencing successfully identified small subsets (as low as 2%) of abnormal cell types in a cell suspension. Massively parallel single cell sequencing may be used in cancer diagnostics (e.g., biopsy/circulating tumor cells). Since cancer cells are larger in size and carry more mRNA, they may be easily differentiated from normal cells.

Example 12

Figure 29:
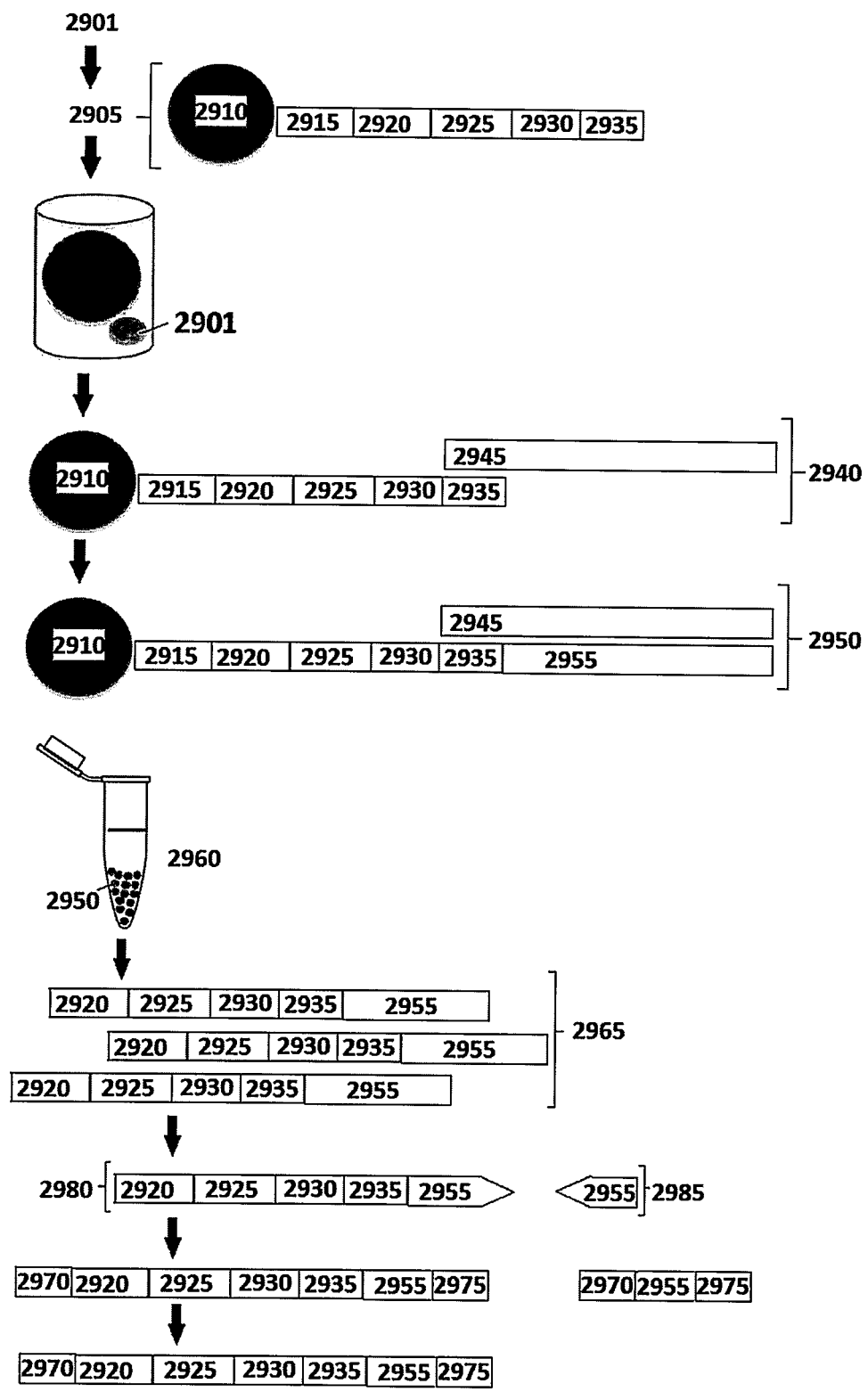
FIG. 29 shows a workflow for Example 12.

Massively Parallel Single Cell Whole Genome and Multiplex Amplification of gDNA Targets Using RESOLVE FIG. 29 shows a workflow for this example. As shown in FIG. 29, a cell suspension is applied to a microwell array (2901). The number of cells in the cell suspension is less than the number of wells in the microwell array, such that application of the cell suspension to the microwell array results in a well in the microwell array containing 1 or fewer cells. Oligonucleotide-conjugated beads (2905) are applied to the microwell array. An oligonucleotide-conjugated bead (2905) contains a bead (2910) attached to an oligonucleotide comprising a 5' amine (2915), universal primer sequence (2920), cell label (2925), molecular label (2930) and randomer (2935). The oligonucleotide-conjugated bead contains approximately 1 billion oligonucleotides. An oligonucleotide contains a 5' amine, universal primer sequence, cell label, molecular label, and randomer. Each oligonucleotide on a single bead contains the same cell label. However, two or more oligonucleotides on a single bead may contain two or more different molecular labels. A bead may contain multiple copies of oligonucleotides containing the same molecular label.

After the oligonucleotide-conjugated beads are added to the microwell array, a cell lysis buffer is applied to the array surface. As shown in FIG. 29, the genomic DNA (2945) from the cell hybridizes to the randomer sequence (2935) of the oligonucleotide-conjugated beads (2940). A neutralization buffer is added to the array surface. A DNA polymerase (e.g., Phi29) and dNTPs are added to the array surface. The randomer sequence (2935) acts as a primer for amplification of the genomic DNA, thereby produce a gDNA-conjugated bead (2555). The gDNA-conjugated bead (2955) contains an oligonucleotide comprising a 5' amine (2915), universal primer sequence (2920), cell label (2925), molecular label (2925), randomer (2935) and copy of the genomic DNA (2955). The original genomic DNA (2945) is hybridized to the randomer (2935) and the copy of the genomic DNA (2955). For a single bead, there are multiple different genomic DNA molecules attached to the oligonucleotides.

As shown in FIG. 29, the gDNA-conjugated beads (2950) from the wells are combined into an eppendorf tube (2960). The genomic DNA on the gDNA MDA mix containing randomers, dNTPs and a DNA polymerase (e.g., Phi29) is added to the eppendorf tube containing the combined gDNA-conjugated beads. The labeled genomic DNA is further amplified to yield labeled amplicons (2965) in solution. A labeled amplicon (2965) comprises a universal primer sequence (2920), cell label (2925), molecular label (2930), randomer (2935), and copy of the genomic DNA (2955). The labeled amplicons are sheared to smaller pieces of approximately 1 kb or less. Alternatively, the labeled amplicons may be fragmented by to Tagmentation (Nextera). Shearing or fragmenting the labeled amplicons results in labeled-fragments (2980) and unlabeled fragments (2985). The labeled fragment (2980) contains the universal primer sequence (2920), cell label (2925), molecular label (2930), randomer (2935), and fragment of the copy of the genomic DNA (2955). Adaptors (2970, 7975) are added to the fragments. The universal primer sequence may be used to select for labeled fragments (2980) via hybridization pulldown or PCR using the universal primer sequence and a primer against one of the adaptors (2970, 2975).

The labeled fragments may be sequenced. Sequence reads comprising a sequence of the cell label, molecular label and genomic fragment may be used to identify cell populations from the cell suspension. Principal component analysis may be used to generate scatterplots of the cells based on known cell markers. Alternatively, or additionally, SPADE may be used to produce cell cluster plots. A computer software program may be used to generate a list comprising a cell label and the molecular labels and genomic fragments associated with the cell label.

Example 13

Massively Parallel Sequencing to Identify Cells in a Heterogeneous Population

Figure 30:
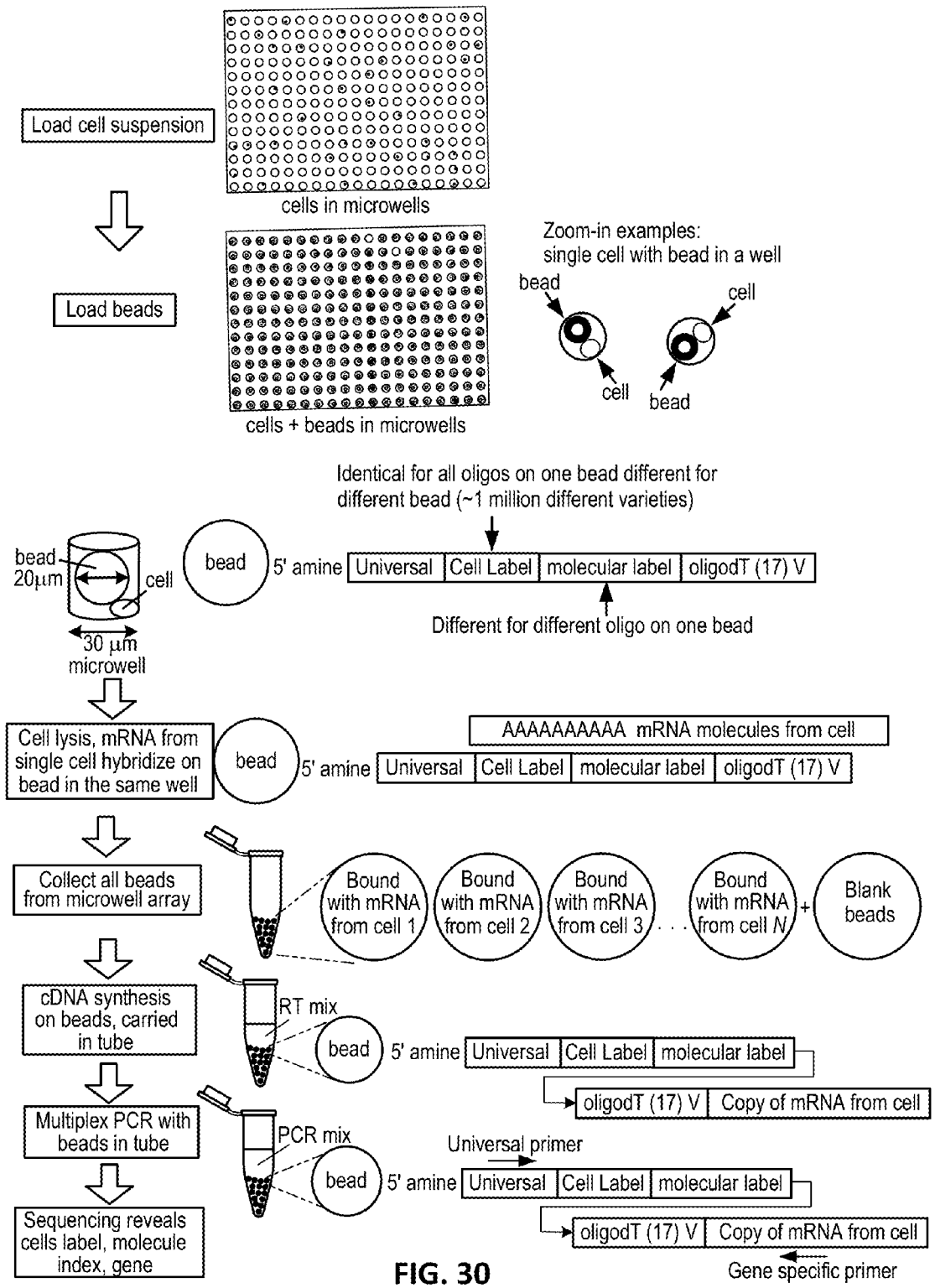
FIG. 30 shows a workflow for Example 13.
Figure 31A:
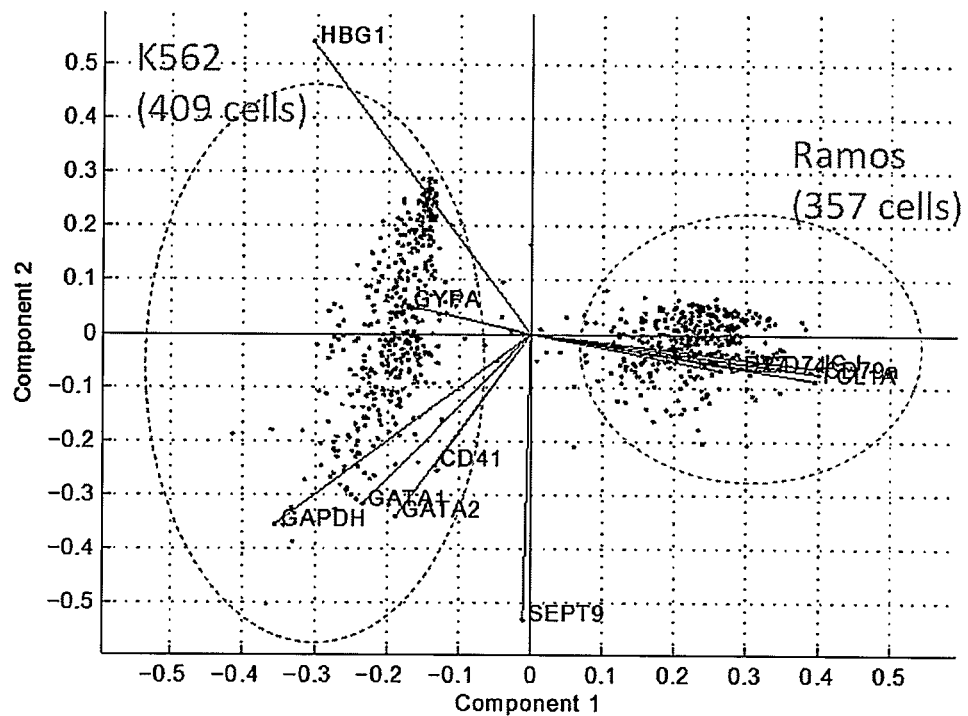
FIGS. 31A-C. Clustering of single cells in controlled mixtures containing two distinct cell types. A. Clustering of a 1:1 mixture of K562 and Ramos cells by principal component analysis of the expression of 12 genes. The biplot shows two distinct clusters, with one cluster expressing Ramos specific genes and the other expressing K562 specific genes. B. Principal component analysis of a mixture containing a small percentage of Ramos cells in a background of primary B cells from a healthy individual using a panel of 111 genes. The color of each data point indicates the total number of unique transcript molecules detected across the entire gene panel. A set of 18 cells (circled) out of 1198 cells displays a distinct gene expression profile and with much higher transcription levels. C. Heatmap showing expression level of each gene in the top 100 cells in the sample of FIG. 31B, ranked by the total number of transcript molecules detected in the gene panel. Genes are ordered via hierarchical clustering in terms of correlation. The top 18 cells, indicated by the horizontal red bar, expressed preferentially a set of genes known to be associated with follicular lymphoma, as indicated by the vertical red bar.

The experimental workflow for this example is shown in FIG. 30. As shown in FIG. 30, a mixed population of cells was stochastically dispersed onto a microwell array. In this example, the mixed population of cells comprises a mixture of Ramos cells and K562 cells. The cell suspension comprises a low concentration of cells such that each microwell in the array contains 1 or fewer cells. After the cells were applied to the microwell array, a plurality of oligonucleotide conjugated beads was stochastically dispersed onto the microwell array. The oligonucleotide bead contains a plurality of oligonucleotides comprising a 5' amine, universal primer sequence, cell label, molecular label, and oligodT. The cell labels of the plurality of oligonucleotides from a single bead are identical. A single bead may comprise multiple oligonucleotides comprising the same molecular label. In addition, a single bead may comprise multiple oligonucleotides comprising different molecular labels. A cell label of an oligonucleotide conjugated to a first bead is different from a cell label of an oligonucleotide conjugated to a second bead. Thus, the cell label may be used to differentiate two or more oligonucleotide conjugated beads. The cells were lysed and the RNA molecules from a single cell were attached to the oligonucleotide conjugated beads in the same well. FIG. 30 shows the attachment of the polyA sequence of a RNA to the oligodT sequence of the oligonucleotide. After attachment of the RNA molecules from the individual cells to the oligonucleotide conjugated beads in the same well, the beads were combined into a single sample. A cDNA synthesis reaction was carried out on the beads in the single sample. FIG. 30 shows the product of the cDNA synthesis comprises a bead attached to an oligonucleotide, the oligonucleotide comprising the 5' amine, universal primer sequence, cell label, molecular label, oligodT and a copy of the RNA molecule. For simplicity, only one oligonucleotide is depicted in FIG. 30, however, in this example, each oligonucleotide conjugated bead comprises approximately 1 billion oligonucleotides. As shown in FIG. 30, multiplexed PCR was performed with the beads in the single sample using a universal primer that hybridized to the universal primer sequence and a gene-specific primer that hybridized to the copy of the RNA molecule. The gene-specific primers were designed to bind to Ramos-specific genes or K562-specific genes from the gene panel shown in Table 16. As a control, a GAPDH gene-specific primer was also used in the multiplexed PCR reaction. Lastly, next-generation sequencing was used to sequence the amplified products. The sequencing reads included information pertaining to the cell label, molecular label and the gene. Using principal component analysis, a scatter plot of the cells was constructed based on the sequencing information pertaining to the cell label, molecular label and the gene. Analogous to how FACs is used to sort cells and scatter plots based on the surface markers is used to group cells, the cell label is used to identify genes from a single cell and the molecular label is used to determine the quantity of the genes. This combined information is then used to relate the gene expression profile individual cells. As shown in FIG. 31A, massively parallel single cell sequencing with cell and molecular labels was able to successfully identify the two cell populations (K562 and Ramos cells) in the mixed cell population.

TABLE 16

| Gene | Cell | Gene | Cell |
|---|---|---|---|
| CD74 | Ramos specific | CD41 | K562 specific |
| CD79a | Ramos specific | GYPA | K562 specific |
| IGJ | Ramos specific | GATA2 | K562 specific |
| TCL1A | Ramos specific | GATA1 | K562 specific |
| SEPT9 | Ramos specific | HBG1 | K562 specific |
| CD27 | Ramos specific | GAPDH | Common |

Example 14

Massively Parallel Single Cell Sequencing with Principal Component Analysis

In this example, mRNA molecules from individual cells were stochastically labeled with oligonucleotide conjugated beads in parallel. PBMCs were isolated from blood and frozen at 80° C. in RPMI1640 plus FBS and DMSO. The PMBCs were thawed and washed three times with PBS. A PBMC sample comprising a mixture of cell types (4000 total cells) was stochastically applied to an agarose microwell array. The agarose microwell array contained 37,500 cells. A mixture of 150,000 oligonucleotide conjugated beads was stochastically applied to the microwell array via a PDMS gasket that surrounded the microwell array. The oligonucleotide conjugated bead is depicted in FIG. 1. For simplicity, only one oligonucleotide is shown to be attached to the bead, however, the oligonucleotide conjugated beads contained approximately 1 billion oligonucleotides.

Cells were lysed by placing the microwell array on a cold block for 10 minutes and by applying lysis buffer to the array surface. Once the cells in the wells were lysed, the mRNA molecules from the single cells were attached to the oligonucleotide conjugated bead via the oligodT sequence. A magnet was applied to the array and the array was washed twice with wash buffer.

The beads with the attached mRNA molecules were combined into an eppendorf tube. The mRNA molecules attached to the beads were reverse transcribed to produce cDNA. The following cDNA synthesis mixture was prepared as follows:

| Component | Volume (uL) |
|---|---|
| Water | 8 |
| dNTP (10 mM) | 2 |
| 5x first strand buffer | 4 |
| MgCl2 | 2.4 |
| SuperRase In | 1 |
| SMART oligo (50 uM) | 0.4 |
| 0.1M DTT | 1 |
| 100x BSA | 0.2 |
| SSII | 1 |
| total | 20 |

The cDNA synthesis mixture was added to the eppendorf tube containing the beads with the attached mRNA molecules. The eppendorf tube was incubated at 40° C. for 90 minutes on a rotor. The cDNA synthesis reaction occurred on the beads. After 90 minutes, a magnet was applied to the tube and the cDNA mix was removed and replaced with the following ExoI reaction mixture:

| Component | Volume (uL) |
|---|---|
| ExoI buffer | 2 |
| water | 17 |
| ExoI | 1 |

The tubes were incubated at 37° C. for 30 minutes on a rotor. The tubes were then transferred to a thermal cycler for 15 minutes at 80° C. After incubating the tube at 80° C. for 15 minutes, 70 microliters of TE+Tween20 was added to the tube. A magnet was applied to the tube and the buffer was removed. The beads were then resuspended in 50 microliters TE+Tween20.

The cDNA attached to the beads were amplified by real-time PCR using the following amplification mixture:

| Component | Volume (uL) |
|---|---|
| 2x iTaq mix | 10 |
| GAPDH ILMN (10 uM) | 0.6 |
| ILR2 (10 uM) | 0.6 |
| bead | 2 |
| water | 6.8 |
| total | 20 |

The labeled cDNA amplicons were sequenced to detect the cell label, molecular index, and gene. Sequencing reads were aligned to the cell label, then the gene, and lastly the molecular label. A cell label associated with 4 or more genes or associated with 10 or more unique transcript molecules, with each unique transcript molecule sequenced more than once, was designated a cell. Principal component analysis with all of genes from Table 9 detected was used to identify the set of genes that had the greatest contribution to the variation in data. 632 single cells were used in the principal component analysis. Based on the sequencing results, 81 out of the 98 genes were detected.

Figure 32:
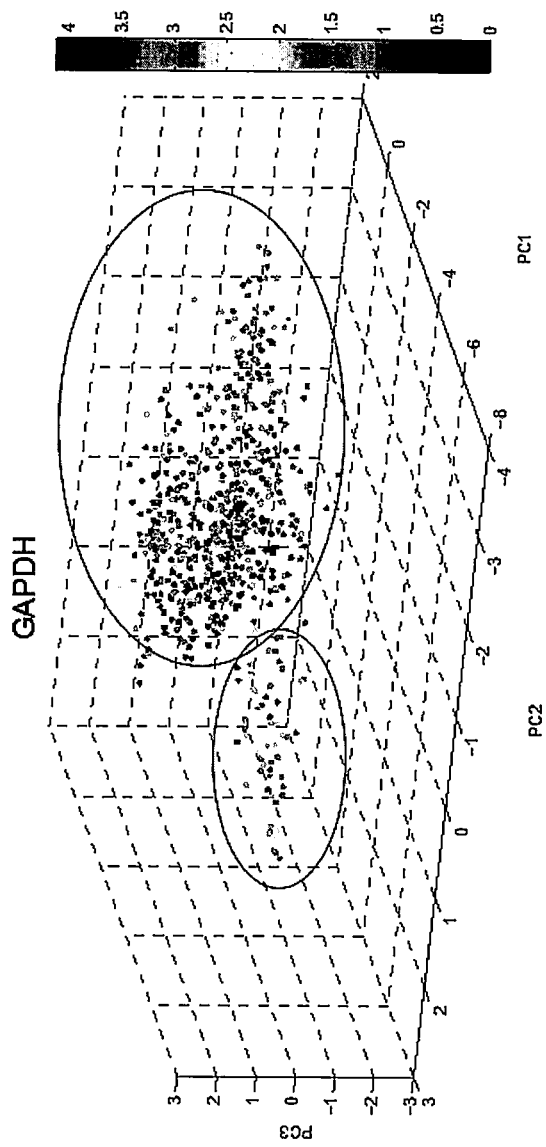
FIG. 32 Expression of GAPDH. Color indicates natural log of the number of unique transcript molecules observed per cell.

FIG. 32 shows a principal component analysis plot for GAPDH expression. As shown in FIG. 32, two cell clusters were observed based on the location of the principal component space.

Figure 33E:
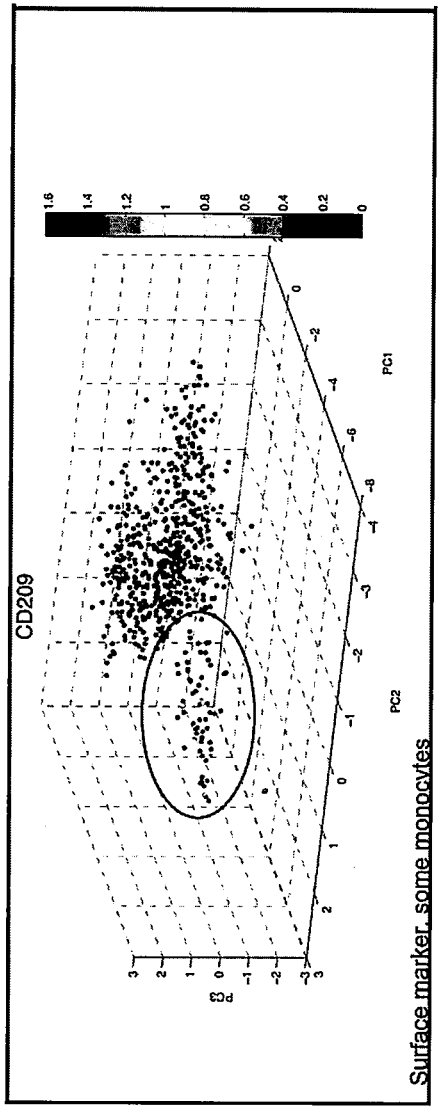
Figure 33F:
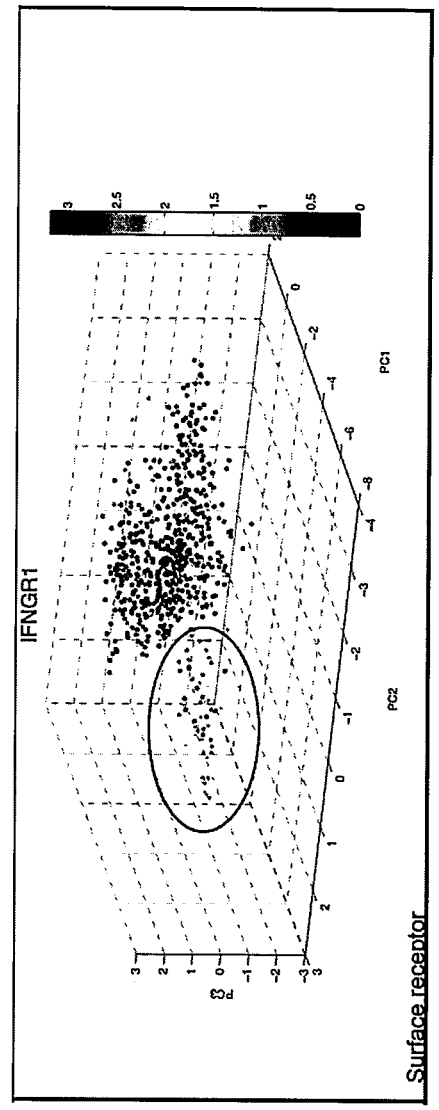

FIG. 33A-F shows the principal component analysis (PCA) for monocyte associated genes. FIG. 33A shows the PCA for CD16. FIG. 33B shows the PCA for CCRvarA. FIG. 33C shows the PCA for CD14. FIG. 33D shows the PCA for S100A12. FIG. 33E shows the PCA for CD209. FIG. 33F shows the PCA for IFNGR1.

FIG. 34A-B shows the principal component analysis (PCA) for pan-T cell markers (CD3). FIG. 34A shows the PCA for CD3D and FIG. 34B shows the PCA for CD3E.

Figure 35A:
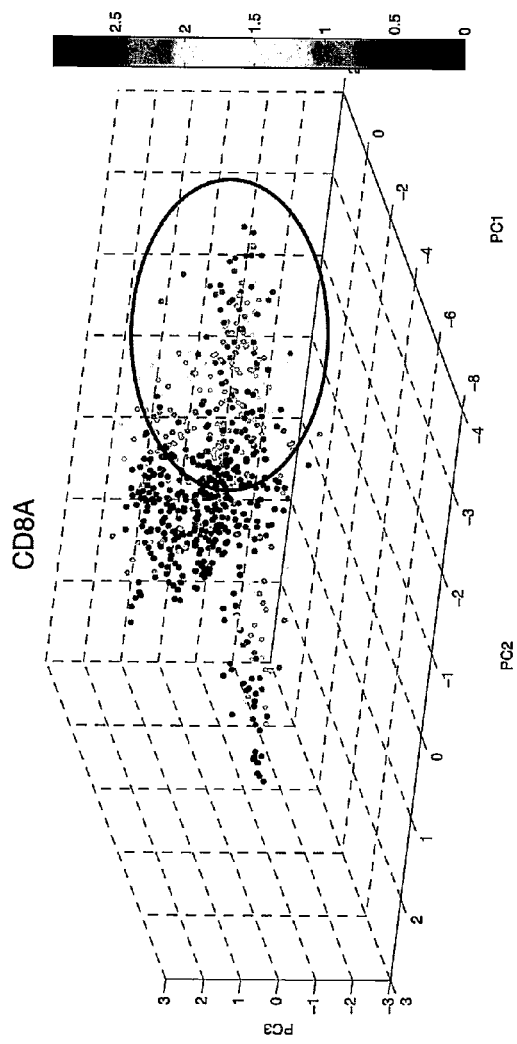
FIGS. 35A-E shows the principal component analysis (PCA) for CD8 T cell associated genes.
Figure 35B:
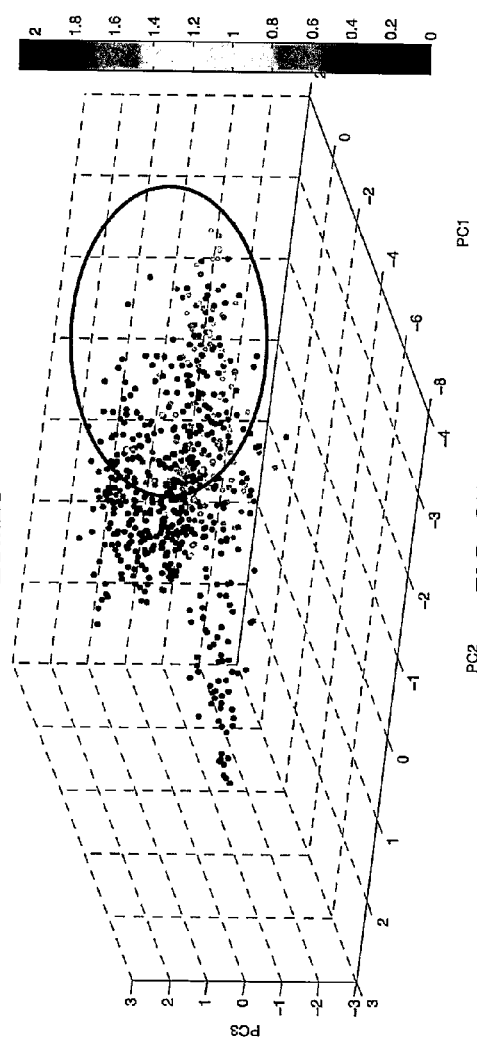
Figure 35C:
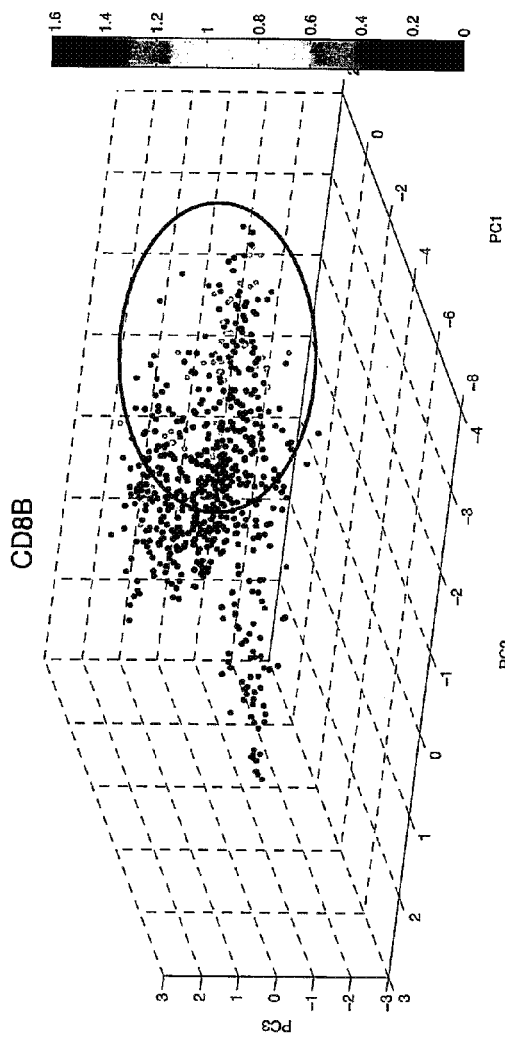
Figure 35D:
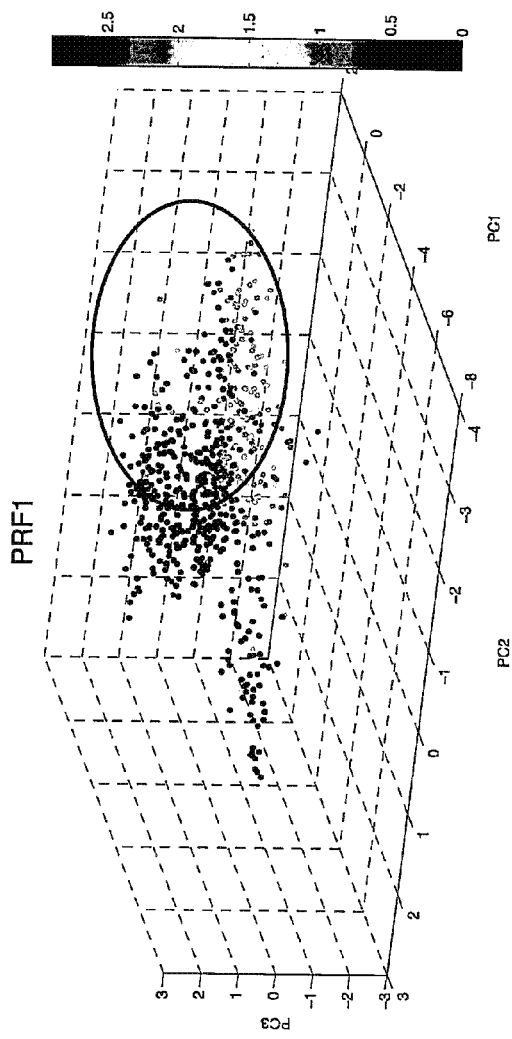
Figure 35E:
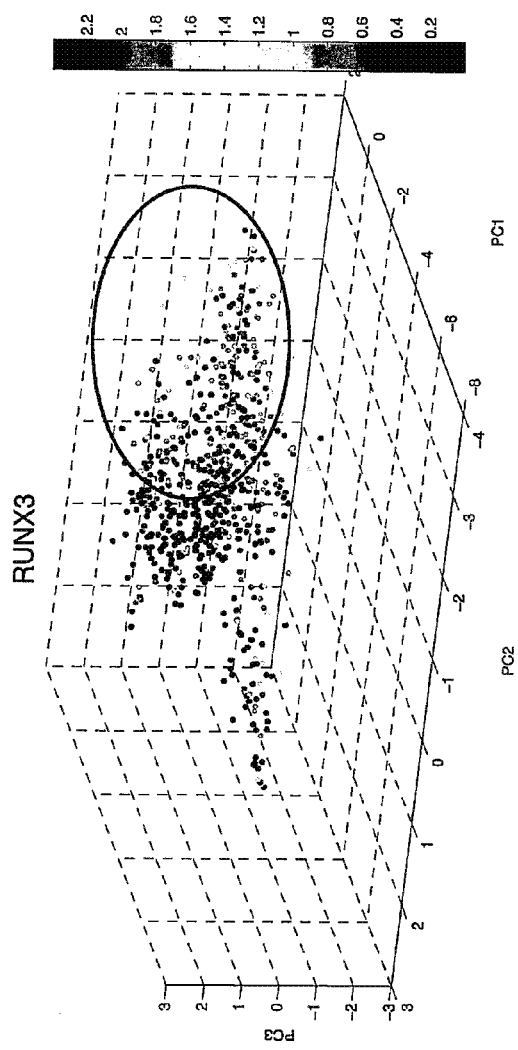

FIG. 35A-E shows the principal component analysis (PCA) for CD8 T cell associated genes. FIG. 35A shows the PCA for CD8A. FIG. 35B shows the PCA for EOMES. FIG. 35C shows the PCA for CD8B. FIG. 35D shows the PCA for PRF1. FIG. 35E shows the PCA for RUNX3.

Figure 36A:
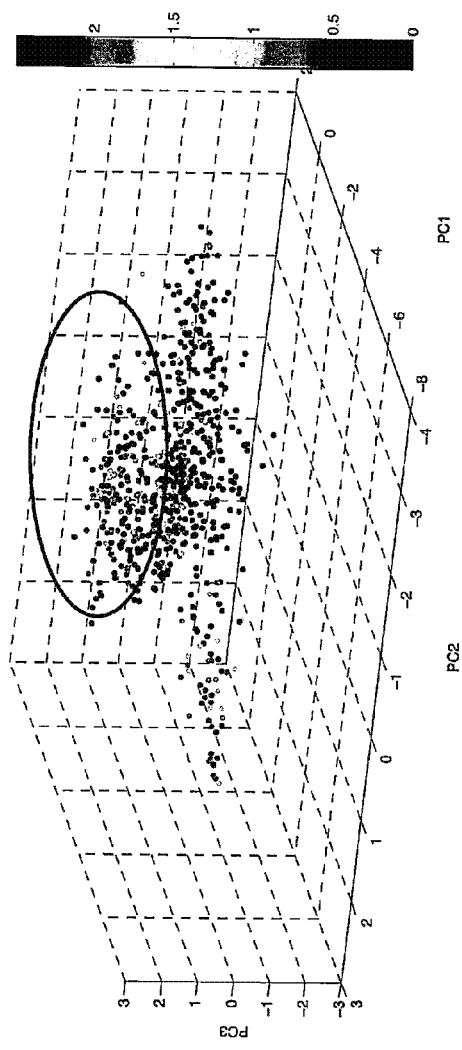
FIGS. 36A-C shows the principal component analysis (PCA) for CD4 T cell associated genes.
Figure 36B:
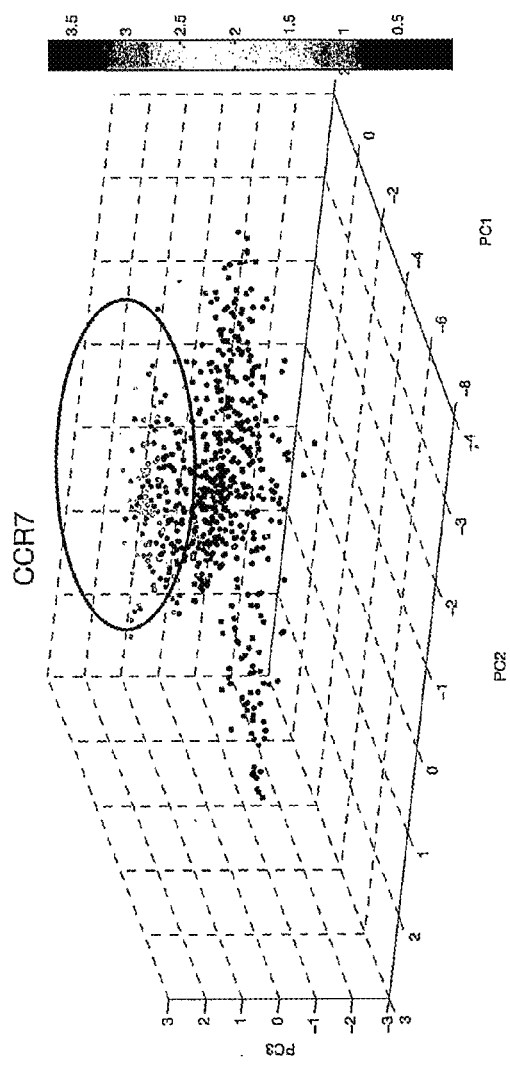
Figure 36C:
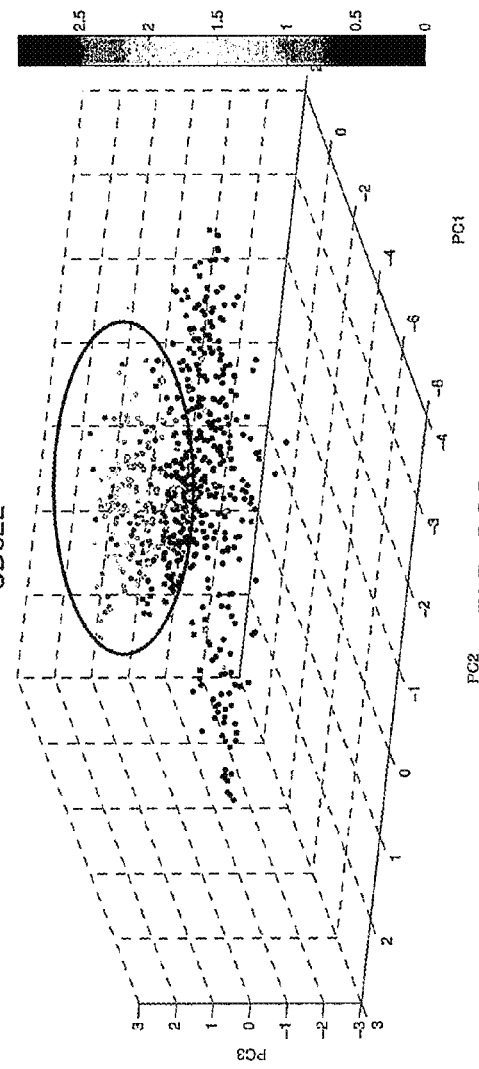

FIG. 36A-C shows the principal component analysis (PCA) for CD4 T cell associated genes. FIG. 36A shows the PCA for CD4. FIG. 36B shows the PCA for CCR7. FIG. 36C shows the PCA for CD62L.

Figure 37A:
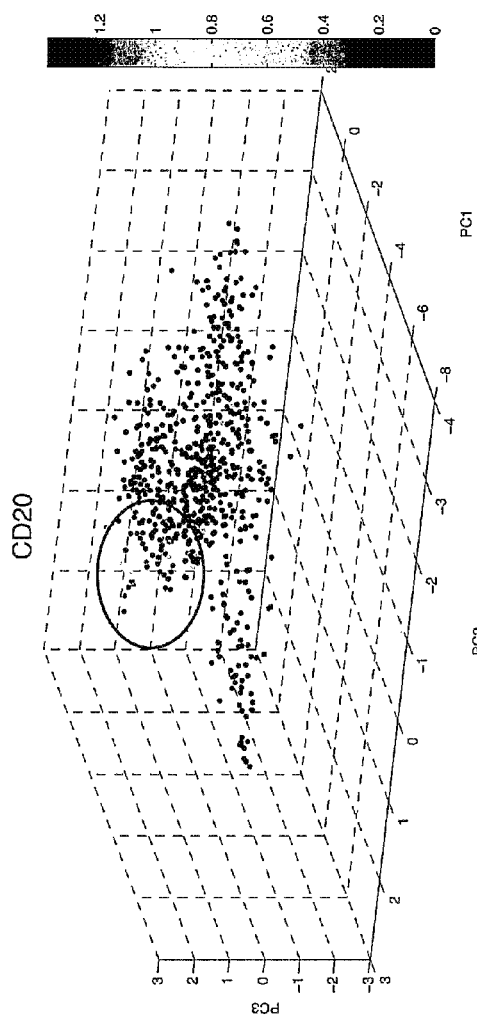
Figure 37B:
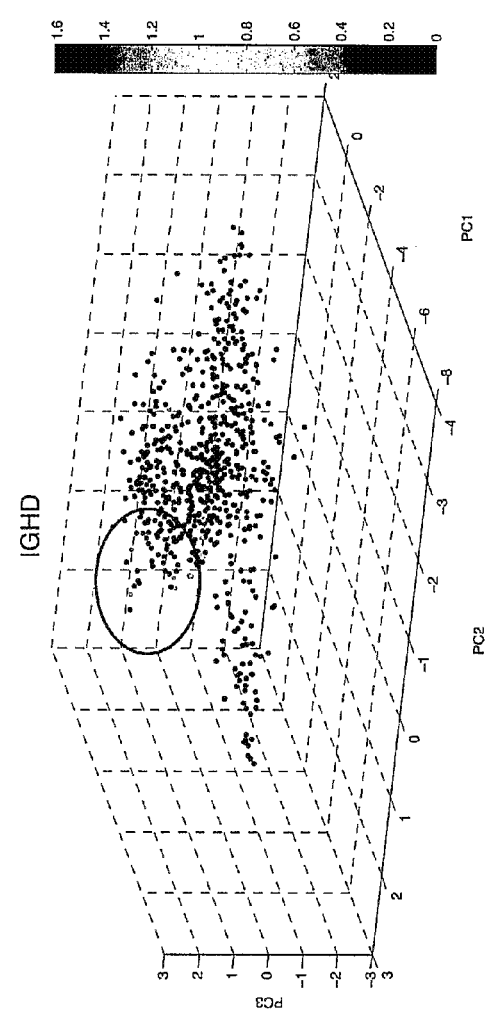
Figure 37C:
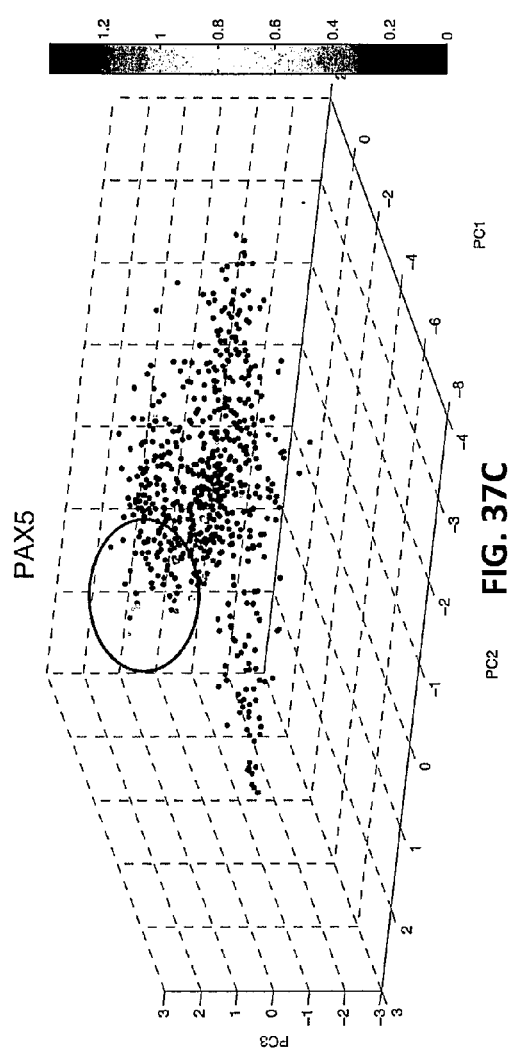
Figure 37D:
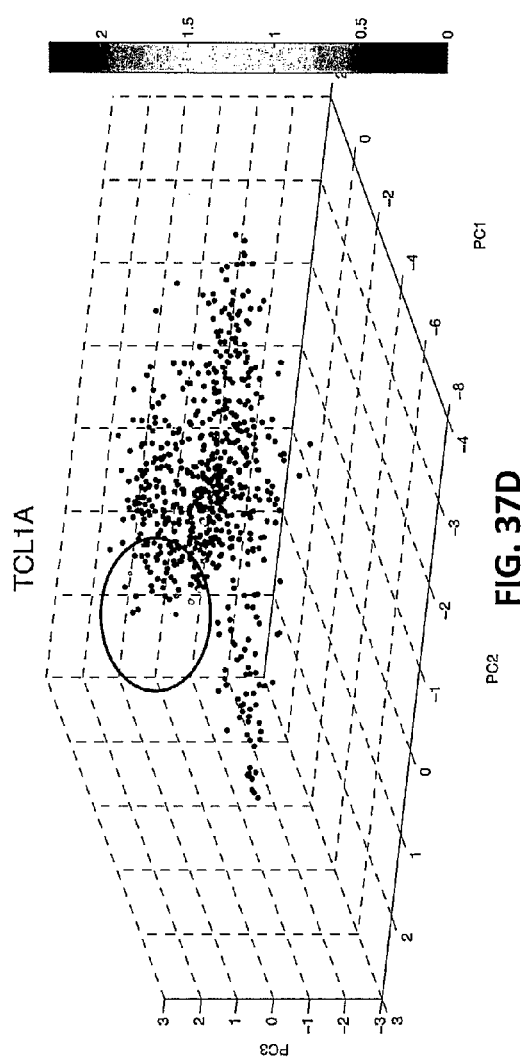

FIG. 37A-F shows the principal component analysis (PCA) for B cell associated genes. FIG. 37A shows the PCA for CD20. FIG. 37B shows the PCA for IGHD. FIG. 37C shows the PCA for PAX5. FIG. 37D shows the PCA for TCL1A. FIG. 37E shows the PCA for IGHM. FIG. 37F shows the PCA for CD24.

Figure 38C:
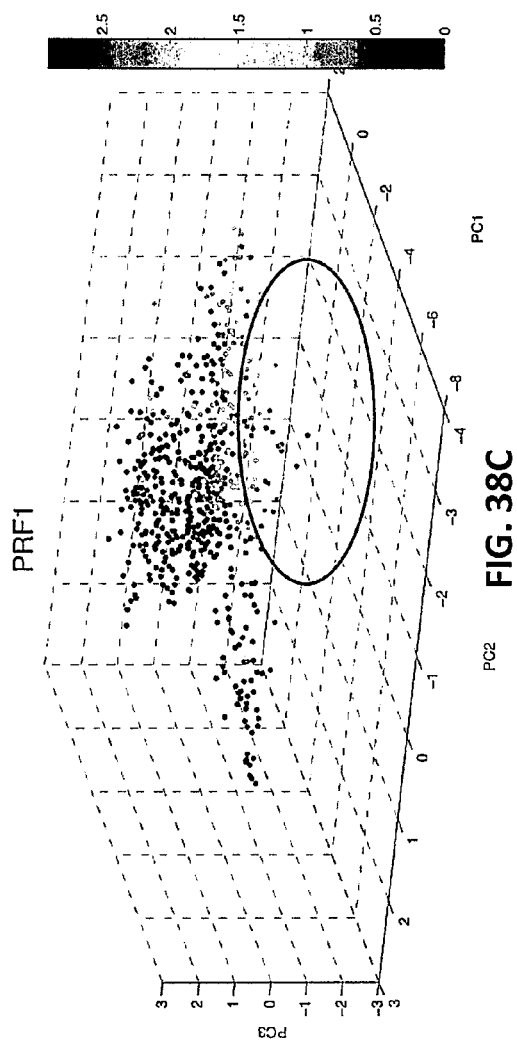

FIG. 38A-C shows the principal component analysis (PCA) for Natural Killer cell associated genes. FIG. 38A shows the PCA for KIR2DS5. FIG. 38B shows the PCA for CD16. FIG. 38C shows the PCA for CD62L.

Figure 39:
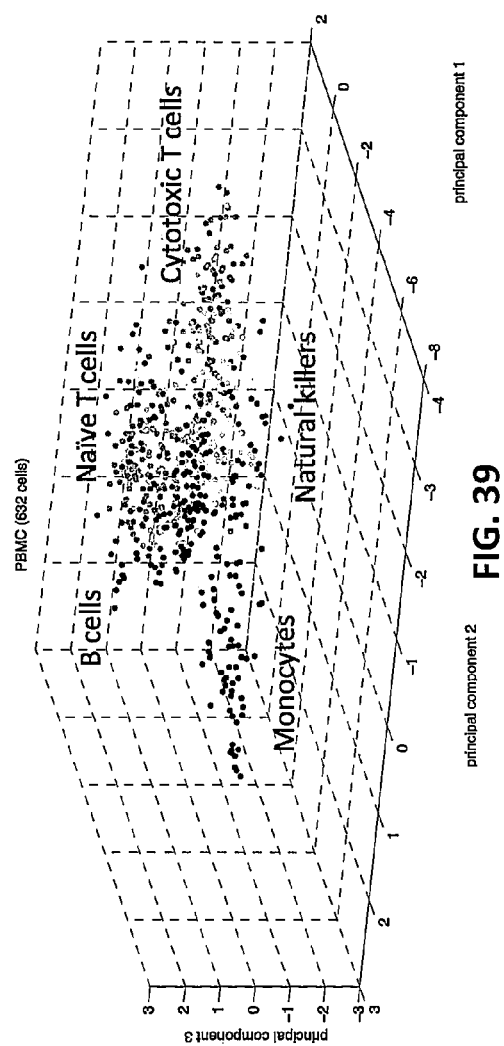
FIG. 39 Simultaneous identification of major cell types in a human PBMC sample (632 cells) by PCA analysis of 81 genes assayed by CytoSeq Cells with highly correlated expression profile are coded with similar color.
Figure 40A:
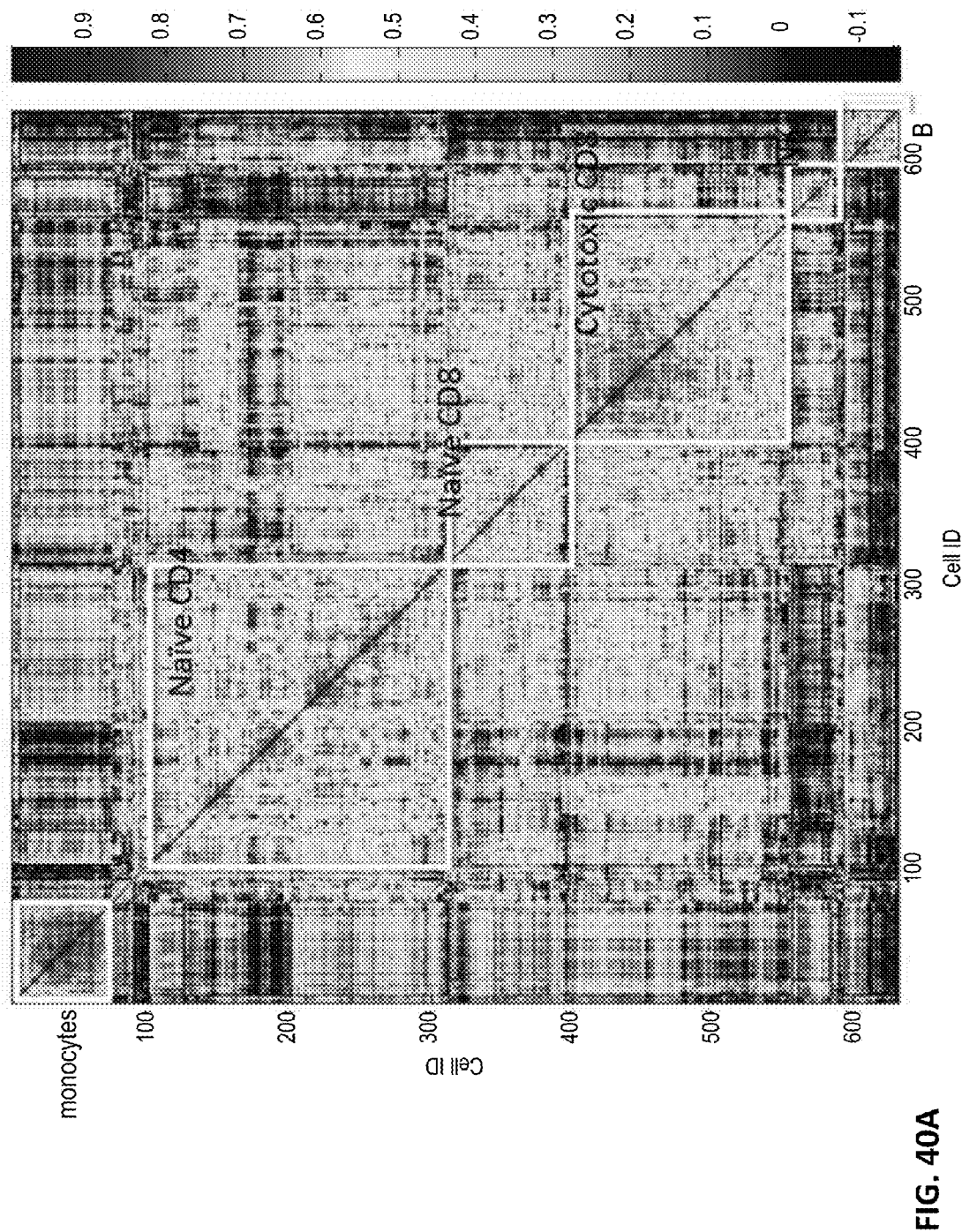
FIGS. 40A-B Correlation analysis of single cell gene expression profile of PBMC sample. 40A. A matrix showing the pairwise correlation coefficient across 632 cells in the sample. The cells are ordered such that those with highly correlated gene expression profile are grouped together. 40B. Heatmap showing the expression of each gene by each cell. The cells (columns) are ordered in the same manner as the correlation matrix above. The genes (rows) are ordered such that genes that share highly similar expression pattern across the cells are grouped together. The cell type of each cluster of cells may be identified by the group of genes the cells co-expressed. Within each major cell cluster, there is substantial degree of heterogeneity in terms of gene expression.
Figure 40B:
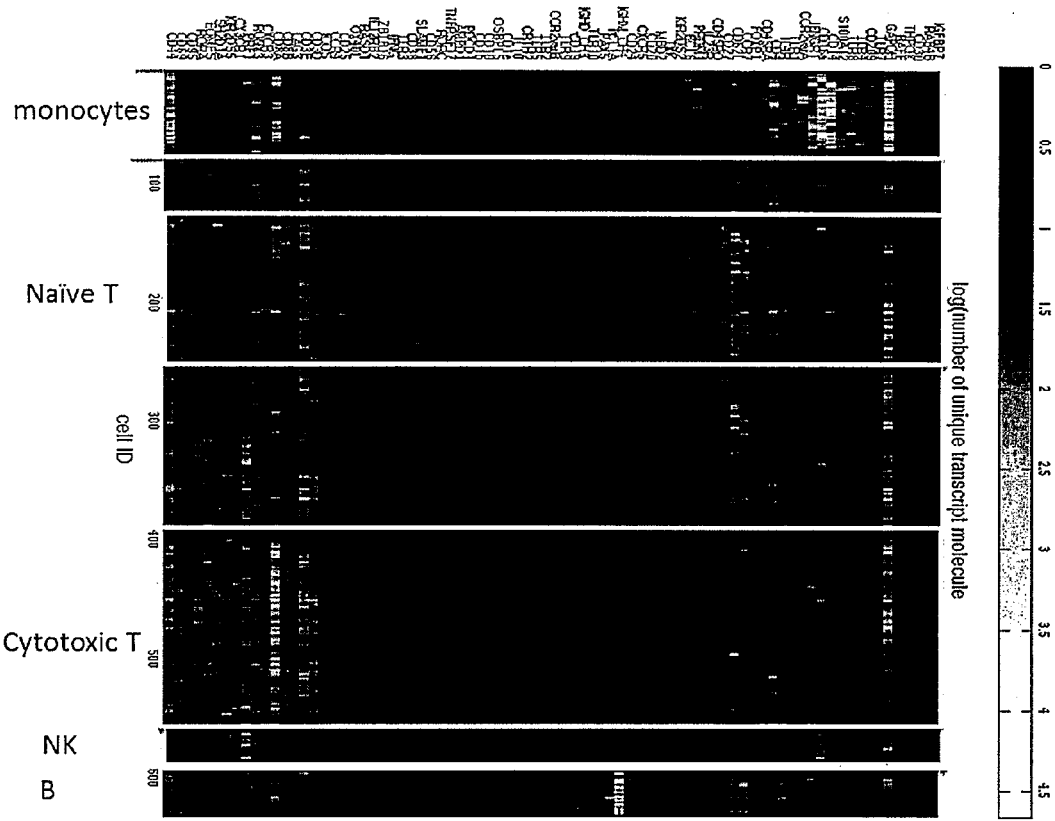
Figure 41:
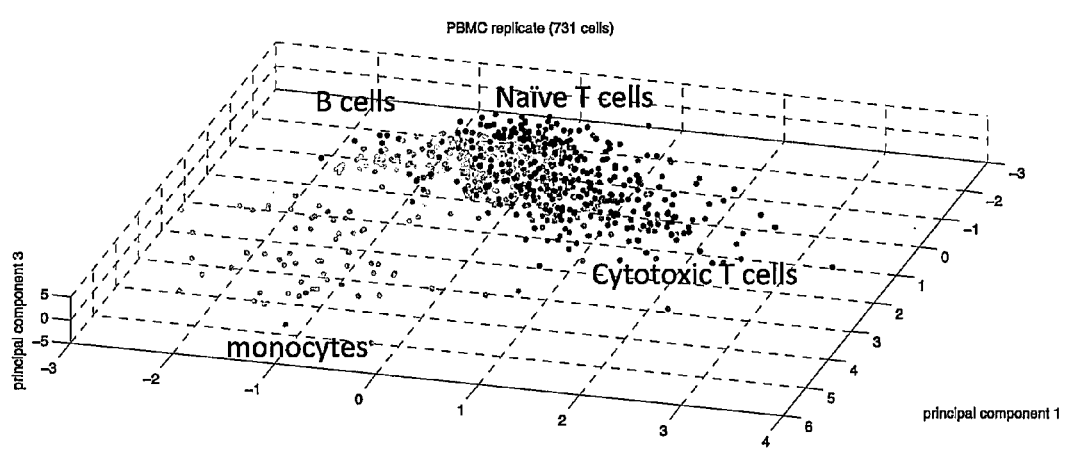
FIG. 41 data represents that of 731 cells from a replicate experiment of PBMC sample from the same donor. Cells with similar gene expression profile (based on hierarchical clustering using correlation coefficient) are plotted with similar color.
Figure 42:
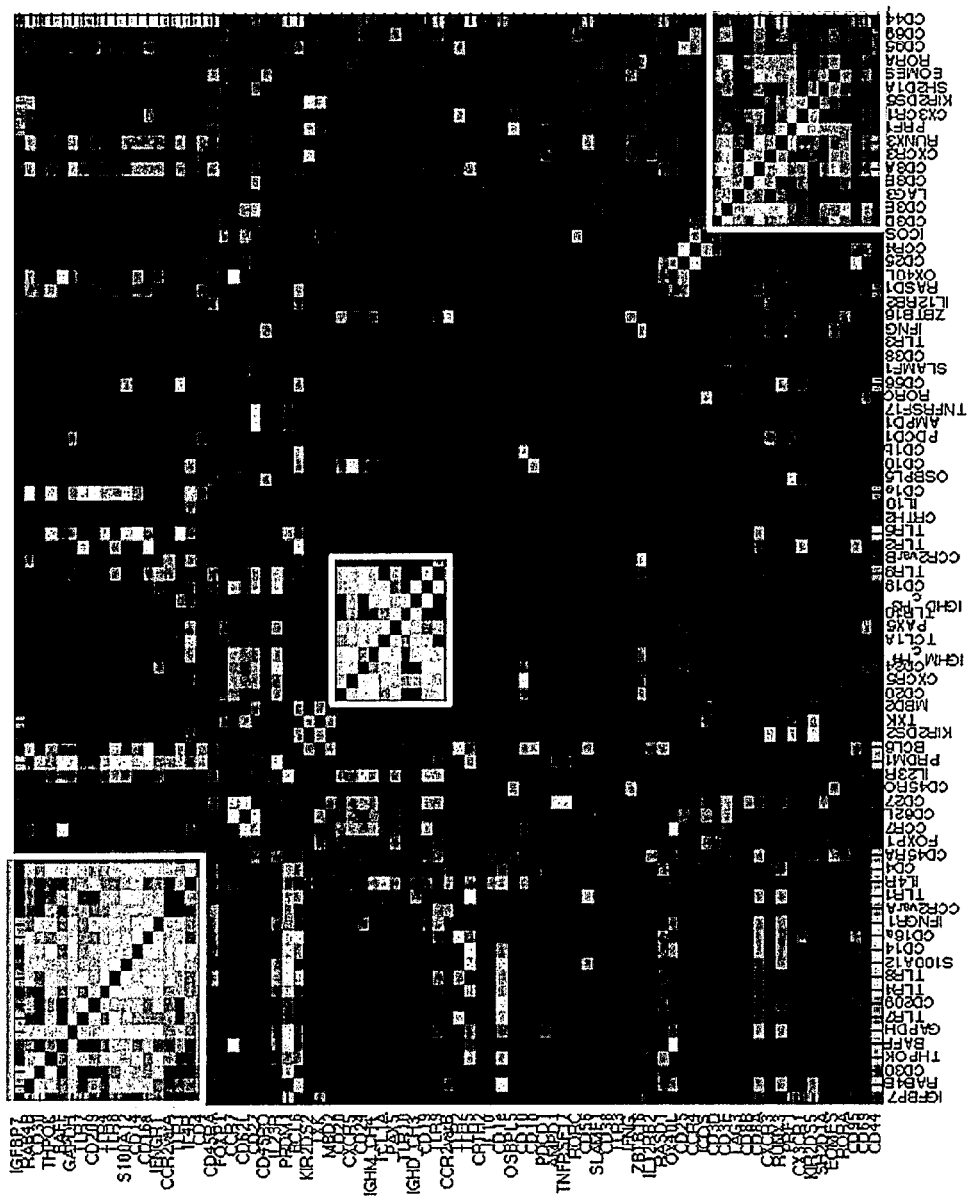
FIG. 42 shows a heat map demonstrating the correlation in gene expression profile between genes.

Based on the principal component analyses, monocytes and lymphocytes formed two distinct clusters on PC1. B, T, and NK cells formed another cluster that resided as a continuum in the cluster along PC2. FIG. 39 shows the PCA analysis of GAPDH expression with annotations for the cell types and cell subtypes. FIG. 40 depicts a heat map that shows the correlation in gene expression profile between cells. Along the diagonal starting with the left upper corner, the cells are monocytes, naive CD4 T cells, naive CD8 T cells, cytotoxic CD8 T cells, NK cells, and B cells. FIG. 41 shows another version of a heat map demonstrating the correlation between gene expression and cell type. FIG. 42 shows a heat map demonstrating the correlation in gene expression profile between genes.

Example 15

Uncovering Cellular Heterogeneity by Digital Gene Expression Cytometry

An approach for gene expression cytometry is presented combining next-generation sequencing with stochastic barcoding of single cells. Thousands of cells were deposited randomly onto an array of approximately 150,000 microwells. A library of beads bearing cell- and transcript-barcoding capture probes was added so that each cell is partitioned alongside a bead with a unique cell barcode. Following cell lysis, mRNAs were hybridized to beads, and were pooled for reverse transcription, amplification, and sequencing. The digital gene expression profile for each cell was reconstructed when barcoded transcripts were counted and assigned to the cell of origin. We applied the technology to dissect the human hematopoietic system into cell subpopulations, and to characterize the heterogeneous response of immune cells to in vitro stimulation. Furthermore, the high sensitivity of the method was demonstrated by the detection of rare cells, such as antigen-specific T cells, and tumor cells in a high background of normal cells.

Introduction

Understanding cellular diversity and function in a large collection of cells requires the measurement of specific genes or proteins expressed by individual cells. Flow cytometry is well established for measuring protein expression of single cells, yet mRNA expression measurements are typically conducted in bulk samples, obscuring individual cell contributions. While single cell mRNA expression measurements using microtiter plates or commercial microfluidic chips have recently been reported (1-5), these approaches are extremely low-throughput and difficult to scale. Because of these limitations, most studies to date are restricted in both the number of cells interrogated and the number of conditions explored.

Here, we have developed a highly scalable approach that enables routine, digital gene expression profiling of thousands of single cells across an arbitrary number of genes. Microscale engineering and combinatorial chemistry were used to label all mRNA molecules in a cell with a unique cellular barcode in a massively parallel manner. In addition, each transcript copy within a cell was tagged with a molecular barcode, allowing absolute digital gene expression measurements (6). Tagged mRNA molecules from all cells were pooled, amplified, and sequenced. The digital gene expression profile of each cell was reconstructed using the cell and molecular barcodes on each sequence. This highly scalable technology enables gene expression cytometry, which we term CytoSeq. We have applied the technique to multiparameter genetic classification of the hematopoietic system and demonstrated its use for studying cellular heterogeneity and detecting rare cells in a population.

Results

CytoSeq

Figure 43:
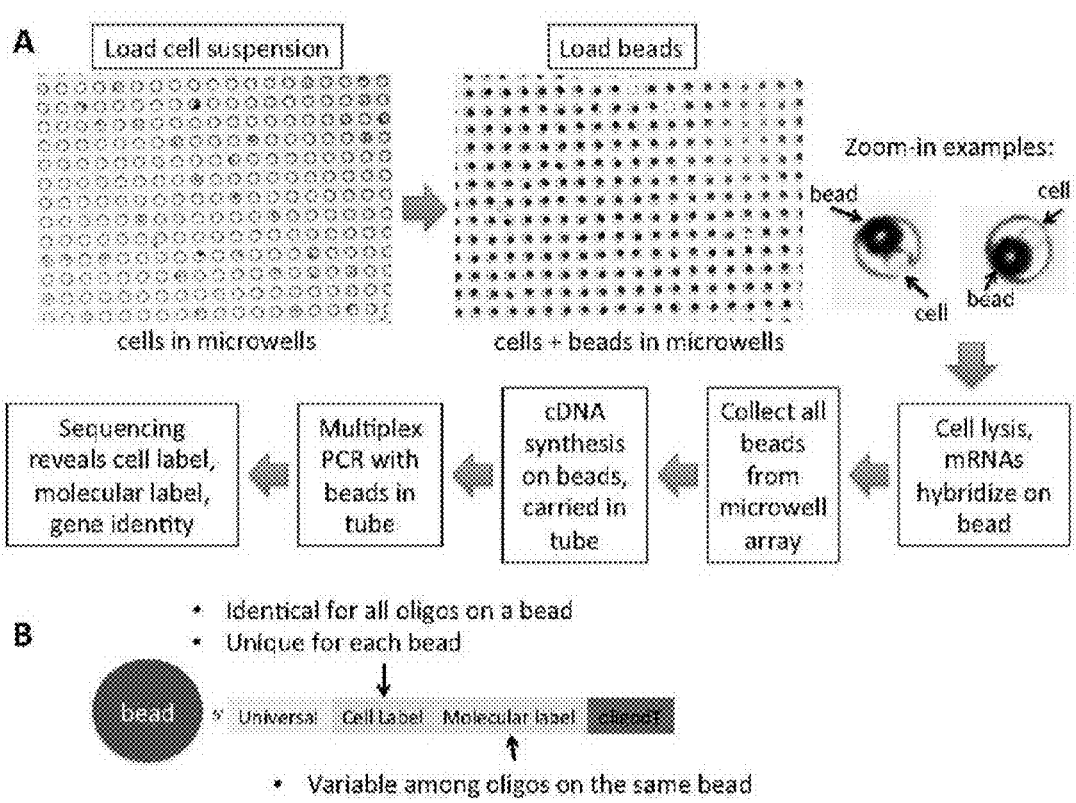
FIGS. 43 A-B illustrate the CytoSeq process.

The procedure was outlined in FIG. 43A. A cell suspension was first loaded onto a microfabricated surface with up to 150,000 microwells. Each 30 micron diameter microwell has a volume of ~20 picoliters. The number of cells was adjusted so that only ~1 out of 10 or more wells receives a cell. The cells settled within the wells by gravity.

Magnetic beads were loaded onto the microwell array to saturation, such that a bead sat partially on top of, or adjacent to, each cell within a well. The dimension of the bead was chosen such that each microwell may hold only one bead. Each magnetic bead carried approximately one billion oligonucleotide templates with the structure outlined in FIG. 43B. Each oligonucleotide displayed a universal priming site, followed by a cell label, a molecular label, and a capture sequence of oligo(dT). All the oligonucleotides on each bead have the same cell label but contain a diversity of molecular labels. We have devised a combinatorial split-pool method to synthesize beads with a diversity of close to one million. The probability of having two single cells being tagged with the same cell label was low (on the order of $10^{-4}$) because only ~10% of the wells were occupied by a single cell. Similarly, the diversity of the molecular labels on a single bead was on the order of $10^4$, and the likelihood of two transcript molecules of the same gene in the same cell being tagged with the same molecular label was also low.

Lysis buffer was applied onto the surface of the microwell array and diffuses into the microwells. The poly(dA) tailed mRNA molecules released from a cell hybridize to the oligo(dT) on the 3' end of the oligonucleotides on the bead. Because the cell was adjacent to the bead, under the high salt conditions of the lysis buffer and high local concentration of mRNA (tens of nanomolar), mRNA molecules were captured on the bead.

Figure 55:
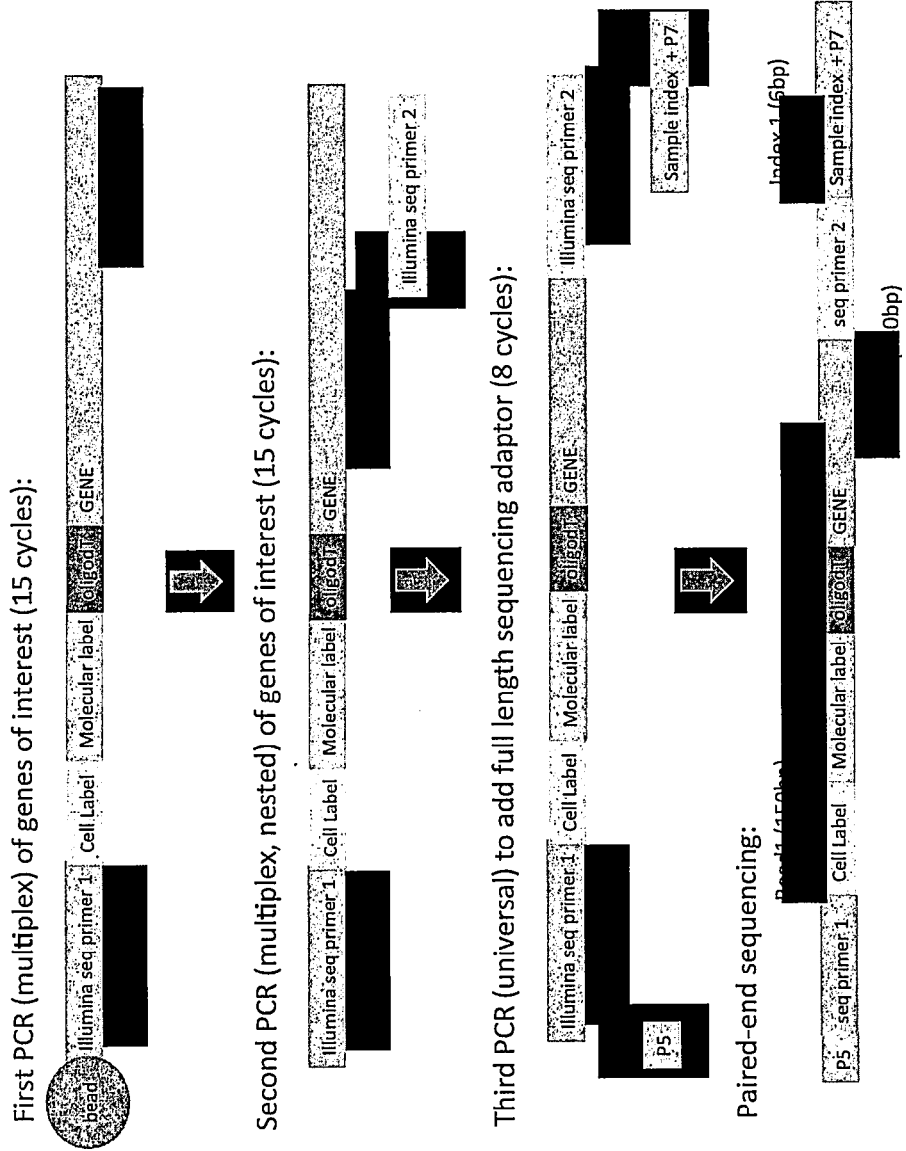
FIG. 55. Amplification scheme. The first PCR amplifies molecules attached to the bead using a gene specific primer and a primer against the universal Illumina sequencing primer 1 sequence. The second PCR amplifies the first PCR products using a nested gene specific primer flanked by Illumina sequencing primer 2 sequence, and a primer against the universal Illumina sequencing primer 1 sequence. The third PCR adds P5 and P7 and sample index to turn PCR products into Illumina sequencing library. 150 bp×2 sequencing reveals the cell label and molecule label on read 1, the gene on read 2, and the sample index on index 1 read.

After lysis and hybridization, all beads were collected from the microwell array into a tube using a magnet. From this point forward, all reactions were carried out in a single tube. cDNA synthesis was performed on the beads using conventional protocols (Methods). The cDNA molecules derived from each cell were covalently attached to their corresponding bead, each tagged on the 5'end with a cell label and a molecular label. Nested multiplex PCRs were carried out to amplify genes of interest (FIG. 55). Because the mRNA from each cell had been copied onto a bead as cDNA, the beads may be repeatedly amplified and analyzed, for example, for a different set of genes.

Sequencing of the amplicons revealed the cell label, the molecular label, and the gene identity (FIG. 55). Computational analysis grouped the reads based on the cell label, and collapsed the reads with the same molecular label and gene sequence into a single entry to suppress any amplification bias. The use of molecular label enabled us to measure the absolute number of molecules per gene per cell, and therefore allowed the direct comparison of cellular expression level across biological samples that may have undergone different depths of sequencing.

Identification of Distinct Cell Types in Controlled Cell Mixtures

In order to measure the ability of the method to separate two cell types, a ~1:1 mixture of K562 and Ramos cells was loaded onto the microwell array with 10,000 wells. Approximately 6000 cells were used to capture ~1000 cells. A panel of 12 genes was selected and amplified from the beads. The panel consists of 5 genes specific for K562 (myelogenous leukemia) cells, 6 genes specific for Ramos (follicular lymphoma) cells, and the housekeeping gene GAPDH (Table 18). With approximately 1000 cells captured on a 10,000-well array each with a single bead, only 10% of the beads should carry mRNA and one should in theory observe only a maximum of 1000 unique cell labels in the sequencing data. Indeed, we found 768 cell labels that were associated with significant number of reads after data filtering (see Methods for filtering criteria). As a comparison, we carried out bulk cell lysis and mRNA capture in a microcentrifuge tube with similar number of cells and beads, and observed a large number of cell labels with mostly only one read associated with each cell label. This demonstrates that the microwell array was effective in confining hybridization of mRNA from a single cell to the bead in the same well.

The gene expression profile of each of the 768 single cells was clustered using principal component analysis (PCA) (FIG. 31A). The first principal component (PC) clearly separated the single cells into two major clusters based on the cell type. The genes that contributed to the positive side of the first principal component were those that are specific to Ramos, while the genes that contributed to the negative side of the same principal component were those that are specific to K562. This successful clustering of cells into groups based on their specific expression showed that inter-well contamination, if any, was negligible. The second principal component highlighted the high degree of variability in fetal hemoglobin (HBG1) within the K562 cells, which had been observed previously (7).

TABLE 18

| Gene | Outer Primer | SEQ ID NO: | Nested Primer with Common 5' Flanking Sequence | SEQ ID NO: |
|---|---|---|---|---|
| CD41 | CCCCTGGAAGAAGATGATGA | 2 | CAGACGTGTGCTCTTCCGATCTTTCTCCAACA AGTTGCCTCC | 3 |
| GYPD | GAGGAAATGAAGCCAAACA CA | 4 | CAGACGTGTGCTCTTCCGATCTAATCGTGACC TTAAAGGCCC | 5 |
| GATA1 | TTAGCCACCTCATGCCTTTC | 6 | CAGACGTGTGCTCTTCCGATCTCTACTGTGGT GGCTCCGCT | 7 |
| GATA2 | GGAGGAGGATTGTGCTGATG | 8 | CAGACGTGTGCTCTTCCGATCTGTGTCCGCAT AAGAAAAGAATC | 9 |
| HBG1 | GCAAGAAGGTGCTGACTTCC | 10 | CAGACGTGTGCTCTTCCGATCTCTGCATGTGG ATCCTGAGAA | 11 |
| CD27 | CTGCAGTCCCATCCTCTTGT | 12 | CAGACGTGTGCTCTTCCGATCTGATGAGGTG GAGAGTGGGAA | 13 |
| IGJ | GGACATAACAGACTTGGAA GCA | 14 | CAGACGTGTGCTCTTCCGATCTCAATCCATTT TGTAACTGAACCTT | 15 |
| TCL1A | AAGCCTCTGGGTCAGTGGT | 16 | CAGACGTGTGCTCTTCCGATCTTGGAAAAGG GATAGAGGTTGG | 17 |
| CD74 | TAGACAGATCCCCGTTCCTG | 18 | CAGACGTGTGCTCTTCCGATCTACAGGGAGA AGGGATAACCC | 19 |
| SEPT9 | CAGCATCCCAGCCTTGAG | 20 | CAGACGTGTGCTCTTCCGATCTCCTCAATGGC CTTTTGCTAC | 21 |
| CD79a | CCTCTAAACTGCCCCACCTC | 22 | CAGACGTGTGCTCTTCCGATCTCCTTAATCGC TGCCTCTAGG | 23 |
| GAPDH | CACATGGCCUCCAAGGAGU AA | 24 | CAGACGTGTGCTCTTCCGATCTCAGCAAGAG CACAAGAGGAA | 25 |

Figure 31B:
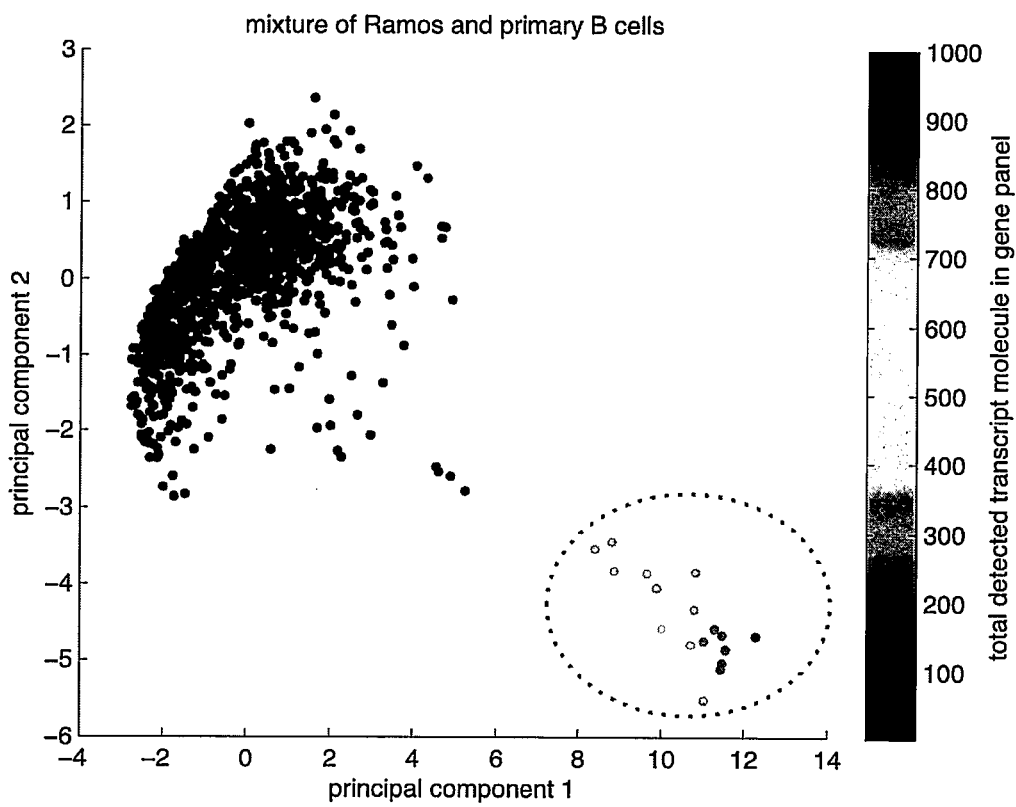
Figure 31C:
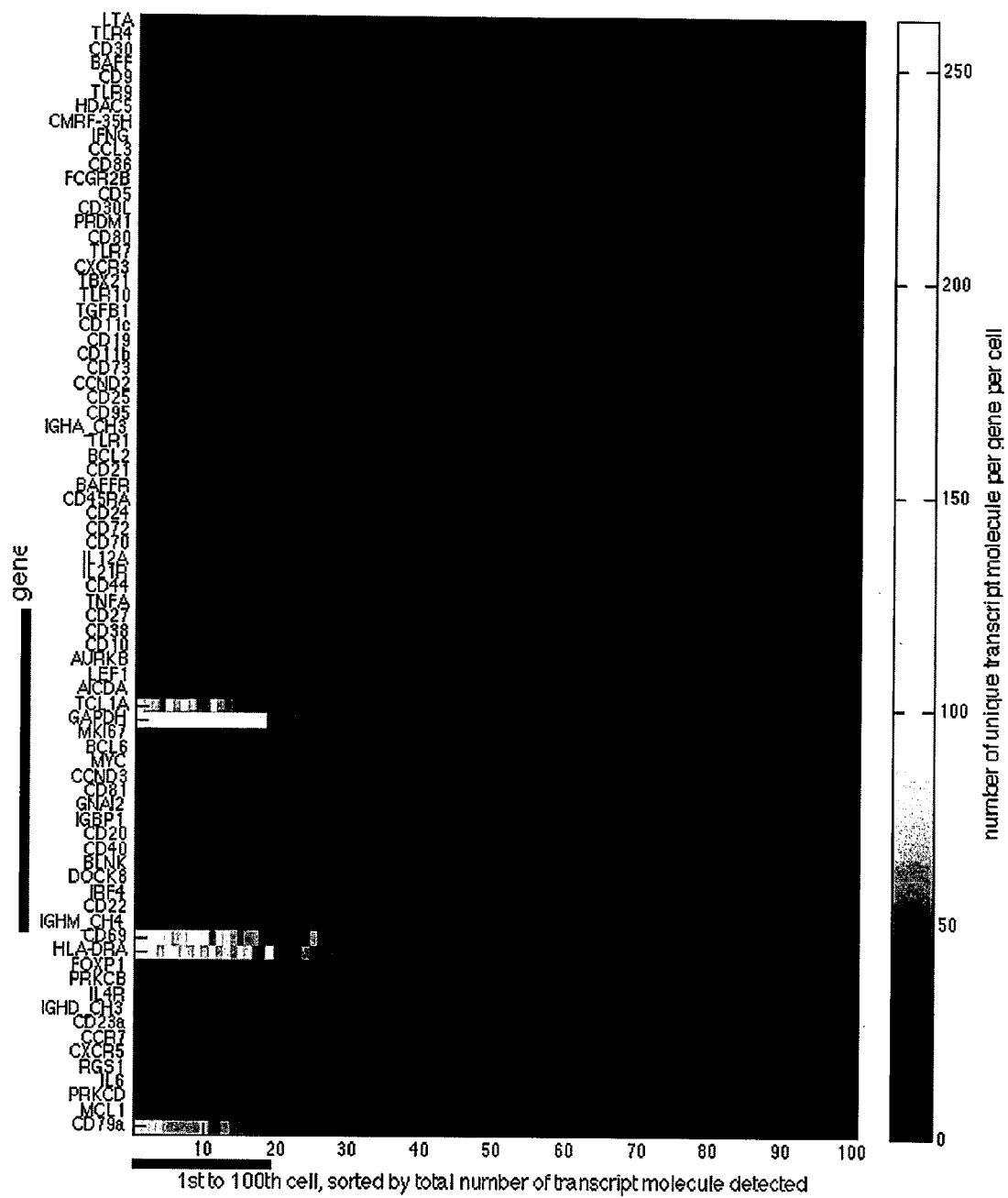
Figure 31D:
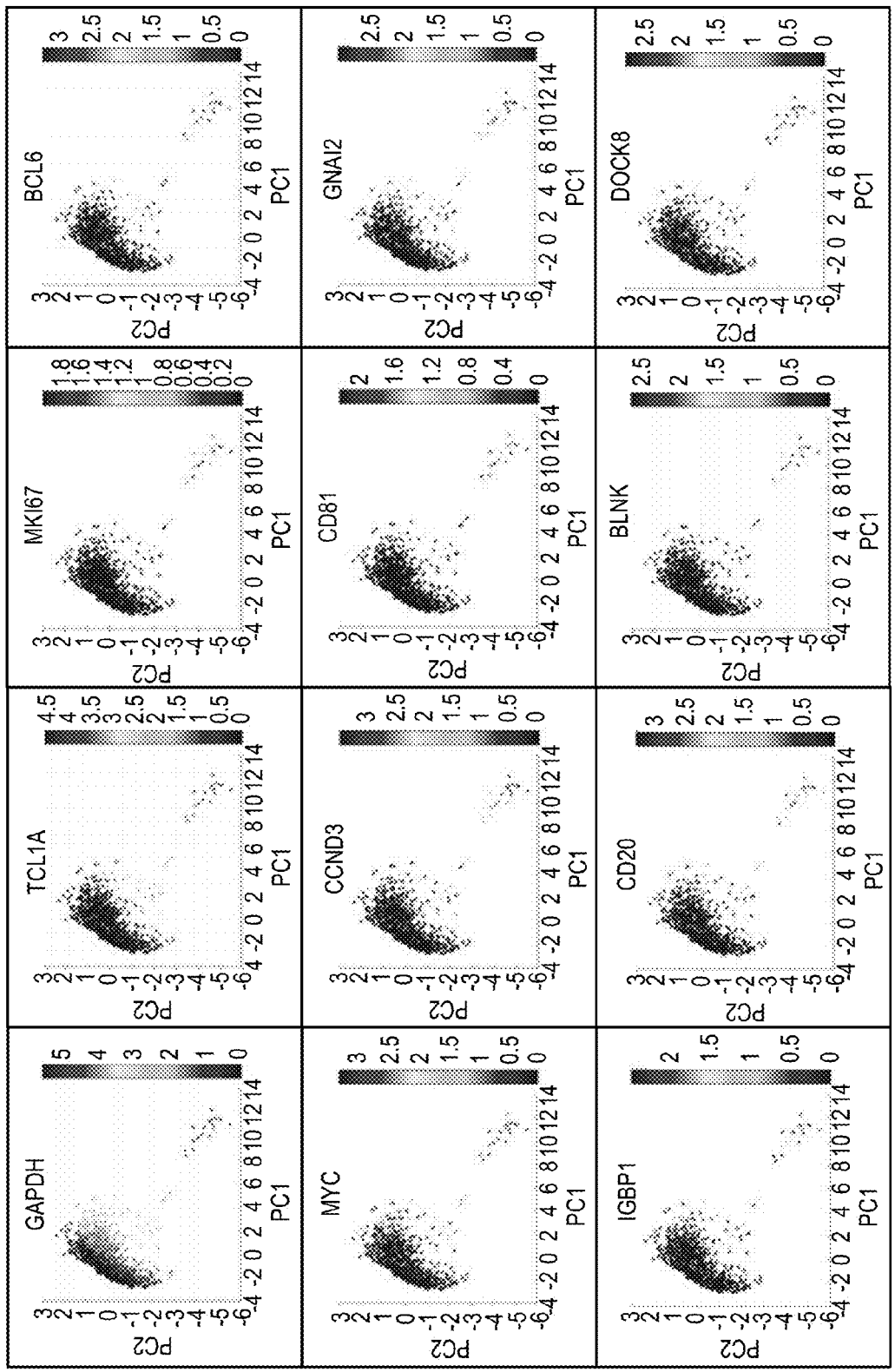
FIG. 31D. PCA analysis of primary B cells with spiked in Ramos cells. Color of each data point (single cell) indicates the log of the number of transcript molecules each cell carries for the particular gene. Top 7 rows: Genes that are preferentially expressed by the subset of 18 cells that are likely Ramos cells. First row genes (from left to right) include GAPDH, TCL1A, MKI67 and BCL6. Second row genes (from left to right) include MYC, CCND3, CD81 and GNAI2. Third row of genes (from left to right) include IGBP1, CD20, BLNK and DOCK8. Fourth row of genes (from left to right) include IRF4, CD22, IGHM and AURKB. Fifth row of genes (from left to right) include CD38, CD10, LEF1 and AICDA. Sixth row of genes (from left to right) include CD40, CD27, IL4R and PRKCD. Seventh row of genes (from left to right) include RGS1, MCL1, CD79a and HLA-DRA. Last row: Genes that are expressed preferentially by a subset of primary B cells but not especially enriched in those 18 cells. Genes in the last row (from left to right) include IL6, CD23a, CCR7 and CXCR5.
Figure 31D:
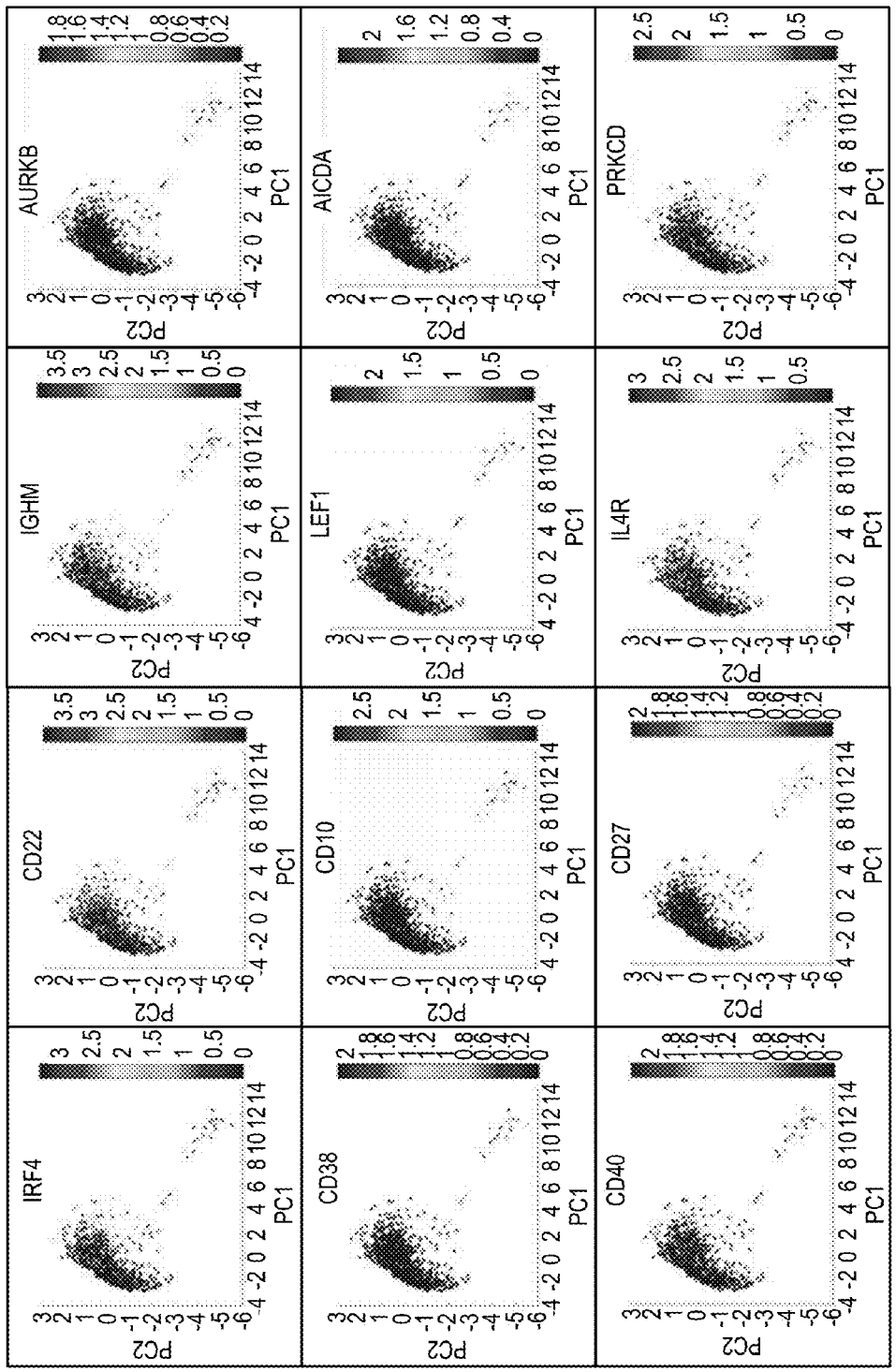
Figure 31D:
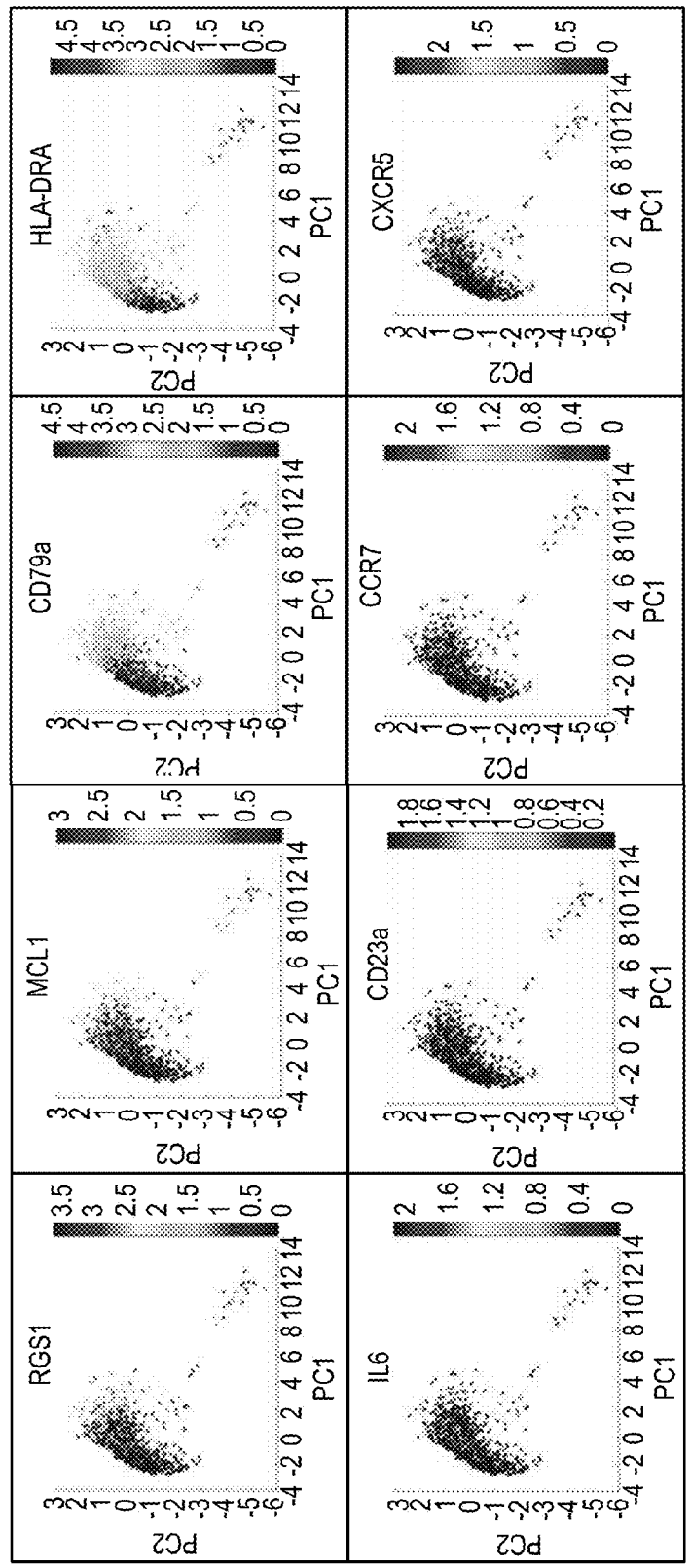

In another experiment, we spiked in Ramos (Burkitt lymphoma) cells at a few percentage into primary B cells from a healthy individual. A panel of 111 genes (Table 22) was designed to represent different states of B cells. 1198 single cells were analyzed. A small group of the population, constituting 18 single cells (~1.5% of the population), was found to have a distinct gene expression pattern as compared to the rest (FIG. 31B). The genes that were preferentially expressed by this group are known to be associated with Burkitt lymphoma, such as MYC and IgM, as well as B cell differentiation markers (CD10, CD20, CD22, BCL6) that are expressed specifically by follicular B cells, which are the subset of B cells that Burkitt lymphoma originates (FIGS. 31C and 31D). In addition, this group of cells carried higher level of CCND3 and GAPDH, as well as an overall higher mRNA content, as determined by the total number of unique mRNA molecules detected based on analyzing the molecular indices (FIG. 31B). This finding was consistent with the fact that lymphoma cells are physically larger than the primary B cells in normal individuals, and that they are rapidly proliferating and producing larger amount of transcripts.

Simultaneous Identification of Multiple Cell Types in Human PBMCs

While the controlled experiments involved artificial mixtures of two distinct types of cells, most naturally occurring biological samples contain diverse populations with numerous cell types and states with more subtle differences in gene expression profile. A prominent example is blood. We carried out an experiment in which we aimed to simultaneously identify all of the major cell types in human peripheral blood mononuclear cells (PBMCs), including monocytes, NK cells, and the different T and B cell subsets, by measuring the expression profile of a panel of 98 genes (Table 19) that are specific to each of the major cell type. Unlike traditional immunophenotyping that is limited mostly to surface protein markers, we included genes that encode cytokines, transcription factors, and intracellular proteins of various cellular functions in addition to surface proteins. We analyzed with PCA the digital gene expression profile of 632 single PBMCs using 81 genes present (FIG. 32-39). The first principal component clearly separated monocytes and lymphocytes into two orthogonal clusters, as evidenced by the expression of CD16a, CD14, S100A12, and CCR2 in one cluster, and lymphocyte associated genes in the other. The different subtypes of lymphocytes lay in a continuum along the second principal component, with B cells (expressing IgM, IgD, TCL1A, CD20, CD24, PAX5) at one end, naïve T cells (expressing CD4, CCR7, CD62L) in the middle, and cytotoxic T cells (expressing CD8A, CD8B, EOMES, PRF1) at the other end. Natural killer cells that express killer-like immunoglobulin receptor, CD16a, and perforin (PRF1) lay in the space between monocytes and cytotoxic T cells. We also observed that GAPDH, an indicator of cellular metabolism, was expressed at highest levels in monocytes and lowest in B cells, which are presumably mostly resting. Correlation analysis of gene expression profile across cells reiterated observations with PCA and revealed additional smaller subsets of cells within each major cell type (FIG. 40A-B). A replicate experiment of the same PBMC sample with 731 cells yielded largely similar segregation and cell type frequency (FIG. 41).

TABLE 22

| Gene | Outer Primer | SEQ ID NO: | Nested Primer with Common 5' Flanking Sequence | SEQ ID NO: |
|---|---|---|---|---|
| CD19 | GCAGGGTCCCAGTCCTATG | 26 | CAGACGTGTGCTCTTCCGATCTCCAATCATGAGGAAGATGCA | 27 |
| CD27 | TCCAGGAGGATTACCGAAAA | 28 | CAGACGTGTGCTCTTCCGATCTCCATCCAAGGGAGAGTGAGA | 29 |
| CD138 | AATGGCAAAGGAAGGTGGAT | 30 | CAGACGTGTGCTCTTCCGATCTGCAGACACCTTGGACATCCT | 31 |
| CD38 | AGATCTGAGCCAGTCGCTGT | 32 | CAGACGTGTGCTCTTCCGATCTTGGTGCAGAGCTGAAGATTTT | 33 |
| CD24 | AAAAGTGGGCTTGATTCTGC | 34 | CAGACGTGTGCTCTTCCGATCTTTTTGTTCGCATGGTCACAC | 35 |
| CD10 | ATATTCCTTTGGGCCTCTGC | 36 | CAGACGTGTGCTCTTCCGATCTTCAAGTTTGGGTCTGTGCTG | 37 |
| CD95 | CCCCCGAAAATGTTCAATAA | 38 | CAGACGTGTGCTCTTCCGATCTTGCTCTTGTCATACCCCCA | 39 |
| CD21 | TAGCTTCCTCCTCTGGTGGT | 40 | CAGACGTGTGCTCTTCCGATCTTTTGCCTTTCCATAATCACTCA | 41 |
| CXCR3 | CTGGCTCTCCCCAATATCCT | 42 | CAGACGTGTGCTCTTCCGATCTGCTCTGAGGACTGCACCATT | 43 |
| CD40 | GTGGTGTTGGGGTATGGTTT | 44 | CAGACGTGTGCTCTTCCGATCTATACACAGATGCCCATTGCA | 45 |
| CD69 | AGACAGGTCCTTTTCGATGG | 46 | CAGACGTGTGCTCTTCCGATCTTGTGCAATATGTGATGTGGC | 47 |
| CD1c | TTGAGACAGGCACATACAGCTT | 48 | CAGACGTGTGCTCTTCCGATCTTTGCTTCCTCAATCTGTCCA | 49 |
| IL10 | CCCCAACCACTTCATTCTTG | 50 | CAGACGTGTGCTCTTCCGATCTTTCAATTCCTCTGGGAATGTT | 51 |
| IL4R | TGCCTAGAGGTGCTCATTCA | 52 | CAGACGTGTGCTCTTCCGATCTGTTGATGCTGGAGGCAGAAT | 53 |
| IL21R | AGCCTGGGTCACAGATCAAG | 54 | CAGACGTGTGCTCTTCCGATCTAGGTAGGAGGGTGGATGGAG | 55 |
| IL6R | CCAGCACCAGGGAGTTTCTA | 56 | CAGACGTGTGCTCTTCCGATCTAGGAAAGGATTGGAACAGCA | 57 |
| CXCL12 | GGGTTTCAGGTTCCAATCAG | 58 | CAGACGTGTGCTCTTCCGATCTTTTGTAACTTTTTGCAAGGCA | 59 |
| CCL3 | GTGAGGAGTGGGTCCAGAAA | 60 | CAGACGTGTGCTCTTCCGATCTAGTGGGAGGAGCAGGAG | 61 |
| CCL14 | CCATTCCCTTCTTCCTCCTC | 62 | CAGACGTGTGCTCTTCCGATCTTACCTACAAGATCCCGCGTC | 63 |
| CCL20 | TTGGACATAGCCCAAGAACA | 64 | CAGACGTGTGCTCTTCCGATCTTGTGCCTCACTGGACTTGTC | 65 |
| CCL18 | ACCTGAAGCTGAATGCCTGA | 66 | CAGACGTGTGCTCTTCCGATCTCTGGAGGCCACCTCTTCTAA | 67 |
| TCL1A | GGTAAACACGCCTGCAAAC | 68 | CAGACGTGTGCTCTTCCGATCTCAGGACTCAGAAGCCTCTGG | 69 |
| TACI | CAACAAAGCACAGTGTTAAATGAA | 70 | CAGACGTGTGCTCTTCCGATCTTGTGTCAGCTACTGCGGAAA | 71 |
| AICDA | TGAGCAGATCCACAGGAAAA | 72 | CAGACGTGTGCTCTTCCGATCTGAAATGGAGTCTCAAAGCTTCA | 73 |
| FCRL4 | TCCCAACTACGCTGATTTGA | 74 | CAGACGTGTGCTCTTCCGATCTGACCAAAAGGAATGTGTGGG | 75 |
| BCL2 | TGCAAGAGTGACAGTGGATTG | 76 | CAGACGTGTGCTCTTCCGATCTTCAACCAAGGTTTGCTTTTGT | 77 |
| FASLG | AGAGGCTGAAAGAGGCCAAT | 78 | CAGACGTGTGCTCTTCCGATCTAATATGGGTTGCATTTGGTCA | 79 |

TABLE 22-continued

| Gene | Outer Primer | SEQ ID NO: | Nested Primer with Common 5' Flanking Sequence | SEQ ID NO: |
|---|---|---|---|---|
| BCL6 | AAATCTGCAGAAGGAAAAATGTG | 80 | CAGACGTGTGCTCTTCCGATCTAGTTTTCAATGATGGGCGAG | 81 |
| AURKB | GCTCAAGGGAGAGCTGAAGA | 82 | CAGACGTGTGCTCTTCCGATCTGACTACCTGCCCCCAGAGAT | 83 |
| CD81 | GTGGCGTGTATGAGTGGAGA | 84 | CAGACGTGTGCTCTTCCGATCTCACTCGCCCAGAGACTCAG | 85 |
| CD80 | GCACATCTCATGGCAGCTAA | 86 | CAGACGTGTGCTCTTCCGATCTGCTTCACAAACCTTGCTCCT | 87 |
| CD23a | ACATTTTCTGCCACCCAAAC | 88 | CAGACGTGTGCTCTTCCGATCTAACAGCACCCTCTCCAGATG | 89 |
| CD44 | GCCTGGTAGAATTGGCTTTTC | 90 | CAGACGTGTGCTCTTCCGATCTTTTTGTAGCCAACATTCATTCAA | 91 |
| LEF1 | CAATTGGCAGCCCTATTTCA | 92 | CAGACGTGTGCTCTTCCGATCTGTTCAGCAGACTGGTTTGCA | 93 |
| CXCR5 | CCGTGAGGATGTCACTCAGA | 94 | CAGACGTGTGCTCTTCCGATCTACGAGGAAGCCCTAAGACGT | 95 |
| PRKCB | TTGAGCCTGGGGTGTAAGAC | 96 | CAGACGTGTGCTCTTCCGATCTGTCTTCCAGGATTCACGGTG | 97 |
| PRKCD | GAGCACCTCCTGGAAGATTG | 98 | CAGACGTGTGCTCTTCCGATCTTAAGCACCAGTGGGACTGTG | 99 |
| CD20 | TAGGAGCAGGCCTGAGAAAA | 100 | CAGACGTGTGCTCTTCCGATCTGATTCCTCTCCAAACCCATG | 101 |
| CD30 | TGTTTTGGGGAAAGTTGGAG | 102 | CAGACGTGTGCTCTTCCGATCTCTGTTTGCCCAGTGTTTGTG | 103 |
| CD30L | TGCAACCCAACTGTGTGTTA | 104 | CAGACGTGTGCTCTTCCGATCTTTTCACCAACTGTTCTCTGAGC | 105 |
| BAFFR | GCCCTGAGCAACAATAGCAG | 106 | CAGACGTGTGCTCTTCCGATCTTTCAGCTCTTCACTCCAGCA | 107 |
| CMRF-35H | AGGAAAAGATGTGGCTCACG | 108 | CAGACGTGTGCTCTTCCGATCTGGAGTTGGGGAGAACTGTCA | 109 |
| PRDM1 | TCGAATAATCCAGGGAAACC | 110 | CAGACGTGTGCTCTTCCGATCTACCAAAGCATCACGTTGACA | 111 |
| HLA-DRA | GGCTTTACAAAGCTGGCAAT | 112 | CAGACGTGTGCTCTTCCGATCTTATGCCTCTTCGATTGCTCC | 113 |
| GNAI2 | CCTTGAGTGTGTCTGCGTGT | 114 | CAGACGTGTGCTCTTCCGATCTCCACAGAATTGGGTTCCAAG | 115 |
| RGS1 | AACTGGGAAGGCCAGGTAAC | 116 | CAGACGTGTGCTCTTCCGATCTTGTTTTCAAATTGCCATTGC | 117 |
| CD5 | CTTTCTCCACGCCATTTGAT | 118 | CAGACGTGTGCTCTTCCGATCTACTAGGATATGGGTGGGCT | 119 |
| CD22 | GGGATCTGCTCGTCATCATT | 120 | CAGACGTGTGCTCTTCCGATCTGTTTCTGCCTCTGAGGGAAA | 121 |
| PIK3CD | GCGTGCGCGTTATTTATTTA | 122 | CAGACGTGTGCTCTTCCGATCTTGTCTGGGGAAGGCAAGTTA | 123 |
| DOCK8 | GCAGTCAGCCAGAAATCACA | 124 | CAGACGTGTGCTCTTCCGATCTTTTTTCTCCTCTCTGGGACCA | 125 |
| CD11b | TGAAAAGTCTCCCTTTCCAGA | 126 | CAGACGTGTGCTCTTCCGATCTCCTTCAGACAGATTCCAGGC | 127 |
| FCGR2B | GGAGAGGAGAGATGGGGATT | 128 | CAGACGTGTGCTCTTCCGATCTGAGTGAGTGCCCCTTTTCTT | 129 |
| CD72 | CTCATGCCAACAAGAACCTG | 130 | CAGACGTGTGCTCTTCCGATCTTGACCCACACCTGACACTTC | 131 |
| BCL11B | TCGTGGAACACAGGCAAAC | 132 | CAGACGTGTGCTCTTCCGATCTTTGCATTTGTACTGGCAAGG | 133 |
| CD86 | TCAAGGCAACCAGAGGAAAC | 134 | CAGACGTGTGCTCTTCCGATCTACTAAGGGATGGGCAGTCT | 135 |
| TBX21 | ACCTTTTCGTTGGCATGTGT | 136 | CAGACGTGTGCTCTTCCGATCTTCAGGGAAAGGACTCACCTG | 137 |
| FOXP1 | ATGCTGAAGGCATTTCTTGG | 138 | CAGACGTGTGCTCTTCCGATCTCTGTGAGCATGGTGCTTCAT | 139 |
| MCL1 | GAGGGGAGTGGTGGGTTTAT | 140 | CAGACGTGTGCTCTTCCGATCTCAAAAGGGAAAGGGAGGATT | 141 |
| IFNB1 | AGGGGAAAACTCATGAGCAG | 142 | CAGACGTGTGCTCTTCCGATCTTCACTGTGCCTGGACCATAG | 143 |
| BLNK | TTGGGCAGAAAGAAAAATGG | 144 | CAGACGTGTGCTCTTCCGATCTCAAAAGATTCCACCAGACTGAA | 145 |
| CD40LG | CCTCCCCCAGTCTCTCTTCT | 146 | CAGACGTGTGCTCTTCCGATCTGAGTCAGGCCGTTGCTAGTC | 147 |
| IGBP1 | GGCTGATCTTCCCACAACAC | 148 | CAGACGTGTGCTCTTCCGATCTACGAGGGCAAAGATGCTAAA | 149 |
| IRF4 | ATTCCCGTGTTGCTTCAAAC | 150 | CAGACGTGTGCTCTTCCGATCTAGAACTGCCAGCAGGTAGGA | 151 |
| CD79a | CACTTCCCTGGGACATTCTC | 152 | CAGACGTGTGCTCTTCCGATCTCTCACTCTTCTCCAGGCCAG | 153 |
| LTA | TGATGTCTGTCTGGCTGAGG | 154 | CAGACGTGTGCTCTTCCGATCTCCACACACAGAGGAAGAGCA | 155 |

TABLE 22-continued

| Gene | Outer Primer | SEQ ID NO: | Nested Primer with Common 5' Flanking Sequence | SEQ ID NO: |
|---|---|---|---|---|
| HDAC5 | CCAGCCTGTAGGAAACCAAA | 156 | CAGACGTGTGCTCTTCCGATCTCTCCTTCTATCTCCAGGGCC | 157 |
| RAG1 | GGATGCAGGTGGTTTTTGAT | 158 | CAGACGTGTGCTCTTCCGATCTCATTGTACCCATTTTACATTTTCTT | 159 |
| RAG2 | CAAACCTTAAACACCCAGAAGC | 160 | CAGACGTGTGCTCTTCCGATCTATAACAATTCGGCAGTTGGC | 161 |
| CD1d | GAACCAGTTTCCTCCTGTGC | 162 | CAGACGTGTGCTCTTCCGATCTAAGATGTGGAGGCTGTTGCT | 163 |
| TGFB1 | GACTGCGGATCTCTGTGTCA | 164 | CAGACGTGTGCTCTTCCGATCTTCTGCACTATTCCTTTGCCC | 165 |
| CD9 | TCAGTATGATCTTGTGCTGTGCT | 166 | CAGACGTGTGCTCTTCCGATCTTACCCATGAAGATTGGTGGG | 167 |
| CD11c | CACAGCATGAGAGGCTCTGT | 168 | CAGACGTGTGCTCTTCCGATCTTCTCAGTTCCGATTTCCCAG | 169 |
| FOXP3 | TCAGGATCTGAGGTCCCAAC | 170 | CAGACGTGTGCTCTTCCGATCTTCACCTGTGTATCTCACGCA | 171 |
| LAG3 | AGAGCTGTCTAGCCCAGGTG | 172 | CAGACGTGTGCTCTTCCGATCTTGGTGTCCTTTCTCTGCTCC | 173 |
| CD73 | CTTAACGTGGGAGTGGAACC | 174 | CAGACGTGTGCTCTTCCGATCTGTGTGCAAATGGCAGCTAGA | 175 |
| CD70 | TCTCAGCTTCCACCAAGGTT | 176 | CAGACGTGTGCTCTTCCGATCTTCACTGGGACACTTTTGCCT | 177 |
| CCR7 | CAGGGGAGAGTGTGGTGTTT | 178 | CAGACGTGTGCTCTTCCGATCTGACATGCACTCAGCTCTTGG | 179 |
| CD45RA | TGCATAGTTCCCATGTTAAATCC | 180 | CAGACGTGTGCTCTTCCGATCTTACCAGGAATGGATGTCGCT | 181 |
| PDCD1 | ACATCCTACGGTCCCAAGGT | 182 | CAGACGTGTGCTCTTCCGATCTGCAGAAGTGCAGGCACCTA | 183 |
| MYC | TGCATGATCAAATGCAACCT | 184 | CAGACGTGTGCTCTTCCGATCTTTGGACTTTGGGCATAAAGA | 185 |
| CD25 | AAATCACGGCAGTTTTCAGC | 186 | CAGACGTGTGCTCTTCCGATCTCTCATCTGTGCACTCTCCCC | 187 |
| FCAMR | GTGGGAAGAGAAGCTGATGC | 188 | CAGACGTGTGCTCTTCCGATCTTCAAGCATTATCCACGTCCA | 189 |
| CCND2 | TGTGATGCCATATCAAGTCCA | 190 | CAGACGTGTGCTCTTCCGATCTTCAGTGTATGCGAAAAGGTTTTT | 191 |
| MKI67 | AGCCTCTCTTGGGCTTTCTT | 192 | CAGACGTGTGCTCTTCCGATCTGTTTTCCCTGCCTGGAACTT | 193 |
| CCND3 | CTTTGCTGCTGAAGGCTCAT | 194 | CAGACGTGTGCTCTTCCGATCTACAAGTGGTGGTAACCCTGG | 195 |
| IL12A | TGCTTCCTAAAAAGCGAGGT | 196 | CAGACGTGTGCTCTTCCGATCTGAACTAGGGAGGGGAAAGA | 197 |
| IFNG | GCAGCCAACCTAAGCAAGAT | 198 | CAGACGTGTGCTCTTCCGATCTATCCAGTTACTGCCGGTTTG | 199 |
| TNFA | GAATGCTGCAGGACTTGAGA | 200 | CAGACGTGTGCTCTTCCGATCTACTTCCTTGAGACACGGAGC | 201 |
| IL2 | ACCCAGGGACTTAATCAGCA | 202 | CAGACGTGTGCTCTTCCGATCTGCTGATGAGACAGCAACCATT | 203 |
| IL4 | GACATCTTTGCTGCCTCCA | 204 | CAGACGTGTGCTCTTCCGATCTATGAGAAGGACACTCGCTGC | 205 |
| IL6 | TTAAGGAGTTCCTGCAGTCCA | 206 | CAGACGTGTGCTCTTCCGATCTTCCACTGGGCACAGAACTTA | 207 |
| BAFF | TCCTTCGCTTTGCTTGTCTT | 208 | CAGACGTGTGCTCTTCCGATCTAGGTGGAAAAATAGATGCCAGTC | 209 |
| IGHE | CCCGGAAGTCTATGCGTTT | 210 | CAGACGTGTGCTCTTCCGATCTAGGACATCTCGGTGCAGTG | 211 |
| IGHD | TGTGTGAGGTGTCTGGCTTC | 212 | CAGACGTGTGCTCTTCCGATCTAGGAGCACCACGTTCTGG | 213 |
| IGHM | CCCGGAGAAGTATGTGACCA | 214 | CAGACGTGTGCTCTTCCGATCTGTACTTCGCCCACAGCATC | 215 |
| IGHA | CTGAACGAGCTGGTGACG | 216 | CAGACGTGTGCTCTTCCGATCTAGTACCTGACTTGGGCATCC | 217 |
| IGHG1 | CAAGGGCCCATCGGTCTT | 218 | CAGACGTGTGCTCTTCCGATCTTTGTGACAAAACTCACACATGC | 219 |
| IGHG4 | CAAGGGCCCATCGGTCTT | 220 | CAGACGTGTGCTCTTCCGATCTCAAATATGGTCCCCCATGC | 221 |
| IGHG2 | CAAGGGCCCATCGGTCTT | 222 | CAGACGTGTGCTCTTCCGATCTGCAAATGTTGTGTCGAGTGC | 223 |
| IGHG3 | CAAGGGCCCATCGGTCTT | 224 | CAGACGTGTGCTCTTCCGATCTACCCCACTTGGTGACACAAC | 225 |
| TLR1 | CCATTCCGCAGTACTCCATT | 226 | CAGACGTGTGCTCTTCCGATCTAAGGAAAAGAGCAAACGTGG | 227 |
| TLR2 | TTGGTTGACTTCATGGATGC | 228 | CAGACGTGTGCTCTTCCGATCTGGAAACAGCACAAATGAACTTAA | 229 |
| TLR3 | CATCATGCAGTTCAACAAGC | 230 | CAGACGTGTGCTCTTCCGATCTATGCACTCTGTTTGCGAAGA | 231 |

TABLE 22-continued

| Gene | Outer Primer | SEQ ID NO: | Nested Primer with Common 5' Flanking Sequence | SEQ ID NO: |
|---|---|---|---|---|
| TLR4 | GGGTGTGTTTCCATGTCTCA | 232 | CAGACGTGTGCTCTTCCGATCTTTGAAAGTGTGTGTCCGC | 233 |
| TLR5 | TCAGGCTGTTGCATGAAGAA | 234 | CAGACGTGTGCTCTTCCGATCTGTATGCCCTTGCTGGACCTA | 235 |
| TLR6 | ATGCGCAGTAAAAACTCGTG | 236 | CAGACGTGTGCTCTTCCGATCTTACAGTTCCACGCTGAGCTG | 237 |
| TLR7 | GCCTGTACTTTCAGCTGGGTA | 238 | CAGACGTGTGCTCTTCCGATCTAAGGTGTTTGTGCCATTTGG | 239 |
| TLR8 | GGTGAGCTCTGATTGCTTCA | 240 | CAGACGTGTGCTCTTCCGATCTTATCAGGAGGCAGGGATCAC | 241 |
| TLR9 | GACCGGGTCAGTGGTCTCT | 242 | CAGACGTGTGCTCTTCCGATCTGGTGATCCTGAGCCCTGAC | 243 |
| TLR10 | TGCAGTGAGCTGAGATCGAG | 244 | CAGACGTGTGCTCTTCCGATCTATGGAAAACATCCTCATGGC | 245 |
| GAPDH | CACATGGCCUCCAAGGAGUAA | 246 | CAGACGTGTGCTCTTCCGATCTCAGCAAGAGCACAAGAGGAA | 247 |

TABLE 19

| Gene | Outer Primer | SEQ ID NO: | Nested Primer with Common 5' Flanking Sequence | SEQ ID NO: |
|---|---|---|---|---|
| CD19 | GCAGGGTCCCAGTCCTATG | 248 | CAGACGTGTGCTCTTCCGATCTCCAATCATGAGGAAGATGCA | 249 |
| CD20 | TAGGAGCAGGCCTGAGAAAA | 250 | CAGACGTGTGCTCTTCCGATCTGATTCCTCTCCAAACCCATG | 251 |
| BAFF | TCCTTCGCTTTGCTTGTCTT | 252 | CAGACGTGTGCTCTTCCGATCTAGGTGGAAAAATAGATGCCAGTC | 253 |
| TCL1A | GGTAAACACGCCTGCAAAC | 254 | CAGACGTGTGCTCTTCCGATCTCAGGACTCAGAAGCCTCTGG | 255 |
| TACI | CAACAAAGCACAGTGTTAAATGAA | 256 | CAGACGTGTGCTCTTCCGATCTTGTGTCAGCTACTGCGGAAA | 257 |
| IGHD | TGTGTGAGGTGTCTGGCTTC | 258 | CAGACGTGTGCTCTTCCGATCTAGGAGCACCACGTTCTGG | 259 |
| IGHM | CCCGGAGAAGTATGTGACCA | 260 | CAGACGTGTGCTCTTCCGATCTGTACTTCGCCCACAGCATC | 261 |
| CD27 | TCCAGGAGGATTACCGAAAA | 262 | CAGACGTGTGCTCTTCCGATCTCCATCCAAGGGAGAGTGAGA | 263 |
| CD38 | AGATCTGAGCCAGTCGCTGT | 264 | CAGACGTGTGCTCTTCCGATCTTGGTGCAGAGCTGAAGATTTT | 265 |
| CD24 | AAAAGTGGGCTTGATTCTGC | 266 | CAGACGTGTGCTCTTCCGATCTTTTTGTTCGCATGGTCACAC | 267 |
| AICDA | TGAGCAGATCCACAGGAAAA | 268 | CAGACGTGTGCTCTTCCGATCTGAAATGGAGTCTCAAAGCTTCA | 269 |
| CD95 | CCCCCGAAAATGTTCAATAA | 270 | CAGACGTGTGCTCTTCCGATCTTGCTCTTGTCATACCCCCA | 271 |
| CD10 | ATATTCCTTTGGGCCTCTGC | 272 | CAGACGTGTGCTCTTCCGATCTTCAAGTTTGGGTCTGTGCTG | 273 |
| IL10 | CCCCAACCACTTCATTCTTG | 274 | CAGACGTGTGCTCTTCCGATCTTTCAATTCCTCTGGGAATGTT | 275 |
| CD138 | AATGGCAAAGGAAGGTGGAT | 276 | CAGACGTGTGCTCTTCCGATCTGCAGACACCTTGGACATCCT | 277 |
| CD45RA | TGCATAGTTCCCATGTTAAATCC | 278 | CAGACGTGTGCTCTTCCGATCTTACCAGGAATGGATGTCGCT | 279 |
| BCL6 | AAATCTGCAGAAGGAAAAATGTG | 280 | CAGACGTGTGCTCTTCCGATCTAGTTTTCAATGATGGGCGAG | 281 |
| PRDM1 | TCGAATAATCCAGGGAAACC | 282 | CAGACGTGTGCTCTTCCGATCTACCAAAGCATCACGTTGACA | 283 |
| CXCR3 | CTGGCTCTCCCCAATATCCT | 284 | CAGACGTGTGCTCTTCCGATCTGCTCTGAGGACTGCACCATT | 285 |
| IFNG | GCAGCCAACCTAAGCAAGAT | 286 | CAGACGTGTGCTCTTCCGATCTATCCAGTTACTGCCGGTTTG | 287 |
| IL4R | TGCCTAGAGGTGCTCATTCA | 288 | CAGACGTGTGCTCTTCCGATCTGTTGATGCTGGAGGCAGAAT | 289 |
| IL4 | GACATCTTTGCTGCCTCCA | 290 | CAGACGTGTGCTCTTCCGATCTATGAGAAGGACACTCGCTGC | 291 |
| CCL20 | TTGGACATAGCCCAAGAACA | 292 | CAGACGTGTGCTCTTCCGATCTTGTGCCTCACTGGACTTGTC | 293 |
| CD25 | AAATCACGGCAGTTTTCAGC | 294 | CAGACGTGTGCTCTTCCGATCTCTCATCTGTGCACTCTCCCC | 295 |
| FOXP1 | ATGCTGAAGGCATTTCTTGG | 296 | CAGACGTGTGCTCTTCCGATCTCTGTGAGCATGGTGCTTCAT | 297 |
| TGFB1 | GACTGCGGATCTCTGTGTCA | 298 | CAGACGTGTGCTCTTCCGATCTTCTGCACTATTCCTTTGCCC | 299 |

TABLE 19-continued

| Gene | Outer Primer | SEQ ID NO: | Nested Primer with Common 5' Flanking Sequence | SEQ ID NO: |
|---|---|---|---|---|
| CXCR5 | CCGTGAGGATGTCACTCAGA | 300 | CAGACGTGTGCTCTTCCGATCTACGAGGAAGCCCTAAGACGT | 301 |
| CD69 | AGACAGGTCCTTTTCGATGG | 302 | CAGACGTGTGCTCTTCCGATCTTGTGCAATATGTGATGTGGC | 303 |
| CD30 | TGTTTTGGGGAAAGTTGGAG | 304 | CAGACGTGTGCTCTTCCGATCTCTGTTTGCCCAGTGTTTGTG | 305 |
| PDCD1 | ACATCCTACGGTCCCAAGGT | 306 | CAGACGTGTGCTCTTCCGATCTGCAGAAGTGCAGGCACCTA | 307 |
| LAG3 | AGAGCTGTCTAGCCCAGGTG | 308 | CAGACGTGTGCTCTTCCGATCTTGGTGTCCTTTCTCTGCTCC | 309 |
| PAX5 | TGACGTGTGTTGCTTTTGTG | 310 | CAGACGTGTGCTCTTCCGATCTACTTGGGAGAAAACAGGGGT | 311 |
| TNFRSF17 | GCTTTCCACTCCCAGCTATG | 312 | CAGACGTGTGCTCTTCCGATCTTGCTTTGAGTGCTACGGAGA | 313 |
| RASD1 | GGGGGAGGGATGTGAAGTTA | 314 | CAGACGTGTGCTCTTCCGATCTATCTTGTCTGTGATTCCGGG | 315 |
| AMPD1 | ACAGATGACCCAATGCAATTC | 316 | CAGACGTGTGCTCTTCCGATCTGAGCACCTGTGATATGTGCG | 317 |
| OSBPL5 | AGACCGATGCACAGTCTTCC | 318 | CAGACGTGTGCTCTTCCGATCTCTTCACGTCTGGCCTCAGTC | 319 |
| CD56 | GGAGCACTCAAGTGTGACGA | 320 | CAGACGTGTGCTCTTCCGATCTTTTTCTATGGAGCCTTCCGA | 321 |
| IGFBP7 | CATCCAATTCCCAAGGACAG | 322 | CAGACGTGTGCTCTTCCGATCTGGTGAAGGTGCCGAGCTATA | 323 |
| KIR2DS5 | GCTCTTCCTCAAACCACGAA | 324 | CAGACGTGTGCTCTTCCGATCTCACACTCCTTTGCTTAGCCC | 325 |
| KIR2DS2 | TCCTCACACCACGAATCTGA | 326 | CAGACGTGTGCTCTTCCGATCTCACTCCTTTGCTTAGCCCAC | 327 |
| RAB4B | CCAGCTCACCTGTTCTCCAG | 328 | CAGACGTGTGCTCTTCCGATCTGAATCCCGTACCTGCTGCT | 329 |
| CD14 | CTAAAGGACTGCCAGCCAAG | 330 | CAGACGTGTGCTCTTCCGATCTATAACCTGACACTGGACGGG | 331 |
| S100A12 | CACATTCCTGTGCATTGAGG | 332 | CAGACGTGTGCTCTTCCGATCTATACTCAGTTCGGAAGGGGC | 333 |
| CCR2variantB | GAAGGAGGGAGACATGAGCA | 334 | CAGACGTGTGCTCTTCCGATCTACTGGTCCTTAGCCCCATCT | 335 |
| CD62L | TCAGTTGGCTGACTTCCACA | 336 | CAGACGTGTGCTCTTCCGATCTTTAGTTTGGGGGTTTTGCTG | 337 |
| CD16 | TCTTGGCCAGGGTAGTAAGAA | 338 | CAGACGTGTGCTCTTCCGATCTGTCAGTTCCAATGAGGTGGG | 339 |
| CX3CR1 | CGTCCAGACCTTGTTCACAC | 340 | CAGACGTGTGCTCTTCCGATCTCCACAAATAGTGCTCGCTTTC | 341 |
| CD1b | TAGAGGGCCAGGACATCATC | 342 | CAGACGTGTGCTCTTCCGATCTTTGCTCCTTTTGCTATGCCT | 343 |
| FOXQ1 | TGCTATTGACCGATGCTTCA | 344 | CAGACGTGTGCTCTTCCGATCTGCAACGGGCTACAGCTTTAT | 345 |
| CD209 | GCTCTTGTTCTTGCCGTTTT | 346 | CAGACGTGTGCTCTTCCGATCTGAGTCCCTCAGTGGAGCAAG | 347 |
| CD1e | CACAAGCACATTCATCTCTTCC | 348 | CAGACGTGTGCTCTTCCGATCTATTCAGGGCCAGCTTCATAA | 349 |
| CCL17 | TACTTCAAGGGAGCCATTCC | 350 | CAGACGTGTGCTCTTCCGATCTTTTGTAACTGTGCAGGGCAG | 351 |
| DTNA | AGCAACGTGGAGTCAGTCTGT | 352 | CAGACGTGTGCTCTTCCGATCTCTCACCTTCTCTTGCCTTGG | 353 |
| CLEC4C | TTATTTTCTGGGGCTGTCAGA | 354 | CAGACGTGTGCTCTTCCGATCTCATTCTGGCACTCAGGTGAA | 355 |
| ZBTB16 | TGATCAAGCACCTGAGAACG | 356 | CAGACGTGTGCTCTTCCGATCTTACCAGTGCACCATCTGCAC | 357 |
| SLAMF1 | TGCAAAACCCAGAAGCTAAAA | 358 | CAGACGTGTGCTCTTCCGATCTGTTCTGTGCAAATGGCATTC | 359 |
| CD3D | AGAGCTGTGTGGAGCTGGAT | 360 | CAGACGTGTGCTCTTCCGATCTGGAGTCTTCTGCTTTGCTGG | 361 |
| CD3E | GCCCTCTTGCCAGGATATTT | 362 | CAGACGTGTGCTCTTCCGATCTGCATGTAAGTTGTCCCCCAT | 363 |
| CD8A | CTGGCCTCTGCTCAACTAGC | 364 | CAGACGTGTGCTCTTCCGATCTATGGTACAAGCAATGCCTGC | 365 |
| CD8B | CAGCCTCAAGGGGAAGGTAT | 366 | CAGACGTGTGCTCTTCCGATCTTGCTTAACCCATGGATCCTG | 367 |
| PRF1 | CCCTGCAGTCACAGCTACAC | 368 | CAGACGTGTGCTCTTCCGATCTTCAGGGCTGGTCTTTTAGGA | 369 |
| EOMES | TGGGATAATGTAAAACTGGTGCT | 370 | CAGACGTGTGCTCTTCCGATCTCATCCCCATGATATTTGGGA | 371 |
| CD4 | AGCTAGCCTGAGAGGGAACC | 372 | CAGACGTGTGCTCTTCCGATCTTCCTCCAGACCATTCAGGAC | 373 |
| THPOK | GGCTCTGCCTTGCACTATTT | 374 | CAGACGTGTGCTCTTCCGATCTCTCTTCCTCCCTTCCATGC | 375 |

TABLE 19-continued

| Gene | Outer Primer | SEQ ID NO: | Nested Primer with Common 5' Flanking Sequence | SEQ ID NO: |
|---|---|---|---|---|
| RUNX3 | TAAGGCCCAAAGTGGGTACA | 376 | CAGACGTGTGCTCTTCCGATCTTAGGAAGCACGAGGAAAGGA | 377 |
| CD45RO | ACCCTCTCTCCCTCCCTTTC | 378 | CAGACGTGTGCTCTTCCGATCTTAGTTGGCTATGCTGGCATG | 379 |
| CD44 | GCCTGGTAGAATTGGCTTTTC | 380 | CAGACGTGTGCTCTTCCGATCTTTTTGTAGCCAACATTCATTCAA | 381 |
| CCR7 | CAGGGGAGAGTGTGGTGTTT | 382 | CAGACGTGTGCTCTTCCGATCTACTCAGCTCTTGGCTCCACT | 383 |
| TXK | ACATCAAGCTCCATTGTTTCG | 384 | CAGACGTGTGCTCTTCCGATCTTTTGCCTGCACTCTTTGTAGG | 385 |
| MBD2 | GCCTGGCACGTAATAGCTTG | 386 | CAGACGTGTGCTCTTCCGATCTAGGAAAGAAATGCCCTTGGT | 387 |
| IFNGR1 | GAGGATGTGTGGCATTTTCA | 388 | CAGACGTGTGCTCTTCCGATCTGGTTCCTAGGTGAGCAGGTG | 389 |
| IL12RB2 | AGCAGGCTGTACACAGCAGA | 390 | CAGACGTGTGCTCTTCCGATCTGACACTAGGCACATTGGCTG | 391 |
| IL33R | ACTGTGCCCTCATCCAGAAC | 392 | CAGACGTGTGCTCTTCCGATCTAACGACGCCAAGGTGATACT | 393 |
| CCR4 | TGGTGAAATGCAGAGTCAATG | 394 | CAGACGTGTGCTCTTCCGATCTTCAGGAGGAAGGCTTACACC | 395 |
| CRTH2 | TGAATTTTGCTTGGTGGATG | 396 | CAGACGTGTGCTCTTCCGATCTTGTCAGTGGAAGAAGCAGATG | 397 |
| IL5 | CAGTGAGAATGAGGGCCAAG | 398 | CAGACGTGTGCTCTTCCGATCTGAATGAGGGCCAAGAAAGAG | 399 |
| IL17A | AAAATGAAACCCTCCCCAAA | 400 | CAGACGTGTGCTCTTCCGATCTTCCTTTGGAGATTAAGGCCC | 401 |
| IL17F | CTGCATCAATGCTCAAGGAA | 402 | CAGACGTGTGCTCTTCCGATCTCCAAGGCTGCTCTGTTTCTT | 403 |
| IL21 | AAATCAAGCTCCCAAGGTCA | 404 | CAGACGTGTGCTCTTCCGATCTTGTGAATGACTTGGTCCCTG | 405 |
| IL22 | ATGCCCCAAAGCGATTTTT | 406 | CAGACGTGTGCTCTTCCGATCTCAAAGGAAACCAATGCCACT | 407 |
| IL23R | TCCCTCATTGAAAGATGCAA | 408 | CAGACGTGTGCTCTTCCGATCTTAGAATCATTAGGCCAGGCG | 409 |
| RORA | TGCAAGCCATTTATGGGAAT | 410 | CAGACGTGTGCTCTTCCGATCTCCTTGGGTTTTCTTTTCAATTC | 411 |
| RORC | ATTTCCATGGTGCTCCAGTC | 412 | CAGACGTGTGCTCTTCCGATCTAGAGAAGCAGAAGTCGCTCG | 413 |
| OX40L | CTGCTGGCCCTGTACCTG | 414 | CAGACGTGTGCTCTTCCGATCTCTCCACCCTGGCCAAGAT | 415 |
| ICOS | TTCAGCTGACTTGGACAACCT | 416 | CAGACGTGTGCTCTTCCGATCTGGACAACCTGACTGGCTTTG | 417 |
| SH2D1A | GGGTGTTGGTGAACTTGGTT | 418 | CAGACGTGTGCTCTTCCGATCTTTTAATATGGATGCCGTGGG | 419 |
| CCR2variantA | GTTGCCCAGTGTGTTTCTGA | 420 | CAGACGTGTGCTCTTCCGATCTAACCAGGCAACTTGGGAACT | 421 |
| TLR1 | CCATTCCGCAGTACTCCATT | 422 | CAGACGTGTGCTCTTCCGATCTAAGGAAAAGAGCAAACGTGG | 423 |
| TLR2 | TTGGTTGACTTCATGGATGC | 424 | CAGACGTGTGCTCTTCCGATCTGGAAACAGCACAAATGAACTTAA | 425 |
| TLR3 | CATCATGCAGTTCAACAAGC | 426 | CAGACGTGTGCTCTTCCGATCTATGCACTCTGTTTGCGAAGA | 427 |
| TLR4 | GGGTGTGTTTCCATGTCTCA | 428 | CAGACGTGTGCTCTTCCGATCTTTGAAAGTGTGTGTCCGC | 429 |
| TLR5 | TCAGGCTGTTGCATGAAGAA | 430 | CAGACGTGTGCTCTTCCGATCTGTATGCCCTTGCTGGACCTA | 431 |
| TLR6 | ATGCGCAGTAAAAACTCGTG | 432 | CAGACGTGTGCTCTTCCGATCTTACAGTTCCACGCTGAGCTG | 433 |
| TLR7 | GCCTGTACTTTCAGCTGGGTA | 434 | CAGACGTGTGCTCTTCCGATCTAAGGTGTTTGTGCCATTTGG | 435 |
| TLR8 | GGTGAGCTCTGATTGCTTCA | 436 | CAGACGTGTGCTCTTCCGATCTTATCAGGAGGCAGGGATCAC | 437 |
| TLR9 | GACCGGGTCAGTGGTCTCT | 438 | CAGACGTGTGCTCTTCCGATCTGGTGATCCTGAGCCCTGAC | 439 |
| TLR10 | TGCAGTGAGCTGAGATCGAG | 440 | CAGACGTGTGCTCTTCCGATCTATGGAAAACATCCTCATGGC | 441 |
| GAPDH | CACATGGCCUCCAAGGAGUAA | 442 | CAGACGTGTGCTCTTCCGATCTCAGCAAGAGCACAAGAGGAA | 443 |

Studying Diversity of Response of Human T Cells to In Vitro Stimulus

When examining the gene expression pattern of a bulk sample, the observed pattern was contributed by both the sample's cell composition and the expression level of each gene in each cell type or subtype. These two effects cannot be deconvoluted by bulk analysis but only with large-scale single cell analysis. To illustrate, we utilized our platform to study the variability of response of human T cells to an in vitro stimulus.

We purified CD3+ T cells by negative selection from a blood donor and stimulated them with anti-CD28/anti-CD3 beads for 6 hours, and performed experiments with the stimulated and a separate aliquot of unstimulated cells. We designed a panel of 93 genes (Table 20) that encompassed surface proteins, cytokines, chemokines, and effector molecules expressed by the different T cell subsets. A total of 3517 and 1478 single cells were analyzed for the stimulated and unstimulated samples, respectively.

TABLE 20

| Gene | Outer Primer | SEQ ID NO: | Nested Primer with Common 5' Flanking Sequence | SEQ ID NO: |
|---|---|---|---|---|
| GAPDH | GACTTCAACAGCGACACCCA | 444 | CAGACGTGTGCTCTTCCGATCTGCCCTCAACGACCACTTTGT | 445 |
| CD3D | GAAAACGCATCCTGGACCCA | 446 | CAGACGTGTGCTCTTCCGATCTTGATGTCATTGCCACTCTGCT | 447 |
| CD3E | AAGTTGTCCCCCATCCCAAA | 448 | CAGACGTGTGCTCTTCCGATCTCTGGGGATGGACTGGGTAAAT | 449 |
| CD8A | ACTGCTGTCCCAAACATGCA | 450 | CAGACGTGTGCTCTTCCGATCTATGCCTGCCCATTGGAGAGAA | 451 |
| CD8B | CCACCATCTTTGCAGGTTGC | 452 | CAGACGTGTGCTCTTCCGATCTGCTGTCCAGTTCCCAGAAGG | 453 |
| CD4 | CTGGGAGAGGGGTAGCTAG | 454 | CAGACGTGTGCTCTTCCGATCTACCACTTCCCTCAGTCCCAA | 455 |
| FOXP3 | ACAGAAGCAGCGTCAGTACC | 456 | CAGACGTGTGCTCTTCCGATCTGGGTCTCTTGAGTCCCGTG | 457 |
| CCR7 | GGGGAGAGTGTGGTGTTTCC | 458 | CAGACGTGTGCTCTTCCGATCTCTCTTGGCTCCACTGGGATG | 459 |
| CD5 | ATCAATGGTCCAAGCCGCAT | 460 | CAGACGTGTGCTCTTCCGATCTAGGTCACAGATCTTCCCCCG | 461 |
| IL32 | CTTTCCAGTCCTACGGAGCC | 462 | CAGACGTGTGCTCTTCCGATCTTGCTCTGAACCCCAATCCTC | 463 |
| CD28 | ACCATCACAGGCATGTTCCT | 464 | CAGACGTGTGCTCTTCCGATCTTGTAGATGACCTGGCTTGCC | 465 |
| SELL | GCATCTCATGAGTGCCAAGC | 466 | CAGACGTGTGCTCTTCCGATCTCCTGCCCCAGACCTTTTATC | 467 |
| CD27 | TGCAGAGCCTTGTCGTTACA | 468 | CAGACGTGTGCTCTTCCGATCTCGTGACAGAGTGCCTTTTCG | 469 |
| GZMB | AGGTGAAGATGACAGTGCAGG | 470 | CAGACGTGTGCTCTTCCGATCTAGGCCCTCTTGTGTGTAACA | 471 |
| GZMA | GGAACCATGTGCCAAGTTGC | 472 | CAGACGTGTGCTCTTCCGATCTCCTTTGTTGTGCGAGGGTGT | 473 |
| GZMH | AGTGTTGCTGACAGTGCAGA | 474 | CAGACGTGTGCTCTTCCGATCTCCAAAGAAGACACAGACCGGT | 475 |
| GZMK | TTGCCACAAAGCCTGGAATC | 476 | CAGACGTGTGCTCTTCCGATCTAAAGCAACCTTGTCCCGCCT | 477 |
| PRF1 | GGAGTCCAGCGAATGACGTC | 478 | CAGACGTGTGCTCTTCCGATCTCATGGCCACGTTGTCATTGT | 479 |
| NKG2D | CAACACCCAGGGGATCAGTG | 480 | CAGACGTGTGCTCTTCCGATCTCCACCCTCCACAGGAAATTG | 481 |
| LAG3 | AGCTGTACCAGGGGGAGAG | 482 | CAGACGTGTGCTCTTCCGATCTCTTTGGAGAAGACAGTGGCGA | 483 |
| CD160 | GGAAGACAGCCAGATCCAGTG | 484 | CAGACGTGTGCTCTTCCGATCTTTGTGCAGACCAAGAGCACC | 485 |
| CD244 | GGGCTGAGAATGAGGCAGTT | 486 | CAGACGTGTGCTCTTCCGATCTGGAAAGCGACAAGGGTGAAC | 487 |
| EOMES | ACTTAACAGCTGCAGGGGC | 488 | CAGACGTGTGCTCTTCCGATCTACTAACTTGAACCGTGTTTAAGG | 489 |
| TBX21 | TTATAACCATCAGCCCGCCA | 490 | CAGACGTGTGCTCTTCCGATCTAGAAAAGGGGCTGGAAAGGG | 491 |
| PRDM1 | ACCAAAGCATCACGTTGACAT | 492 | CAGACGTGTGCTCTTCCGATCTACATGTGAATGTTGAGCCCA | 493 |
| IRF4 | CTCTTCAGCATCCCCCGTAC | 494 | CAGACGTGTGCTCTTCCGATCTGCCCCCAAATGAAAGCTTGA | 495 |
| ZNF683 | GGAGAGCGTCCATTCCAGTG | 496 | CAGACGTGTGCTCTTCCGATCTATCCACCTGAAGCTGCACC | 497 |
| ZBED2 | AATGTACCAGCCAGTCAGCG | 498 | CAGACGTGTGCTCTTCCGATCTGGTTTTGGTGGAGCTGACGA | 499 |
| CD30 | TTTACTCATCGGGCAGCCAC | 500 | CAGACGTGTGCTCTTCCGATCTTGTTTGCCCAGTGTTTGTGC | 501 |
| CD69 | GCTGTAGACAGGTCCTTTTCG | 502 | CAGACGTGTGCTCTTCCGATCTAGTGTTGGAAAATGTGCAATATGTG | 503 |
| HLA-DRA | GGGTCTGGTGGGCATCATTA | 504 | CAGACGTGTGCTCTTCCGATCTGCCTCTTCGATTGCTCCGTA | 505 |
| CD38 | AGGTCAATGCCAGAGACGGA | 506 | CAGACGTGTGCTCTTCCGATCTATCAGCATACCTTTATTGTGATCTATC | 507 |
| TNFRSF9 | TGGCATGTGAGTCATTGCTC | 508 | CAGACGTGTGCTCTTCCGATCTTTTTGATGTGAGGGCGGAT | 509 |
| MKI67 | TACTTTTTCGCCTCCCAGGG | 510 | CAGACGTGTGCTCTTCCGATCTCCTGCCCCACCAAGATCAT | 511 |

TABLE 20-continued

| Gene | Outer Primer | SEQ ID NO: | Nested Primer with Common 5' Flanking Sequence | SEQ ID NO: |
|---|---|---|---|---|
| BIRC5 | TGCCACGGCCTTTCCTTAAA | 512 | CAGACGTGTGCTCTTCCGATCTTTGTCTAAGTGCAACCGCCT | 513 |
| FOSL1 | CTCCTGACAGAAGGTGCCAC | 514 | CAGACGTGTGCTCTTCCGATCTGGTGATTGGACCAGGCCATT | 515 |
| MCL1 | GACTGGCTACGTAGTTCGGG | 516 | CAGACGTGTGCTCTTCCGATCTTTTGCTTAGAAGGATGGCGC | 517 |
| MYC | AGCTACGGAACTCTTGTGCG | 518 | CAGACGTGTGCTCTTCCGATCTCAACCTTGGCTGAGTCTTGA | 519 |
| TYMS | TCAGTCTTTAGGGGTTGGGC | 520 | CAGACGTGTGCTCTTCCGATCTATGTGCATTTCAATCCCACGTAC | 521 |
| CDCA7 | CCAGTCTAGTTTCTGGGCAGG | 522 | CAGACGTGTGCTCTTCCGATCTATGTAAACCATTGCTGTGCCATT | 523 |
| UHRF1 | CCAGTTCTTCCTGACACCGG | 524 | CAGACGTGTGCTCTTCCGATCTCCAAAGTTTGCAGCCTATACC | 525 |
| SAP30 | ACCAACCAGACCAGGACTTA | 526 | CAGACGTGTGCTCTTCCGATCTTCACTAGGAGACGTGGAATTG | 527 |
| CX3CR1 | CACCCGTCCAGACCTTGTT | 528 | CAGACGTGTGCTCTTCCGATCTTGTTTTCCTCTTAACGTTAGACCAC | 529 |
| BCL2 | TGCAAGAGTGACAGTGGATTG | 530 | CAGACGTGTGCTCTTCCGATCTGCTGATATTCTGCAACACTGTACA | 531 |
| BCL6 | TGTCCTCACGGTGCCTTTT | 532 | CAGACGTGTGCTCTTCCGATCTGTAGGCAGACACAGGGACTT | 533 |
| FASLG | CCTCAAGGGGACTGTCTTTC | 534 | CAGACGTGTGCTCTTCCGATCTGCATATCCTGAGCCATCGGT | 535 |
| FAS | ATTGCTGGTAGAGACCCCCA | 536 | CAGACGTGTGCTCTTCCGATCTCCCCCATTTCCCCGATGT | 537 |
| CCL4 | CCCAGCCAGCTGTGGTATTC | 538 | CAGACGTGTGCTCTTCCGATCTTGGAACTGAACTGAGCTGCT | 539 |
| IFNG | CTAGGCAGCCAACCTAAGCA | 540 | CAGACGTGTGCTCTTCCGATCTCCTGCAATCTGAGCCAGTGC | 541 |
| TNF | AGTGGACCTTAGGCCTTCCT | 542 | CAGACGTGTGCTCTTCCGATCTGGCTCAGACATGTTTTCCGTG | 543 |
| IL2 | TCACTTAAGACCCAGGGACTT | 544 | CAGACGTGTGCTCTTCCGATCTAAGCATCATCTCAACACTGACTT | 545 |
| IL4 | ACCATGAGAAGGACACTCGC | 546 | CAGACGTGTGCTCTTCCGATCTCGGGCTTGAATTCCTGTCCT | 547 |
| IL6 | CGGCAAATGTAGCATGGGC | 548 | CAGACGTGTGCTCTTCCGATCTGGAAAGTGGCTATGCAGTTTG | 549 |
| IL1A | GGCATCCTCCACAATAGCAGA | 550 | CAGACGTGTGCTCTTCCGATCTGCATTTTGGTCCAAGTTGTGC | 551 |
| IL1B | CTTAAAGCCCGCCTGACAGA | 552 | CAGACGTGTGCTCTTCCGATCTACATTCTGATGAGCAACCGC | 553 |
| IL3 | ACAGACGACTTTGAGCCTCG | 554 | CAGACGTGTGCTCTTCCGATCTATTTCACCTTTTCCTGCGGC | 555 |
| IL13 | GGAGCCAAGGGTTCAGAGAC | 556 | CAGACGTGTGCTCTTCCGATCTTGCTACCTCACTGGGGTCCT | 557 |
| IL31 | GGCCATCTCTTCCTTTCGGA | 558 | CAGACGTGTGCTCTTCCGATCTGTGTGGGAACTCTGCCGTG | 559 |
| IL24 | CTCACCCCATCATCCCTTTCC | 560 | CAGACGTGTGCTCTTCCGATCTGCCCAGTGAGACTGTGTTGT | 561 |
| IL26 | TACTGACGGCATGTTAGGTG | 562 | CAGACGTGTGCTCTTCCGATCTTGTGTGTGGAGTGGGATGTG | 563 |
| LTA | AGGCAGGGAGGGACTATTT | 564 | CAGACGTGTGCTCTTCCGATCTGGAGAAACAGAGACAGGCCC | 565 |
| IL5 | GCAGTGAGAATGAGGGCCA | 566 | CAGACGTGTGCTCTTCCGATCTAGGCATACTGACACTTTGCC | 567 |
| CSF2 | AGCCAGTCCAGGAGTGAGAC | 568 | CAGACGTGTGCTCTTCCGATCTGGCCACACTGACCCTGATAC | 569 |
| IL21 | CCCAAGGTCAAGATCGCCAC | 570 | CAGACGTGTGCTCTTCCGATCTCTGCCAGCTCCAGAAGATGT | 571 |
| IL22 | TGGGAAGCCAAACTCCATCAT | 572 | CAGACGTGTGCTCTTCCGATCTGGAAACCAATGCCACTTTGT | 573 |
| IL17A | GCCTTCAAGACTGAACACCGA | 574 | CAGACGTGTGCTCTTCCGATCTGCCCCTCAGAGATCAACAGAC | 575 |
| IL17F | TTGGAGAAGGTGCTGGTGAC | 576 | CAGACGTGTGCTCTTCCGATCTCTTACCCAGTGCTCTGCAAC | 577 |
| TGFB1 | TATTCCTTTGCCCGGCATCA | 578 | CAGACGTGTGCTCTTCCGATCTACCTTGGGCACTGTTGAAGT | 579 |
| CCL20 | ACTTGCACATCATGGAGGGT | 580 | CAGACGTGTGCTCTTCCGATCTTCCATAAGCTATTTTGGTTTAGTGC | 581 |
| IL12A | GGTCCCTCCAAACCGTTGTC | 582 | CAGACGTGTGCTCTTCCGATCTGAACTAGGGAGGGGAAAGAAG | 583 |
| CXCL12 | TGGGAGTTGATCGCCTTTCC | 584 | CAGACGTGTGCTCTTCCGATCTCTCATTCTGAAGGAGCCCCAT | 585 |

TABLE 20-continued

| Gene | Outer Primer | SEQ ID NO: | Nested Primer with Common 5' Flanking Sequence | SEQ ID NO: |
|---|---|---|---|---|
| CCL3 | TGGACTGGTTGTTGCCAAAC | 586 | CAGACGTGTGCTCTTCCGATCTCTCTGAGAGTTCCCCTGTCC | 587 |
| CCL14 | TTCCTCCTCATCACCATCGC | 588 | CAGACGTGTGCTCTTCCGATCTCTTACCACCCCTCAGAGTGC | 589 |
| CCL18 | GAAGCTGAATGCCTGAGGGG | 590 | CAGACGTGTGCTCTTCCGATCTGTCCCATCTGCTATGCCCA | 591 |
| CCL17 | GAGTGCTGCCTGGAGTACTT | 592 | CAGACGTGTGCTCTTCCGATCTCTCACCCCAGACTCCTGACT | 593 |
| IL12B | GCTATGGTGAGCCGTGATTG | 594 | CAGACGTGTGCTCTTCCGATCTTCCTCACCCCCACCTCTCTA | 595 |
| CXCR3 | GACCTCAGAGGCCTCCTACT | 596 | CAGACGTGTGCTCTTCCGATCTCCAATATCCTCGCTCCCGG | 597 |
| IL33R | TTCAGGACTCCCTCCAGCAT | 598 | CAGACGTGTGCTCTTCCGATCTAGGTACCAAATGCCTGTGCC | 599 |
| IL4R | TGAACTTCAGGGAGGGTGGT | 600 | CAGACGTGTGCTCTTCCGATCTTCCTCGTATGCATGGAACCC | 601 |
| CCR4 | CCAAAGGGAAGAGTGCAGGG | 602 | CAGACGTGTGCTCTTCCGATCTATTCTGTATAACACTCATATCTTTGCC | 603 |
| IL23R | AGAATCATTAGGCCAGGCGTG | 604 | CAGACGTGTGCTCTTCCGATCTCTGGCCAATATGCTGAAACCC | 605 |
| IL21R | ATTTGAGGCTGCAGTGAGCT | 606 | CAGACGTGTGCTCTTCCGATCTAGACAAGAGCTGGCTCACCT | 607 |
| CXCR5 | CCTCCCCAGCCTTTGATCAG | 608 | CAGACGTGTGCTCTTCCGATCTTCCTCGCAAGCTGGGTAATC | 609 |
| IL6R | CCAGCACCAGGGAGTTTCTA | 610 | CAGACGTGTGCTCTTCCGATCTACAGCATGTCACAAGGCTGT | 611 |
| CXCL13 | AGGCAGATGGAACTTGAGCC | 612 | CAGACGTGTGCTCTTCCGATCTGCATTCGAAGATCCCCAGACTT | 613 |
| LIF | TCCCCATCGTCCTCCTTGTC | 614 | CAGACGTGTGCTCTTCCGATCTTTGCCGGCTCTCCAGAGTA | 615 |
| PTPRCv1 (CD45RA) | GTTCCCATGTTAAATCCCATTCAT | 616 | CAGACGTGTGCTCTTCCGATCTTACCAGGAATGGATGTCGCTAATCA | 617 |
| PTPRCv2 (CD45RO) | ACCCTCTCTCCCTCCCTTTC | 618 | CAGACGTGTGCTCTTCCGATCTTAGTTGGCTATGCTGGCATG | 619 |
| IL10 | CCCCAACCACTTCATTCTTG | 620 | CAGACGTGTGCTCTTCCGATCTTTCAATTCCTCTGGGAATGTT | 621 |
| CD40LG | CCTCCCCAGTCTCTCTTCT | 622 | CAGACGTGTGCTCTTCCGATCTGAGTCAGGCCGTTGCTAGTC | 623 |

Figure 44A:
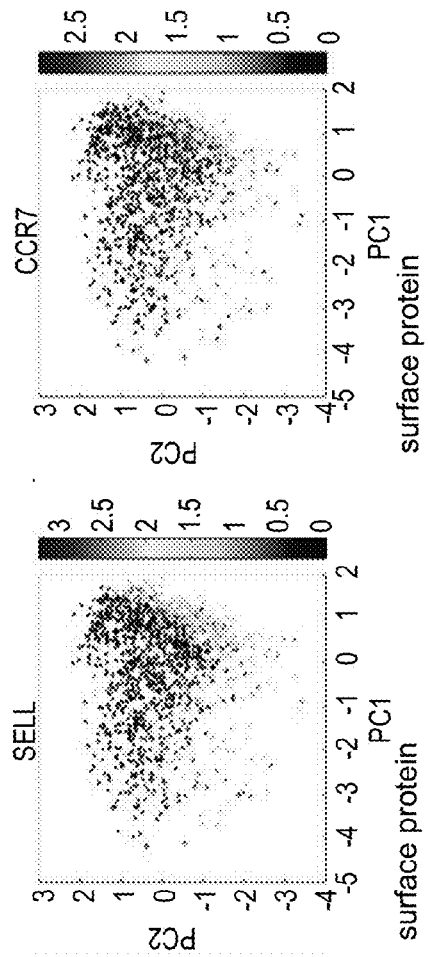
FIGS. 44AA-AF. PCA of Donor 1 unstimulated sample reveals two major branches of cells. The expression level (log of unique transcript molecule) of a particular gene within each cell is indicated with color. Helper T cell associated cytokine and effector genes are enriched in cells in the lower branch, while cytotoxic T cell associated genes are enriched in the upper branch. Shown here are representative genes. First row shows helper T cell related genes and include (from left to right) CD4, SELL and CCR7. Second row shows cytotoxic T cell related genes and include (from left to right) CD8A, NKG2D and EOMES.
Figure 44A:
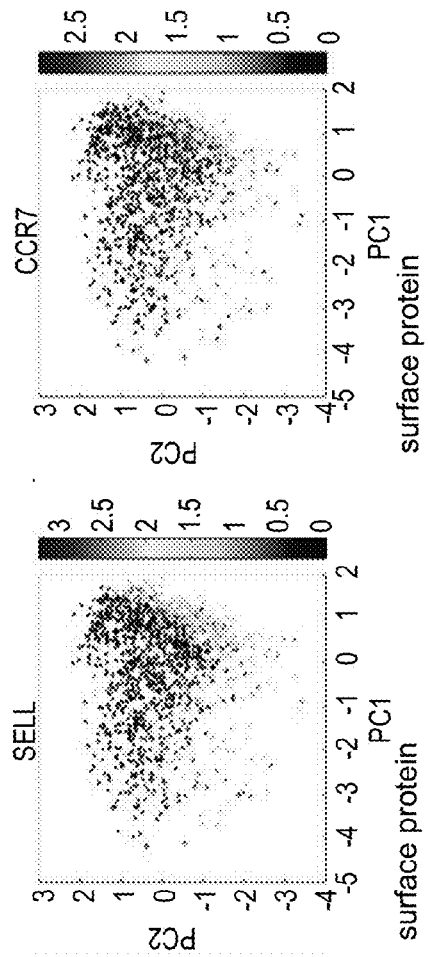
Figure 44A:
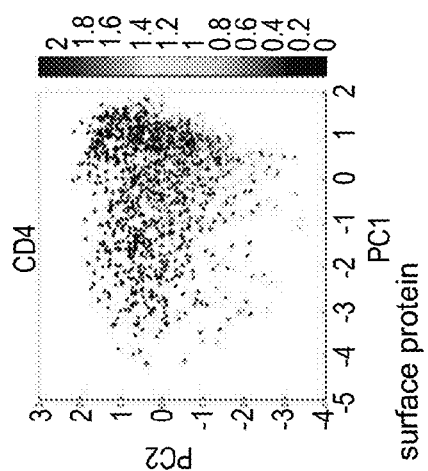
Figure 44A:
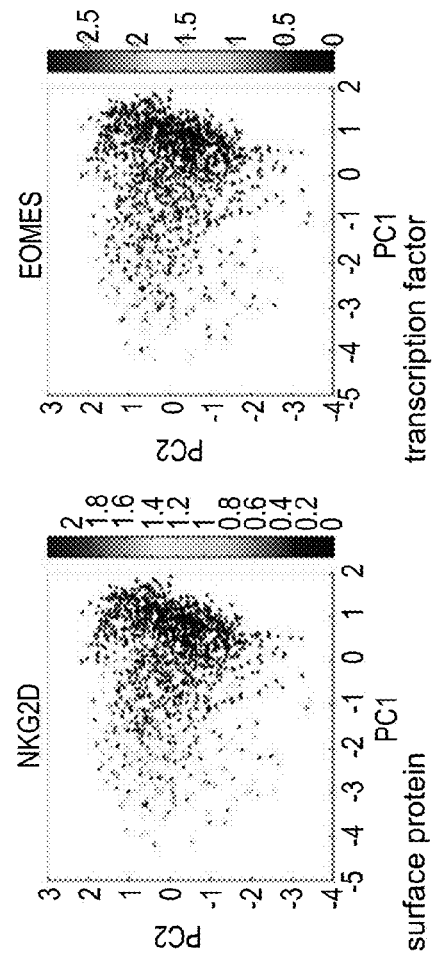
Figure 44A:
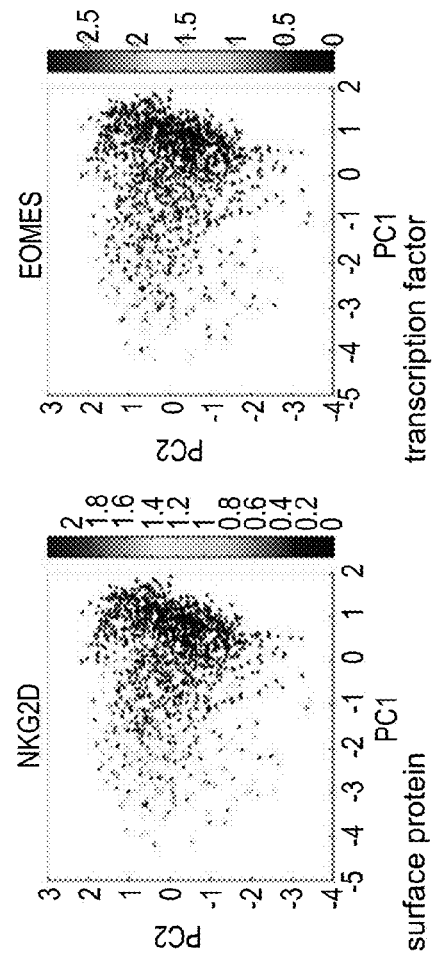
Figure 44A:
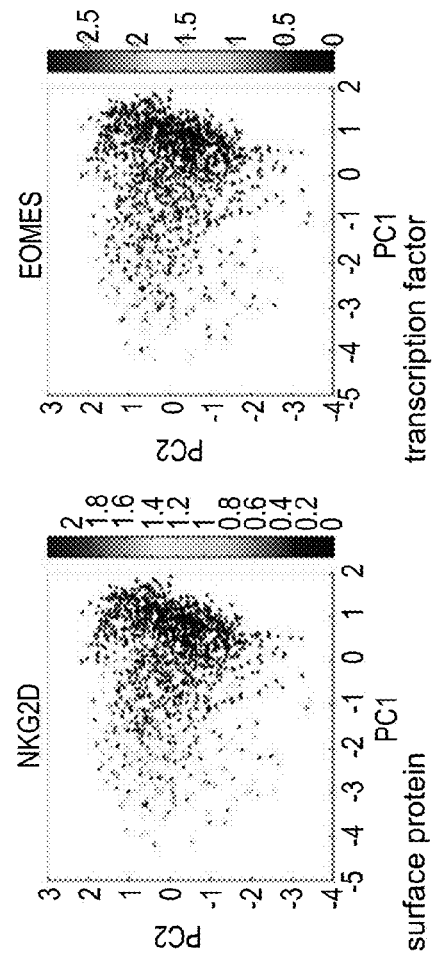

In the unstimulated sample, PCA analysis revealed two major subsets of cells. A closer look at the genes enriched in each subset showed that one subset represented CD8+ cells with expression of CD8A, CD8B, NKG2D, GZMA, GZMH, GZMK, and EOMES, and the other subset represented CD4+ cells with expression of CD4, CCR7 and SELL (FIGS. 44AA-AF and FIGS. 45AA-CL).

In the stimulated sample, two branches of cells were immediately clear on the PCA plot (FIGS. 44BA-BL and FIG. 46A-D). The first principal component represented the degree of response of individual cells to stimulant in terms of varying level of expression of IFNG, TNF, CD69, and GAPDH. Expression of CCL3, CCL4, and GZMB, which are cytokines and effector molecules associated with cytotoxic T cells, and LAG3, a marker associated with exhausted cells, was localized to cells in the upper branch. Expression of IL2, LTA, CD40LG, and CCL20, which are cytokines associated with helper T cells, was localized to the lower branch. Other genes that have been known to be upregulated in activated T cells, including ZBED2, IL4R, PRDM1, TBX21, MYC, FOSL1, CSF2, TNFRSF9, BCL2 and FASLG, were expressed in various degrees in a smaller number of cells (FIG. 46A-D). Most of these cytokines, effector molecules, and transcription factors were not expressed or were expressed at very low levels by cells in the unstimulated sample. While most of the cells that responded within this short period of stimulation were presumably memory cells, we observed a small population of cells that produced lower level of IL2 and not other cytokines nor effector molecules, and may represent naïve cells (FIG. 44BG, arrow).

Figure 47:
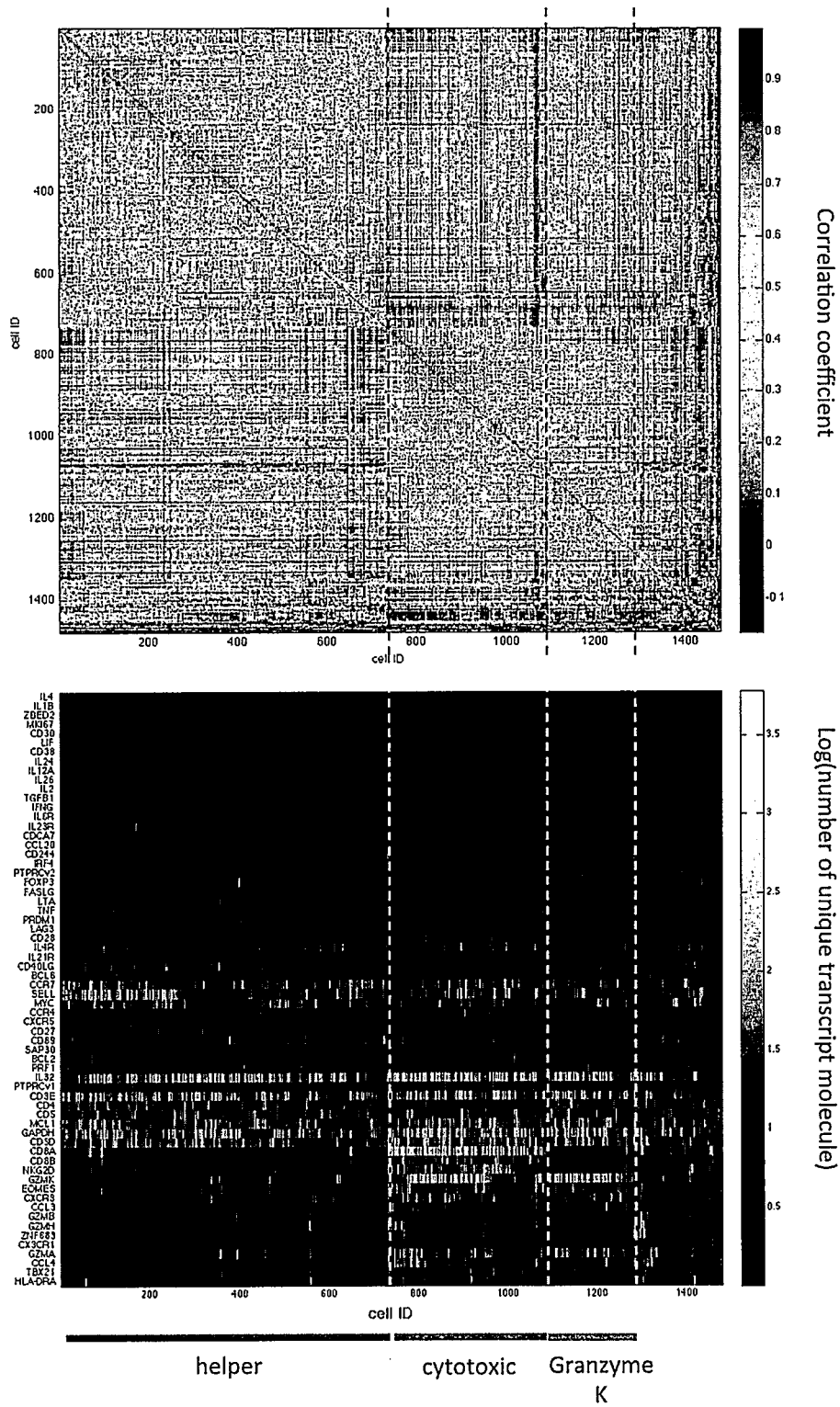
FIG. 47 Clustering of data from Donor 1's unstimulated CD3+ T cells shows separations of CD4 and CD8 cells, as well as a group of cells that express Granzyme K and Granzyme A but little CD8.
Figure 48:
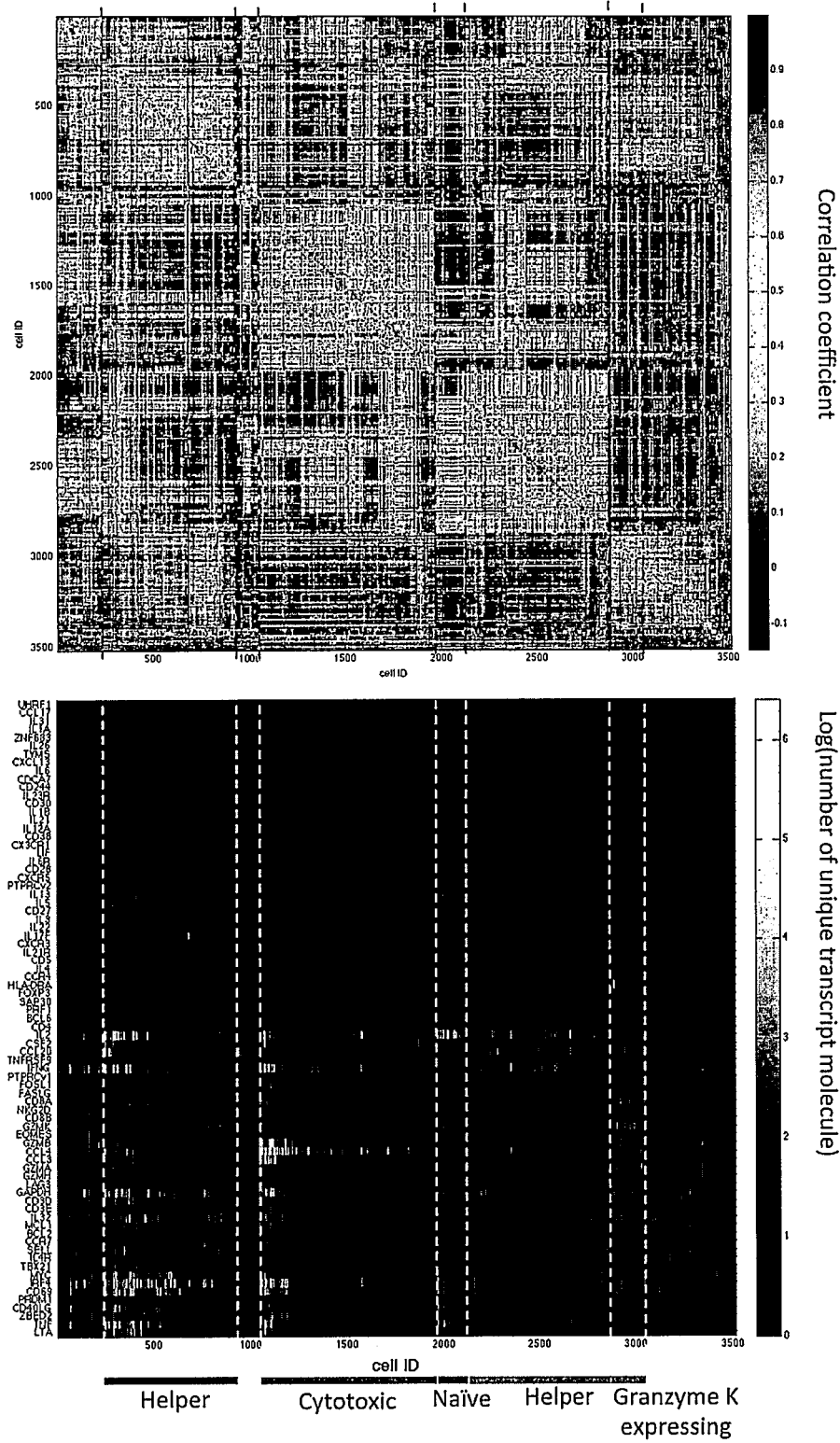
FIG. 48. Similar to FIG. 47, but showing data from anti-CD3/anti-CD28 stimulated CD3+ T cell sample of Donor 1.

To fully appreciate the heterogeneity in response, we clustered the cells based on a pairwise correlation coefficient. While the two main groups of CD4 and CD8 cells were obvious, there was considerable diversity within each set in terms of the combination and level of activated genes expressed (FIG. 47 and FIG. 48).

Figure 44C:
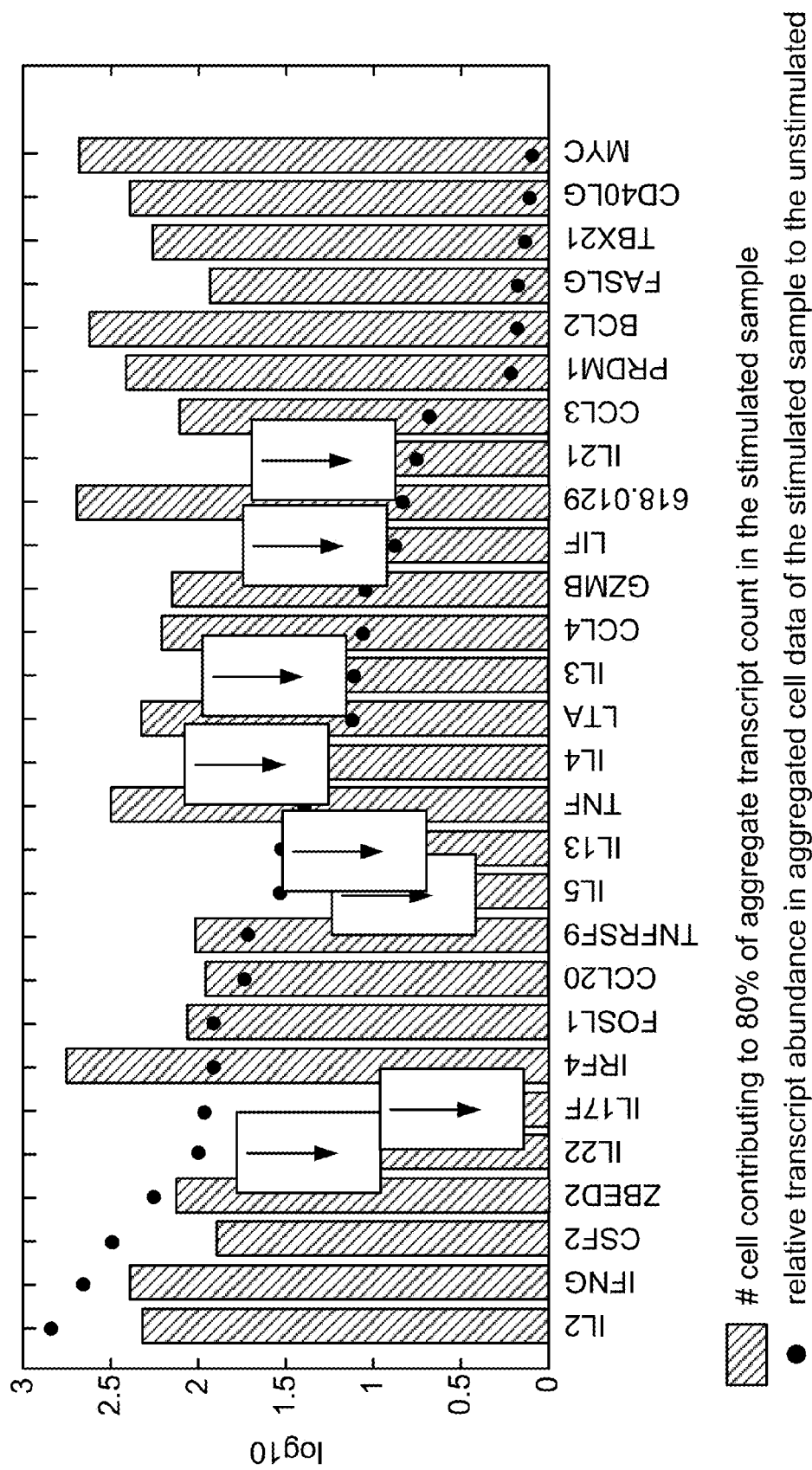
FIG. 44C. Number of cells that contribute to the overall expression level of genes that exhibit large fold-changes when comparing stimulated over unstimulated samples in aggregate data. For several cytokines (red arrows), the contribution from only a small number of cells is responsible for large overall gene expression change in the entire population.
Figure 46A:
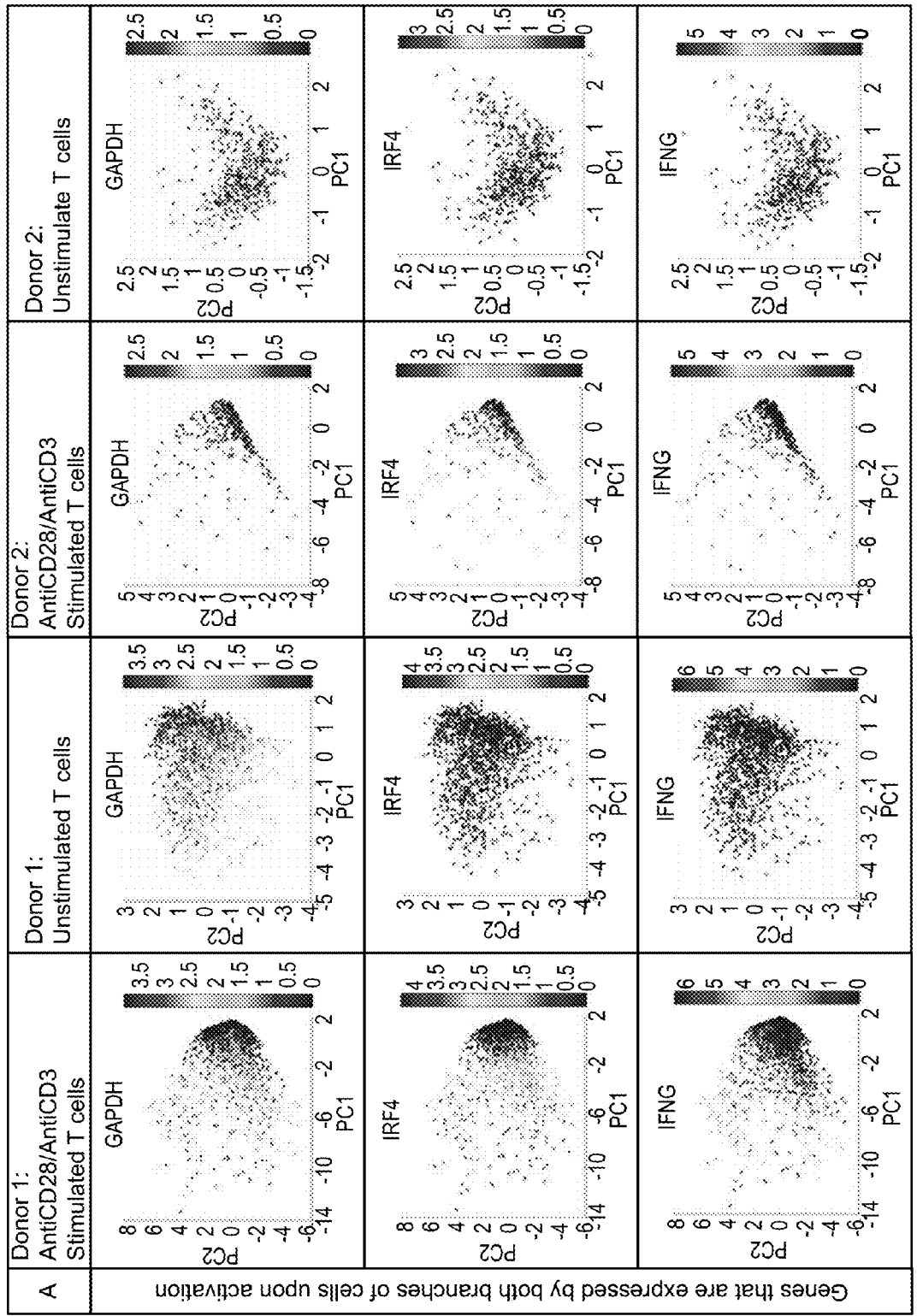
FIGS. 46A-D PCA plots of T cell samples that have undergone stimulation with anti-CD28/anti-CD3 beads in the two donors, and the corresponding unstimulated samples, with emphasis on the expression of genes that are expressed in the stimulated samples but at low or undetectable level in the unstimulated samples. The color of each data point (single cell) indicates log (number of unique transcript molecule) per cell for the indicated gene. For each pair of stimulated and unstimulated graphs in each donor, the color range is adjusted to be the same. 46A and 46D. Genes that are expressed by both branches of cells upon activation. 46B. Genes that are expressed preferentially by cells in the upper branch upon activation. These genes are known to be associated with activated cytotoxic T cells. 46C. Genes that are expressed preferentially by cells in the lower branch upon activation. These genes are known to be associated with activated helper T cells.
Figure 46A:
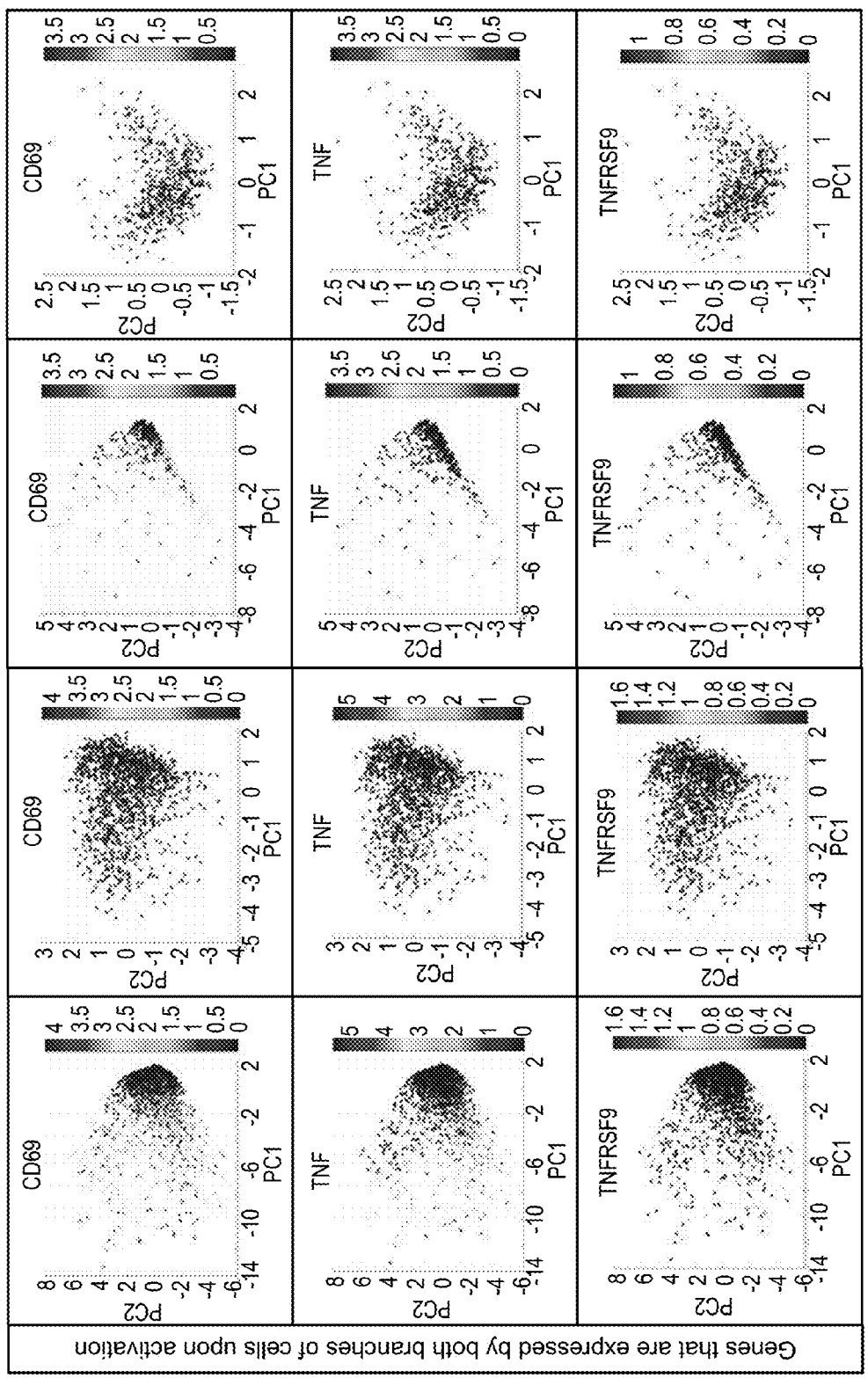
Figure 46A:
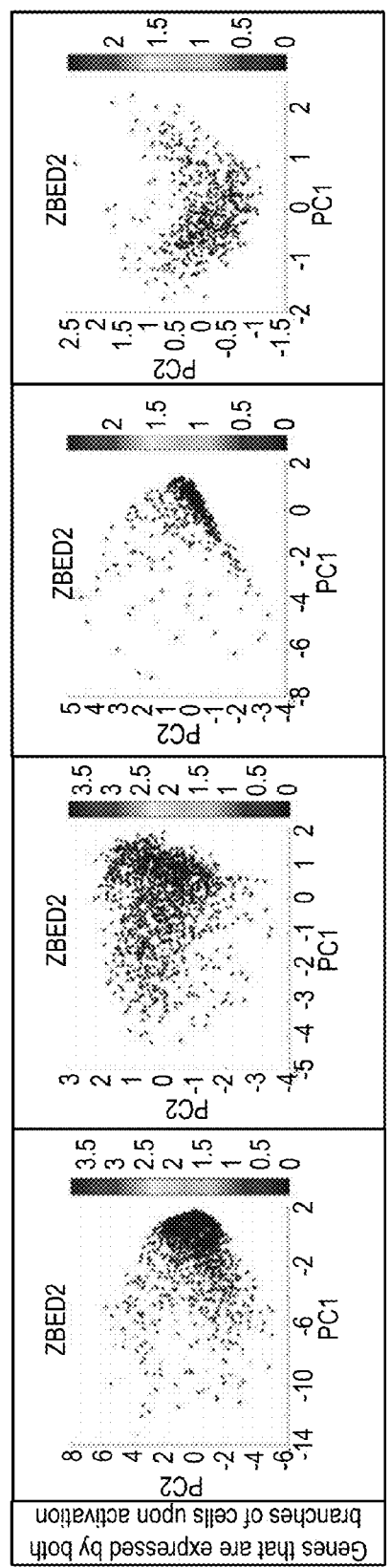
Figure 46B:
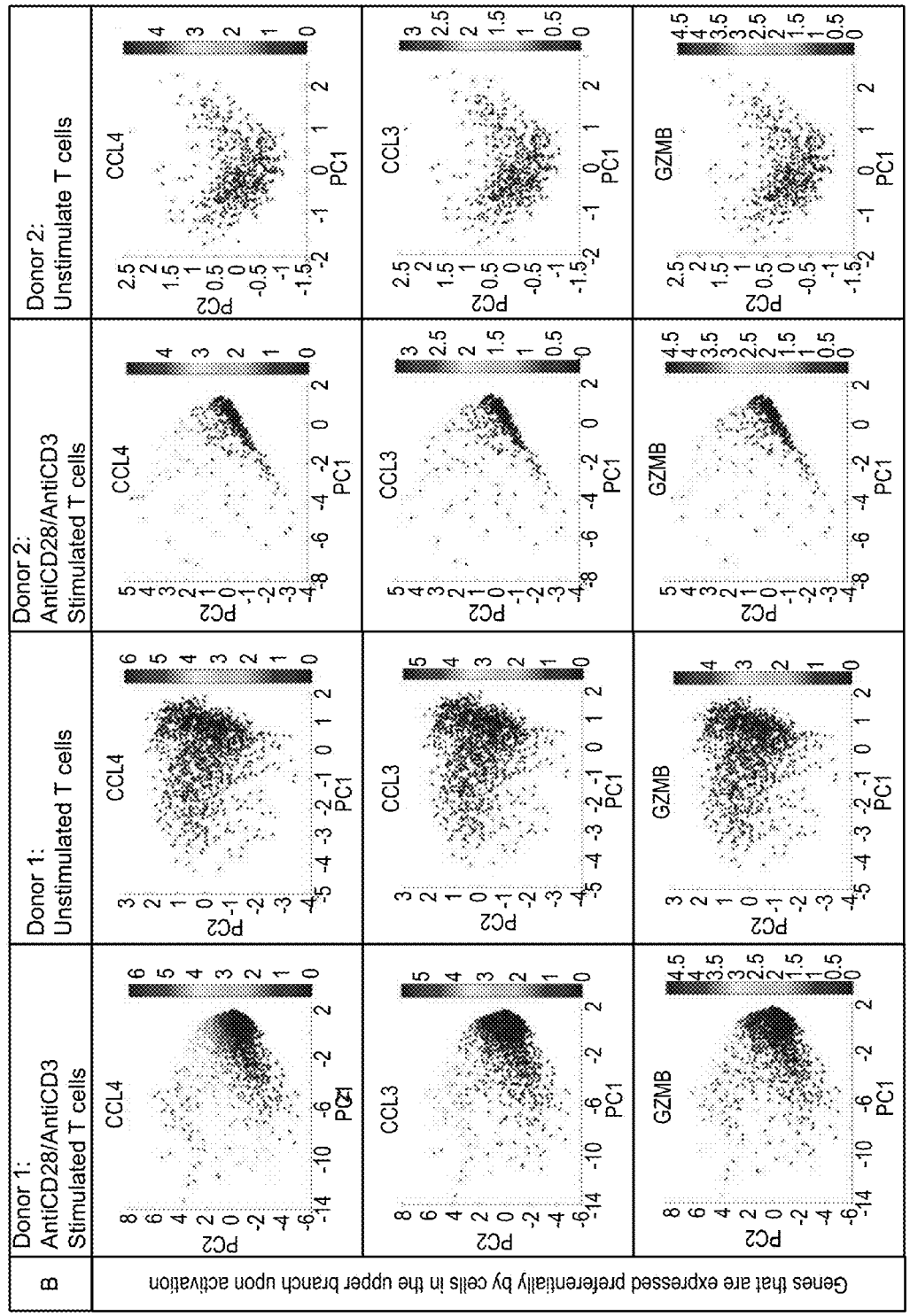
Figure 46B:
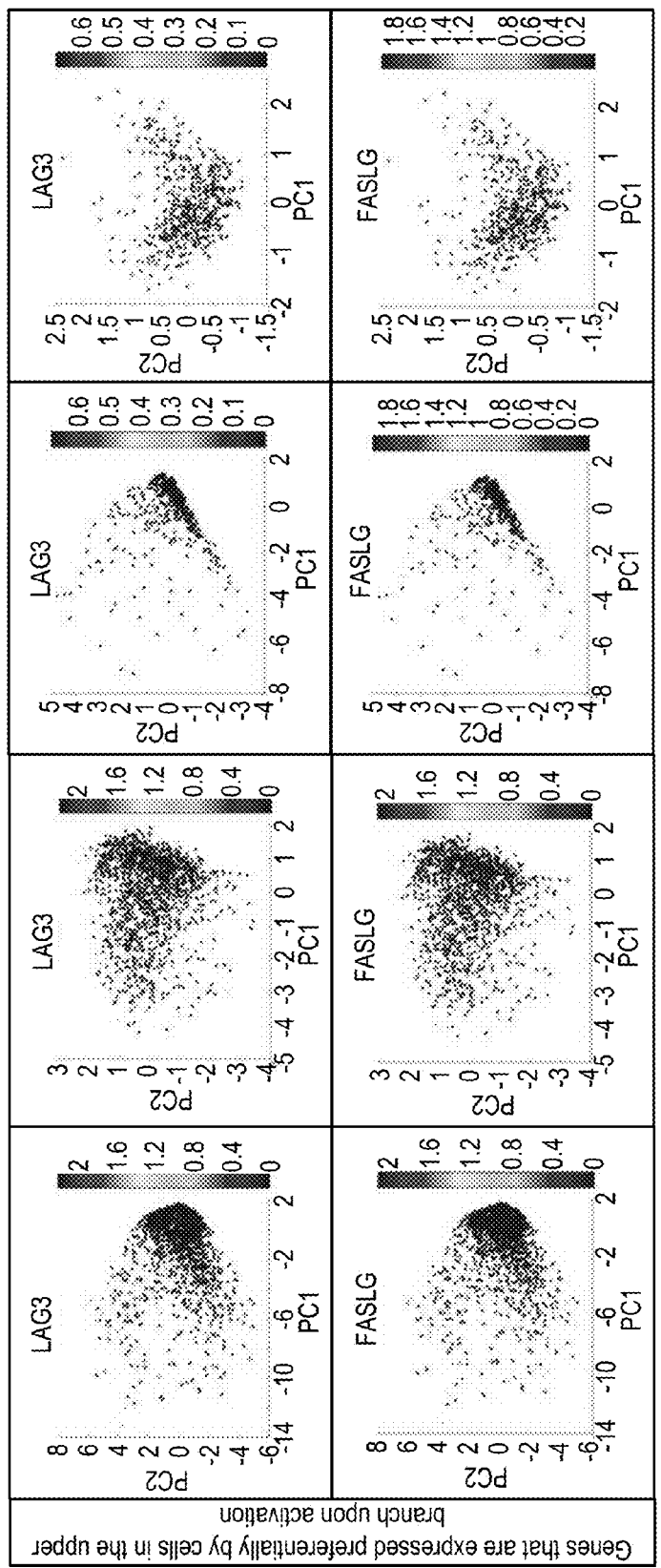
Figure 46C:
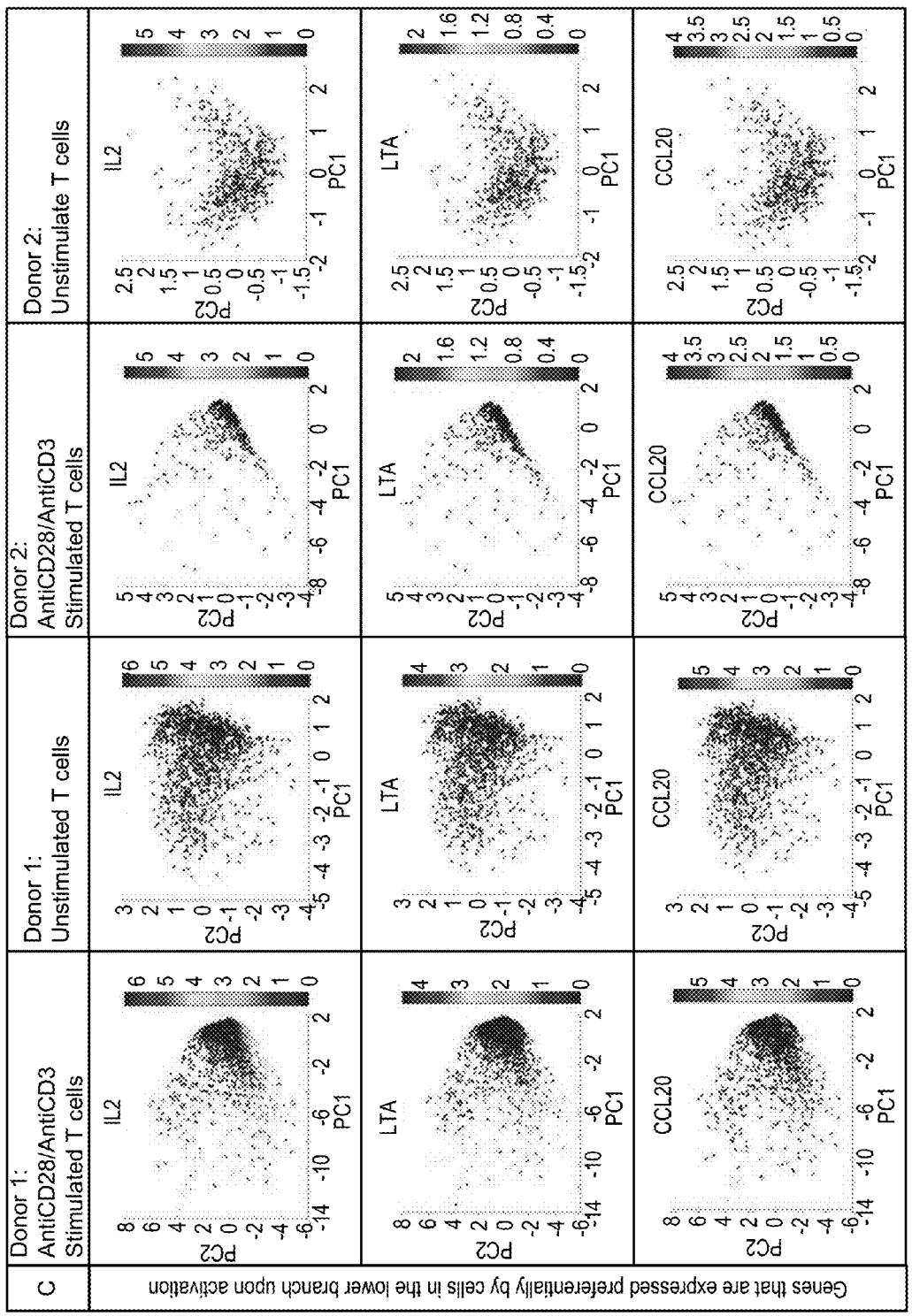
Figure 46C:
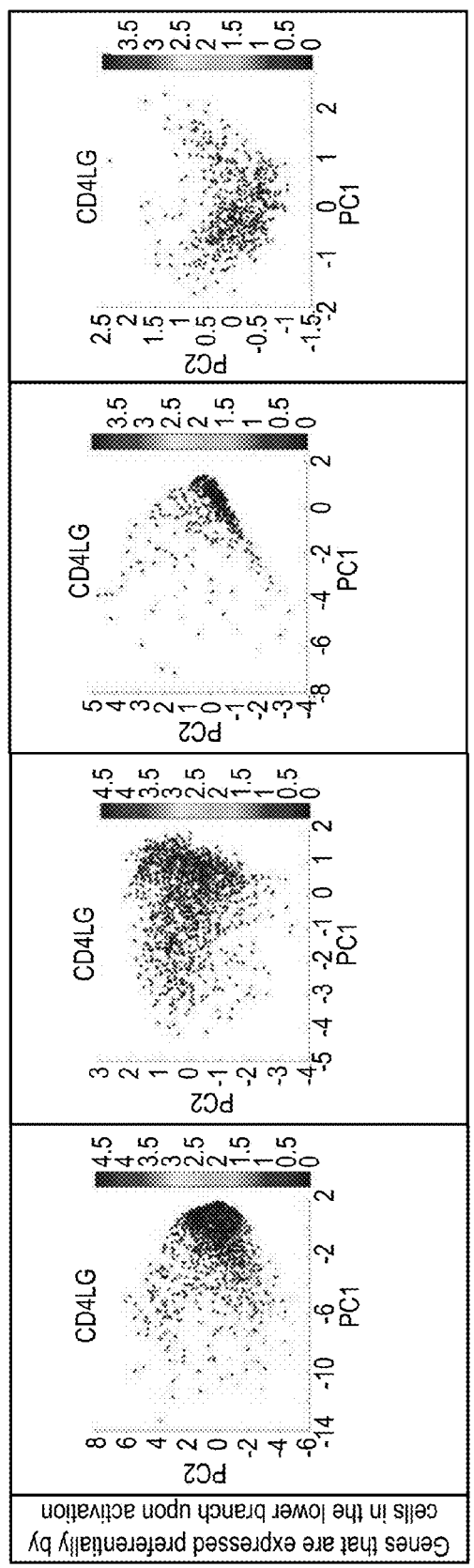
Figure 46D:
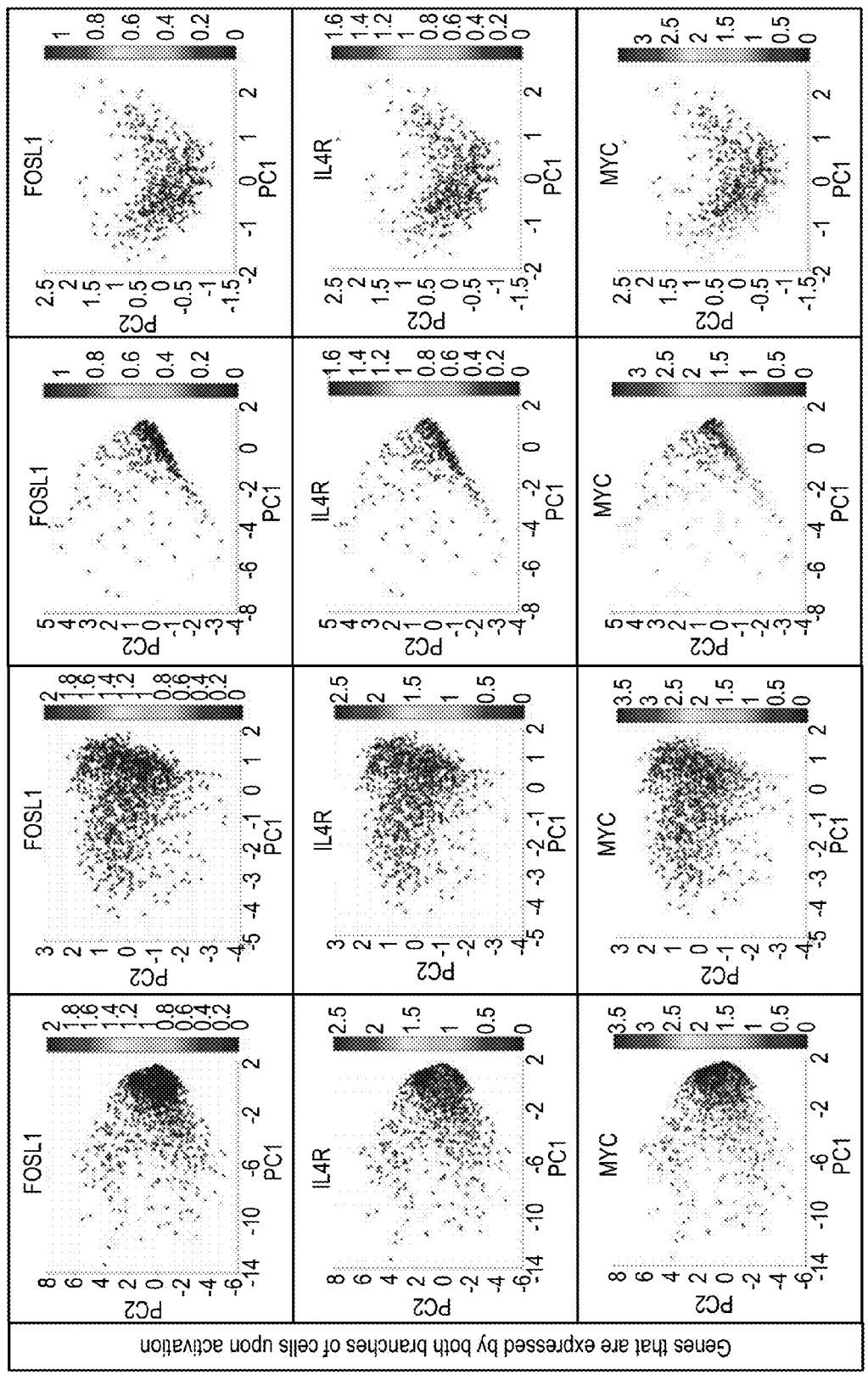
Figure 46D:
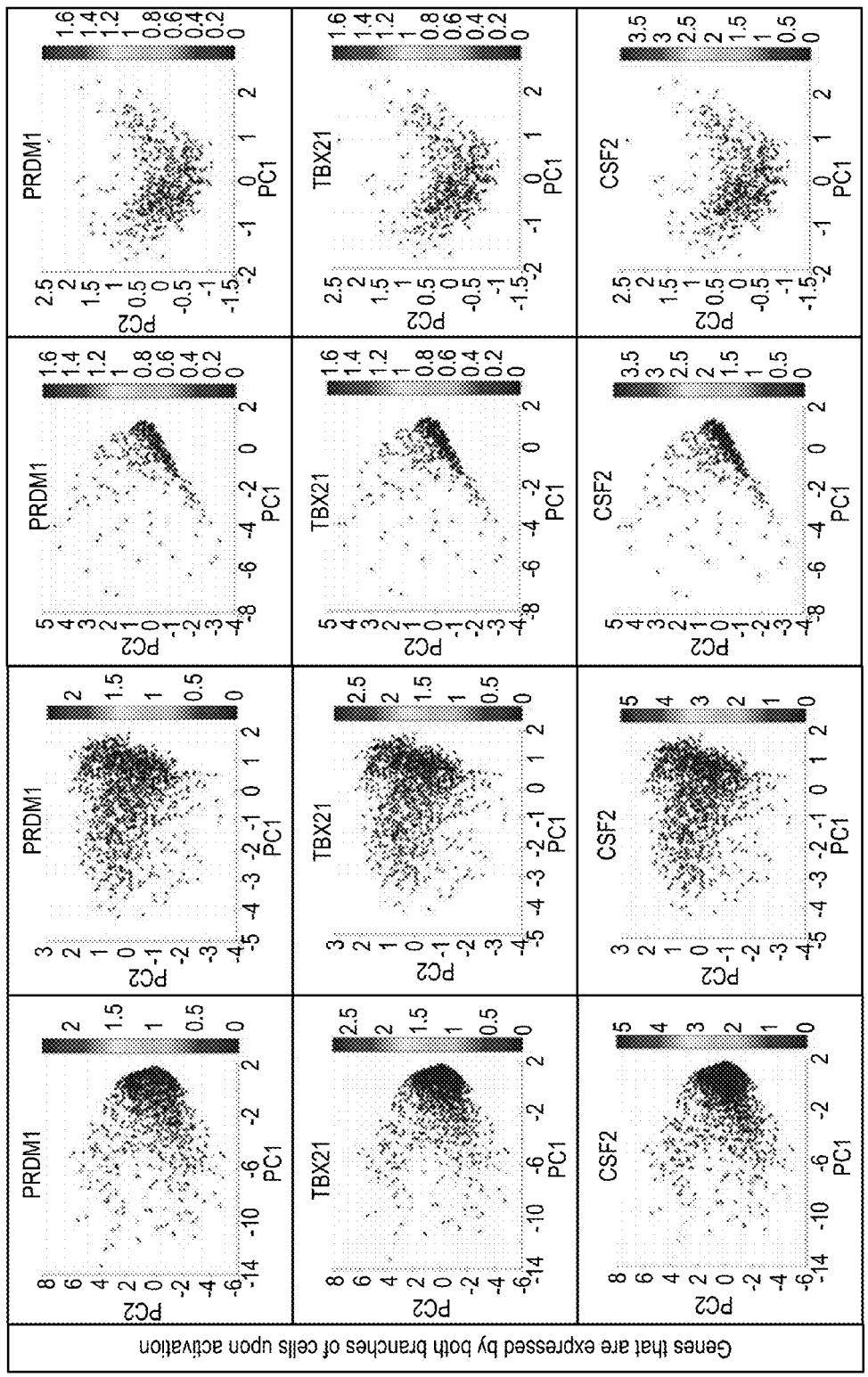
Figure 46D:
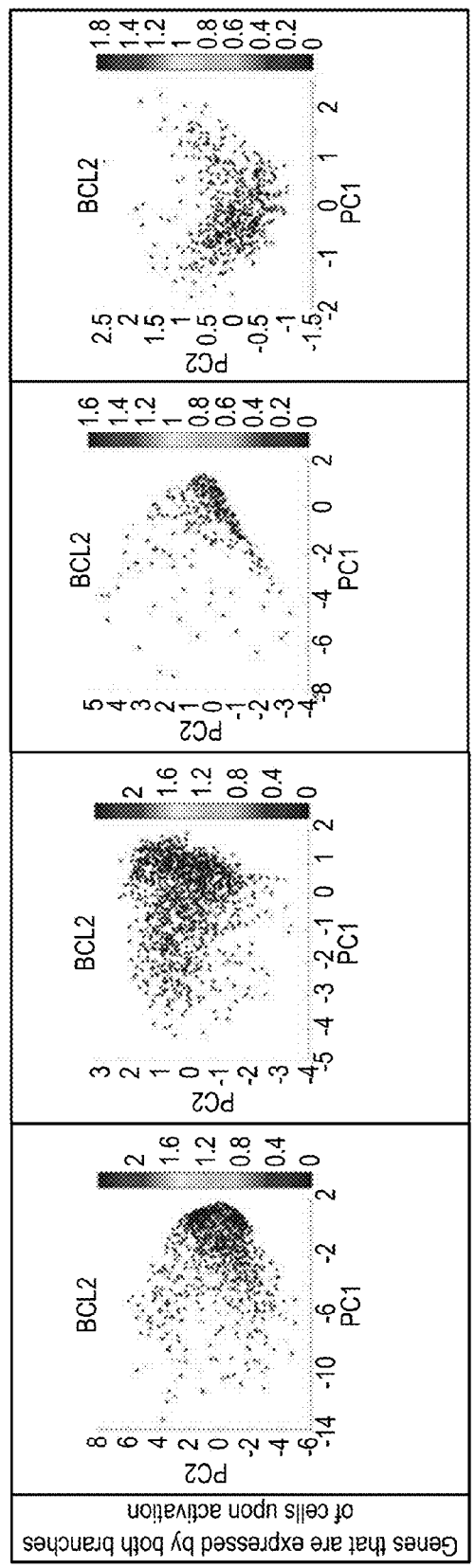
Figure 49A:
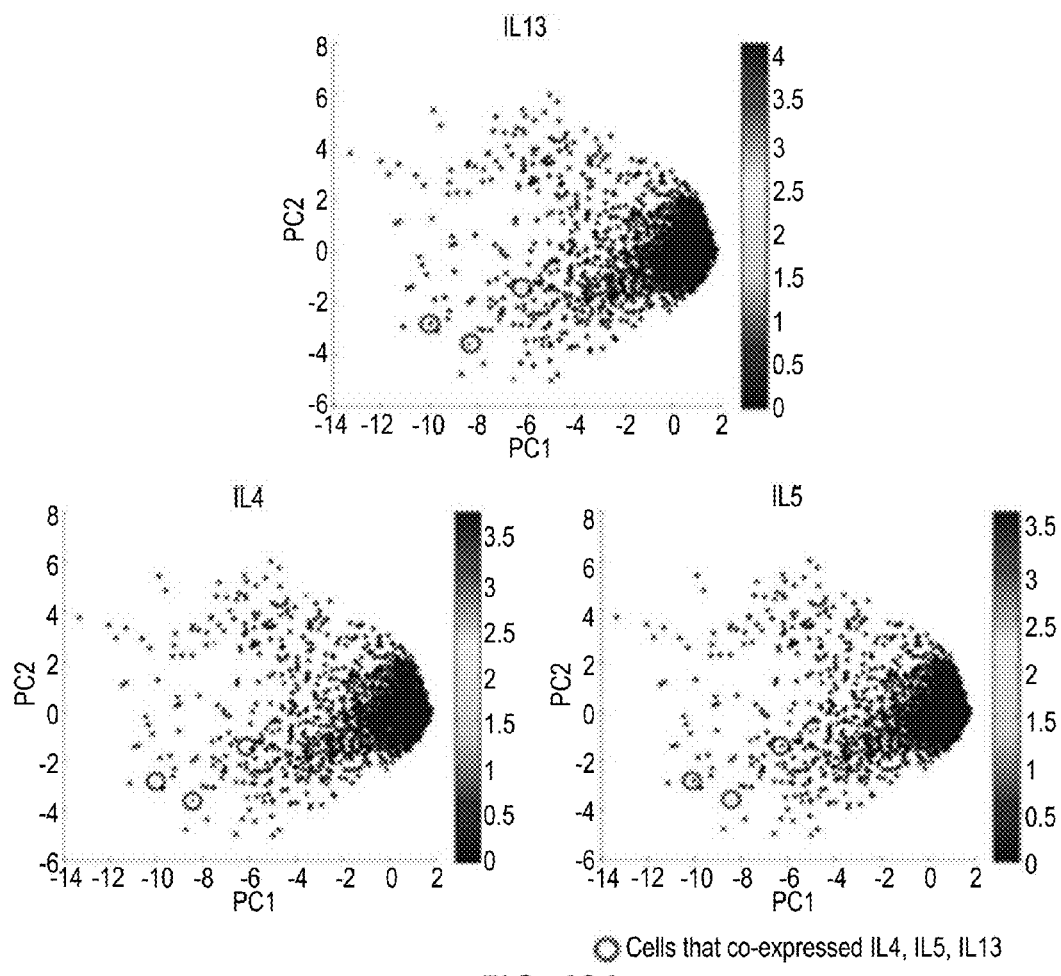
Figure 49B:
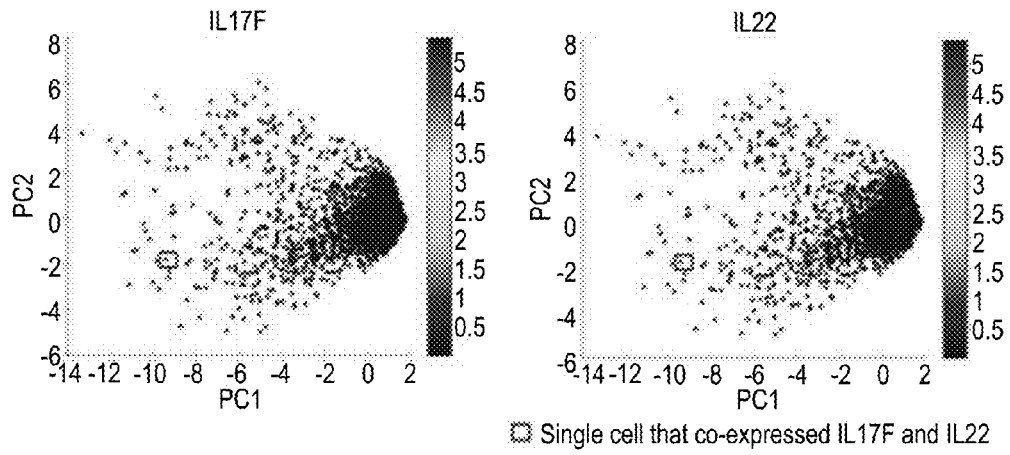

We observed that there were a few cytokines, namely IL4, IL5, IL13, IL17F, IL22, LIF, IL3, and IL21, that were upregulated by a few hundred or more folds in the stimulated sample as a whole as compared to the unstimulated one, but were contributed only by a few cells in the sample (FIG. 44C). Subsets of these cytokines were expressed by the same cells (FIG. 49A-C). For instance, the same single cell contributed to most of the counts of IL17F and IL22, which were signatures for Th17 cells. Another 7 cells expressed various combinations of IL4, IL5, IL13, which were signatures of Th2 cells, and expressed various combinations of them. Such observation highlights the importance of large-scale single cell analysis, especially when the contribution to overall expression changes was derived from a rare subpopulation.

We repeated the same stimulation experiment with T cells from a second blood donor and analyzed the profile of 669 and 595 single cells in the stimulated and unstimulated sample, respectively. While the overall level of activation was lower (smaller magnitude in terms of change in expression) in this individual (possibly indicating inter-individual variability to stimulation), we observed the same trends in PCA analysis, as well as heterogeneity in individual cell's response to stimulus (FIG. 48).

Identification of Rare Antigen Specific T Cells

We demonstrated the utility of our platform to identify rare cells using the model of antigen specific cells in CD8+ T cell population. We exposed fresh blood of the same two blood donors who were seropositive for cytomegalovirus (CMV) to CMV pp65 peptide pool. A separate untreated blood aliquot of each donor served as negative control. We subsequently isolated CD8+ T cells and analyzed the response of stimulated and unstimulated cells on our platform. We obtained data from 2274, 2337, 581, and 253 cells in donor 2's CMV stimulated and unstimulated, and donor 1's CMV stimulated and unstimulated samples, respectively.

Figure 50A:
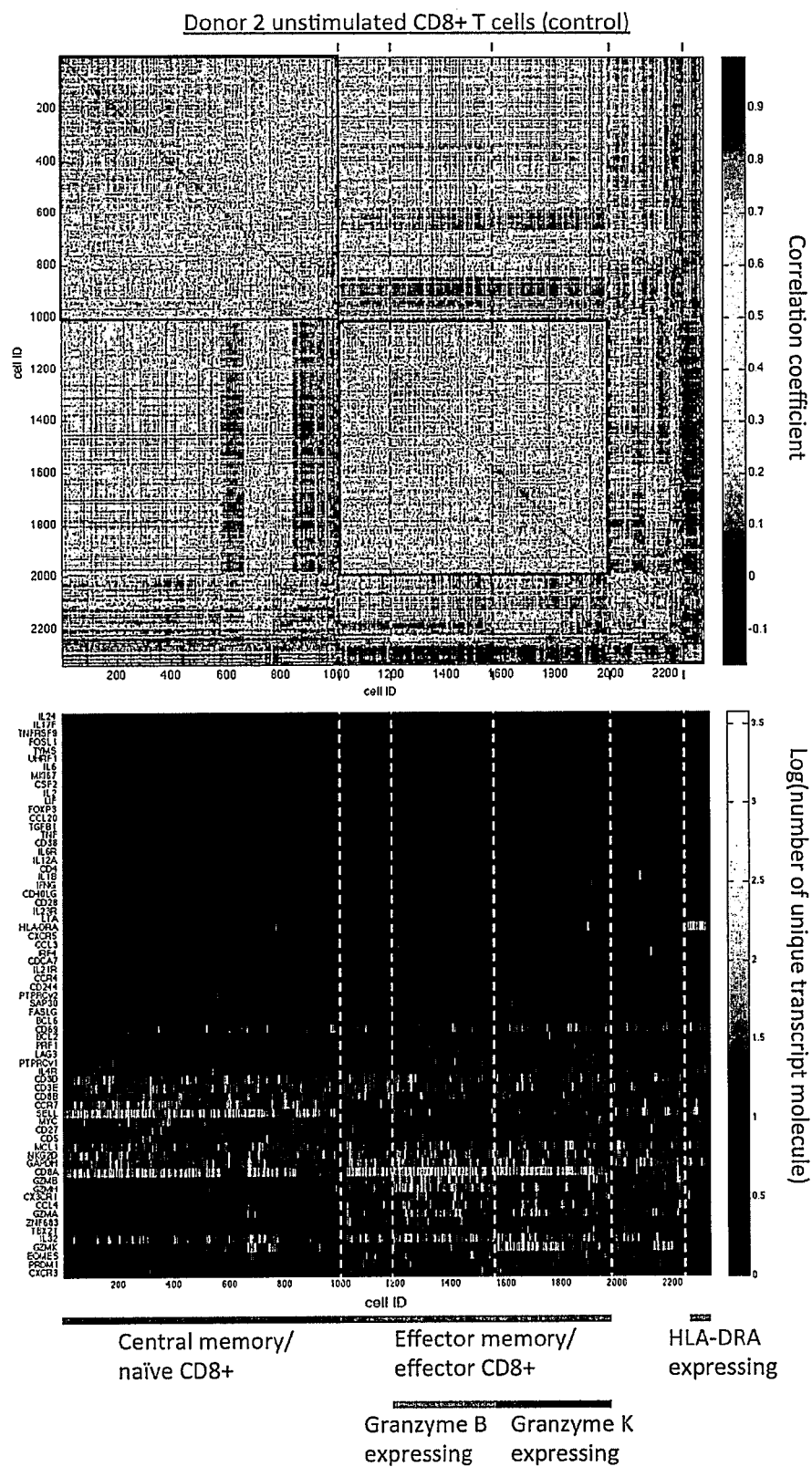
FIGS. 50A-B. Dissecting sub-populations of CD8+ T cells.
Figure 51:
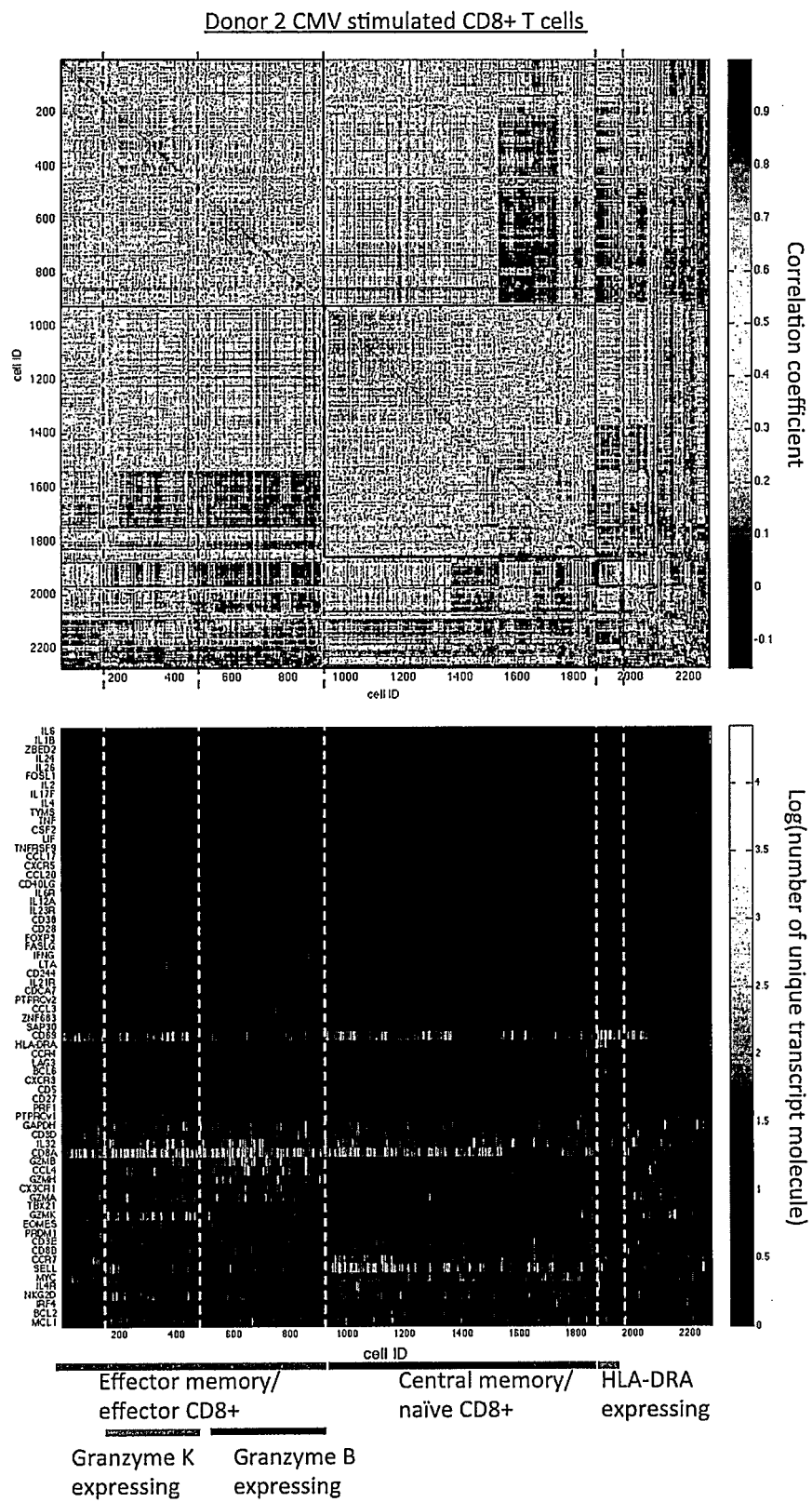
FIG. 51. Similar to FIG. 50A except the data here represents that of Donor 2 CMV stimulated sample. Clustering of CytoSeq data defines two major groups of CD8+ cells—one group expresses genes shared by central memory/naïve cells, and the other group expresses genes shared by effector memory/effector cells.
Figure 52F:
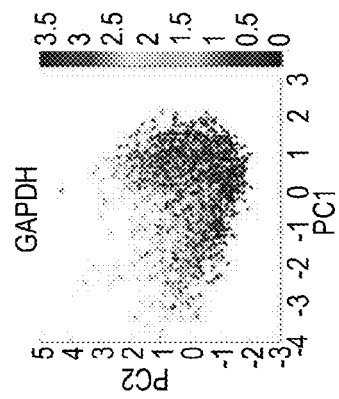
FIGS. 52FA-FX. Genes that are expressed in both branches of cells.
Figure 52F:
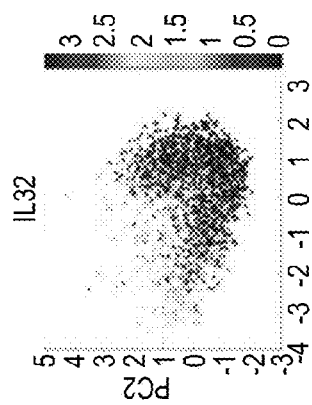
Figure 52F:
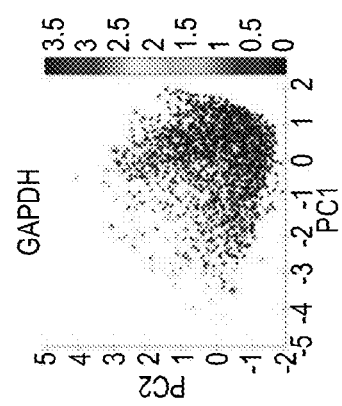
Figure 52F:
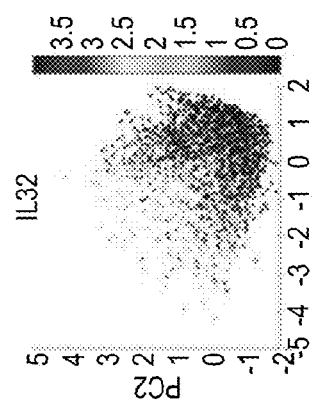
Figure 52F:
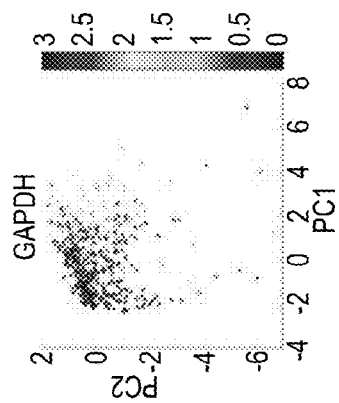
Figure 52F:
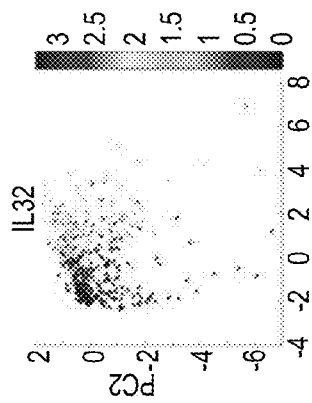

Except for donor 1's negative control that yielded relatively small number of cells to form obvious clusters in clustering analysis, all the rest of the samples showed two main groups of cells (FIGS. 50A, 51 and 52). Cells in one group expressed naïve cell and central memory associated markers SELL, CCR7, and CD27, while cells in the other group expressed effector memory cell (CCL4, CX3CR1, CXCR3) and effector cell associated genes (EOMES, GZMA, GZMB, GZMH, TBX21, ZNF683). There was a distinct small subset of cells that occupy space in between the two branches and express granzyme K (GZMK), as well as another subset of HLA-DRA expressing cells. The differential expression of the different types of granzymes has previously been reported (8). Our results recapitulated those observed in previous CyTOF experiments with CD8+ T cells (9).

Figure 50B:
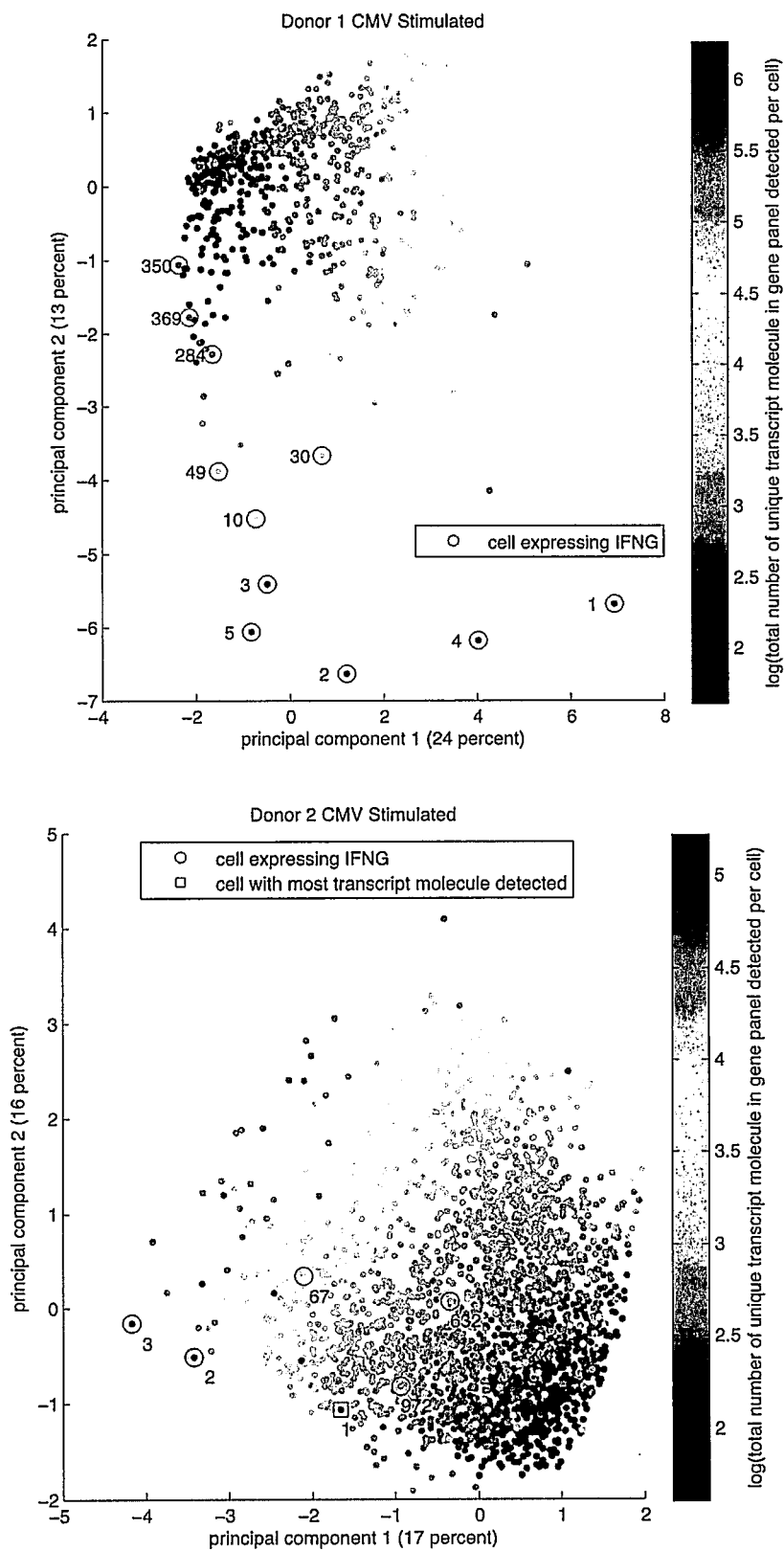
Figure 53:
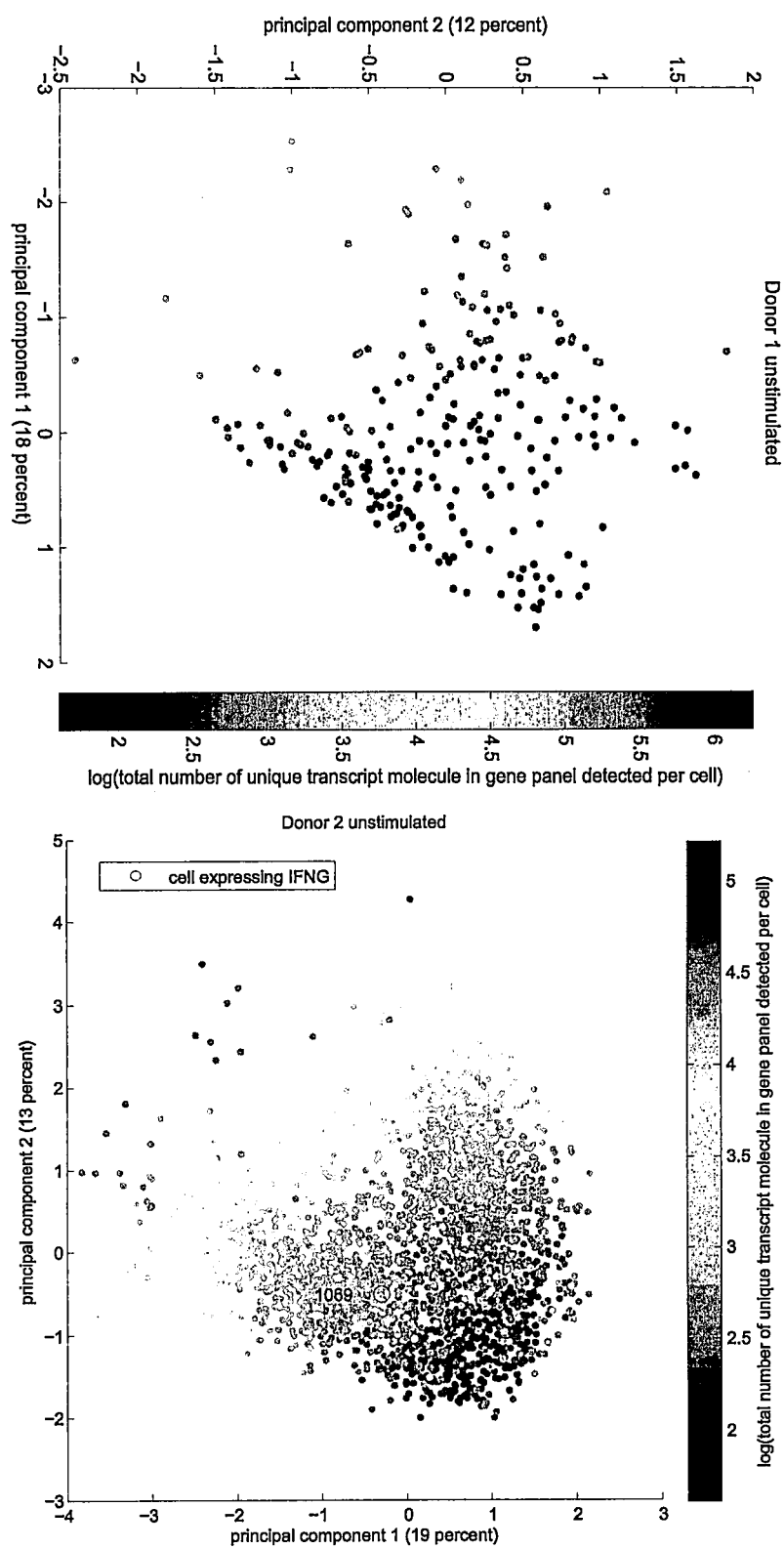
FIG. 53. Same as FIG. 50B, except the data represents those of the unstimulated controls.
Figure 54:
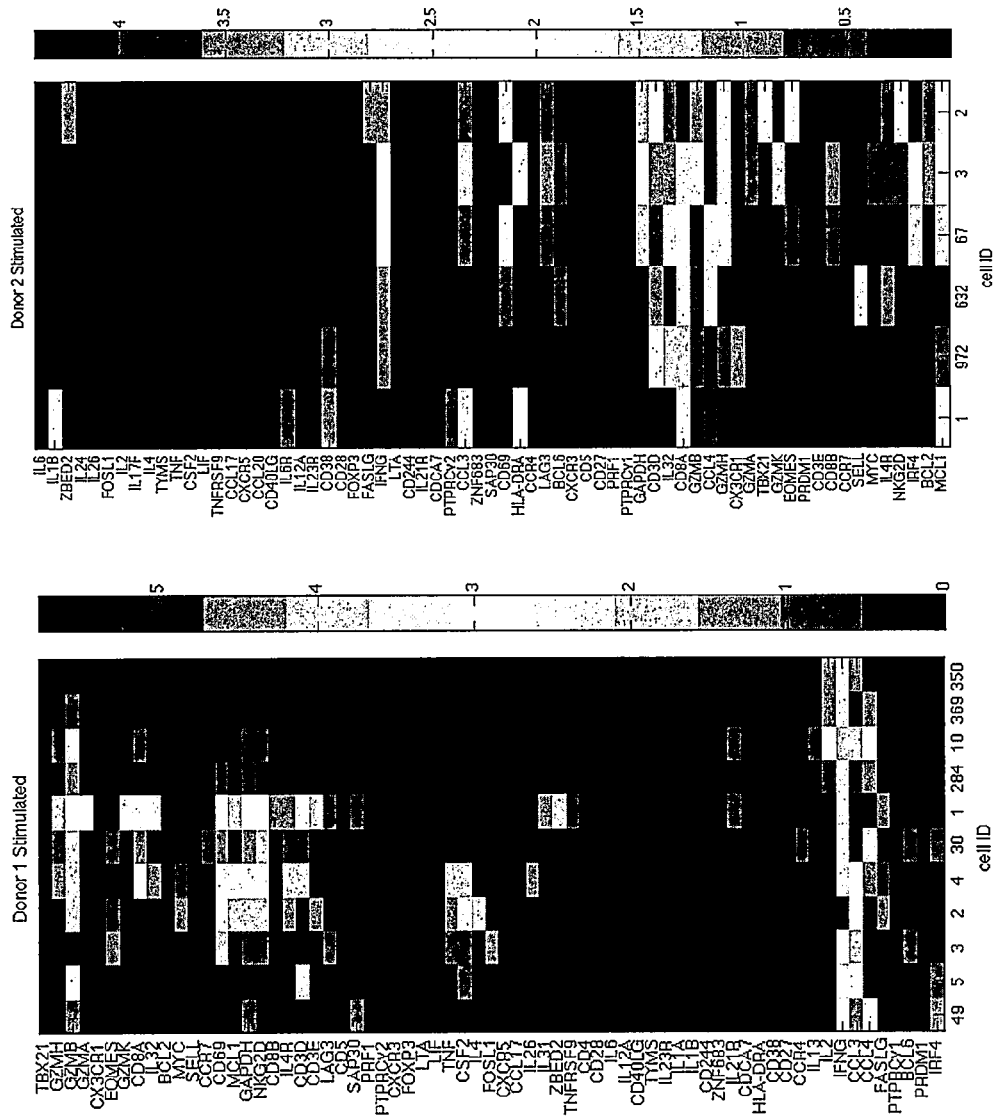
FIG. 54. Heatmaps showing the heterogeneous expression of the gene panel in cells that express gamma interferon (IFNG) in CMV stimulated CD8+ T cells of Donors 1 and 2.

While a considerable proportion of cells seemed to respond to the exposure to the antigen via expression CD69 and MYC (FIGS. 52AA-FX), we found only a few cells that expressed IFNG, a signature cytokine for activated antigen specific cell. Most of the IFNG expressing cells were also among those cells carried the most total detected transcript molecules in the gene panel, an indication of active cell state, and belong to the effector memory/effector cell cluster (FIGS. 50B and 53). We identified 5 out of 581 (0.86%) and 2 out of 2274 (0.09%) cells in donors 1 and 2 respectively that were likely to be CMV specific based on IFNG expression and overall transcription level. Among those cells, there was substantial amount of heterogeneity in terms of combinations and levels of effector molecules (e.g., granzymes) and cytokines (e.g., IFNG, IL2, CCL3, CCL4, TNF, CSF2, IL4) expressed (FIG. 54). Interesting, the single cell that expressed most transcripts in donor 2 expressed both IL6 and IL1B but not IFNG.

Discussion

In this example, we presented highly scalable mRNA cytometry that used a recursive Poisson strategy to isolate single cells, to uniquely barcode cellular content, and to barcode individual molecules for quantitative analysis. We have shown that we may simultaneously identify and count transcript molecules belonging to each cell in a sample containing a few thousands cells. Further, we have demonstrated to use of this technique to characterize individual cells based on their expression profiles in naturally occurring heterogeneous systems, and detection of rare cells in a large background population.

The throughput and simplicity of CytoSeq presents a major advance over existing approaches involving microtiter plates or microfluidic chips for sequencing based measurement of gene expression of single cells. Because the experimental procedure is simple and reagent consumption per cell is low (in the nanoliter range), it enables one to readily carry out single cell analysis for large number of cells across multiple conditions. In this study alone, we performed gene expression profiling of a total of ~14,600 single cell across 12 experiments, which would be costly and time-consuming if carried out by existing approaches. The number of cells measured by CytoSeq may be further scaled up simply by increasing the size of the microwell array and the library size of the barcoded beads, which is readily achieved by combinatorial synthesis. In addition, there is no restriction on the uniformity of cell sizes, thus allowing direct analysis of complex samples containing cells with a variety of cell sizes and shapes, such as PBMCs shown in this example, without any pre-sorting.

CytoSeq data resembled those of flow cyometry (FC), but with important differences. First, CytoSeq offers more versatility in terms of the number and type of gene products studied. Unlike flow cytometry that is confined mostly to a handful of surface proteins and requires optimally binding antibodies, CytoSeq allowed measurement of any transcribed mRNAs via nucleic acid amplification techniques. Optimal primer design and assay conditions enable us to routinely achieve ~88% mapped rate via multiplex PCR for an arbitrarily chosen panel of 100 or more genes (Table 21). Additionally, the entire transcriptome of each single cell in the sample may also be measured via universal amplification of the bead bound cDNA, although one has to be mindful with the relatively low efficiency of commonly used universal amplification techniques (7) and the high sequencing depth required for measuring the whole transcriptome across thousands of cells.

Second, in contrast to flow cytometry that relies on the kinetics of antibody binding, CytoSeq provides digital, absolute readout of gene expression level through molecular indexing. It has higher sensitivity and specificity to a single rare cell event because the detection was achieved by the co-expression of large number of genes specific to the rare cells. It therefore consumes much smaller amount of sample as compared to flow cytometry that requires certain number of events in order to form reliable clusters for gating.

Our data illustrates the importance of single cell versus bulk analysis. For instance, we showed scenarios where the most highly expressed genes in a sample of thousands of cells as whole were contributed by only one or a few cells. Most importantly, our experiments illustrate the importance of examining both large number of cells and large number of genes in single cell gene expression studies, an ability that is extremely limiting in prior approaches. The availability of such a tool for the routine measurement of expression across thousands of single cells in a biological sample may help accelerate the understanding of complex biological systems and drive novel applications in clinical diagnostics, such as circulating tumor cell analysis and immune responses monitoring. We envision that our massive parallel single cell barcoding regime may also be adopted to measure the genome, as well as the genome and the transcriptome simultaneously, for studying single cell genome instability in areas such as cancer biology and neuroscience.

TABLE 21

| Experiment | total number of reads | number of reads with exactly 1 match to gene in panel | % reads aligned to one gene in the panel | number of reads with exact match to a cell barcode and alignment to one gene | % read after gene and barcode alignment | number of unique cell barcodes that satisfy filtering criteria | number of reads associated with those cell barcodes |
|---|---|---|---|---|---|---|---|
| K562 + Ramos | 2399025 | 2154454 | 90% | 1175715 | 49% | 768 | 859470 |
| Primary B + Ramos | 5711013 | 5203308 | 91% | 3495392 | 61% | 1198 | 2868577 |
| PBMC | 1270214 | 1105687 | 87% | 803151 | 63% | 632 | 670576 |
| PBMC replicate | 3927672 | 3468538 | 88% | 2459367 | 63% | 731 | 1920956 |
| Donor 1 antiCD3/antiCD28 stimulated | 3529898 | 3249998 | 92% | 2122416 | 60% | 3517 | 1466000 |
| Donor 1 antiCD3/antiCD28 negative control | 1557996 | 1292211 | 83% | 939094 | 60% | 1478 | 719351 |
| Donor 2 antiCD3/antiCD28 stimulated | 606865 | 552877 | 91% | 403943 | 67% | 669 | 246234 |
| Donor 2 antiCD3/antiCD28 negative control | 332951 | 283723 | 85% | 205762 | 62% | 595 | 86866 |
| Donor 1 CMV stimulated | 1064648 | 958410 | 90% | 697057 | 65% | 581 | 401629 |
| Donor 1 CMV negative control | 619957 | 547259 | 88% | 406801 | 66% | 253 | 192605 |
| Donor 2 CMV stimulated | 1902977 | 1692734 | 89% | 1229667 | 65% | 2274 | 688296 |
| Donor 2 CMV negative control | 1671419 | 1346637 | 81% | 977344 | 58% | 2337 | 715453 |

Synthesis of Bead Library

Beads were manufactured by Cellular Research, Inc. using a split-pool combinatorial approach. Briefly, twenty-micron magnetic beads functionalized with carboxyl groups were distributed into a 96 tubes containing oligos with 5' amine, followed by a universal sequence, first part of the cell label that is different for different tubes, and a linker sequence. The oligos were covalently coupled onto the beads by carbodiimide chemistry. Beads were pooled and split into a second set of 96 tubes containing oligos with a second linker sequence on the 5' end, followed by the second part of the cell label that is different for different tubes, and complementary sequence to the first linker. Oligos on the beads were extended by DNA polymerase upon hybridization to oligos in solution via the first linker. Beads were pooled and split into a third set of 96 tubes containing oligos with oligo(dA) on the 5' end, followed by a randomer sequence that serves as the molecular label, the third part of the cell label, and a complementary sequence to the second linker. Oligos on the beads were extended by DNA polymerase upon hybridization to oligos in solution via the second linker. The final bead library has a size of 96×96×96 (884,736) cell labels.

Fabrication of Microwell Array

Microwell arrays were fabricated using standard photolithography. Arrays of pillars were patterned on photoresist on silicon wafer. PDMS was poured onto the wafer to create arrays of microwells. Replicas of the wafer were made with NOA63 optical adhesive using PDMS microwell array as template. Agarose (5%, type IX-A, Sigma) microwell arrays were casted from the NOA63 replica before each experiment.

Sample Preparation

K562 and Ramos cells were cultured in RPMI-1640 with 10% FBS and 1× antibiotic-antimycotic. Primary B cells from a healthy donor were purchased from Sanguine Biosciences. PBMCs from a healthy donor were isolated from fresh whole blood in sodium heparin tube acquired from the Stanford Blood Center using Lymphoprep solution (StemCell).

T Cell Stimulation

Heparinized whole blood of two CMV seropositive blood donors was obtained from the Stanford Blood Center. For CMV stimulation, 1 ml of whole blood was stimulated with CMV pp65 peptide pool diluted in PBS (Miltenyi Biotec) at a final concentration of 1.81 µg/ml for 6 hours at 37 C. A separate aliquot of whole blood of each donor was incubated with PBS as negative controls. CD8+ T cells were isolated using RosetteSep cocktail (StemCell) and subsequently deposited onto microwell arrays. For anti-CD3/anti-CD28 stimulation, T cells from the same two donors were isolated from whole blood using RosetteSep T cell enrichment cocktail and resusupended in RPMI-1640 with 10% FBS and 1× antibiotic-antimycotic. One aliquot of cells from each donor was incubated with Dynabeads Human T-Activator CD3/CD28 (Life Technologies) at ~1:1 bead to cell ratio at 37 C for 6 hours. A separate aliquot of cells from each donor were placed in incubator with no stimulation and served as negative control.

Single Cell Capture

Single cell suspension was pipetted on to the microwell array at a density of ~1 cell per 10 microwells. After washing to remove uncaptured cells, magnetic beads were loaded at a density of ~5 beads per well to saturate the microwell array. After washing to remove excess beads, cold lysis buffer (0.1M Tris-HCl pH 7.5, 0.5M LiCl, 1% LiSDS, 10 mM EDTA, 5 mM DTT) was pipetted over the surface of the microwell array. After 10 minutes of incubation on a slide magnet, beads were retrieved from the microwell array. Beads were collected in a microcentrifuge tube, and washed twice with wash A buffer (0.1M Tris-HCl, 0.5M LiCl, 1 mM EDTA) and once with wash B buffer (20 mM Tris-HCl pH 7.5, 50 mM KCl, 3 mM MgCl2). From this point forward, all reactions were carried out in a single tube.

cDNA Synthesis

Washed beads were resuspended in 40 µL RT mix (1× First Strand buffer, 14 SuperRase Inhibitor, 1 µL SuperScript II or SuperScript III, 3 mM additional MgCl2, 1 mM dNTP, 0.2 ug/µL BSA) in a microcentrifuge tube placed on a rotor in a hybridization oven at temperatures 50 C for 50 minutes (when using SuperScript III for the early experiment with K562 and Ramos cells) or 42 C for 90 minutes (when using Superscript II for the rest of the experiments). Beads were treated with 1 µL of ExoI (NEB) in 20 µL of 1× ExoI buffer at 37° C. for 30 minutes, and 80° C. for 15 minutes.

Multiplex PCR and Sequencing

Each gene panel contained two sets of gene specific primers designed by Primer3. A custom MATLAB script was written to select PCR primers such that there was minimal 3' end complementarity across the primers within the set. Primers in each panel are listed in Table 21. The amplification scheme is shown in FIG. 55. PCR were performed with the beads with KAPA Fast Multiplex Kit, with 50 nM of each gene specific primer in the first primer set and 400 nM universal primer, in a volume of 100 µL or 200 µL, with the following cycling protocol: 3 min at 95 C; 15 cycles of 15 s at 95 C, 60 s at 60 C, 90 s at 72 C; 5 min at 72 C. Magnetic beads were recovered and PCR products were purified with 0.7× Ampure XP. Half of the purified products were used for the next round of nested PCR with the second primer set using the same KAPA kit and cycling protocol. After clean up with 0.7× Ampure XP, $1/10^{th}$ of the product was input into a final PCR reaction whereby the full-length Illumina adaptors were appended (1× KAPA HiFi Ready Mix, 200 nM of P5, 200 nM of P7. 95 C 5 min; 8 cycles of 98 C 15 s, 60 C 30 s, 72 C 30 s; 72 C 5 min).

Data Analysis

Sequencing of library was performed on Illumina MiSeq instrument with 150×2 bp chemistry at a median depth of 1.6 million reads per sample. Sequencing revealed the cell label, the molecular label, and the gene of each read (FIG. 55). The assignment of gene of each read was done with the alignment software 'bowtie' (ref). The cell and molecular labels of each read were analyzed using custom MATLAB scripts. Reads were grouped first by cell label, then by gene and molecular label. To calculate the number of unique molecules per gene per cell, the molecular labels of reads with the same cell label and gene assignment were clustered. Edit distance greater than 1 base was considered as a unique cluster, and thus a unique transcript molecule. A table containing digital gene expression information of each cell was constructed for each sample—each row in the table represented a unique cell label, each column represented a gene, and each entry in the table represented the count of unique molecules within a gene per cell label. The table was filtered such that unique molecules that were sequenced only once (i.e. redundancy=1) were removed. Subsequently, cells with a sum of unique molecules less than 10 or with co-expression of 4 or less genes in the panel were removed. The filtered table was then used for clustering analysis. Principal component analysis and hierarchical clustering was performed on log-transformed transcript count (with pseudocount of 1 added) with built-in functions in MATLAB.

References cited in Example 15, all of which are incorporated by reference in their entireties:

1. A. K. Shalek et al., Single-cell transcriptomics reveals bimodality in expression and splicing in immune cells. Nature 498, 236 (Jun. 13, 2013).
2. S. C. Bendall et al., Single-cell mass cytometry of differential immune and drug responses across a human hematopoietic continuum. Science 332, 687 (May 6, 2011).
3. A. R. Wu et al., Quantitative assessment of single-cell RNA-sequencing methods. Nature methods 11, 41 (January, 2014).
4. B. Treutlein et al., Reconstructing lineage hierarchies of the distal lung epithelium using single-cell RNA-seq. Nature 509, 371 (May 15, 2014).
5. S. Islam et al., Characterization of the single-cell transcriptional landscape by highly multiplex RNA-seq. Genome research 21, 1160 (July, 2011).
6. G. K. Fu, J. Hu, P. H. Wang, S. P. Fodor, Counting individual DNA molecules by the stochastic attachment of diverse labels. Proceedings of the National Academy of Sciences of the United States of America 108, 9026 (May 31, 2011).
7. G. K. Fu, J. Wilhelmy, D. Stern, H. C. Fan, S. P. Fodor, Digital encoding of cellular mRNAs enabling precise and absolute gene expression measurement by single-molecule counting. Analytical chemistry 86, 2867 (Mar. 18, 2014).
8. K. Bratke, M. Kuepper, B. Bade, J. C. Virchow, Jr., W. Luttmann, Differential expression of human granzymes A, B, and K in natural killer cells and during CD8+ T cell differentiation in peripheral blood. European journal of immunology 35, 2608 (September, 2005).
9. E. W. Newell, N. Sigal, S. C. Bendall, G. P. Nolan, M. M. Davis, Cytometry by time-of-flight shows combinatorial cytokine expression and virus-specific cell niches within a continuum of CD8+ T cell phenotypes. Immunity 36, 142 (Jan. 27, 2012).

Example 16

Development of Single Cell Quantification Protocol

FIG. 56 depicts a general workflow for the quantification of RNA molecules in a sample. In this example, the total number of RNA molecules in the sample was equivalent to the total number of RNA molecules in a single cell. As shown in Step 1 of FIG. 56, RNA molecules (110) were reverse transcribed to produce cDNA molecules (105) by the stochastic hybridization of a set of molecular identifier labels (115) to the polyA tail region of the RNA molecules. The molecular identifier labels (115) comprised an oligodT region (120), label region (125), and universal PCR region (130). The set of molecular identifier labels contained 960 different types of label regions.

Part I. Reverse Transcription and Labeling of RNA Molecules

An RNA sample was prepared by mixing the following:

| Genes | number of RNA molecules |
|---|---|
| Lys (spike-in control) | 456 |
| Phe (spike-in control) | 912 |
| Thr (spike-in control) | 1824 |
| Dap (spike-in control) | 6840 |
| Kan (spike-in control) | 7352 |
| Lymphocyte cell line RNA | 10 pg (1 cell equivalent) |
| MS2 carrier (no polyA) | $6 \times 10^{11}$ |

RNA molecules were labeled by preparing in an eppendorf tube a labeling mix as follows:

|  | Amount (μL) |
| --- | --- |
| RNA sample | 2 |
| ms2 RNA 1 μg/μL | 1 |
| 10 mM dNTP | 1 |
| 960 dT oligos pool (set#4) 10 μM | 0.4 |
| water | 9.1 |

Note: dT oligos pool (set #4) refers to the set of molecular identifier labels.

The molecular identifier labels were hybridized to the RNA molecules by incubation at 65° C. for 5 minutes. The labeling mix was stored on ice for at least 1 minute.

The labeled RNA molecules were reverse transcribed by the addition of the reverse transcription mix as described below:

|  | Amount (μL) |
| --- | --- |
| 5X first strand buffer | 4 |
| 0.1M DTT | 1 |
| superase-in 20 u/μL | 0.5 |
| superscript III RT | 1 |

Once the reverse transcription mix was added to the eppendorf tube containing labeling mix reaction, the reverse transcription reaction was conducted by incubating the sample at 37° C. for 5 minutes, followed by incubation at 50° C. for 30 minutes, and lastly incubation at 75° C. for 15 minutes. Reverse transcription of the labeled RNA molecules produced labeled cDNA molecules (170).

Once the RNA molecules were reverse transcribed and labeled, excess oligos were removed from the sample by Ampure bead purification (Step 2 of FIG. 1). Ampure bead purification was performed by adding 20 μl of ampure beads to the eppendorf tube containing the reverse transcribed and labeled RNA molecules and incubating the tube at room temperature for 5 minutes, The beads were washed twice with 70% ethanol to remove the excess oligos. Once the excess oligos were removed by the ethanol washes, 20 μl of 10 mM Tris was added to the tube containing the bead-bound labeled cDNA molecules.

As shown in Step 3 of FIG. 56, the labeled cDNA molecules (170) were amplified by multiplex PCR. Custom amplification of the labeled cDNA molecules was performed by using a custom forward primer (F1, 135 in FIG. 1) and a universal PCR primer (140). Table 23 lists the 96 different custom forward primers that were used to amplify 96 different genes to produce labeled amplicons (180) in a single reaction volume.

In order to optimize multiplex PCR reactions, 3 multiplex PCR reactions mixtures were prepared. Multiplex PCR reaction 1 was prepared as follows:

|  | Reaction 1 Amount (μL) |
| --- | --- |
| 10X titanium | 5 |
| 10 mM dNTP | 1.5 |
| water | 35.5 |
| 1 μM each F1 primer pool | 5 |
| PCR004 10 μM | 1 |
| purified cDNA | 1 |
| Titanium polymerase | 1 |

The reaction condition for Multiplex PCR reaction was 1 cycle at 94° C. for 2 min, followed by 25 cycles of 94° C. for 30 sec, 57° C. for 60 sec, and 68° C. for 1 min, then 1 cycle of 68° C. for 7 min and 1 hold cycle at 4° C.

Multiplex PCR reactions 2 and 3 were prepared as follows:

|  | Reaction 2 Amount (μL) | Reaction 3 Amount (μL) |
| --- | --- | --- |
| 2X Qiagen Multiplex mix | 25 | 25 |
| 1 μM each F1 primer pool | 5 | 5 |
| PCR004 10 μM | 1 | 1 |
| Q solution |  | 5 |
| water | 18 | 13 |
| purified cDNA | 1 | 1 |

The multiplex PCR reaction condition for Reactions 2 and 3 was 1 cycle at 95° C. for 15 min, followed by 25 cycles of 94° C. for 30 sec, 57° C. for 90 sec, and 72° C. for 1 min, then 1 cycle of 68° C. for 7 min and 1 hold cycle at 4° C.

The F1 primer pools contained the following primers:

| F1 PCR Primers | Sequence | SEQ ID NO: |
| --- | --- | --- |
| 100611KanF2 | CTGCCTCGGTGAGTTTTCTC | 624 |
| Lys_L_269 | CTTCCCGTTACGGTTTTGAC | 625 |
| phe_L_177 | AAAACCGGATTAGGCCATTA | 626 |
| thrL_332 | TCTCGTCATGACCGAAAAAG | 627 |
| dap_L_276 | CAACGCCTACAAAAGCCAGT | 628 |

Kan, Phe and Dap control genes were selectively amplified by nested PCR. Nested PCR amplification reactions were prepared as follows:

|  | Multiplex PCR Rxn # | | | | | | | | |
| --- | --- | --- | --- | --- | --- | --- | --- | --- | --- |
|  | 1 | 2 | 3 | 1 | 2 | 3 | 1 | 2 | 3 |
|  | PCR Rxn # | | | | | | | | |
|  | 1 μL | 2 μL | 3 μL | 4 μL | 5 μL | 6 μL | 7 μL | 8 μL | 9 μL |
| 10x Taq | 2.5 | 2.5 | 2.5 | 2.5 | 2.5 | 2.5 | 2.5 | 2.5 | 2.5 |
| 10 mM dNTP | 0.5 | 0.5 | 0.5 | 0.5 | 0.5 | 0.5 | 0.5 | 0.5 | 0.5 |
| water | 22.25 | 22.25 | 22.25 | 22.25 | 22.25 | 22.25 | 22.25 | 22.25 | 22.25 |
| Cy3 PCR004 10 μM | 0.5 | 0.5 | 0.5 | 0.5 | 0.5 | 0.5 | 0.5 | 0.5 | 0.5 |
| KanF3_5P 5 μM | 1 | 1 | 1 |  |  |  |  |  |  |
| Phe_L_215 5 μM |  |  |  | 1 | 1 | 1 |  |  |  |

-continued

| | Multiplex PCR Rxn # | | | | | | | | |
|---|---|---|---|---|---|---|---|---|---|
| | 1 | 2 | 3 | 1 | 2 | 3 | 1 | 2 | 3 |
| | | | | PCR Rxn # | | | | | |
| | 1 μL | 2 μL | 3 μL | 4 μL | 5 μL | 6 μL | 7 μL | 8 μL | 9 μL |
| Dap_L_290 5 μM | | | | | | | 1 | 1 | 1 |
| Multiplex PCR Rxn | 0.5 | 0.5 | 0.5 | 0.5 | 0.5 | 0.5 | 0.5 | 0.5 | 0.5 |
| USB taq | 0.25 | 0.25 | 0.25 | 0.25 | 0.25 | 0.25 | 0.25 | 0.25 | 0.25 |

Note:
The multiplex PCR reaction used for PCR reactions 1, 4, and 7 was multiplex PCR reaction # 1.
The multiplex PCR reaction used for PCR reactions 2, 5 and 8 was multiplex PCR reaction # 2.
The multiplex PCR reaction used for PCR reactions 3, 6 and 9 was multiplex PCR reaction # 3.

The primers used for nested PCR are disclosed as follows:

| Nested PCR primer | Sequence | SEQ ID NO: |
|---|---|---|
| KanF4_5P | /5Phos/GTGGCAAAGCAAAAGTTCAA | 629 |
| Phe_L_215 | TGAGAAAGCGTTTGATGATGTA | 630 |
| Dap_L_290 | GCCAGTTTATCCCGTCAAAG | 631 |

The PCR amplification reaction condition for Reactions 1-9 was 1 cycle of 94° C. for 2 min, 30 cycles of 94° C. for 20 sec, 55° C. for 20 sec, and 72° C. for 20 sec, then 1 cycle at 72° C. for 4 min and 1 hold cycle at 4° C.

Figure 58B:
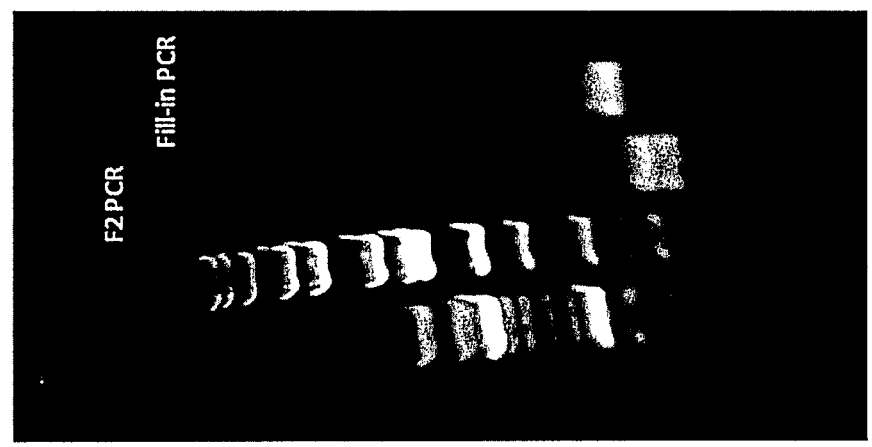
FIGS. 58A-B depict agarose gels of PCR products.
Figure 58A:
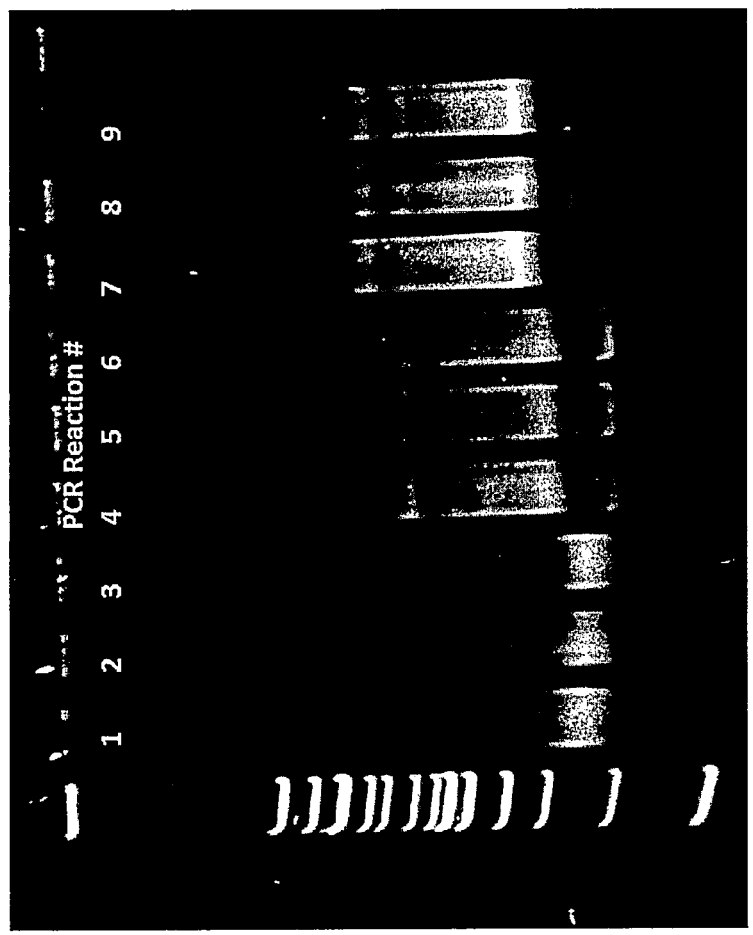

The 4 μl of PCR products of PCR amplification reactions 1-9 were run on an agarose gel. As shown in FIG. 58A, Reactions 1-3 showed the presence of the Kan control gene, Reactions 4-6 showed the presence of the Phe control gene, and Reactions 7-9 showed the presence of the Dap control gene.

The PCR products from PCR reactions 1-9 were prepared for hybridization to an Applied Microarray Inc. (AMI) array. Hybridization mixtures were prepared as follows:

| | μL |
|---|---|
| PCR product | 20 |
| Wash A (6X SSPE + 0.01% Triton X-100) | 55 |
| Cy3 Oligo (760 pM) | 1 |

The hybridization mixtures 1-9, corresponding to the mixtures containing PCR products from PCR reactions 1-9, respectively, were denatured at 95° C. for 5 minutes and then placed at 4° C. The hybridization mixtures were transferred to an AMI array slide and incubated overnight at 37° C.

After the overnight hybridization, the AMI array slide was washed and then scanned. Theoretical and actual measurements and percent accuracy are depicted below:

| | Hybridization mixtures # | | | | | | | | |
|---|---|---|---|---|---|---|---|---|---|
| | 1 | 2 | 3 | 4 | 5 | 6 | 7 | 8 | 9 |
| Multiplex PCR condition (Rxn #) | Titanium (1) | Qiagen (2) | Qiagen + Q (3) | Titanium (1) | Qiagen (2) | Qiagen + Q (3) | Titanium (1) | Qiagen (2) | Qiagen + Q (3) |
| Theoretical measurement | 3676 (bioanalyzer) | | | 912 | | | 6840 | | |
| Actual measurement | 1826 | 1740 | 2116 | 299 | 235 | 251 | 1165 | 1077 | 172 |
| % detection | 49.7 | 47.3 | 57.6 | 32.8 | 25.8 | 27.5 | 17 | 15.7 | 2.5 |

Note:
The theoretical measurement is based on detection of 100% of the Kan, Phe and Dap control genes.

PCR products from Reaction 2 were purified by Ampure purification. Ampure purification was performed as follows:

| | μL |
|---|---|
| F1 PCR products from X01 sample 2 | 30 |
| Ampure beads | 30 |

Ampure purification reactions were incubated at room temperature for 5 min and then washed in 70% ethanol. Purified PCR products were eluted from the beads in 30 μL of water. The concentration of the PCR products was 6 ng/μL as determined by a Nanodrop spectrometer.

Part II: Library Preparation Protocol

PCR products purified from the X01 sample 2 (see Example 1) were used to prepare a DNA library. An F2 primer pool was created from mixing the following primers:

| F2 PCR Primers | Sequence | SEQ ID NO: |
|---|---|---|
| Lys_L_269 | CTTCCCGTTACGGTTTTGAC | 632 |
| phe_L_177 | AAAACCGGATTAGGCCATTA | 633 |
| thrL_332 | TCTCGTCATGACCGAAAAAG | 634 |
| dap_L_276 | CAACGCCTACAAAAGCCAGT | 635 |

An F2 primer mix was prepared by mixing the following

| F2 primer mix | µL |
|---|---|
| water | 750 |
| F2 primer pool 1 uM each/100 uM total | 100 |

The F2 primer mix was incubated at 95° C. for 3 min and then stored on ice. The following ligation mix was added to the F2 primer mix to produce an F2 primer ligation mix:

| Ligation mix | µL |
|---|---|
| 10X DNA ligase buffer NEB | 100 |
| T4 PNK USB | 50 |

The F2 primer ligation mix was incubated at 37° C. for 1 hour, followed by an incubation at 65° C. for 20 min. The F2 PCR primers were ethanol precipitated and the concentration of the primer pool was determined by a Nanodrop spectrophotometer. The F2 primer pool was resuspended to produce a final concentration of 1 uM each/100 uM total.

As shown in Step 4 of FIG. 56, the labeled amplicons (180) were amplified by multiplex PCR. 96 different custom forward primers (F2, 145 in FIG. 1) and a universal PCR primer (140) were used to amplify the labeled amplicons (X01 sample 2 from Example 1) in a single reaction volume. Table 24 lists the 96 different custom forward primers.

The multiplex PCR reaction was prepared as follows:

| Multiplex PCR mix | µL |
|---|---|
| 2X Qiagen Multiplex mix | 25 |
| 1 µM each F2 primer pool kinase | 5 |
| PCR004 5'P 10 µM | 1 |
| water | 18 |
| purified first PCR X01 sample 2 | 1 |

The multiplex PCR condition was 1 cycle at 95° C. for 15 min, followed by 18 cycles of 94° C. for 30 sec, 57° C. for 90 sec, and 72° C. for 1 min, then 1 cycle of 68° C. for 7 min and 1 hold cycle at 4° C. The multiplexed amplicons were purified by Ampure purification and eluted with 50 µL of water. The concentration of the amplicons was determined to be 30 ng/µL by a Nanodrop spectrophotometer. 5 µL of the amplicons was run on an agarose gel (FIG. 58B).

As shown in Step 5 of FIG. 56, adaptors (150, 155) were ligated to the labeled amplicons (180) to produce adaptor labeled amplicons (190). Adaptor labeled amplicons were produced as follows:

| Adaptor mix | µL |
|---|---|
| 10X T4 ligase USB | 10 |
| water | 60 |
| purified nested PCR product | 10 |
| annealed, pooled 96 ABC adaptors 50 µM | 10 |
| T4 DNA ligase (3 µl neb hc, 7 µl usb) | 10 |

The adaptor mix was incubated at 16° C. for 4 hours. The adaptor labeled amplicons were purified by Ampure purification and eluted in 20 µL of 10 mM Tris.

The purified adaptor labeled amplicons were gap-repaired and PCR amplified as follows:

| Fill-in and PCR mix | µL |
|---|---|
| 10x thermoPol buffer | 5 |
| 10 mM dNTP | 1.5 |
| water | 32 |
| CR P1 10 µM | 3 |
| CR IDX D1 10 µM | 3 |
| purified adaptor labeled amplicons | 5 |
| Vent exo- 2 u/µL | 0.5 |

The PCR condition was 1 cycle of 72° C. for 2 min, followed by 94° C. for 1 min, 12 cycles of 94° C. for 15 sec, 60° C. for 15 sec and 72° C. for 30 sec, 1 cycle of 72° C. for 4 min and 1 hold cycle at 4° C. The PCR products were purified by Ampure purification and eluted in 30 µL of TE. The concentration of the purified PCR product was 22 ng/µL (83 nM) as determined by Nanodrop spectroscopy. 5 µL of the PCR purified products were run on a 1% agarose gel (FIG. 58B)

Part III. Sequencing of the Adaptor Labeled Amplicon Library

The adaptor labeled amplicon library was sequenced using a MiSeq Sequencer.

A sequence mapping summary is shown below:

|  | Require Perfect Match | Allow 1 bp mismatch |
|---|---|---|
| Total Read Pairs | 7,724,955 | |
| # of RNA with universal primer and polyA match | 2,499,444 (32%) | 4,716,378 (61%) |
| # of RNA mapped to targets (96 genes) | 2,373,700 | 4,489,485 |

Figure 59:
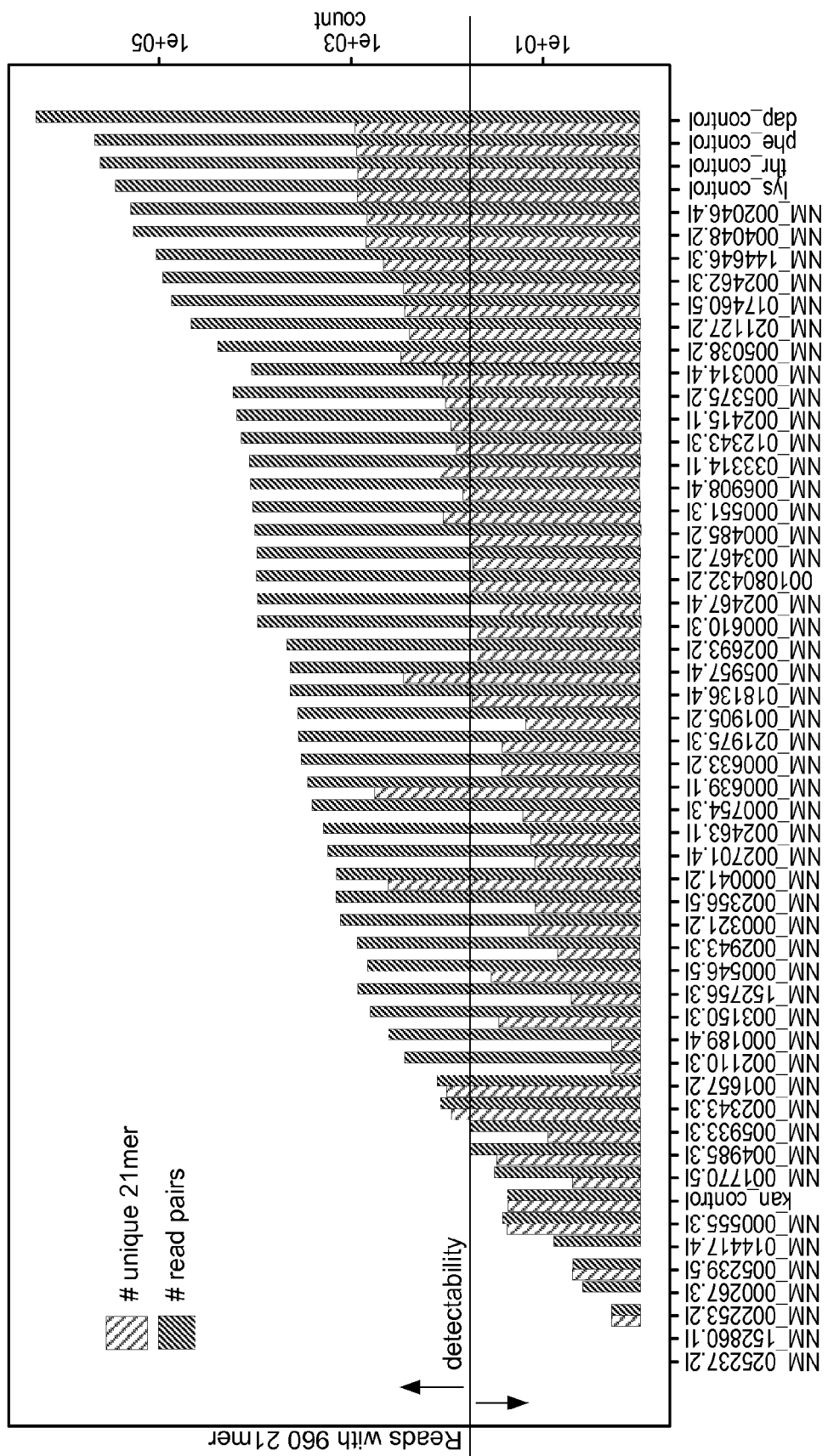
FIG. 59 depicts a plot of sequencing reads for a plurality of genes.

As shown in the sequence mapping summary above, many reads were lost due to the stringent polyA matching criteria. FIG. 59 shows the reads and counts across all detected genes.

Figure 61:
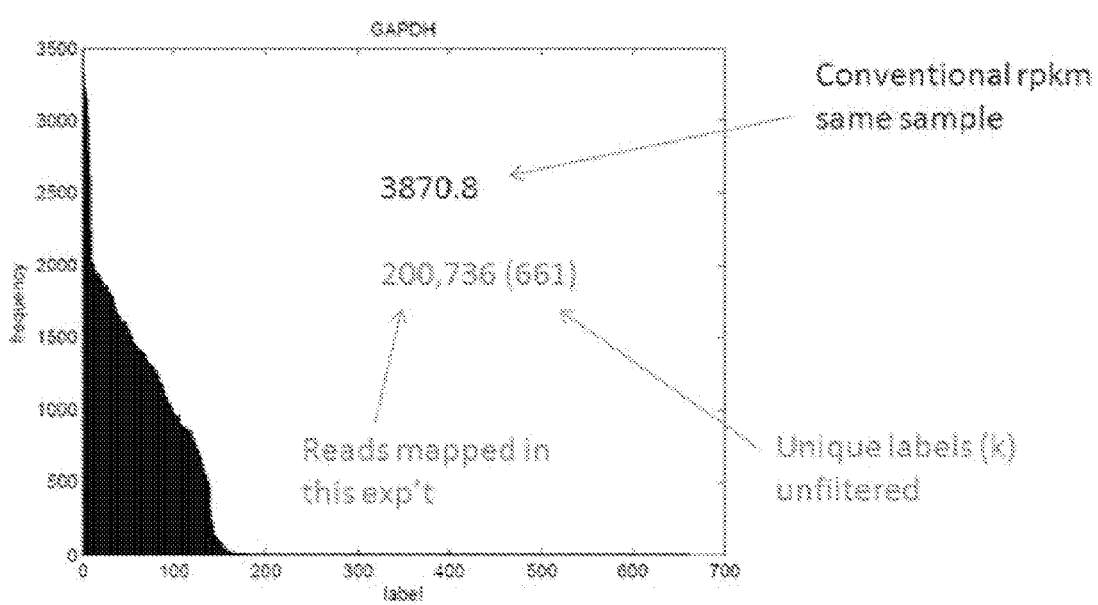
FIG. 61 depicts a plot of the reads observed per label detected (RPLD) for various genes.

Sequencing reads were also used to quantify specific genes. FIG. 61-62 depict a plot of the reads observed per label detected (RPLD) for various genes. Conventional rpkm values are also shown in the plots depicted in FIGS. 61-62A-AX. FIG. 59 summarizes a comparison of RPLD and RPKM for various genes.

FIGS. 63A-AX depict plots of total reads (labels) versus rpld for various genes.

Figure 4:
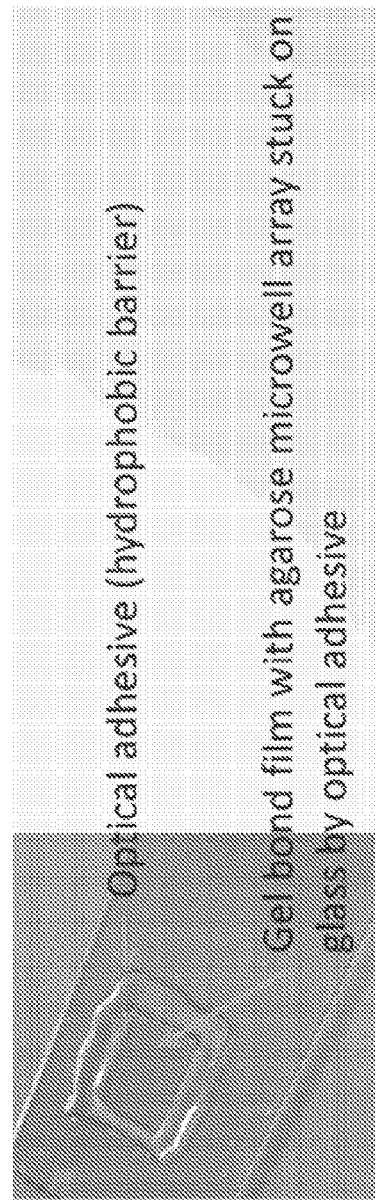
FIG. 4 illustrates an exemplary embodiment of a microwell array.
Figure 8B:
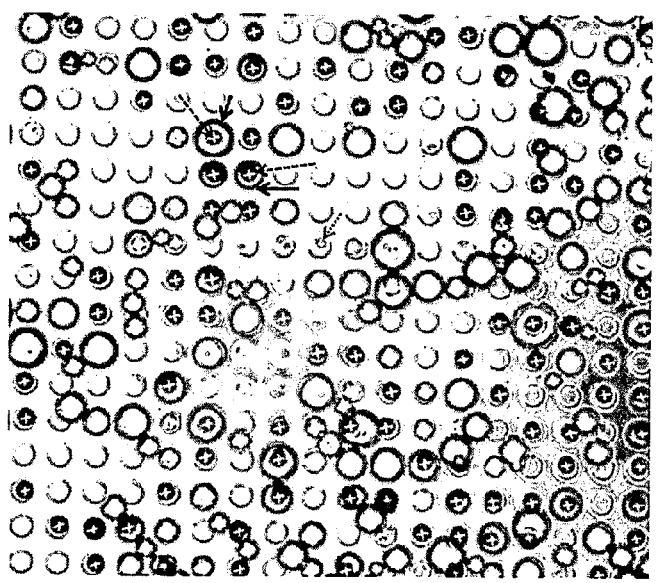
Figure 8C:
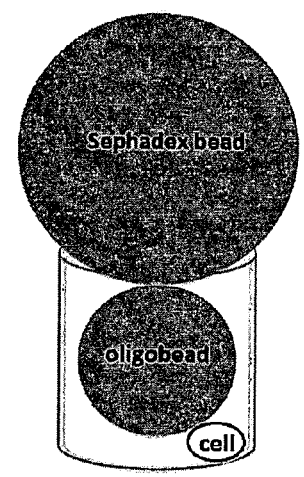

The data represented in FIGS. 4, 7 and 8 are also shown in numerical form in Table 25.

Figure 64:
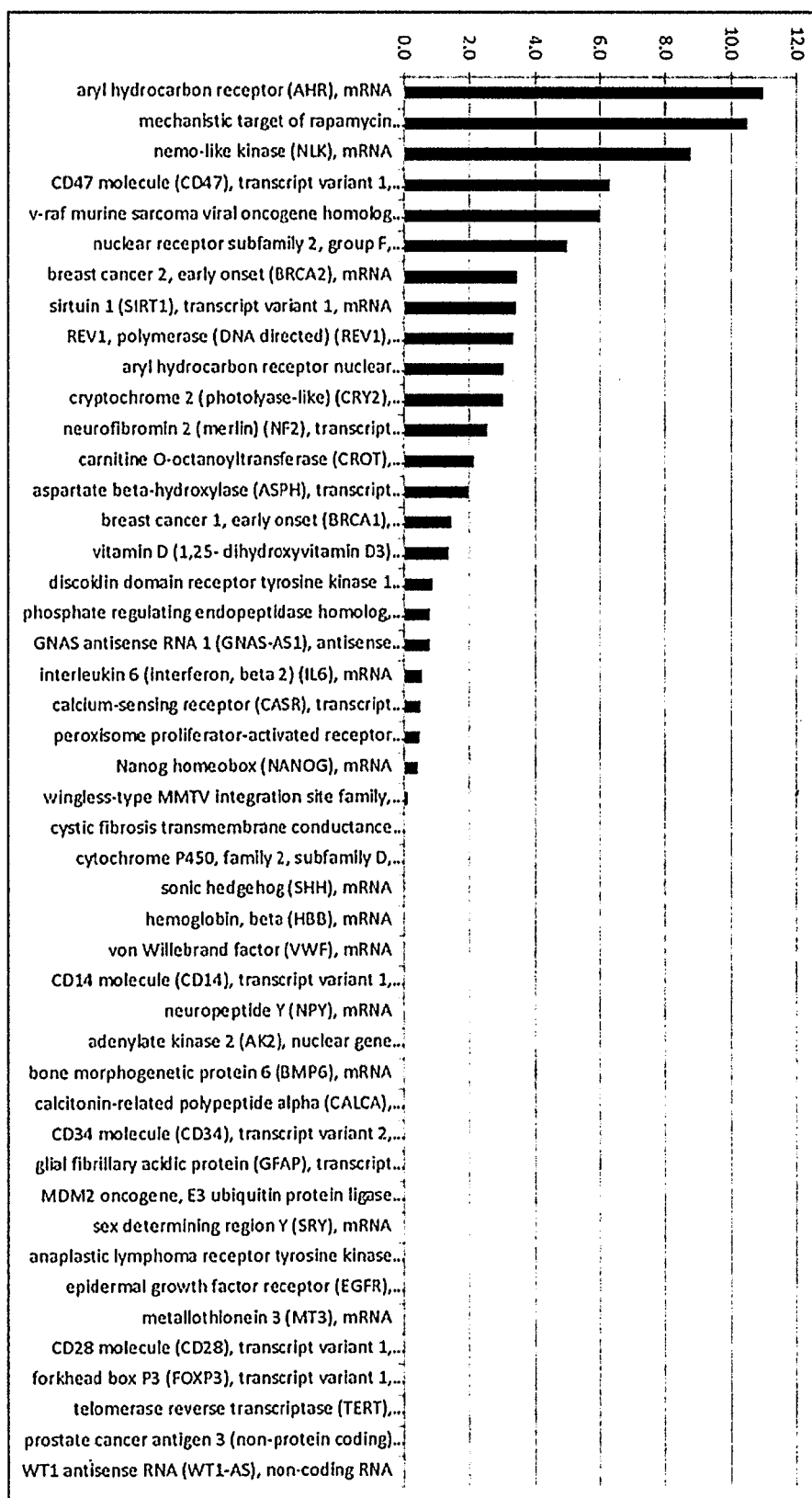
FIG. 64 depicts a plot of RPKM for undetected genes.

FIG. 64 depicts a plot of RPKM for undetected genes.

The quantity of the spike-in controls in the adaptor labeled amplicon library was determined by MiSeq sequencing. Results from MiSeq sequencing of the spike-in controls are shown in the table below.

| Spike-in Control | input N (mfg) | Reads | Labels (K) |
|---|---|---|---|
| Dap | 6840 | 1,920,503 | 893 |
| Phe | 912 | 470,738 | 859 |
| Thr | 1824 | 410,664 | 847 |
| Lys | 456 | 282,174 | 847 |
| Kan | 7352 | 24 | 23 |

Figure 60A:
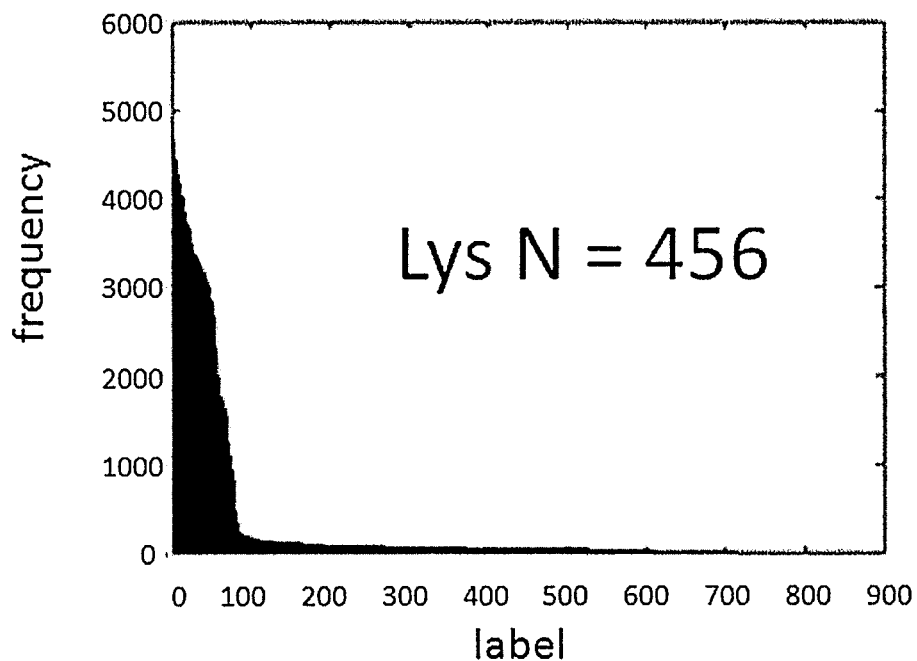
FIGS. 60A-D depicts plots of the reads observed per label detected (RPLD) for Lys, Phe, Thr, and Dap spike-in controls, respectively.
Figure 60B:
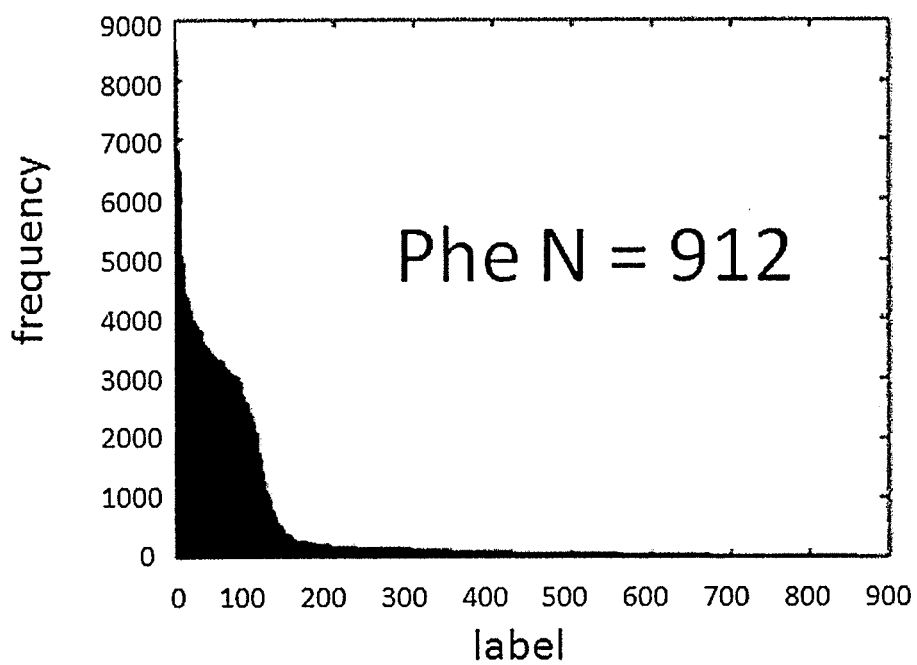
Figure 60C:
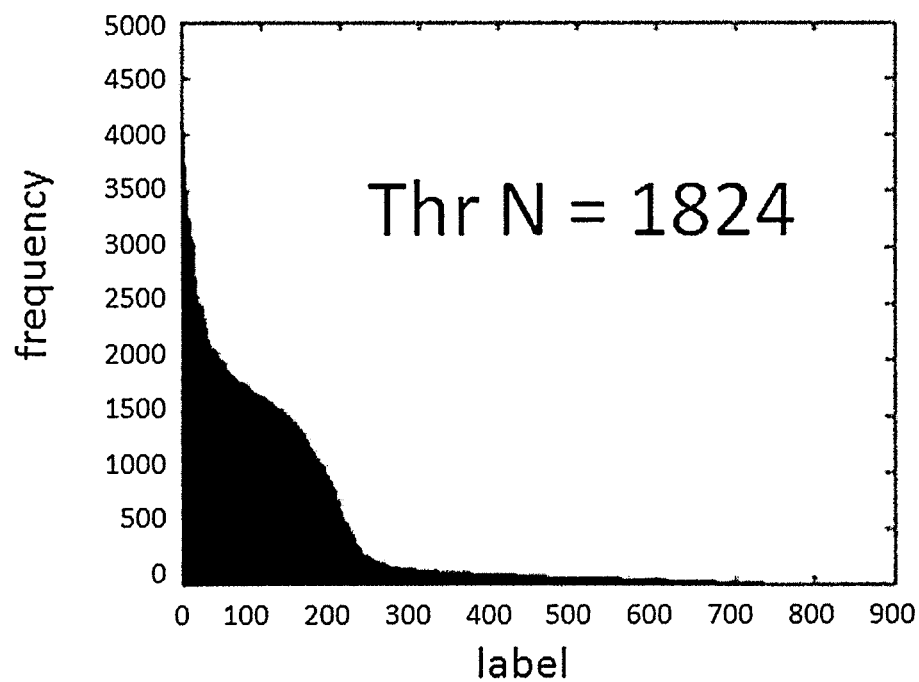
Figure 60D:
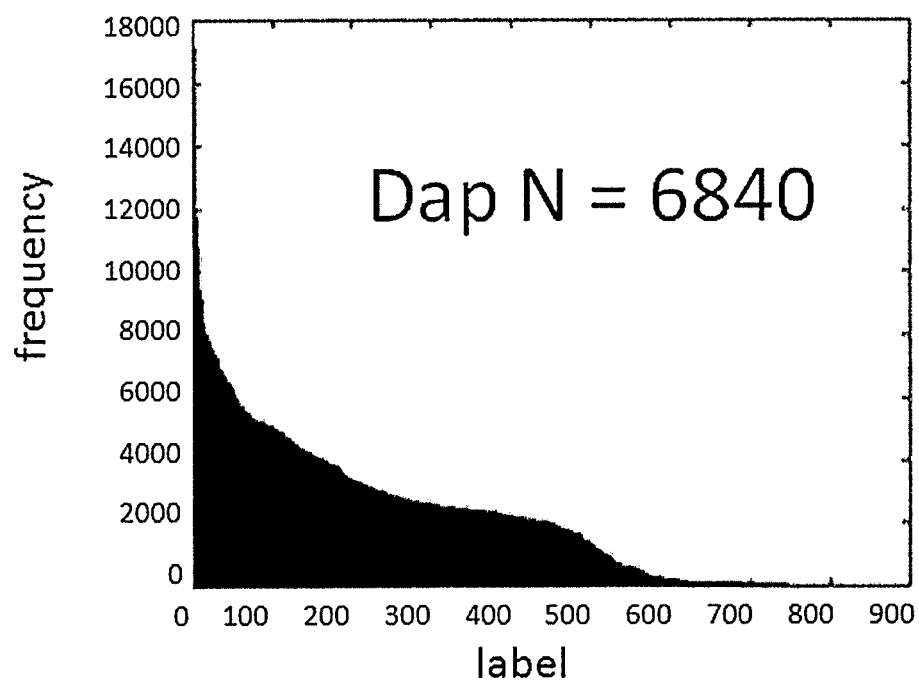
Figure 60E:
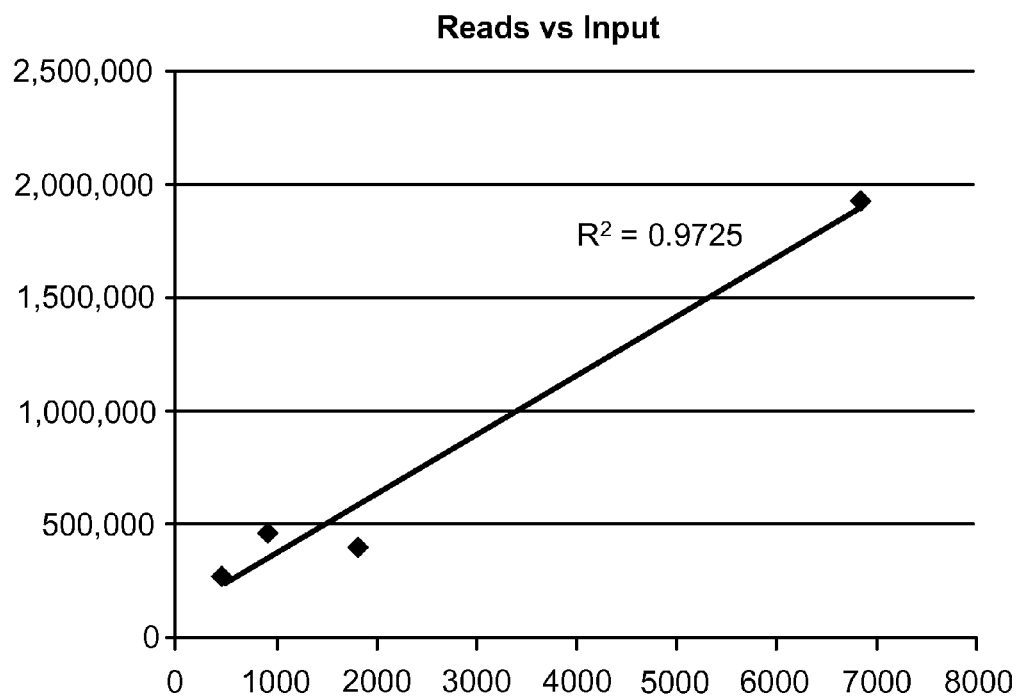
FIG. 60E depicts a plot of Reads versus Input.

In the table above, input N refers to the original number of the spike-in control; Reads refers to the total number of read pairs; and Labels (K) refers to the number of different labels detected by sequencing. FIG. 60A-D depicts a plot of the reads observed per label detected (RPLD) for Lys, Phe, Thr, and Dap spike-in controls, respectively. FIG. 60E depicts a plot of Reads versus Input.

TABLE 23

| Name | Sequence | SEQ ID NO: |
|---|---|---|
| NM_144646.3F1 | TTGACTTTGCCTTGGAGAGC | 636 |
| NR_015342.1F1 | TTTTTCTTACAGTGTCTTGGCATA | 637 |
| NM_000193.2F1 | CGTGACCCTAAGCGAGGAG | 638 |
| NM_001777.3F1 | TTTGCAGTGATTTGAAGACCA | 639 |
| NM_000600.3F1 | GGCATTCCTTCTTCTGGTCA | 640 |
| NM_021127.2F1 | CTGGGCTATATACAGTCCTCAAA | 641 |
| NM_004318.3F1 | GGGGTGATTATGACCAGTTGA | 642 |
| NM_002467.4F1 | TGCATGATCAAATGCAACCT | 643 |
| NM_001773.2F1 | TCTTCCGAAAAATCCTCTTCC | 644 |
| NM_001770.5F1 | CTGGGGTCCCAGTCCTATG | 645 |
| NM_001718.4F1 | TGTACTGGGAAGGCAATTTCA | 646 |
| NR_023920.1F1 | GAGCCGCTGGGGTTACTC | 647 |
| NM_000267.3F1 | CAGTTAGTTGCTGCACATGGA | 648 |
| NM_000633.2F1 | TTGCATTTCTTTTGGGGAAG | 649 |
| NM_000314.4F1 | GTCATGCATGCAGATGGAAG | 650 |
| NM_021151.3F1 | GCTGCAGTGAGCTGTGATGT | 651 |
| NM_002415.1F1 | GTTCCTCTCCGAGCTCACC | 652 |
| NM_004985.3F1 | TCCGAAAGTTTCCAATTCCA | 653 |
| NM_005375.2F1 | TTGTTTGGGAGACTCTGCATT | 654 |
| NM_000555.3F1 | GACCCCACTTGGACTGGTAG | 655 |
| NM_001668.3F1 | GTGATCTTGATTGCGGCTTT | 656 |
| NM_025237.2F1 | GGGGGAAAAACTACAAGTGC | 657 |
| NM_021117.3F1 | TGATTCCTTTTCCTGCCTGT | 658 |
| NM_016316.2F1 | AAAAACCTCCAGGCCAGACT | 659 |
| NM_021975.3F1 | AATCAAAATAACGCCCCAGA | 660 |
| NM_004333.4F1 | TTGCTAAAAATTGGCAGAGC | 661 |
| NM_001621.4F1 | TTGTTAAGTGCCAAACAAGGA | 662 |
| NM_005239.5F1 | AAGCTGGGAAGAGCAAAGC | 663 |
| NM_000485.2F1 | AGGACAGAGGGTGGTCGTC | 664 |
| NM_004048.2F1 | TGAGTGCTGTCTCCATGTTTG | 665 |
| NM_001657.2F1 | CCTCACAGCTGTTGCTGTTATT | 666 |
| NM_012238.4F1 | AAAACACCCAGCTAGGACCA | 667 |
| NM_002055.4F1 | AACTGAGGCACGAGCAAAGT | 668 |
| NM_002392.4F1 | GCTTTATGGGTGGATGCTGA | 669 |
| NM_001625.3F1 | ATAATATCGCCAGCCTCAGC | 670 |
| NM_002110.3F1 | TCCAGAGTGTGCTGGATGAC | 671 |
| NM_002943.3F1 | TGCAAGCCATTTATGGGAAT | 672 |
| NM_000059.3F1 | TGGAATGAGGTCTCTTAGTACAGTT | 673 |
| NM_018136.4F1 | TCCCAGAAACACCTGTAAGGA | 674 |
| NM_003467.2F1 | TGTCTAGGCAGGACCTGTGG | 675 |
| NM_004958.3F1 | AGTGATGCTGCGACTCACAC | 676 |
| NM_006139.3F1 | GGCTCAGAAAGTCTCTCTTTCC | 677 |
| NM_002693.2F1 | CTCCCAAACTCAGGCTTTCA | 678 |
| NM_001080432.2F1 | AAAGCGCTGGGATTACAGG | 679 |
| NM_005954.2F1 | CGTCCAGTTGCTTGGAGAAG | 680 |
| NM_024865.2F1 | AATAACCTTGGCTGCCGTCT | 681 |
| NM_001905.2F1 | GGGAATTCTCAGTGCCAACT | 682 |
| NM_002046.4F1 | GCATCCTGGGCTACACTGAG | 683 |
| NM_002253.2F1 | TGCTGGGAACAATGACTATAAGA | 684 |
| NM_002356.5F1 | GCCTAAAACACTTTGGGTGGT | 685 |
| NM_000189.4F1 | GGGTGCCCACAAAATAGAGA | 686 |
| NM_000546.5F1 | GAGACTGGGTCTCGCTTTGT | 687 |
| NM_152860.1F1 | TGGGGAAGGCTTTCTCTAGG | 688 |
| NM_016231.4F1 | TTCAACTTGAGTGATCTGAGCTG | 689 |
| NM_000518.4F1 | TATGGGCAACCCTAAGGTGA | 690 |
| NM_000905.3F1 | CGCTGCGACACTACATCAAC | 691 |
| NM_005038.2F1 | TGGAGTCTTGCTCTGTCACC | 692 |
| NM_000041.2F1 | ACGAGGTGAAGGAGCAGGT | 693 |
| NM_005957.4F1 | CGATGCCTTTGGGTAGAGAG | 694 |
| NR_002785.2F1 | ACTGATCGTCCAAGGACTGG | 695 |
| NM_000321.2F1 | AAAAGAAATCTGGTCTTGTTAGAAAA | 696 |
| NM_152756.3F1 | TTGAAAAGTGGTAAGGAATTGTGA | 697 |
| NM_000610.3F1 | CACCAAGAATTGATTTTGTAGCC | 698 |
| NR_033314.1F1 | AAAAATGGGGAAAATGGTG | 699 |
| NM_017460.5F1 | CATGGTTGAAACCCCATCTC | 700 |
| NR_002196.1F1 | TTCAAAGCCTCCACGACTCT | 701 |

TABLE 23-continued

| Name | Sequence | SEQ ID NO: |
|---|---|---|
| NM_000591.3F1 | GCTGGAACAGGTGCCTAAAG | 702 |
| NM_000106.5F1 | CCCTAAGGGAACGACACTCA | 703 |
| NM_138712.3F1 | ACCTGCTACAAGCCCTGGA | 704 |
| NM_004304.4F1 | GGATCCCTAAGACCGTGGAG | 705 |
| NM_000754.3F1 | CCACCTCAGAGGCTCCAA | 706 |
| NM_000492.3F1 | TGCTGTATTTTAAAAGAATGATTATGA | 707 |
| NM_000444.4F1 | GTAGCTGGGACGCTGGTTTA | 708 |
| NM_002463.1F1 | ATTCCCTTCCCCCTACAAGA | 709 |
| NM_000552.3F1 | CCTGAGTGCAACGACATCAC | 710 |
| NM_005430.3F1 | GGGGGAACCAGCAGAAAT | 711 |
| NM_003150.3F1 | GACCTAGGGCGAGGGTTC | 712 |
| NM_000388.3F1 | AATTCCTGAAGCCAGATCCA | 713 |
| NM_007294.3F1 | AAAATGTTTATTGTTGTAGCTCTGG | 714 |
| NM_005933.3F1 | TTTCAAGAGCTCAACAGATGACA | 715 |
| NM_002343.3F1 | GACTGCCCGGACAAGTTTT | 716 |
| NM_000376.2F1 | GAGAAGGTGCCCCAAAATG | 717 |
| NM_002462.3F1 | AGCCACTGGACTGACGACTT | 718 |
| NM_021005.3F1 | GGAGGACTAGTGAGGGAGGTG | 719 |
| NM_012343.3F1 | GGCAAGTGATGTGGCAATTA | 720 |
| NM_001741.2F1 | GTTGGAGCACCTGGAAAGAA | 721 |
| NM_014417.4F1 | ATGCCTGCCTCACCTTCAT | 722 |
| NM_014009.3F1 | ACAGGGGCACTGTCAACAC | 723 |
| NM_006908.4F1 | AAAAATCATGTGTTGCAGCTTT | 724 |
| NM_005228.3F1 | TGCTTTCACAACATTTGCAG | 725 |
| NM_013994.2F1 | AATGTTTCCTTGTGCCTGCT | 726 |
| NM_000639.1F1 | ATATCCTGAGCCATCGGTGA | 727 |
| NM_002701.4F1 | TTTTGGTACCCCAGGCTATG | 728 |
| NM_000268.3F1 | ACCCCGTGGCATTACATAAC | 729 |
| NM_003140.1F1 | CTTCCAGGAGGCACAGAAAT | 730 |
| NM_000551.3F1 | CTAACCTGGGCGACAGAGTG | 731 |

TABLE 24

| Name | Sequence | SEQ ID NO: |
|---|---|---|
| NM_144646.3F2 | ATATTTGGACATAACAGACTTGGAA | 732 |
| NR_015342.1F2 | TGCTGACTTTTAAAATAAGTGATTCG | 733 |
| NM_000193.2F2 | GCGGCAGAGTAGCCCTAAC | 734 |
| NM_001777.3F2 | TGGGCTATTTCTATTGCTGCT | 735 |

TABLE 24-continued

| Name | Sequence | SEQ ID NO: |
|---|---|---|
| NM_000600.3F2 | AATGGAAAGTGGCTATGCAG | 736 |
| NM_021127.2F2 | GGTTGTAGTCACTTTAGATGGAAAA | 737 |
| NM_004318.3F2 | TTTGTTTGACTTTGAGCACCA | 738 |
| NM_002467.4F2 | AATGTTTCTCTGTAAATATTGCCATT | 739 |
| NM_001773.2F2 | CACCCCCATATGGTCATAGC | 740 |
| NM_001770.5F2 | AGCACCAGGTGATCCTCAG | 741 |
| NM_001718.4F2 | TGTTTTGCTGTAACATTGAAGGA | 742 |
| NR_023920.1F2 | TAATGCCACAGTGGGGATG | 743 |
| NM_000267.3F2 | GGGCCTAAACTTTGGCAGTT | 744 |
| NM_000633.2F2 | TTTTACCTTCCATGGCTCTTTT | 745 |
| NM_000314.4F2 | GCCTTACTCTGATTCAGCCTCTT | 746 |
| NM_021151.3F2 | CGTAACAAAATTCATTGTGGTGT | 747 |
| NM_002415.1F2 | AGAACCGCTCCTACAGCAAG | 748 |
| NM_004985.3F2 | GTGCTTTCTTTTGTGGGACA | 749 |
| NM_005375.2F2 | GGGAGTTCTGCATTTGATCC | 750 |
| NM_000555.3F2 | TGGGTCAGAGGACTTCAAGG | 751 |
| NM_001668.3F2 | AGGGTTCTGATCACATTGCAC | 752 |
| NM_025237.2F2 | CTGCAGGACTGGTCGTTTTT | 753 |
| NM_021117.3F2 | AGGGCAGGGTAGAGAGGGTA | 754 |
| NM_016316.2F2 | TTCTTCCATGCGGAGAAATC | 755 |
| NM_021975.3F2 | CATGGCTGAAGGAAACCAGT | 756 |
| NM_004333.4F2 | TTGCCAGCTATCACATGTCC | 757 |
| NM_001621.4F2 | TCTTTTCCTGTACCAGGTTTTC | 758 |
| NM_005239.5F2 | TGACTGGGAACATCTTGCTG | 759 |
| NM_000485.2F2 | TGGCACCTGTACCCTTCTTC | 760 |
| NM_004048.2F2 | TTCAATCTCTTGCACTCAAAGC | 761 |
| NM_001657.2F2 | TGGAGTCACTGCCAAGTCAT | 762 |
| NM_012238.4F2 | TTTGCATGATGTTTGTGTGC | 763 |
| NM_002055.4F2 | GCACCCACTCTGCTTTGACT | 764 |
| NM_002392.4F2 | ACCATGTAGCCAGCTTTCAA | 765 |
| NM_001625.3F2 | GCAACTGGGCATGAGTACCT | 766 |
| NM_002110.3F2 | CCACACCCCCTTCCTACTC | 767 |
| NM_002943.3F2 | AGTCTGCTTATTTCCAGCTGTTT | 768 |
| NM_000059.3F2 | TCCTGTTCAAAAGTCAGGATGA | 769 |
| NM_018136.4F2 | AAATCACAAATCCCCTGCAA | 770 |
| NM_003467.2F2 | CTGAACATTCCAGAGCGTGT | 771 |
| NM_004958.3F2 | CAGTGGGACCACCCTCACT | 772 |
| NM_006139.3F2 | TCTGTAGATGACCTGGCTTGC | 773 |

TABLE 24-continued

| Name | Sequence | SEQ ID NO: |
|---|---|---|
| NM_002693.2F2 | TCAGAACCAAGATGCCAACA | 774 |
| NM_001080432.2F2 | CATGACCCAGCCTATGGTTT | 775 |
| NM_005954.2F2 | ACCTCCTGCAAGAAGAGCTG | 776 |
| NM_024865.2F2 | TTGGGAGGCTTTGCTTATTTT | 777 |
| NM_001905.2F2 | CTGGGAAACACTCCTTGCAT | 778 |
| NM_002046.4F2 | CAACGAATTTGGCTACAGCA | 779 |
| NM_002253.2F2 | CAAAGGTCATAATGCTTTCAGC | 780 |
| NM_002356.5F2 | TTTGACGTATCTTTTCATCCAA | 781 |
| NM_000189.4F2 | TGTTGTTGGTTTCCAAAAAGG | 782 |
| NM_000546.5F2 | GCCAACTTTTGCATGTTTTG | 783 |
| NM_152860.1F2 | CCCAAGCTGATCTGGTGGT | 784 |
| NM_016231.4F2 | TGCTGTGAAAGAAACAAACATTG | 785 |
| NM_000518.4F2 | GCACGTGGATCCTGAGAACT | 786 |
| NM_000905.3F2 | CCAGCCCAGAGACACTGATT | 787 |
| NM_005038.2F2 | CACGCCCAGCTAATTTTTGT | 788 |
| NM_000041.2F2 | CCTGGTGGAAGACATGCAG | 789 |
| NM_005957.4F2 | TCACACCTGTAATCCCAGCA | 790 |
| NR_002785.2F2 | CAGAGCTCCGCCTCATTAGT | 791 |
| NM_000321.2F2 | TCCATTTCATCATTGTTTCTGC | 792 |
| NM_152756.3F2 | TGGTGTTTGTAGGTCACTGAACA | 793 |
| NM_000610.3F2 | AACATGGTCCATTCACCTTTATG | 794 |
| NR_033314.1F2 | AGAGCGAGACTCCGTCTCAA | 795 |
| NM_017460.5F2 | AGTGAGCTGAGATTGCACCA | 796 |
| NR_002196.1F2 | AGACGGCCTTGAGTCTCAGT | 797 |
| NM_000591.3F2 | GGGAATCCCTTCCTGGTC | 798 |
| NM_000106.5F2 | CTTCCTGCCTTTCTCAGCAG | 799 |
| NM_138712.3F2 | TGCAGGTGATCAAGAAGACG | 800 |
| NM_004304.4F2 | GGTTTTGAGCATGGGTTCAT | 801 |
| NM_000754.3F2 | CCAGCCCACTCCTATGGAT | 802 |
| NM_000492.3F2 | AAACTGGGACAGGGGAGAAC | 803 |
| NM_000444.4F2 | TTTGGGTAGGTGACCTGCTT | 804 |
| NM_002463.1F2 | TCACTGAACGAATGAGTGCTG | 805 |
| NM_000552.3F2 | ACGATGTGCAGGACCAGTG | 806 |
| NM_005430.3F2 | AATTTGCACTGAAACGTGGA | 807 |
| NM_003150.3F2 | CTGTTGTGGCCCATTAAAGAA | 808 |
| NM_000388.3F2 | TTCCCTCCAGCAGTGGTATT | 809 |
| NM_007294.3F2 | CACCAGGAAGGAAGCTGTTG | 810 |
| NM_005933.3F2 | TTTCCTTGTGTTCTTCCAAGC | 811 |
| NM_002343.3F2 | TCGCAGGCATTACTAATCTGAA | 812 |
| NM_000376.2F2 | CTCTGGCTGGCTAACTGGAA | 813 |
| NM_002462.3F2 | AGAGCCCCACCCTCAGAT | 814 |
| NM_021005.3F2 | TGTGCAGAGTTCTCCATCTGA | 815 |
| NM_012343.3F2 | TGCCTGTTACAAATATCAAGGAA | 816 |
| NM_001741.2F2 | TTTCCCTTCTTGCATCCTTC | 817 |
| NM_014417.4F2 | TGTGACCACTGGCATTCATT | 818 |
| NM_014009.3F2 | CTCACACACACGGCCTGTTA | 819 |
| NM_006908.4F2 | CACTTGACCAATACTGACCCTCT | 820 |
| NM_005228.3F2 | GTGTGTGCCCTGTAACCTGA | 821 |
| NM_013994.2F2 | CCACTTCCCACTTGCAGTCT | 822 |
| NM_000639.1F2 | TGTGTGTGTGTGTGTGTGT | 823 |
| NM_002701.4F2 | TCTCCCATGCATTCAAACTG | 824 |
| NM_000268.3F2 | TCTAAGTGTTCCTCACTGACAGG | 825 |
| NM_003140.1F2 | TACTCTGCAGCGAAGTGCAA | 826 |
| NM_000551.3F2 | CCAAGATCACACCATTGCAC | 827 |
| NM_144646.3F2 | ATATTTGGACATAACAGACTTGGAA | 828 |

TABLE 25

| Gene | Number of reads | Number of labels | reads per kb/million (RPKM) |
|---|---|---|---|
| APOE | 1585 | 408 | 0.2 |
| APRT | 11280 | 56 | 103.4 |
| AREG | 147 | 102 | 0.0 |
| ASPM | 4683 | 53 | 4.4 |
| B2M | 209362 | 698 | 3891.7 |
| BBC3 | 8 | 1 | 0.0 |
| BCL2 | 3627 | 27 | 33.2 |
| BDNF | 12778 | 116 | 0.3 |
| CD19 | 38 | 5 | 43.1 |
| CD44 | 6789 | 47 | 8.1 |
| COMT | 2828 | 16 | 10.7 |
| CTPS1 | 3998 | 15 | 25.4 |
| CXCR4 | 10547 | 54 | 19.2 |
| CYP3A4 | 80982 | 267 | 0.1 |
| DCX | 28 | 24 | 0.0 |
| ETS2 | 6 | 5 | 0.0 |
| FASLG | 3182 | 565 | 0.2 |
| FTO | 8877 | 58 | 11.3 |
| GAPDH | 227129 | 661 | 3870.8 |
| HCK | 294 | 2 | 2.4 |
| HK2 | 593 | 2 | 12.7 |
| IGJ | 119449 | 454 | 438.9 |
| KDR | 2 | 2 | 0.0 |
| KRAS | 64 | 31 | 6.8 |
| LTF | 126 | 90 | 0.0 |
| MARCKS | 1563 | 12 | 36.9 |
| MIF | 17775 | 89 | 760.4 |
| MLL | 72 | 9 | 2.6 |
| MTHFR | 4854 | 282 | 3.9 |
| MX1 | 100701 | 285 | 119.0 |
| MX2 | 2145 | 13 | 45.2 |
| MYB | 18361 | 100 | 2.8 |
| MYC | 6859 | 27 | 130.5 |

TABLE 25-continued

| Gene | Number of reads | Number of labels | reads per kb/million (RPKM) |
|---|---|---|---|
| NF1 | 4 | 1 | 3.7 |
| NNT | 15673 | 78 | 14.1 |
| PMAIP1 | 50604 | 244 | 126.9 |
| POLG | 5163 | 46 | 7.4 |
| POU5F1 | 1924 | 12 | 1.0 |
| PPID | 27354 | 303 | 39.0 |
| PTEN | 20884 | 109 | 51.6 |
| RAC1 | 12454 | 67 | 44.8 |
| RB1 | 1420 | 14 | 46.1 |
| RELA | 3893 | 26 | 17.9 |
| RICTOR | 898 | 5 | 5.2 |
| RORA | 954 | 7 | 0.1 |
| SOST | 1 | 1 | 0.0 |
| SP7 | 1 | 1 | 0.0 |
| STAT3 | 706 | 28 | 16.9 |
| TP53 | 900 | 34 | 14.6 |
| VHL | 11576 | 106 | 0.0 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Embodiments

Disclosed herein are methods for analyzing molecules in two or more samples. The method may comprise: a) producing a plurality of sample-tagged nucleic acids by: i) contacting a first sample comprising a plurality of nucleic acids with a plurality of first sample tags to produce a plurality of first sample-tagged nucleic acids; and ii) contacting a second sample comprising a plurality of nucleic acids with a plurality of second sample tags to produce a plurality of second sample-tagged nucleic acids, wherein the plurality of second sample tags are different from the first sample tags; b) contacting the plurality of sample-tagged nucleic acids with a plurality of molecular identifier labels to produce a plurality of labeled nucleic acids; and c) detecting at least one of the labeled nucleic acids, thereby determining a count of a plurality of nucleic acids in a plurality of samples. One or more of the plurality of samples may comprise a single cell or cell lysate. One or more of the plurality of samples may consist of a single cell. The sample tag may comprise a cellular label that identifies the cell from which the labeled nucleic acids originated from. The plurality of samples consisting of a single cell may be from one or more sources. The sample tag may comprise a sample index region that identifies the source of the single cell. The molecular identifier labels may be referred to as a molecular label. One or more of the plurality of samples may comprise fewer than 1,000,000 cells. One or more of the plurality of samples may comprise fewer than 100,000 cells. One or more of the plurality of samples may comprise fewer than 10,000 cells. One or more of the plurality of samples may comprise fewer than 1,000 cells. One or more of the plurality of samples may comprise fewer than 100 cells. One or more of the plurality of samples may comprise a cell lysate.

Alternatively, the method for analyzing molecules in a plurality of samples may comprise: a) producing a plurality of labeled nucleic acids comprising: i) contacting a first sample with a first plurality of sample tags, wherein the first plurality of sample tags comprise identical nucleic acid sequences; ii) contacting the first sample with a first plurality of molecular identifier labels comprising different nucleic acid sequences, thereby producing a plurality of first-labeled nucleic acids; iii) contacting a second sample with a second plurality of sample tags, wherein the second plurality of sample tags comprise identical nucleic acid sequences; iv) contacting the second sample with a second plurality of molecular identifier labels comprising different nucleic acid sequences, thereby producing a plurality of second-labeled nucleic acids, wherein the plurality of labeled nucleic acids comprises the plurality of first-labeled nucleic acids and the second-labeled nucleic acids; and b) determining a number of different labeled nucleic acids, thereby determining a count of a plurality of nucleic acids in a plurality of samples. The sample tag may comprise a cellular label that identifies the cell from which the labeled nucleic acids originated from. The sample tag may comprise a sample index region that identifies the source of the single cell. The molecular identifier labels may be referred to as a molecular label.

Alternatively, the method for analyzing molecules in a plurality of samples may comprise: a) contacting a plurality of samples comprising two or more different nucleic acids with a plurality of sample tags and a plurality of molecular identifier labels to produce a plurality of labeled nucleic acids, wherein: i) the plurality of labeled nucleic acids comprise two or more nucleic acids attached to two or more sample tags and two or more molecular identifier labels; ii) the sample tags attached to nucleic acids from a first sample of the plurality of samples are different from the sample tags attached to nucleic acid molecules from a second sample of the plurality of samples; and iii) two or more identical nucleic acids in the same sample are attached to two or more different molecular identifier labels; and b) detecting at least a portion of the labeled nucleic acids, thereby determining a count of two or more different nucleic acids in the plurality of samples. The sample tag may comprise a cellular label that identifies the cell from which the labeled nucleic acids originated from. The sample tag may comprise a sample index region that identifies the source of the single cell. The molecular identifier labels may be referred to as a molecular label.

Further disclosed herein are methods for analyzing molecules in a plurality of samples comprising: a) contacting a first plurality of molecules from a first sample of a plurality of samples with a first set of molecular barcodes to produce a first plurality of labeled molecules, wherein a molecular barcode of the first plurality of molecular barcodes comprises a label region and a sample index region; b) contacting a second plurality of molecules from a second sample of the plurality of samples with a second set of molecular barcodes to produce a second plurality of labeled molecules, wherein a molecular barcodes of the second plurality of molecular barcodes comprises a label region and a sample index region, and wherein the first plurality of molecular barcodes and the second plurality of molecular barcodes differ at least by the sample index region of the molecular barcodes; and c) detecting at least a portion of two or more molecules of the first plurality of labeled molecules and at least a portion of two or more molecules of the second plurality of labeled molecules, thereby determining a count of the two or more molecules in the plurality of samples. The first plurality of molecules may comprise nucleic acid molecules. The second plurality of molecules may comprise nucleic acid molecules. The label region may be referred to as a molecular label. The molecular barcode may further comprise a cellular label. In instances in which a sample of the plurality of samples consists of a single cell, the sample index region may refer to the cellular label.

Disclosed herein is a method of selecting a custom primer, comprising: a) a first pass, wherein primers chosen comprise: i) no more than three sequential guanines, no more than three sequential cytosines, no more than four sequential adenines, and no more than four sequential thymines; ii) at least 3, 4, 5, or 6 nucleotides that are guanines or cytosines; and iii) a sequence that does not easily form a hairpin structure; b) a second pass, comprising: i) a first round of choosing a plurality of sequences that have high coverage of all transcripts; and ii) one or more subsequent rounds, selecting a sequence that has the highest coverage of remaining transcripts and a complementary score with other chosen sequences of no more than 4; and c) adding sequences to a picked set until a coverage saturates or a total number of customer primers is less than or equal to about 96.

Further disclosed herein is a method for producing a labeled molecule library comprising: a) producing a plurality of sample-tagged nucleic acids by: i) contacting a first sample comprising a plurality of nucleic acids with a plurality of first sample tags to produce a plurality of first sample-tagged nucleic acids; and ii) contacting a second sample comprising a plurality of nucleic acids with a plurality of second sample tags to produce a plurality of second sample-tagged nucleic acids, wherein the plurality of first sample tags are different from the second sample tags; and b) contacting the plurality of sample-tagged nucleic acids with a plurality of molecular identifier labels to produce a plurality of labeled nucleic acids, thereby producing a labeled nucleic acid library.

Disclosed herein are kits for use in analyzing molecules in a plurality of samples. The kit may comprise: a) two or more sets of molecular barcodes, wherein a molecular barcode of the set of one or more molecular barcodes comprise a sample index region and a label region, wherein (i) the sample index regions of the molecular barcodes of a set of molecular barcodes is the same; and (ii) the sample index regions of a first set of molecular barcodes are different from the sample index regions of a second set of molecular barcodes; and b) a plurality of beads. The two or more sets of molecular barcodes may be attached to the plurality of beads. The two or more sets of molecular barcodes may be conjugated to the bead. The label region may be referred to as a molecular label. The molecular barcode may further comprise a cellular label. In instances in which a sample of the plurality of samples consists of a single cell, the sample index region may refer to a cellular label.

The kit for analyzing molecules in a plurality of samples may comprise: a) a first container comprising a first plurality of molecular barcodes, wherein: (i) a molecular barcode comprises a sample index region and a label region; (ii) the sample index regions of at least about 80% of the total number of molecular barcodes of the first plurality of molecular barcodes are identical; and (iii) the label regions of two or more barcodes of the first plurality of molecular barcodes are different; and (b) a second container comprising a second plurality of molecular barcodes, wherein: (i) a molecular barcode comprises a sample index region and a label region; (ii) the sample index regions of at least about 80% of the total number of molecular barcodes of the first plurality of molecular barcodes are identical; and (iii) the label regions of two or more barcodes of the first plurality of molecular barcodes are different; wherein the sample index regions of the first plurality of molecular barcodes is different from the sample index regions of the second plurality of molecular barcodes. The label region may be referred to as a molecular label. The molecular barcode may further comprise a cellular label. In instances in which a sample of the plurality of samples consists of a single cell, the sample index region may refer to a cellular label.

Alternatively, the kit for analyzing molecules in a plurality of samples comprises: a) a first container comprising a first plurality of sample tags, wherein the plurality of sample tags comprises the same nucleic acid sequence; and b) a second container comprising a first plurality of molecular identifier labels, wherein the plurality of molecular identifier labels comprises two or more different nucleic acid sequences. The label region may be referred to as a molecular label. In instances in which a sample of the plurality of samples consists of a single cell, the sample tag may refer to a cellular label. The kit may further comprise a third container comprising a first plurality of cellular labels, wherein the plurality of cellular labels comprises two or more different nucleic acid sequences.

The kits and methods disclosed herein may comprise one or more sets of molecular barcodes. The kits and methods disclosed herein may comprise one or more molecular barcodes. The molecular barcodes may comprise a sample index region, molecular label region, cellular label region, or a combination thereof. At least two molecular barcodes of a set of molecular barcodes may comprise two or more different label regions. Label regions of two or more molecular barcodes of two or more sets of molecular barcodes may be identical. Two or more sets of molecular barcodes may comprise molecular barcodes comprising the same label region. In instances in which a sample of the plurality of samples consists of a single cell, the sample tag may refer to a cellular label.

The molecular barcodes disclosed herein may comprise a sample index region. The sample index region of molecular barcodes of two or more sets of molecular barcodes may be different. The sample index region may comprise one or more nucleotides. Two or more sequences of sample index regions of two or more different sets of molecular barcodes may be less than about 90%, 85%, 80%, 75%, 70%, 65%, 60%, 55%, 50%, 45%, 40%, 35%, 30%, 25%, 20%, 15%, 10%, or 5% homologous. Two or more sequences of sample index regions of two or more different sets of molecular barcodes may be less than about 80% homologous. Two or more sequences of sample index regions of two or more different sets of molecular barcodes may be less than about 60% homologous. Two or more sequences of sample index regions of two or more different sets of molecular barcodes may be less than about 40% homologous. Two or more sequences of sample index regions of two or more different sets of molecular barcodes may be less than about 20% homologous.

The molecular barcodes disclosed herein may comprise a cellular label. The cellular label of molecular barcodes of two or more sets of molecular barcodes may be different. The cellular label may comprise one or more nucleotides. Two or more sequences of cellular labels of two or more different sets of molecular barcodes may be less than about 90%, 85%, 80%, 75%, 70%, 65%, 60%, 55%, 50%, 45%, 40%, 35%, 30%, 25%, 20%, 15%, 10%, or 5% homologous. Two or more sequences of cellular labels of two or more different sets of molecular barcodes may be less than about 80% homologous. Two or more sequences of cellular labels of two or more different sets of molecular barcodes may be less than about 60% homologous. Two or more sequences of cellular labels of two or more different sets of molecular barcodes may be less than about 40% homologous. Two or more sequences of cellular labels of two or more different sets of molecular barcodes may be less than about 20% homologous.

The molecular barcode disclosed herein may further comprise a universal PCR region. The molecular barcode may further comprise a target-specific region. The molecular barcode may comprise one or more nucleotides. The label region may comprise one or more nucleotides. The sample index region may comprise one or more nucleotides. The universal PCR region may comprise one or more nucleotides. The target-specific region may comprise one or more nucleotides.

The kits and methods disclosed herein may comprise one or more sets of sample tags. The kits and methods disclosed herein may comprise one or more sample tags. The sample tags may comprise a sample index region. The sample index region of the sample tags of a first set of sample tags may be different from the sample index region of the sample tags of a second set of sample tags. The sample index region may comprise one or more nucleotides. Two or more sequences of sample index regions of two or more different sets of sample tags may be less than about 90%, 85%, 80%, 75%, 70%, 65%, 60%, 55%, 50%, 45%, 40%, 35%, 30%, 25%, 20%, 15%, 10%, or 5% homologous. Two or more sequences of sample index regions of two or more different sets of sample tags may be less than about 80% homologous. Two or more sequences of sample index regions of two or more different sets of sample tags may be less than about 60% homologous. Two or more sequences of sample index regions of two or more different sets of sample tags may be less than about 40% homologous. Two or more sequences of sample index regions of two or more different sets of sample tags may be less than about 20% homologous.

The kits and methods disclosed herein may comprise one or more sets of molecular identifier labels. The kits and methods disclosed herein may comprise one or more molecular identifier labels. The molecular identifier labels may comprise a label region. The label regions of two or more molecular identifier labels of a set of molecular identifier labels may be different. The label region may comprise one or more nucleotides. A sequence of label regions of two or more molecular identifier labels of a set of molecular identifier labels may be less than about 90%, 85%, 80%, 75%, 70%, 65%, 60%, 55%, 50%, 45%, 40%, 35%, 30%, 25%, 20%, 15%, 10%, or 5% homologous. A sequence of label regions of two or more molecular identifier labels of a set of molecular identifier labels may be less than about 80% homologous. A sequence of label regions of two or more molecular identifier labels of a set of molecular identifier labels may be less than about 60% homologous. A sequence of label regions of two or more molecular identifier labels of a set of molecular identifier labels may be less than about 40% homologous. A sequence of label regions of two or more molecular identifier labels of a set of molecular identifier labels may be less than about 20% homologous. A label region may be referred to as a cellular label region.

The kits and methods disclosed herein may further comprise one or more primers. The one or more primers may comprise a sequence that is at least partially complementary to the universal PCR region. The one or more primers may comprise a sequence that is at least about 50% complementary to the universal PCR region. The one or more primers may comprise a sequence that is at least about 80% complementary to the universal PCR region.

The kits and methods disclosed herein may further comprise one or more amplification agents. The amplification agents may comprise a fixed panel of primers. The amplification agents may comprise one or more custom primers. The amplification agents may comprise one or more control primers. The amplification agents may comprise one or more housekeeping gene primers. The amplification agents may comprise one or more PCR reagents. The one or more PCR reagents may comprise polymerases, deoxyribonucleotide triphosphates (dNTPs), buffers, or a combination thereof.

The kits and methods disclosed herein may further comprise one or more beads. The molecular barcodes may be attached to the one or more beads. The sample tags may be attached to the one or more beads. The molecular identifier labels may be attached to the one or more beads.

Further disclosed herein are methods for generating one or more sets of beads. The method may comprise: a) depositing a plurality of first nucleic acids into a plurality of wells, wherein two or more different wells of the plurality of wells may comprise two or more different nucleic acids of the plurality of nucleic acids; b) contacting one or more wells of the plurality of wells with one or fewer beads to produce a plurality of single label beads, wherein a single label bead of the plurality of first labeled beads comprises a bead attached to a nucleic acid of the plurality of first nucleic acids; c) pooling the plurality of first labeled beads from the plurality of wells to produce a pool of first labeled beads; d) distributing the pool of first labeled beads to a subsequent plurality of wells, wherein two or more wells of the subsequent plurality of wells comprise two or more different nucleic acids of a plurality of subsequent nucleic acids; and e) attaching one or more nucleic acids of the plurality of subsequent nucleic acids to one or more first labeled beads to produce a plurality of uniquely labeled beads.

The methods and kits disclosed herein may be used to analyze a plurality of nucleic acids. The methods and kits disclosed herein may be used to analyze less than about 100,000,000 nucleic acids. The methods and kits disclosed herein may be used to analyze less than about 10,000,000 nucleic acids. The methods and kits disclosed herein may be used to analyze less than about 1,000,000 nucleic acids. Further disclosed herein are methods of analyzing a plurality of proteins. The method may comprise: a) producing a plurality of sample-tagged polypeptides by: i) contacting a first sample comprising a plurality of polypeptides with a plurality of first sample tags to produce a plurality of first sample-tagged polypeptides; and ii) contacting a second sample comprising a plurality of polypeptides with a plurality of second sample tags to produce a plurality of second sample-tagged polypeptides, wherein the plurality of first sample tags are different from the plurality of second sample tags; b) contacting the plurality of sample-tagged polypeptides with a plurality of molecular identifier labels to produce a plurality of labeled polypeptides; and c) detecting at least a portion of the labeled polypeptides, thereby determining a count of the plurality of polypeptides in the plurality of samples.

The methods of analyzing polypeptides in a plurality of samples may further comprise determining the identity of one or more labeled polypeptides. Determining the identity of the one or more labeled polypeptides may comprise mass spectrometry. The method may further comprise combining the labeled polypeptides of the first sample with the labeled polypeptides of the second sample. The labeled polypeptides may be combined prior to determining the number of different labeled polypeptides. The method may further comprise combining the first sample-tagged polypeptides and the second sample-tagged polypeptides. The first sample-tagged polypeptides and the second sample-tagged polypeptides may be combined prior to contact with the plurality of molecular identifier labels. Determining the number of different labeled polypeptides may comprise detecting at least a portion of the tagged labeled polypeptide. Detecting at least a portion of the tagged labeled polypeptide may comprise detecting at least a portion of the sample tag, molecule-specific tag, polypeptide, or a combination thereof.

The methods disclosed herein may comprise contacting a plurality of samples with a plurality of sample tags and a plurality of molecular identifier labels. Contacting the plurality of samples with the plurality of sample tags and the plurality of molecular identifier labels may occur simultaneously. Contacting the plurality of samples with the plurality of sample tags and the plurality of molecular identifier labels may occur concurrently. Contacting the plurality of samples with the plurality of sample tags and the plurality of molecular identifier labels may occur sequentially. Contacting the plurality of samples with the plurality of sample tags may occur prior to contacting the plurality of samples with the plurality of molecular identifier labels. Contacting the plurality of samples with the plurality of sample tags may occur after contacting the plurality of samples with the plurality of molecular identifier labels.

The methods disclosed herein may comprise contacting a first sample with a first plurality of sample tags and a first plurality of molecular identifier labels. Contacting the first sample with the first plurality of sample tags and the first plurality of molecular identifier labels may occur simultaneously. Contacting the first sample with the first plurality of sample tags and the first plurality of molecular identifier labels may occur concurrently. Contacting the first sample with the first plurality of sample tags and the first plurality of molecular identifier labels may occur sequentially. Contacting the first sample with the first plurality of sample tags may occur prior to contacting the first sample with the first plurality of molecular identifier labels. Contacting the first sample with the first plurality of sample tags may occur after contacting the first sample with the first plurality of molecular identifier labels.

The methods disclosed herein may comprise contacting a second sample with a second plurality of sample tags and a second plurality of molecular identifier labels. Contacting the second sample with the second plurality of sample tags and the second plurality of molecular identifier labels may occur simultaneously. Contacting the second sample with the second plurality of sample tags and the second plurality of molecular identifier labels may occur concurrently. Contacting the second sample with the second plurality of sample tags and the second plurality of molecular identifier labels may occur sequentially. Contacting the second sample with the second plurality of sample tags may occur prior to contacting the second sample with the second plurality of molecular identifier labels. Contacting the second sample with the second plurality of sample tags may occur after contacting the second sample with the second plurality of molecular identifier labels.

The methods and kits disclosed herein may further comprise combining two or more samples. The methods and kits disclosed herein may further comprise combining the first sample and the second sample. The first and second samples may be combined prior to contact with the plurality of molecular identifier labels. The first and second samples may be combined prior to detecting the labeled nucleic acids. The two or more samples may be combined prior to stochastically labeling two or more molecules in the two or more samples. The two or more samples may be combined after stochastically labeling two or more molecules in the two or more samples. The two or more samples may be combined prior to detecting two or more molecules in the two or more samples. The two or more samples may be combined after detecting two or more molecules in the two or more samples. The two or more samples may be combined prior to analyzing two or more molecules in the two or more samples. The two or more samples may be combined after analyzing two or more molecules in the two or more samples. The two or more samples may be combined prior to conducting one or more assays on two or more molecules in the two or more samples. The two or more samples may be combined after conducting one or more assays on two or more molecules in the two or more samples.

The methods and kits disclosed herein may comprise conducting one or more assays on two or more molecules in a sample. The one or more assays may comprise one or more amplification reactions. The methods and kits disclosed herein may further comprise conducting one or more amplification reactions to produce labeled nucleic acid amplicons. The labeled nucleic acids may be amplified prior to detecting the labeled nucleic acids. The method may further comprise combining the first and second samples prior to conducting the one or more amplification reactions.

The amplification reactions may comprise amplifying at least a portion of the sample tag. The amplification reactions may comprise amplifying at least a portion of the label. The amplification reactions may comprise amplifying at least a portion of the sample tag, label, nucleic acid, or a combination thereof. The amplification reactions may comprise amplifying at least about 1%, 5%, 10%, 15%, 20%, 25%, 30%, 35%, 40%, 45%, 50%, 55%, 60%, 65%, 70%, 75%, 80%, 85%, 90%, 95%, or 100% of the total number of nucleic acids of the plurality of nucleic acids. The amplification reactions may comprise amplifying at least about 1% of the total number of nucleic acids of the plurality of nucleic acids. The amplification reactions may comprise amplifying at least about 5% of the total number of nucleic acids of the plurality of nucleic acids. The amplification reactions may comprise amplifying at least about 1%, 5%, 10%, 15%, 20%, 25%, 30%, 35%, 40%, 45%, 50%, 55%, 60%, 65%, 70%, 75%, 80%, 85%, 90%, 95%, or 100% of the total number of labeled nucleic acids of the plurality of labeled nucleic acids. The amplification reactions may comprise amplifying at least about 1% of the total number of labeled nucleic acids of the plurality of labeled nucleic acids. The amplification reactions may comprise amplifying at least about 5% of the total number of labeled nucleic acids of the plurality of labeled nucleic acids. The amplification reactions may comprise amplifying at least about 10% of the total number of labeled nucleic acids of the plurality of labeled nucleic acids. The amplification reactions may comprise amplifying less than about 95%, 90%, 80%, 70%, 60% or 50% of the total number of nucleic acids of the plurality of nucleic acids. The amplification reactions may comprise amplifying less than about 50% of the total number of nucleic acids of the plurality of nucleic acids. The amplification reactions may comprise amplifying less than about 20% of the total number of nucleic acids of the plurality of nucleic acids. The amplification reactions may comprise amplifying less than about 10% of the total number of nucleic acids of the plurality of nucleic acids. The amplification reactions may comprise amplifying less than about 95%, 90%, 80%, 70%, 60% or 50% of the total number of labeled nucleic acids of the plurality of labeled nucleic acids. The amplification reactions may comprise amplifying less than about 40% of the total number of labeled nucleic acids of the plurality of labeled nucleic acids. The amplification reactions may comprise amplifying less than about 25% of the total number of labeled nucleic acids of the plurality of labeled nucleic acids. The amplification reactions may comprise amplifying less than about 10% of the total number of labeled nucleic acids of the plurality of labeled nucleic acids.

The one or more amplification reactions may result in amplification of about 1, 2, 5, 10, 15, 20, 25, 30, 35, 40, 45, 50, 55, 60, 65, 70, 75, 80, 85, 90, 95, 100, 200, 300, 400, 500, 600, 700, 800, 900 or 1000 targeted nucleic acids in a sample. The one or more amplification reactions may result in amplification of about 2000 targeted nucleic acids in a sample. The one or more amplification reactions may result in amplification of about 1000 targeted nucleic acids in a sample. The one or more amplification reactions may result in amplification of about 2000 targeted molecules. The one or more amplification reactions may result in amplification of about 100 targeted nucleic acids in a sample.

The amplification reactions may comprise one or more polymerase chain reactions (PCRs). The one or more polymerase chain reactions may comprise multiplex PCR, nested PCR, absolute PCR, HD-PCR, Next Gen PCR, digital RTA, or any combination thereof. The one or more polymerase chain reactions may comprise multiplex PCR. The one or more polymerase chain reactions may comprise nested PCR.

Conducting the one or more amplification reactions may comprise the use of one or more primers. The one or more primers may comprise one or more oligonucleotides. The one or more oligonucleotides may comprise at least about 7-9 nucleotides. The one or more oligonucleotides may comprise less than 12-15 nucleotides. The one or more primers may anneal to at least a portion of the plurality of labeled nucleic acids. The one or more primers may anneal to the 3' end and/or 5' end of the plurality of labeled nucleic acids. The one or more primers may anneal to an internal region of the plurality of labeled nucleic acids. The internal region may be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The internal region may be at least about 2000 nucleotides from the 3' ends the plurality of labeled nucleic acids. The one or more primers may comprise a fixed panel of primers. The one or more primers may comprise at least one or more custom primers. The one or more primers may comprise at least one or more control primers. The one or more primers may comprise at least one or more housekeeping gene primers. The one or more oligonucleotides may comprise a sequence selected from a group consisting of sequences in Table 1. The one or more primers may comprise a universal primer. The universal primer may anneal to a universal primer binding site. The universal primer may anneal to a universal PCR region. The one or more custom primers may anneal to at least a portion of a sample tag. The one or more custom primers may anneal to at least a portion of a molecular identifier label. The one or more custom primers may anneal to at least a portion of a molecular barcode. The one or more custom primers may anneal to the first sample tag, the second sample tag, the molecular identifier label, the nucleic acid or a product thereof. The one or more primers may comprise a universal primer and a custom primer. The one or more primers may comprise at least about 96 or more custom primers. The one or more primers may comprise at least about 960 or more custom primers. The one or more primers may comprise at least about 9600 or more custom primers. The one or more custom primers may anneal to two or more different labeled nucleic acids. The two or more different labeled nucleic acids may correspond to one or more genes.

Multiplex PCR reactions may comprise a nested PCR reaction. The nested PCR reaction may comprise a pair of primers comprising a first primer and a second primer. The first primer may anneal to a region of one or more nucleic acids of the plurality of nucleic acids. The region of the one or more nucleic acids may be at least about 300 to 400 nucleotides from the 3' end of the one or more nucleic acids. The second primer may anneal to a region of one or more nucleic acids of the plurality of nucleic acids. The region of the one or more nucleic acids may be at least 200 to 300 nucleotides from the 3' end of the one or more nucleic acids.

The methods and kits disclosed herein may further comprise conducting one or more cDNA synthesis reactions to produce one or more cDNA copies of the molecules or derivatives thereof (e.g., labeled molecules). The one or more cDNA synthesis reactions may comprise one or more reverse transcription reactions.

The methods and kits disclosed herein may comprise one or more samples. The methods and kits disclosed herein may comprise a plurality of samples. The plurality of samples may comprise at least about 2, 3, 4, 5, 10, 20, 30, 40, 50, 60, 70, 80, 90 or 100 or more samples. The plurality of samples may comprise at least about 100, 200, 300, 400, 500, 600, 700, 800, 900 or 1000 or more samples. The plurality of samples may comprise at least about 1000, 2000, 3000, 4000, 5000, 6000, 7000, 8000 samples, 9000, or 10,000 samples, or 100,000 samples, or 1,000,000 or more samples. The plurality of samples may comprise at least about 10,000 samples. The plurality of samples may comprise at least about 2 samples. The plurality of samples may comprise at least about 5 samples. The plurality of samples may comprise at least about 10 samples. The plurality of samples may comprise at least about 50 samples. The plurality of samples may comprise at least about 100 samples.

The methods and kits disclosed herein may comprise one or more samples comprising one or more cells. The methods and kits disclosed herein may comprise two or more samples comprising one or more cells. A first sample may comprise one or more cells. A second sample may comprise one or more cells. The one or more cells of the first sample may be of the same cell type as the one or more cells of the second sample.

The methods and kits disclosed herein may comprise a plurality of samples. The plurality of samples may be from one or more subjects. The plurality of samples may be from two or more subjects. The plurality of samples may be from the same subject. The two or more subjects may be from the same species. The two or more subjects may be from different species. The plurality of samples may be from one or more sources. The plurality of samples may be from two or more sources. The plurality of samples may be from the same subject. The two or more sources may be from the same species. The two or more sources may be from different species.

The plurality of samples may be obtained concurrently. The plurality of samples may be obtained sequentially. The plurality of samples may be obtained over two or more time periods. The two or more time periods may be one or more hours apart. The two or more time periods may be one or more days apart. The two or more time periods may be one or more weeks apart. The two or more time periods may be one or more months apart. The two or more time periods may be one or more years apart.

The plurality of samples may be from one or more bodily fluids, tissues, cells, organs, or muscles. The plurality of samples may comprise one or more blood samples.

The methods and kits disclosed herein may comprise one or more samples comprising one or more nucleic acids. Two or more samples may comprise one or more nucleic acids. Two or more samples may comprise two or more nucleic acids. The one or more nucleic acids of a first sample may be different from one or more nucleic acids of a second sample. The nucleic acids in a first sample may be at least about 50% identical to the nucleic acids in a second sample. The nucleic acids in a first sample may be at least about 70% identical to the nucleic acids in a second sample. The nucleic acids in a first sample may be at least about 80% identical to the nucleic acids in a second sample.

The plurality of nucleic acids in the one or more samples may comprise two or more identical sequences. At least about 5%, 10%, 15%, 20%, 25%, 30%, 35%, 40%, 45%, 50%, 55%, 60%, 65%, 70%, 75%, 80%, 85%, 90%, 95%, 100% of the total nucleic acids in the one or more samples may comprise the same sequence. The plurality of nucleic acids in one or more samples may comprise at least two different sequences. At least about 5%, 10%, 15%, 20%, 25%, 30%, 35%, 40%, 45%, 50%, 55%, 60%, 65%, 70%, 75%, 80%, 85%, 90%, 95%, 100% of the total nucleic acids in the one or more samples may comprise different sequences.

The plurality of nucleic acids may comprise RNA, DNA, cDNA, mRNA, genomic DNA, small RNA, non-coding RNA, or other nucleic acid contents of a cell. The plurality of nucleic acids may comprise mRNA. The plurality of nucleic acids may comprise RNA. The plurality of nucleic acids may comprise mRNA. The plurality of nucleic acids may comprise DNA.

The methods and kits disclosed herein may comprise one or more sample tags. The methods and kits disclosed herein may comprise one or more pluralities of sample tags. The sample tags may comprise a sample index region. The sample index region of a first plurality of sample tags may be different from the sample index region of a second plurality of sample tags. The sample tags may comprise one or more nucleotides.

The sample tags may comprise at least about 5, 10, 15, 20, 25, 30, 35, 40, 45, 50, 55, 60, 65, 70, 75, 80, 85, 90, 95 or 100 nucleotides. The sample tags may comprise at least about 5 or more nucleotides. The sample tags may comprise at least about 10 or more nucleotides. The sample tags may comprise less than about 200 nucleotides. The sample tags may comprise less than about 100 nucleotides. The sample tags may comprise less than about 60 nucleotides.

The sample tags may further comprise a universal primer binding site. The sample tags may further comprise a universal PCR region. The sample tags may further comprise one or more adaptor regions. The sample tags may further comprise one or more target-specific regions.

The methods and kits disclosed herein may comprise one or more molecular identifier labels. The methods and kits disclosed herein may comprise one or more pluralities of molecular identifier labels. The one or more pluralities of molecular identifier labels may comprise two or more different molecular identifier labels. The one or more pluralities of molecular identifier labels may comprise 50 or more different molecular identifier labels. The one or more pluralities of molecular identifier labels may comprise 90 or more different molecular identifier labels. The one or more pluralities of molecular identifier labels may comprise 100 or more different molecular identifier labels. The one or more pluralities of molecular identifier labels may comprise 300 or more different molecular identifier labels. The one or more pluralities of molecular identifier labels may comprise 500 or more different molecular identifier labels. The one or more pluralities of molecular identifier labels may comprise 960 or more different molecular identifier labels. The one or more pluralities of molecular identifier labels may comprise multiple copies of one or more molecular identifier labels. Two or more pluralities of molecular identifier labels may comprise one or more identical molecular identifier labels. Two or more pluralities of molecular identifier labels may comprise 10 or more identical molecular identifier labels. The molecular identifier labels of a first plurality of molecular identifier labels may be at least about 30% identical to the molecular identifier labels of a second plurality of molecular identifier labels. The molecular identifier labels of a first plurality of molecular identifier labels may be at least about 50% identical to the molecular identifier labels of a second plurality of molecular identifier labels. The molecular identifier labels of a first plurality of molecular identifier labels may be at least about 80% identical to the molecular identifier labels of a second plurality of molecular identifier labels.

The molecular identifier labels may comprise a label region (e.g., molecular label region, molecular index region). The label region of two or more molecular identifier labels of a first plurality of molecular identifier labels may be different. One or more pluralities of molecular identifier labels may comprise at least about 20 different label regions. One or more pluralities of molecular identifier labels may comprise at least about 50 different label regions. One or more pluralities of molecular identifier labels may comprise at least about 96 different label regions. One or more pluralities of molecular identifier labels may comprise at least about 200 different label regions. One or more pluralities of molecular identifier labels may comprise at least about 500 different label regions. One or more pluralities of molecular identifier labels may comprise at least about 960 different label regions.

The molecular identifier labels may comprise at least about 1, 2, 3, 4, 5, 6, 7, 8, 9, 10 or more nucleotides. The molecular identifier labels may comprise at least about 20, 30, 40, 50 or more nucleotides. The molecular identifier labels may comprise at least about 21 nucleotides.

The molecular identifier labels may further comprise a target-specific region. The target-specific region may comprise an oligodT sequence.

The molecular identifier labels may further comprise one or more dye labels. The molecular identifier labels may further comprise a Cy3 dye. The molecular identifier labels may further comprise a Tye563 dye.

The methods and kits disclosed herein may comprise one or more labeled molecules. The one or more labeled molecules may be produced by contacting a plurality of molecules with a plurality of sample tags. The one or more labeled molecules may be produced by contacting a plurality of nucleic acids with a plurality of sample tags. Contacting the plurality of nucleic acids with the plurality of sample tags may comprise ligating one or more sample tags to one or more nucleic acids. Contacting the plurality of nucleic acids with the plurality of sample tag may comprise hybridizing one or more sample tags to one or more nucleic acids. Contacting the plurality of nucleic acids with the plurality of sample tag may comprise performing one or more nucleic acid extension reactions. The one or more nucleic acid extension reactions may comprise reverse transcription.

The methods and kits disclosed herein may further comprise attaching one or more oligonucleotide linkers to the plurality of nucleic acids. The method and kits may further comprise attaching one or more oligonucleotide linkers to the sample tagged nucleic acids. The methods and kits may further comprise attaching one or more oligonucleotide linkers to the labeled nucleic acids. The one or more linkers may comprise at least about 10 nucleotides.

The methods and kits disclosed herein may further comprise attaching one or more labeled nucleic acids to a support. The support may comprise a solid support. The support may comprise a bead. The support may comprise an array. The support may comprise a glass slide.

Attachment of the labeled nucleic acids to the support may comprise amine-thiol crosslinking, maleimide crosslinking, N-hydroxysuccinimide or N-hydroxysulfosuccinimide, Zenon, SiteClick, or a combination thereof. Attaching the labeled nucleic acids to the support may comprise attaching biotin to the one or more labeled nucleic acids.

The support may comprise one or more beads. The one or more beads may be a coated bead. The coated bead may be coated with streptavadin.

The support may comprise an array. The array may comprise one or more probes. The labeled nucleic acids may be attached to the one or more probes. The one or more probes may comprise one or more oligonucleotides. The one or more probes may be attached to at least a portion of the labeled nucleic acids. The portion of the labeled nucleic acids attached to the one or more probes may comprise at least a portion of the sample tag, molecular identifier label, molecular barcode, nucleic acid, or a combination thereof.

The support may comprise a glass slide. The glass slide may comprise one or more wells. The one or more wells may be etched on the glass slide. The one or more wells may comprise at least 960 wells. The glass slide may comprise one or more probes. The one or more probes may be printed onto the glass slide. The one or more wells may further comprise one or more probes. The one or more probes may be printed within the one or more wells. The one or more probes may comprise 960 nucleic acids. The nucleic acids may be different. The nucleic acids may be the same.

The methods and kits disclosed herein may be used to determine a count of one or more molecules in one or more samples. Determining the count of one or more molecules may comprise determining the number of different labeled nucleic acids. Determining the number of different labeled nucleic acids may comprise detecting at least a portion of the labeled nucleic acid. Detecting at least a portion of the labeled nucleic acid may comprise detecting at least a portion of the sample tag, molecular identifier label, molecular barcode, nucleic acid, or a combination thereof.

Determining the number of different labeled nucleic acids may comprise sequencing. Sequencing may comprise MiSeq sequencing. Sequencing may comprise HiSeq sequencing. Determining the number of different labeled nucleic acids may comprise an array. Determining the number of different labeled nucleic acids may comprise contacting the labeled nucleic acids with the one or more probes.

Determining the number of different labeled nucleic acids may comprise contacting the labeled nucleic acids with an array. The array may comprise a plurality of probes. Determining the number of different labeled nucleic acids may comprise contacting the labeled nucleic acids with a glass slide of a plurality of probes.

Determining the number of different labeled nucleic acids may comprise labeled probe hybridization, target-specific amplification, target-specific sequencing, sequencing with labeled nucleotides specific for target small nucleotide polymorphism, sequencing with labeled nucleotides specific for restriction enzyme digest patterns, sequencing with labeled nucleotides specific for mutations, or a combination thereof.

Determining the number of different labeled nucleic acids may comprise flow cytometry sorting of a sequence-specific label. Determining the number of different labeled nucleic acids may comprise detection of the labeled nucleic acids attached to the beads. Detection of the labeled nucleic acids attached to the beads may comprise fluorescence detection.

Determining the number of different labeled nucleic acids may comprise counting the plurality of labeled nucleic acids by fluorescence resonance energy transfer (FRET), between a target-specific probe and a labeled nucleic acid or a target-specific labeled probe. Determining the number of different labeled nucleic acids may comprise attaching the labeled nucleic acid to the support.

The methods and kits disclosed herein may further comprise immunoprecipitation of a target sequence with a nucleic-acid binding protein.

The methods and kits disclosed herein may further comprise distributing the plurality of samples into a plurality of wells of a microwell plate. One or more of the plurality of samples may comprise a plurality of cells. One or more of the plurality of samples may comprise a plurality of nucleic acids. The methods and kits disclosed herein may further comprise distributing one or fewer cells to the plurality of wells. The plurality of cells may be lysed in the microwell plate. The methods and kits disclosed herein may further comprise synthesizing cDNA in the microwell plate. Synthesizing cDNA may comprise reverse transcription of mRNA.

The methods and kits disclosed herein may further comprise distributing the plurality of first sample tags, the plurality of second sample tags, the plurality of molecular identifier labels, or any combination thereof into a microwell plate.

The methods and kits disclosed herein may further comprise distributing one or more beads in the microwell plate. The microwell plate may comprise a microwell plate fabricated on PDMS by soft lithography, etched on a silicon wafer, etched on a glass slide, patterned photoresist on a glass slide, or a combination thereof. The microwell may comprise a hole on a microcapillary plate. The microwell plate may comprise a water-in-oil emulsion. The microwell plate may comprise at least one or more wells. The microwell plate may comprise at least about 6 wells, 12 wells, 48 wells, 96 wells, 384 wells, 960 wells or 1000 wells.

The methods and kits disclosed herein may further comprise a chip. The microwell plate may be attached to the chip. The chip may comprise at least about 6 wells, 12 wells, 48 wells, 96 wells, 384 wells, 960 wells, 1000 wells, 2000 wells, 3000 wells, 4000 wells, 5000 wells, 6000 wells, 7000 wells, 8000 wells, 9000 wells, 10,000 wells, 20,000 wells, 30,000 wells, 40,000 wells, 50,000 wells, 60,000 wells, 70,000 wells, 80,000 wells, 90,000 wells, 100,000 wells, 200,000 wells, 500,000 wells, or a million wells. The wells may comprise an area of at least about 300 microns$^2$, 400 microns$^2$, 500 microns$^2$, 600 microns$^2$, 700 microns$^2$, 800 microns$^2$, 900 microns$^2$, 1000 microns$^2$, 1100 microns$^2$, 1200 microns$^2$, 1300 microns$^2$, 1400 microns$^2$, 1500 microns$^2$. The methods and kits disclosed herein may further comprise distributing between about 10,000 and 30,000 samples on the chip.

The methods and kits disclosed herein may further comprise diagnosing a condition, disease, or disorder in a subject in need thereof.

The methods and kits disclosed herein may further comprise prognosing a condition, disease, or disorder in a subject in need thereof. The methods and kits disclosed herein may further comprise determining a treatment for a condition, disease, or disorder in a subject in need thereof.

The plurality of samples may comprise one or more samples from a subject suffering from a disease or condition. The plurality of samples may comprise one or more samples from a healthy subject.

Further disclosed herein is a method of forensic analysis comprising: a) stochastically labeling two or more molecules in two or more samples to produce two or more labeled molecules; and b) detecting the two or more labeled molecules.

The method of selecting the custom primer may further comprise selecting the custom primer based on one or more nucleic acids. The one or more nucleic acids may comprise mRNA transcripts, non-coding transcripts including structural RNAs, transcribed pseudogenes, model mRNA provided by a genome annotation process, sequences corresponding to a genomic contig, or any combination thereof. The one or more nucleic acids may be RNA. The one or more nucleic acids may be mRNA. The one or more nucleic acids may comprise one or more exons. The method of selecting the custom primer may further comprise enriching for one or more subsets of nucleic acids. The one or more subsets comprise low abundance mRNAs. The method of selecting the custom primer may further comprise a computational algorithm.

The methods and kits disclosed herein may comprise the use of one or more controls. The one or more controls may be spiked in controls. The one or more controls may comprise nucleic acids. The one or more samples comprising a plurality of nucleic acids may be spiked with one or more control nucleic acids. The one or more control nucleic acids may be used to measure an efficiency of producing the labeled nucleic acid library.

The methods and kits disclosed herein may be used in the production of one or more nucleic acid libraries. The one or more nucleic acid libraries may comprise a plurality of labeled nucleic acids or derivatives thereof (e.g., labeled amplicons). The method of producing the labeled nucleic acid library may comprise stochastically labeling two or more nucleic acids in two or more samples with two or more sets of molecular barcodes to produce a plurality of labeled nucleic acids. The method of producing a labeled nucleic acid library may comprise contacting two or more samples with a plurality of sample tags and a plurality of molecule specific labels to produce a plurality of labeled nucleic acids. The labeled nucleic acids may comprise a sample index region, a label region and a nucleic acid region. The sample index region may be used to confer a sample or sub-sample identity to the nucleic acid. The sample index region may be used to determine the source of the nucleic acid. The label region may be used to confer a unique identity to the nucleic acid, thereby enabling differentiation of two or more identical nucleic acids in the same sample or sub-sample.

The method of producing a nucleic acid library may further comprise amplifying one or more labeled nucleic acids to produce one or more enriched labeled nucleic acids. The method may further comprise conducting one or more pull-down assays of the one or more enriched labeled nucleic acids. The method may further comprise purifying the one or more enriched labeled nucleic acids.

The kits disclosed herein may comprise a plurality of beads, a primer and/or amplification agents. One or more kits may be used in the analysis of at least about 10, 20, 30, 40, 50, 60, 70, 80, 90, or 100 or more samples or subsamples. One or more kits may be used in the analysis of at least about 96 samples. One or more kits may be used in the analysis of at least about 384 samples. The kit may further comprise instructions for primer design and optimization.

The kit may further comprise one or more microwell plates. The one or more microwell plates may be used for the distribution of one or more beads. The one or more microwell plates may be used for the distribution of one or more molecules or derivatives thereof (e.g., labeled molecules, labeled amplicons) from one or more samples.

The kit may further comprise one or more additional containers. The one or more additional containers may comprise one or more additional pluralities of sample tags. The one or more additional pluralities of sample tags in the one or more additional containers may be different from the first plurality of sample tags in the first container. The one or more additional containers may comprise one or more additional pluralities of molecular identifier labels. The one or more additional pluralities of molecular identifier labels of the one or more additional containers may be at least about 50% identical to the one or more additional molecular identifier labels of the second container. The one or more additional pluralities of molecular identifier labels of the one or more additional containers may be at least about 80% identical to the one or more additional molecular identifier labels of the second container. The one or more additional pluralities of molecular identifier labels of the one or more additional containers may be at least about 90% identical to the one or more additional molecular identifier labels of the second container.

Further disclosed herein are methods of producing one or more sets of labeled beads. The method of producing the one or more sets of labeled beads may comprise attaching one or more nucleic acids to one or more beads, thereby producing one or more sets of labeled beads. The one or more nucleic acids may comprise one or more molecular barcodes. The one or more nucleic acids may comprise one or more sample tags. The one or more nucleic acids may comprise one or more molecular identifier labels. The one or more nucleic acids may comprise a) a primer region; b) a sample index region; and c) a linker or adaptor region. The one or more nucleic acids may comprise a) a primer region; b) a label region; and c) a linker or adaptor region. The one or more nucleic acids may comprise a) a sample index region; and b) a label region. The one or more nucleic acids may further comprise a primer region. The one or more nucleic acids may further comprise a target specific region. The one or more nucleic acids may further comprise a linker region. The one or more nucleic acids may further comprise an adaptor region. The one or more nucleic acids may further comprise a sample index region. The one or more nucleic acids may further comprise a label region.

The primer region of the nucleic acids for a set of labeled beads may be at least about 70% identical. The primer region of the nucleic acids for a set of labeled beads may be at least about 90% identical. The primer region of the nucleic acids for a set of labeled beads may be the same.

The sample index region of the nucleic acids for a set of labeled beads may be at least about 70% identical. The sample index region of the nucleic acids for a set of labeled beads may be at least about 90% identical. The sample index region of the nucleic acids for a set of labeled beads may be the same. The sample index region of the nucleic acids for two or more sets of sample indexed beads may be less than about 40% identical. The sample index region of the nucleic acids for two or more sets of sample indexed beads may be less than about 50% identical. The sample index region of the nucleic acids for two or more sets of sample indexed beads may be less than about 60% identical. The sample index region of nucleic acids for two or more sets of sample indexed beads may be different.

The label region of the nucleic acids for two or more sets of labeled beads may be at least about 70% identical. The label region of the nucleic acids for two or more sets of labeled beads may be at least about 90% identical. The label region of the nucleic acids for two or more sets of labeled beads may be the same. The label region of the nucleic acids for a set of labeled beads may be less than about 40% identical. The label region of the nucleic acids for a set of labeled beads may be less than about 50% identical. The label region of the nucleic acids for a set of labeled beads may be less than about 60% identical. The label region of two or more nucleic acids for a set of labeled beads may be different.

The linker or adaptor region of the nucleic acids for a set of labeled beads may be at least about 70% identical. The linker or adaptor region of the nucleic acids for a set of labeled beads may be at least about 90% identical. The linker or adaptor region of the nucleic acids for a set of labeled beads may be the same.

The target specific region of the nucleic acids for two or more sets of target specified beads may be at least about 70% identical. The target specific region of the nucleic acids for two or more sets of target specified beads may be at least about 90% identical. The target specific region of the nucleic acids for two or more sets of target specified beads may be the same. The target specific region of the nucleic acids for a set of target specified beads may be less than about 40% identical. The target specific region of the nucleic acids for a set of target specified beads may be less than about 50% identical. The target specific region of the nucleic acids for a set of target specified beads may be less than about 60% identical. The target specific region of two or more nucleic acids for a set of target specified beads may be different.

The one or more sets of labeled beads may comprise one million or more labeled beads. The one or more sets of labeled beads may comprise ten million or more labeled beads.

Attaching the one or more nucleic acids to the beads may comprise covalent attachment. Attaching the one or more nucleic acids to the beads may comprise conjugation. Attaching the one or more nucleic acids to the beads may comprise ionic interactions.

The beads may be coated beads. The nucleic acids may be attached to one or more tags. The beads may be coated with streptavidin. The nucleic acids may be attached to biotin. The beads may also be coated with antibodies or nucleic acids, and the nucleic acids may be attached to the beads indirectly via such surface coated materials.

In one aspect, the disclosure provides for a composition comprising: a solid support, wherein said solid support comprises a plurality of oligonucleotides, wherein at least two of said plurality of oligonucleotides comprises a cellular label and a molecular label, wherein said cellular labels of said at least two of said plurality of oligonucleotides are the same, and wherein said molecular labels of said at least two of said plurality of oligonucleotides are different. In some embodiments, the plurality of oligonucleotide further comprises a sample label. In some embodiments, the plurality of oligonucleotides further comprises a target binding region. In some embodiments, the target binding region comprises a sequence is adapted to hybridize to a target nucleic acid. In some embodiments, the target binding region comprises a sequence selected from the group consisting of: a random multimer e.g., a random dimer, trimer, quatramer, pentamer, hexamer, septamer, octamer, nonamer, decamer, or higher multimer sequence of any length; a gene-specific primer; and oligo dT; or any combination thereof. In some embodiments, the plurality of oligonucleotides comprises a universal label. In some embodiments, the universal label comprises a binding site for a sequencing primer. In some embodiments, the plurality of oligonucleotides comprises a linker. In some embodiments, the linker comprises a functional group. In some embodiments, the linker is located 5' to said oligonucleotide. In some embodiments, the linker is selected from the group consisting of: C6, biotin, streptavidin, primary amines, aldehydes, and ketones, or any combination thereof. In some embodiments, the solid support is comprised of polystyrene. In some embodiments, the in solid support is magnetic. In some embodiments, the solid support is selected from the group consisting of: a PDMS solid support, a glass solid support, a polypropylene solid support, an agarose solid support, a gelatin solid support, a magnetic solid support, and a pluronic solid support, or any combination thereof. In some embodiments, the solid support comprises a bead. In some embodiments, the solid support comprises a diameter of about 20 microns. In some embodiments, the solid support comprises a diameter from about 5 microns to about 40 microns. In some embodiments, the solid support comprises a functional group. In some embodiments, the functional group is selected from the group consisting of: C6, biotin, streptavidin, primary amines, aldehydes, and ketones, or any combination thereof. In some embodiments, the cellular label comprises a plurality of cellular labels. In some embodiments, the plurality of cellular labels are interspersed with a plurality of linker label sequences. In some embodiments, the plurality of oligonucleotides comprises from 10,000 to 1 billion oligonucleotides.

In one aspect the disclosure provides for a solid support comprising: a first oligonucleotide comprising: a first cellular label comprising a first random sequence, a second random sequence, and a first linker label sequence, wherein said first linker label sequence connects said first random sequence and said second random sequence; and a first molecular label comprising a random sequence; and a second oligonucleotide comprising: a second cellular label comprising a third random sequence, a fourth random sequence, and a second linker label sequence, wherein said second linker label sequence connects said third random sequence and said fourth random sequence; and a second molecular label comprising a random sequence, wherein said first cellular label and said second cellular label are the same and said first molecular label and said second molecular label are different. In some embodiments, the first and second oligonucleotides further comprise identical sample index regions. In some embodiments, the sample index region comprises a random sequence. In some embodiments, the sample index region is 4-12 nucleotides in length. In some embodiments, the cellular label is directly attached to said molecular label. In some embodiments, the cellular label and said molecular label are attached through a linker label sequence. In some embodiments, the random sequence of said cellular label is from 4-12 nucleotides in length. In some embodiments, the constant sequence of said cellular label is at least 4 nucleotides in length. In some embodiments, the cellular label has a total length of at least 12 nucleotides. In some embodiments, the cellular label further comprises one or more additional random sequences. In some embodiments, the cellular label further comprises one or more additional linker label sequences. In some embodiments, the one or more additional linker label sequences connect the one or more additional random sequences. In some embodiments, the random sequence of the molecular label is 4-12 nucleotides in length.

In one aspect the disclosure provides for a composition comprising: a solid support, wherein said solid support comprises a plurality of oligonucleotides, wherein at least two of said plurality of oligonucleotides comprises: a cellular label, a molecular label; and a target binding region; and a plurality of a target nucleic acids, wherein said cellular labels of said at least two of said plurality of oligonucleotides are the same, and wherein said molecular labels of said at least two of said plurality of oligonucleotides are different. In some embodiments, the target binding region comprises a sequence that is adapted to hybridize to at least one of said plurality of target nucleic acids. In some embodiments, the target binding region comprises a sequence selected from the group consisting of: a random a random multimer e.g., a random dimer, trimer, quatramer, pentamer, hexamer, septamer, octamer, nonamer, decamer, or higher multimer sequence of any length; a gene-specific primer; and oligo dT; or any combination thereof. In some embodiments, the plurality of oligonucleotides comprises from 10,000 to 1 billion oligonucleotides. In some embodiments, the plurality of oligonucleotides comprises a number of oligonucleotides greater than the number of target nucleic acids of said plurality of target nucleic acids. In some embodiments, the plurality of target nucleic acids comprises multiple copies of a same target nucleic acid. In some embodiments, the plurality of target nucleic acids comprises multiple copies of different target nucleic acids. In some embodiments, the plurality of target nucleic acids are bound to said plurality of oligonucleotides. In some embodiments, the oligonucleotide further comprises a sample label. In some embodiments, the plurality of oligonucleotides comprises a universal label. In some embodiments, the universal label comprises a binding site for a sequencing primer. In some embodiments, the plurality of oligonucleotides comprises a linker. In some embodiments, the linker comprises a functional group. In some embodiments, the linker is located 5' to said oligonucleotide. In some embodiments, the functional group comprises an amino group. In some embodiments, the linker is selected from the group consisting of: C6, biotin, streptavidin, primary amines, aldehydes, and ketones, or any combination thereof. In some embodiments, the solid support is comprised of polystyrene. In some embodiments, the solid support is magnetic. In some embodiments, the solid support is selected from the group consisting of: a PDMS solid support, a glass solid support, a polypropylene solid support, an agarose solid support, a gelatin solid support, a magnetic solid support, and a pluronic solid support, or any combination thereof. In some embodiments, the solid support comprises a bead. In some embodiments, the solid support comprises a diameter of about 20 microns. In some embodiments, the solid support comprises a diameter from about 5 microns to about 40 microns. In some embodiments, the solid support comprises a functional group. In some embodiments, the functional group comprises a carboxy group. In some embodiments, the functional group is selected from the group consisting of: C6, biotin, streptavidin, primary amines, aldehydes, and ketones, or any combination thereof. In some embodiments, the cellular label comprises a plurality of cellular labels. In some embodiments, the plurality of cellular labels is interspersed with a plurality of linker label sequences.

In one aspect the disclosure provides for a kit comprising: a first solid support, wherein said first solid support comprises a first plurality of oligonucleotides, wherein said first plurality of oligonucleotides comprises the same first cellular label, a second solid support, wherein said second solid support comprises a second plurality of oligonucleotides, wherein said second plurality of oligonucleotides comprises the same second cellular label, instructions for use, wherein said first cellular label and said second cellular label are different. In some embodiments, oligonucleotides form said first plurality of oligonucleotides and said second plurality of oligonucleotides comprises a molecular label. In some embodiments, the molecular labels of said oligonucleotides are different. In some embodiments, the molecular labels of said oligonucleotides are the same. In some embodiments, the molecular label of some of said oligonucleotides are different and some are the same. In some embodiments, the oligonucleotides from said first plurality of oligonucleotides and said second plurality of oligonucleotides comprise a target binding region. In some embodiments, the kit further comprises: a microwell array. In some embodiments, the kit further comprises: a buffer. In some embodiments, the buffer is selected from the group consisting of: a reconstitution buffer, a dilution buffer, and a stabilization buffer, or any combination thereof.

In one aspect the disclosure provides for a method for determining an amount of a target nucleic acid comprising: contacting a sample with a solid support, wherein said solid support comprises a plurality of oligonucleotides, wherein at least two of said plurality of oligonucleotides comprises a cellular label and a molecular label, wherein said cellular labels of said at least two of said plurality of oligonucleotides are the same, and wherein said molecular labels of said at least two of said plurality of oligonucleotides are different; and hybridizing said target nucleic acid from said sample to an oligonucleotide of said plurality of oligonucleotides. In some embodiments, the sample comprises cells. In some embodiments, the sample is lysed prior to said hybridizing. In some embodiments, the hybridizing comprising hybridizing multiple copies of a same target nucleic acid to said plurality of oligonucleotides. In some embodiments, the method further comprises: amplifying said target nucleic acid. In some embodiments, the amplifying comprises reverse transcribing said target nucleic acid. In some embodiments, the amplifying comprises amplification using a method selected from the group consisting of: PCR, quantitative PCR, real-time PCR, and digital PCR, or any combination thereof. In some embodiments, the amplifying is performed directly on said solid support. In some embodiments, the amplifying is performed on a template transcribed from said solid support. In some embodiments, the method further comprises: sequencing said target nucleic acid. In some embodiments, the sequencing comprises sequencing said target nucleic acid and said molecular label. In some embodiments, the method further comprises: determining an amount of said target nucleic acid. In some embodiments, the determining comprises quantifying levels of said target nucleic acid. In some embodiments, the determining comprises counting the number of sequenced molecular labels for said target nucleic acid. In some embodiments, the contacting occurs in a microwell. In some embodiments, the microwell is made from a material selected from the group consisting of: hydrophilic plastic, plastic, elastomer, and hydrogel, or any combination thereof. In some embodiments, the microwell comprises agarose. In some embodiments, the microwell is one microwell of a microwell array. In some embodiments, the microwell array comprises at least 90 microwells. In some embodiments, the microwell array comprises at least 150,000 microwells. In some embodiments, the microwell comprises at least one solid support per well. In some embodiments, the microwell comprises at most two solid supports per well. In some embodiments, the microwell is of a size that accommodates at most two of said solid support. In some embodiments, the microwell is of a size that accommodates at most one solid support. In some embodiments, the microwell is at least 25 microns deep. In some embodiments, the microwell is at least 25 microns in diameter.

In one aspect the disclosure provides for a method to reduce amplification bias of a target nucleic acid comprising: contacting a sample to a solid support, wherein said solid support comprises a plurality of oligonucleotides, wherein at least two of said plurality of oligonucleotides comprises a cellular label and a molecular label, wherein said cellular labels of said at least two of said plurality of oligonucleotides are the same, and wherein said molecular labels of said at least two of said plurality of oligonucleotides are different; and hybridizing a target nucleic acid from said sample to said plurality of oligonucleotides; amplifying said target nucleic acidl; sequencing said target nucleic acid, wherein said sequencing sequences said target nucleic acid and said molecular label of said oligonucleotide to which said target nucleic acid is bound; and determining an amount of said target nucleic acid. In some embodiments, the hybridizing comprising hybridizing multiple copies of a same target nucleic acid to said plurality of oligonucleotides. In some embodiments, the determining comprises counting a number of sequenced molecular labels for a same target nucleic acid. In some embodiments, the counting counts the number of copies of said same target nucleic acid. In some embodiments, the sample comprises cells. In some embodiments, the amplifying comprises reverse transcribing said target nucleic acid. In some embodiments, the amplifying comprises amplification using a method selected from the group consisting of: PCR, quantitative PCR, real-time PCR, and digital PCR, or any combination thereof. In some embodiments, the amplifying is performed directly on said solid support. In some embodiments, the amplifying is performed on a template transcribed from said solid support.

In one aspect the disclosure provides for a composition comprising: a microwell; a cell; and a solid support, wherein said solid support comprises a plurality of oligonucleotides, wherein at least two of said plurality of oligonucleotides comprises a cellular label and a molecular label, wherein said cellular labels of said at least two of said plurality of oligonucleotides are the same, and wherein said molecular labels of said at least two of said plurality of oligonucleotides are different. In some embodiments, the at least two of said plurality of oligonucleotides further comprises a sample label. In some embodiments, the at least two of said plurality of oligonucleotides further comprises a target binding region. In some embodiments, the target binding region comprises a sequence selected from the group consisting of: a random multimer e.g., a random dimer, trimer, quatramer, pentamer, hexamer, septamer, octamer, nonamer, decamer, or higher multimer sequence of any length; a gene-specific primer; and oligo dT; or any combination thereof. In some embodiments, the plurality of oligonucleotides comprises a universal label. In some embodiments, the universal label comprises a binding site for a sequencing primer. In some embodiments, the solid support is comprised of polystyrene. In some embodiments, the solid support is magnetic. In some embodiments, the solid support is selected from the group consisting of: a PDMS solid support, a glass solid support, a polypropylene solid support, an agarose solid support, a gelatin solid support, a magnetic solid support, and a pluronic solid support, or any combination thereof. In some embodiments, the solid support comprises a bead. In some embodiments, the solid support has a diameter of about 20 microns. In some embodiments, the solid support has a diameter from about 5 microns to about 40 microns. In some embodiments, the cellular label comprises a plurality of cellular labels. In some embodiments, the plurality of cellular labels is interspersed with a plurality of linker sequences. In some embodiments, the microwell is made from a material selected from the group consisting of: hydrophilic plastic, plastic, elastomer, and hydrogel, or any combination thereof. In some embodiments, the microwell comprises agarose. In some embodiments, the microwell is a microwell of a microwell array. In some embodiments, the microwell comprises at least one solid support per well. In some embodiments, the microwell comprises at most two solid supports per well. In some embodiments, the microwell is of a size that accommodates at least one of said solid support and at least one of said cell. In some embodiments, the microwell is of a size that accommodates at most one of said solid support and at least one of said cell. In some embodiments, the microwell is at least 25 microns deep. In some embodiments, the microwell is at least 25 microns in diameter. In some embodiments, the microwell is flat.

In one aspect the disclosure provides for a device comprising: a first substrate comprising a first microwell array; wherein said first microwell array comprises a plurality of first microwells in a first pre-determined spatial arrangement configured to perform multiplexed, single cell stochastic labeling and molecular indexing assays.

In some embodiments, the device comprises a first substrate comprising at least a second microwell array, wherein said at least second microwell array comprises a plurality of at least second microwells in an at least second pre-determined spatial arrangement. In some embodiments, the first microwells and the at least second microwells are the same. In some embodiments, the first microwells and the at least second microwells are different. In some embodiments, the first pre-determined spatial arrangement and the at least second pre-determined spatial arrangement are the same. In some embodiments, the first pre-determined spatial arrangement and the at least second pre-determined spatial arrangement are different. In some embodiments, a pre-determined spatial arrangement comprises a one dimensional or two dimensional array pattern. In some embodiments, the two dimensional array pattern comprises a square grid, a rectangular grid, or a hexagonal grid. In some embodiments, the microwells comprise a cylindrical geometry, a conical geometry, a hemispherical geometry, a rectangular geometry, a polyhedral geometry, or a combination thereof. In some embodiments, a diameter of the microwells is between about 5 microns and about 50 microns. In some embodiments, a depth of the microwells is between about 10 microns and about 60 microns. In some embodiments, a center-to-center spacing between two adjacent microwells is between about 15 microns and about 75 microns. In some embodiments, a total number of microwells in a first or at least second microwell array is between about 96 and about 5,000,000. In some embodiments, the first substrate comprises silicon, fused-silica, glass, a polymer, a metal, or a combination thereof. In some embodiments, the first substrate further comprises agarose or a hydrogel. In some embodiments, a microwell array further comprises at least one surface feature, wherein said surface feature surrounds one or more individual microwells or straddles a surface between individual microwells, and wherein said surface feature is domed, ridged, or peaked.

In one aspect the disclosure provides for a device comprising: a first substrate comprising at least a first microwell array; and a mechanical fixture comprising a top plate, a bottom plate, and a gasket; wherein when the first substrate and mechanical fixture are in assembled form, the first substrate is positioned between the gasket and the bottom plate, the gasket forms a leak-proof seal with the first substrate, and the top plate and gasket form at least a first chamber encompassing said at least first microwell array such that a cell sample and a bead-based oligonucleotide label may be dispensed into said at least first chamber to perform multiplexed, single cell stochastic labeling and a molecular indexing assays.

In some embodiments, the at least first microwell array is any described herein. In some embodiments, the gasket is fabricated from polydimethylsiloxane (PDMS) or a similar elastomeric material. In some embodiments, the top and bottom plates are fabricated from aluminum, anodized aluminum, stainless steel, teflon, polymethylmethacrylate, polycarbonate, or a similar rigid polymer material.

In one aspect the disclosure provides for a device comprising: at least one substrate further comprising at least one microwell array; and a flow cell; wherein the flow cell encloses or is attached to said at least one substrate, and includes at least one inlet port and at least one outlet port for the purpose of delivering fluids to said microwell arrays; and wherein the device is configured to perform multiplexed, single cell stochastic labeling and molecular indexing assays.

In some embodiments, said at least one substrate comprise at least one microwell array as described herein. In some embodiments, the flow cell further comprises a plurality of microarray chambers that interface with a plurality of microwell arrays such that one or more samples may be processed in parallel. In some embodiments, the flow cell further comprises a porous barrier or flow diffuser to provide more uniform delivery of cells and beads to the at least one microwell array. In some embodiments, the flow cell further comprises dividers that divide each chamber containing a microwell array into subsections that collectively cover the same total array area and provide for more uniform delivery of cells and beads to the at least one microwell array. In some embodiments, the width of fluid channels incorporated into the device is between about 50 microns and 20 mm. In some embodiments, the depth of fluid channels incorporated into the device is between about 50 microns and about 2 mm. In some embodiments, the flow cell is fabricated from a material selected from the group consisting of silicon, fused-silica, glass, polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resin, metal, or a combination of these materials. In some embodiments, the device comprises a fixed component of an instrument system configured to perform automated multiplexed, single cell stochastic labeling and molecular indexing assays. In some embodiments, the device comprises a removable component of an instrument system configured to perform automated multiplexed, single cell stochastic labeling and molecular indexing assays.

In one aspect the disclosure provides for a cartridge comprising: at least a first substrate further comprising at least a first microwell array; at least a first flow cell or microwell array chamber; one or more sample or reagent reservoirs; and wherein the cartridge further comprises at least one inlet port and at least one outlet port for the purpose of delivering fluids to said at least first microwell array; and wherein the cartridge is configured to perform multiplexed, single cell stochastic labeling and molecular indexing assays.

In some embodiments, said at least first substrate comprises at least a first microwell array as described herein. In some embodiments, the cartridge comprises a plurality of microwell arrays and is configured to process one or more samples in parallel. In some embodiments, the at least first flow cell or microwell array chamber further comprises a porous barrier or flow diffuser to provide more uniform delivery of cells and beads to the at least first microwell arrays. In some embodiments, the at least first flow cell or microwell array chamber further comprises dividers that divide the at least first flow cell or microwell array chamber into subsections that collectively cover the same total array area and provide for more uniform delivery of cells and beads to the microwell arrays. In some embodiments, the width of fluid channels incorporated into the cartridge is between about 50 microns and 200 microns. In some embodiments, the width of the fluid channels incorporated into the cartridge is between about 200 microns and 2 mm. In some embodiments, the width of the fluid channels incorporated into the cartridge is between about 2 mm and 10 mm. In some embodiments, the width of the fluid channels incorporated into the cartridge is between about 10 mm and 20 mm. In some embodiments, the depth of fluid channels incorporated into the cartridge is between about 50 microns and about 2 mm. In some embodiments, the depth of fluid channels incorporated into the cartridge is between about 500 microns and 1 mm. In some embodiments, the depth of fluid channels incorporated into the cartridge is between about 1 mm and about 2 mm. In some embodiments, the one or more flow cells or microwell array chambers are fabricated from a material selected from the group consisting of silicon, fused-silica, glass, polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resin, metal, or a combination of these materials. In some embodiments, the device comprises a removable, consumable component of an instrument system configured to perform automated multiplexed, single cell stochastic labeling and molecular indexing assays. In some embodiments, the cartridge further comprises bypass channels or other design features for providing self-metering of cell samples or bead suspensions dispensed or injected into the cartridge. In some embodiments, the cartridge further comprises integrated miniature pumps for controlling fluid flow through the device. In some embodiments, the cartridge further comprises integrated miniature valves for compartmentalizing pre-loaded reagents and for controlling fluid flow through the device. In some embodiments, the cartridge further comprises vents for providing an escape path for trapped air. In some embodiments, the cartridge further comprises design elements for creating physical or chemical barriers that effectively increase pathlength and prevent or minimize diffusion of molecules between microwells, wherein the design elements are selected from the group consisting of: a pattern of serpentine channels for delivery of cells and beads to the at least first microwell array, a retractable platen or deformable membrane that is pressed into contact with the surface of the at least first microwell array, or the release of an immiscible, hydrophobic fluid from a reservoir within the cartridge. In some embodiments, the cartridge further comprises integrated temperature control components or an integrated thermal interface for providing good thermal contact with an external instrument system. In some embodiments, the cartridge further comprises an optical interface or window for optical imaging of the at least first microwell array. In some embodiments, the cartridge further comprises one or more removable sample collection chambers that are configured to interface with stand-alone PCR thermal cyclers and/or sequencing instruments. In some embodiments, the cartridge itself is configured to interface directly with stand-alone PCR thermal cyclers and/or sequencing instruments.

In one aspect the disclosure provides for an instrument system comprising: at least a first flow cell or cartridge further comprising at least a first microwell array; and a flow controller; wherein the flow controller controls the delivery of cell samples, bead-based oligonucleotide labeling reagents, and other assay reagents to the at least first microwell array, and the instrument system is configured to perform multiplexed, single cell stochastic labeling and molecular indexing assays.

In some embodiments, the at least first microwell array as described herein. In some embodiments, the at least first flow cell is a fixed component of the system. In some embodiments, the at least first flow cell is a removable, consumable component of the system. In some embodiments, the at least first cartridge is a removable, consumable component of the system. In some embodiments, cell samples and bead-based oligonucleotide reagents are dispensed or injected directly into the cartridge by the user. In some embodiments, assay reagents other than cell samples are preloaded in the cartridge. In some embodiments, the instrument system further comprises an imaging system for imaging the at least first microwell array. In some embodiments, the instrument system further comprises a cell or bead distribution system for facilitating uniform distribution of cells and beads across the at least first microwell array, wherein the mechanism underlying said distribution system is selected from the group consisting of rocking, shaking, swirling, recirculating flow, low frequency agitation, or high frequency agitation. In some embodiments, the instrument system further comprises a cell lysis system wherein the system uses a high frequency piezoelectric transducer for sonicating the cells. In some embodiments, the instrument system further comprises a temperature controller for maintaining a user-specified temperature, or for ramping temperature between two or more specified temperatures over two or more specified time intervals. In some embodiments, the instrument system further comprises a magnetic field controller for use in eluting beads from microwells. In some embodiments, the instrument system further comprises a computer or processor programmed to provide a user interface and control of system functions. In some embodiments, the instrument system further comprises program code for providing real-time image analysis capability. In some embodiments, the real-time image analysis and instrument control functions are coupled, so that cell and bead sample loading steps can be prolonged or repeated until optimal cell/bead distributions are achieved. In some embodiments, the instrument system further comprises an integrated PCR thermal cycler for amplification of oligonucleotide labels. In some embodiments, the instrument system further comprises an integrated sequencer for sequencing of oligonucleotide libraries, thereby providing sample-to-answer capability. In some embodiments, the cell samples comprise patient samples and the results of the multiplexed, single cell stochastic labeling and molecular indexing assay are used for clinical diagnostic applications. In some embodiments, the cell samples comprise patient samples and the results of the multiplexed, single cell stochastic labeling and molecular indexing assay are used by a healthcare provider to make informed healthcare treatment decisions.

In one aspect the disclosure provides for software residing in a computer readable medium programmed to perform one or more of the following sequence data analysis functions: determining the number of reads per gene per cell, and the number of unique transcript molecules per gene per cell; principal component analysis or other statistical analysis to predict confidence intervals for determinations of the number of transcript molecules per gene per cell; alignment of gene sequence data with known reference sequences; decoding/demultiplexing of sample barcodes, cell barcodes, and molecular barcodes; and automated clustering of molecular labels to compensate for amplification or sequencing errors; wherein the sequence data is generated by performing multiplexed, single cell stochastic labeling and molecular indexing assays.

In one aspect the disclosure provides for a composition comprising: a solid support, wherein the solid support comprises a plurality of oligonucleotides, wherein at least two of the plurality of oligonucleotides comprises a cellular label and a molecular label, wherein the cellular labels of the at least two of the plurality of oligonucleotides are the same, and wherein the molecular labels of the at least two of the plurality of oligonucleotides are different.

In some embodiments, the plurality of oligonucleotide further comprises a sample label. In some embodiments, the plurality of oligonucleotides further comprises a target binding region. In some embodiments, the target binding region comprises a sequence is adapted to hybridize to a target nucleic acid. In some embodiments, the target nucleic acid comprises a plurality of target nucleic acids comprising at least 0.01%, 0.02%, 0.05%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the transcripts of a transcriptome of an organism. In some embodiments, the target nucleic acid is DNA. In some embodiments, the target nucleic acid is RNA. In some embodiments, the target nucleic acid is mRNA. In some embodiments, the DNA is genomic DNA. In some embodiments, the genomic DNA is sheared. In some embodiments, the sheared genomic DNA comprises at least 0.01%, 0.02%, 0.05%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the genes of a genome of an organism. In some embodiments, the target binding region comprises a sequence selected from the group consisting of: a random multimer e.g., a random dimer, trimer, quatramer, pentamer, hexamer, septamer, octamer, nonamer, decamer, or higher multimer sequence of any length; a gene-specific primer; and oligo dT; or any combination thereof. In some embodiments, the plurality of oligonucleotides comprises a universal label. In some embodiments, the universal label comprises a binding site for a sequencing primer. In some embodiments, the plurality of oligonucleotides comprises a linker. In some embodiments, the linker comprises a functional group. In some embodiments, the linker is located 5' to the oligonucleotide. In some embodiments, the linker is selected from the group consisting of: C6, biotin, streptavidin, primary amines, aldehydes, and ketones, or any combination thereof. In some embodiments, the solid support is comprised of polystyrene. In some embodiments, in solid support is magnetic. In some embodiments, the solid support is selected from the group consisting of: a PDMS solid support, a glass solid support, a polypropylene solid support, an agarose solid support, a gelatin solid support, a magnetic solid support, and a pluronic solid support, or any combination thereof. In some embodiments, the solid support comprises a bead. In some embodiments, the solid support comprises a diameter of about 20 microns. In some embodiments, the solid support comprises a diameter from about 5 microns to about 40 microns. In some embodiments, the solid support comprises a functional group. In some embodiments, the functional group is selected from the group consisting of: C6, biotin, streptavidin, primary amines, aldehydes, and ketones, or any combination thereof. In some embodiments, the cellular label comprises a plurality of cellular labels. In some embodiments, the plurality of cellular labels is interspersed with a plurality of linker label sequences. In some embodiments, the plurality of oligonucleotides comprises from 10,000 to 1 billion oligonucleotides. In some embodiments, the plurality of oligonucleotides comprises from 10,000 to 1 billion target binding regions. In some embodiments, the plurality of oligonucleotides comprises from 10,000 to 1 billion different target binding regions. In some embodiments, the plurality of oligonucleotides comprises from 10,000 to 1 billion same target binding regions. In some embodiments, the different target binding regions can hybridize to at least 0.01%, 0.02%, 0.05%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the transcripts of a transcriptome of an organism. In some embodiments, the different target binding regions can hybridize to at least 0.01%, 0.02%, 0.05%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the transcripts of a transcriptome of an organism.

In one aspect the disclosure provides for a composition comprising: a solid support, wherein the solid support comprises a plurality of oligonucleotides, wherein at least two of the plurality of oligonucleotides comprises a cellular label and a molecular label, wherein the cellular labels of the at least two of the plurality of oligonucleotides are the same, and wherein the molecular labels of the at least two of the plurality of oligonucleotides are different.

In some embodiments, the plurality of oligonucleotide further comprises a sample label. In some embodiments, the plurality of oligonucleotides further comprises a target binding region. In some embodiments, the target binding region comprises a sequence is adapted to hybridize to a target nucleic acid. In some embodiments, the target nucleic acid comprises a plurality of target nucleic acids comprising at least 0.01%, 0.02%, 0.05%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the transcripts of a transcriptome of an organism. In some embodiments, the target nucleic acid comprises sheared genomic DNA wherein the wherein the sheared genomic DNA comprises at least 0.01%, 0.02%, 0.05%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, or 100% of the genes of a genome of an organism. In some embodiments, the target binding region comprises an oligo dT. In some embodiments, the at least two of the plurality of oligonucleotides comprises a first oligonucleotide and a second oligonucleotide, wherein the first oligonucleotide comprises a first cellular label and a first molecular label, wherein the first cellular label comprises a first random sequence, a second random sequence, and a first linker label sequence, wherein the first linker label sequence connects the first random sequence and the second random sequence; and the first molecular label comprises a random sequence; and the second oligonucleotide comprises a second cellular label and a second molecular label, wherein the second cellular label comprises a third random sequence, a fourth random sequence, and a second linker label sequence, wherein the second linker label sequence connects the third random sequence and the fourth random sequence; and the second molecular label comprising a random sequence, and wherein the first cellular label and the second cellular label are the same and the first molecular label and the second molecular label are different.

In one aspect the disclosure provides for a kit comprising any composition described herein and instructions for use.

In one aspect the disclosure provides for a method, comprising: contacting a sample with a solid support, wherein the solid support comprises a plurality of oligonucleotides, wherein at least two of the plurality of oligonucleotides comprises a cellular label and a molecular label, wherein the cellular labels of the at least two of the plurality of oligonucleotides are the same, and wherein the molecular labels of the at least two of the plurality of oligonucleotides are different; and hybridizing the target nucleic acid from the sample to an oligonucleotide of the plurality of oligonucleotides.

In some embodiments, the sample comprises cells. In some embodiments, the sample is lysed prior to the hybridizing. In some embodiments, the hybridizing comprising hybridizing multiple copies of a same target nucleic acid to the plurality of oligonucleotides. In some embodiments, the method further comprises reverse transcribing the target nucleic acid. In some embodiments, the method further comprises performing an oligonucletide amplification. In some embodiments, the amplifying comprises amplification using a method selected from the group consisting of: PCR, quantitative PCR, real-time PCR, and digital PCR, or any combination thereof.

In one aspect the disclosure provides for a A solid support comprising: a first oligonucleotide comprising: a first cellular label comprising a first random sequence, a second random sequence, and a first linker label sequence, wherein the first linker label sequence connects the first random sequence and the second random sequence; and a first molecular label comprising a random sequence; and a second oligonucleotide comprising: a second cellular label comprising a third random sequence, a fourth random sequence, and a second linker label sequence, wherein the second linker label sequence connects the third random sequence and the fourth random sequence; and a second molecular label comprising a random sequence, wherein the first cellular label and the second cellular label are the same and the first molecular label and the second molecular label are different. In some embodiments, the first and second oligonucleotides further comprise identical sample index regions. In some embodiments, the sample index region comprises a random sequence. In some embodiments, the sample index region is 4-12 nucleotides in length. In some embodiments, the cellular label is directly attached to the molecular label. In some embodiments, the cellular label and the molecular label are attached through a linker label sequence. In some embodiments, the random sequence of the cellular label is from 4-12 nucleotides in length. In some embodiments, the constant sequence of the cellular label is at least 4 nucleotides in length. In some embodiments, the cellular label has a total length of at least 12 nucleotides. In some embodiments, the cellular label further comprises one or more additional random sequences. In some embodiments, the cellular label further comprises one or more additional linker label sequences. In some embodiments, the one or more additional linker label sequences connect the one or more additional random sequences. In some embodiments, the random sequence of the molecular label is 4-12 nucleotides in length.

In one aspect the disclosure provides for a composition comprising: a solid support, wherein the solid support comprises a plurality of oligonucleotides, wherein at least two of the plurality of oligonucleotides comprises: a cellular label, a molecular label; and a target binding region; and a plurality of a target nucleic acids, wherein the cellular labels of the at least two of the plurality of oligonucleotides are the same, and wherein the molecular labels of the at least two of the plurality of oligonucleotides are different.

In some embodiments, the target binding region comprises a sequence that is adapted to hybridize to at least one of the plurality of target nucleic acids. In some embodiments, the target binding region comprises a sequence selected from the group consisting of: a random multimer e.g., a random dimer, trimer, quatramer, pentamer, hexamer, septamer, octamer, nonamer, decamer, or higher multimer sequence of any length; a gene-specific primer; and oligo dT; or any combination thereof. In some embodiments, the plurality of oligonucleotides comprises from 10,000 to 1 billion oligonucleotides. In some embodiments, the plurality of oligonucleotides comprises a number of oligonucleotides greater than the number of target nucleic acids of the plurality of target nucleic acids. In some embodiments, the plurality of target nucleic acids comprises multiple copies of a same target nucleic acid. In some embodiments, the plurality of target nucleic acids comprises multiple copies of different target nucleic acids. In some embodiments, the plurality of target nucleic acids are bound to the plurality of oligonucleotides. In some embodiments, the oligonucleotide further comprises a sample label. In some embodiments, the plurality of oligonucleotides comprises a universal label. In some embodiments, the universal label comprises a binding site for a sequencing primer. In some embodiments, the plurality of oligonucleotides comprises a linker. In some embodiments, the linker comprises a functional group. In some embodiments, the linker is located 5' to the oligonucleotide. In some embodiments, the functional group comprises an amino group. In some embodiments, the linker is selected from the group consisting of: C6, biotin, streptavidin, primary amines, aldehydes, and ketones, or any combination thereof. In some embodiments, the solid support is comprised of polystyrene. In some embodiments, in solid support is magnetic. In some embodiments, the solid support is selected from the group consisting of: a PDMS solid support, a glass solid support, a polypropylene solid support, an agarose solid support, a gelatin solid support, a magnetic solid support, and a pluronic solid support, or any combination thereof. In some embodiments, the solid support comprises a bead. In some embodiments, the solid support comprises a diameter of about 20 microns. In some embodiments, the solid support comprises a diameter from about 5 microns to about 40 microns. In some embodiments, the solid support comprises a functional group. In some embodiments, the functional group comprises a carboxy group. In some embodiments, the functional group is selected from the group consisting of: C6, biotin, streptavidin, primary amines, aldehydes, and ketones, or any combination thereof. In some embodiments, the cellular label comprises a plurality of cellular labels. In some embodiments, the plurality of cellular labels is interspersed with a plurality of linker label sequences.

In one aspect the disclosure provides for a kit comprising: a first solid support, wherein the first solid support comprises a first plurality of oligonucleotides, wherein the first plurality of oligonucleotides comprises a same first cellular label, a second solid support, wherein the second solid support comprises a second plurality of oligonucleotides, wherein the second plurality of oligonucleotides comprises a same second cellular label, and instructions for use, wherein the first cellular label and the second cellular label are different.

In some embodiments, oligonucleotides from the first plurality of oligonucleotides and the second plurality of oligonucleotides comprises a molecular label. In some embodiments, the molecular label of the oligonucleotides are different. In some embodiments, the molecular label of the oligonucleotides are the same. In some embodiments, the molecular label of some of the oligonucleotides are different and some are the same. In some embodiments, oligonucleotides from the first plurality of oligonucleotides and the second plurality of oligonucleotides comprise a target binding region. In some embodiments, the kit further comprises a microwell array. In some embodiments, the kit further comprises a buffer. In some embodiments, the buffer is selected from the group consisting of: a reconstitution buffer, a dilution buffer, and a stabilization buffer, or any combination thereof.

In one aspect the disclosure provides for a method for determining an amount of a target nucleic acid comprising: contacting a sample with a solid support, wherein the solid support comprises a plurality of oligonucleotides, wherein at least two of the plurality of oligonucleotides comprises a cellular label and a molecular label, wherein the cellular labels of the at least two of the plurality of oligonucleotides are the same, and wherein the molecular labels of the at least two of the plurality of oligonucleotides are different; and hybridizing the target nucleic acid from the sample to an oligonucleotide of the plurality of oligonucleotides.

In some embodiments, the sample comprises cells. In some embodiments, the sample is lysed prior to the hybridizing. In some embodiments, the hybridizing comprising hybridizing multiple copies of a same target nucleic acid to the plurality of oligonucleotides. In some embodiments, the method further comprises amplifying the target nucleic acid. In some embodiments, the amplifying comprises reverse transcribing the target nucleic acid. In some embodiments, the amplifying comprises amplification using a method selected from the group consisting of: PCR, quantitative PCR, real-time PCR, and digital PCR, or any combination thereof. In some embodiments, the amplifying is performed directly on the solid support. In some embodiments, the amplifying is performed on a template transcribed from the solid support. In some embodiments, the method further comprises sequencing the target nucleic acid. In some embodiments, the sequencing comprises sequencing the target nucleic acid and the molecular label. In some embodiments, the method further comprises determining an amount of the target nucleic acid. In some embodiments, the determining comprises quantifying levels of the target nucleic acid. In some embodiments, the determining comprises counting the number of sequenced molecular labels for the target nucleic acid. In some embodiments, the contacting occurs in a microwell. In some embodiments, the microwell is made from a material selected from the group consisting of: hydrophilic plastic, plastic, elastomer, and hydrogel, or any combination thereof. In some embodiments, the microwell comprises agarose. In some embodiments, the microwell is one microwell of a microwell array. In some embodiments, the microwell array comprises at least 90 microwells. In some embodiments, the microwell array comprises at least 150,000 microwells. In some embodiments, the microwell comprises at least one solid support per well. In some embodiments, the microwell comprises at most two solid supports per well. In some embodiments, the microwell is of a size that accommodates at most two of the solid support. In some embodiments, the microwell is of a size that accommodates at most one solid support. In some embodiments, the microwell is at least 25 microns deep. In some embodiments, the microwell is at least 25 microns in diameter.

In one aspect the disclosure provides for a method to reduce amplification bias of a target nucleic acid comprising: contacting a sample to a solid support, wherein the solid support comprises a plurality of oligonucleotides, wherein at least two of the plurality of oligonucleotides comprises a cellular label and a molecular label, wherein the cellular labels of the at least two of the plurality of oligonucleotides are the same, and wherein the molecular labels of the at least two of the plurality of oligonucleotides are different; and hybridizing a target nucleic acid from the sample to the plurality of oligonucleotides; amplifying the target nucleic acid or compliment thereof. sequencing the target nucleic acid or compliment thereof, wherein the sequencing sequences the target nucleic acid or compliment thereof and the molecular label of the oligonucleotide to which the target nucleic acid or compliment thereof is bound. determining an amount of the target nucleic acid.

In some embodiments, the hybridizing comprising hybridizing multiple copies of a same target nucleic acid to the plurality of oligonucleotides. In some embodiments, the determining comprises counting a number of sequenced molecular labels for a same target nucleic acid. In some embodiments, the counting counts the number of copies of the same target nucleic acid. In some embodiments, the sample comprises cells. In some embodiments, the amplifying comprises reverse transcribing the target nucleic acid. In some embodiments, the amplifying comprises amplification using a method selected from the group consisting of: PCR, quantitative PCR, real-time PCR, and digital PCR, or any combination thereof. In some embodiments, the amplifying is performed directly on the solid support. In some embodiments, the amplifying is performed on a template transcribed from the solid support.

In one aspect the disclosure provides for a composition comprising a microwell; a cell; and a solid support, wherein the solid support comprises a plurality of oligonucleotides, wherein at least two of the plurality of oligonucleotides comprises a cellular label and a molecular label, wherein the cellular labels of the at least two of the plurality of oligonucleotides are the same, and wherein the molecular labels of the at least two of the plurality of oligonucleotides are different.

In some embodiments, the at least two of the plurality of oligonucleotides further comprises a sample label. In some embodiments, the at least two of the plurality of oligonucleotides further comprises a target binding region. In some embodiments, the target binding region comprises a sequence selected from the group consisting of: a random multimer e.g., a random dimer, trimer, quatramer, pentamer, hexamer, septamer, octamer, nonamer, decamer, or higher multimer sequence of any length; a gene-specific primer; and oligo dT; or any combination thereof. In some embodiments, the plurality of oligonucleotides comprises a universal label. In some embodiments, the universal label comprises a binding site for a sequencing prumer. In some embodiments, the solid support is comprised of polystyrene. In some embodiments, in solid support is magnetic. In some embodiments, the solid support is selected from the group consisting of: a PDMS solid support, a glass solid support, a polypropylene solid support, an agarose solid support, a gelatin solid support, a magnetic solid support, and a pluronic solid support, or any combination thereof. In some embodiments, the solid support comprises a bead. In some embodiments, the solid support has a diameter of about 20 microns. In some embodiments, the solid support has a diameter from about 5 microns to about 40 microns. In some embodiments, the cellular label comprises a plurality of cellular labels. In some embodiments, the plurality of cellular labels is interspersed with a plurality of linker sequences. In some embodiments, the microwell is made from a material selected from the group consisting of: hydrophilic plastic, plastic, elastomer, and hydrogel, or any combination thereof. In some embodiments, the microwell comprises agarose. In some embodiments, the microwell is a microwell of a microwell array. In some embodiments, the microwell comprises at least one solid support per well. In some embodiments, the microwell comprises at most two solid supports per well. In some embodiments, the microwell is of a size that accommodates at least one of the solid support and at least one of the cell. In some embodiments, the microwell is of a size that accommodates at most one of the solid support and at least one of the cell. In some embodiments, the microwell is at least 25 microns deep. In some embodiments, the microwell is at least 25 microns in diameter. In some embodiments, the microwell is flat In one aspect the disclosure provides for a device, comprising a plurality of microwells, wherein the plurality of microwells comprises at least two microwells; and wherein each microwell of the plurality of microwells has a volume ranging from about 1,000 $\mu m^3$ to about 120,000 $\mu m^3$. In some embodiments, each microwell of the plurality of microwells has a volume of about 20,000 $\mu m^3$. In some embodiments, the plurality of microwells comprises from about 1,000 to about 5,000,000 microwells. In some embodiments, the plurality of microwells comprises about 100,000 to about 200,000 microwells. In some embodiments, the microwells are comprised in a single layer of a material. In some embodiments, at least about 10% of the microwells further comprise a cell. In some embodiments, at least about 10% of the microwells further comprise a solid support which comprises a plurality of oligonucleotides, wherein at least two of the plurality of oligonucleotides comprise a cellular label and a molecular label, wherein the cellular labels of the at least two of the plurality of oligonucleotides are the same, and wherein the molecular labels of the at least two of the plurality of oligonucleotides are different. In some embodiments, the solid supports are magnetized.

In one aspect the disclosure provides for an apparatus comprising any device described herein, and a liquid handler.

In some embodiments, the liquid handler delivers liquid to the plurality of microwells in about 1 second. In some embodiments, the apparatus delivers liquid to the plurality of microwells from a single input port. In some embodiments, the apparatus further comprises a magnet. In some embodiments, the apparatus further comprises at least one of: an inlet port, an outlet port, a pump, a valve, a vent, a reservoir, a sample collection chamber, a temperature control apparatus, or any combination thereof. In some embodiments, the apparatus comprises the sample collection chamber, wherein the sample collection chamber is removable from the apparatus. In some embodiments, the apparatus further comprises an optical imager. In some embodiments, the optical imager produces an output signal which is used to control the liquid handler. In some embodiments, the apparatus further comprises a thermal cycling mechanism configured to perform polymerase chain reaction (PCR) amplification of oligonucleotides.

In one aspect the disclosure provides for a method of producing a clinical diagnostic test result, comprising producing the clinical diagnostic test result with any device or apparatus described herein. In some embodiments, the clinical diagnostic test result is transmitted via a communication medium.

In one aspect the disclosure provides for a device comprising: one or more substrates further comprising one or more microwell arrays; wherein the microwell arrays are used to perform multiplexed, single cell stochastic labeling and molecular indexing assays.

In some embodiments, the microwell arrays of the substrates comprise microwells arranged in a one dimensional or two dimensional array pattern. In some embodiments, the two dimensional array pattern of microwells is selected from the group including a square grid, a rectangular grid, or a hexagonal grid.

In some embodiments, the microwells of the microwell arrays are fabricated using a well geometry selected from the group including cylindrical, conical, hemispherical, rectangular, or polyhedral. In some embodiments, the microwells of the microwell arrays are fabricated using a overall geometry that comprises two or more component geometries selected from the group including cylindrical, conical, hemispherical, rectangular, or polyhedral. In some embodiments, the diameter of the microwells in the microwell arrays is between about 5 microns and about 50 microns. In some embodiments, the depth of the microwells in the microwell arrays is between about 10 microns and about 60 microns. In some embodiments, the center-to-center spacing between microwells in the microwell arrays is between about 15 microns an about 75 microns. In some embodiments, the total number of microwells in each of the microwell arrays is between about 96 and about 5,000,000. In some embodiments, the one or more substrates are fabricated from a material selected from the group including silicon, fused-silica, glass, a polymer, or a metal. In some embodiments, the one or more substrates are fabricated from agarose or a hydrogel. In some embodiments, the microwell arrays further comprise surface features between microwells that surround the microwells or straddle the surface between microwells, and are selected from the group including domed, ridged, or peaked surface features.

In one aspect the disclosure provides for a device comprising: a substrate further comprising one or more microwell arrays; and a mechanical fixture comprising a top plate, a bottom plate, and a gasket; wherein when assembled the substrate is positioned between the gasket and the bottom plate, the gasket forms a leak-proof seal with the substrate, and the top plate and gasket form one or more chambers encompassing the microwell arrays such that one or more cell samples and bead-based oligonucleotide labels may be dispensed into the chambers for the purpose of performing multiplexed, single cell stochastic labeling and molecular indexing assays.

In some embodiments, the substrate comprises any one or more microwell arrays as described herein. In some embodiments, the gasket is fabricated from polydimethylsiloxane (PDMS) or a similar elastomeric material. In some embodiments, the top and bottom plates are fabricated from aluminum, anodized aluminum, stainless steel, teflon, polymethylmethacrylate, polycarbonate, or a similar rigid polymer material.

In one aspect the disclosure provides for a device comprising: one or more substrates further comprising one or more microwell arrays; and one or more flow cells; wherein the one or more flow cells enclose or are attached to the one or more substrates, and include at least one inlet port and at least one outlet port for the purpose of delivering fluids to the microwell arrays; and wherein the device is used to perform multiplexed, single cell stochastic labeling and molecular indexing assays.

In some embodiments, the one or more substrates comprise any one or more microwell arrays as described herein. In some embodiments, each of the one or more flow cells further comprise a plurality of microarray chambers that interface with a plurality of microwell arrays such that one or more samples may be processed in parallel. In some embodiments, the one or more flow cells further comprise a porous barrier or flow diffuser to provide more uniform delivery of cells and beads to the microwell arrays. In some embodiments, the one or more flow cells further comprise dividers that divide chambers containing microwell arrays into subsections that collectively cover the same total array area and provide for more uniform delivery of cells and beads to the microwell arrays. In some embodiments, the width of fluid channels incorporated into the device is between about 50 microns and 20 mm. In some embodiments, the depth of fluid channels incorporated into the device is between about 50 microns and about 2 mm. In some embodiments, the one or more flow cells are fabricated from a material selected from the group consisting of silicon, fused-silica, glass, polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resin, metal, or a combination of these materials. In some embodiments, the device comprises a fixed component of an instrument system for performing automated multiplexed, single cell stochastic labeling and molecular indexing assays. In some embodiments, the device comprises a removable component of an instrument system for performing automated multiplexed, single cell stochastic labeling and molecular indexing assays.

In one aspect the disclosure provides for a cartridge comprising: one or more substrates further comprising one or more microwell arrays; one or more flow cells or microwell array chambers; one or more sample or reagent reservoirs; and wherein the cartridge further comprises at least one inlet port and at least one outlet port for the purpose of delivering fluids to the microwell arrays; and wherein the cartridge is used to perform multiplexed, single cell stochastic labeling and molecular indexing assays.

In some embodiments, the one or more substrates comprise any one or more microwell arrays as described herein. In some embodiments, the one or more flow cells or microwell array chambers interface with a plurality of microwell arrays such that one or more samples may be processed in parallel. In some embodiments, the one or more flow cells or microwell array chambers further comprise a porous barrier or flow diffuser to provide more uniform delivery of cells and beads to the microwell arrays. In some embodiments, the one or more flow cells or microwell array chambers further comprise dividers that divide the flow cells or chambers into subsections that collectively cover the same total array area and provide for more uniform delivery of cells and beads to the microwell arrays. In some embodiments, the width of fluid channels incorporated into the cartridge is between about 50 microns and 200 microns. In some embodiments, the width of the fluid channels incorporated into the cartridge is between about 200 microns and 2 mm. In some embodiments, the width of the fluid channels incorporated into the cartridge is between about 2 mm and 10 mm. In some embodiments, the width of the fluid channels incorporated into the cartridge is between about 10 mm and 20 mm. In some embodiments, the depth of fluid channels incorporated into the cartridge is between about 50 microns and about 10 mm. In some embodiments, the depth of fluid channels incorporated into the cartridge is between about 500 microns and 1 mm. In some embodiments, the depth of fluid channels incorporated into the cartridge is between about 1 mm and about 2 mm. In some embodiments, the one or more flow cells or microwell array chambers are fabricated from a material selected from the group consisting of silicon, fused-silica, glass, polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resin, metal, or a combination of these materials. In some embodiments, the device comprises a removable, consumable component of an instrument system for performing automated multiplexed, single cell stochastic labeling and molecular indexing assays. In some embodiments, the cartridge further comprises bypass channels or other design features for providing self-metering of cell samples or bead suspensions dispensed or injected into the cartridge. In some embodiments, the cartridge further comprises integrated miniature pumps for controlling fluid flow through the device. In some embodiments, the cartridge further comprises integrated miniature valves for compartmentalizing pre-loaded reagents and for controlling fluid flow through the device. In some embodiments, the cartridge further comprises vents for providing an escape path for trapped air. In some embodiments, the cartridge further comprises comprise design elements for creating physical or chemical barriers that effectively increase pathlength and prevent or minimize diffusion of molecules between microwells, wherein the design elements are selected from the group consisting of: a pattern of serpentine channels for delivery of cells and beads to the microwell array, a retractable platen or deformable membrane that is pressed into contact with the surface of the microwell array, or the release of an immiscible, hydrophobic fluid from a reservoir within the cartridge. In some embodiments, the cartridge further comprises integrated temperature control components or an integrated thermal interface for providing good thermal contact with an external instrument system. In some embodiments, the cartridge further comprises an optical interface or window for optical imaging of the one or more microwell arrays. In some embodiments, the cartridge further comprises one or more removable sample collection chambers that are configured to interface with stand-alone PCR thermal cyclers and/or sequencing instruments. In some embodiments, the cartridge itself is configured to interface directly with stand-alone PCR thermal cyclers and/or sequencing instruments.

In one aspect the disclosure provides for an instrument system comprising: one or more flow cells or cartridges further comprising one or more microwell arrays; and a flow controller; wherein the flow controller controls the delivery of cell samples, bead-based oligonucleotide labeling reagents, and other assay reagents to the microwell arrays, and the instrument system is used to perform multiplexed, single cell stochastic labeling and molecular indexing assays.

In some embodiments, the one or more microwell arrays are any described herein. In some embodiments, the one or more flow cells are a fixed component of the system. In some embodiments, the one or more flow cells are a removable, consumable component of the system. In some embodiments, the one or more cartridges are removable, consumable components of the system. In some embodiments, cell samples and bead-based oligonucleotide reagents are dispensed or injected directly into the cartridge by the user. In some embodiments, assay reagents other than cell samples are preloaded in the cartridge. In some embodiments, the ainstrument system further comprises an imaging system for imaging the the microwell arrays. In some embodiments, the ainstrument system further comprises a cell or bead distribution system for facilitating uniform distribution of cells and beads across the microwell arrays, wherein the mechanism underlying the distribution system is selected from the group consisting of rocking, shaking, swirling, recirculating flow, low frequency agitation, or high frequency agitation. In some embodiments, the ainstrument system further comprises a cell lysis system wherein the system uses a high frequency piezoelectric transducer for sonicating the cells. In some embodiments, the ainstrument system further comprises a temperature controller for maintaining a user-specified temperature, or for ramping temperature between two or more specified temperatures over two or more specified time intervals. In some embodiments, the ainstrument system further comprises a magnetic field controller for use in eluting beads from microwells. In some embodiments, the ainstrument system further comprises a computer or processor programmed to provide a user interface and control of system functions. In some embodiments, the ainstrument system further comprises program code for providing real-time image analysis capability. In some embodiments, the real-time image analysis and instrument control functions are coupled, so that cell and bead sample loading steps can be prolonged or repeated until optimal cell/bead distributions are achieved. In some embodiments, the ainstrument system further comprises an integrated PCR thermal cycler for amplification of oligonucleotide labels. In some embodiments, the ainstrument system further comprises an integrated sequencer for sequencing of oligonucleotide libraries, thereby providing sample-to-answer capability. In some embodiments, the cell samples comprise patient samples and the results of the multiplexed, single cell stochastic labeling and molecular indexing assay are used for clinical diagnostic applications. In some embodiments, the cell samples comprise patient samples and the results of the multiplexed, single cell stochastic labeling and molecular indexing assay are used by a healthcare provider to make informed healthcare treatment decisions.

In one aspect the disclosure provides for software residing in a computer readable medium programmed to perform one or more of the following sequence data analysis: determining the number of reads per gene per cell, and the number of unique transcript molecules per gene per cell; principal component analysis or other statistical analysis to predict confidence intervals for determinations of the number of transcript molecules per gene per cell; alignment of gene sequence data with known reference sequences; decoding/demultiplexing of sample barcodes, cell barcodes, and molecular barcodes; and automated clustering of molecular labels to compensate for amplification or sequencing errors; wherein the sequence data is generated by performing multiplexed, single cell stochastic labeling and molecular indexing assays.

What is claimed is:

1. A composition comprising:
a single cell and a single bead,
wherein said single bead comprises a plurality of oligonucleotides,
wherein each of said plurality of oligonucleotides comprises an identical cellular label sequence, a molecular label sequence, and a target-binding region, and
wherein at least 100 of said plurality of oligonucleotides comprise different molecular label sequences.

2. The composition of claim 1, wherein said plurality of oligonucleotides comprises at least 100,000 oligonucleotides.

3. The composition of claim 1, wherein said plurality of oligonucleotides each comprises a universal label sequence.

4. The composition of claim 1, wherein said target-binding region comprises a sequence selected from the group consisting of an oligo-dT sequence, a gene-specific sequence, and a random multimer sequence.

5. The composition of claim 1, wherein said single cell is a cell selected from the group consisting of a rare cell, a tumor cell, and an immune cell.

6. The composition of claim 1, wherein said single cell is from a human.

7. The composition of claim 1, wherein said single cell is from a tissue.

8. The composition of claim 1, wherein said single cell is infected with viral polynucleotides.

9. The composition of claim 1, wherein said single bead is magnetic.

10. A composition comprising:
a lysate from a single cell and a single bead,
wherein said single bead comprises a plurality of oligonucleotides,
wherein each of said plurality of oligonucleotides comprises an identical cellular label sequence, a molecular label sequence, and a target-binding region, and
wherein at least 100 of said plurality of oligonucleotides comprise different molecular label sequences.

11. The composition of claim 10, wherein the nucleic acid contents of said lysate from a single cell are associated with a plurality of oligonucleotides.

12. The composition of claim 1, wherein at least 1,000 of said plurality of oligonucleotides comprise different molecular label sequences.

13. The composition of claim 1, wherein at least 10,000 of said plurality of oligonucleotides comprise different molecular label sequences.

14. The composition of claim 10, wherein at least 1,000 of said plurality of oligonucleotides comprise different molecular label sequences.

15. The composition of claim 10, wherein at least 10,000 of said plurality of oligonucleotides comprise different molecular label sequences.

16. The composition of claim 1, wherein said plurality of oligonucleotides is capable of labeling individual occurrences of target molecules of said single cell.

17. The composition of claim 1, wherein said plurality of oligonucleotides is capable of labeling individual occurrences of mRNA molecules of said single cell via reverse transcription.

18. The composition of claim 1, wherein said bead comprises silica gel, controlled pore glass, Dynabead, Wang resin, Merrifield resin, Sephadex/Sepharose bead, cellulose bead, polystyrene bead, or any combination thereof.

19. The composition of claim 10, wherein said plurality of oligonucleotides is capable of labeling individual occurrences of target molecules of said lysate from a single cell.

20. The composition of claim 10, wherein said plurality of oligonucleotides is capable of labeling individual occurrences of mRNA molecules of said lysate from a single cell via reverse transcription.

21. The composition of claim 10, wherein said plurality of oligonucleotides comprises at least 100,000 oligonucleotides.

22. The composition of claim 10, wherein said single cell is a cell selected from the group consisting of a rare cell, a tumor cell, and an immune cell.

23. The composition of claim 10, wherein said single cell is from a human.

24. The composition of claim 10, wherein said single cell is from a tissue.

25. The composition of claim 10, wherein said single cell is infected with viral polynucleotides.

26. The composition of claim 10, wherein said bead is magnetic.

27. The composition of claim 10, wherein said bead comprises silica gel, controlled pore glass, Dynabead, Wang resin, Merrifield resin, Sephadex/Sepharose bead, cellulose bead, polystyrene bead, or any combination thereof.

* * * * *

UNITED STATES PATENT AND TRADEMARK OFFICE
CERTIFICATE OF CORRECTION

PATENT NO. : 9,567,646 B2
APPLICATION NO. : 14/800526
DATED : February 14, 2017
INVENTOR(S) : Christina Fan et al.

It is certified that error appears in the above-identified patent and that said Letters Patent is hereby corrected as shown below:

On the Title Page

Item (72), Inventors at Line 1, Change "Fremont, CA (US);" for Christina Fan to --San Jose, CA (US);--.

In the Drawings

Sheet 23 of 135 (Y-Axis, FIG. 12L) at Line 1, Above "Graphs Tables" insert --Number of unique molecules per gene--.

Sheet 76 of 135 (FIG. 44C) at Line 10 (approx.), After "unstimulated" insert --sample--.

In the Specification

In Column 2 at Line 22, Change "vericella" to --varicella--.

In Column 19 at Line 3, After "different" insert --.--.

In Column 21 at Line 60, Change "streptavadin." to --streptavidin.--.

In Column 23 at Line 46, Change "diameterA" to --diameter. A--.

In Column 23 at Line 67, Change "denderimer," to --dendrimer,--.

In Column 24 at Line 9, Change "dendrom." to --dendron.--.

In Column 24 at Line 17, Change "hyberbranched" to --hyperbranched--.

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,567,646 B2

In Column 24 at Line 20, Change "hyberbranched" to --hyperbranched--.

In Column 28 at Lines 7-8, Change "4-(N-mafeimidomethyl)-" to --4-(N-maleimidomethyl)- --.

In Column 28 at Line 9, Change "6-hydrazinonicotimide (HYNIC)," to --6-hydrazinonicotinamide (HYNIC)),--.

In Column 29 at Lines 2-3, Change "4-(N-mafeimidomethyl)-" to --4-(N-maleimidomethyl)- --.

In Column 29 at Line 4, Change "6-hydrazinonicotimide (HYNIC)." to --6-hydrazinonicotinamide (HYNIC)).--.

In Column 32 at Line 27, Change "hydropillic." to --hydrophilic--.

In Column 36 at Line 4, After "micromachining" insert --.--.

In Column 38 at Line 66, Change "acutation," to --actuation,--.

In Column 45 at Line 32, Change "302a-fIn" to --302a-f. In--.

In Column 49 at Line 17, Change "microwall" to --microwell--.

In Column 62 at Line 33, Change "HCL." to --HCl.--.

In Column 71 at Line 40, Change "Nat." to --Natl.--.

In Column 71 at Line 56, Change "based sequence" to --sequence based--.

In Column 71 at Line 56, Change "(NABSA)." to --(NASBA).--.

In Column 71 at Line 58, Change "reference)," to --reference).--.

In Column 72 at Line 64, After "samples" insert --.--.

In Column 73 at Line 34 (approx.), Change "Primer 3," to --Primer3,--.

In Column 77 at Line 57, Change "HLPC" to --HPLC--.

In Column 78 at Line 24, Change "Fluoremeter" to --Fluorometer--.

In Column 78 at Line 25, Change "Fluoremeter," to --Fluorometer,--.

In Column 78 at Line 27, Change "Muliskan" to --Multiskan--.

In Column 78 at Line 28, Change "Muliskan" to --Multiskan--.

In Column 80 at Line 5, Change "to to" to --to--.

In Column 83 at Line 61, Change "pluoronic" to --pluronic--.

In Column 84 at Line 8, Change "wafter" to --wafer--.

In Column 84 at Line 26, Change "4 5," to --4, 5,--.

In Column 84 at Line 52, Change "archae," to --archaea,--.

In Column 85 at Line 38 (approx.), Change "Actinomedurae," to --Actinomadura,--.

In Column 85 at Lines 47-48 (approx.), Change "Bortadella" to --Bordetella--.

In Column 85 at Line 51 (approx.), Change "Haemophilius" to --Haemophilus--. (First Occurrence)

In Column 85 at Line 51 (approx.), Change "Haemophilius" to --Haemophilus--. (Second Occurrence)

In Column 85 at Line 52 (approx.), Change "Haemophilius influenziae," to --Haemophilus influenzae--.

In Column 85 at Line 52 (approx.), Change "Heliobacter" to --Helicobacter--.

In Column 85 at Line 54 (approx.), Change "sturti," to --stuartii,--.

In Column 85 at Line 55 (approx.), Change "enteridis" to --enteritidis--.

In Column 85 at Line 60, Change "Myobacterium" to --Mycobacterium--.

In Column 85 at Line 61, Change "Myobacterium" to --Mycobacterium--. (First Occurrence)

In Column 85 at Line 61, Change "Myobacterium" to --Mycobacterium--. (Second Occurrence)

In Column 85 at Line 62, Change "henseiae," to --henselae,--.

In Column 85 at Line 66, Change "chafensis," to --chaffeensis,--.

In Column 86 at Line 7, Change "cayatanensis," to --cayetanensis,--.

In Column 86 at Line 8, Change "Encephalitozoa," to --Encephalitozoon,--.

In Column 86 at Line 9, Change "Plasmodia" to --Plasmodium--.

In Column 86 at Line 11, Change "helminthes)," to --helminths),--.

In Column 86 at Line 22, Change "archae," to --archaea,--.

In Column 93 at Line 66, Change "6-carboxyfluoroscein)," to --6-carboxyfluorescein),--.

In Column 95 at Line 57, Before "The" delete "may".

In Column 96 at Line 19, Change "phylloides," to --phyllodes,--.

In Column 96 at Lines 52-53, Change "mesotheliomia." to --mesothelioma.--.

In Column 96 at Line 65, Change "astocytoma" to --astrocytoma--.

In Column 97 at Line 4, Change "oligodendriogliomas" to --oligodendrogliomas--.

In Column 97 at Line 39, Change "B" to --B.--.

In Column 97 at Line 65, Change "metavirirus," to --metavirus,--.

In Column 97 at Line 67, Change "hepadenovirus" to --hepadnavirus--.

In Column 99 at Line 29, Change "Chrohn's" to --Crohn's--.

In Column 99 at Line 30, Change "neorlogical" to --neurological--.

In Column 99 at Line 31, Change "neorlogical" to --neurological--.

In Column 99 at Line 42, Before "Pain," insert --Back--.

In Column 100 at Line 37, Change "Menieres" to --Meniere's- --.

In Column 101 at Line 7, Change "Rombergs Syndrome," to --Rombergs_Syndrome,--.

In Column 101 at Lines 15-16, Change "Romberg_s Syndrome," to --Rombergs_Syndrome,--.

In Column 103 at Line 25, Change "xantine," to --xanthine,--.

In Column 103 at Lines 28-29, Change "beta-D-galactosylqueosine," to --beta-D-galactosylqueuosine,--.

In Column 103 at Lines 33-34, Change "beta-D-mannosylqueosine," to --beta-D-mannosylqueuosine,--.

CERTIFICATE OF CORRECTION (continued)
U.S. Pat. No. 9,567,646 B2

In Column 103 at Line 36, Change "queosine," to --queuosine,--.

In Column 116 at Line 23, Change "(PMBCs)" to --(PBMCs)--.

In Column 116 at Line 24, Change "(PMBCs)" to --(PBMCs)--.

In Column 116 at Line 25, Change "(PMBCs)" to --(PBMCs)--.

In Column 116 at Line 27, Change "(PMBCs)" to --(PBMCs)--.

In Column 118 at Line 34 (approx.), Change "myeoloid" to --myeloid--.

In Column 119 at Line 28, Change "PMBCs" to --PBMCs--.

In Column 119 at Line 36, Change "PMBC" to --PBMC--.

In Column 121 at Line 64, Change "PMBCs." to --PBMCs.--.

In Column 125 at Line 49, Change "by to" to --to--.

In Column 127 at Line 24 (approx.), Change "PMBCs" to --PBMCs--.

In Column 127 at Line 53 (approx.), Change "SuperRase" to --SupeRase--.

In Column 152 at Line 21, Change "cyometry" to --cytometry--.

In Column 154 at Line 46, Change "resusupended" to --resuspended--.

In Column 155 at Line 3, Change "14" to --1 µL--.

In Column 155 at Line 3, Change "SuperRase" to --SupeRase--.

In Column 157 at Line 38 (approx.), Change "minutes," to --minutes.--.

In Column 158 at Line 45, Change "thrL_332" to --thr_L_332--.

In Column 161 at Line 6 (approx.), Change "thrL_332" to --thr_L_332--.

In Column 161 at Line 11, After "following" insert --:--.

In Column 162 at Line 33, After "(FIG. 58B)" insert --.--.

In Column 181 at Line 28, Change "streptavadin" to --streptavidin--.

CERTIFICATE OF CORRECTION (continued)
U.S. Pat. No. 9,567,646 B2

In Column 189 at Line 28, Change "acidl;" to --acid;--.

In Column 196 at Line 53, Change "a A" to --a--.
In Column 199 at Line 44, Change "bound." to --bound,--.

In Column 200 at Line 16 (approx.), Change "prumer." to --primer.--.

In Column 200 at Line 47, After "flat" insert --.--.

In Column 204 at Line 33, Change "the the" to --the--.

In the Claims

In Column 483 at Line 53, In Claim 11, change "a" to --the--.